(12) United States Patent
Scharenberg et al.

(10) Patent No.: US 11,400,169 B2
(45) Date of Patent: Aug. 2, 2022

(54) LONG POLY(A) PLASMIDS AND METHODS FOR INTRODUCTION OF LONG POLY(A) SEQUENCES INTO THE PLASMID

(71) Applicant: Seattle Children's Hospital, Seattle, WA (US)

(72) Inventors: Andrew M. Scharenberg, Seattle, WA (US); Kyle Jacoby, Seattle, WA (US); Alexandra E. Grier, Seattle, WA (US)

(73) Assignee: SEATTLE CHILDREN'S HOSPITAL, Seattle, WA (US)

( * ) Notice: Subject to any disclaimer, the term of this patent is extended or adjusted under 35 U.S.C. 154(b) by 232 days.

(21) Appl. No.: 15/950,562

(22) Filed: Apr. 11, 2018

(65) Prior Publication Data

US 2018/0272007 A1 Sep. 27, 2018

Related U.S. Application Data

(62) Division of application No. 14/879,023, filed on Oct. 8, 2015, now Pat. No. 9,943,612.

(60) Provisional application No. 62/161,107, filed on May 13, 2015, provisional application No. 62/062,098, filed on Oct. 9, 2014.

(51) Int. Cl.
| | |
|---|---|
| *A61K 48/00* | (2006.01) |
| *C12N 15/63* | (2006.01) |
| *C12N 15/67* | (2006.01) |
| *C12P 19/34* | (2006.01) |
| *A61K 41/00* | (2020.01) |

(52) U.S. Cl.
CPC ...... *A61K 48/0066* (2013.01); *A61K 41/0047* (2013.01); *C12N 15/63* (2013.01); *C12N 15/67* (2013.01); *C12P 19/34* (2013.01); *C12N 2710/10343* (2013.01); *C12N 2750/14143* (2013.01)

(58) Field of Classification Search
CPC ............ A61K 48/0066; A61K 41/0047; C12N 15/63; C12N 15/67
See application file for complete search history.

(56) References Cited

U.S. PATENT DOCUMENTS

| 6,130,040 | A | 10/2000 | Lin |
| 7,723,103 | B2 | 5/2010 | Mead et al. |
| 9,029,134 | B2 | 5/2015 | Godiska et al. |
| 2001/0000077 | A1 | 3/2001 | Engelhardt et al. |
| 2008/0260706 | A1 | 10/2008 | Rabinovich et al. |
| 2009/0093433 | A1 | 4/2009 | Woolf et al. |
| 2009/0263873 | A1 | 10/2009 | Godiska et al. |
| 2010/0129877 | A1† | 5/2010 | Sahin |
| 2014/0179770 | A1 | 6/2014 | Zhang et al. |
| 2014/0242579 | A1 | 8/2014 | Zhou et al. |

FOREIGN PATENT DOCUMENTS

| EP | 2357230 B1 | 9/2006 |
| WO | WO 99/61605 A2 | 12/1999 |
| WO | 2007036366 A2 † | 4/2007 |
| WO | WO 2007/087478 | 11/2007 |
| WO | WO 2013/123559 A1 | 8/2013 |
| WO | WO 2014/089290 A1 | 6/2014 |
| WO | WO 2016/005004 A1 | 1/2016 |

OTHER PUBLICATIONS

Krieg et al.; In Vitro RNA synthesis with SP6 RNA polymerase; Methods in Enzymology; vol. 155, pp. 397-415, published 1987 (Year: 1987).*
"PSP64 Poly(A) Vector" Promega, Technical Bulletin, pSP64 Poly(A) Vector, Instructions for use of product P1241, Dec. 2005.
Chang et al. "TAIL-seq: Genome-wide Determination of Poly(A) Tail Length and 3' End Modifications." Molecular Cell (Mar. 2014) 53: 1044-1052.
Elango et al., "Optimized transfection of mRNA transcribed from a d(A/T)$_{100}$tail-containing vector", Biochem Biophys Res Comm. (2005) 330: 958-966.
Godiska et al., "Linear plasmid vector for cloning of repetitive or unstable sequences in *Escherichia coli*," Nucleic Acids Res. Apr. 2010; 38(6), Epub Dec. 29, 2009.
Holtkamp et al., "Modification of antigen-encoding RNA increases stability, translational efficacy, and T-cell stimulatory capacity of dendritic cells", Blood (Dec. 2006) 108(13): 4009-4017.
Invitation to Pay Additional Fees of the International application PCT/US2015/54780, dated Dec. 21, 2015.
Promega Corporation; Technical Bulletin No. 052: "pSP64 Poly(A) Vector Sequence and Map", (May 2000); 8 pages.
Rouet, Philippe, et al., "Expression of a site-specific endonuclease stimulates homologous recombination in mammalian cells," Proc. Natl. Acad. Sci. USA, vol. 91, pp. 6064-6068, Jun. 1994.
Van Der Velden et al., "Vector Design for Optimal Protein Expression", BioTechniques (Sep. 2001) 31(3): 572-582.
Weill et al., "Translational control by changes in poly(A) tail length: recycling mRNAs"; Nat Struct Mol Biol. (Jun. 2012) 19(6): 577-585.
Written Opinion and Search report of the International application PCT/US2015/54780 dated Feb. 11, 2016.
Ikegami et al., "Enhanced Transfection of MRNA Transcribed From Elongated-poly(A/T) Tail-Containing Vector," Molecular Therapy (May 2014) vol. 22, Supp. 1, p. S43. © The American Society of Gene & Cell Therapy.

(Continued)

*Primary Examiner* — Antonio Galisteo Gonzalez
(74) *Attorney, Agent, or Firm* — Knobbe, Martens, Olson & Bear LLP

(57) ABSTRACT

Disclosed herein are polynucleotides having a plurality of thymine nucleotides and an endonuclease recognition site inserted therein, methods of engineering the polynucleotides having a plurality of thymine nucleotides and an endonuclease recognition site inserted therein, and methods of enhancing transcription, translation, and increasing stability of a polynucleotide.

20 Claims, 25 Drawing Sheets

Specification includes a Sequence Listing.

(56) References Cited

OTHER PUBLICATIONS

Kühn et al., "Poly(A) Tail Length Is Controlled by the Nuclear Poly(A)-binding Portein Regulating the Interaction between Poly(A) Polymerase and the Cleavage and Polyadenylation Specificity Factor," The Journal of Biological Chemistry (Aug. 21, 2009) vol. 284, No. 34, pp. 22803-22814.
Schlake et al., "Developing mRNA-vaccine technologies," RNA Biology (Nov. 2012) 9:11, 1319-1330, © 2012 Landes Bioscience.
Ford et al. "The Poly(A) Tail Inhibits the Assembly of a 3'-To-5' Exonuclease in an Vitro RNA Stability System" Molecular and Cellular Biology, Amercian Society for Microbiology, vol. 17, No. 1, Jan. 1, 1997 (Jan. 1, 1997), pp. 398-406, XP000857790.
D R Galli E: "The cap and poly(A) tail 1-15 function synergistically to regulate mRNA translational efficiency.", Genes and Development., vol. 5, No. 11, Nov. 1, 1991 (Nov. 1, 1991), pp. 2108-2116, XP055452703.
Extended Search Report in European application No. 15848462.6, dated Mar. 22, 2018.
Holtcamp, et al., Modification of antigen-encoding RNA increases stability, translational efficacy, and T-cell stimulatory capacity of dendritic cells, Blood (2006), 108(13): 4009-4017.
Iskakova et al., "Troubleshooting coupled in vitro transcription-translation system derived from *Escherichia coli* cells: synthesis of high-yield fully active proteins", Nucleic Acids Research, 34(19): e135, 2006.†
Elango et al., "Optimized transfection of mRNA transcribed from a d(A/T) 100 tail-containing vector", Biochemical and Biophysical Research Communications, 330: 958-966, 2005.†

\* cited by examiner
† cited by third party

Gel analysis of tail lengths of pEVL-300 derivatives with defined non-adenosine 3'termini

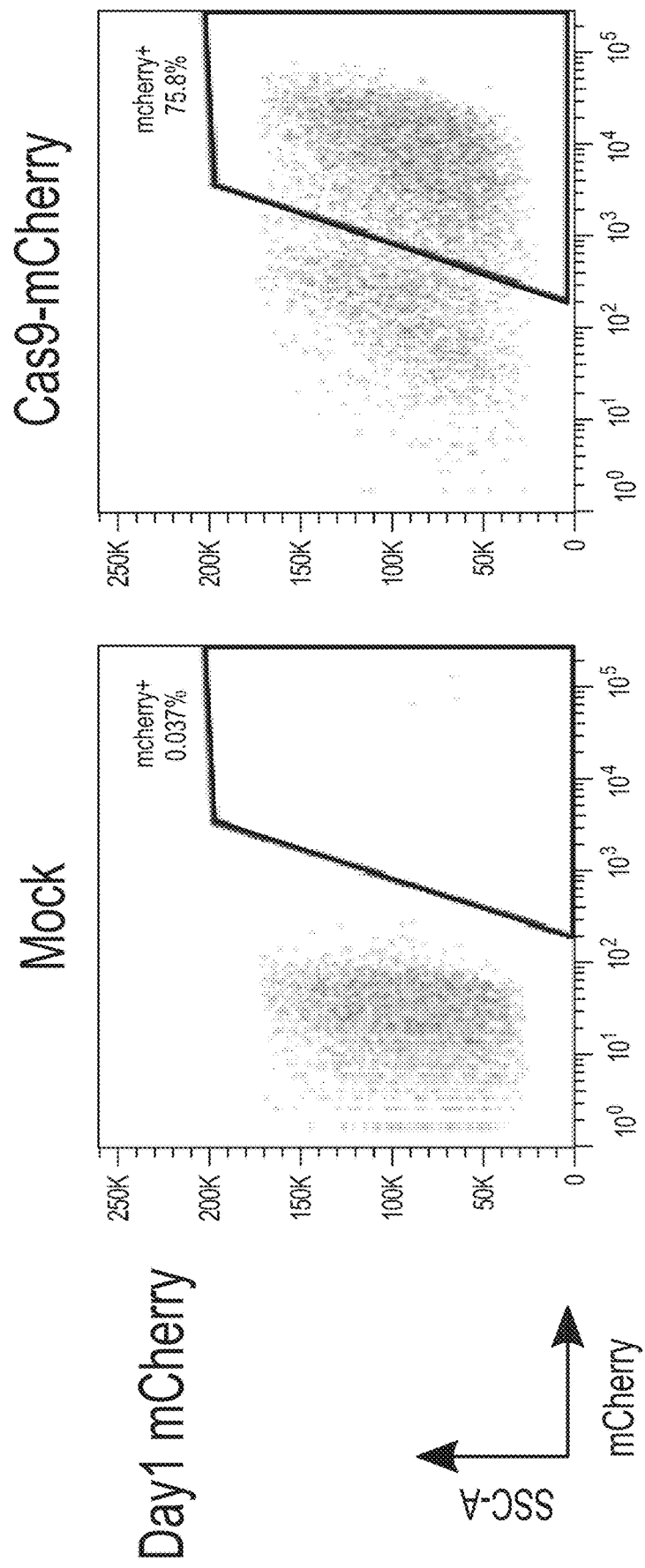

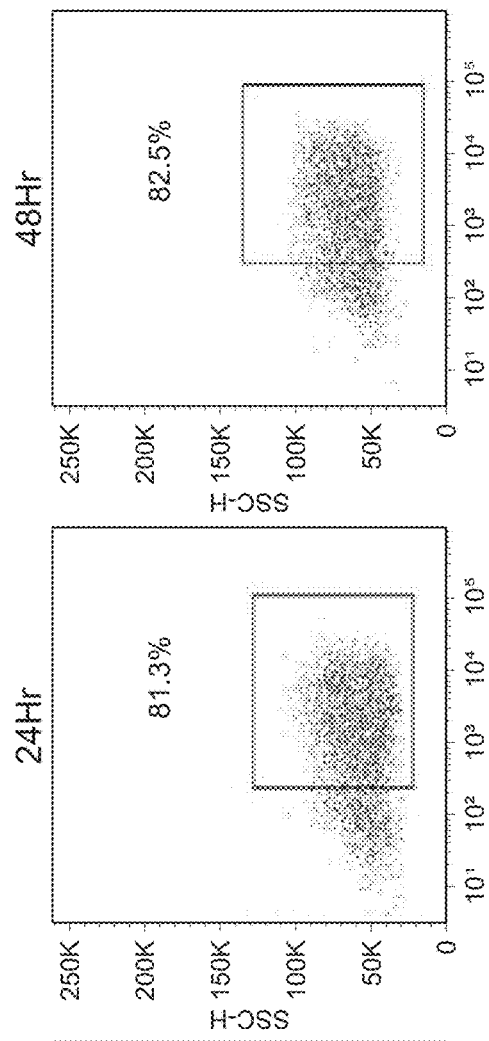
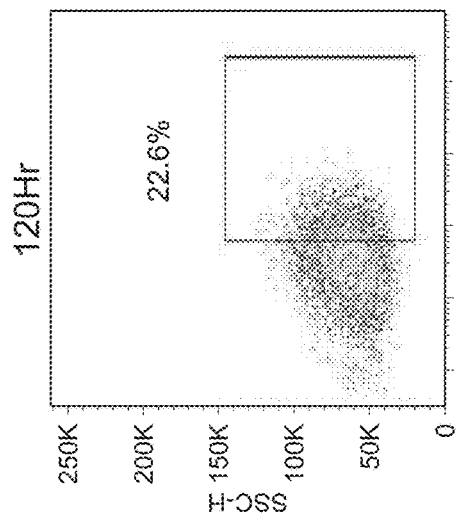
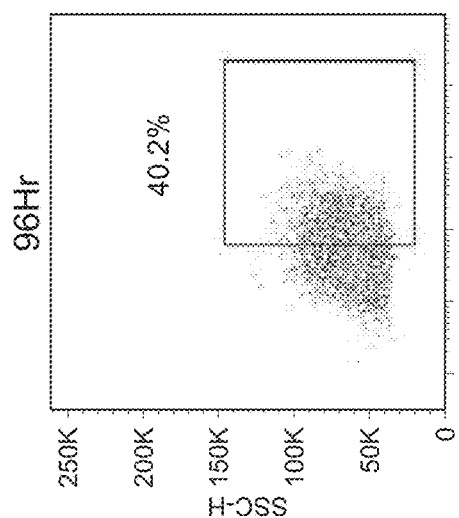
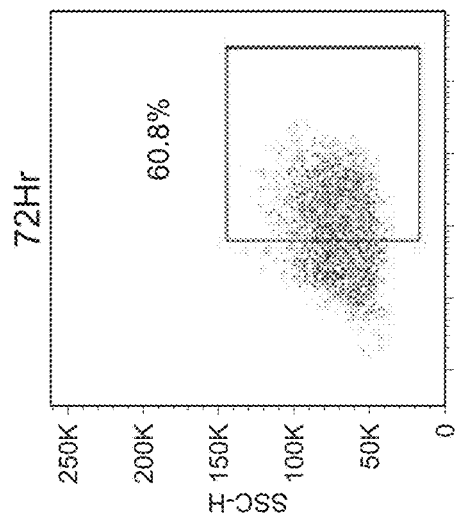

us 11,400,169 B2

LONG POLY(A) PLASMIDS AND METHODS FOR INTRODUCTION OF LONG POLY(A) SEQUENCES INTO THE PLASMID

CROSS-REFERENCED TO RELATED APPLICATIONS

The present application is a division of U.S. application Ser. No. 14/879,023 filed on Oct. 8, 2015, now U.S. Pat. No. 9,943,612 which issued Apr. 17, 2018 which claims priority to U.S. Provisional Application Ser. No. 62/062,098, entitled "LONG POLY(A) PLASMIDS AND METHOD FOR INTRODUCTION OF LONG POLY(A) SEQUENCES INTO THE PLASMID" filed Oct. 9, 2014, and U.S. Provisional Application Ser. No. 62/161,107 entitled "LONG POLY(A) PLASMIDS AND METHOD FOR INTRODUCTION OF LONG POLY(A) SEQUENCES INTO THE PLASMID" filed May 13, 2015, the contents of which are hereby expressly incorporated by reference in their entireties.

STATEMENT REGARDING FEDERALLY SPONSORED R&D

This invention was made with partial support under NICHD U19 AI096111, awarded by the US Department of Health and Human Services and the National Institutes of Health.

REFERENCE TO SEQUENCE LISTING, TABLE, OR COMPUTER PROGRAM LISTING

The present application is being filed along with a Sequence Listing in electronic format. The Sequence Listing is provided as a file entitled SCRI098C1SEQLIST, created Sep. 3, 2020, which is approximately 180,000 bytes in size. The information is the electronic format of the Sequence Listing is incorporated herein by reference in its entirety.

FIELD OF THE INVENTION

Aspects of the invention as described herein, include compositions and methods relating to genes that allow for the generation of a nucleic acid having a poly(T) tract or poly(A) tract of a desired length. Included herein are methods of increasing the stability of a nucleic acid transcript, enhancing gene transcription, and enhancing protein translation by providing one or more of the aforementioned nucleic acids, and methods of treating, ameliorating, inhibiting and/or eliminating a disease in a subject. Also included herein, are methods of enhancing gene transcription, and enhancing protein translation by providing one or more of the aforementioned nucleic acids comprising a gene encoding a nuclease and methods of treating a disease with compositions or cells comprising the nucleic acids.

BACKGROUND OF THE INVENTION

Increased demand for large scale synthesis of in vitro transcribed (IVT) mRNA is being driven by an increasing use of mRNA for transient gene expression in ex vivo cell engineering or direct in vivo therapeutic applications. One of the most important determinants of potency of an IVT mRNA is the 3' poly-adenosine (poly(A)) tail, the length of which directly correlates with efficiency of translation. However, present methods for large scale generation of IVT mRNA rely on templates derived from circular plasmids, in which homolypolymeric tracts are highly unstable, thus limiting encoded poly(A) tail lengths to less than approximately 120 base pairs. Thus methods are needed to generate mRNA that are highly stable for translation.

SUMMARY OF THE INVENTION

In a first aspect, a polynucleotide is provided. The polynucleotide can comprise a first nucleic acid sequence that comprises at least one endonuclease recognition site and a second nucleic acid sequence that comprises a plurality of thymine nucleotides, wherein said plurality of thymine nucleotides comprises at least, greater than, equal to, or any number in between 20, 30, 40, 50, 60, 70, 80, 90, 100, 110, 120, 130, 140, 150, 175, 200, 225, 250, 275, 300, 325, 350, 375, 400, 425, 450, 475, 500 or 550 covalently linked thymine nucleotides, wherein the second nucleic acid comprises an endonuclease cleavage site that is within the plurality of thymine nucleotides or within 1, 2, 3, 4, 5, 6, 7, 7, 8, 9, 10, 11, 12, 13, 14, 15, 16, 17, 18, 19 or 20 nucleotides from the 5' terminal thymine in the plurality of thymine nucleotides, and wherein said first nucleic acid is covalently linked to said second nucleic acid at one end of said second nucleic acid and, wherein said endonuclease recognition site is within 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54 or 55 nucleotides of the endonuclease cleavage site and said endonuclease cleavage site is within 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 nucleotides of the 5' terminal thymine in the plurality of thymine nucleotides. In some alternatives, the polynucleotide comprises a left arm that comprises a left telomere; a right arm comprising a right telomere; and a cloning region located between the left arm and the right arm. In some alternatives, the polynucleotide further comprises a third nucleic acid and, wherein the third nucleic acid comprises a gene. In some alternatives, the gene encodes a protein, a nuclease, or an endonuclease. In some alternatives, the nuclease comprises an amino acid sequence set forth in SEQ ID NO. 6 or is encoded by a nucleic acid sequence set forth in SEQ ID NO: 7-14. In some alternatives, the at least one endonuclease recognition site is a restriction endonuclease recognition site. In some alternatives, the restriction endonuclease recognition site is a Type II restriction endonuclease recognition site or a Type IIS restriction endonuclease recognition site. In some alternatives, the at least one endonuclease recognition site is a BsaI restriction endonuclease recognition site or a StuI restriction endonuclease recognition site. In some alternatives, the endonuclease recognition site is inverted. In some alternatives, the plurality of thymine nucleotides terminates in a cysteine, adenine, or a guanine. In some alternatives, the polynucleotide is a linear polynucleotide.

In a second aspect, a method of making a nucleic acid is provided. Some methods can comprise providing the polynucleotide of any of the alternatives herein and contacting said polynucleotide with a polymerase in the presence of nucleotides. Some polynucleotides can comprise a first nucleic acid sequence that comprises at least one endonuclease recognition site and a second nucleic acid sequence that comprises a plurality of thymine nucleotides, wherein said plurality of thymine nucleotides comprises at least, greater than, equal to, or any number in between 20, 30, 40, 50, 60, 70, 80, 90, 100, 110, 120, 130, 140, 150, 175, 200, 225, 250, 275, 300, 325, 350, 375, 400, 425, 450, 475, 500 or 550 covalently linked thymine nucleotides, wherein the second nucleic acid comprises an endonuclease cleavage site that is within the plurality of thymine nucleotides or within 1, 2, 3, 4, 5, 6, 7, 8, 9, 10, 11, 12, 13, 14, 15, 16, 17, 18, 19 or 20 nucleotides from the 5' terminal thymine in the plurality of thymine nucleotides, and wherein said first nucleic acid is covalently linked to said second nucleic acid at one end of said second nucleic acid and, wherein said endonuclease recognition site is within 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54 or 55 nucleotides of the endonuclease cleavage site and said endonuclease cleavage site is within 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 nucleotides of the 5' terminal thymine in the plurality of thymine nucleotides. In some alternatives, the polynucleotide comprises a left arm that comprises a left telomere; a right arm comprising a right telomere; and a cloning region located between the left arm and the right arm. In some alternatives, the polynucleotide further comprises a third nucleic acid and, wherein the third nucleic acid comprises a gene. In some alternatives, the gene encodes a protein, a nuclease, or an endonuclease. In some alternatives, the nuclease comprises an amino acid sequence set forth in SEQ ID NO. 6 or is encoded by a nucleic acid sequence set forth in SEQ ID NO: 7-14. In some alternatives, the at least one endonuclease recognition site is a restriction endonuclease recognition site. In some alternatives, the restriction endonuclease recognition site is a Type II restriction endonuclease recognition site or a Type IIS restriction endonuclease recognition site. In some alternatives, the at least one endonuclease recognition site is a BsaI restriction endonuclease recognition site or a StuI restriction endonuclease recognition site. In some alternatives, the endonuclease recognition site is inverted. In some alternatives, the plurality of thymine nucleotides terminates in a cysteine, adenine, or a guanine. In some alternatives, the polynucleotide is a linear polynucleotide. In some alternatives of making the nucleic acid, the nucleic acid is RNA. In some alternatives of making the nucleic acid, the RNA comprises a plurality of adenine nucleotides, wherein the plurality of adenine nucleotides comprises at least, greater than, equal to, or any number in between 20, 30, 40, 50, 60, 70, 80, 90, 100, 110, 120, 130, 140, 150, 175, 200, 225, 250, 275, 300, 325, 350, 375, 400, 425, 450, 475, or 500 covalently linked adenines.

In a third aspect, a method of stabilizing an RNA during in vitro translation at 30-37 degrees Celsius for at least 100 hours, is provided. Some methods can comprise providing the nucleic acid manufactured by a method of any of the alternatives herein, and contacting said nucleic acid with a RNA polymerase in the presence of nucleotides, wherein said RNA is stable at 30-37 degrees Celsius for at least, greater than, equal to, or time in between 1, 5, 10, 20, 30, 40, 50, 60, 70, 80, 90 or 100 hours (e.g., at least, or equal to 1, 5, 10, 20, 30, 40, 50, 60, 70, 80, 90 or 100 hours or within a range defined by any two of the aforementioned times). In some methods of making the nucleic acid, the method can comprise providing the polynucleotide of any of the alternatives herein and contacting said nucleic acid with a ribosome, in the presence of amino acids and tRNAs, wherein said RNA is stable at 30-37 degrees Celsius at least, greater than, equal to, or time in between 1, 5, 10, 20, 30, 40, 50, 60, 70, 80, 90 or 100 hours (e.g., at least, or equal to 1, 5, 10, 20, 30, 40, 50, 60, 70, 80, 90 or 100 hours or within a range defined by any two of the aforementioned times).

Some polynucleotides can comprise a first nucleic acid sequence that comprises at least one endonuclease recognition site and a second nucleic acid sequence that comprises a plurality of thymine nucleotides, wherein said plurality of thymine nucleotides comprises at least, greater than, equal to, or any number in between 20, 30, 40, 50, 60, 70, 80, 90, 100, 110, 120, 130, 140, 150, 175, 200, 225, 250, 275, 300, 325, 350, 375, 400, 425, 450, 475, 500 or 550 covalently linked thymine nucleotides, wherein the second nucleic acid comprises an endonuclease cleavage site that is within the plurality of thymine nucleotides or within 1, 2, 3, 4, 5, 6, 7, 7, 8, 9, 10, 11, 12, 13, 14, 15, 16, 17, 18, 19 or 20 nucleotides from the 5' terminal thymine in the plurality of thymine nucleotides, and wherein said first nucleic acid is covalently linked to said second nucleic acid at one end of said second nucleic acid and, wherein said endonuclease recognition site is within 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54 or 55 nucleotides of the endonuclease cleavage site and said endonuclease cleavage site is within 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 nucleotides of the 5' terminal thymine in the plurality of thymine nucleotides. In some alternatives, the polynucleotide comprises a left arm that comprises a left telomere; a right arm comprising a right telomere; and a cloning region located between the left arm and the right arm. In some alternatives, the polynucleotide further comprises a third nucleic acid and, wherein the third nucleic acid comprises a gene. In some alternatives, the gene encodes a protein, a nuclease, or an endonuclease. In some alternatives, the nuclease comprises an amino acid sequence set forth in SEQ ID NO. 6 or is encoded by a nucleic acid sequence set forth in SEQ ID NO: 7-14. In some alternatives, the at least one endonuclease recognition site is a restriction endonuclease recognition site. In some alternatives, the restriction endonuclease recognition site is a Type II restriction endonuclease recognition site or a Type IIS restriction endonuclease recognition site. In some alternatives, the at least one endonuclease recognition site is a BsaI restriction endonuclease recognition site or a StuI restriction endonuclease recognition site. In some alternatives, the endonuclease recognition site is inverted. In some alternatives, the plurality of thymine nucleotides terminates in a cysteine, adenine, or a guanine. In some alternatives, the polynucleotide is a linear polynucleotide. In some alternatives of making the nucleic acid, the nucleic acid is RNA. In some alternatives of making the nucleic acid, the RNA comprises a plurality of adenine nucleotides, wherein the plurality of adenine nucleotides comprises at least, greater than, equal to, or any number in between 20, 30, 40, 50, 60, 70, 80, 90, 100, 110, 120, 130, 140, 150, 175, 200, 225, 250, 275, 300, 325, 350, 375, 400, 425, 450, 475, or 500 covalently linked adenines. In some alternatives of the method of stabilizing an RNA during in vitro translation at 30-37 degrees Celcius for at least 100 hours, the nucleic acid is an RNA. In some alternatives, the plurality of adenine nucleotides comprises at least, greater than, equal to, or any number in between 20, 30, 40, 50, 60, 70, 80, 90, 100, 110, 120, 130, 140, 150, 175, 200, 225, 250, 275, 300, 325, 350, 375, 400, 425, 450, 475, or 500 covalently linked adenines. In some alternatives, the RNA further comprises a gene and, wherein the gene encodes, a protein for therapy, an endonuclease or a nuclease. In some alternatives, the method is performed for at least, greater than, equal to, or time in between 1, 5, 10, 20, 30, 40, 50, 60, 70, 80, 90 or 100 hours.

In a fourth aspect, a method of stabilizing an RNA during in vivo translation at 30-37 degrees Celsius for at least 100 hours in a cell is provided. The method can comprise transfecting into a cell the nucleic acid providing the nucleic acid manufactured by a method of any of the alternatives described herein, placing the cell into a culture vessel with media, supplying the cell with nutrients and amino acids for translation and incubating the cell for at least, greater than, equal to, or time in between 1, 5, 10, 20, 30, 40, 50, 60, 70, 80, 90 or 100 hours (e.g., at least, or equal to 1, 5, 10, 20, 30, 40, 50, 60, 70, 80, 90 or 100 hours or within a range defined by any two of the aforementioned times) so as to allow for translation. In some methods of making the nucleic acid, the method can comprise providing the polynucleotide of any of the alternatives herein and contacting said polynucleotide with a polymerase in the presence of nucleotides. Some polynucleotides can comprise a first nucleic acid sequence that comprises at least one endonuclease recognition site and a second nucleic acid sequence that comprises a plurality of thymine nucleotides, wherein said plurality of thymine nucleotides comprises at least, greater than, equal to, or any number in between 20, 30, 40, 50, 60, 70, 80, 90, 100, 110, 120, 130, 140, 150, 175, 200, 225, 250, 275, 300, 325, 350, 375, 400, 425, 450, 475, 500 or 550 covalently linked thymine nucleotides, wherein the second nucleic acid comprises an endonuclease cleavage site that is within the plurality of thymine nucleotides or within 1, 2, 3, 4, 5, 6, 7, 7, 8, 9, 10, 11, 12, 13, 14, 15, 16, 17, 18, 19 or 20 nucleotides from the 5' terminal thymine in the plurality of thymine nucleotides, and wherein said first nucleic acid is covalently linked to said second nucleic acid at one end of said second nucleic acid and, wherein said endonuclease recognition site is within 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54 or 55 nucleotides of the endonuclease cleavage site and said endonuclease cleavage site is within 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 nucleotides of the 5' terminal thymine in the plurality of thymine nucleotides. In some alternatives, the polynucleotide comprises a left arm that comprises a left telomere; a right arm comprising a right telomere; and a cloning region located between the left arm and the right arm. In some alternatives, the polynucleotide further comprises a third nucleic acid and, wherein the third nucleic acid comprises a gene. In some alternatives, the gene encodes a protein, a nuclease, or an endonuclease. In some alternatives, the nuclease comprises an amino acid sequence set forth in SEQ ID NO. 6 or is encoded by a nucleic acid sequence set forth in SEQ ID NO: 7-14. In some alternatives, the at least one endonuclease recognition site is a restriction endonuclease recognition site. In some alternatives, the restriction endonuclease recognition site is a Type II restriction endonuclease recognition site or a Type IIS restriction endonuclease recognition site. In some alternatives, the at least one endonuclease recognition site is a BsaI restriction endonuclease recognition site or a StuI restriction endonuclease recognition site. In some alternatives, the endonuclease recognition site is inverted. In some alternatives, the plurality of thymine nucleotides terminates in a cysteine, adenine, or a guanine. In some alternatives, the polynucleotide is a linear polynucleotide. In some alternatives of making the nucleic acid, the nucleic acid is RNA. In some alternatives of making the nucleic acid, the RNA comprises a plurality of adenine nucleotides, wherein the plurality of adenine nucleotides comprises at least, greater than, equal to, or any number in between 20, 30, 40, 50, 60, 70, 80, 90, 100, 110, 120, 130, 140, 150, 175, 200, 225, 250, 275, 300, 325, 350, 375, 400, 425, 450, 475, or 500 covalently linked adenines. In some alternatives of the method of stabilizing an RNA during in vivo translation at 30-37 degrees Celcius for at least 100 hours, the cell is a human cell. In some alternatives, the cell is selected from the group consisting of primary cells, human primary T cells, CD4+ cells and CD8+ cells.

In a fifth aspect, a method of increasing and/or stabilizing expression of a protein is provided. Some methods comprise generating an RNA from the polynucleotide of any of the alternatives described herein and translating said RNA into a peptide. The polynucleotide can comprise a first nucleic acid sequence that comprises at least one endonuclease recognition site and a second nucleic acid sequence that comprises a plurality of thymine nucleotides, wherein said plurality of thymine nucleotides comprises at least, greater than, equal to, or any number in between 20, 30, 40, 50, 60, 70, 80, 90, 100, 110, 120, 130, 140, 150, 175, 200, 225, 250, 275, 300, 325, 350, 375, 400, 425, 450, 475, 500 or 550 covalently linked thymine nucleotides, wherein the second nucleic acid comprises an endonuclease cleavage site that is within the plurality of thymine nucleotides or within 1, 2, 3, 4, 5, 6, 7, 7, 8, 9, 10, 11, 12, 13, 14, 15, 16, 17, 18, 19 or 20 nucleotides from the 5' terminal thymine in the plurality of thymine nucleotides, and wherein said first nucleic acid is covalently linked to said second nucleic acid at one end of said second nucleic acid and, wherein said endonuclease recognition site is within 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54 or 55 nucleotides of the endonuclease cleavage site and said endonuclease cleavage site is within 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 nucleotides of the 5' terminal thymine in the plurality of thymine nucleotides. In some alternatives, the polynucleotide comprises a left arm that comprises a left telomere; a right arm comprising a right telomere; and a cloning region located between the left arm and the right arm. In some alternatives, the polynucleotide further comprises a third nucleic acid and, wherein the third nucleic acid comprises a gene. In some alternatives, the gene encodes a protein, a nuclease, or an endonuclease. In some alternatives, the nuclease comprises an amino acid sequence set forth in SEQ ID NO. 6 or is encoded by a nucleic acid sequence set forth in SEQ ID NO: 7-14. In some alternatives, the at least one endonuclease recognition site is a restriction endonuclease recognition site. In some alternatives, the restriction endonuclease recognition site is a Type II restriction endonuclease recognition site or a Type IIS restriction endonuclease recognition site. In some alternatives, the at least one endonuclease recognition site is a BsaI restriction endonuclease recognition site or a StuI restriction endonuclease recognition site. In some alternatives, the endonuclease recognition site is inverted. In some alternatives, the plurality of thymine nucleotides terminates in an cysteine, adenine, or a guanine. In some alternatives, the polynucleotide is a linear polynucleotide. In some alternatives of the method of increasing and/or stabilizing expression of a protein, the translating further comprises providing an RNA polymerase. In some alternatives, the method further comprises providing an endonuclease. In some alternatives, the endonuclease is a Type II restriction endonuclease or a Type IIS restriction endonuclease. In some alternatives, the endonuclease is BsaI or StuI. In some alternatives, the RNA comprises a plurality of adenine nucleotides, wherein the plurality of adenine nucleotides comprises at least, greater than, equal to, or any number in between 20, 30, 40, 50, 60, 70, 80, 90, 100, 110, 120, 130, 140, 150, 175, 200, 225, 250, 275, 300, 325, 350, 375, 400, 425, 450, 475, or 500 covalently linked adenines.

In a sixth aspect, a method of treating, ameliorating, or a inhibiting disease in a subject is provided. Some methods can comprise introducing into a cell the RNA manufactured by the method of any of the alternatives described herein and delivering the cell to the subject. In some alternatives, the RNA is manufactured by a method comprising providing the polynucleotide of any of the alternatives herein and contacting said polynucleotide with a polymerase in the presence of nucleotides. Some polynucleotides can comprise a first nucleic acid sequence that comprises at least one endonuclease recognition site and a second nucleic acid sequence that comprises a plurality of thymine nucleotides, wherein said plurality of thymine nucleotides comprises at least, greater than, equal to, or any number in between 20, 30, 40, 50, 60, 70, 80, 90, 100, 110, 120, 130, 140, 150, 175, 200, 225, 250, 275, 300, 325, 350, 375, 400, 425, 450, 475, 500 or 550 covalently linked thymine nucleotides, wherein the second nucleic acid comprises an endonuclease cleavage site that is within the plurality of thymine nucleotides or within 1, 2, 3, 4, 5, 6, 7, 7, 8, 9, 10, 11, 12, 13, 14, 15, 16, 17, 18, 19 or 20 nucleotides from the 5' terminal thymine in the plurality of thymine nucleotides, and wherein said first nucleic acid is covalently linked to said second nucleic acid at one end of said second nucleic acid and, wherein said endonuclease recognition site is within 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54 or 55 nucleotides of the endonuclease cleavage site and said endonuclease cleavage site is within 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 nucleotides of the 5' terminal thymine in the plurality of thymine nucleotides. In some alternatives, the polynucleotide comprises a left arm that comprises a left telomere; a right arm comprising a right telomere; and a cloning region located between the left arm and the right arm. In some alternatives, the polynucleotide further comprises a third nucleic acid and, wherein the third nucleic acid comprises a gene. In some alternatives, the gene encodes a protein, a nuclease, or an endonuclease. In some alternatives, the nuclease comprises an amino acid sequence set forth in SEQ ID NO. 6 or is encoded by a nucleic acid sequence set forth in SEQ ID NO: 7-14. In some alternatives, the at least one endonuclease recognition site is a restriction endonuclease recognition site. In some alternatives, the restriction endonuclease recognition site is a Type II restriction endonuclease recognition site or a Type IIS restriction endonuclease recognition site. In some alternatives, the at least one endonuclease recognition site is a BsaI restriction endonuclease recognition site or a StuI restriction endonuclease recognition site. In some alternatives, the endonuclease recognition site is inverted. In some alternatives, the plurality of thymine nucleotides terminates in a cysteine, adenine, or a guanine. In some alternatives, the polynucleotide is a linear polynucleotide. In some alternatives of making the nucleic acid, the nucleic acid is RNA. In some alternatives of making the nucleic acid, the RNA comprises a plurality of adenine nucleotides, wherein the plurality of adenine nucleotides comprises at least, greater than, equal to, or any number in between 20, 30, 40, 50, 60, 70, 80, 90, 100, 110, 120, 130, 140, 150, 175, 200, 225, 250, 275, 300, 325, 350, 375, 400, 425, 450, 475, or 500 covalently linked adenines. In some alternatives of the method of treating, ameliorating, or a inhibiting disease in a subject, the introducing is performed by electroporation. In some alternatives, the cell is a T-cell or a primary cell. In some alternatives, the cell is a human cell. In some alternatives, the cell is CD4+ and/or CD8+.

BRIEF DESCRIPTION OF THE DRAWINGS

FIG. 2 demonstrates the shortening poly(A) encoding region of the DNA vector itself for the plasmids pEVL100, pEVL200, pEVL300, and pEVL500, when the plasmids are continuously replicated in bacteria grown at temperatures of 30° C. and 37° C., and for times of 1 day, 6 days and 14 days.

FIG. 6B: Quantification of TCRa knockout using pEVL and other vectors encoding a T7 promoter that were enzymatically poly-adenylated. TCRa knockout was achieved using TALEN, electroporating primary human CD4+ T cells using the amount of RNA as indicated in the figure. pEVL constructs are able to achieve 90% knockout when cells are cultured at 37 degrees Celsius, and when incubated at 30° C. for 24 hours following electroporation, the lowest dose of TALEN provided by pEVL performs better than both enzymatically tailed mRNA.

FIGS. 12A, 12B, 12C and 12D show the generation and characterization of mRNA from pEVL-encoded templates 12A) IVT mRNA encoding blue fluorescent protein (BFP) generated from pWNY with enzymatic tailing and pEVL-100 through pEVL-500 BFP-pEVL-100 to -500 were digested with XbaI and BsaI, and pWNY with ScaI and BsiWI, to generate template for IVT. IVT was carried out with ARCA capping, and for pWNY, enzymatic tailing with EPAP. After purification, 200 ng of each transcript was imaged on a FlashGel (Lonza) system. Typically, pEVL produces a single band of defined length, whereas pWNY with enzymatic tailing produces transcripts of a more heterogenous length. 12B) and 12D) Relative potency and representative flow plots generated by mRNA encoding BFP generated from a circular plasmid vector with enzymatic poly-adenylation or from pEVL-100/pEVL-200. 1 μg of IVT mRNA from the indicated template was electroporated into pre-stimulated primary human T-cells. After 24 hr at 30° C., the cells were analyzed by flow cytometry for the percentage of cells expressing BFP as well as the MFI of the BFP. 12C) Relative potency and representative flow plots from generated by mRNA encoding BFP generated from pEVL-100 through pEVL-500 Equimolar amounts of IVT mRNA from BFP-pEVL-100 to 500 was electroporated into pre-stimulated primary human T-cells. After 24 hr at 30 C, the percentage of cells expressing BFP and the BFI MFI was analyzed by flow cytometry.

FIG. 14B depicts SEQ ID NO:637, and FIG. 14C depicts SEQ ID NO:638. Note that with a homopolymeric tract of this size, clear 3' boundaries are not expected due to polymerase slippage, thus explaining the gradual diminishment of the sequence and wavy appearance of the processed electropherogram that occur around the end of the tract.

FIGS. 18A and 18B show Jurkat cells growth after transfection with the pEVL-encoded mRNA.]]

FIGS. 20A, 20B, 20C, 20D, 20E and 20F show CD34 cells that were transfected with BFP mRNA.

DEFINITIONS

Figure 1A:
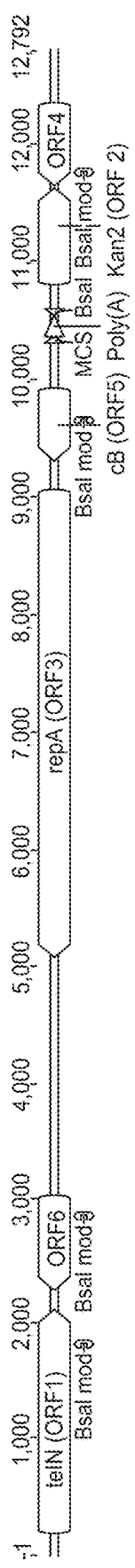
FIGS. 1A and 1B are illustrations of the linear DNA vector comprising a site encoding a poly(A) tail and a BsaI endonuclease cleavage site within the poly(A) tail encoding region (FIGS. 1A and 1B). As shown, the BsaI cut site is within the polyA encoding region. The BsaI recognition site is inverted and lies downstream from the polyA encoding region so that the endonuclease can cut within the polyA encoding region. A zoomed-in region of FIG. 1A is shown in FIG. 1B, which illustrates the region of interest, the multicloning site (MCS) with a poly (A) tail encoding region.

"Template strand" as defined herein, refers to the one strand of DNA that is used as a template for RNA synthesis and can also be referred to as the "noncoding strand." During the process of transcription, the RNA polymerase traverses the template strand and uses base pairing complementarity with the template strand to create an RNA copy. The RNA polymerase traverses the template strand in a 3' to 5' direction producing an RNA molecule from 5' to 3' as an exact copy of the coding strand, in the exception that the thymines are replaced with uracils in the RNA strand. In some alternatives, a template strand is provided, wherein the template strand can comprise a plurality of thymine nucleotides. In some alternatives, a nucleic acid is provided, wherein the nucleic acid is a DNA, wherein the DNA is a double stranded DNA comprising the template strand. a polynucleotide comprising a template strand, an endonuclease recognition site and an endonuclease cleavage site for an endonuclease inserted therein, wherein said template strand comprises a plurality of thymine nucleotides. Some polynucleotides comprise a first nucleic acid sequence comprising at least one restriction endonuclease recognition site and a second nucleic acid sequence, wherein the second nucleic acid sequence comprises the template strand, wherein the template strand comprises a plurality of thymine nucleotides, wherein said plurality of thymine nucleotides comprises at least, greater than, equal to, or any number in between 20, 30, 40, 50, 60, 70, 80, 90, 100, 110, 120, 130, 140, 150, 175, 200, 225, 250, 275, 300, 325, 350, 375, 400, 425, 450, 475, 500 or 550 covalently linked thymine nucleotides, wherein the second nucleic acid comprises the restriction endonuclease cleavage site, and wherein the restriction endonuclease cleavage site is within the plurality of thymine nucleotides or within 1, 2, 3, 4, 5, 6, 7, 7, 8, 9, 10, 11, 12, 13, 14, 15, 16, 17, 18, 19 or 20 base pairs away from the most 5' thymine (or 5' terminal thymine) in the plurality of thymine nucleotides and wherein said first nucleic acid is covalently linked to said second nucleic acid at one end of said second nucleic acid, and wherein the said restriction endonuclease recognition site is located within 1-55 base pairs such as, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54 or 55 base pairs, of the restriction endonuclease cleavage site for the restriction endonuclease and said restriction endonuclease cleavage site is within 1 to 40 base pairs, such as 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 base pairs, of a most 5' thymine (or 5' terminal thymine) in the plurality of thymine nucleotides.

"Coding strand" as defined herein, refers to the DNA strand which has the same base sequence as the RNA transcript (mRNA) that is produced during transcription. The coding strand is the strand used when displaying a DNA sequence in the 5' to 3' direction.

As used herein, "nucleic acid" or "nucleic acid molecule" refers to polynucleotides, such as deoxyribonucleic acid (DNA) or ribonucleic acid (RNA), oligonucleotides, fragments generated by the polymerase chain reaction (PCR), and fragments generated by any of ligation, scission, endonuclease action, and exonuclease action. Nucleic acid molecules can be composed of monomers that are naturally-occurring nucleotides (such as DNA and RNA), or analogs of naturally-occurring nucleotides (e.g., enantiomeric forms of naturally-occurring nucleotides), or a combination of both. Modified nucleotides can have alterations in sugar moieties and/or in pyrimidine or purine base moieties. Sugar modifications include, for example, replacement of one or more hydroxyl groups with halogens, alkyl groups, amines, and azido groups, or sugars can be functionalized as ethers or esters. Moreover, the entire sugar moiety can be replaced with sterically and electronically similar structures, such as aza-sugars and carbocyclic sugar analogs. Examples of modifications in a base moiety include alkylated purines and pyrimidines, acylated purines or pyrimidines, or other well-known heterocyclic substitutes. Nucleic acid monomers can be linked by phosphodiester bonds or analogs of such linkages. Analogs of phosphodiester linkages include phosphorothioate, phosphorodithioate, phosphoroselenoate, phosphorodiselenoate, phosphoroanilothioate, phosphoranilidate, phosphoramidate, and the like. The term "nucleic acid molecule" also includes so-called "peptide nucleic acids," which comprise naturally-occurring or modified nucleic acid bases attached to a polyamide backbone. Nucleic acids can be either single stranded or double stranded. As referenced above, in some alternatives, the CRISPR/Cas9 system described herein, whereby the polynucleotide encoding the Cas9 nuclease or a derivative or functional fragment thereof (e.g., SEQ ID NOs. 6-14) is provided with a poly(T) or poly(A) tail of a desired length and prepared in accordance with the teachings described herein, is provided with a guide RNA that comprises one or more modified bases, such as any one or more of the modified bases described above. Exemplary guide RNAs useful with the alternatives described herein, which may contain one or more of the modified bases set forth above are provided in SEQ ID Nos. 5, 15, 16, and 17.

A nucleotide is composed of a nucleobase, a five-carbon sugar (i.e., either ribose or 2-deoxyribose), and one or more than one phosphate groups (i.e., two or three phosphate groups). Thus, the term "nucleotide" generally refers to a nucleoside monophosphate, but a nucleoside diphosphate or nucleoside triphosphate can be considered a nucleotide as well.

Without the phosphate group, the nucleobase and sugar compose a nucleoside. The phosphate groups form bonds with either the 2, 3, or 5-carbon of the sugar, with the 5-carbon site most common. Cyclic nucleotides form when the phosphate group is bound to two of the sugar's hydroxyl groups. Nucleotides contain either a purine or a pyrimidine base. Ribonucleotides are nucleotides in which the sugar is ribose. Deoxyribonucleotides are nucleotides which has deoxyribose as the sugar. Nucleic acids are polymeric macromolecules made from nucleotide monomers. In DNA, the purine bases are adenine (A) and guanine (G), while the pyrimidines are thymine (T) and cytosine (C). RNA uses uracil (U) in place of thymine (T). Adenine always pairs with thymine by two hydrogen bonds, while guanine always pairs with cytosine through three hydrogen bonds, each due to their unique structures.

"Nucleosides" as described herein, are glycosylamines that can be thought of as nucleotides without a phosphate group. A nucleotide is composed of a nucleobase, also referred to a nitrogenous base, a five-carbon sugar (i.e., ribose or deoxyribose), and one or more phosphate groups while a nucleoside consists simply of a nucleobase and a 5-carbon sugar. However, in a nucleoside, the base is bound to either ribose or deoxyribose via a beta-glycosidic linkage. Examples of nucleosides include cytidine, uridine, adenosine, guanosine, thymidine and inosine.

"Adenine" is a nucleobase, and is a chemical component of DNA and RNA. As used herein, adenines can refer to polyadenosine ribonucleotides, polyadenosine monophosphates or polyadenylyls. The shape of adenine is complementary to either thymine in DNA or uracil in RNA. Thymine, is one of the four nucleobases in the nucleic acid of DNA. As used herein, thymines can refer to polythymidine ribonucleotides, polythymidine monophosphates or polythymidyls. As used herein, the term "covalently linked adenines," as referred to in the term "poly(A) tract" in reference to a polynucleotide comprising DNA or RNA, can refer to a polymer of covalently linked deoxyadenosine nucleotides comprising moieties of polyadenosine ribonucleotides, polyadenosine monophosphates, or polyadenylyls. As used herein the term "covalently linked thymines," as referred to in a poly(T) tract, can refer to a polymer of covalently linked deoxythymidine nucleotides comprising moieties of polythymidine ribonucleotides, polythymidine monophosphates, or polythymidyls.

"Polyadenylation" as described herein, refers to the addition of covalently linked adenines at the 3'-end of a primary, or pre-messenger RNA (pre-mRNA). The addition of a stretch of covalently linked adenine residues (poly(A) tail) is a process that produces a mature messenger RNA (mRNA) for translation. Polyadenylation, a eukaryotic mechanism, is initiated in vivo when transcription of a gene is terminated and the pre-mRNA is cleaved by a protein, Cleavage and Polyadenylation Specificity Factor (CPSF). Following cleavage, polyadenylate polymerase polymerizes the poly (A) tail and can add up to 200-250 covalently linked adenine residues.

A "telomere" as described herein is a region of repetitive nucleotide sequences at each end of a nucleic acid, which protects the ends from deterioration. In some alternatives, a polynucleotide is provided wherein the polynucleotide comprises telomeres. In some alternatives, the polynucleotide comprises a left arm wherein the left arm comprises a left telomere, a right arm wherein the right arm comprises a right telomere and a cloning region located between the left arm and the right arm. In some alternatives, the polynucleotide comprises a first protelomerase target site in the left arm and a second protelomerase target site in the right arm.

An untranslated region (or UTR) refers to either of two sections, one on each side of a coding sequence on a strand of mRNA. If it is found on the 5' side, it is called the 5' UTR (or leader sequence), or if it is found on the 3' side, it is called the 3' UTR (or trailer sequence). UTRs are found in naturally occurring mRNAs. In some alternatives, the RNA does not have a 3' UTR or a 5' UTR. In some alternatives, the RNA lacks a 5' and/or 3' UTR or lacks a native 5' and/or 3' UTR and/or lacks one or more sequences required for native polyadenylation such as, a cleavage/polyadenylation specificity factor (CPSF) binding site, a cleavage stimulation factor binding site (CstF), a cleavage factor I binding site (CFI), or a cleavage factor II binding site (CFII).

"Nuclease" or "endonuclease" as described herein, refers to an enzyme capable of cleaving the phosphodiester bonds between the nucleotide subunits of nucleic acids. In some alternatives a polynucleotide encoding a nuclease is provided. Without being limiting, examples of endonucleases can include for example, a CRISPR enzyme or a restriction endonuclease.

A "restriction enzyme" or "restriction endonuclease" is an enzyme that recognize and bind DNA at or near specific recognition nucleotide sequences so that it can cut at a restriction cleavage sites. In some alternatives, a polynucleotide comprising a template strand, an endonuclease recognition site and an endonuclease cleavage site for an endonuclease inserted therein, wherein said template strand comprises a plurality of thymine nucleotides, is provided. In some alternatives the endonuclease recognition site is specific for a restriction endonuclease. Without being limiting, examples of Type II restriction endonucleases can include, for example, AatII, AbaSI, Acc65I, AccI, AciI, AclI, AfeI, AflII, AflIII, AgeI, AhdI, AleI, AluI, AlwI, AlwNI, ApaI, ApaLI, ApeKI, ApoI, AscI, AseI, AsiSI, AvaI, AvaII, AvrII, BaeGI, BaeI, BamHI, BanI, BanII, BbsI, BbvCI, BbvI, BccI, BceAI, BcgI, BciVI, BclI, BcoDI, BfaI, BfuAI, BfuCI, BglI, BglII, BlpI, BmgBI, BmrI, BmtI, BpmI, Bpu10I, BpuEI, BsaAI, BsaBI, BsaHI, BsaI, BsaJI, BsaWI, BsaXI, BseRI, BseYI, BsgI, BsiEI, BsiHKAI, BsiWI, BslI, BsmAI, BsmBI, BsmFI, BsmI, BsoBI, Bsp1286I, BspCNI, BspDI, BspEI, BspHI, BspMI, BspQI, BsrBI, BsrDI, BsrFI, BsrGI, BsrI, BssHII, BssKI, BssSI, BstAPI, BstBI, BstEII, BstNI, BstUI, BstXI, BstYI, BstZ17I, Bsu36I, BtgI, BtgZI, BtsCI, BtsI, BtsIMutI, Cac8I, ClaI, CspCI, CviAII, CviKI-1, CviQI, DdeI, DpnI, DpnII, DraI, DrdI, EaeI, EagI, EarI, EciI, Eco53kI, EcoNI, EcoO109I, EcoP15I, EcoRI, EcoRV, FatI, FauI, Fnu4HI, FokI, FseI, FspEI, FspI, HaeII, HaeIII, HgaI, HhaI, HincII, HindIII, HinfI, HinP1I, HpaI, HpaII, HphI, Hpy166II, Hpy188I, Hpy188III, Hpy99I, HpyA, HpyCH4III, HpyCH4IV, HpyCH4V, I-CeuI, I-SceI, KasI, KpnI, LpnPI, MboI, MboII, MfeI, MluCI, MluI, MlyI, MmeI, MnlI, MscI, MseI, MslI, MspA1I, MspI, MspJI, MwoI, NaeI, NarI, BbvCI, BsmI, BsrDI, BtsI, NciI, NcoI, NdeI, NgoMIV, NheI, NlaIII, NlaIV, NmeAIII, NotI, NruI, NsiI, NspI, Nt.AlwI, Nt.BbvCI, Nt.BsmAI, Nt.BspQI, Nt.BstNBI, Nt.CviPII, PacI, PaeR7I, PciI, PfMFI, PflMI, PI-PspI, PI-SceI, PleI, PluTI, PmeI, PmlI, PpuMI, PshAI, PsiI, PspGI, PspOMI, PspXI, PstI, PvuI, PvuII, RsaI, RsrII, SacI, SacII, SalI, SapI, Sau3AI, Sau96I, SbfI, ScrFI, SexAI, SfaNI, SfcI, SfiI, SfoI, SgrAI, SmaI, SmlI, SnaBI, SpeI, SphI, SspI, StuI, StyD4I, StyI, SwaI, TaqαI, TfiI, TliI, TseI, Tsp45I, Tsp509I, TspMI TspRI, Tth111I, XbaI, XcmI, XhoI, XmaI, XmnI, and ZraI. In some alternatives, the restriction endonuclease is AatII, AbaSI, Acc65I, AccI, AciI, AclI, AfeI, AflII, AflIII, AgeI, AhdI, AleI, AluI, AlwI, AlwNI, ApaI, ApaLI, ApeKI, ApoI, AscI, AseI, AsiSI, AvaI, AvaII, AvrII, BaeGI, BaeI, BamHI, BanI, BanII, BbsI, BbvCI, BbvI, BccI, BceAI, BcgI, BciVI, BclI, BcoDI, BfaI, BfuAI, BfuCI, BglI, BglII, BlpI, BmgBI, BmrI, BmtI, BpmI, Bpu10I, BpuEI, BsaAI, BsaBI, BsaHI, BsaI, BsaJI, BsaWI, BsaXI, BseRI, BseYI, BsgI, BsiEI, BsiHKAI, BsiWI, BslI, BsmAI, BsmBI, BsmFI, BsmI, BsoBI, Bsp1286I, BspCNI, BspDI, BspEI, BspHI, BspMI, BspQI, BsrBI, BsrDI, BsrFI, BsrGI, BsrI, BssHII, BssKI, BssSI, BstAPI, BstBI, BstEII, BstNI, BstUI, BstXI, BstYI, BstZ17I, Bsu36I, BtgI, BtgZI, BtsCI, BtsI, BtsIMutI, Cac8I, ClaI, CspCI, CviAII, CviKI-1, CviQI, DdeI, DpnI, DpnII, DraI, DrdI, EaeI, EagI, EarI, EciI, Eco53kI, EcoNI, EcoO109I, EcoP15I, EcoRI, EcoRV, FatI, FauI, Fnu4HI, FokI, FseI, FspEI, FspI, HaeII, HaeIII, HgaI, HhaI, HincII, HindIII, HinfI, HinP1I, HpaI, HpaII, HphI, Hpy166II, Hpy188I, Hpy188III, Hpy99I, HpyA, HpyCH4III, HpyCH4IV, HpyCH4V, I-CeuI, I-SceI, KasI, KpnI, LpnPI, MboI, MboII, MfeI, MluCI, MluI, MlyI, MmeI, MnlI, MscI, MseI, MslI, MspA1I, MspI, MspJI, MwoI, NaeI, NarI, BbvCI, BsmI, BsrDI, BtsI, NciI, NcoI, NdeI, NgoMIV, NheI, NlaIII, NlaIV, NmeAIII, NotI, NruI, NsiI, NspI, Nt.AlwI, Nt.BbvCI, Nt.BsmAI, Nt.BspQI, Nt.B- stNBI, Nt.CviPII, PacI, PaeR7I, PciI, PflFI, PflMI, PI-PspI, PI-SceI, PleI, PluTI, PmeI, PmlI, PpuMI, PshAI, PsiI, PspGI, PspOMI, PspXI, PstI, PvuI, PvuII, RsaI, RsrII, SacI, SacII, SalI, SapI, Sau3AI, Sau96I, SbfI, ScrFI, SexAI, SfaNI, SfcI, SfiI, SfoI, SgrAI, SmaI, SmlI, SnaBI, SpeI, SphI, SspI, StuI, StyD4I, StyI, SwaI, TaqαI, TfiI, TliI, TseI, Tsp45I, Tsp509I, TspMI TspRI, Tth111I, XbaI, XcmI, XhoI, XmaI, XmnI, or ZraI. In some alternatives, the restriction endonuclease is BsaI. In some alternatives, the restriction endonuclease is StuI. In some alternatives, the restriction site is inverted and the restriction endonuclease cleavage site is inverted.

A type II restriction endonuclease as described herein, refers to an endonuclease that form homodimers, with recognition sites that are usually undivided and palindromic and 4-8 nucleotides in length. They recognize and cleave DNA at the same site, and they do not use ATP or AdoMet for their activity.

A "Type IIS restriction endonuclease," as described herein, refers an endonuclease that cleaves DNA at a defined distance from their palindromic or a non-palindromic asymmetric recognition sites. Examples of Type IIS restriction endonucleases include but are not limited to include but are not limited to AciI, MnlI, AlwI, BbvI, BccI, BceAI, BsmAI, BsmFI, BspCNI, BsrI, BtsCI, FokI, HgaI, HphI, HpyAV, MboII, MlyI, PleI, SfaNI, AcuI, BciVI, BfuAI, BmgBI, BmrI, BpmI, BpuEI, BsaI, BseRI, BsgI, BsmI, BspMI, BsrBI, BsrDI, BtgZI, BtsI, EarI, EciI, MmeI, NmeAIII, BbvCI, Bpu10I, BspQI, SapI, BaeI, BsaXI, CspCI, AfaI, AluBI, AspLEI, BscFI, Bsh1236I, BshFI, BshI, BsiSI, BsnI, Bsp143I, BspANI, BspFNI, BssMI, BstENII, BstFNI, BstHHI, BstKTI, BstMBI, BsuRI, CfoI, Csp6I, FaeI, FaiI, FnuDII, FspBI, GlaI, HapII, Hin1II, R9529, Hsp92II, HspAI, MaeI, MaeII, MvnI, PalI, RsaNI, SetI, SgeI, Sse9I, TruII, Tru9I, TscI, TspEI, TthHB8I, XspI, AflI, AgsI, AspS9I, AsuC2I, AsuI, BcefI, BcnI, BisI, BlsI, Bme1390I, Bme18I, BmrFI, BscGI, BseBI, BsiLI, BsiZI, BslFI, BsoMAI, BspNCI, Bst2UI, Bst71I, BstDEI, BstOI,BstSCI, CauII, CdiI, Cfr13I, Eco47I, EcoRII, FaqI, FinI, Fsp4HI, GluI, Hin4II, HpyF3I, ItaI, MaeIII, MspR9I, MvaI, NmuCI, Psp6I, PspPI, SatI, SinI, TscAI, VpaK11BI, AanI, AatI, AauI, Acc113I, Acc16I, AccB1I, AceIII, AcsI, AcvI, AcyI, AhlI, Alw21I, Alw44I, Ama87I, Aor51HI, AsiAI, AsnI, Asp718I, AspHI, AsuII, AsuNHI, AvaII, AviII, BanIII, BauI, BbeI, BbrPI, BbuI, Bbv12I, BbvII, Bce83I, BcoI, BcuI, BfmI, BfrB1,BfrI, BlnI, BmcAI, BmeT110I, BmiI, BmuI, BmyI, Bpu14I, BpvUI, Bsa29I, BsaOI, BsbI, BscBI, BscCI, Bse118I, BseAI, BseCI, BseDI, BsePI, BseSI, BseX3I, Bsh1285I, BshNI, BshTI, BshVI, BsiCI, BsiHKCI, BsiMI, BsiQI, BsiXI, Bsp106I, Bsp119I, Bsp120I, Bsp13I, Bsp1407I, Bsp143II, Bsp19I, Bsp68I, BspA2I, BspCI, BspGI, BspLU11I, BspMAI, BspMII, BspOI, BspT104I, BspT107I, BspTI, BspXI, BssAI, BssHI, BssNAI, BssNI, BssT1I, Bst1107I, Bst98I, BstACI, BstAFI, BstAUI, BstBAI, BstC8I, BstDSI, BstH2I, BstHPI, BstNSI, BstSFI, BstSLI, BstSNI, BstX2I, BstZI, BsuTUI, BtuMI, BveI, CciI, Cfr10I, Cfr42I, Cfr9I, CfrI, Csp45I, CspAI, DinI, DrdII, DsaI, Ecl136II, EclXI, Eco105I, Eco130I, Eco147I, Eco24I, Eco32I, Eco47III, Eco52I, Eco72I, Eco88I, EcoICRI, EcoT14I, EcoT22I, EcoT38I, EgeI, EheI, ErhI, FauNDI, FbaI, FblI, FriOI, FunI, FunII, GdiII, GsaI, HaeI, HgiAI, Hin1I, HindII, Hpy178III, Hpy8I, Hsp92I, Kpn2I, Ksp22I, KspAI, KspI, MflI, MhlI, MisI, MluNI, Mly113I, Mph1103I, MroI, MroNI, Msp20I, MspCI, MstI, MunI, MvrI, NgoAIV, NsbI, NspIII, NspV, PaeI, PagI, PauI, PceI, Pfl23II, PinAI, Ple19I, PmaCI, PshBI, Psp124BI, Psp1406I, PspAI, PspLI, PspN4I, PsuI, RcaI, SduI, Sfr274I, Sfr303I, SfuI, SgrBI, SlaI, SpaHI, SseBI, SspBI, SstI, SstII, SunI, TatI, Vha464I, VneI, XapI, XhoII, XmaCI, XmaIII, XmaJI, XmiI, ZhoI, Zsp2I, AocI, AxyI, Bpu1102I, Bse21I, Bsp1720I, BstPI, CelII, CpoI, CspI, DraII, Eco065I, Eco81I, Eco91I, EspI, KflI, LguI, MabI, PpuXI, Psp5II, PspEI, Rsr2I, SauI, AbsI, CciNI, FspAI, MauBI, MreI, MssI, RgaI, SdaI, SfaAI, SgfI, SmiI, Sse232I, AdeI, AspI, CaiI, PsyI, TelI, Asp700I, BoxI, Bse8I, BseJI, BsiBI, BsrBRI, BstPAI, CjeNII, MamI, MroXI, OliI, PdmI, RseI, SmiMI, AccB7I, AspEI, BasI, BmeRI, BplI, Bsc4I, BseLI, BsiYI, BstENI, BstMWI, CjeI, CjuI, CjuII, DriI, Eam1105I, EclHKI, FalI, HpyF10VI, NgoAVIII, NruGI, PflBI, UbaF14I, XagI, AasI, BdaI, Bsp24I, CjePI, DseDI, UbaF9I, ArsI, BarI, PcsI and UbaF13I. The Type II restriction endonuclease cleavage site and recognition sites are shown in Table 1 (SEQ ID NOs: 18-632, 634-636, 634-636). a polynucleotide comprising a template strand, an endonuclease recognition site and an endonuclease cleavage site for an endonuclease inserted therein, wherein said template strand comprises a plurality of thymine nucleotides. Some polynucleotides comprise a first nucleic acid sequence comprising at least one restriction endonuclease recognition site and a second nucleic acid sequence, wherein the second nucleic acid sequence comprises the template strand, wherein the template strand comprises a plurality of thymine nucleotides, wherein said plurality of thymine nucleotides comprises at least, greater than, equal to, or any number in between 20, 30, 40, 50, 60, 70, 80, 90, 100, 110, 120, 130, 140, 150, 175, 200, 225, 250, 275, 300, 325, 350, 375, 400, 425, 450, 475, 500 or 550 covalently linked thymine nucleotides, wherein the second nucleic acid comprises the restriction endonuclease cleavage site, and wherein the restriction endonuclease cleavage site is within the plurality of thymine nucleotides or within 1, 2, 3, 4, 5, 6, 7, 7, 8, 9, 10, 11, 12, 13, 14, 15, 16, 17, 18, 19 or 20 base pairs away from the most 5' thymine (or 5' terminal thymine) in the plurality of thymine nucleotides and wherein said first nucleic acid is covalently linked to said second nucleic acid at one end of said second nucleic acid, and wherein the said restriction endonuclease recognition site is located within 1-55 base pairs such as, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54 or 55 base pairs, of the restriction endonuclease cleavage site for the restriction endonuclease and said restriction endonuclease cleavage site is within 1 to 40 base pairs, such as 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 base pairs, of a most 5' thymine (or 5' terminal thymine) in the plurality of thymine nucleotides. In some alternatives, the endonuclease is a Type IIS restriction endonuclease. In some alternatives, the Type IIS restriction endonuclease is AciI, MnlI, AlwI, BbvI, BccI, BceAI, BsmAI, BsmFI, BspCNI, BsrI, BtsCI, FokI, HgaI, HphI, HpyAV, MboII, MlyI, PleI, SfaNI, AcuI, BciVI, BfuAI, BmgBI, BmrI, BpmI, BpuEI, BsaI, BseRI, BsgI, BsmI, BspMI, BsrBI, BsrDI, BtgZI, BtsI, EarI, EciI, MmeI, NmeAIII, BbvCI, Bpu10I, BspQI, SapI, BaeI, BsaXI, CspCI, AfaI, AluBI, AspLEI, BscFI, Bsh1236I, BshFI, BshI, BsiSI, BsnI, Bsp143I, BspANI, BspFNI, BssMI, BstENII, BstFNI, BstHHI, BstKTI, BstMBI, BsuRI, CfoI, Csp6I, FaeI, FaiI, FnuDII, FspBI, GlaI, HapII, Hin1II, R9529, Hsp92II, HspAI, MaeI, MaeII, MvnI, PalI, RsaNI, SetI, SgeI, Sse9I, TruII, Tru9I, TscI, TspEI, TthHB8I, XspI, AflI, AgsI, AspS9I, AsuC2I, AsuI, BcefI, BcnI, BisI, BlsI, Bme1390I, Bme18I, BmrFI, BscGI, BseBI, BsiLI, BsiZI, BslFI, BsoMAI, BspNCI, Bst2UI, Bst71I, BstDEI, BstOI, BstSCI, CauII, CdiI, Cfr13I, Eco47I, EcoRII, FaqI, FinI, Fsp4HI, GluI, Hin4II, HpyF3I, ItaI, MaeIII, MspR9I, MvaI, NmuCI, Psp6I, PspPI, SatI, SinI, TscAI, VpaK11BI, AanI, AatI, AauI, Acc113I, Acc16I, AccB1I, AceIII, AcsI, AcvI, AcyI, AhlI, Alw21I, Alw44I, Ama87I, Aor51HI, AsiAI, AsnI, Asp718I, AspHI, AsuII, AsuNHI, AvaIII, AviII, BanIII, BauI, BbeI, BbrPI, BbuI, Bbv12I, BbvII, Bce83I, BcoI, BcuI, BfmI, BfrB1,BfrI, BlnI, BmcAI, BmeT110I, BmiI, BmuI, BmyI, Bpu14I, BpvUI, Bsa29I, BsaOI, BsbI, BscBI, BscCI, Bse118I, BseAI, BseCI, BseDI, BsePI, BseSI, BseX3I, Bsh1285I, BshNI, BshTI, BshVI, BsiCI, BsiHKCI, BsiMI, BsiQI, BsiXI, Bsp106I, Bsp119I, Bsp120I, Bsp13I, Bsp1407I, Bsp143II, Bsp19I, Bsp68I, BspA2I, BspCI, BspGI, BspLU11I, BspMAI, BspMII, BspOI, BspT104I, BspT107I, BspTI, BspXI, BssAI, BssHI, BssNAI, BssNI, BssT1I, Bst1107I, Bst98I, BstACI, BstAFI, BstAUI, BstBAI, BstC8I, BstDSI, BstH2I, BstHPI, BstNSI, BstSFI, BstSLI, BstSNI, BstX2I, BstZI, BsuTUI, BtuMI, BveI, CciI, Cfr10I, Cfr42I, Cfr9I, CfrI, Csp45I, CspAI, DinI, DrdII, DsaI, Ec1136II, EcIXI, Eco105I, Eco130I, Eco147I, Eco24I, Eco32I, Eco47III, Eco52I, Eco72I, Eco88I, EcoICRI, EcoT14I, EcoT22I, EcoT38I, EgeI, EheI, ErhI, FauNDI, FbaI, FblI, FriOI, FunI, FunII, GdiII, GsaI, HaeI, HgiAI, Hin1I, HindII, Hpy178III, Hpy8I, Hsp92I, Kpn2I, Ksp22I, KspAI, KspI, MflI, MhlI, MlsI, MluNI, Mly113I, Mph1103I, MroI, MroNI, Msp20I, MspCI, MstI, MunI, MvrI, NgoAIV, NsbI, NspIII, NspV, PaeI, PagI, Paul, PceI, Pfl23II, PinAI, Ple19I, PmaCI, PshBI, Psp124BI, Psp1406I, PspAI, PspLI, PspN4I, PsuI, RcaI, SduI, Sfr274I, Sfr303I, SfuI, SgrBI, SlaI, SpaHI, SseBI, SspBI, SstI, SstII, SunI, TatI, Vha464I, VneI, XapI, XhoII, XmaCI, XmaIII, XmaJI, XmiI, ZhoI, Zsp2I, AocI, AxyI, Bpu1102I, Bse21I, Bsp1720I, BstPI, CelII, CpoI, CspI, DraII, Eco065I, Eco81I, Eco91I, EspI, KflI, LguI, MabI, PpuXI, Psp5II, PspEI, Rsr2I, SauI, AbsI, CciNI, FspAI, MauBI, MreI, MssI, RgaI, SdaI, SfaAI, SgfI, SmiI, Sse232I, AdeI, AspI, CaiI, PsyI, TelI, Asp700I, BoxI, Bse8I, BseJI, BsiBI, BsrBRI, BstPAI, CjeNII, MamI, MroXI, OliI, PdmI, RseI, SmiMI, AccB7I, AspEI, BasI, BmeRI, BplI, Bsc4I, BseLI, BsiYI, BstENI, BstMWI, CjeI, CjuI, CjuII, DriI, Eam1105I, EclHKI, FalI, HpyF10VI, NgoAVIII, NruGI, PflBI, UbaF14I, XagI, AasI, BdaI, Bsp24I, CjePI, DseDI, UbaF9I, ArsI, BarI, PcsI or UbaF13I. In some alternatives, the endonuclease recognition site is inverted. In some alternatives, said endonuclease recognition site is located within 1, 5, 10, 15, 20, 25, 30, 35, 40, 45 or 55 base pairs of the endonuclease cleavage site for the endonuclease or any number of base pairs between two aforementioned values, and said endonuclease cleavage site is within 1, 5, 10, 15, 20, 25, 30, 35 or 40 base pairs of the most 5' thymine of the plurality of thymine nucleotides or any number of base pairs between any two aforementioned values. In some alternatives, the endonuclease recognition site is inverted and the endonuclease cleavage site is inverted. In some alternatives, the endonuclease recognition site and endonuclease cleavage site comprise a sequence set forth in Table 1 (SEQ ID NOs: 18-632, 634-636, 634-636), wherein the endonuclease recognition site and endonuclease cleavage site are specific for the Type II restriction endonuclease AciI, MnlI, AlwI, BbvI, BccI, BceAI, BsmAI, BsmFI, BspCNI, BsrI, BtsCI, FokI, HgaI, HphI, HpyAV, MboII, MlyI, PleI, SfaNI, AcuI, BciVI, BfuAI, BmgBI, BmrI, BpmI, BpuEI, BsaI, BseRI, BsgI, BsmI, BspMI, BsrBI, BsrDI, BtgZI, BtsI, EarI, EciI, MmeI, NmeAIII, BbvCI, Bpu10I, BspQI, SapI, BaeI, BsaXI, CspCI, AfaI, AluBI, AspLEI, BscFI, Bsh1236I, BshFI, BshI, BsiSI, BsnI, Bsp143I, BspANI, BspFNI, BssMI, BstENII, BstFNI, BstHHI, BstKTI, BstMBI, BsuRI, CfoI, Csp6I, FaeI, FaiI, FnuDII, FspBI, GlaI, HapII, Hin1II, R9529, Hsp92II, HspAI, MaeI, MaeII, MvnI, PalI, RsaNI, SetI, SgeI, Sse9I, Tru1I, Tru9I, TscI, TspEI, TthHB8I, XspI, AflI, AgsI, AspS9I, AsuC2I, AsuI, BcefI, BcnI, BisI, BlsI, Bme1390I, Bme18I, BmrFI, BscGI, BseBI, BsiLI, BsiZI, BslFI, BsoMAI, BspNCI, Bst2UI, Bst71I, BstDEI, BstOI, BstSCI, CauII, CdiI, Cfr13I, Eco47I, EcoRII, FaqI, FinI, Fsp4HI, GluI, Hin4II, HpyF3I, ItaI, MaeIII, MspR9I, MvaI, NmuCI, Psp6I, PspPI, SatI, SinI, TscAI, VpaK11BI, AanI, AatI, AauI, Acc113I, Acc16I, AccB1I, AceIII, AesI, AcvI, AcyI, AhlI, Alw21I, A1w44I, Ama87I, Aor51HI, AsiAI, AsnI, Asp718I, AspHI, AsuII, AsuNHI, AvaIII, AviII, BanIII, BauI, BbeI, BbrPI, BbuI, Bbv12I, BbvII, Bce83I, BeoI, BcuI, BfmI, BfrB1, BfrI, B1nI, BmcAI, BmeT110I, BmiI, BmuI, BmyI, Bpu14I, BpvUI, Bsa29I, BsaOI, BsbI, BscBI, BscCI, Bse118I, BseAI, BseCI, BseDI, BsePI, BseSI, BseX3I, Bsh1285I, BshNI, BshTI, BshVI, BsiCI, BsiHKCI, BsiMI, BsiQI, BsiXI, Bsp106I, Bsp119I, Bsp120I, Bsp13I, Bsp1407I, Bsp143II, Bsp19I, Bsp68I, BspA2I, BspCI, BspGI, BspLU11I, BspMAI, BspMII, BspOI, BspT104I, BspT107I, BspTI, BspXI, BssAI, BssHI, BssNAI, BssNI, BssT1I, Bst1107I, Bst98I, BstACI, BstAFI, BstAUI, BstBAI, BstC8I, BstDSI, BstH2I, BstHPI, BstNSI, BstSFI, BstSLI, BstSNI, BstX2I, BstZI, BsuTUI, BtuMI, BveI, CciI, Cfr10I, Cfr42I, Cfr9I, CfrI, Csp45I, CspAI, DinI, DrdII, DsaI, Ec1136II, EcIXI, Eco105I, Eco130I, Eco147I, Eco24I, Eco32I, Eco47III, Eco52I, Eco72I, Eco88I, EcoICRI, EcoT14I, EcoT22I, EcoT38I, EgeI, EheI, ErhI, FauNDI, FbaI, FblI, FriOI, FunI, FunII, GdiII, GsaI, HaeI, HgiAI, Hin1I, HindII, Hpy178III, Hpy8I, Hsp92I, Kpn2I, Ksp22I, KspAI, KspI, MflI, MhlI, MlsI, MluNI, Mly113I, Mph1103I, MroI, MroNI, Msp20I, MspCI, MstI, MunI, MvrI, NgoAIV, NsbI, NspIII, NspV, PaeI, PagI, Paul, PeeI, Pfl23II, PinAI, Ple19I, PmaCI, PshBI, Psp124BI, Psp1406I, PspAI, PspLI, PspN4I, PsuI, RcaI, SduI, Sfr274I, Sfr303I, SfuI, SgrBI, SlaI, SpaHI, SseBI, SspBI, SstI, SstII, SunI, TatI, Vha464I, VneI, XapI, XhoII, XmaCI, XmaIII, XmaJI, XmiI, ZhoI, Zsp2I, AocI, AxyI, Bpu1102I, Bse21I, Bsp1720I, BstPI, CelII, CpoI, CspI, DraII, Eco065I, Eco81I, Eco91I, EspI, KflI, LguI, MabI, PpuXI, Psp5II, PspEI, Rsr2I, SauI, AbsI, CciNI, FspAI, MauBI, MreI, MssI, RgaI, SdaI, SfaAI, SgfI, SmiI, Sse232I, AdeI, AspI, CaiI, PsyI, TelI, Asp700I, BoxI, Bse8I, BseJI, BsiBI, BsrBRI, BstPAI, CjeNII, MamI, MroXI, OliI, PdmI, RseI, SmiMI, AccB7I, AspEI, BasI, BmeRI, BplI, Bsc4I, BseLI, BsiYI, BstENI, BstMWI, CjeI, CjuI, CjuII, DriI, Eam1105I, EclHKI, FalI, HpyF10VI, NgoAVIII, NruGI, PflBI, UbaF14I, XagI, AasI, BdaI, Bsp24I, CjePI, DseDI, UbaF9I, ArsI, BarI, PcsI or UbaF13I. As shown in Table 1, the endonuclease, or restriction endonuclease can cleave between 1 and 50 bases away from a recognition site (SEQ ID NOs: 18-632, 634-636, 634-636). In some alternatives, the endonuclease cleavage site is located 1, 2, 3, 4, 5, 6, 7, 7, 8, 9, 10, 11, 12, 13, 14, 15, 16, 17, 18, 19 or 20 base pairs away from the most 5' thymine (or 5' terminal thymine) in the plurality of thymine nucleotides. In some alternatives, the endonuclease recognition site is located 1, 2, 3, 4, 5, 6, 7, 7, 8, 9 or 10 base pairs from the endonuclease cleavage site of from the most 5' thymine (or 5' terminal thymine) in the plurality of thymine nucleotides.

A "recognition site" as described herein, refers to a sequence on a nucleic acid site that is recognized and bound by a restriction enzyme, nuclease, or a restriction endonuclease.

A "cleavage site" as described herein, is a site on a nucleic acid that is cleaved by a restriction endonuclease or endonuclease. In some alternatives, the endonuclease is a Type IIS endonuclease. In some alternatives, the recognition site and cleavage site are inverted.

A "palindromic sequence" as described herein, refers to a nucleic acid sequence on double-stranded DNA or RNA wherein reading 5' (five-prime) to 3' (three prime) forward on one strand matches the sequence reading backward 5' to 3' on the complementary strand or on itself. Complimentary strands can bind to the compliment in a palindromic sequence leading to a "hairpin" structure.

"A promoter" refers to a region of DNA that initiates replication. Promoters can be 100-1000 base pairs long. In some alternatives, of the polynucleotide, the polynucleotide further comprises a DNA polymerase promoter.

"Tertiary structure" is the 3D structure formed by a double stranded or a single stranded nucleic acid and is dependent on the sequences. Examples of tertiary structures seen in nucleic acid include but are not limited to a double helix, stem loops, hairpins, major and minor grove triplexes (RNA), quadruplexes, coaxial stacking, tetraloops, A-minor motifs and ribose zippers. In some alternatives of the polynucleotide, the polynucleotide further comprises a sixth sequence, wherein the sixth sequence is capable of forming a tertiary structure. In some alternatives, the tertiary structure comprises a double helix, stem loops, hairpins, major and minor grove triplexes (RNA), quadruplexes, coaxial stacking, tetraloops, A-minor motifs and/or ribose zippers.

"Specific" or "Specificity" as described herein, refers to the ability of a protein to bind to a defined binding site. As described herein, an enzyme can be specific for binding to a specific sequence, for example, a specific sequence on a nucleic acid.

"Upstream" and "downstream" as used herein, refers to relative positions in either DNA or RNA. Each strand of DNA or RNA has a 5' end and a 3' end, so named for the carbon position on the deoxyribose (or ribose) ring. Upstream and downstream relate to the 5' to 3' direction in which RNA transcription takes place. Upstream is toward the 5' end of the RNA molecule and downstream is toward the 3' end. When considering double-stranded DNA, upstream is toward the 5' end of the coding strand for the gene in question and downstream is toward the 3' end. Due to the anti-parallel nature of DNA, this means the 3' end of the template strand is upstream of the gene and the 5' end is downstream.

"Sticky end" as referred herein refers to an overhang, which is a stretch of unpaired nucleotides in the end of a DNA molecule. Sticky ends can be created with an endonuclease, such as a restriction endonuclease. For example some endonucleases cleave a palindromic sequence and can leave an overhang, or a sticky end.

"Blunt end" as referred herein, refers o a blunt-ended molecule in which both strands of in a nucleic acid terminate in a base pair. Some alternatives relate to a polynucleotide comprising a template strand, an endonuclease recognition site and an endonuclease cleavage site for an endonuclease inserted therein, wherein said template strand comprises a plurality of thymine nucleotides. The polynucleotide can comprise a first nucleic acid sequence encoding a nuclease, a second nucleic acid sequence comprising at least one restriction endonuclease recognition site and a third nucleic acid sequence, wherein the third nucleic acid sequence comprises the template strand, wherein said plurality of thymine nucleotides comprises at least, greater than, equal to, or any number in between 20, 30, 40, 50, 60, 70, 80, 90, 100, 110, 120, 130, 140, 150, 175, 200, 225, 250, 275, 300, 325, 350, 375, 400, 425, 450, 475, 500 or 550 covalently linked thymine nucleotides and wherein the third nucleic acid comprises the restriction endonuclease cleavage site, wherein the restriction endonuclease cleavage site is located within the plurality of thymine nucleotides or within 1, 2, 3, 4, 5, 6, 7, 7, 8, 9, 10, 11, 12, 13, 14, 15, 16, 17, 18, 19 or 20 base pairs away from the most 5' thymine (or 5' terminal thymine) in the plurality of thymine nucleotides and wherein said second nucleic acid is covalently linked to one end of said third nucleic acid sequence, and wherein the said restriction endonuclease recognition site is located within 55 base pairs of the restriction endonuclease cleavage site for the restriction endonuclease and said restriction endonuclease cleavage site is within 1 to 40 base pairs of a most 5' thymine in the plurality of thymine nucleotides. In some alternatives, the endonuclease produces a blunt end during cleavage. In some alternatives, the endonuclease is StuI.

DETAILED DESCRIPTION

In vitro transcribed (IVT) mRNA has emerged as an important modality of transient heterologous protein expression for therapeutic applications. Electroporation of IVT mRNA's is presently being applied in translational contexts ranging from in vivo expression of antigenic proteins in dendritic cells for cancer and infectious disease vaccine purposes, to ex vivo expression of nucleases in primary hematopoietic stem cells and T-cells for gene editing, and expression of chimeric antigen receptors in primary human T-cells for cancer immunotherapy. Nano-particle based IVT mRNA-mediated transient gene expression is under development for in vivo administration as a novel modality for protein replacement therapies.

An important issue in any IVT mRNA application is to obtain efficient protein expression. Increased efficiency of expression reduces costs by directly reducing the quantity of mRNA necessary for a required level of expression, and can also reduce the potential for antigenicity of the mRNA due to the reduced exposure of a patient's cells to a foreign nucleic acid. Numerous determinants of the efficiency of expression of an mRNA have been identified, including the nature of the 5' cap, the efficiency of capping, nature of 5' and 3' UTR's, codon optimization of protein coding sequence, presence of miRNA target sequences in the protein coding sequence and UTR's, and the length of the polyadenosine (poly(A)) tail. Of these determinants, the length of the poly(A) tail is most problematic to optimize: although poly(A) tail length is known to be one of the most important physiological determinants of translational efficiency and mRNA stability, existing technologies do not allow for production of IVT mRNA with defined length poly(A) tails in the physiological (>200 base pairs) range.

The alternatives described herein demonstrate a novel method for generation of homopolymeric tracts of arbitrary length and content, and demonstrate that a previously described linear plasmid, linear plasmid, is capable of propagating poly(A) tracts up to at least 500 base pairs in length. Further, in an exemplary alternative, linear plasmid is modified by removing extraneous BsaI sites while incorporating a unique BsaI site downstream from the poly(A) tract to create pEVL, a linear plasmid that allows for facile generation of IVT mRNA's with defined, extended poly(A) tails using standard T7 phage RNA polymerase chemistry.

Described herein are methods for making a polynucleotide having a polymer of covalently linked deoxyadenosine nucleotides, which can be extended to a desired length by virtue of the presence of an endonuclease site within or upstream of said polymer of covalently linked deoxyadenosine nucleotides such that a poly(A) insert of a desired length can be ligated to the polynucleotide having the polymer of covalently linked deoxyadenosine nucleotides and endonuclease site thereby extending the poly(A) tract to the desired length. The polynucleotide having a polymer of covalently linked deoxyadenosine nucleotides can also be referred to as a polymer of covalently linked deoxythymidines or a polymer of covalently linked deoxythymidine monophosphates, when referencing to the antisense or template strand. The polynucleotide strand can be digested and ligated to extend the length further to 500 thymine nucleotides or more. This polynucleotide can serve as the "antisense" or template strand that can then be transcribed so as to generate an RNA having a poly(A) tract of a desired length, e.g., the length of the poly(T) polymer after ligation with the poly(T) insert. The polynucleotide as described herein can serve as a DNA template for transcription with increased stability, and can improve gene transcription with fewer steps leading to improved protein translation due to a longer poly(A) tract in the transcribed RNA which would be a more pure product, e.g., the lengths of the transcribed RNA would all be one size. Accordingly, several compositions and methods for generating nucleic acids having a poly(T) tract and poly(A) tract nucleic acids are described herein. As used herein, in some aspects, poly(A) and poly(T) are used interchangeably in the same context depending on reference to a sense or anti-sense strand. The use of these compositions and methods to increase the stability of a nucleic acid transcript, such as a DNA template used for transcription, enhance and improve gene transcription such as allowing fewer steps for generating a homogeneous RNA product, and/or improve protein translation such as a more efficacious product, are contemplated. In some alternatives, the RNA lacks a 5' and/or 3' UTR or lacks a native 5' and/or 3' UTR and/or lacks one or more sequences required for native polyadenylation such as, a cleavage/polyadenylation specificity factor (CPSF) binding site, a cleavage stimulation factor binding site (CstF), a cleavage factor I binding site (CFI), or a cleavage factor II binding site (CFII). Endonucleases can be an enzyme that can enzymes that cleave the phosphodiester bond within a polynucleotide. Without being limiting an endonuclease can include, for example, a CRISPR, a restriction endonuclease, a Type II restriction endonuclease and a Type IIS restriction endonuclease. In some alternatives, the endonuclease is a CRISPR, a restriction endonuclease, a Type II restriction endonuclease or a Type IIS restriction endonuclease. In some alternatives, wherein StuI is provided, the endonuclease cleavage site is a StuI cleavage site, AGGCCT (SEQ ID NO: 633), and StuI cleaves between the G and C, leaving a blunt end that terminates in a GG. In some alternatives, the endonuclease cleavage site is AGGCCT (SEQ ID NO: 633). In some alternatives, the endonuclease is StuI. In some alternatives, the plurality of adenines terminates in GG. In some alternatives, the StuI cleavage site is inverted. In some alternatives, the endonuclease cleavage site is located 1, 2, 3, 4, 5, 6, 7, 7, 8, 9, 10, 11, 12, 13, 14, 15, 16, 17, 18, 19 or 20 base pairs away from the most 5' thymine (or 5' terminal thymine) in the plurality of thymine nucleotides. In some alternatives, the endonuclease cleavage site is located 1, 2, 3, 4, 5, 6, 7, 7, 8, 9 or 10 base pairs away from the most 5' thymine (or 5' terminal thymine) in the plurality of thymine nucleotides. In some alternatives, translation is performed for at least, greater than, equal to, or time in between 1, 5, 10, 20, 30, 40, 50, 60, 70, 80, 90 or 100 hours (e.g., at least, or equal to 1, 5, 10, 20, 30, 40, 50, 60, 70, 80, 90 or 100 hours or within a range defined by any two of the aforementioned times).

The polynucleotide described herein, can further comprise genes for expression. Examples of genes can include but are not limited to transcriptional regulators (e.g., eukaryotic histone remodeling enzymes, transcription factors, enhancers and repressors), chimeric antigen receptors (CARS), T-cell receptors (TCR), nucleases (e.g., Cas9 or a derivative thereof or active fragment thereof, see e.g., SEQ ID. Nos. 6-14, MegaTAL, TALEN), epigenetic modulators (e.g., DNA methylation proteins, histone modification proteins, chromatin remodeling proteins, methyl-CpG binding proteins) and vaccine antigens (e.g., cancer vaccine antigens and infectious disease antigens). Accordingly, in some alternatives, the polynucleotide encodes a gene. In some alternatives, the gene encodes eukaryotic histone remodeling enzymes, transcription factors, enhancers, repressors, CARs, TCR's, Cas9 or derivatives thereof or active fragments thereof see e.g., SEQ ID. Nos. 6-14, MegaTAL, TALEN, DNA methylation proteins, histone modification proteins, chromatin remodeling proteins, methyl-CpG binding proteins, or a vaccine antigen. In many of the alternatives described herein, the polynucleotide described herein having a poly(T) or poly(A) tail encodes a Cas9 nuclease and said polynucleotide is delivered to a cell with a guide RNA so as to allow for CRISPR/Cas9 gene editing. The basic components of CRISPR/Cas9 system comprise a target gene, a guide RNA, and a Cas9 endonuclease. An important aspect of applying CRISPR/Cas9 for gene editing is the need for a system to deliver the guide RNAs efficiently to a wide variety of cell types. This could for example involve delivery of an in vitro generated guide RNA as a nucleic acid (the guide RNA generated by in vitro transcription or chemical synthesis). In some alternatives the nucleic acid encoding the guide RNA is rendered nuclease resistant by incorporation of modified bases, such as 2'O-methyl bases. An important system for expressing guide RNAs in this context is based on the use of adeno-associated virus (AAV) vectors because AAV vectors are able to transduce a wide range of primary cells. AAV vectors do not cause infection and are not known to integrate into the genome. Therefore, the use of AAV vectors has the benefits of being both safe and efficacious.

The 3'-termini of eukaryotic RNAs reflects their regulatory status and plays an important role in determining the fate of RNAs. The function of the poly(A) tail in mRNA is important for nuclear export, facilitating translation initiation and efficiency, and ensuring the stability of the mRNA, all of which is dependent on the length of the poly-A tail. In eukaryotes, the polyadenylation protects the mRNA molecule from exonucleases and is important for transcription termination, for export of the mRNA from the nucleus, and for translation efficiency. Some prokaryotic mRNAs are also polyadenylated, although the poly(A) tail function is different from that in eukaryotes. For example in prokaryotes, polyadenylation promotes the degradation of a regulatory RNA that inhibits the replication of bacterial plasmids and may play a similar role in the degradation of mRNA.

Due to the benefits of adding a poly(A) tail to an mRNA, techniques have been reported in which poly(A) tails have been added through a commercial polyadenylate enzyme (e.g., E-PAP), and PCR methods using a specific 5'-specific primer and a poly(A) tail-specific primer. However, there are many undesirable aspects to these techniques. Use of a polyadenylate enzyme, such as E-PAP, will generate poly(A) tails of varying lengths, for example, which is not desired in some applications. Furthermore, enzymatic approaches are an additional costly step and usually require extensive purification procedures, which can lead to a significant loss of the product. Although the addition of a poly (A) tail to the mRNA by PCR avoids the extra enzymatic step, PCR methodologies can also bring additional problems, such as length variation, as well as amplification abnormalities, which can stem from specific genes that are not readily amplified by PCR. PCR is also restricted by the number of adenine residues that can be contained in a primer (~120). More importantly, it is also limited to genes that can be amplified by PCR. Genes that are refractory to PCR include but are not limited to genes with repetitive elements (including TAL effector nucleases, which are currently used in genome editing), secondary structure, skewed GC ratios, and other recalcitrant features. Still further, the specific PCR conditions required for certain genes can also affect amplification (e.g., TAL Effector Nucleases).

The addition of short poly(A) sequences can also be performed through commercially available circular *Escherichia coli* plasmids that contain poly-thymine (poly (T)) tracts for transcribing an mRNA with a poly(A) tract. However, commercially available plasmids only contain poly(T) tracts of 30 bases in length, which are not effective for in vivo use (only in vitro). Plasmids can be custom-ordered to have up to 100 poly(T) tracts, but the poly(T) tracts can rapidly shorten to about 30-40 bases under normal growth conditions. Another undesired aspect can arise from the use of circular plasmids required by these methodologies, such as supercoiling and the consequent inability to clone large or "difficult" polynucleotide sequences that are not easily maintained or unstable in the supercoiled plasmid form. Further complicating these approaches, is that the template is very unstable during the propagation in *E. coli*, leading to tracts that can only transcribe poly(A) tails of about 30 adenines, which can spontaneously shorten again leading to the problem of different poly(A) tail lengths in the product mRNA. Sustaining a much longer length of poly(A) tract is correlated with translational efficiency, and in order to maintain a poly(A) tail length greater than 30 adenines requires a 25° C. growth condition so as to prevent shortening. However, low temperatures can also extend the propagation time significantly.

In the present disclosure, the addition of a poly(A) tract of a desired length has been made possible by generating a poly(T) containing polynucleotide having one or more endonuclease sites (e.g., within the poly(T) domain itself or juxtaposed to the poly(T) domain, such as within 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50 or 55 nucleotides or a number of nucleotides within a range defined by any two of the aforementioned values from the most 5' thymine residue of the poly(T) domain in the template strand, but configured or spaced to permit enzymatic cleavage within the poly(T) domain) thereby allowing the introduction of an insert comprising an additional poly (T) tract and ligation, which when transcribed, allows one to control the length of the poly(A) tract in a resultant RNA. New approaches to add a poly(A) tail to a "difficult" or large gene are also described herein. Endonucleases can be an enzyme that can enzymes that cleave the phosphodiester bond within a polynucleotide. Without being limiting an endonuclease can include, for example, a CRISPR, a restriction endonuclease, a Type II restriction endonuclease and a Type IIS restriction endonuclease. In some alternatives, the endonuclease is a CRISPR, a restriction endonuclease, a Type II restriction endonuclease or a Type IIS restriction endonuclease. In some alternatives, wherein StuI is provided, the endonuclease cleavage site is a StuI cleavage site, AGGCCT (SEQ ID NO: 633), and StuI cleaves between the G and C, leaving a blunt end that terminates in a GG. In some alternatives, the endonuclease cleavage site is AGGCCT (SEQ ID NO: 633). In some alternatives, the endonuclease is StuI. In some alternatives, the plurality of adenines terminates in GG. In some alternatives, the StuI cleavage site is inverted. In some alternatives, the endonuclease cleavage site is located 1, 2, 3, 4, 5, 6, 7, 7, 8, 9, 10, 11, 12, 13, 14, 15, 16, 17, 18, 19 or 20 base pairs away from the most 5' thymine (or 5' terminal thymine) in the plurality of thymine nucleotides. In some alternatives, the endonuclease cleavage site is located 1, 2, 3, 4, 5, 6, 7, 7, 8, 9 or 10 base pairs away from the most 5' thymine (or 5' terminal thymine) in the plurality of thymine nucleotides.

For quite some time the field has desired the ability to control the length of a poly(A) tract so as to increase the polynucleotide stability during replication, increase transcriptional efficiency, increase half-life or stability of an RNA molecule, as well as to increase the translational efficiency of a gene. An increased half-life of RNA can also allow for the use of RNA for increased protein production. RNA can also be used as a therapeutic mRNA in which its increased half-life can lead to production of a protein that is needed in therapy, and the breakdown of the therapeutic mRNA can be controlled by using a determined poly(A) tail length in order to lengthen the time of treatment.

Poly(A) tails with alternative termination bases can also be achieved by the methods described herein. To date, there are no methods described in which a poly(A) tail can end in an alternative nucleotide base such as guanine, cytosine, thymine, or uracil by use of an enzyme or an available plasmid. Creating a poly(A) tail with alternative terminal sequences can allow one to test the influence of various tails. In some alternatives, a polynucleotide having a plurality of thymine nucleotides is made and an endonuclease recognition site is inserted therein or juxtaposed to the poly(T) tract (e.g., within 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50 or 55 nucleotides or a number of nucleotides within a range defined by any two of the aforementioned values from the most 5' thymine residue of the poly(T) domain in the template strand, but configured or spaced to permit enzymatic cleavage within the poly(T) domain) thereby allowing the introduction of an insert comprising an additional poly(T) tract and ligation, which when transcribed, allows one to control the length of the poly(A) tract in a resultant RNA. In some alternatives, the polynucleotide is extended by insertion and ligation of a polymer of covalently linked thymine residues terminating in a guanine, cytosine, or an adenine. Without being limiting an endonuclease can include, for example, a CRISPR, a restriction endonuclease, a Type II restriction endonuclease and a Type IIS restriction endonuclease. In some alternatives, the endonuclease is a CRISPR, a restriction endonuclease, a Type II restriction endonuclease or a Type IIS restriction endonuclease. In some alternatives, wherein StuI is provided, the endonuclease cleavage site is a StuI cleavage site, AGGCCT (SEQ ID NO: 633), and StuI cleaves between the G and C, leaving a blunt end that terminates in a GG. In some alternatives, the endonuclease cleavage site is AGGCCT (SEQ ID NO: 633). In some alternatives, the endonuclease is StuI. In some alternatives, the plurality of adenines terminates in GG. In some alternatives, the StuI cleavage site is inverted. In some alternatives, the endonuclease cleavage site is located 1, 2, 3, 4, 5, 6, 7, 7, 8, 9, 10, 11, 12, 13, 14, 15, 16, 17, 18, 19 or 20 base pairs away from the most 5' thymine (or 5' terminal thymine) in the plurality of thymine nucleotides. In some alternatives, the endonuclease cleavage site is located 1, 2, 3, 4, 5, 6, 7, 7, 8, 9 or 10 base pairs away from the most 5' thymine (or 5' terminal thymine) in the plurality of thymine nucleotides.

Important factors for mRNA production can include, but are not limited to, the stability of the tail length, the purity and uniformity of the mRNA, and the cost and time factors. Described herein are methods, wherein the addition of a poly(A) tract to an mRNA is realized in a one step process. A one step process is highly desirable over the multi-step processes that involve the use of PCR and enzymes to add on a poly(A) tract. Additionally, the mRNA produced from a polynucleotide comprising a poly(T) tract having one or more endonuclease cleavage sites allowing the introduction of an insert, can be used in both biotechnology and therapeutic approaches. The polynucleotide that generates the resultant polypeptide, e.g., a vector, can also have a consensus sequence for initiating the translation process. Without being limiting, such consensus sequences can include Kozak, T3, SP6, and/or T7 consensus sequences. The polynucleotide that generates the resultant nucleic acid can also include stop codons and/or mammalian expression sequences, such as activation sequences or enhancer sequences. Without being limiting, the stop codons can include TAG, TAA, and TGA sequences. Without being limiting, stop codons in RNA can include UAG, UAA, and UGA sequences. In some alternatives of the polynucleotide, the polynucleotide comprises stop codons. In some alternatives, the stop codons are TAG, TAA, or TGA sequences. Without being limiting an endonuclease can include, for example, a CRISPR, a restriction endonuclease, a Type II restriction endonuclease and a Type IIS restriction endonuclease. In some alternatives, the endonuclease is a CRISPR, a restriction endonuclease, a Type II restriction endonuclease or a Type IIS restriction endonuclease. In some alternatives, wherein StuI is provided, the endonuclease cleavage site is a StuI cleavage site, AGGCCT (SEQ ID NO: 633), and StuI cleaves between the G and C, leaving a blunt end that terminates in a GG. In some alternatives, the endonuclease cleavage site is AGGCCT (SEQ ID NO: 633). In some alternatives, the endonuclease is StuI. In some alternatives, the plurality of adenines terminates in GG. In some alternatives, the StuI cleavage site is inverted. In some alternatives, the endonuclease cleavage site is located 1, 2, 3, 4, 5, 6, 7, 7, 8, 9, 10, 11, 12, 13, 14, 15, 16, 17, 18, 19 or 20 base pairs away from the most 5' thymine (or 5' terminal thymine) in the plurality of thymine nucleotides. In some alternatives, the endonuclease cleavage site is located 1, 2, 3, 4, 5, 6, 7, 7, 8, 9 or 10 base pairs away from the most 5' thymine (or 5' terminal thymine) in the plurality of thymine nucleotides.

By one approach, a polynucleotide having a plurality of thymine nucleotides is made and an endonuclease recognition site is inserted therein or within 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50 or 55 nucleotides or a number of nucleotides within a range defined by any two of the aforementioned values from the most 5' thymine residue of the poly(T) domain of the template strand, but configured or spaced to permit enzymatic cleavage within the poly(T) domain) thereby allowing the introduction of an insert comprising an additional poly(T) tract and ligation, which when transcribed, allows one to control the length of the poly(A) tract in a resultant RNA. Accordingly, methods for making a nucleic acid from a polynucleotide having a plurality of thymine nucleotides and an endonuclease recognition site disposed within or juxtaposed to (e.g., 1-55 nucleotides downstream from the most downstream or most 5' thymine of the poly(T) tract) said plurality of thymine nucleotides of the template strand) is provided herein. Methods for enhancing transcription and translation utilizing said compositions are also alternatives. Without being limiting an endonuclease can include, for example, a CRISPR, a restriction endonuclease, a Type II restriction endonuclease and a Type IIS restriction endonuclease. In some alternatives, the endonuclease is a CRISPR, a restriction endonuclease, a Type II restriction endonuclease or a Type IIS restriction endonuclease. In some alternatives, wherein StuI is provided, the endonuclease cleavage site is a StuI cleavage site, AGGCCT (SEQ ID NO: 633), and StuI cleaves between the G and C, leaving a blunt end that terminates in a GG. In some alternatives, the endonuclease cleavage site is AGGCCT (SEQ ID NO: 633). In some alternatives, the endonuclease is StuI. In some alternatives, the plurality of adenines terminates in GG. In some alternatives, the StuI cleavage site is inverted. In some alternatives, the endonuclease cleavage site is located 1, 2, 3, 4, 5, 6, 7, 7, 8, 9, 10, 11, 12, 13, 14, 15, 16, 17, 18, 19 or 20 base pairs away from the most 5' thymine (or 5' terminal thymine) in the plurality of thymine nucleotides. In some alternatives, the endonuclease cleavage site is located 1, 2, 3, 4, 5, 6, 7, 7, 8, 9 or 10 base pairs away from the most 5' thymine (or 5' terminal thymine) in the plurality of thymine nucleotides.

In some alternatives, a polynucleotide comprising a template strand, an endonuclease recognition site and an endonuclease cleavage site for an endonuclease inserted therein, wherein said template strand comprises a plurality of thymine nucleotides is provided. The polynucleotide can comprise a first nucleic acid sequence comprising at least one endonuclease recognition site and a second nucleic acid sequence, wherein the second nucleic acid sequence comprises the template strand, wherein the template strand comprises a plurality of thymine nucleotides, wherein said plurality of thymine nucleotides comprises at least at least 5, 10, 20, 50, 100, 200, 300, 400, 500 or 550 covalently linked thymine nucleotides and wherein the second nucleic acid comprises the endonuclease cleavage site, wherein the endonuclease cleavage site is within the plurality of thymine nucleotides and wherein said first nucleic acid is covalently linked to said second nucleic acid at one end of said second nucleic acid, and wherein the said endonuclease recognition site is located within 1 to 55 base pairs (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54 or 55 base pairs) of the endonuclease cleavage site for the endonuclease and said endonuclease cleavage site is within 1 to 40 base pairs (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 base pairs) of a most 5' thymine (or 5' terminal thymine) of the plurality of thymine nucleotides. In some alternatives, the polynucleotide further comprises a T3, SP6, and/or a T7 sequence. In some alternatives, the polynucleotide may further comprise a Kozak sequence. In some alternatives, the polynucleotide may further comprise a stop codon. In some alternatives, the endonuclease cleavage site comprises at least one guanine, cytosine, or an adenine, wherein the endonuclease cleaves between a thymine and the at least one guanine, cytosine or adenine. In some alternatives, the covalently linked thymines terminate in a guanine, adenine, or cytosine after cleavage by the endonuclease. In some alternatives, there exists a sequence that is complimentary to an endonuclease site (on the single strand), wherein the sequence is complimentary to any one of the restriction endonuclease recognition sites set forth in Table 1 (SEQ ID NOs: 18-632, 634-636, 634-636) and SEQ ID NO: 633. In some alternatives, the endonuclease recognition sites and the complimentary sequence is inverted. Endonucleases can be an enzyme that cleave the phosphodiester bond within a polynucleotide. Without being limiting an endonuclease can include, for example, a CRISPR, a restriction endonuclease, a Type II restriction endonuclease and a Type IIS restriction endonuclease. In some alternatives, the endonuclease is a CRISPR, a restriction endonuclease, a Type II restriction endonuclease or a Type IIS restriction endonuclease. In some alternatives, wherein StuI is provided, the endonuclease cleavage site is a StuI cleavage site, AGGCCT (SEQ ID NO: 633), and StuI cleaves between the G and C, leaving a blunt end that terminates in a GG. In some alternatives, the endonuclease cleavage site is AGGCCT (SEQ ID NO: 633). In some alternatives, the endonuclease is StuI. In some alternatives, the plurality of adenines terminates in GG. In some alternatives, the StuI cleavage site is inverted. In some alternatives, the endonuclease cleavage site is located 1, 2, 3, 4, 5, 6, 7, 8, 9, 10, 11, 12, 13, 14, 15, 16, 17, 18, 19 or 20 base pairs away from the most 5' thymine (or 5' terminal thymine) in the plurality of thymine nucleotides. In some alternatives, the endonuclease cleavage site is located 1, 2, 3, 4, 5, 6, 7, 7, 8, 9 or 10 base pairs away from the most 5' thymine (or 5' terminal thymine) in the plurality of thymine nucleotides.

In some alternatives, the resultant polynucleotide comprising said template strand, comprises a first and second nucleic acid. The second nucleic acid comprises a plurality of thymine nucleotides, wherein said plurality of thymine nucleotides comprises at least at least 5, 10, 20, 50, 100, 200, 300, 400, 500 or 550 covalently linked thymine nucleotides or any number of thymine nucleotides between any two aforementioned values, and the second nucleic acid further comprises the endonuclease cleavage site, wherein the endonuclease cleavage site is within the plurality of thymine nucleotides. The first nucleic acid comprises the endonuclease recognition site, wherein the first nucleic acid is covalently linked to said second nucleic acid at one end of said second nucleic acid, and wherein the said endonuclease recognition site is located within 1, 5, 10, 15, 20, 25, 30, 35, 40, 45, 50 or 55 base pairs of the endonuclease cleavage site for the endonuclease or any number of base pairs between any two aforementioned values, and said endonuclease cleavage site is within 1 to 40 base pairs of the most 5' thymine (or 5' terminal thymine) of the plurality of thymine nucleotides. In some alternatives, this allows enzymatic cleavage within the plurality of thymine nucleotides (poly (T) domain) leaving a poly (T) insert of a desired length comprising a final polymer of covalently linked thymine residues that is at least, greater than, equal to, or any number in between 20, 30, 40, 50, 60, 70, 80, 90, 100, 110, 120, 130, 140, 150, 175, 200, 225, 250, 275, 300, 325, 350, 375, 400, 425, 450, 475 or 500 thymine residues or any number of thymine residues between any two aforementioned values. As shown in Table 1 (SEQ ID Nos: 18-632, 634-636) and SEQ ID NO: 633, an endonuclease recognition site can reside between 1 and 50 nucleic acids away from a cleavage site, therefore in order to achieve a poly(A) tail of 500 adenines, the poly(T) must be longer than 500 thymines in length, depending on the endonuclease used. In some alternatives, the resultant polynucleotide having a polymer of covalently linked thymine nucleotides, an endonuclease recognition site within said polymer of covalently linked thymine nucleotides or within 1, 5, 10, 15, 20, 25, 30, 35, 40, 45, 50 or 55 nucleotides or a number of nucleotides within a range defined by any two of the aforementioned values from the most 5' thymine residue (or 5'terminal thymine) of the poly(T) domain but configured or spaced to permit enzymatic cleavage within the poly(T) domain), and a poly (T) insert of a desired length comprises a final polymer of covalently linked thymine residues that is at least, greater than, equal to, or any number in between 200 or 550 thymine residues, is provided. In some alternatives, the resultant polynucleotide having a polymer of covalently linked thymine nucleotides, an endonuclease site within said polymer of covalently linked thymine nucleotides or within 1, 5, 10, 15, 20, 25, 30, 35, 40, 45 or 55 nucleotides or a number of nucleotides within a range defined by any two of the aforementioned values from most 5' thymine residue (or 5' terminal thymine) of the poly(T) domain in the template strand, but configured or spaced to permit enzymatic cleavage within the poly(T) domain), and a poly (T) insert of a desired length comprises a final polymer of covalently linked thymine residues that is at least, greater than, equal to, or any number in between 200, 250, 300, 350, 400, 450, 500 or 550 thymine residues. In some alternatives, the plurality of thymine nucleotides comprises at least one covalently linked guanine, cytosine, or an adenine, wherein the at least one covalently linked guanine, cytosine or adenine is optionally joined to the most 5' thymine (or 5' terminal thymine) in the plurality of thymine nucleotides. In some alternatives, the endonuclease cleavage site comprises at least one guanine, cytosine, or an adenine, wherein the endonuclease cleaves between a thymine and the at least one guanine, cytosine or adenine. In some alternatives, the covalently linked thymines terminate in a guanine, adenine, or cytosine after cleavage by the endonuclease. In some alternatives, the polynucleotide can further encode a gene. In some alternatives, the gene is an endonuclease. In some alternatives, the gene is Cas9 or a derivative thereof or active fragment thereof, see e.g., SEQ ID. Nos. 6-14. In some alternatives, the gene is a TALEN. In some alternatives, the gene is a MegaTAL. In some alternatives, the endonuclease cleavage site comprises at least one guanine, cytosine, or an adenine, wherein the endonuclease cleaves between a thymine and the at least one guanine, cytosine or adenine. In some alternatives, the covalently linked thymines terminate in a guanine, adenine, or cytosine after cleavage by the endonuclease. In some alternatives, the endonuclease recognition sites and the complimentary sequence are inverted. In some alternatives, the endonuclease recognition site is a sequence set forth in Table 1 (SEQ ID Nos: 18-632, 634-636). In some alternatives, the endonuclease recognition site set forth in Table 1 is inverted. Without being limiting an endonuclease can include, for example, a CRISPR, a restriction endonuclease, a Type II restriction endonuclease and a Type IIS restriction endonuclease. In some alternatives, the endonuclease is a CRISPR, a restriction endonuclease, a Type II restriction endonuclease or a Type IIS restriction endonuclease. In some alternatives, wherein StuI is provided, the endonuclease cleavage site is a StuI cleavage site, AGGCCT (SEQ ID NO: 633), and StuI cleaves between the G and C, leaving a blunt end that terminates in a GG. In some alternatives, the endonuclease cleavage site is AGGCCT (SEQ ID NO: 633). In some alternatives, the endonuclease is StuI. In some alternatives, the plurality of adenines terminates in GG. In some alternatives, the StuI cleavage site is inverted. In some alternatives, the endonuclease cleavage site is located 1, 2, 3, 4, 5, 6, 7, 7, 8, 9, 10, 11, 12, 13, 14, 15, 16, 17, 18, 19 or 20 base pairs away from the most 5' thymine (or 5' terminal thymine) in the plurality of thymine nucleotides. In some alternatives, the endonuclease cleavage site is located 1, 2, 3, 4, 5, 6, 7, 7, 8, 9 or 10 base pairs away from the most 5' thymine (or 5' terminal thymine) in the plurality of thymine nucleotides. In some alternatives, wherein the plurality of thymine nucleotides comprises at least one covalently linked guanine, cytosine, or an adenine, wherein the at least one covalently linked guanine, cytosine or adenine is optionally joined to the most 5' thymine (or 5' terminal thymine) in the plurality of thymine nucleotides, the endonuclease cleaves at the at the 5' side of the guanine, cytosine or adenine.

Disclosed herein are methods of making such a nucleic acid, such as RNA, as well. By some approaches, the method comprises providing the polynucleotide of any of the alternatives described above, and contacting said polynucleotide with a polymerase in the presence of nucleotides. In some alternatives, the polynucleotide further comprises a promoter for a DNA or RNA polymerase or both. In some alternatives, the nucleotides that are included in the reaction with the polymerase are adenine, cytosine, guanine, thymine, and/or uracil. In some alternatives, the method further comprises providing an endonuclease. In some alternatives, the endonuclease is a Type II restriction endonuclease. In some alternatives the endonuclease is a Type IIS restriction endonuclease. In some alternatives, the endonuclease is AciI, MnlI, AlwI, BbvI, BccI, BceAI, BsmAI, BsmFI, BspCNI, BsrI, BtsCI, FokI, HgaI, HphI, HpyAV, MboII, MlyI, PleI, SfaNI, AcuI, BciVI, BfuAI, BmgBI, BmrI, BpmI, BpuEI, BsaI, BseRI, BsgI, BsmI, BspMI, BsrBI, BsrDI, BtgZI, BtsI, EarI, EciI, MmeI, NmeAIII, BbvCI, Bpu10I, BspQI, SapI, BaeI, BsaXI, CspCI, AfaI, AluBI, AspLEI, BscFI, Bsh1236I, BshFI, BshI, BsiSI, BsnI, Bsp143I, BspANI, BspFNI, BssMI, BstENII, BstFNI, BstHHI, BstKTI, BstMBI, BsuRI, CfoI, Csp6I, FaeI, FaiI, FnuDII, FspBI, GlaI, HapII, Hin1II, R9529, Hsp92II, HspAI, MaeI, MaeII, MvnI, PalI, RsaNI, SetI, SgeI, Sse9I, Tru1I, Tru9I, TscI, TspEI, TthHB8I, XspI, AflI, AgsI, AspS9I, AsuC2I, AsuI, BcefI, BcnI, BisI, BlsI, Bme1390I, Bme18I, BmrFI, BscGI, BseBI, BsiLI, BsiZI, BslFI, BsoMAI, BspNCI, Bst2UI, Bst71I, BstDEI, BstOI, BstSCI, CauII, CdiI, Cfr13I, Eco47I, EcoRII, FaqI, FinI, Fsp4HI, GluI, Hin4II, HpyF3I, ItaI, MaeIII, MspR9I, MvaI, NmuCI, Psp6I, PspPI, SatI, SinI, TscAI, VpaK11BI, AanI, AatI, AauI, Acc113I, Acc16I, AccB1I, AceIII, AesI, AcvI, AcyI, AhlI, Alw21I, Alw44I, Ama87I, Aor51HI, AsiAI, AsnI, Asp718I, AspHI, AsuII, AsuNHI, AvaIII, AviII, BanIII, BauI, BbeI, BbrPI, BbuI, Bbv12I, BbvII, Bce83I, BeoI, BcuI, BfmI, BfrB1I,BfrI, BlnI, BmeAI, BmeT110I, BmiI, BmuI, BmyI, Bpu14I, BpvUI, Bsa29I, BsaOI, BsbI, BscBI, BscCI, Bse118I, BseAI, BseCI, BseDI, BsePI, BseSI, BseX3I, Bsh1285I, BshNI, BshTI, BshVI, BsiCI, BsiHKCI, BsiMI, BsiQI, BsiXI, Bsp106I, Bsp119I, Bsp120I, Bsp13I, Bsp1407I, Bsp143II, Bsp19I, Bsp68I, BspA2I, BspCI, BspGI, BspLU11I, BspMAI, BspMII, BspOI, BspT104I, BspT107I, BspTI, BspXI, BssAI, BssHI, BssNAI, BssNI, BssT1I, Bst1107I, Bst98I, BstACI, BstAFI, BstAUI, BstBAI, BstC8I, BstDSI, BstH2I, BstHPI, BstNSI, BstSFI, BstSLI, BstSNI, BstX2I, BstZI, BsuTUI, BtuMI, BveI, CciI, Cfr10I, Cfr42I, Cfr9I, CfrI, Csp45I, CspAI, DinI, DrdII, DsaI, Ec1136II, EcIXI, Eco105I, Eco130I, Eco147I, Eco24I, Eco32I, Eco47III, Eco52I, Eco72I, Eco88I, EcoICRI, EcoT14I, EcoT22I, EcoT38I, EgeI, EheI, ErhI, FauNDI, FbaI, FblI, FriOI, FunI, FunII, GdiII, GsaI, HaeI, HgiAI, Hin1I, HindII, Hpy178III, Hpy8I, Hsp92I, Kpn2I, Ksp22I, KspAI, KspI, MflI, MhlI, MlsI, MluNI, Mly113I, Mph1103I, MroI, MroNI, Msp20I, MspCI, MstI, MunI, MvrI, NgoAIV, NsbI, NspIII, NspV, PaeI, PagI, PauI, PceI, Pfl23II, PinAI, Ple19I, PmaCI, PshBI, Psp124BI, Psp1406I, PspAI, PspLI, PspN4I, PsuI, RcaI, SduI, Sfr274I, Sfr303I, SfuI, SgrBI, SlaI, SpaHI, SseBI, SspBI, SstI, SstII, SunI, TatI, Vha464I, VneI, XapI, XhoII, XmaCI, XmaIII, XmaJI, XmiI, ZhoI, Zsp2I, AocI, AxyI, Bpu1102I, Bse21I, Bsp1720I, BstPI, CelII, CpoI, CspI, DraII, Eco065I, Eco81I, Eco91I, EspI, KflI, LguI, MabI, PpuXI, Psp5II, PspEI, Rsr2I, SauI, AbsI, CciNI, FspAI, MauBI, MreI, MssI, RgaI, SdaI, SfaAI, SgfI, SmiI, Sse232I, AdeI, AspI, CaiI, PsyI, TelI, Asp700I, BoxI, Bse8I, BseJI, BsiBI, BsrBRI, BstPAI, CjeNII, MamI, MroXI, OliI, PdmI, RseI, SmiMI, AccB7I, AspEI, BasI, BmeRI, BplI, Bsc4I, BseLI, BsiYI, BstENI, BstMWI, CjeI, CjuI, CjuII, DriI, Eam1105I, EclHKI, FalI, HpyF10VI, NgoAVIII, NruGI, PflBI, UbaF14I, XagI, AasI, BdaI, Bsp24I, CjePI, DseDI, UbaF9I, ArsI, BarI, PcsI or UbaF13I. In some alternatives, the resultant RNA obtained after transcription of the aforementioned poly(T) containing constructs comprises at least, greater than, equal to, or any number in between 20, 30, 40, 50, 60, 70, 80, 90, 100, 110, 120, 130, 140, 150, 175, 200, 225, 250, 275, 300, 325, 350, 375, 400, 425, 450, 475, 500 or 550 covalently linked adenine residues and said RNA can contain a sequence complimentary to an endonuclease recognition site (on the single strand), such as StuI or BsaI, within said poly(A) tail or juxtaposed to said poly(A) tail (e.g., within 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50 or 55 nucleotides or a number of nucleotides within a range defined by any two of the aforementioned values upstream (5' in orientation) from the first adenine residue of the poly(A) domain), when the polynucleotide is not cleaved by the endonuclease. In some alternatives, wherein the polynucleotide is not cleaved by the endonuclease, the resulting nucleic acid (RNA) comprises at least, greater than, equal to, or any number in between 20, 30, 40, 50, 60, 70, 80, 90, 100, 110, 120, 130, 140, 150, 175, 200, 225, 250, 275, 300, 325, 350, 375, 400, 425, 450, 475 or 500 covalently linked adenine residues. In some alternatives, the resultant RNA (mRNA) terminates in a guanine, cytosine or a uracil. In some alternatives, the mRNA comprises a poly(A) tail, wherein within said poly(A) tail there exists a sequence that is complimentary to an endonuclease site (on the single strand), such as StuI or BsaI site. In some alternatives, there exists a sequence that is complimentary to an endonuclease site (on the single strand), wherein the sequence is complimentary to any one of the endonuclease recognition sites set forth in Table 1 (SEQ ID NOs: 18-632, 634-636). In some alternatives, the endonuclease recognition sites and the complimentary sequence is inverted. In some alternatives, the mRNA comprises a first sequence encoding an RNA compliment to at least one endonuclease site, such as StuI or BsaI site, wherein the sequence encoding the RNA compliment is covalently linked to a plurality of adenine nucleotides at the 3' end of said plurality of adenine nucleotides. In some alternatives, the mRNA further comprises or encodes a gene. In some alternatives, the gene is an endonuclease gene. In some alternatives, the gene encodes Cas9 or a derivative thereof or active fragment thereof, see e.g., SEQ ID. Nos. 6-14, TALEN or a MegaTAL. In some alternatives, the at least one endonuclease recognition site is inverted, and the sequence encoding an RNA compliment is a compliment to the inverted endonuclease site (on the single strand). In some alternatives, the endonuclease recognition site is a sequence set forth in Table 1 (SEQ ID NOs: 18-632, 634-636). In some alternatives, the at least one endonuclease is a Type II restriction endonuclease recognition site, such as StuI or BsaI site. In some alternatives, the one endonuclease is a Type IIS restriction endonuclease recognition site. In some alternatives, a pharmaceutical composition is provided, wherein the pharmaceutical composition comprises a pharmaceutical vehicle and a nucleic acid. In some alternatives, methods are provided for delivering a pharmaceutical composition to a subject in need. In some alternatives, methods are provided for introducing an mRNA into a cell for delivery to a subject in need. In these alternatives, the cell is provided for translation of a protein for therapy in the subject in need. In some alternatives, the protein is a nuclease, such as Cas 9 or a derivative thereof, see e.g., SEQ ID. Nos. 6-14, TALEN or MegaTAL. In some alternatives, a method of delivering a pharmaceutical composition comprising the nucleic acid is provided, wherein the method comprises delivering the pharmaceutical composition to a subject in need. Without being limiting an endonuclease can include, for example, a CRISPR, a restriction endonuclease, a Type II restriction endonuclease and a Type IIS restriction endonuclease. In some alternatives, the endonuclease is a CRISPR, a restriction endonuclease, a Type II restriction endonuclease or a Type IIS restriction endonuclease. In some alternatives, wherein StuI is provided, the endonuclease cleavage site is a StuI cleavage site, AGGCCT (SEQ ID NO: 633), and StuI cleaves between the G and C, leaving a blunt end that terminates in a GG. In some alternatives, the endonuclease cleavage site is AGGCCT (SEQ ID NO: 633). In some alternatives, the endonuclease is StuI. In some alternatives, the plurality of adenines terminates in GG. In some alternatives, the StuI cleavage site is inverted. In some alternatives, the endonuclease cleavage site is located 1, 2, 3, 4, 5, 6, 7, 7, 8, 9, 10, 11, 12, 13, 14, 15, 16, 17, 18, 19 or 20 base pairs away from the most 5' thymine (or 5' terminal thymine) in the plurality of thymine nucleotides. In some alternatives, the endonuclease cleavage site is located 1, 2, 3, 4, 5, 6, 7, 7, 8, 9 or 10 base pairs away from the most 5' thymine (or 5' terminal thymine) in the plurality of thymine nucleotides. In some alternatives, wherein the plurality of thymine nucleotides comprises at least one covalently linked guanine, cytosine, or an adenine, wherein the at least one covalently linked guanine, cytosine or adenine is optionally joined to the most 5' thymine (or 5' terminal thymine) in the plurality of thymine nucleotides, the endonuclease cleaves at the at the 5' side of the guanine, cytosine or adenine.

Endonuclease Sites, Restriction Endonuclease Sites and Enzymes (Endonucleases)

A gene can be added to a plasmid by the amplification of the gene utilizing PCR methods, wherein endonuclease recognition sites are added to the gene by way of primers and said gene is then inserted into the plasmid by molecular cloning techniques, e.g., ligation reactions. "Restriction sites," "endonuclease recognition sites," or "endonuclease cleavage sites" or "restriction enzyme binding domains" are locations on a nucleic acid that contain specific sequences of nucleotides that are recognized and cleaved by restriction enzymes and such restriction recognition sites can vary from 4 to 10 bases in length. Restriction sites can be palindromic, and depending on the type of restriction enzyme the restriction enzyme can cut the sequence between two nucleotides within the recognition site, or it can cut upstream or downstream from the recognition site, such that the endonuclease cleavage site is a specific distance away from an endonuclease recognition site. "Restriction enzyme" as described herein, refers to an enzyme that can cut nucleic acid at or near specific recognition nucleotide sequences known as restriction sites. Restriction enzymes are commonly classified into three types, which differ in their structure and whether they cut their nucleic acid substrate at their recognition site, or if the recognition and cleavage sites are separate from one another. To cut a nucleic acid, all restriction enzymes make two incisions, once through each sugar-phosphate backbone (i.e. each strand) of a double stranded nucleic acid sequence. There are over 3000 restriction enzymes, of which over 600 are commercially available. There are 5 types of restriction enzymes (Type I, II, III, IV, and V). Type II enzymes are homodimers, in which the recognition sites are usually undivided and palindromic and 4-8 nucleotides in length. They recognize and cleave DNA at the same site, and they do not use ATP or AdoMet for their activity and many require only $Mg^{2+}$ as a cofactor. Without being limiting an endonuclease can include, for example, a CRISPR, a restriction endonuclease, a Type II restriction endonuclease and a Type IIS restriction endonuclease. In some alternatives, the endonuclease is a CRISPR, a restriction endonuclease, a Type II restriction endonuclease or a Type IIS restriction endonuclease. In some alternatives, wherein StuI is provided, the endonuclease cleavage site is a StuI cleavage site, AGGCCT (SEQ ID NO: 633), and StuI cleaves between the G and C, leaving a blunt end that terminates in a GG. In some alternatives, the endonuclease cleavage site is AGGCCT (SEQ ID NO: 633). In some alternatives, the endonuclease is StuI. In some alternatives, the plurality of adenines terminates in GG. In some alternatives, the StuI cleavage site is inverted. In some alternatives, the endonuclease cleavage site is located 1, 2, 3, 4, 5, 6, 7, 7, 8, 9, 10, 11, 12, 13, 14, 15, 16, 17, 18, 19 or 20 base pairs away from the most 5' thymine (or 5' terminal thymine) in the plurality of thymine nucleotides. In some alternatives, the endonuclease cleavage site is located 1, 2, 3, 4, 5, 6, 7, 7, 8, 9 or 10 base pairs away from the most 5' thymine (or 5' terminal thymine) in the plurality of thymine nucleotides. In some alternatives, wherein the plurality of thymine nucleotides comprises at least one covalently linked guanine, cytosine, or an adenine, wherein the at least one covalently linked guanine, cytosine or adenine is optionally joined to the most 5' thymine (or 5' terminal thymine) in the plurality of thymine nucleotides, the endonuclease cleaves at the at the 5' side of the guanine, cytosine or adenine.

Additionally, there are also subgroups under the Type II, such as Type IIS restriction endonucleases. Type IIS restriction endonucleases can cleave DNA at a defined distance from their non-palindromic asymmetric recognition sites. Accordingly, in some alternatives provided herein, the endonuclease recognition site or binding site for the enzyme is within 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50 or 55 nucleotides (or a number of nucleotides within a range defined by any two of the aforementioned values) from the most 5' thymine on the plurality of thymine residues in the template strand, which then becomes the plurality of adenine residues of the poly(A) tail upon transcription of the sequence, and upon binding of the endonuclease to said endonuclease recognition site or binding site for the enzyme, cleavage within the poly(T) domain occurs. Cleavage within the plurality of thymine residues can occur when the endonuclease recognition site is inverted. Additionally, the enzymes can also function as dimers. Without being limiting an endonuclease can include, for example, a CRISPR, a restriction endonuclease, a Type II restriction endonuclease and a Type IIS restriction endonuclease. In some alternatives, the endonuclease is a CRISPR, a restriction endonuclease, a Type II restriction endonuclease or a Type IIS restriction endonuclease. In some alternatives, wherein StuI is provided, the endonuclease cleavage site is a StuI cleavage site, AGGCCT (SEQ ID NO: 633), and StuI cleaves between the G and C, leaving a blunt end that terminates in a GG. In some alternatives, the endonuclease cleavage site is AGGCCT (SEQ ID NO: 633). In some alternatives, the endonuclease is StuI. In some alternatives, the plurality of adenines terminates in GG. In some alternatives, the StuI cleavage site is inverted. In some alternatives, the endonuclease cleavage site is located 1, 2, 3, 4, 5, 6, 7, 7, 8, 9, 10, 11, 12, 13, 14, 15, 16, 17, 18, 19 or 20 base pairs away from the most 5' thymine (or 5' terminal thymine) in the plurality of thymine nucleotides. In some alternatives, the endonuclease cleavage site is located 1, 2, 3, 4, 5, 6, 7, 7, 8, 9 or 10 base pairs away from the most 5' thymine (or 5' terminal thymine) in the plurality of thymine nucleotides. In some alternatives, wherein the plurality of thymine nucleotides comprises at least one covalently linked guanine, cytosine, or an adenine, wherein the at least one covalently linked guanine, cytosine or adenine is optionally joined to the most 5' thymine (or 5' terminal thymine) in the plurality of thymine nucleotides, the endonuclease cleaves at the at the 5' side of the guanine, cytosine or adenine.

Without being limiting, examples of endonuclease sites that can be incorporated into one or more of the nucleic acids described herein, which have the capacity to generate a poly(T) region of a desired size or have the capacity to generate an RNA having a poly(A) region of a desired length after transcription include: AatII, AbaSI, Acc65I, AccI, AciI, AclI, AfeI, AflII, AflIII, AgeI, AhdI, AleI, AluI, AlwI, AlwNI, ApaI, ApaLI, ApeKI, ApoI, AscI, AseI, AsiSI, AvaI, AvaII, AvrII, BaeGI, BaeI, BamHI, BanI, BanII, BbsI, BbvCI, BbvI, BccI, BceAI, BcgI, BciVI, BclI, BcoDI, BfaI, BfuAI, BfuCI, BglI, BglII, BlpI, BmgBI, BmrI, BmtI, BpmI, Bpu10I, BpuEI, BsaAI, BsaBI, BsaHI, BsaI, BsaJI, BsaWI, BsaXI, BseRI, BseYI, BsgI, BsiEI, BsiHKAI, BsiWI, BslI, BsmAI, BsmBI, BsmFI, BsmI, BsoBI, Bsp1286I, BspCNI, BspDI, BspEI, BspHI, BspMI, BspQI, BsrBI, BsrDI, BsrFI, BsrGI, BsrI, BssHII, BssKI, BssSI, BstAPI, BstBI, BstEII, BstNI, BstUI, BstXI, BstYI, BstZ17I, Bsu36I, BtgI, BtgZI, BtsCI, BtsI, BtsIMutI, Cac8I, ClaI, CspCI, CviAII, CviKI-1, CviQI, DdeI, DpnI, DpnII, DraI, DrdI, EaeI, EagI, EarI, EciI, Eco53kI, EcoNI, EcoO109I, EcoP15I, EcoRI, EcoRV, FatI, FauI, Fnu4HI, FokI, FseI, FspEI, FspI, HaeII, HaeIII, HgaI, HhaI, HincII, HindIII, HinfI, HinPII, HpaI, HpaII, HphI, Hpy166II, Hpy188I, Hpy188III, Hpy99I, HpyA, HpyCH4III, HpyCH4IV, HpyCH4V, I-CeuI, I-SceI, KasI, KpnI, LpnPI, MboI, MboII, MfeI, MluCI, MluI, MlyI, MmeI, MnlI, MscI, MseI, MslI, MspA1I, MspI, MspJI, MwoI, NaeI, NarI, BbvCI, BsmI, BsrDI, BtsI, NciI, NcoI, NdeI, NgoMIV, NheI, NlaIII, NlaIV, NmeAIII, NotI, NruI, NsiI, NspI, Nt.AlwI, Nt.BbvCI, Nt.BsmAI, Nt.BspQI, Nt.BstNBI, Nt.CviPII, PacI, PaeR7I, PciI, PflFI, PflMI, PI-PspI, PI-SceI, PleI, PluTI, PmeI, PmlI, PpuMI, PshAI, PsiI, PspGI, PspOMI, PspXI, PstI, PvuI, PvuII, RsaI, RsrII, SacI, SacII, SalI, SapI, Sau3AI, Sau96I, SbfI, ScrFI, SexAI, SfaNI, SfcI, SfiI, SfoI, SgrAI, SmaI, SmlI, SnaBI, SpeI, SphI, SspI, StuI, StyD4I, StyI, SwaI, TaqαI, TfiI, TliI, TseI, Tsp45I, Tsp509I, TspMI TspRI, Tth111I, XbaI, XcmI, XhoI, XmaI, XmnI, and/or ZraI restriction sites.

Examples of Type IIS restriction enzymes can include but are not limited to AciI, MnlI, AlwI, BbvI, BccI, BceAI, BsmAI, BsmFI, BspCNI, BsrI, BtsCI, FokI, HgaI, HphI, HpyAV, MboII, MlyI, PleI, SfaNI, AcuI, BciVI, BfuAI, BmgBI, BmrI, BpmI, BpuEI, BsaI, BseRI, BsgI, BsmI, BspMI, BsrBI, BsrDI, BtgZI, BtsI, EarI, EciI, MmeI, NmeAIII, BbvCI, Bpu10I, BspQI, SapI, BaeI, BsaXI, CspCI, AfaI, AluBI, AspLEI, BscFI, Bsh1236I, BshFI, BshI, BsiSI, BsnI, Bsp143I, BspANI, BspFNI, BssMI, BstENII, BstFNI, BstHHI, BstKTI, BstMBI, BsuRI, CfoI, Csp6I, FaeI, FaiI, FnuDII, FspBI, GlaI, HapII, Hin1II, R9529, Hsp92II, HspAI, MaeI, MaeII, MvnI, PalI, RsaNI, SetI, SgeI, Sse9I, Tru1I, Tru9I, TscI, TspEI, TthHB8I, XspI, AflI, AgsI, AspS9I, AsuC2I, AsuI, BcefI, BcnI, BisI, BlsI, Bme1390I, Bme18I, BmrFI, BscGI, BseBI, BsiLI, BsiZI, BslFI, BsoMAI, BspNCI, Bst2UI, Bst71I, BstDEI, BstOI, BstSCI, CauII, CdiI, Cfr13I, Eco47I, EcoRII, FaqI, FinI, Fsp4HI, GluI, Hin4II, HpyF3I, ItaI, MaeIII, MspR9I, MvaI, NmuCI, Psp6I, PspPI, SatI, SinI, TscAI, VpaK11BI, AanI, AatI, AauI, Acc113I, Acc16I, AccB1I, AceIII, AesI, AcvI, AcyI, AhlI, Alw21I, Alw44I, Ama87I, Aor51HI, AsiAI, AsnI, Asp718I, AspHI, AsuII, AsuNHI, AvaIII, AviII, BanIII, BauI, BbeI, BbrPI, BbuI, Bbv12I, BbvII, Bce83I, BeoI, BcuI, BfmI, BfrB1,BfrI, BlnI, BmeAI, BmeT110I, BmiI, BmuI, BmyI, Bpu14I, BpvUI, Bsa29I, BsaOI, BsbI, BscBI, BscCI, Bse118I, BseAI, BseCI, BseDI, BsePI, BseSI, BseX3I, Bsh1285I, BshNI, BshTI, BshVI, BsiCI, BsiHKCI, BsiMI, BsiQI, BsiXI, Bsp106I, Bsp119I, Bsp120I, Bsp13I, Bsp1407I, Bsp143II, Bsp19I, Bsp68I, BspA2I, BspCI, BspGI, BspLU11I, BspMAI, BspMII, BspOI, BspT104I, BspT107I, BspTI, BspXI, BssAI, BssHI, BssNAI, BssNI, BssT1I, Bst1107I, Bst98I, BstACI, BstAFI, BstAUI, BstBAI, BstC8I, BstDSI, BstH2I, BstHPI, BstNSI, BstSFI, BstSLI, BstSNI, BstX2I, BstZI, BsuTUI, BtuMI, BveI, CciI, Cfr10I, Cfr42I, Cfr9I, CfrI, Csp45I, CspAI, DinI, DrdII, DsaI, Ec1136II, EcIXI, Eco105I, Eco130I, Eco147I, Eco24I, Eco32I, Eco47III, Eco52I, Eco72I, Eco88I, EcoICRI, EcoT14I, EcoT22I, EcoT38I, EgeI, EheI, ErhI, FauNDI, FbaI, FblI, FriOI, FunI, FunII, GdiII, GsaI, HaeI, HgiAI, Hin1I, HindII, Hpy178III, Hpy8I, Hsp92I, Kpn2I, Ksp22I, KspAI, KspI, MflI, MhlI, MlsI, MluNI, Mly113I, Mph1103I, MroI, MroNI, Msp20I, MspCI, MstI, MunI, MvrI, NgoAIV, NsbI, NspIII, NspV, PaeI, PagI, Paul, Peel, Pfl23II, PinAI, Ple19I, PmaCI, PshBI, Psp124BI, Psp1406I, PspAI, PspLI, PspN4I, PsuI, RcaI, SduI, Sfr274I, Sfr303I, SfuI, SgrBI, SlaI, SpaHI, SseBI, SspBI, SstI, SstII, SunI, TatI, Vha464I, VneI, XapI, XhoII, XmaCI, XmaIII, XmaJI, XmiI, ZhoI, Zsp2I, AocI, AxyI, Bpu1102I, Bse21I, Bsp1720I, BstPI, CelII, CpoI, CspI, DraII, Eco065I, Eco81I, Eco91I, EspI, KflI, LguI, MabI, PpuXI, Psp5II, PspEI, Rsr2I, SauI, AbsI, CciNI, FspAI, MauBI, MreI, MssI, RgaI, SdaI, SfaAI, SgfI, SmiI, Sse232I, AdeI, AspI, CaiI, PsyI, TelI, Asp700I, BoxI, Bse8I, BseJI, BsiBI, BsrBRI, BstPAI, CjeNII, MamI, MroXI, OliI, PdmI, RseI, SmiMI, AccB7I, AspEI, BasI, BmeRI, BplI, Bsc4I, BseLI, BsiYI, BstENI, BstMWI, CjeI, CjuI, CjuII, DriI, Eam1105I, EcIHKI, FaII, HpyF10VI, NgoAVIII, NruGI, PflBI, UbaF14I, XagI, AasI, BdaI, Bsp24I, CjePI, DseDI, UbaF9I, ArsI, BarI, PcsI and UbaF13I. As shown in Table 1, these enzymes have a recognition site that is several base pairs away from the enzyme cleavage site. As shown in Table 1, below, the Type IIS restriction will recognize a sequence recognition site and can cut away from the sequence recognition site. In alternatives described herein, these sequence recognition sites can be inverted so that the cleavage site will be within the plurality of thymine residues.

As shown for MnlI for example, in Table 1, MnlI will recognize CCTC bound to its complement on a double stranded nucleic acid and will cleave 7 nucleotides away from the recognition site. As shown in Table 1, there are enzymes that can also cleave about 40 or more nucleic acid residues away from the recognition site. In some alternatives described herein, the sequence recognition site comprises a sequence recognition site of any one of the sequence recognition sites described in Table 1. In some alternatives, the sequence recognition site is inverted for a Type IIs restriction endonuclease. In some alternatives, the cut site, or endonuclease cleavage site is inverted. In some alternatives, the endonuclease recognition site comprises any one of the endonuclease recognition sites described in Table 1. In some alternatives, the endonuclease is AciI, MnlI, AlwI, BbvI, BccI, BceAI, BsmAI, BsmFI, BspCNI, BsrI, BtsCI, FokI, HgaI, HphI, HpyAV, MboII, MlyI, PleI, SfaNI, AcuI, BciVI, BfuAI, BmgBI, BmrI, BpmI, BpuEI, BsaI, BseRI, BsgI, BsmI, BspMI, BsrBI, BsrDI, BtgZI, BtsI, EarI, EciI, MmeI, NmeAIII, BbvCI, Bpu10I, BspQI, SapI, BaeI, BsaXI, CspCI, AfaI, AluBI, AspLEI, BscFI, Bsh1236I, BshFI, BshI, BsiSI, BsnI, Bsp143I, BspANI, BspFNI, BssMI, BstENII, BstFNI, BstHHI, BstKTI, BstMBI, BsuRI, CfoI, Csp6I, FaeI, FaiI, FnuDII, FspBI, GlaI, HapII, Hin1III, R9529, Hsp92II, HspAI, MaeI, MaeII, MvnI, PalI, RsaNI, SetI, SgeI, Sse9I, Tru1I, Tru9I, TscI, TspEI, TthHB8I, XspI, AflI, AgsI, AspS9I, AsuC2I, AsuI, BcefI, BcnI, BisI, BlsI, Bme1390I, Bme18I, BmrFI, BscGI, BseBI, BsiLI, BsiZI, BslFI, BsoMAI, BspNCI, Bst2UI, Bst71I, BstDEI, BstOI, BstSCI, CauII, CdiI, Cfr13I, Eco47I, EcoRII, FaqI, FinI, Fsp4HI, GluI, Hin4II, HpyF3I, ItaI, MaeIII, MspR9I, MvaI, NmuCI, Psp6I, PspPI, SatI, SinI, TscAI, VpaK11BI, AanI, AatI, AauI, Acc113I, Acc16I, AccB1I, AceIII, AcsI, AcvI, AcyI, AhlI, Alw21I, Alw44I, Ama87I, Aor51HI, AsiAI, AsnI, Asp718I, AspHI, AsuII, AsuNHI, AvaIII, AviII, BanIII, BauI, BbeI, BbrPI, BbuI, Bbv12I, BbvII, Bce83I, BcoI, BcuI, BfmI, BfrBI, BfrI, BlnI, BmcAI, BmeT110I, BmiI, BmuI, BmyI, Bpu14I, BpvUI, Bsa29I, BsaOI, BsbI, BscBI, BscCI, Bse118I, BseAI, BseCI, BseDI, BsePI, BseSI, BseX3I, Bsh1285I, BshNI, BshTI, BshVI, BsiCI, BsiHKCI, BsiMI, BsiQI, BsiXI, Bsp106I, Bsp119I, Bsp120I, Bsp13I, Bsp1407I, Bsp143II, Bsp19I, Bsp68I, BspA2I, BspCI, BspGI, BspLU11I, BspMAI, BspMII, BspOI, BspT104I, BspT107I, BspTI, BspXI, BssAI, BssHI, BssNAI, BssNI, BssT1I, Bst1107I, Bst98I, BstACI, BstAFI, BstAUI, BstBAI, BstC8I, BstDSI, BstH2I, BstHPI, BstNSI, BstSFI, BstSLI, BstSNI, BstX2I, BstZI, BsuTUI, BtuMI, BveI, CciI, Cfr10I, Cfr42I, Cfr9I, CfrI, Csp45I, CspAI, DinI, DrdII, DsaI, Ecl136II, EclXI, Eco105I, Eco130I, Eco147I, Eco24I, Eco32I, Eco47III, Eco52I, Eco72I, Eco88I, EcoICRI, EcoT14I, EcoT22I, EcoT38I, EgeI, EheI, ErhI, FauNDI, FbaI, FblI, FriOI, FunI, FunII, GdiII, GsaI, HaeI, HgiAI, Hin1I, HindII, Hpy178III, Hpy8I, Hsp92I, Kpn2I, Ksp22I, KspAI, KspI, MflI, MhlI, MlsI, MluNI, Mly113I, Mph1103I, MroI, MroNI, Msp20I, MspCI, MstI, MunI, MvrI, NgoAIV, NsbI, NspIII, NspV, PaeI, PagI, PauI, PceI, Pfl23II, PinAI, Ple19I, PmaCI, PshBI, Psp124BI, Psp1406I, PspAI, PspLI, PspN4I, PsuI, RcaI, SduI, Sfr274I, Sfr303I, SfuI, SgrBI, SlaI, SpaHI, SseBI, SspBI, SstI, SstII, SunI, TatI, Vha464I, VneI, XapI, XhoII, XmaCI, XmaIII, XmaJI, XmiI, ZhoI, Zsp2I, AocI, AxyI, Bpu1102I, Bse21I, Bsp1720I, BstPI, CelII, CpoI, CspI, DraII, Eco65I, Eco81I, Eco91I, EspI, KflI, LguI, MabI, PpuXI, Psp5II, PspEI, Rsr2I, SauI, AbsI, CciNI, FspAI, MauBI, MreI, MssI, RgaI, SdaI, SfaAI, SgfI, SmiI, Sse232I, AdeI, AspI, CaiI, PsyI, TelI, Asp700I, BoxI, Bse8I, BseJI, BsiBI, BsrBRI, BstPAI, CjeNII, MamI, MroXI, OliI, PdmI, RseI, SmiMI, AccB7I, AspEI, BasI, BmeRI, BplI, Bsc4I, BseLI, BsiYI, BstENI, BstMWI, CjeI, CjuI, CjuII, DriI, Eam1105I, EclHKI, FalI, HpyF10VI, NgoAVIII, NruGI, PflBI, UbaF14I, XagI, AasI, BdaI, Bsp24I, CjePI, DseDI, UbaF9I, ArsI, BarI, PcsI or UbaF13I.

Without being limiting an endonuclease can include, for example, a CRISPR, a restriction endonuclease, a Type II restriction endonuclease and a Type IIS restriction endonuclease. In some alternatives, the endonuclease is a CRISPR, a restriction endonuclease, a Type II restriction endonuclease or a Type IIS restriction endonuclease. In some alternatives, wherein StuI is provided, the endonuclease cleavage site is a StuI cleavage site, AGGCCT (SEQ ID NO: 633), and StuI cleaves between the G and C, leaving a blunt end that terminates in a GG. In some alternatives, the endonuclease cleavage site is AGGCCT (SEQ ID NO: 633). In some alternatives, the endonuclease is StuI. In some alternatives, the plurality of adenines terminates in GG. In some alternatives, the StuI cleavage site is inverted. In some alternatives, the endonuclease cleavage site is located 1, 2, 3, 4, 5, 6, 7, 7, 8, 9, 10, 11, 12, 13, 14, 15, 16, 17, 18, 19 or 20 base pairs away from the most 5' thymine (or 5' terminal thymine) in the plurality of thymine nucleotides. In some alternatives, the endonuclease cleavage site is located 1, 2, 3, 4, 5, 6, 7, 7, 8, 9 or 10 base pairs away from the most 5' thymine (or 5' terminal thymine) in the plurality of thymine nucleotides. In some alternatives, wherein the plurality of thymine nucleotides comprises at least one covalently linked guanine, cytosine, or an adenine, wherein the at least one covalently linked guanine, cytosine or adenine is optionally joined to the most 5' thymine (or 5' terminal thymine) in the plurality of thymine nucleotides, the endonuclease cleaves at the at the 5' side of the guanine, cytosine or adenine.

| Type IIS Restriction Enzyme | Sequence recognition site | Cut Site |
|---|---|---|
| AciI | CCGC (SEQ ID No. 18) | C/CGC (SEQ ID No. 18)<br>GGC/G (SEQ ID No. 19) |
| MnlI | CCTC (SEQ ID No. 20) | CCTCNNNNNNN/ (SEQ ID No. 21)<br>GGAGNNNNNN/N (SEQ ID No. 22) |
| AlwI | GGATC (SEQ ID No. 23) | GGATCNNNN/N (SEQ ID No. 24)<br>CCTAGNNNNN/ (SEQ ID No. 25) |
| BbvI | GCAGC (SEQ ID No. 26) | GCAGCNNNNNNNN/NNNN (SEQ ID No. 27)<br>CGTCGNNNNNNNNNNNN/ (SEQ ID No. 28) |
| BccI | CCATC (SEQ ID No. 29) | GCAGCNNNNNNN/NNNN (SEQ ID No. 30)<br>CGTCGNNNNNNNNNNN/ (SEQ ID No. 31) |
| BceAI | ACGGC (SEQ ID No. 32) | ACGGCNNNNNNNNNNNNN/NN (SEQ ID No. 33)<br>TGCCGNNNNNNNNNNNNNN/ (SEQ ID No. 34) |
| BsmAI | GTCTC (SEQ ID No. 35) | GTCTCN/NNNN (SEQ ID No. 36)<br>CAGAGNNNNN/ (SEQ ID No. 37) |

-continued

| Type IIS Restriction Enzyme | Sequence recognition site | Cut Site |
|---|---|---|
| BsmFI | GGGAC (SEQ ID No. 38) | GGGACNNNNNNNNNN/NNNN (SEQ ID No. 39)<br>CCCTGNNNNNNNNNNNNNN/ (SEQ ID No. 40) |
| BspCNI | CTCAG (SEQ ID No. 41) | CTCAGNNNNNNNNN/ (SEQ ID No. 42)<br>GAGTCNNNNNNN/NN (SEQ ID No. 43) |
| BsrI | ACTGG (SEQ ID No. 44) | ACTGGN/ (SEQ ID No. 45)<br>TGAC/CN (SEQ ID No. 46) |
| BtsCI | GGATG (SEQ ID No. 47) | GGATGNN/ (SEQ ID No. 48)<br>CCTAC/NN (SEQ ID No. 49) |
| FokI | GGATG (SEQ ID No. 50) | GGATGNNNNNNNNN/NNNN (SEQ ID No. 51)<br>CCTACNNNNNNNNNNNNN/ (SEQ ID No. 52) |
| HgaI | GACGC (SEQ ID No. 53) | GACGCNNNNN/NNNNN (SEQ ID No. 54)<br>CTGCGNNNNNNNNNN/ (SEQ ID No. 55) |
| HphI | GGTGA (SEQ ID No. 56) | GGTGANNNNNNNN/ (SEQ ID No. 57)<br>CCACTNNNNNNN/N (SEQ ID No. 58) |
| HpyAV | CCTTC (SEQ ID No. 59) | CCTTCNNNNNN/ (SEQ ID No. 60)<br>GGAAGNNNNN/N (SEQ ID No. 61) |
| MboII | GAAGA (SEQ ID No. 62) | GAAGANNNNNNNN/ (SEQ ID No. 63)<br>CTTCTNNNNNNN/N (SEQ ID No. 64) |
| MlyI | GAGTC (SEQ ID No. 65) | GAGTCNNNNN/ (SEQ ID No. 66)<br>CTCAGNNNNN/ (SEQ ID No. 67) |
| PleI | GAGTC (SEQ ID No. 68) | GAGTCNNNN/N (SEQ ID No. 69)<br>CTCAGNNNNN/ (SEQ ID No. 70) |
| SfaNI | GCATC (SEQ ID No. 71) | GCATCNNNNN/NNNN (SEQ ID No. 72)<br>CGTAGNNNNNNNNN/ (SEQ ID No. 73) |
| AcuI | CTGAAG (SEQ ID No. 74) | CTGAAGNNNNNNNNNNNNNNNN/ (SEQ ID No. 75)<br>GACTTCNNNNNNNNNNNNNN/NN (SEQ ID No. 76) |
| BciVI | GTATCC (SEQ ID No. 77) | GTATCCNNNNNN/ (SEQ ID No. 78)<br>CATAGGNNNNN/N (SEQ ID No. 79) |
| BfuAI | ACCTGC (SEQ ID No. 80) | ACCTGCNNNN/NNNN (SEQ ID No. 81)<br>TGGACGNNNNNNNN/ (SEQ ID No. 82) |
| BmgBI | CACGTC (SEQ ID No. 83) | CAC/GTC (SEQ ID No. 84)<br>GTG/CAG (SEQ ID No. 85) |
| BmrI | ACTGGG (SEQ ID No. 86) | ACTGGGNNNNN/ (SEQ ID No. 87)<br>TGACCCNNNN/N (SEQ ID No. 88) |
| BpmI | CTGGAG (SEQ ID No. 89) | CTGGAGNNNNNNNNNNNNNNNN/ (SEQ ID No. 90)<br>GACCTCNNNNNNNNNNNNNN/NN (SEQ ID No. 91) |
| BpuEI | CTTGAG (SEQ ID No. 92) | CTTGAGNNNNNNNNNNNNNNNN/ (SEQ ID No. 93)<br>GAACTCNNNNNNNNNNNNNN/NN (SEQ ID No. 94) |
| BsaI | GGTCTC (SEQ ID No. 95) | GGTCTCN/NNNN (SEQ ID No. 96)<br>CCAGAGNNNNN/ (SEQ ID No. 97) |
| BseRI | GAGGAG (SEQ ID No. 98) | GAGGAGNNNNNNNNNN/ (SEQ ID No. 99)<br>CTCCTCNNNNNNNN/NN (SEQ ID No. 100) |
| BsgI | GTGCAG (SEQ ID No. 101) | GTGCAGNNNNNNNNNNNNNNNN/ (SEQ ID No. 102)<br>CACGTCNNNNNNNNNNNNNN/NN (SEQ ID No. 103) |
| BsmI | GAATGC (SEQ ID No. 104) | GAATGCN/ (SEQ ID No. 105)<br>CTTAC/GN (SEQ ID No. 106) |
| BspMI | ACCTGC (SEQ ID No. 107) | ACCTGCNNNN/NNNN (SEQ ID No. 108)<br>TGGACGNNNNNNNN/ (SEQ ID No. 109) |
| BsrBI | CCGCTC (SEQ ID No. 110) | CCG/CTC (SEQ ID No. 110)<br>GGC/GAG (SEQ ID No. 111) |

-continued

| Type IIS Restriction Enzyme | Sequence recognition site | Cut Site |
|---|---|---|
| BsrDI | GCAATG (SEQ ID No. 112) | GCAATGNN/ (SEQ ID No. 113)<br>CGTTAC/NN (SEQ ID No. 114) |
| BtgZI | GCGATG (SEQ ID No. 115) | GCGATGNNNNNNNNNN/NNNN (SEQ ID No. 116)<br>CGCTACNNNNNNNNNNNNNN/ (SEQ ID No. 117) |
| BtsI | GCAGTG (SEQ ID No. 118) | GCAGTGNN/ (SEQ ID No. 119)<br>CGTCAC/NN (SEQ ID No. 120) |
| EarI | CTCTTC (SEQ ID No. 121) | CTCTTCN/NNN (SEQ ID No. 122)<br>GAGAAGNNNN/ (SEQ ID No. 123) |
| EciI | GGCGGA (SEQ ID No. 124) | GGCGGANNNNNNNNNNN/ (SEQ ID No. 125)<br>CCGCCTNNNNNNNNN/NN (SEQ ID No. 126) |
| MmeI | TCCRAC (SEQ ID No. 127) | TCCRACNNNNNNNNNNNNNNNNNNNN/ (SEQ ID No. 128)<br>AGGYTGNNNNNNNNNNNNNNNNNN/NN (SEQ ID No. 129) |
| NmeAIII | GCCGAG (SEQ ID No. 130) | GCCGAGNNNNNNNNNNNNNNNNNNNN/ (SEQ ID No. 131)<br>CGGCTCNNNNNNNNNNNNNNNNNN/NN (SEQ ID No. 132) |
| BbvCI | CCTCAGC (SEQ ID No. 133) | CC/TCAGC (SEQ ID No. 133)<br>GGAGT/CG (SEQ ID No. 134) |
| Bpu10I | CCTNAGC (SEQ ID No. 135) | CC/TNAGC (SEQ ID No. 135)<br>GGANT/CG (SEQ ID No. 136) |
| BspQI | GCTCTTC (SEQ ID No. 137) | GCTCTTCN/NNN (SEQ ID No. 138)<br>CGAGAAGNNNN/(SEQ ID No. 139) |
| SapI | GCTCTTC (SEQ ID No. 140) | GCTCTTCN/NNN (SEQ ID No. 141)<br>CGAGAAGNNNN/ (SEQ ID No. 142) |
| BaeI | ACNNNNGTAYC (SEQ ID No. 143) | NN/NNNNNNNNNNNCAANNNNNGTGGNNNNNNNNNNNN/ (SEQ ID No. 144)<br>/NNNNNNNNNNNNNNGTTNNNNNCACCNNNNNNNNNN/NN (SEQ ID No. 145) |
| BsaXI | ACNNNNNCTCC (SEQ ID No. 146) | NNN/NNNNNNNNNNACNNNNNCTCCNNNNNNNNNNN/ (SEQ ID No. 147)<br>/NNNNNNNNNNNTGNNNNNGAGGNNNNNNNNN/NNN (SEQ ID No. 148) |
| CspCI | CAANNNNNGTGG (SEQ ID No. 149) | NN/NNNNNNNNNNNCAANNNNNGTGGNNNNNNNNNNNN/ (SEQ ID No. 150)<br>/NNNNNNNNNNNNNNGTTNNNNNCACCNNNNNNNNNN/NN (SEQ ID No. 151) |
| AccII | CGCG (SEQ ID No. 152) | CG/CG (SEQ ID No. 152)<br>GC/GC (SEQ ID No. 152) |
| AfaI | GTAC (SEQ ID No. 153) | GT/AC (SEQ ID No. 153)<br>CA/TG (SEQ ID No. 153) |
| AluBI | AGCT (SEQ ID No. 154) | AG/CT (SEQ ID No. 154)<br>TC/GA (SEQ ID No. 154) |
| AspLEI | GCGC (SEQ ID No. 155) | GCG/C (SEQ ID No. 155)<br>C/GCG (SEQ ID No. 155) |
| BscFI | GATC (SEQ ID No. 156) | /GATC (SEQ ID No. 156)<br>CTAG/ (SEQ ID No. 156) |
| Bsh1236I | CGCG (SEQ ID No. 157) | CG/CG (SEQ ID No. 157)<br>GC/GC (SEQ ID No. 157) |
| BshFI | GGCC (SEQ ID No. 158) | GG/CC (SEQ ID No. 158)<br>CC/GG (SEQ ID No. 158) |
| BshI | GGCC (SEQ ID No. 159) | GG/CC (SEQ ID No. 159)<br>CC/GG (SEQ ID No. 159) |
| BsiSI | CCGG (SEQ ID No. 160) | C/CGG (SEQ ID No. 160)<br>GGC/C (SEQ ID No. 160) |
| BsnI | GGCC SEQ ID No. 161) | GG/CC (SEQ ID No. 161)<br>CC/GG (SEQ ID No. 161) |
| Bsp143I | GATC (SEQ ID No. 162) | /GATC (SEQ ID No. 162)<br>CTAG/ (SEQ ID No. 162) |

-continued

| Type IIS Restriction Enzyme | Sequence recognition site | Cut Site |
|---|---|---|
| BspACI | CCGC (SEQ ID No. 163) | C/CGC (SEQ ID No. 163) GGC/G (SEQ ID No. 163) |
| BspANI | GGCC (SEQ ID No. 164) | GG/CC (SEQ ID No. 164) CC/GG (SEQ ID No. 164) |
| BspFNI | CGCG (SEQ ID No. 165) | CG/CG (SEQ ID No. 165) GC/GC (SEQ ID No. 165) |
| BssMI | GATC (SEQ ID No. 166) | /GATC (SEQ ID No. 166) CTAG/ (SEQ ID No. 166) |
| BstENII | GATC (SEQ ID No. 167) | /GATC (SEQ ID No. 167) CTAG/ (SEQ ID No. 167) |
| BstFNI | CGCG (SEQ ID No. 168) | CG/CG (SEQ ID No. 168) GC/GC (SEQ ID No. 168) |
| BstHHI | GCGC (SEQ ID No. 169) | GCG/C (SEQ ID No. 169) C/GCG (SEQ ID No. 169) |
| BstKTI | GATC (SEQ ID No. 170) | GAT/C (SEQ ID No. 170) C/TAG (SEQ ID No. 170) |
| BstMBI | GATC (SEQ ID No. 171) | /GATC (SEQ ID No. 171) CTAGN SEQ ID No. 171) |
| BsuRI | GGCC (SEQ ID No. 172) | GG/CC (SEQ ID No. 172) CC/GG (SEQ ID No. 172) |
| CfoI | GCGC (SEQ ID No. 173) | GCG/C (SEQ ID No. 173) C/GCG (SEQ ID No. 173) |
| Csp6I | GTAC (SEQ ID No. 174) | G/TAC (SEQ ID No. 174) CAT/G (SEQ ID No. 174) |
| FaeI | CATG (SEQ ID No. 175) | CATG/ (SEQ ID No. 175) /GTAC (SEQ ID No. 175) |
| FaiI | YATR (SEQ ID No. 176) | YA/TR (SEQ ID No. 176) RT/AY (SEQ ID No. 176) |
| FnuDII | CGCG (SEQ ID No. 177) | CG/CG (SEQ ID No. 177) GC/GC (SEQ ID No. 177) |
| FspBI | CTAG (SEQ ID No. 178 | C/TAG (SEQ ID No. 178) GAT/C (SEQ ID No. 178) |
| GlaI | GCGC (SEQ ID No. 179) | GC/GC (SEQ ID No. 179) CG/CG (SEQ ID No. 179) |
| HapII | CCGG (SEQ ID No. 180) | C/CGG (SEQ ID No. 180) GGC/C (SEQ ID No. 180) |
| Hin1II | CATG (SEQ ID No. 181) | CATG/ (SEQ ID No. 181) /GTAC (SEQ ID No. 181) |
| R9529 | GCGC (SEQ ID No. 182) | G/CGC (SEQ ID No. 182) CGC/G (SEQ ID No. 182) |
| Hsp92II | CATG (SEQ ID No. 183) | CATG/ (SEQ ID No. 183) /GTAC (SEQ ID No. 183) |
| HspAI | GCGC (SEQ ID No. 184) | G/CGC (SEQ ID No. 184) CGC/G (SEQ ID No. 184) |
| MaeI | CTAG (SEQ ID No. 185) | C/TAG (SEQ ID No. 185) GAT/C (SEQ ID No. 185) |
| MaeII | ACGT (SEQ ID No. 186) | A/CGT (SEQ ID No. 186) TGC/A (SEQ ID No. 186) |
| MvnI | CGCG (SEQ ID No. 187) | CG/CG (SEQ ID No. 187) GC/GC (SEQ ID No. 187) |

-continued

| Type IIS Restriction Enzyme | Sequence recognition site | Cut Site |
|---|---|---|
| PalI | GGCC (SEQ ID No. 188) | GG/CC (SEQ ID No. 188)<br>CC/GG (SEQ ID No. 188) |
| RsaNI | GTAC (SEQ ID No. 189) | G/TAC (SEQ ID No. 189)<br>CAT/G (SEQ ID No. 189) |
| SetI | ASST (SEQ ID No. 190) | ASST/ (SEQ ID No. 190)<br>/TSSA (SEQ ID No. 190) |
| SgeI | CNNG (SEQ ID No. 191) | CNNGNNNNNNNNN/NNNN (SEQ ID No. 192)<br>GNNCNNNNNNNNNNNNN/ (SEQ ID No. 193) |
| Sse9I | AATT (SEQ ID No. 194) | /AATT (SEQ ID No. 194)<br>TTAA/ (SEQ ID No. 194) |
| ThaI | CGCG (SEQ ID No. 195) | CG/CG (SEQ ID No. 195)<br>GC/GC (SEQ ID No. 195) |
| Tru1I | TTAA (SEQ ID No. 196) | T/TAA (SEQ ID No. 196)<br>AAT/T (SEQ ID No. 196) |
| Tru9I | TTAA (SEQ ID No. 197) | T/TAA (SEQ ID No. 197)<br>AAT/T (SEQ ID No. 197) |
| TscI | ACGT (SEQ ID No. 198) | ACGT/ (SEQ ID No. 198)<br>/TGCA (SEQ ID No. 198) |
| TspEI | AATT (SEQ ID No. 199) | /AATT (SEQ ID No. 199)<br>TTAA/ (SEQ ID No. 199) |
| TthHB8I | TCGA (SEQ ID No. 200) | T/CGA (SEQ ID No. 200)<br>AGC/T (SEQ ID No. 200) |
| XspI | CTAG (SEQ ID No. 201) | C/TAG (SEQ ID No. 201)<br>GAT/C (SEQ ID No. 201) |
| AflI | GGWCC (SEQ ID No. 202) | G/GWCC (SEQ ID No. 202)<br>CCWG/G (SEQ ID No. 202) |
| AgsI | TTSAA (SEQ ID No. 203) | TTS/AA (SEQ ID No. 203)<br>A/ASTT (SEQ ID No. 203) |
| AspS9I | GGNCC (SEQ ID No. 204) | G/GNCC (SEQ ID No. 204)<br>CCNG/G (SEQ ID No. 204) |
| AsuC2I | CCSGG (SEQ ID No. 205) | CC/SGG (SEQ ID No. 205)<br>GGS/CC (SEQ ID No. 205) |
| AsuI | GGNCC (SEQ ID No. 206) | G/GNCC (SEQ ID No. 206)<br>CCNG/G (SEQ ID No. 206) |
| BcefI | ACGGC (SEQ ID No. 207) | ACGGCNNNNNNNNNNNN/N (SEQ ID No. 208)<br>TGCCGNNNNNNNNNNNNN/ (SEQ ID No. 209) |
| BcnI | CCSGG (SEQ ID No. 230) | CC/SGG (SEQ ID No. 230)<br>GGS/CC (SEQ ID No. 230) |
| BisI | GCNGC (SEQ ID No. 231) | GC/NGC (SEQ ID No. 231)<br>CGN/CG (SEQ ID No. 231) |
| BlsI | GCNGC (SEQ ID No. 232) | GCN/GC (SEQ ID No. 232)<br>CG/NCG (SEQ ID No. 232) |
| Bme1390I | CCNGG (SEQ ID No. 233) | CC/NGG (SEQ ID No. 233)<br>GGN/CC (SEQ ID No. 233) |
| Bme18I | GGWCC (SEQ ID No. 234) | G/GWCC (SEQ ID No. 234)<br>CCWG/G (SEQ ID No. 234) |
| BmrFI | CCNGG (SEQ ID No. 235) | CC/NGG (SEQ ID No. 235)<br>GGN/CC (SEQ ID No. 235) |
| BscGI | CCCGT (SEQ ID No. 236) | CCCGTN (SEQ ID No. 237)<br>GGGCA/N (SEQ ID No. 238) |

-continued

| Type IIS Restriction Enzyme | Sequence recognition site | Cut Site |
|---|---|---|
| BseBI | CCWGG (SEQ ID No. 239) | CC/WGG (SEQ ID No. 239)<br>GGW/CC (SEQ ID No. 239) |
| BsiLI | CCWGG (SEQ ID No. 240) | CC/WGG (SEQ ID No. 240)<br>GGW/CC (SEQ ID No. 240) |
| BsiZI | GGNCC (SEQ ID No. 241) | G/GNCC (SEQ ID No. 241)<br>CCNG/G (SEQ ID No. 241) |
| BslFI | GGGAC (SEQ ID No. 242) | GGGACNNNNNNNNNN/NNNN (SEQ ID No. 243)<br>CCCTGNNNNNNNNNNNNNN/ (SEQ ID No. 244) |
| BsoMAI | GTCTC (SEQ ID No. 245) | GTCTCN/NNNN (SEQ ID No. 246)<br>CAGAGNNNNN/ (SEQ ID No. 247) |
| BspNCI | CCAGA (SEQ ID No. 248) | CCAGAN (SEQ ID No. 249)<br>GGTCT/N (SEQ ID No. 250) |
| Bst2UI | CCWGG (SEQ ID No. 251) | CC/WGG (SEQ ID No. 251)<br>GGW/CC (SEQ ID No. 251) |
| Bst71I | GCAGC (SEQ ID No. 252) | GCAGCNNNNNNNN/NNNN (SEQ ID No. 253)<br>CGTCGNNNNNNNNNNNN/ (SEQ ID No. 254) |
| BstDEI | CTNAG (SEQ ID No. 255) | C/TNAG (SEQ ID No. 255)<br>GANT/C (SEQ ID No. 255) |
| BstOI | CCWGG (SEQ ID No. 356) | CC/WGG (SEQ ID No. 356)<br>GGW/CC (SEQ ID No. 356) |
| BstSCI | CCNGG (SEQ ID No. 257) | /CCNGG (SEQ ID No. 257)<br>GGNCC/ (SEQ ID No. 257) |
| CauII | CCSGG (SEQ ID No. 258) | CC/SGG (SEQ ID No. 258)<br>GGS/CC (SEQ ID No. 258) |
| CdiI | CATCG (SEQ ID No. 259) | CATC/G (SEQ ID No. 259)<br>GTAG/C (SEQ ID No. 260) |
| Cfr13I | GGNCC (SEQ ID No. 261) | G/GNCC (SEQ ID No. 261)<br>CCNG/G (SEQ ID No. 261) |
| Eco47I | GGWCC (SEQ ID No. 262) | G/GWCC (SEQ ID No. 262)<br>CCWG/G (SEQ ID No. 262) |
| EcoRII | CCWGG (SEQ ID No. 263) | /CCWGG (SEQ ID No. 263)<br>GGWCC/ (SEQ ID No. 263) |
| FaqI | GGGAC (SEQ ID No. 264) | GGGACNNNNNNNNNN/NNNN (SEQ ID No. 265)<br>CCCTGNNNNNNNNNNNNNN/ (SEQ ID No. 266) |
| FinI | GGGAC (SEQ ID No. 267) | GGGACN (SEQ ID No. 268)<br>CCCTG/N (SEQ ID No. 269) |
| Fsp4HI | GCNGC (SEQ ID No. 270) | GC/NGC (SEQ ID No. 270)<br>CGN/CG (SEQ ID No. 270) |
| GluI | GCNGC (SEQ ID No. 271) | GC/NGC (SEQ ID No. 271)<br>CGN/CG (SEQ ID No. 271) |
| Hin4II | CCTTC (SEQ ID No. 272) | CCTTCNNNNNN/ (SEQ ID No. 273)<br>GGAAGNNNNN/N (SEQ ID No. 274) |
| HpyF3I | CTNAG (SEQ ID No. 275) | C/TNAG (SEQ ID No. 275)<br>GANT/C (SEQ ID No. 275) |
| ItaI | GCNGC (SEQ ID No. 276) | GC/NGC (SEQ ID No. 276)<br>CGN/CG (SEQ ID No. 276) |
| MaeIII | GTNAC (SEQ ID No. 277) | /GTNAC (SEQ ID No. 277)<br>CANTG/ (SEQ ID No. 277) |
| MspR9I | CCNGG (SEQ ID No. 278) | CC/NGG (SEQ ID No. 278)<br>GGN/CC (SEQ ID No. 278) |

-continued

| Type IIS Restriction Enzyme | Sequence recognition site | Cut Site |
|---|---|---|
| MvaI | CCWGG (SEQ ID No. 279) | CC/WGG (SEQ ID No. 279)<br>GGW/CC (SEQ ID No. 279) |
| NmuCI | GTSAC (SEQ ID No. 280) | /GTSAC (SEQ ID No. 280)<br>CASTG/ (SEQ ID No. 280) |
| Psp6I | CCWGG (SEQ ID No. 281) | /CCWGG (SEQ ID No. 281)<br>GGWCC/ (SEQ ID No. 281) |
| PspPI | GGNCC (SEQ ID No. 282) | G/GNCC (SEQ ID No. 282)<br>CCNG/G (SEQ ID No. 282) |
| SatI | GCNGC (SEQ ID No. 283) | GC/NGC (SEQ ID No. 283)<br>CGN/CG (SEQ ID No. 283) |
| SinI | GGWCC (SEQ ID No. 284) | G/GWCC SEQ ID No. 284)<br>CCWG/G SEQ ID No. 284) |
| TscAI | CASTG SEQ ID No. 285) | NNCASTGNN/ (SEQ ID No. 286)<br>/NNGTSACNN (SEQ ID No. 286) |
| VpaK11BI | GGWCC (SEQ ID No. 287) | G/GWCC (SEQ ID No. 287)<br>CCWG/G (SEQ ID No. 287) |
| AanI | TTATAA (SEQ ID No. 288) | TTA/TAA (SEQ ID No. 288)<br>AAT/ATT (SEQ ID No. 288) |
| AatI | AGGCCT (SEQ ID No. 289) | AGG/CCT (SEQ ID No. 289)<br>TCC/GGA (SEQ ID No. 289) |
| AauI | TGTACA (SEQ ID No. 290) | T/GTACA (SEQ ID No. 290)<br>ACATG/T (SEQ ID No. 290) |
| Acc113I | AGTACT (SEQ ID No. 291) | AGT/ACT (SEQ ID No. 291)<br>TCA/TGA (SEQ ID No. 291) |
| Acc16I | TGCGCA (SEQ ID No. 292) | TGC/GCA (SEQ ID No. 292)<br>ACG/CGT (SEQ ID No. 292) |
| AccBII | GGYRCC (SEQ ID No. 293) | G/GYRCC (SEQ ID No. 293)<br>CCRYG/G (SEQ ID No. 293) |
| AceIII | CAGCTC (SEQ ID No. 294) | CAGCTCNNNNNNN/NNNN (SEQ ID No. 295)<br>GTCGAGNNNNNNNNNNN/ (SEQ ID No. 296) |
| AcsI | RAATTY (SEQ ID No. 297) | R/AATTY (SEQ ID No. 298)<br>YTTAA/R (SEQ ID No. 298) |
| AcvI | CACGTG (SEQ ID No. 299) | CAC/GTG (SEQ ID No. 299)<br>GTG/CAC (SEQ ID No. 299) |
| AcyI | GRCGYC (SEQ ID No. 300) | GR/CGYC (SEQ ID No. 300)<br>CYGC/RG (SEQ ID No. 300) |
| AhlI | ACTAGT (SEQ ID No. 301) | A/CTAGT (SEQ ID No. 301)<br>TGATC/A (SEQ ID No. 301) |
| Alw21I | GWGCWC (SEQ ID No. 302) | GWGCW/C (SEQ ID No. 302)<br>C/WCGWG (SEQ ID No. 302) |
| Alw44I | GTGCAC (SEQ ID No. 303) | G/TGCAC (SEQ ID No. 303)<br>CACGT/G (SEQ ID No. 303) |
| Ama87I | CYCGRG (SEQ ID No. 304) | C/YCGRG (SEQ ID No. 304)<br>GRGCY/C (SEQ ID No. 304) |
| Aor51HI | AGCGCT (SEQ ID No. 305) | AGC/GCT (SEQ ID No. 305)<br>TCG/CGA (SEQ ID No. 305) |
| AsiAI | ACCGGT (SEQ ID No. 306) | A/CCGGT (SEQ ID No. 306)<br>TGGCC/A (SEQ ID No. 306) |
| AsnI | ATTAAT (SEQ ID No. 307) | AT/TAAT (SEQ ID No. 307)<br>TAAT/TA (SEQ ID No. 307) |

-continued

| Type IIS Restriction Enzyme | Sequence recognition site | Cut Site |
|---|---|---|
| Asp718I | GGTACC (SEQ ID No. 308) | G/GTACC (SEQ ID No. 308)<br>CCATG/G (SEQ ID No. 308) |
| AspHI | GWGCWC (SEQ ID No. 309) | GWGCW/C (SEQ ID No. 309)<br>C/WCGWG (SEQ ID No. 309) |
| AsuII | TTCGAA (SEQ ID No. 310) | TT/CGAA (SEQ ID No. 310)<br>AAGC/TT (SEQ ID No. 310) |
| AsuNHI | GCTAGC (SEQ ID No. 311) | G/CTAGC (SEQ ID No. 311)<br>CGATC/G (SEQ ID No. 311) |
| AvaIII | ATGCAT (SEQ ID No. 312) | ATGCAT (SEQ ID No. 312)<br>TACGTA (SEQ ID No. 312) |
| AviII | TGCGCA (SEQ ID No. 313) | TGC/GCA (SEQ ID No. 313)<br>ACG/CGT (SEQ ID No. 313) |
| BalI | TGGCCA (SEQ ID No. 314) | TGG/CCA (SEQ ID No. 314)<br>ACC/GGT (SEQ ID No. 314) |
| BanIII | ATCGAT (SEQ ID No. 315) | AT/CGAT (SEQ ID No. 315)<br>TAGC/TA (SEQ ID No. 315) |
| BauI | CACGAG (SEQ ID No. 316) | C/ACGAG (SEQ ID No. 317)<br>GTGCT/C (SEQ ID No. 318) |
| BbeI | GGCGCC (SEQ ID No. 319) | GGCGC/C (SEQ ID No. 320)<br>C/CGCGG (SEQ ID No. 320) |
| BbrPI | CACGTG (SEQ ID No. 321) | CAC/GTG (SEQ ID No. 321)<br>GTG/CAC (SEQ ID No. 321) |
| BbuI | GCATGC (SEQ ID No. 322) | GCATG/C (SEQ ID No. 322)<br>C/GTACG (SEQ ID No. 322) |
| Bbv12I | GWGCWC (SEQ ID No. 323) | GWGCW/C (SEQ ID No. 323)<br>C/WCGWG (SEQ ID No. 323) |
| BbvII | GAAGAC (SEQ ID No. 324) | GAAGACNN/NNNN (SEQ ID No. 325)<br>CTTCTGNNNNNN/ (SEQ ID No. 326) |
| Bce83I | CTTGAG (SEQ ID No. 327) | CTTGAGNNNNNNNNNNNNNNNN/ (SEQ ID No. 328)<br>GAACTCNNNNNNNNNNNNNNNN/NN (SEQ ID No. 329) |
| BcoI | CYCGRG (SEQ ID No. 330) | C/YCGRG (SEQ ID No. 330)<br>GRGCY/C (SEQ ID No. 330) |
| BcuI | ACTAGT (SEQ ID No. 331) | A/CTAGT (SEQ ID No. 331)<br>TGATC/A (SEQ ID No. 331) |
| BfmI | CTRYAG (SEQ ID No. 332) | C/TRYAG (SEQ ID No. 332)<br>GAYRT/C (SEQ ID No. 332) |
| BfrBI | ATGCAT (SEQ ID No. 333) | ATGCA/T (SEQ ID No. 333)<br>T/ACGTA (SEQ ID No. 333) |
| BfrI | CTTAAG (SEQ ID No. 334) | C/TTAAG (SEQ ID No. 334)<br>GAATT/C (SEQ ID No. 334) |
| BlnI | CCTAGG (SEQ ID No. 335) | C/CTAGG (SEQ ID No. 335)<br>GGATC/C (SEQ ID No. 335) |
| BmcAI | AGTACT (SEQ ID No. 336) | AGT/ACT (SEQ ID No. 336)<br>TCA/TGA (SEQ ID No. 336) |
| BmeT11I | CYCGRG (SEQ ID No. 337) | C/YCGRG (SEQ ID No. 337)<br>GRGCY/C (SEQ ID No. 337) |
| BmiI | GGNNCC (SEQ ID No. 338) | GGN/NCC (SEQ ID No. 338)<br>CCN/NGG (SEQ ID No. 338) |
| BmuI | ACTGGG (SEQ ID No. 339) | ACTGGGNNNNN/ (SEQ ID No. 339)<br>TGACCCNNNN/N (SEQ ID No. 339) |

-continued

| Type IIS Restriction Enzyme | Sequence recognition site | Cut Site |
|---|---|---|
| BmyI | GDGCHC (SEQ ID No. 340) | GDGCH/C (SEQ ID No. 340)<br>C/HCGDG (SEQ ID No340) |
| Bpu14I | TTCGAA (SEQ ID No. 341) | TT/CGAA (SEQ ID No. 341)<br>AAGC/TT (SEQ ID No. 341) |
| BpvUI | CGATCG (SEQ ID No. 342) | CGAT/CG (SEQ ID No. 342)<br>GC/TAGC (SEQ ID No. 342) |
| Bsa29I | ATCGAT (SEQ ID No. 343) | AT/CGAT (SEQ ID No. 343)<br>TAGC/TA (SEQ ID No. 343) |
| BsaOI | CGRYCG (SEQ ID No. 344) | CGRY/CG (SEQ ID No. 344)<br>GC/YRGC (SEQ ID No. 344) |
| BsbI | CAACAC (SEQ ID No. 345) | CAACACNNNNNNNNNNNNNNNNNNNN/ (SEQ ID No. 346)<br>GTTGTGNNNNNNNNNNNNNNNNNN/NN (SEQ ID No. 347)) |
| BscBI | GGNNCC (SEQ ID No. 348) | GGN/NCC (SEQ ID No. 348)<br>CCN/NGG (SEQ ID No. 348) |
| BscCI | GAATGC (SEQ ID No. 349) | GAATGCN/ (SEQ ID No. 350)<br>CTTAC/GN (SEQ ID No. 351) |
| Bse118I | RCCGGY (SEQ ID No. 352) | R/CCGGY (SEQ ID No. 352)<br>YGGCC/R (SEQ ID No. 352) |
| BseAI | TCCGGA (SEQ ID No. 353) | T/CCGGA (SEQ ID No. 353)<br>AGGCC/T (SEQ ID No. 353) |
| BseCI | ATCGAT (SEQ ID No. 354) | AT/CGAT (SEQ ID No. 354)<br>TAGC/TA (SEQ ID No. 354) |
| BseDI | CCNNGG (SEQ ID No. 355) | C/CNNGG (SEQ ID No. 355)<br>GGNNC/C (SEQ ID No. 355) |
| BsePI | GCGCGC (SEQ ID No. 356) | G/CGCGC (SEQ ID No. 356)<br>CGCGC/G (SEQ ID No. 356) |
| BseSI | GKGCMC (SEQ ID No. 357) | GKGCM/C (SEQ ID No. 357)<br>C/MCGKG (SEQ ID No. 357) |
| BseX3I | CGGCCG (SEQ ID No. 358) | C/GGCCG (SEQ ID No. 358)<br>GCCGG/C (SEQ ID No. 358) |
| Bsh1285I | CGRYCG (SEQ ID No. 359) | CGRY/CG (SEQ ID No. 359)<br>GC/YRGC (SEQ ID No. 359) |
| BshNI | GGYRCC (SEQ ID No. 360) | G/GYRCC (SEQ ID No. 360)<br>CCRYG/G (SEQ ID No. 360) |
| BshTI | ACCGGT (SEQ ID No. 361) | A/CCGGT (SEQ ID No. 361)<br>TGGCC/A (SEQ ID No. 361) |
| BshVI | ATCGAT (SEQ ID No. 362) | AT/CGAT (SEQ ID No. 362)<br>TAGC/TA (SEQ ID No. 362) |
| BsiCI | TTCGAA (SEQ ID No. 363) | TT/CGAA (SEQ ID No. 363)<br>AAGC/TT (SEQ ID No. 363) |
| BsiHKCI | CYCGRG (SEQ ID No. 364) | C/YCGRG (SEQ ID No. 364)<br>GRGCY/C (SEQ ID No. 364) |
| BsiMI | TCCGGA (SEQ ID No. 365) | T/CCGGA (SEQ ID No. 365)<br>AGGCC/T (SEQ ID No. 365) |
| BsiQI | TGATCA (SEQ ID No. 366) | T/GATCA (SEQ ID No. 366)<br>ACTAG/T (SEQ ID No. 366) |
| BsiXI | ATCGAT (SEQ ID No. 367) | AT/CGAT (SEQ ID No. 367)<br>TAGC/TA (SEQ ID No. 367) |
| Bsp106I | ATCGAT (SEQ ID No. 368) | AT/CGAT (SEQ ID No. 368)<br>TAGC/TA (SEQ ID No. 368) |

-continued

| Type IIS Restriction Enzyme | Sequence recognition site | Cut Site |
|---|---|---|
| Bsp119I | TTCGAA (SEQ ID No. 369) | TT/CGAA (SEQ ID No. 369)<br>AAGC/TT(SEQ ID No. 369) |
| Bsp120I | GGGCCC (SEQ ID No. 370) | G/GGCCC (SEQ ID No. 370)<br>CCCGG/G (SEQ ID No. 370) |
| Bsp13I | TCCGGA (SEQ ID No. 371) | T/CCGGA (SEQ ID No. 371)<br>AGGCC/T(SEQ ID No. 371) |
| Bsp1407I | TGTACA (SEQ ID No. 372) | T/GTACA SEQ ID No. 372)<br>ACATG/T SEQ ID No. 372) |
| Bsp143II | RGCGCY (SEQ ID No. 373) | RGCGC/Y (SEQ ID No. 373)<br>Y/CGCGR(SEQ ID No. 373) |
| Bsp19I | CCATGG (SEQ ID No. 374) | C/CATGG (SEQ ID No. 374)<br>GGTAC/C(SEQ ID No. 374) |
| Bsp68I | TCGCGA (SEQ ID No. 375) | TCG/CGA (SEQ ID No. 375)<br>AGC/GCT(SEQ ID No. 375) |
| BspA2I | CCTAGG (SEQ ID No. 376) | C/CTAGG (SEQ ID No. 376)<br>GGATC/C (SEQ ID No. 376) |
| BspCI | CGATCG (SEQ ID No. 377) | CGAT/CG (SEQ ID No. 377)<br>GC/TAGC (SEQ ID No. 377) |
| BspGI | CTGGAC (SEQ ID No. 378) | CTGGACN (SEQ ID No. 379)<br>GACCTG/N (SEQ ID No. 380) |
| BspLU11I | ACATGT (SEQ ID No. 381) | A/CATGT (SEQ ID No. 381)<br>TGTAC/A (SEQ ID No. 381) |
| BspMAI | CTGCAG (SEQ ID No. 382) | CTGCA/G (SEQ ID No. 382)<br>G/ACGTC (SEQ ID No. 382) |
| BspMII | TCCGGA (SEQ ID No. 383) | T/CCGGA (SEQ ID No. 383)<br>AGGCC/T (SEQ ID No. 383) |
| BspOI | GCTAGC (SEQ ID No. 384) | GCTAG/C SEQ ID No. 384)<br>C/GATCG SEQ ID No. 384) |
| BspT104I | TTCGAA SEQ ID No. 385) | TT/CGAA (SEQ ID No. 385)<br>AAGC/TT (SEQ ID No. 385) |
| BspT107I | GGYRCC (SEQ ID No. 386) | G/GYRCC (SEQ ID No. 386)<br>CCRYG/G (SEQ ID No. 386) |
| BspTI | CTTAAG (SEQ ID No. 387) | C/TTAAG (SEQ ID No. 387)<br>GAATT/C (SEQ ID No. 387) |
| BspXI | ATCGAT (SEQ ID No. 388) | AT/CGAT (SEQ ID No. 388)<br>TAGC/TA (SEQ ID No. 388) |
| BssAI | RCCGGY (SEQ ID No. 389) | R/CCGGY (SEQ ID No. 389)<br>YGGCC/R (SEQ ID No. 389) |
| BssHI | CTCGAG (SEQ ID No. 390) | C/TCGAG (SEQ ID No. 390)<br>GAGCT/C (SEQ ID No. 390) |
| BssNAI | GTATAC (SEQ ID No. 391) | GTA/TAC (SEQ ID No. 391)<br>CAT/ATG (SEQ ID No. 391) |
| BssNI | GRCGYC (SEQ ID No. 392) | GR/CGYC (SEQ ID No. 392)<br>CYGC/RG (SEQ ID No. 392) |
| BssT1I | CCWWGG (SEQ ID No. 393) | C/CWWGG (SEQ ID No. 393)<br>GGWWC/C (SEQ ID No. 393) |
| Bst1107I | GTATAC (SEQ ID No. 394) | GTA/TAC (SEQ ID No. 394)<br>CAT/ATG (SEQ ID No. 394) |
| Bst98I | CTTAAG (SEQ ID No. 395) | C/TTAAG (SEQ ID No. 395)<br>GAATT/C (SEQ ID No. 395) |

-continued

| Type IIS Restriction Enzyme | Sequence recognition site | Cut Site |
|---|---|---|
| BstACI | GRCGYC (SEQ ID No. 396) | GR/CGYC (SEQ ID No. 396)<br>CYGC/RG (SEQ ID No. 396) |
| BstAFI | CTTAAG (SEQ ID No. 397) | C/TTAAG (SEQ ID No. 397)<br>GAATT/C (SEQ ID No. 397) |
| BstAUI | TGTACA (SEQ ID No. 398) | T/GTACA (SEQ ID No. 398)<br>ACATG/T (SEQ ID No. 398) |
| BstBAI | YACGTR (SEQ ID No. 399) | YAC/GTR (SEQ ID No. 399)<br>RTG/CAY (SEQ ID No. 399) |
| BstC8I | GCNNGC (SEQ ID No. 400) | GCN/NGC (SEQ ID No. 400)<br>CGN/NCG (SEQ ID No. 400) |
| BstDSI | CCRYGG (SEQ ID No. 401) | C/CRYGG (SEQ ID No. 401)<br>GGYRC/C (SEQ ID No. 401) |
| BstH2I | RGCGCY (SEQ ID No. 402) | RGCGC/Y (SEQ ID No. 402)<br>Y/CGCGR (SEQ ID No. 402) |
| BstHPI | GTTAAC (SEQ ID No. 403) | GTT/AAC (SEQ ID No. 403)<br>CAA/TTG (SEQ ID No. 403) |
| BstNSI | RCATGY (SEQ ID No. 404) | RCATG/Y (SEQ ID No. 404)<br>Y/GTACR (SEQ ID No. 404) |
| BstSFI | CTRYAG (SEQ ID No. 405) | C/TRYAG (SEQ ID No. 405)<br>GAYRT/C (SEQ ID No. 405) |
| BstSLI | GKGCMC (SEQ ID No. 406) | GKGCM/C (SEQ ID No. 406)<br>C/MCGKG (SEQ ID No. 406) |
| BstSNI | TACGTA (SEQ ID No. 407) | TAC/GTA (SEQ ID No. 407)<br>ATG/CAT (SEQ ID No. 407) |
| BstX2I | RGATCY (SEQ ID No. 408) | R/GATCY (SEQ ID No. 408)<br>YCTAG/R (SEQ ID No. 408) |
| BstZI | CGGCCG (SEQ ID No. 409) | C/GGCCG (SEQ ID No. 409)<br>GCCGG/C (SEQ ID No. 409) |
| BsuTUI | ATCGAT (SEQ ID No. 410) | AT/CGAT (SEQ ID No. 410)<br>TAGC/TA (SEQ ID No. 410) |
| BtuMI | TCGCGA (SEQ ID No. 411) | TCG/CGA (SEQ ID No. 411)<br>AGC/GCT (SEQ ID No. 411) |
| BveI | ACCTGC (SEQ ID No. 412) | ACCTGCNNNN/NNNN (SEQ ID No. 413)<br>TGGACGNNNNNNNN/ (SEQ ID No. 414) |
| CciI | TCATGA (SEQ ID No. 415) | T/CATGA (SEQ ID No. 415)<br>AGTAC/T (SEQ ID No. 415) |
| Cfr10I | RCCGGY (SEQ ID No. 416) | R/CCGGY (SEQ ID No. 416)<br>YGGCC/R (SEQ ID No. 416) |
| Cfr42I | CCGCGG (SEQ ID No. 417) | CCGC/GG (SEQ ID No. 417)<br>GG/CGCC (SEQ ID No. 417) |
| Cfr9I | CCCGGG (SEQ ID No. 418) | C/CCGGG (SEQ ID No. 418)<br>GGGCC/C (SEQ ID No. 418) |
| CfrI | YGGCCR (SEQ ID No. 419) | Y/GGCCR (SEQ ID No. 419)<br>RCCGG/Y (SEQ ID No. 419) |
| Csp45I | TTCGAA (SEQ ID No. 420) | TT/CGAA (SEQ ID No. 420)<br>AAGC/TT (SEQ ID No. 420) |
| CspAI | ACCGGT (SEQ ID No. 421) | A/CCGGT (SEQ ID No. 421)<br>TGGCC/A (SEQ ID No. 421) |
| DinI | GGCGCC (SEQ ID No. 422) | GGC/GCC (SEQ ID No. 422)<br>CCG/CGG (SEQ ID No. 422) |

-continued

| Type IIS Restriction Enzyme | Sequence recognition site | Cut Site |
|---|---|---|
| DrdII | GAACCA (SEQ ID No. 423) | GAACCAN (SEQ ID No. 424)<br>CTTGGT/N (SEQ ID No. 425) |
| DsaI | CCRYGG (SEQ ID No. 426) | C/CRYGG (SEQ ID No. 426)<br>GGYRC/C (SEQ ID No. 426) |
| EcI1361I | GAGCTC (SEQ ID No. 427) | GAG/CTC (SEQ ID No. 427)<br>CTC/GAG (SEQ ID No. 427) |
| EcIXI | CGGCCG (SEQ ID No. 428) | C/GGCCG (SEQ ID No. 428)<br>GCCGG/C (SEQ ID No. 428) |
| Eco105I | TACGTA (SEQ ID No. 429) | TAC/GTA (SEQ ID No. 429)<br>ATG/CAT (SEQ ID No. 429) |
| Eco130I | CCWWGG (SEQ ID No. 430) | C/CWWGG (SEQ ID No. 430)<br>GGWWC/C (SEQ ID No. 430) |
| Eco147I | AGGCCT (SEQ ID No. 431) | AGG/CCT (SEQ ID No. 431)<br>TCC/GGA (SEQ ID No. 431) |
| Eco24I | GRGCYC (SEQ ID No. 432) | GRGCY/C (SEQ ID No. 432)<br>C/YCGRG (SEQ ID No. 432) |
| Eco32I | GATATC (SEQ ID No. 433) | GAT/ATC (SEQ ID No. 433)<br>CTA/TAG (SEQ ID No. 433) |
| Eco47III | AGCGCT (SEQ ID No. 434) | AGC/GCT (SEQ ID No. 434)<br>TCG/CGA (SEQ ID No. 434) |
| Eco52I | CGGCCG (SEQ ID No. 435) | C/GGCCG (SEQ ID No. 435)<br>GCCGG/C (SEQ ID No. 435) |
| Eco72I | CACGTG (SEQ ID No. 436) | CAC/GTG (SEQ ID No. 436)<br>GTG/CAC (SEQ ID No. 436) |
| Eco88I | CYCGRG (SEQ ID No. 437) | C/YCGRG (SEQ ID No. 437)<br>GRGCY/C (SEQ ID No. 437) |
| EcolCRI | GAGCTC (SEQ ID No. 438) | GAG/CTC (SEQ ID No. 438)<br>CTC/GAG (SEQ ID No. 438) |
| EcoT14I | CCWWGG (SEQ ID No. 439) | C/CWWGG (SEQ ID No. 439)<br>GGWWC/C (SEQ ID No. 439) |
| EcoT22I | ATGCAT (SEQ ID No. 440) | ATGCA/T (SEQ ID No. 440)<br>T/ACGTA (SEQ ID No. 440) |
| EcoT38I | GRGCYC (SEQ ID No. 441) | GRGCY/C (SEQ ID No. 441)<br>C/YCGRG (SEQ ID No. 441) |
| EgeI | GGCGCC (SEQ ID No. 442) | GGC/GCC (SEQ ID No. 442)<br>CCG/CGG (SEQ ID No. 442) |
| EheI | GGCGCC (SEQ ID No. 443) | GGC/GCC (SEQ ID No. 443)<br>CCG/CGG (SEQ ID No. 443) |
| ErhI | CCWWGG (SEQ ID No. 444) | C/CWWGG (SEQ ID No. 444)<br>GGWWC/C (SEQ ID No. 444) |
| FauNDI | CATATG (SEQ ID No. 445) | CA/TATG (SEQ ID No. 445)<br>GTAT/AC (SEQ ID No. 445) |
| FbaI | TGATCA (SEQ ID No. 446) | T/GATCA (SEQ ID No. 446)<br>ACTAG/T (SEQ ID No. 446) |
| FbiI | GTMKAC (SEQ ID No. 447) | GT/MKAC (SEQ ID No. 447)<br>CAKM/TG (SEQ ID No. 447) |
| FriOI | GRGCYC (SEQ ID No. 448) | GRGCY/C (SEQ ID No. 448)<br>C/YCGRG (SEQ ID No. 448) |
| FunI | AGCGCT (SEQ ID No. 449) | AGC/GCT (SEQ ID No. 449)<br>TCG/CGA (SEQ ID No. 449) |

-continued

| Type IIS Restriction Enzyme | Sequence recognition site | Cut Site |
|---|---|---|
| FunII | GAATTC (SEQ ID No. 450) | G/AATTC (SEQ ID No. 450)<br>CTTAA/G (SEQ ID No. 450) |
| GdiII | CGGCCR (SEQ ID No. 451) | C/GGCCR (SEQ ID No. 451)<br>GCCGG/Y (SEQ ID No. 452) |
| GsaI | CCCAGC (SEQ ID No. 453) | CCCAG/C (SEQ ID No. 453)<br>G/GGTCG (SEQ ID No. 454) |
| HaeI | WGGCCW (SEQ ID No. 455) | WGG/CCW (SEQ ID No. 455)<br>WCC/GGW (SEQ ID No. 455) |
| HgiAI | GWGCWC (SEQ ID No. 456) | GWGCW/C (SEQ ID No. 456)<br>C/WCGWG (SEQ ID No. 456) |
| Hin1I | GRCGYC (SEQ ID No. 457) | GR/CGYC (SEQ ID No. 457)<br>CYGC/RG (SEQ ID No. 457) |
| HindII | GTYRAC (SEQ ID No. 458) | GTY/RAC (SEQ ID No. 458)<br>CAR/YTG (SEQ ID No. 458) |
| Hpy178II | TCNNGA (SEQ ID No. 459) | TC/NNGA (SEQ ID No. 459)<br>AGNN/CT (SEQ ID No. 459) |
| Hpy8I | GTNNAC (SEQ ID No. 460) | GTN/NAC (SEQ ID No. 460)<br>CAN/NTG (SEQ ID No. 460) |
| Hsp92I | GRCGYC (SEQ ID No. 461) | GR/CGYC (SEQ ID No. 461)<br>CYGC/RG (SEQ ID No. 461) |
| Kpn2I | TCCGGA (SEQ ID No. 462) | T/CCGGA (SEQ ID No. 462)<br>AGGCC/T (SEQ ID No. 462) |
| Ksp22I | TGATCA (SEQ ID No. 463) | T/GATCA (SEQ ID No. 463)<br>ACTAG/T (SEQ ID No. 463) |
| KspAI | GTTAAC (SEQ ID No. 464) | GTT/AAC SEQ ID No. 464)<br>CAA/TTG SEQ ID No. 464) |
| KspI | CCGCGG SEQ ID No. 631) | CCGC/GG SEQ ID No. 631)<br>GG/CGCC SEQ ID No. 631) |
| MflI | RGATCY (SEQ ID No. 465) | R/GATCY (SEQ ID No. 465)<br>YCTAG/R (SEQ ID No. 465) |
| MhiI | GDGCHC (SEQ ID No. 466) | GDGCH/C (SEQ ID No. 466)<br>C/HCGDG (SEQ ID No. 466) |
| MlsI | TGGCCA (SEQ ID No. 467) | TGG/CCA (SEQ ID No. 467)<br>ACC/GGT (SEQ ID No. 467) |
| MluNI | TGGCCA (SEQ ID No. 468) | TGG/CCA (SEQ ID No. 468)<br>ACC/GGT (SEQ ID No. 468) |
| Mly113I | GGCGCC (SEQ ID No. 469) | GG/CGCC (SEQ ID No. 469)<br>CCGC/GG (SEQ ID No. 469) |
| Mph1103I | ATGCAT (SEQ ID No. 470) | ATGCA/T (SEQ ID No. 470)<br>T/ACGTA (SEQ ID No. 470) |
| MroI | TCCGGA (SEQ ID No. 471) | T/CCGGA SEQ ID No. 471)<br>AGGCC/T SEQ ID No. 471) |
| MroNI | GCCGGC (SEQ ID No. 472) | G/CCGGC (SEQ ID No. 472)<br>CGGCC/G (SEQ ID No. 472) |
| Msp20I | TGGCCA (SEQ ID No. 473) | TGG/CCA (SEQ ID No. 473)<br>ACC/GGT (SEQ ID No. 473) |
| MspCI | CTTAAG (SEQ ID No. 474) | C/TTAAG (SEQ ID No. 474)<br>GAATT/C (SEQ ID No. 474) |
| MstI | TGCGCA (SEQ ID No. 475) | TGC/GCA (SEQ ID No. 475)<br>ACG/CGT (SEQ ID No. 475) |

-continued

| Type IIS Restriction Enzyme | Sequence recognition site | Cut Site |
|---|---|---|
| MunI | CAATTG (SEQ ID No. 476) | C/AATTG (SEQ ID No. 476)<br>GTTAA/C (SEQ ID No. 476) |
| MyrI | CGATCG (SEQ ID No. 477) | CGAT/CG (SEQ ID No. 477)<br>GC/TAGC (SEQ ID No. 477) |
| NgoAIV | GCCGGC (SEQ ID No. 478) | G/CCGGC (SEQ ID No. 478)<br>CGGCC/G (SEQ ID No. 478) |
| NsbI | TGCGCA (SEQ ID No. 479) | TGC/GCA (SEQ ID No. 479)<br>ACG/CGT (SEQ ID No. 479) |
| NspIII | CYCGRG (SEQ ID No. 480) | C/YCGRG (SEQ ID No. 480)<br>GRGCY/C (SEQ ID No. 480) |
| NspV | TTCGAA (SEQ ID No. 481) | TT/CGAA (SEQ ID No. 481)<br>AAGC/TT (SEQ ID No. 481) |
| PaeI | GCATGC (SEQ ID No. 632) | GCATG/C (SEQ ID No. 632)<br>C/GTACG (SEQ ID No. 632) |
| PagI | TCATGA (SEQ ID No. 482) | T/CATGA (SEQ ID No. 482)<br>AGTAC/T (SEQ ID No. 482) |
| PauI | GCGCGC (SEQ ID No. 483) | G/CGCGC (SEQ ID No. 483)<br>CGCGC/G (SEQ ID No. 483) |
| PceI | AGGCCT (SEQ ID No. 484) | AGG/CCT (SEQ ID No. 484)<br>TCC/GGA (SEQ ID No. 484) |
| PdiI | GCCGGC (SEQ ID No. 485) | GCC/GGC (SEQ ID No. 485)<br>CGG/CCG (SEQ ID No. 485) |
| Pf123II | CGTACG (SEQ ID No. 486) | C/GTACG (SEQ ID No. 486)<br>GCATG/C (SEQ ID No. 486) |
| PinAI | ACCGGT (SEQ ID No. 487) | A/CCGGT (SEQ ID No. 487)<br>TGGCC/A (SEQ ID No. 487) |
| Ple19I | CGATCG (SEQ ID No. 488) | CGAT/CG (SEQ ID No. 488)<br>GC/TAGC (SEQ ID No. 488) |
| PmaCI | CACGTG (SEQ ID No. 489) | CAC/GTG (SEQ ID No. 489)<br>GTG/CAC (SEQ ID No. 489) |
| PshBI | ATTAAT (SEQ ID No. 490) | AT/TAAT (SEQ ID No. 490)<br>TAAT/TA (SEQ ID No. 490) |
| Psp124BI | GAGCTC (SEQ ID No. 491) | GAGCT/C (SEQ ID No. 491)<br>C/TCGAG (SEQ ID No. 491) |
| Psp1406I | AACGTT (SEQ ID No. 492) | AA/CGTT (SEQ ID No. 492)<br>TTGC/AA (SEQ ID No. 492) |
| PspAI | CCCGGG (SEQ ID No. 493) | C/CCGGG (SEQ ID No. 493)<br>GGGCC/C (SEQ ID No. 493) |
| PspLI | CGTACG (SEQ ID No. 494) | C/GTACG (SEQ ID No. 494)<br>GCATG/C (SEQ ID No. 494) |
| PspN4I | GGNNCC (SEQ ID No. 495) | GGN/NCC (SEQ ID No. 495)<br>CCN/NGG (SEQ ID No. 495) |
| PsuI | RGATCY (SEQ ID No. 496) | R/GATCY (SEQ ID No. 496)<br>YCTAG/R (SEQ ID No. 496) |
| RcaI | TCATGA (SEQ ID No. 497) | T/CATGA (SEQ ID No. 497)<br>AGTAC/T (SEQ ID No. 497) |
| SduI | GDGCHC (SEQ ID No. 498) | GDGCH/C (SEQ ID No. 498)<br>C/HCGDG (SEQ ID No. 498) |
| Sfr274I | CTCGAG (SEQ ID No. 499) | C/TCGAG (SEQ ID No. 499)<br>GAGCT/C (SEQ ID No. 499) |

| Type IIS Restriction Enzyme | Sequence recognition site | Cut Site |
|---|---|---|
| Sfr303I | CCGCGG (SEQ ID No. 500) | CCGC/GG (SEQ ID No. 500)<br>GG/CGCC (SEQ ID No. 500) |
| SfuI | TTCGAA (SEQ ID No. 501) | TT/CGAA (SEQ ID No. 501)<br>AAGC/TT (SEQ ID No. 501) |
| SgrBI | CCGCGG (SEQ ID No. 502) | CCGC/GG (SEQ ID No. 502)<br>GG/CGCC (SEQ ID No. 502) |
| SlaI | CTCGAG (SEQ ID No. 503) | C/TCGAG (SEQ ID No. 503)<br>GAGCT/C (SEQ ID No. 503) |
| SpaHI | GCATGC (SEQ ID No. 504) | GCATG/C (SEQ ID No. 504)<br>C/GTACG (SEQ ID No. 504) |
| SseBI | AGGCCT (SEQ ID No. 505) | AGG/CCT (SEQ ID No. 505)<br>TCC/GGA (SEQ ID No. 505) |
| SspBI | TGTACA (SEQ ID No. 506) | T/GTACA (SEQ ID No. 506)<br>ACATG/T (SEQ ID No. 506) |
| SstI | GAGCTC (SEQ ID No. 507) | GAGCT/C (SEQ ID No. 507)<br>C/TCGAG (SEQ ID No. 507) |
| SstII | CCGCGG (SEQ ID No. 508) | CCGC/GG (SEQ ID No. 508)<br>GG/CGCC (SEQ ID No. 508) |
| SunI | CGTACG (SEQ ID No. 509) | C/GTACG (SEQ ID No. 509)<br>GCATG/C (SEQ ID No. 509) |
| TatI | WGTACW (SEQ ID No. 510) | W/GTACW (SEQ ID No. 510)<br>WCATG/W (SEQ ID No. 510) |
| Vha464I | CTTAAG (SEQ ID No. 511) | C/TTAAG (SEQ ID No. 511)<br>GAATT/C (SEQ ID No. 511) |
| VneI | GTGCAC (SEQ ID No. 512) | G/TGCAC (SEQ ID No. 512)<br>CACGT/G (SEQ ID No. 512) |
| VspI | ATTAAT (SEQ ID No. 513) | AT/TAAT (SEQ ID No. 513)<br>TAAT/TA (SEQ ID No. 513) |
| XapI | RAATTY (SEQ ID No. 514) | R/AATTY (SEQ ID No. 514)<br>YTTAA/R (SEQ ID No. 514) |
| XhoII | RGATCY (SEQ ID No. 515) | R/GATCY (SEQ ID No. 515)<br>YCTAG/R (SEQ ID No. 515) |
| XmaCI | CCCGGG (SEQ ID No. 516) | C/CCGGG (SEQ ID No. 516)<br>GGGCC/C (SEQ ID No. 516) |
| XmaIII | CGGCCG (SEQ ID No. 517) | C/GGCCG (SEQ ID No. 517)<br>GCCGG/C (SEQ ID No. 517) |
| XmaJI | CCTAGG (SEQ ID No. 518) | C/CTAGG (SEQ ID No. 518)<br>GGATC/C (SEQ ID No. 518) |
| XmiI | GTMKAC (SEQ ID No. 519) | GT/MKAC (SEQ ID No. 519)<br>CAKM/TG (SEQ ID No. 519) |
| ZhoI | ATCGAT (SEQ ID No. 520) | AT/CGAT (SEQ ID No. 520)<br>TAGC/TA (SEQ ID No. 520) |
| Zsp2I | ATGCAT (SEQ ID No. 521) | ATGCA/T (SEQ ID No. 521)<br>T/ACGTA (SEQ ID No. 521) |
| AocI | CCTNAGG (SEQ ID No. 522) | CC/TNAGG (SEQ ID No. 522)<br>GGANT/CC (SEQ ID No. 522) |
| AxyI | CCTNAGG (SEQ ID No. 523) | CC/TNAGG (SEQ ID No. 523)<br>GGANT/CC (SEQ ID No. 523) |
| Bpu1102I | GCTNAGC (SEQ ID No. 524) | GC/TNAGC (SEQ ID No. 524)<br>CGANT/CG (SEQ ID No. 524) |

-continued

| Type IIS Restriction Enzyme | Sequence recognition site | Cut Site |
|---|---|---|
| Bse21I | CCTNAGG (SEQ ID No. 525) | CC/TNAGG (SEQ ID No. 525)<br>GGANT/CC (SEQ ID No. 525) |
| Bsp1720I | GCTNAGC (SEQ ID No. 526) | GC/TNAGC (SEQ ID No. 526)<br>CGANT/CG (SEQ ID No. 526) |
| BstPI | GGTNACC (SEQ ID No. 527) | G/GTNACC (SEQ ID No. 527)<br>CCANTG/G (SEQ ID No. 527) |
| CelII | GCTNAGC (SEQ ID No. 528) | GC/TNAGC (SEQ ID No. 528)<br>CGANT/CG (SEQ ID No. 528) |
| CpoI | CGGWCCG (SEQ ID No. 529) | CG/GWCCG (SEQ ID No. 529)<br>GCCWG/GC (SEQ ID No. 529) |
| CspI | CGGWCCG (SEQ ID No. 530) | CG/GWCCG (SEQ ID No. 530)<br>GCCWG/GC (SEQ ID No. 530) |
| DraII | RGGNCCY (SEQ ID No. 531) | RG/GNCCY (SEQ ID No. 531)<br>YCCNG/GR (SEQ ID No. 531) |
| Eco065I | GGTNACC (SEQ ID No. 532) | G/GTNACC (SEQ ID No. 532)<br>CCANTG/G (SEQ ID No. 532) |
| Eco81I | CCTNAGG (SEQ ID No. 533) | CC/TNAGG (SEQ ID No. 533)<br>GGANT/CC (SEQ ID No. 533) |
| Eco91I | GGTNACC (SEQ ID No. 534) | G/GTNACC (SEQ ID No. 534)<br>CCANTG/G (SEQ ID No. 534) |
| EspI | GCTNAGC (SEQ ID No. 535) | GC/TNAGC (SEQ ID No. 535)<br>CGANT/CG (SEQ ID No. 535) |
| KflI | GGGWCCC (SEQ ID No. 536) | GG/GWCCC (SEQ ID No. 536)<br>CCCWG/GG (SEQ ID No. 536) |
| LguI | GCTCTTC (SEQ ID No. 634) | GCTCTTCN/NNN (SEQ ID No. 635)<br>CGAGAAGNNNN/ (SEQ ID No. 636) |
| MabI | ACCWGGT (SEQ ID No. 539) | A/CCWGGT (SEQ ID No. 539)<br>TGGWCC/A (SEQ ID No. 539) |
| PpuXI | RGGWCCY (SEQ ID No. 540) | RG/GWCCY (SEQ ID No. 540)<br>YCCWG/GR (SEQ ID No. 540) |
| Psp5II | RGGWCCY (SEQ ID No. 541) | RG/GWCCY (SEQ ID No. 541)<br>YCCWG/GR (SEQ ID No. 541) |
| PspEI | GGTNACC (SEQ ID No. 542) | G/GTNACC (SEQ ID No. 542)<br>CCANTG/G (SEQ ID No. 542) |
| Rsr2I | CGGWCCG (SEQ ID No. 543) | CG/GWCCG (SEQ ID No. 543)<br>GCCWG/GC (SEQ ID No. 543) |
| SauI | CCTNAGG (SEQ ID No. 544) | CC/TNAGG (SEQ ID No. 544)<br>GGANT/CC (SEQ ID No. 544) |
| AbsI | CCTCGAGG (SEQ ID No. 545) | CC/TCGAGG (SEQ ID No. 545)<br>GGAGCT/CC (SEQ ID No. 545) |
| CciNI | GCGGCCGC (SEQ ID No. 546) | GC/GGCCGC (SEQ ID No. 546)<br>CGCCGG/CG (SEQ ID No. 546) |
| FspAI | RTGCGCAY (SEQ ID No. 547) | RTGC/GCAY (SEQ ID No. 547)<br>YACG/CGTR (SEQ ID No. 547) |
| MauBI | CGCGCGCG (SEQ ID No. 548) | CG/CGCGCG (SEQ ID No. 548)<br>GCGCGC/GC (SEQ ID No. 548) |
| MreI | CGCCGGCG (SEQ ID No. 549) | CG/CCGGCG (SEQ ID No. 549)<br>GCGGCC/GC (SEQ ID No. 549) |
| MssI | GTTTAAAC (SEQ ID No. 550) | GTTT/AAAC (SEQ ID No. 550)<br>CAAA/TTTG (SEQ ID No. 550) |

-continued

| Type IIS Restriction Enzyme | Sequence recognition site | Cut Site |
|---|---|---|
| RgaI | GCGATCGC (SEQ ID No. 551) | GCGAT/CGC (SEQ ID No. 551)<br>CGC/TAGCG (SEQ ID No. 551) |
| SdaI | CCTGCAGG (SEQ ID No. 552) | CCTGCA/GG (SEQ ID No. 552)<br>GG/ACGTCC (SEQ ID No. 552) |
| SfaAI | GCGATCGC (SEQ ID No. 553) | GCGAT/CGC (SEQ ID No. 553)<br>CGC/TAGCG (SEQ ID No. 553) |
| SgfI | GCGATCGC (SEQ ID No. 554) | GCGAT/CGC (SEQ ID No. 554)<br>CGC/TAGCG (SEQ ID No. 554) |
| SmiI | ATTTAAAT (SEQ ID No. 555) | ATTT/AAAT (SEQ ID No. 555)<br>TAAA/TTTA (SEQ ID No. 555) |
| Sse232I | CGCCGGCG (SEQ ID No. 556) | CG/CCGGCG (SEQ ID No. 556)<br>GCGGCC/GC (SEQ ID No. 556) |
| AdeI | CACNNNGTG (SEQ ID No. 557) | CACNNN/GTG (SEQ ID No. 557)<br>GTG/NNNCAC (SEQ ID No. 557) |
| AspI | GACNNNGTC (SEQ ID No. 558) | GACN/NNGTC (SEQ ID No. 558)<br>CTGNN/NCAG (SEQ ID No. 558) |
| CaiI | CAGNNNCTG (SEQ ID No. 559) | CAGNNN/CTG (SEQ ID No. 559)<br>GTC/NNNGAC (SEQ ID No. 559) |
| PsyI | GACNNNGTC (SEQ ID No. 560) | GACN/NNGTC (SEQ ID No. 560)<br>CTGNN/NCAG (SEQ ID No. 560) |
| TelI | GACNNNGTC (SEQ ID No. 561) | GACN/NNGTC (SEQ ID No. 561)<br>CTGNN/NCAG (SEQ ID No. 561) |
| Asp700I | GAANNNNTTC (SEQ ID No. 562) | GAANN/NNTTC (SEQ ID No. 562)<br>CTTNN/NNAAG (SEQ ID No. 562) |
| BoxI | GACNNNNGTC (SEQ ID No. 563) | GACNN/NNGTC (SEQ ID No. 563)<br>CTGNN/NNCAG (SEQ ID No. 563) |
| Bse8I | GATNNNNATC (SEQ ID No. 564) | GATNN/NNATC (SEQ ID No. 564)<br>CTANN/NNTAG (SEQ ID No. 564) |
| BseJI | GATNNNNATC (SEQ ID No. 565) | GATNN/NNATC (SEQ ID No. 565)<br>CTANN/NNTAG (SEQ ID No. 565) |
| BsiBI | GATNNNNATC (SEQ ID No. 566) | GATNN/NNATC (SEQ ID No. 566)<br>CTANN/NNTAG (SEQ ID No. 566) |
| BsrBRI | GATNNNNATC (SEQ ID No. 567) | GATNN/NNATC (SEQ ID No. 567)<br>CTANN/NNTAG (SEQ ID No. 567) |
| BstPAI | GACNNNNGTC (SEQ ID No. 568) | GACNN/NNGTC (SEQ ID No. 568)<br>CTGNN/NNCAG (SEQ ID No. 568) |
| CjeNII | GAGNNNNNGT (SEQ ID No. 569) | GAGNNNNNGT (SEQ ID No. 569)<br>CTCNNNNNCA (SEQ ID No. 569) |
| MamI | GATNNNNATC (SEQ ID No. 570) | GATNN/NNATC (SEQ ID No. 570)<br>CTANN/NNTAG (SEQ ID No. 570) |
| MroXI | GAANNNNTTC (SEQ ID No. 571) | GAANN/NNTTC (SEQ ID No. 571)<br>CTTNN/NNAAG (SEQ ID No. 571) |
| OliI | CACNNNNGTG (SEQ ID No. 572) | CACNN/NNGTG (SEQ ID No. 572)<br>GTGNN/NNCAC (SEQ ID No. 572) |
| PdmI | GAANNNNTTC (SEQ ID No. 573) | GAANN/NNTTC (SEQ ID No. 573)<br>CTTNN/NNAAG (SEQ ID No. 573) |
| RseI | CAYNNNNRTG (SEQ ID No. 574) | CAYNN/NNRTG (SEQ ID No. 574)<br>GTRNN/NNYAC (SEQ ID No. 574) |
| SmiMI | CAYNNNNRTG (SEQ ID No. 575) | CAYNN/NNRTG (SEQ ID No. 575)<br>GTRNN/NNYAC (SEQ ID No. 575) |

-continued

| Type IIS Restriction Enzyme | Sequence recognition site | Cut Site |
|---|---|---|
| AccB7I | CCANNNNNTGG (SEQ ID No. 576) | CCANNNN/NTGG (SEQ ID No. 576)<br>GGTN/NNNNACC (SEQ ID No. 576) |
| AspEI | GACNNNNNGTC (SEQ ID No. 577) | GACNNN/NNGTC (SEQ ID No. 577)<br>CTGNN/NNNCAG (SEQ ID No. 577) |
| BasI | CCANNNNNTGG (SEQ ID No. 578) | CCANNNN/NTGG (SEQ ID No. 578)<br>GGTN/NNNNACC (SEQ ID No. 578) |
| BmeRI | GACNNNNNGTC (SEQ ID No. 579) | GACNNN/NNGTC (SEQ ID No. 579)<br>CTGNN/NNNCAG (SEQ ID No. 579) |
| BpiI | GAGNNNNNCTC (SEQ ID No. 580) | NNNNN/NNNNNNNNGAGNNNNNCTCNNNNNNNNNNNNN/ (SEQ ID No. 581)<br>/NNNNNNNNNNNNNCTCNNNNNGAGNNNNNNNN/NNNNN (SEQ ID No. 582) |
| Bsc4I | CCNNNNNNNGG (SEQ ID No. 583) | CCNNNNN/NNGG (SEQ ID No. 583)<br>GGNN/NNNNNCC (SEQ ID No. 583) |
| BseLI | CCNNNNNNNGG (SEQ ID No. 584) | CCNNNNN/NNGG (SEQ ID No. 584)<br>GGNN/NNNNNCC (SEQ ID No. 584) |
| BsiYI | CCNNNNNNNGG (SEQ ID No. 585) | CCNNNNN/NNGG (SEQ ID No. 585)<br>GGNN/NNNNNCC (SEQ ID No. 585) |
| BstENI | CCTNNNNNAGG (SEQ ID No. 586) | CCTNN/NNNAGG (SEQ ID No. 586)<br>GGANNN/NNTCC (SEQ ID No. 586) |
| BstMWI | GCNNNNNNNGC (SEQ ID No. 587) | GCNNNNN/NNGC (SEQ ID No. 587)<br>CGNN/NNNNNCG (SEQ ID No. 587) |
| CjeI | CCANNNNNNGT (SEQ ID No. 588) | NNNNNN/NNNNNNNNNCCANNNNNNGTNNNNNNNNNNNNNNN/ (SEQ ID No. 589)<br>/NNNNNNNNNNNNNNNGGTNNNNNNCANNNNNNNNN/NNNNNN (SEQ ID No. 590) |
| CjuI | CAYNNNNNRTG (SEQ ID No. 591) | CAYNNNNNRTG (SEQ ID No. 591)<br>GTRNNNNNYAC (SEQ ID No. 591) |
| CjuII | CAYNNNNNCTC (SEQ ID No. 592) | CAYNNNNNCTC (SEQ ID No. 592)<br>GTRNNNNNGAG (SEQ ID No. 593) |
| DriI | GACNNNNNGTC (SEQ ID No. 594) | GACNNN/NNGTC (SEQ ID No. 594)<br>CTGNN/NNNCAG (SEQ ID No. 594) |
| Eam1105I | GACNNNNNGTC (SEQ ID No. 595) | GACNNN/NNGTC (SEQ ID No. 595)<br>CTGNN/NNNCAG (SEQ ID No. 595) |
| EcIHKI | GACNNNNNGTC (SEQ ID No. 596) | GACNNN/NNGTC (SEQ ID No. 596)<br>CTGNN/NNNCAG (SEQ ID No. 596) |
| FalI | AAGNNNNNCTT (SEQ ID No. 597) | NNNNN/NNNNNNNNAAGNNNNNCTTNNNNNNNNNNNNN/ (SEQ ID No. 598)<br>/NNNNNNNNNNNNNTTCNNNNNGAANNNNNNNN/NNNNN (SEQ ID No. 599) |
| HpyF10VI | GCNNNNNNNGC (SEQ ID No. 600) | GCNNNNN/NNGC (SEQ ID No. 600)<br>CGNN/NNNNNCG (SEQ ID No. 600) |
| NgoAVIII | GACNNNNNTGA (SEQ ID No. 601) | NN/NNNNNNNNNNNNGACNNNNNTGANNNNNNNNNNNNNN/ (SEQ ID No. 602)<br>/NNNNNNNNNNNNNNCTGNNNNNACTNNNNNNNNNNNN/NN (SEQ ID No. 603) |
| NruGI | GACNNNNNGTC (SEQ ID No. 604) | GACNNN/NNGTC (SEQ ID No. 604)<br>CTGNN/NNNCAG (SEQ ID No. 604) |
| PfIBI | CCANNNNNTGG (SEQ ID No. 605) | CCANNNN/NTGG (SEQ ID No. 605)<br>GGTN/NNNNACC (SEQ ID No. 605) |
| UbaF14I | CCANNNNNTCG (SEQ ID No. 606) | CCANNNNNTCG (SEQ ID No. 606)<br>GGTNNNNNAGC (SEQ ID No. 607) |
| XagI | CCTNNNNNAGG (SEQ ID No. 608) | CCTNN/NNNAGG (SEQ ID No. 608)<br>GGANNN/NNTCC (SEQ ID No. 608) |
| AasI | GACNNNNNNGTC (SEQ ID No. 609) | GACNNNN/NNGTC (SEQ ID No. 609)<br>CTGNN/NNNNCAG (SEQ ID No. 609) |
| BdaI | TGANNNNNNTCA (SEQ ID No. 610) | NN/NNNNNNNNNNNTGANNNNNNTCANNNNNNNNNNNNN/ (SEQ ID No. 611)<br>/NNNNNNNNNNNNNACTNNNNNNAGTNNNNNNNNN/NN (SEQ ID No. 612) |

-continued

| Type IIS Restriction Enzyme | Sequence recognition site | Cut Site |
|---|---|---|
| Bsp24I | GACNNNNNNTGG (SEQ ID No. 613) | NNNNN/NNNNNNNNGACNNNNNNTGGNNNNNNNNNNNN/ (SEQ ID No. 614)<br>/NNNNNNNNNNNNNNCTGNNNNNNACCNNNNNNNN/NNNNN (SEQ ID No. 615) |
| CjePI | CCANNNNNNNTC (SEQ ID No. 616) | NNNNNN/NNNNNNNNCCANNNNNNNNTCNNNNNNNNNNNNNNN/ (SEQ ID No. 617)<br>/NNNNNNNNNNNNNNNGGTNNNNNNNAGNNNNNNNN/NNNNNN (SEQ ID No. 618) |
| DseDI | GACNNNNNNGTC (SEQ ID No. 619) | GACNNNN/NNGTC (SEQ ID No. 619)<br>CTGNN/NNNNCAG (SEQ ID No. 619) |
| UbaF9I | TACNNNNNRTGT (SEQ ID No. 620) | TACNNNNNRTGT (SEQ ID No. 620)<br>ATGNNNNNYACA (SEQ ID No. 621) |
| ArsI | GACNNNNNNTTYG (SEQ ID No. 622) | NNNNN/NNNNNNNNGACNNNNNNTTYGNNNNNNNNNNNN/ (SEQ ID No. 623)<br>/NNNNNNNNNNNNNNCTGNNNNNNAARCNNNNNNN/NNNNN (SEQ ID No. 624) |
| BanI | GAAGNNNNNNTAC (SEQ ID No. 625) | NNNNN/NNNNNNNGAAGNNNNNNTACNNNNNNNNNNNN/ (SEQ ID No. 626)<br>/NNNNNNNNNNNNNCTTCNNNNNNATGNNNNNNN/NNNNN (SEQ ID No. 627) |
| PcsI | WCGNNNNNNNCGW (SEQ ID No. 628) | WCGNNNNN/NNNCGW (SEQ ID No. 628)<br>WGCNNN/NNNNGCW (SEQ ID No. 628) |
| UbaF13I | GAGNNNNNNCTGG (SEQ ID No. 629) | GAGNNNNNNCTGG (SEQ ID No. 629)<br>CTCNNNNNNGACC (SEQ ID No. 630) |

In some alternatives, a polynucleotide comprising a template strand, an endonuclease recognition site and an endonuclease cleavage site for an endonuclease inserted therein, wherein said template strand comprises a plurality of thymine nucleotides is provided. The polynucleotide can comprise a first nucleic acid sequence comprising at least one endonuclease recognition site and a second nucleic acid sequence, wherein the second nucleic acid sequence comprises the template strand, wherein the template strand comprises a plurality of thymine nucleotides, wherein said plurality of thymine nucleotides comprises at least at least 5, 10, 20, 50, 100, 200, 300, 400, 500 or 550 covalently linked thymine nucleotides covalently linked thymine nucleotides and wherein the second nucleic acid comprises the endonuclease cleavage site, wherein the endonuclease cleavage site is within the plurality of thymine nucleotides and wherein said first nucleic acid is covalently linked to said second nucleic acid at one end of said second nucleic acid, and wherein the said endonuclease recognition site is located within 1-55 base pairs (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54 or 55 base pairs) of the endonuclease cleavage site for the endonuclease and said endonuclease cleavage site is within 1 to 40 base pairs (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 base pairs) of a most 5' thymine (or 5' terminal thymine) in the plurality of thymine nucleotides. Some alternatives include a polynucleotide having a plurality of thymine nucleotides and an endonuclease recognition site within 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54 or 55 nucleotides or a number of nucleotides within a range defined by any two of the aforementioned values from the most 5' thymine residue of the poly(T) domain of the template strand, but configured or spaced to permit enzymatic cleavage within the poly(T) domain. In some alternatives the endonuclease recognition site is specific for an endonuclease. In some alternatives, the endonuclease is AatII, AbaSI, Acc65I, AccI, AciI, AclI, AfeI, AflII, AflIII, AgeI, AhdI, AleI, AluI, AlwI, AlwNI, ApaI, ApaLI, ApeKI, ApoI, AscI, AseI, AsiSI, AvaI, AvaII, AvrII, BaeGI, BaeI, BamHI, BanI, BanII, BbsI, BbvCI, BbvI, BccI, BceAI, BcgI, BciVI, BclI, BcoDI, BfaI, BfuAI, BfuCI, BglI, BglII, BlpI, BmgBI, BmrI, BmtI, BpmI, Bpu10I, BpuEI, BsaAI, BsaBI, BsaHI, BsaI, BsaJI, BsaWI, BsaXI, BseRI, BseYI, BsgI, BsiEI, BsiHKAI, BsiWI, BslI, BsmAI, BsmBI, BsmFI, BsmI, BsoBI, Bsp1286I, BspCNI, BspDI, BspEI, BspHI, BspMI, BspQI, BsrBI, BsrDI, BsrFI, BsrGI, BsrI, BssHII, BssKI, BssSI, BstAPI, BstBI, BstEII, BstNI, BstUI, BstXI, BstYI, BstZ17I, Bsu36I, BtgI, BtgZI, BtsCI, BtsI, BtsIMut1, Cac8I, ClaI, CspCI, CviAII, CviKI-1, CviQI, DdeI, DpnI, DpnII, DraI, DrdI, EaeI, EagI, EarI, EciI, Eco53kI, EcoNI, EcoO109I, EcoP15I, EcoRI, EcoRV, FatI, FauI, Fnu4HI, FokI, FseI, FspEI, FspI, HaeII, HaeIII, HgaI, HhaI, HincII, HindIII, HinfI, HinPII, HpaI, HpaII, HphI, Hpy166II, Hpy188I, Hpy188III, Hpy99I, HpyA, HpyCH4III, HpyCH4IV, HpyCH4V, I-CeuI, I-SceI, KasI, KpnI, LpnPI, MboI, MboII, MfeI, MluCI, MluI, MlyI, MmeI, MnlI, MscI, MseI, MslI, MspA1I, MspI, MspJI, MwoI, NaeI, NarI, BbvCI, BsmI, BsrDI, BtsI, NciI, NcoI, NdeI, NgoMIV, NheI, NlaIII, NlaIV, NmeAIII, NotI, NruI, NsiI, NspI, Nt.AlwI, Nt.BbvCI, Nt.BsmAI, Nt.BspQI, Nt.BstNBI, Nt.CviPII, PacI, PaeR7I, PciI, PflFI, PflMI, PI-PspI, PI-SceI, PleI, PluTI, PmeI, PmlI, PpuMI, PshAI, PsiI, PspGI, PspOMI, PspXI, PstI, PvuI, PvuII, RsaI, RsrII, SacI, SacII, SalI, SapI, Sau3AI, Sau96I, SbfI, ScrFI, SexAI, SfaNI, SfcI, SfiI, SfoI, SgrAI, SmaI, SmlI, SnaBI, SpeI, SphI, SspI, StuI, StyD4I, StyI, SwaI, Taqαl, TfiI, TliI, TseI, Tsp45I, Tsp509I, TspMI TspRI, Tth111I, XbaI, XcmI, XhoI, XmaI, XmnI, or ZraI. In some alternatives, the endonuclease is a Type IIS restriction endonuclease. In some alternatives, the endonuclease is BsaI. In some alternatives, the endonuclease is StuI. In some alternatives, the restriction site is an inverted AciI, MnlI, AlwI, BbvI, BccI, BceAI, BsmAI, BsmFI, BspCNI, BsrI, BtsCI, FokI, HgaI, HphI, HpyAV, MboII, MlyI, PleI, SfaNI, AcuI, BciVI, BfuAI, BmgBI, BmrI, BpmI, BpuEI, BsaI, BseRI, BsgI, BsmI, BspMI, BsrBI, BsrDI, BtgZI, BtsI, EarI, EciI, MmeI, NmeAIII, BbvCI, Bpu10I, BspQI, SapI, BaeI, BsaXI, CspCI, AfaI, AluBI, AspLEI, BscFI, Bsh1236I, BshFI, BshI, BsiSI, BsnI, Bsp143I, BspANI, BspFNI, BssMI, BstENII, BstFNI, BstHHI, BstKTI, BstMBI, BsuRI, CfoI, Csp6I, FaeI, FaiI, FnuDII, FspBI, GlaI, HapII, HinIII, R9529, Hsp92II, HspAI, MaeI, MaeII, MvnI, PalI, RsaNI, SetI, SgeI, Sse9I, Tru1I, Tru9I, TscI, TspEI, TthHB8I, XspI, AflI, AgsI, AspS9I, AsuC2I, AsuI, BcefI, BenI, BisI, BlsI, Bme1390I, Bme18I, BmrFI, BscGI, BseBI, BsiLI, BsiZI, BslFI, BsoMAI, BspNCI, Bst2UI, Bst71I, BstDEI, BstOI, BstSCI, CauII, CdiI, Cfr13I, Eco47I, EcoRII, FaqI, FinI, Fsp4HI, GluI, Hin4II, HpyF3I, ItaI, MaeIII, MspR9I, MvaI, NmuCI, Psp6I, PspPI, SatI, SinI, TscAI, VpaK11BI, AanI, AatI, AauI, Acc113I, Acc16I, AccB1I, AceIII, AesI, AcvI, AcyI, AhlI, Alw21I, Alw44I, Ama87I, Aor51HI, AsiAI, AsnI, Asp718I, AspHI, AsuII, AsuNHI, AvaIII, AviII, BanIII, BauI, BbeI, BbrPI, BbuI, Bbv12I, BbvII, Bce83I, BeoI, BcuI, BfmI, BfrB1,BfrI, BlnI, BmeAI, BmeT110I, BmiI, BmuI, BmyI, Bpu14I, BpvUI, Bsa29I, BsaOI, BsbI, BscBI, BscCI, Bse118I, BseAI, BseCI, BseDI, BsePI, BseSI, BseX3I, Bsh1285I, BshNI, BshTI, BshVI, BsiCI, BsiHKCI, BsiMI, BsiQI, BsiXI, Bsp106I, Bsp119I, Bsp120I, Bsp13I, Bsp1407I, Bsp143II, Bsp19I, Bsp68I, BspA2I, BspCI, BspGI, BspLU11I, BspMAI, BspMII, BspOI, BspT104I, BspT107I, BspTI, BspXI, BssAI, BssHI, BssNAI, BssNI, BssT1I, Bst1107I, Bst98I, BstACI, BstAFI, BstAUI, BstBAI, BstC8I, BstDSI, BstH2I, BstHPI, BstNSI, BstSFI, BstSLI, BstSNI, BstX2I, BstZI, BsuTUI, BtuMI, BveI, CciI, Cfr10I, Cfr42I, Cfr9I, CfrI, Csp45I, CspAI, DinI, DrdII, DsaI, Ec1136II, EcIXI, Eco105I, Eco130I, Eco147I, Eco24I, Eco32I, Eco47III, Eco52I, Eco72I, Eco88I, EcoICRI, EcoT14I, EcoT22I, EcoT38I, EgeI, EheI, ErhI, FauNDI, FbaI, FblI, FriOI, FunI, FunII, GdiII, GsaI, HaeI, HgiAI, Hin1I, HindII, Hpy178III, Hpy8I, Hsp92I, Kpn2I, Ksp22I, KspAI, KspI, MflI, MhlI, MisI, MluNI, Mly113I, Mph1103I, MroI, MroNI, Msp20I, MspCI, MstI, MunI, MvrI, NgoAIV, NsbI, NspIII, NspV, PaeI, PagI, PauI, PceI, Pfl23II, PinAI, Ple19I, PmaCI, PshBI, Psp124BI, Psp1406I, PspAI, PspLI, PspN4I, PsuI, Real, SduI, Sfr274I, Sfr303I, SfuI, SgrBI, SlaI, SpaHI, SseBI, SspBI, SstI, SstII, SunI, TatI, Vha464I, VneI, XapI, XhoII, XmaCI, XmaIII, XmaJI, XmiI, ZhoI, Zsp2I, AocI, AxyI, Bpu1102I, Bse21I, Bsp1720I, BstPI, CelII, CpoI, CspI, DraII, Eco065I, Eco81I, Eco91I, EspI, KflI, LguI, MabI, PpuXI, Psp5II, PspEI, Rsr2I, SauI, AbsI, CciNI, FspAI, MauBI, MreI, MssI, RgaI, SdaI, SfaAI, SgfI, SmiI, Sse232I, AdeI, AspI, CaiI, PsyI, TelI, Asp700I, BoxI, Bse8I, BseJI, BsiBI, BsrBRI, BstPAI, CjeNII, MamI, MroXI, OliI, PdmI, RseI, SmiMI, AccB7I, AspEI, BasI, BmeRI, BplI, Bsc4I, BseLI, BsiYI, BstENI, BstMWI, CjeI, CjuI, CjuII, DriI, Eam1105I, EclHKI, FalI, HpyF10VI, NgoAVIII, NruGI, PflBI, UbaF14I, XagI, AasI, BdaI, Bsp24I, CjePI, DseDI, UbaF9I, ArsI, BarI, PcsI or UbaF13I endonuclease restriction recognition site. In some alternatives, the endonuclease recognition site is inverted. In some alternatives, said endonuclease recognition site is located within 1, 5, 10, 15, 20, 25, 30, 35, 40, 45 or 55 base pairs of the endonuclease cleavage site for the endonuclease or any number of base pairs between two aforementioned values, and said endonuclease cleavage site is within 1, 5, 10, 15, 20, 25, 30, 35 or 40 base pairs of a most 5' thymine in the plurality of thymine nucleotides of the template strand or any number of base pairs between any two aforementioned values. In some alternatives, the endonuclease recognition site is inverted and the endonuclease cleavage site is inverted. In some alternatives, the endonuclease recognition site and endonuclease cleavage site comprise a sequence set forth in Table 1 (SEQ ID NOs: 18-632, 634-636). Without being limiting an endonuclease can include, for example, a CRISPR, a restriction endonuclease, a Type II restriction endonuclease and a Type IIS restriction endonuclease. In some alternatives, the endonuclease is a CRISPR, a restriction endonuclease, a Type II restriction endonuclease or a Type IIS restriction endonuclease. In some alternatives, wherein StuI is provided, the endonuclease cleavage site is a StuI cleavage site, AGGCCT (SEQ ID NO: 633), and StuI cleaves between the G and C, leaving a blunt end that terminates in a GG. In some alternatives, the endonuclease cleavage site is AGGCCT (SEQ ID NO: 633). In some alternatives, the endonuclease is StuI. In some alternatives, the plurality of adenines terminates in GG. In some alternatives, the StuI cleavage site is inverted. In some alternatives, the endonuclease cleavage site is located 1, 2, 3, 4, 5, 6, 7, 7, 8, 9, 10, 11, 12, 13, 14, 15, 16, 17, 18, 19 or 20 base pairs away from the most 5' thymine (or 5' terminal thymine) in the plurality of thymine nucleotides. In some alternatives, the endonuclease cleavage site is located 1, 2, 3, 4, 5, 6, 7, 7, 8, 9 or 10 base pairs away from the most 5' thymine (or 5' terminal thymine) in the plurality of thymine nucleotides. In some alternatives, wherein the plurality of thymine nucleotides comprises at least one covalently linked guanine, cytosine, or an adenine, wherein the at least one covalently linked guanine, cytosine or adenine is optionally joined to the most 5' thymine (or 5' terminal thymine) in the plurality of thymine nucleotides, the endonuclease cleaves at the at the 5' side of the guanine, cytosine or adenine.

In some alternatives, the endonuclease is a Type IIS restriction endonuclease, wherein the Type IIS restriction endonuclease cleaves at a distances from the endonuclease recognition site. In some alternatives, the Type IIS restriction endonuclease recognition site, comprises the sequences for the sequence recognition site as set forth in Table 1 (SEQ ID NOs: 18-632, 634-636). In some alternatives, the Type IIS restriction endonuclease is AciI, MnlI, AlwI, BbvI, BccI, BceAI, BsmAI, BsmFI, BspCNI, BsrI, BtsCI, FokI, HgaI, HphI, HpyAV, MboII, MlyI, PleI, SfaNI, AcuI, BciVI, BfuAI, BmgBI, BmrI, BpmI, BpuEI, BsaI, BseRI, BsgI, BsmI, BspMI, BsrBI, BsrDI, BtgZI, BtsI, EarI, EciI, MmeI, NmeAIII, BbvCI, Bpu10I, BspQI, SapI, BaeI, BsaXI, CspCI, AfaI, AluBI, AspLEI, BscFI, Bsh1236I, BshFI, BshI, BsiSI, BsnI, Bsp143I, BspANI, BspFNI, BssMI, BstENII, BstFNI, BstHHI, BstKTI, BstMBI, BsuRI, CfoI, Csp6I, FaeI, FaiI, FnuDII, FspBI, GlaI, HapII, HinIII, R9529, Hsp92II, HspAI, MaeI, MaeII, MvnI, PalI, RsaNI, SetI, SgeI, Sse9I, Tru1I, Tru9I, TscI, TspEI, TthHB8I, XspI, AflI, AgsI, AspS9I, AsuC2I, AsuI, BcefI, BcnI, BisI, BlsI, Bme1390I, Bme18I, BmrFI, BscGI, BseBI, BsiLI, BsiZI, BslFI, BsoMAI, BspNCI, Bst2UI, Bst71I, BstDEI, BstOI, BstSCI, CauII, CdiI, Cfr13I, Eco47I, EcoRII, FaqI, FinI, Fsp4HI, GluI, Hin4II, HpyF3I, ItaI, MaeIII, MspR9I, MvaI, NmuCI, Psp6I, PspPI, SatI, SinI, TscAI, VpaK11BI, AanI, AatI, AauI, Acc113I, Acc16I, AccB1I, AceIII, AesI, AcvI, AcyI, AhlI, Alw21I, Alw44I, Ama87I, Aor51HI, AsiAI, AsnI, Asp718I, AspHI, AsuII, AsuNHI, AvaIII, AviII, BanIII, BauI, BbeI, BbrPI, BbuI, Bbv12I, BbvII, Bce83I, BeoI, BcuI, BfmI, BfrB1,BfrI, BlnI, BmeAI, BmeT110I, BmiI, BmuI, BmyI, Bpu14I, BpvUI, Bsa29I, BsaOI, BsbI, BscBI, BscCI, Bse118I, BseAI, BseCI, BseDI, BsePI, BseSI, BseX3I, Bsh1285I, BshNI, BshTI, BshVI, BsiCI, BsiHKCI, BsiMI, BsiQI, BsiXI, Bsp106I, Bsp119I, Bsp120I, Bsp13I, Bsp1407I, Bsp143II, Bsp19I, Bsp68I, BspA2I, BspCI, BspGI, BspLU11I, BspMAI, BspMII, BspOI, BspT104I, BspT107I, BspTI, BspXI, BssAI, BssHI, BssNAI, BssNI, BssT1I, Bst1107I, Bst98I, BstACI, BstAFI, BstAUI, BstBAI, BstC81, BstDSI, BstH2I, BstHPI, BstNSI, BstSFI, BstSLI, BstSNI, BstX2I, BstZI, BsuTUI, BtuMI, BveI, CciI, Cfr10I, Cfr42I, Cfr9I, CfrI, Csp45I, CspAI, DinI, DrdII, DsaI, Ecl136II, EclXI, Eco105I, Eco130I, Eco147I, Eco24I, Eco32I, Eco47III, Eco52I, Eco72I, Eco88I, EcoICRI, EcoT14I, EcoT22I, EcoT38I, EgeI, EheI, ErhI, FauNDI, FbaI, FblI, FriOI, FunI, FunII, GdiII, GsaI, HaeI, HgiAI, Hin1I, HindII, Hpy178III, Hpy8I, Hsp92I, Kpn2I, Ksp22I, KspAI, KspI, MflI, MhlI, MlsI, MluNI, Mly113I, Mph1103I, MroI, MroNI, Msp20I, MspCI, MstI, MunI, MvrI, NgoAIV, NsbI, NspIII, NspV, PaeI, PagI, PauI, PceI, Pfl23II, PinAI, Ple19I, PmaCI, PshBI, Psp124BI, Psp1406I, PspAI, PspLI, PspN4I, PsuI, ReaI, SduI, Sfr274I, Sfr303I, SfuI, SgrBI, SlaI, SpaHI, SseBI, SspBI, SstI, SstII, SunI, TatI, Vha464I, VneI, XapI, XhoII, XmaCI, XmaIII, XmaJI, XmiI, ZhoI, Zsp2I, AocI, AxyI, Bpu1102I, Bse21I, Bsp1720I, BstPI, CelII, CpoI, CspI, DraII, Eco065I, Eco81I, Eco91I, EspI, KflI, LguI, MabI, PpuXI, Psp5II, PspEI, Rsr2I, SauI, AbsI, CciNI, FspAI, MauBI, MreI, MssI, RgaI, SdaI, SfaAI, SgfI, SmiI, Sse232I, AdeI, AspI, CaiI, PsyI, TelI, Asp700I, BoxI, Bse8I, BseJI, BsiBI, BsrBRI, BstPAI, CjeNII, MamI, MroXI, OliI, PdmI, RseI, SmiMI, AccB7I, AspEI, BasI, BmeRI, BplI, Bsc4I, BseLI, BsiYI, BstENI, BstMWI, CjeI, CjuI, CjuII, DriI, Eam1105I, EclHKI, FalI, HpyF10VI, NgoAVIII, NruGI, PflBI, UbaF14I, XagI, AasI, BdaI, Bsp24I, CjePI, DseDI, UbaF9I, ArsI, BarI, PcsI or UbaF13I. In some alternatives, the sequence recognition site is inverted. In some alternatives, wherein the sequence recognition site is inverted, the Type IIS restriction endonuclease can cleave within the second nucleic acid sequence, wherein the endonuclease can cleave within the plurality of thymine nucleotides. Without being limiting an endonuclease can include, for example, a CRISPR, a restriction endonuclease, a Type II restriction endonuclease and a Type IIS restriction endonuclease. In some alternatives, the endonuclease is a CRISPR, a restriction endonuclease, a Type II restriction endonuclease or a Type IIS restriction endonuclease. In some alternatives, wherein StuI is provided, the endonuclease cleavage site is a StuI cleavage site, AGGCCT (SEQ ID NO: 633), and StuI cleaves between the G and C, leaving a blunt end that terminates in a GG. In some alternatives, the endonuclease cleavage site is AGGCCT (SEQ ID NO: 633). In some alternatives, the endonuclease is StuI. In some alternatives, the plurality of adenines terminates in GG. In some alternatives, the StuI cleavage site is inverted. In some alternatives, the endonuclease cleavage site is located 1, 2, 3, 4, 5, 6, 7, 7, 8, 9, 10, 11, 12, 13, 14, 15, 16, 17, 18, 19 or 20 base pairs away from the most 5' thymine (or 5' terminal thymine) in the plurality of thymine nucleotides. In some alternatives, the endonuclease cleavage site is located 1, 2, 3, 4, 5, 6, 7, 7, 8, 9 or 10 base pairs away from the most 5' thymine (or 5' terminal thymine) in the plurality of thymine nucleotides. In some alternatives, wherein the plurality of thymine nucleotides comprises at least one covalently linked guanine, cytosine, or an adenine, wherein the at least one covalently linked guanine, cytosine or adenine is optionally joined to the most 5' thymine (or 5' terminal thymine) in the plurality of thymine nucleotides, the endonuclease cleaves at the at the 5' side of the guanine, cytosine or adenine.

In some alternatives, a polynucleotide comprising a template strand, an endonuclease recognition site and an endonuclease cleavage site for an endonuclease inserted therein, wherein said template strand comprises a plurality of thymine nucleotides, is provided. The polynucleotide can comprise a first nucleic acid sequence comprising at least one endonuclease recognition site and a second nucleic acid sequence, wherein the second nucleic acid sequence comprises the template strand, wherein the template strand comprises a plurality of thymine nucleotides, wherein said plurality of thymine nucleotides comprises at least 5, 10, 20, 50, 100, 200, 300, 400, 500 or 550 covalently linked thymine nucleotides and wherein the second nucleic acid comprises the endonuclease cleavage site, wherein the endonuclease cleavage site is within the plurality of thymine nucleotides and wherein said first nucleic acid is covalently linked to said second nucleic acid at one end of said second nucleic acid, and wherein the said endonuclease recognition site is located within 1-55 base pairs (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54 or 55 base pairs) of the endonuclease cleavage site for the endonuclease and said endonuclease cleavage site is within 1 to 40 base pairs (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 base pairs) of a most 5' thymine (or 5' terminal thymine) in the plurality of thymine nucleotides. In some alternatives, the polynucleotide further comprises a third nucleic acid sequence encoding a nuclease, such as Cas9, a derivative thereof or active fragment thereof, see e.g., SEQ ID. Nos. 6-14, a TALEN, or a MegaTAL, wherein the third nucleic acid is operably linked to the second nucleic acid sequence comprising the plurality of thymine nucleotides at opposite end of the attached first nucleic acid comprising the endonuclease recognition site. In some alternatives the at least one endonuclease recognition site is specific for an endonuclease. In some alternatives, the endonuclease recognition site is inverted. In some alternatives the endonuclease recognition site is specific for a Type IIS restriction endonuclease. In some alternatives, the recognition site is a Type IIS restriction endonuclease recognition site. In some alternatives, the Type IIS restriction endonuclease recognition site is inverted. In some alternatives, the endonuclease recognition site comprises any one of the endonuclease recognition sites described in Table 1 (SEQ ID NOs: 18-632, 634-636). Some alternatives include a polynucleotide having a plurality of thymine nucleotides, a first nucleic acid sequence encoding a nuclease, such as Cas9, a derivative thereof or active fragment thereof, see e.g., SEQ ID. Nos. 6-14, a TALEN, or a MegaTAL, and an endonuclease recognition site within 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54 or 55 nucleotides or a number of nucleotides within a range defined by any two of the aforementioned values upstream (5' in orientation) from the first thymine residue of the poly(T) domain but configured or spaced to permit enzymatic cleavage within the poly(T) domain. In some alternatives, the endonuclease is AatII, AbaSI, Acc65I, AccI, AciI, AclI, AfeI, AflII, AflIII, AgeI, AhdI, AleI, AluI, AlwI, AlwNI, ApaI, ApaLI, ApeKI, ApoI, AscI, AseI, AsiSI, AvaI, AvaII, AvrII, BaeGI, BaeI, BamHI, BanI, BanII, BbsI, BbvCI, BbvI, BccI, BceAI, BcgI, BciVI, BclI, BcoDI, BfaI, BfuAI, BfuCI, BglI, BglII, BlpI, BmgBI, BmrI, BmtI, BpmI, Bpu10I, BpuEI, BsaAI, BsaBI, BsaHI, BsaI, BsaJI, BsaWI, BsaXI, BseRI, BseYI, BsgI, BsiEI, BsiHKAI, BsiWI, BslI, BsmAI, BsmBI, BsmFI, BsmI, BsoBI, Bsp1286I, BspCNI, BspDI, BspEI, BspHI, BspMI, BspQI, BsrBI, BsrDI, BsrFI, BsrGI, BsrI, BssHII, BssKI, BssSI, BstAPI, BstBI, BstEII, BstNI, BstUI, BstXI, BstYI, BstZ17I, Bsu36I, BtgI, BtgZI, BtsCI, BtsI, BtsIMutI, Cac8I, ClaI, CspCI, CviAII, CviKI-1, CviQI, DdeI, DpnI, DpnII, DraI, DrdI, EaeI, EagI, EarI, EciI, Eco53kI, EcoNI, EcoO109I, EcoP15I, EcoRI, EcoRV, FatI, FauI, Fnu4HI, FokI, FseI, FspEI, FspI, HaeII, HaeIII, HgaI, HhaI, HincII, HindIII, HinfI, HinPII, HpaI, HpaII, HphI, Hpy166II, Hpy188I, Hpy188III, Hpy99I, HpyA, HpyCH4III, HpyCH4IV, HpyCH4V, I-CeuI, I-SceI, KasI, KpnI, LpnPI, MboI, MboII, MfeI, MluCI, MluI, MlyI, MmeI, MnlI, MscI, MseI, MslI, MspA1I, MspI, MspJI, MwoI, NaeI, NarI, BbvCI, BsmI, BsrDI, BtsI, NciI, NcoI, NdeI, NgoMIV, NheI, NlaIII, NlaIV, NmeAIII, NotI, NruI, NsiI, NspI, Nt.AlwI, Nt.BbvCI, Nt.BsmAI, Nt.BspQI, Nt.BstNBI, Nt.CviPII, PacI, PaeR7I, PciI, PflFI, PflMI, PI-PspI, PI-SceI, PleI, PluTI, PmeI, PmlI, PpuMI, PshAI, PsiI, PspGI, PspOMI, PspXI, PstI, PvuI, PvuII, RsaI, RsrII, SacI, SacII, SalI, SapI, Sau3AI, Sau96I, SbfI, ScrFI, SexAI, SfaNI, SfcI, SfiI, SfoI, SgrAI, SmaI, SmlI, SnaBI, SpeI, SphI, SspI, StuI, StyD4I, StyI, SwaI, TaqαI, TfiI, TliI, TseI, Tsp45I, Tsp509I, TspMI TspRI, Tth111I, XbaI, XcmI, XhoI, XmaI, XmnI, or ZraI. In some alternatives, the endonuclease is BsaI. In some alternatives, the endonuclease is StuI. Endonucleases can be an enzyme that can enzymes that cleave the phosphodiester bond within a polynucleotide. Without being limiting an endonuclease can include, for example, a CRISPR, a restriction endonuclease, a Type II restriction endonuclease and a Type IIS restriction endonuclease. In some alternatives, the endonuclease is a CRISPR, a restriction endonuclease, a Type II restriction endonuclease or a Type IIS restriction endonuclease. In some alternatives, the endonuclease is a CRISPR, a restriction endonuclease, a Type II restriction endonuclease or a Type IIS restriction endonuclease. In some alternatives, wherein StuI is provided, the endonuclease cleavage site is a StuI cleavage site, AGGCCT (SEQ ID NO: 633), and StuI cleaves between the G and C, leaving a blunt end that terminates in a GG. In some alternatives, the endonuclease cleavage site is AGGCCT (SEQ ID NO: 633). In some alternatives, the endonuclease is StuI. In some alternatives, the plurality of adenines terminates in GG. In some alternatives, the StuI cleavage site is inverted. In some alternatives, the endonuclease recognition site is a BsaI restriction recognition site, and the endonuclease is BSaI. In some alternatives, the BsaI restriction recognition site is inverted. Without being limiting an endonuclease can include, for example, a CRISPR, a restriction endonuclease, a Type II restriction endonuclease and a Type IIS restriction endonuclease. In some alternatives, the endonuclease is a CRISPR, a restriction endonuclease, a Type II restriction endonuclease or a Type IIS restriction endonuclease. In some alternatives, wherein StuI is provided, the endonuclease cleavage site is a StuI cleavage site, AGGCCT (SEQ ID NO: 633), and StuI cleaves between the G and C, leaving a blunt end that terminates in a GG. In some alternatives, the endonuclease cleavage site is AGGCCT (SEQ ID NO: 633). In some alternatives, the endonuclease is StuI. In some alternatives, the plurality of adenines terminates in GG. In some alternatives, the StuI cleavage site is inverted. In some alternatives, the endonuclease cleavage site is located 1, 2, 3, 4, 5, 6, 7, 7, 8, 9, 10, 11, 12, 13, 14, 15, 16, 17, 18, 19 or 20 base pairs away from the most 5' thymine (or 5' terminal thymine) in the plurality of thymine nucleotides. In some alternatives, the endonuclease cleavage site is located 1, 2, 3, 4, 5, 6, 7, 7, 8, 9 or 10 base pairs away from the most 5' thymine (or 5' terminal thymine) in the plurality of thymine nucleotides. In some alternatives, wherein the plurality of thymine nucleotides comprises at least one covalently linked guanine, cytosine, or an adenine, wherein the at least one covalently linked guanine, cytosine or adenine is optionally joined to the most 5' thymine (or 5' terminal thymine) in the plurality of thymine nucleotides, the endonuclease cleaves at the at the 5' side of the guanine, cytosine or adenine.

Some alternatives relate to an mRNA that comprises a poly A tail, wherein within said poly A tail or upstream of the first adenine residue of said poly(A) tail is the gene. Some of these mRNAs also include a sequence that encodes a gene, such as a nuclease (e.g., Cas9 or derivative thereof or active fragment thereof, see e.g., SEQ ID NOs. 6-14, TALEN, or MegaTAL). In some alternatives, an mRNA having a plurality of adenine nucleotides is provided, wherein the mRNA comprises a first sequence comprising a gene, a second sequence comprising a plurality of adenine nucleotides, and a third sequence that comprises a compliment sequence to an endonuclease recognition site, wherein the first sequence is covalently linked to the second sequence at the 5' end of said plurality of adenine nucleotides and wherein said mRNA comprises a third sequence that comprises a compliment sequence to an endonuclease recognition site wherein the third sequence is covalently linked to said plurality of adenine nucleotides of said second nucleic acid at the 3' end of said plurality of adenine nucleotides of said second nucleic acid. This type of mRNA can occur if the polynucleotide for transcribing the mRNA was not cleaved with the Type IIS restriction endonuclease. Some alternatives include an mRNA having a plurality of adenine nucleotides and at least one complimentary sequence to an endonuclease recognition site, such as StuI or BsaI (on the single strand) within 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 nucleotides or a number of nucleotides within a range defined by any two of the aforementioned values upstream (5' in orientation) from the first adenine residue of the poly(A) domain. In some alternatives, the complimentary sequence is a compliment (on the single strand) to the endonuclease recognition site of AatII, AbaSI, Acc65I, AccI, AciI, AclI, AfeI, AflII, AflIII, AgeI, AhdI, AleI, AluI, AlwI, AlwNI, ApaI, ApaLI, ApeKI, ApoI, AscI, AseI, AsiSI, AvaI, AvaII, AvrII, BaeGI, BaeI, BamHI, BanI, BanII, BbsI, BbvCI, BbvI, BccI, BceAI, BcgI, BciVI, BclI, BcoDI, BfaI, BfuAI, BfuCI, BglI, BglII, BlpI, BmgBI, BmrI, BmtI, BpmI, Bpu10I, BpuEI, BsaAI, BsaBI, BsaHI, BsaI, BsaJI, BsaWI, BsaXI, BseRI, BseYI, BsgI, BsiEI, BsiHKAI, BsiWI, BslI, BsmAI, BsmBI, BsmFI, BsmI, BsoBI, Bsp1286I, BspCNI, BspDI, BspEI, BspHI, BspMI, BspQI, BsrBI, BsrDI, BsrFI, BsrGI, BsrI, BssHII, BssKI, BssSI, BstAPI, BstBI, BstEII, BstNI, BstUI, BstXI, BstYI, BstZ17I, Bsu36I, BtgI, BtgZI, BtsCI, BtsI, BtsIMutI, Cac8I, ClaI, CspCI, CviAII, CviKI-1, CviQI, DdeI, DpnI, DpnII, DraI, DrdI, EaeI, EagI, EarI, EciI, Eco53kI, EcoNI, EcoO109I, EcoP15I, EcoRI, EcoRV, FatI, FauI, Fnu4HI, FokI, FseI, FspEI, FspI, HaeII, HaeIII, HgaI, HhaI, HincII, HindIII, HinfI, HinPII, HpaI, HpaII, HphI, Hpy166II, Hpy188I, Hpy188III, Hpy99I, HpyA, HpyCH4III, HpyCH4IV, HpyCH4V, I-CeuI, I-SceI, KasI, KpnI, LpnPI, MboI, MboII, MfeI, MluCI, MluI, MlyI, MmeI, MnlI, MscI, MseI, MslI, MspA1I, MspI, MspJI, MwoI, NaeI, NarI, BbvCI, BsmI, BsrDI, BtsI, NciI, NcoI, NdeI, NgoMIV, NheI, NlaIII, NlaIV, NmeAIII, NotI, NruI, NsiI, NspI, Nt.AlwI, Nt.BbvCI, Nt.BsmAI, Nt.BspQI, Nt.BstNBI, Nt.CviPII, PacI, PaeR7I, PciI, PflFI, PflMI, PI-PspI, PI-SceI, PleI, PluTI, PmeI, PmlI, PpuMI, PshAI, PsiI, PspGI, PspOMI, PspXI, PstI, PvuI, PvuII, RsaI, RsrII, SacI, SacII, SalI, SapI, Sau3AI, Sau96I, SbfI, ScrFI, SexAI, SfaNI, SfcI, SfiI, SfoI, SgrAI, SmaI, SmlI, SnaBI, SpeI, SphI, SspI, StuI, StyD4I, StyI, SwaI, TaqαI, TfiI, TliI, TseI, Tsp45I, Tsp509I, TspMI TspRI, Tth111I, XbaI, XcmI, XhoI, XmaI, XmnI, or ZraI. In some alternatives, the sequence of the at least one endonuclease site is inverted, wherein the sequence encoding the RNA compliment is a compliment to the inverted sequence of the at least one endonuclease site (on the single strand). In some alternatives, the sequence encoding the RNA compliment is a compliment to any one of the endonuclease recognition sites described in Table 1 (Type IIS restriction endonucleases) (SEQ ID NOs: 18-632, 634-636). In some alternatives, the endonuclease recognition sites described in Table 1 is inverted (SEQ ID NOs: 18-632, 634-636). In some alternatives, wherein the endonuclease site is the Type IIS restriction endonuclease recognition site, the Type IIS restriction endonuclease recognition sites are recognition sites for AciI, MnlI, AlwI, BbvI, BccI, BceAI, BsmAI, BsmFI, BspCNI, BsrI, BtsCI, FokI, HgaI, HphI, HpyAV, MboII, MlyI, PleI, SfaNI, AcuI, BciVI, BfuAI, BmgBI, BmrI, BpmI, BpuEI, BsaI, BseRI, BsgI, BsmI, BspMI, BsrBI, BsrDI, BtgZI, BtsI, EarI, EciI, MmeI, NmeAIII, BbvCI, Bpu10I, BspQI, SapI, BaeI, BsaXI, CspCI, AfaI, AluBI, AspLEI, BscFI, Bsh1236I, BshFI, BshI, BsiSI, BsnI, Bsp143I, BspANI, BspFNI, BssMI, BstENII, BstFNI, BstHHI, BstKTI, BstMBI, BsuRI, CfoI, Csp6I, FaeI, FaiI, FnuDII, FspBI, GlaI, HapII, HinlII, R9529, Hsp92II, HspAI, MaeI, MaeII, MvnI, PalI, RsaNI, SetI, SgeI, Sse9I, Tru1I, Tru9I, TscI, TspEI, TthHB8I, XspI, AflI, AgsI, AspS9I, AsuC2I, AsuI, BcefI, BcnI, BisI, BlsI, Bme1390I, Bme18I, BmrFI, BscGI, BseBI, BsiLI, BsiZI, BslFI, BsoMAI, BspNCI, Bst2UI, Bst71I, BstDEI, BstOI, BstSCI, CauII, CdiI, Cfr13I, Eco47I, EcoRII, FaqI, FinI, Fsp4HI, GluI, Hin4II, HpyF3I, ItaI, MaeIII, MspR9I, MvaI, NmuCI, Psp6I, PspPI, SatI, SinI, TscAI, VpaK11BI, AanI, AatI, AauI, Acc113I, Acc16I, AccB1I, AceIII, AcsI, AcvI, AcyI, AhlI, Alw21I, Alw44I, Ama87I, Aor51HI, AsiAI, AsnI, Asp718I, AspHI, AsuII, AsuNHI, AvaIII, AviII, Ban-III, BauI, BbeI, BbrPI, BbuI, Bbv12I, BbvII, Bce83I, BcoI, BcuI, BfmI, BfrBI,BfrI, BlnI, BmcAI, BmeT110I, BmiI, BmuI, BmyI, Bpu14I, BpvUI, Bsa29I, BsaOI, BsbI, BscBI, BscCI, Bse118I, BseAI, BseCI, BseDI, BsePI, BseSI, BseX3I, Bsh1285I, BshNI, BshTI, BshVI, BsiCI, BsiHKCI, BsiMI, BsiQI, BsiXI, Bsp106I, Bsp119I, Bsp120I, Bsp13I, Bsp1407I, Bsp143II, Bsp19I, Bsp68I, BspA2I, BspCI, BspGI, BspLU11I, BspMAI, BspMII, BspOI, BspT104I, BspT107I, BspTI, BspXI, BssAI, BssHI, BssNAI, BssNI, BssT1I, Bst1107I, Bst98I, BstACI, BstAFI, BstAUI, BstBAI, BstC8I, BstDSI, BstH2I, BstHPI, BstNSI, BstSFI, BstSLI, BstSNI, BstX2I, BstZI, BsuTUI, BtuMI, BveI, CciI, Cfr10I, Cfr42I, Cfr9I, CfrI, Csp45I, CspAI, DinI, DrdII, DsaI, Ec1136II, EcIXI, Eco105I, Eco130I, Eco147I, Eco24I, Eco32I, Eco47III, Eco52I, Eco72I, Eco88I, EcoICRI, EcoT14I, EcoT22I, EcoT38I, EgeI, EheI, ErhI, FauNDI, FbaI, FblI, FriOI, FunI, FunII, GdiII, GsaI, HaeI, HgiAI, Hin1I, HindII, Hpy178III, Hpy8I, Hsp92I, Kpn2I, Ksp22I, KspAI, KspI, MflI, MhlI, MlsI, MluNI, Mly113I, Mph1103I, MroI, MroNI, Msp20I, MspCI, MstI, MunI, MvrI, NgoAIV, NsbI, NspIII, NspV, PaeI, PagI, PauI, PceI, Pfl23II, PinAI, Ple19I, PmaCI, PshBI, Psp124BI, Psp1406I, PspAI, PspLI, PspN4I, PsuI, ReaI, SduI, Sfr274I, Sfr303I, SfuI, SgrBI, SlaI, SpaHI, SseBI, SspBI, SstI, SstII, SunI, TatI, Vha464I, VneI, XapI, XhoII, XmaCI, XmaIII, XmaJI, XmiI, ZhoI, Zsp2I, AocI, AxyI, Bpu1102I, Bse21I, Bsp1720I, BstPI, CelII, CpoI, CspI, DraII, Eco065I, Eco81I, Eco91I, EspI, KflI, LguI, MabI, PpuXI, Psp5II, PspEI, Rsr2I, SauI, AbsI, CciNI, FspAI, MauBI, MreI, MssI, RgaI, SdaI, SfaAI, SgfI, SmiI, Sse232I, AdeI, AspI, CaiI, PsyI, TelI, Asp700I, BoxI, Bse8I, BseJI, BsiBI, BsrBRI, BstPAI, CjeNII, MamI, MroXI, OliI, PdmI, RseI, SmiMI, AccB7I, AspEI, BasI, BmeRI, BplI, Bsc4I, BseLI, BsiYI, BstENI, BstMWI, CjeI, CjuI, CjuII, DriI, Eam1105I, EclHKI, FalI, HpyF10VI, NgoAVIII, NruGI, PflBI, UbaF14I, XagI, AasI, BdaI, Bsp24I, CjePI, DseDI, UbaF9I, ArsI, BarI, PcsI and UbaF13I. In some alternatives, the recognition sites are inverted, thus the complimentary sequence is also inverted. In some alternatives, the RNA lacks a 5' and/or 3' UTR or lacks a native 5' and/or 3' UTR and/or lacks one or more sequences required for native polyadenylation such as, a cleavage/polyadenylation specificity factor (CPSF) binding site, a cleavage stimulation factor binding site (CstF), a cleavage factor I binding site (CFI), or a cleavage factor II binding site (CFII). Without being limiting an endonuclease can include, for example, a CRISPR, a restriction endonuclease, a Type II restriction endonuclease and a Type IIS restriction endonuclease. In some alternatives, the endonuclease is a CRISPR, a restriction endonuclease, a Type II restriction endonuclease or a Type IIS restriction endonuclease. In some alternatives, wherein StuI is provided, the endonuclease cleavage site is a StuI cleavage site, AGGCCT (SEQ ID NO: 633), and StuI cleaves between the G and C, leaving a blunt end that terminates in a GG. In some alternatives, the endonuclease cleavage site is AGGCCT (SEQ ID NO: 633). In some alternatives, the endonuclease is StuI. In some alternatives, the plurality of adenines terminates in GG. In some alternatives, the StuI cleavage site is inverted. In some alternatives, the endonuclease cleavage site is located 1, 2, 3, 4, 5, 6, 7, 7, 8, 9, 10, 11, 12, 13, 14, 15, 16, 17, 18, 19 or 20 base pairs away from the most 5' thymine (or 5' terminal thymine) in the plurality of thymine nucleotides. In some alternatives, the endonuclease cleavage site is located 1, 2, 3, 4, 5, 6, 7, 7, 8, 9 or 10 base pairs away from the most 5' thymine (or 5' terminal thymine) in the plurality of thymine nucleotides. In some alternatives, wherein the plurality of thymine nucleotides comprises at least one covalently linked guanine, cytosine, or an adenine, wherein the at least one covalently linked guanine, cytosine or adenine is optionally joined to the most 5' thymine (or 5' terminal thymine) in the plurality of thymine nucleotides, the endonuclease cleaves at the at the 5' side of the guanine, cytosine or adenine.

BsaI is a Type II restriction endonuclease which also falls in the subgroup for Type IIS endonucleases. Type IIS restriction endonucleases can cleave DNA at a defined distance from their non-palindromic asymmetric recognition sites. This feature can be used, for example, for lengthening a tail for a poly (A) tract. Although a tail, such as a poly (A) tract can be created by insertion of the sequence into any restriction site, only a Type IIS restriction site can be used to lengthen a tail, such as a poly (A) tract once a poly (A) tract is in place. Only a Type II S restriction site can cleave adjacent to and not within the recognition sequence, thereby cleaving in the poly (T) region of the said polynucleotide and ensuring that the poly (A) tail that is transcribed from the said polynucleotide does not terminate in a sequence that is related to the restriction site itself.

StuI is a Type II restriction endonuclease that leaves a blunt end when it cleaves a double stranded DNA. In some alternatives, wherein StuI is provided, the endonuclease cleavage site is a StuI cleavage site, AGGCCT (SEQ ID NO: 633), and StuI cleaves between the G and C, leaving a blunt end that terminates in a GG. In some alternatives, the endonuclease cleavage site is AGGCCT (SEQ ID NO: 633). In some alternatives, the endonuclease is StuI. In some alternatives, the plurality of adenines terminates in GG. In some alternatives, the StuI cleavage site is inverted. In some alternatives, the endonuclease recognition site is a BsaI restriction recognition site, and the endonuclease is BSaI. In some alternatives, the BsaI restriction recognition site is inverted.

In order for the poly(A) tail to terminate without including additional bases beyond it, a Type IIS restriction recognition site can be placed downstream from the intended cut site and within the poly(A) tail, in which the restriction site is "inverted" or "facing the poly(A) site, such that the restriction cleavage site is within the poly(A) encoding region (the plurality of thymine residues in the template strand). Therefore the restriction site can be used to lengthen the tail once it is in place. The restriction site can be encoded within the poly(A) encoding region. In some alternatives of the polynucleotide, the polynucleotide comprises a Type IIS endonuclease recognition site downstream from the intended cut site, thereby creating a Type IIS endonuclease cleavage site upstream from the Type IIS endonuclease recognition site. In some alternatives, the Type IIS restriction is inverted. In some alternatives, the Type IIS endonuclease cleavage site is at a distance of 1-55 bases away from the Type IIS endonuclease recognition site. In some alternatives, the Type IIS endonuclease cleavage site is at a distance of 1, 5, 10, 20, 30, 40 or 55 bases away from the Type IIS endonuclease recognition site or a distance in between any two of the aforementioned bases from the Type IIS endonuclease recognition site.

In some alternatives, a polynucleotide comprising a template strand, an endonuclease recognition site and an endonuclease cleavage site for an endonuclease inserted therein, wherein said template strand comprises a plurality of thymine nucleotides is provided, wherein the polynucleotide comprises a first nucleic acid sequence comprising at least one endonuclease recognition site and a second nucleic acid sequence, wherein the second nucleic acid sequence comprises the template strand, wherein the template strand comprises a plurality of thymine nucleotides, wherein said plurality of thymine nucleotides comprises at least 5, 10, 20, 50, 100, 200, 300, 400, 500 or 550 covalently linked thymine nucleotides and wherein the second nucleic acid comprises the endonuclease cleavage site, wherein the endonuclease cleavage site is within the plurality of thymine nucleotides and wherein said first nucleic acid is covalently linked to said second nucleic acid at one end of said second nucleic acid, and wherein the said endonuclease recognition site is located within 55 base pairs of the endonuclease cleavage site for the endonuclease and said endonuclease cleavage site is within 1 to 40 base pairs of a most 5' thymine in the plurality of thymine nucleotides. In some alternatives, the plurality of thymine nucleotides comprises at least, greater than, equal to, or any number in between 5, 10, 20, 50, 100, 200, 300, 400, 500 or 550 covalently linked thymine nucleotides or any number of covalently linked thymine nucleotides between any two aforementioned values. In some alternatives, the number of covalently linked thymines is greater than 120. In some alternatives, the number of covalently linked thymines is greater than 200. In some alternatives, the number of covalently linked thymines is greater than 300. In some alternatives, the at least one endonuclease recognition site is a Type II restriction endonuclease recognition site, and the endonuclease is a Type II restriction endonuclease. In some alternatives, the at least one endonuclease recognition site is a Type IIS restriction endonuclease recognition site and wherein the endonuclease is a Type IIS restriction endonuclease. In some alternatives, AciI, MnlI, AlwI, BbvI, BccI, BceAI, BsmAI, BsmFI, BspCNI, BsrI, BtsCI, FokI, HgaI, HphI, HpyAV, MboII, MlyI, PleI, SfaNI, AcuI, BciVI, BfuAI, BmgBI, BmrI, BpmI, BpuEI, BsaI, BseRI, BsgI, BsmI, BspMI, BsrBI, BsrDI, BtgZI, BtsI, EarI, EciI, MmeI, NmeAIII, BbvCI, Bpu10I, BspQI, SapI, BaeI, BsaXI, CspCI, AfaI, AluBI, AspLEI, BscFI, Bsh1236I, BshFI, BshI, BsiSI, BsnI, Bsp143I, BspANI, BspFNI, BssMI, BstENII, BstFNI, BstHHI, BstKTI, BstMBI, BsuRI, CfoI, Csp6I, FaeI, FaiI, FnuDII, FspBI, GlaI, HapII, Hin1II, R9529, Hsp92II, HspAI, MaeI, MaeII, MvnI, PalI, RsaNI, SetI, SgeI, Sse9I, Tru1I, Tru9I, TscI, TspEI, TthHB8I, XspI, AflI, AgsI, AspS9I, AsuC2I, AsuI, BcefI, BenI, BisI, BlsI, Bme1390I, Bme18I, BmrFI, BscGI, BseBI, BsiLI, BsiZI, BslFI, BsoMAI, BspNCI, Bst2UI, Bst71I, BstDEI, BstOI,BstSCI, CauII, CdiI, Cfr13I, Eco47I, EcoRII, FaqI, FinI, Fsp4HI, GluI, Hin4II, HpyF3I, ItaI, MaeIII, MspR9I, MvaI, NmuCI, Psp6I, PspPI, SatI, SinI, TscAI, VpaK11BI, AanI, AatI, AauI, Acc113I, Acc16I, AccB1I, AceIII, AesI, AcvI, AcyI, AhlI, Alw21I, Alw44I, Ama87I, Aor51HI, AsiAI, AsnI, Asp718I, AspHI, AsuII, AsuNHI, AvaIII, AviII, BanIII, BauI, BbeI, BbrPI, BbuI, Bbv12I, BbvII, Bce83I, BeoI, BcuI, BfmI, BfrB1,BfrI, BlnI, BmcAI, BmeT110I, BmiI, BmuI, BmyI, Bpu14I, BpvUI, Bsa29I, BsaOI, BsbI, BscBI, BscCI, Bse118I, BseAI, BseCI, BseDI, BsePI, BseSI, BseX3I, Bsh1285I, BshNI, BshTI, BshVI, BsiCI, BsiHKCI, BsiMI, BsiQI, BsiXI, Bsp106I, Bsp119I, Bsp120I, Bsp13I, Bsp1407I, Bsp143II, Bsp19I, Bsp68I, BspA2I, BspCI, BspGI, BspLU11I, BspMAI, BspMII, BspOI, BspT104I, BspT107I, BspTI, BspXI, BssAI, BssHI, BssNAI, BssNI, BssT1I, Bst1107I, Bst98I, BstACI, BstAFI, BstAUI, BstBAI, BstC8I, BstDSI, BstH2I, BstHPI, BstNSI, BstSFI, BstSLI, BstSNI, BstX2I, BstZI, BsuTUI, BtuMI, BveI, CciI, Cfr10I, Cfr42I, Cfr9I, CfrI, Csp45I, CspAI, DinI, DrdII, DsaI, Ec1136II, EcIXI, Eco105I, Eco130I, Eco147I, Eco24I, Eco32I, Eco47III, Eco52I, Eco72I, Eco88I, EcoICRI, EcoT14I, EcoT22I, EcoT38I, EgeI, EheI, ErhI, FauNDI, FbaI, FblI, FriOI, FunI, FunII, GdiII, GsaI, HaeI, HgiAI, Hin1I, HindII, Hpy178III, Hpy8I, Hsp92I, Kpn2I, Ksp22I, KspAI, KspI, MflI, MhlI, MlsI, MluNI, Mly113I, Mph1103I, MroI, MroNI, Msp20I, MspCI, MstI, MunI, MvrI, NgoAIV, NsbI, NspIII, NspV, PaeI, PagI, PauI, PeeI, Pfl23II, PinAI, Ple19I, PmaCI, PshBI, Psp124BI, Psp1406I, PspAI, PspLI, PspN4I, PsuI, ReaI, SduI, Sfr274I, Sfr303I, SfuI, SgrBI, SlaI, SpaHI, SseBI, SspBI, SstI, SstII, SunI, TatI, Vha464I, VneI, XapI, XhoII, XmaCI, XmaIII, XmaJI, XmiI, ZhoI, Zsp2I, AocI, AxyI, Bpu1102I, Bse21I, Bsp1720I, BstPI, CelII, CpoI, CspI, DraII, Eco065I, Eco81I, Eco91I, EspI, KflI, LguI, MabI, PpuXI, Psp5II, PspEI, Rsr2I, SauI, AbsI, CciNI, FspAI, MauBI, MreI, MssI, RgaI, SdaI, SfaAI, SgfI, SmiI, Sse232I, AdeI, AspI, CaiI, PsyI, TelI, Asp700I, BoxI, Bse8I, BseJI, BsiBI, BsrBRI, BstPAI, CjeNII, MamI, MroXI, OliI, PdmI, RseI, SmiMI, AccB7I, AspEI, BasI, BmeRI, BplI, Bsc4I, BseLI, BsiYI, BstENI, BstMWI, CjeI, CjuI, CjuII, DriI, Eam1105I, EclHKI, FalI, HpyF10VI, NgoAVIII, NruGI, PflBI, UbaF14I, XagI, AasI, BdaI, Bsp24I, CjePI, DseDI, UbaF9I, ArsI, BarI, PcsI or UbaF13I. In some alternatives, the sequence recognition site is inverted. In some alternatives, the cut site, or endonuclease cleavage site is inverted. In some alternatives, the endonuclease recognition site comprises any one of the endonuclease recognition sites described in Table 1 (SEQ ID NOs: 18-632, 634-636). In some alternatives, the endonuclease is AciI, MnlI, AlwI, BbvI, BccI, BceAI, BsmAI, BsmFI, BspCNI, BsrI, BtsCI, FokI, HgaI, HphI, HpyAV, MboII, MlyI, PleI, SfaNI, AcuI, BciVI, BfuAI, BmgBI, BmrI, BpmI, BpuEI, BsaI, BseRI, BsgI, BsmI, BspMI, BsrBI, BsrDI, BtgZI, BtsI, EarI, EciI, MmeI, NmeAIII, BbvCI, Bpu10I, BspQI, SapI, BaeI, BsaXI, CspCI, AfaI, AluBI, AspLEI, BscFI, Bsh1236I, BshFI, BshI, BsiSI, BsnI, Bsp143I, BspANI, BspFNI, BssMI, BstENII, BstFNI, BstHHI, BstKTI, BstMBI, BsuRI, CfoI, Csp6I, FaeI, FaiI, FnuDII, FspBI, GlaI, HapII, HinlII, R9529, Hsp92II, HspAI, MaeI, MaeII, MvnI, PalI, RsaNI, SetI, SgeI, Sse9I, Tru1I, Tru9I, TscI, TspEI, TthHB8I, XspI, AflI, AgsI, AspS9I, AsuC2I, AsuI, BcefI, BcnI, BisI, BlsI, Bme1390I, Bme18I, BmrFI, BscGI, BseBI, BsiLI, BsiZI, BslFI, BsoMAI, BspNCI, Bst2UI, Bst71I, BstDEI, BstOI,BstSCI, CauII, CdiI, Cfr13I, Eco47I, EcoRII, FaqI, FinI, Fsp4HI, GluI, Hin4II, HpyF3I, ItaI, MaeIII, MspR9I, MvaI, NmuCI, Psp6I, PspPI, SatI, SinI, TscAI, VpaK11BI, AanI, AatI, AauI, Acc113I, Acc16I, AccB1I, AceIII, AcsI, AcvI, AcyI, AhlI, Alw21I, Alw44I, Ama87I, Aor51HI, AsiAI, AsnI, Asp718I, AspHI, AsuII, AsuNHI, AvaIII, AviII, BanIII, BauI, BbeI, BbrPI, BbuI, Bbv12I, BbvII, Bce83I, BcoI, BcuI, BfmI, BfrB1,BfrI, BlnI, BmcAI, BmeT110I, BmiI, BmuI, BmyI, Bpu14I, BpvUI, Bsa29I, BsaOI, BsbI, BscBI, BscCI, Bse118I, BseAI, BseCI, BseDI, BsePI, BseSI, BseX3I, Bsh1285I, BshNI, BshTI, BshVI, BsiCI, BsiHKCI, BsiMI, BsiQI, BsiXI, Bsp106I, Bsp119I, Bsp120I, Bsp13I, Bsp1407I, Bsp143II, Bsp19I, Bsp68I, BspA2I, BspCI, BspGI, BspLU11I, BspMAI, BspMII, BspOI, BspT104I, BspT107I, BspTI, BspXI, BssAI, BssHI, BssNAI, BssNI, BssT1I, Bst1107I, Bst98I, BstACI, BstAFI, BstAUI, BstBAI, BstC8I, BstDSI, BstH2I, BstHPI, BstNSI, BstSFI, BstSLI, BstSNI, BstX2I, BstZI, BsuTUI, BtuMI, BveI, CciI, Cfr10I, Cfr42I, Cfr9I, CfrI, Csp45I, CspAI, DinI, DrdII, DsaI, Ec1136II, EclXI, Eco105I, Eco130I, Eco147I, Eco24I, Eco32I, Eco47III, Eco52I, Eco72I, Eco88I, EcoICRI, EcoT14I, EcoT22I, EcoT38I, EgeI, EheI, ErhI, FauNDI, FbaI, FbII, FriOI, FunI, FunII, GdiII, GsaI, HaeI, HgiAI, Hin1I, HindII, Hpy178III, Hpy8I, Hsp92I, Kpn2I, Ksp22I, KspAI, KspI, MflI, MhlI, MlsI, MluNI, Mly113I, Mph1103I, MroI, MroNI, Msp20I, MspCI, MstI, MunI, MvrI, NgoAIV, NsbI, NspIII, NspV, PaeI, PagI, PauI, PceI, Pfl23II, PinAI, Ple19I, PmaCI, PshBI, Psp124BI, Psp1406I, PspAI, PspLI, PspN4I, PsuI, ReaI, SduI, Sfr274I, Sfr303I, SfuI, SgrBI, SlaI, SpaHI, SseBI, SspBI, SstI, SstII, SunI, TatI, Vha464I, VneI, XapI, XhoII, XmaCI, XmaIII, XmaJI, XmiI, ZhoI, Zsp2I, AocI, AxyI, Bpu1102I, Bse21I, Bsp1720I, BstPI, CelII, CpoI, CspI, DraII, Eco065I, Eco81I, Eco91I, EspI, KflI, LguI, MabI, PpuXI, Psp5II, PspEI, Rsr2I, SauI, AbsI, CciNI, FspAI, MauBI, MreI, MssI, RgaI, SdaI, SfaAI, SgfI, SmiI, Sse232I, AdeI, AspI, CaiI, PsyI, TelI, Asp700I, BoxI, Bse8I, BseJI, BsiBI, BsrBRI, BstPAI, CjeNII, MamI, MroXI, OliI, PdmI, RseI, SmiMI, AccB7I, AspEI, BasI, BmeRI, BplI, Bsc4I, BseLI, BsiYI, BstENI, BstMWI, CjeI, CjuI, CjuII, DriI, Eam1105I, EclHKI, FalI, HpyF10VI, NgoAVIII, NruGI, PflBI, UbaF14I, XagI, AasI, BdaI, Bsp24I, CjePI, DseDI, UbaF9I, ArsI, BarI, PcsI or UbaF13I. In some alternatives, the at least one endonuclease recognition site is a Type II restriction endonuclease recognition site. In some alternatives, the at least one endonuclease recognition site is a BsaI or a StuI restriction endonuclease recognition site and the endonuclease is BsaI or StuI. In some alternatives, the endonuclease cleavage site is between 1, 2, 3, 4, 5, 6, 7, 8, 9, 10, 20, 30, 40, 50 or 55 nucleotides from the endonuclease recognition site or any number of nucleotides between any two aforementioned values away from the endonuclease recognition site. In some alternatives, the polynucleotide further comprises a gene. In some alternatives, the gene is an endonuclease gene, such as Cas9 or a derivative thereof or active fragment thereof, a TALEN, or MegaTAL, see e.g., SEQ ID. Nos. 6-14. In some alternatives, a method of making a polynucleotide having a template strand, an endonuclease recognition site and an endonuclease cleavage site for an endonuclease inserted therein, and wherein said template strand comprises a plurality of thymine nucleotides is provided, wherein the method comprises providing a first nucleic acid sequence comprising at least one endonuclease recognition site, providing a second nucleic acid sequence, wherein the second nucleic acid sequence comprises the template strand, wherein the template strand comprises a plurality of thymine nucleotides, wherein said plurality of thymine nucleotides comprises at least 5, 10, 20, 50, 100, 200, 300, 400, 500 or 550 covalently linked thymine nucleotides and wherein the second nucleic acid comprises the endonuclease cleavage site and joining said first nucleic acid sequence to said second nucleic acid sequence, wherein said first nucleic acid is covalently linked to said second nucleic acid at one end, and wherein the said endonuclease recognition site is located within 55 base pairs of the endonuclease cleavage site for the endonuclease and said endonuclease cleavage site is within 1 to 40 base pairs of a most 5' thymine in the plurality of thymine nucleotides. In some alternatives, the at least one endonuclease recognition site is a Type II restriction endonuclease recognition site, and the endonuclease is a Type II restriction endonuclease. In some alternatives, the at least one endonuclease recognition site is a Type IIS restriction endonuclease recognition site, and the endonuclease is a Type IIS restriction endonuclease. In some alternatives, the at least one Type II restriction endonuclease recognition site is a BsaI or a StuI restriction endonuclease recognition site, and the endonuclease is BsaI or StuI. In some alternatives, the endonuclease cleavage site is between 1, 2, 3, 4, 5, 6, 7, 8, 9, 10, 20, 30, 40, 50 or 55 nucleotides from the endonuclease recognition site or any number of nucleotides between any two aforementioned values away from the endonuclease recognition site. In some alternatives, the polynucleotide further comprises a gene. In some alternatives, the gene is an endonuclease gene, such as Cas9 or a derivative thereof or active fragment thereof, a TALEN, or MegaTAL, see e.g., SEQ ID. Nos. 6-14. Without being limiting an endonuclease can include, for example, a CRISPR, a restriction endonuclease, a Type II restriction endonuclease and a Type IIS restriction endonuclease. In some alternatives, the endonuclease is a CRISPR, a restriction endonuclease, a Type II restriction endonuclease or a Type IIS restriction endonuclease. In some alternatives, wherein StuI is provided, the endonuclease cleavage site is a StuI cleavage site, AGGCCT (SEQ ID NO: 633), and StuI cleaves between the G and C, leaving a blunt end that terminates in a GG. In some alternatives, the endonuclease cleavage site is AGGCCT (SEQ ID NO: 633). In some alternatives, the endonuclease is StuI. In some alternatives, the plurality of adenines terminates in GG. In some alternatives, the StuI cleavage site is inverted. In some alternatives, the endonuclease cleavage site is located 1, 2, 3, 4, 5, 6, 7, 7, 8, 9, 10, 11, 12, 13, 14, 15, 16, 17, 18, 19 or 20 base pairs away from the most 5' thymine (or 5' terminal thymine) in the plurality of thymine nucleotides. In some alternatives, the endonuclease cleavage site is located 1, 2, 3, 4, 5, 6, 7, 7, 8, 9 or 10 base pairs away from the most 5' thymine (or 5' terminal thymine) in the plurality of thymine nucleotides.

Disclosed herein are methods for making a polynucleotide having a plurality of covalently linked thymine nucleotides (a poly(T) tract) and one or more of the aforementioned endonuclease recognition sites inserted therein or attached thereto, as well as, compositions comprising these polynucleotides and methods of use thereof. In some alternatives, the at least one endonuclease recognition site is a Type II restriction endonuclease recognition site, and the endonuclease is a Type II restriction endonuclease. In some alternatives, the at least one endonuclease recognition site is a Type IIS restriction endonuclease recognition site, and the endonuclease is a Type IIS restriction endonuclease. In some alternatives, the at least one endonuclease recognition site is a BsaI restriction endonuclease recognition site, and the endonuclease is BsaI. In some alternatives, the Type IIS restriction endonuclease recognition site is inverted. In some alternatives, the Type IIS restriction endonuclease site is an inverted BsaI restriction endonuclease restriction site. In some alternatives, the polynucleotide or vector having the plurality of covalently linked thymine residues comprises only one BsaI restriction site such that said BsaI site is unique for a linker domain defined by having 5' and 3' polymers of thymine residues flanking said BsaI site. In some alternatives, the polynucleotide comprises or encodes a gene. In some alternatives, the gene encodes a nuclease. In some alternatives, the nuclease is Cas9 or a derivative thereof or active fragment thereof, a TALEN, or MegaTAL, see e.g., SEQ ID. Nos. 6-14. In some alternatives, the Type IIS restriction is inverted. In some alternatives, the Type IIS endonuclease cleavage site is at a distance of 11, 2, 3, 4, 5, 6, 7, 8, 9, 10, 20, 30, 40, 50 or 55 nucleotide bases away from the Type IIS endonuclease recognition site or any distance between any two aforementioned values. In some alternatives, the Type IIS endonuclease cleavage site is at a distance of 1-4 bases away from the Type IIS endonuclease recognition site. Without being limiting an endonuclease can include, for example, a CRISPR, a restriction endonuclease, a Type II restriction endonuclease and a Type IIS restriction endonuclease. In some alternatives, the endonuclease is a CRISPR, a restriction endonuclease, a Type II restriction endonuclease or a Type IIS restriction endonuclease. In some alternatives, wherein StuI is provided, the endonuclease cleavage site is a StuI cleavage site, AGGCCT (SEQ ID NO: 633), and StuI cleaves between the G and C, leaving a blunt end that terminates in a GG. In some alternatives, the endonuclease cleavage site is AGGCCT (SEQ ID NO: 633). In some alternatives, the endonuclease is StuI. In some alternatives, the plurality of adenines terminates in GG. In some alternatives, the StuI cleavage site is inverted. In some alternatives, the endonuclease cleavage site is located 1, 2, 3, 4, 5, 6, 7, 7, 8, 9, 10, 11, 12, 13, 14, 15, 16, 17, 18, 19 or 20 base pairs away from the most 5' thymine (or 5' terminal thymine) in the plurality of thymine nucleotides. In some alternatives, the endonuclease cleavage site is located 1, 2, 3, 4, 5, 6, 7, 7, 8, 9 or 10 base pairs away from the most 5' thymine (or 5' terminal thymine) in the plurality of thymine nucleotides.

Linear Plasmids

Molecular cloning requires the incorporation of genetic material into a nucleic acid. Despite advances in sequencing and molecular cloning, complete sequencing and analysis of proteins require cloning of specific regions, such as a binding site or a site that confers catalytic activity. Many of these regions are difficult to clone in current vectors, such as circular vectors, however. Difficult coding regions and large inserts can be the cause of superhelical stress in circular plasmids and can generate secondary structures that are substrates for deletion, particularly in regions that contain numerous tandem or inverted repeats. Transcription from cloned promoters can also interfere with plasmid stability.

Linear vectors provide several desirable features to the use of circular supercoiled plasmids for cloning. Linear vectors are not subject to the supercoiling found in circular plasmids and can stably maintain inserts that have primary or secondary structures that are unstable when supercoiled. This additional stability may result in improved sequencing data and reductions in the number of sequence gaps and cloning gaps in genomic assemblies. Linear vectors can also exhibit the ability to clone larger inserts using standard methods. Linear vector cloning systems can stably clone a nucleic acid, such as DNA, in the range of 10 to over 100 kb, without the use of packaging systems required with cosmid cloning. The concept of using a linear vector for cloning is similar to that of a linear plasmid vector, which is described, for example, in WO 2007/087478 and in Godiska et al (Nucleic Acids Research (2010), vol. 38, no. 6), which are both hereby expressly incorporated by reference in their entireties.

In order to create a linear vector from a linear plasmid vector with a unique inverted BsaI restriction site within a multicloning site, extra plurality of BsaI sites had to be removed. Therefore, a linear plasmid vector was used for synthesizing the plasmids with various lengths of poly (A) encoding tracts (pEVL). The linear plasmid vector was used for synthesizing a nucleic acid having a poly (T) tract of a desired length and these experiments are described in greater detail. Linear vector cloning systems can be used to clone difficult polynucleotide sequences that cannot be cloned into conventional circular plasmid vectors. For example, the linear vectors can maintain fragments that are unstable in the supercoiled plasmid form. The linear mode of replication can impart high fidelity replication of repeats, large palindromes, AT-rich DNA, and high repeats, for example a thymine rich region. As disclosed herein, a linear vector can be used for making a polynucleotide having a plurality of covalently linked thymine nucleotides (a poly(T) tract) and one or more of the aforementioned endonuclease recognition sites inserted therein or attached thereto. The use of a circular plasmid is unable to support a template for making a long poly(A) tract and commercially available plasmids for transcribing a poly (A) tract are typically limited to about 30 adenines. The use of a linearized plasmid, or a linear plasmid, can enhance the transcription of difficult genes that are large and have high repeats. A linear cloning vector can include a left telomere and at least one selectable marker, a right arm comprising a right telomere and at least one selectable marker, and a cloning region located between the left arm and the right arm. In some alternatives described herein, the polynucleotide is a linear polynucleotide. In some alternatives, the polynucleotide further comprises a left telomere and at least one selectable marker, a right arm comprising a right telomere and at least one selectable marker, and a cloning region located between the left arm and the right arm. Telomeres can be used for protection of the termini of the linear polynucleotide from recombination and degradation. Telomeres for linearized plasmid vectors can include telomeres derived from bacteriophages lambda N15, K02, PRD1 and PY54, and from linear chromosomes from *Agrobacterium*, for example. "Selectable markers" as described herein, refers to a gene introduced into a nucleic acid to protect a transformed cell from a specific factor in the growth environment, and can be an antibiotic resistance gene, a metabolic marker or a screenable marker. Examples of antibiotic resistance genes that can reside in a linear vector polynucleotide can include kanamycin, ampicillin, tetracycline, and chloramphenicol, for example. Metabolic markers can include amino acid synthesis genes, for example genes for trp synthesis. In some alternatives, the polynucleotide further comprises a selectable marker. In some alternatives, the selectable marker is an antibiotic resistance gene, a metabolic marker or a screenable marker. In some alternatives, the polynucleotide further comprises a metabolic marker. In some alternatives the metabolic marker comprises amino acid synthesis genes, for example genes for trp synthesis. In some alternatives, the polynucleotide comprises an antibiotic resistance gene. In some alternatives, the antibiotic resistance gene is a kanamycin resistant gene, ampicillin resistant gene, tetracycline resistant gene, or chloramphenicol resistant gene. Protelomerase proteins are enzymes that are responsible for the generation of closed hairpinends in linear DNA. The target sites of protelomerases can be inverted repeats. Protelomerase proteins can also process a target site, in which the target site can have dyad symmetrical DNA. Protelomerases are a class of unique proteins that function to generate covalently closed hairpin ends in DNA. These linear DNA ends are arranged such that one strand turns around and becomes the complementary strand. In this manner, these linear DNA molecules do not have free or open ends, and are expected to be stable and not vulnerable to exonuclease degradations. In some alternatives, the polynucleotide is a linear polynucleotide. In some alternatives, the polynucleotide has a protelomerase target site. In some alternatives, the target site has a dyad symmetrical DNA site. Protelomerase function and sites for binding of the protelomerase are discussed in Godiska et al. (U.S. Pat. No. 9,029,134; incorporated by reference in its entirety).

Linear vector cloning systems can be used to clone difficult polynucleotide sequences that cannot be cloned into conventional circular plasmid vectors. For example, the linear vectors can maintain fragments that are unstable in the supercoiled plasmid form. The linear mode of replication can impart high fidelity replication of repeats, large palindromes, AT-rich DNA, and high repeats, for example a thymine rich region. As disclosed herein, a linear vector can be used for making a polynucleotide having a plurality of covalently linked thymine nucleotides (a poly(T) tract) and one or more of the aforementioned endonuclease recognition sites inserted therein or attached thereto. The use of a circular plasmid is unable to support a template for making a long poly(A) tract and commercially available plasmids for transcribing a poly (A) tract are typically limited to about 30 adenines. The use of a linearized plasmid, or a linear plasmid, can enhance the transcription of difficult genes that are large and have high repeats. A linear cloning vector can include a left telomere and at least one selectable marker, a right arm comprising a right telomere and at least one selectable marker, and a cloning region located between the left arm and the right arm. In some alternatives described herein, the polynucleotide is a linear polynucleotide. In some alternatives, the polynucleotide further comprises a left telomere and at least one selectable marker, a right arm comprising a right telomere and at least one selectable marker, and a cloning region located between the left arm and the right arm. Telomeres can be used for protection of the termini of the linear polynucleotide from recombination and degradation. Telomeres for linearized plasmid vectors can include telomeres derived from bacteriophages lambda N15, K02, PRD1 and PY54, and from linear chromosomes from *Agrobacterium*, for example. "Selectable markers" as described herein, refers to a gene introduced into a nucleic acid to protect a transformed cell from a specific factor in the growth environment, and can be an antibiotic resistance gene, a metabolic marker or a screenable marker. Examples of antibiotic resistance genes that can reside in a linear vector polynucleotide can include kanamycin, ampicillin, tetracycline, and chloramphenicol, for example. Metabolic markers can include amino acid synthesis genes, for example genes for trp synthesis. In some alternatives, the polynucleotide further comprises a selectable marker. In some alternatives, the selectable marker is an antibiotic resistance gene, a metabolic marker or a screenable marker. In some alternatives, the polynucleotide further comprises a metabolic marker. In some alternatives the metabolic marker comprises amino acid synthesis genes, for example genes for trp synthesis. In some alternatives, the polynucleotide comprises an antibiotic resistance gene. In some alternatives, the antibiotic resistance gene is a kanamycin resistant gene, ampicillin resistant gene, tetracycline resistant gene, or chloramphenicol resistant gene.

By one approach, a polynucleotide having a plurality of thymine nucleotides is made within a linear vector. The polynucleotide can comprise a first nucleic acid sequence encoding a nuclease, a second nucleic acid sequence comprising at least one restriction endonuclease recognition site and a third nucleic acid sequence, wherein the third nucleic acid sequence comprises the template strand, wherein said plurality of thymine nucleotides comprises at least, greater than, equal to, or any number in between 20, 30, 40, 50, 60, 70, 80, 90, 100, 110, 120, 130, 140, 150, 175, 200, 225, 250, 275, 300, 325, 350, 375, 400, 425, 450, 475, 500 or 550 covalently linked thymine nucleotides and wherein the third nucleic acid comprises the restriction endonuclease cleavage site, wherein the restriction endonuclease cleavage site is located within the plurality of thymine nucleotides or within 1, 2, 3, 4, 5, 6, 7, 7, 8, 9, 10, 11, 12, 13, 14, 15, 16, 17, 18, 19 or 20 base pairs away from the most 5' thymine (or 5' terminal thymine) in the plurality of thymine nucleotides and wherein said second nucleic acid is covalently linked to one end of said third nucleic acid sequence, and wherein the said restriction endonuclease recognition site is located within 55 base pairs of the restriction endonuclease cleavage site for the restriction endonuclease and said restriction endonuclease cleavage site is within 1 to 40 base pairs of a most 5' thymine in the plurality of thymine nucleotides. Accordingly, methods for making a nucleic acid from a linear polynucleotide having a plurality of thymine nucleotides and an endonuclease disposed within said plurality of thymine nucleotides is provided herein. Methods for enhancing transcription and translation utilizing said compositions are also alternatives. In some alternatives, the polynucleotide further comprises telomeres. In some alternatives, the polynucleotide is a linear cloning vector, wherein the linear cloning vector comprises a left telomere and at least one selectable marker, a right arm comprising a right telomere and at least one selectable marker, and a cloning region located between the left arm and the right arm.

In some alternatives, a polynucleotide comprising a template strand, an endonuclease recognition site and an endonuclease cleavage site for an endonuclease inserted therein, wherein said template strand comprises a plurality of thymine nucleotides is provided. The polynucleotide can comprise a first nucleic acid sequence encoding a nuclease, a second nucleic acid sequence comprising at least one restriction endonuclease recognition site and a third nucleic acid sequence, wherein the third nucleic acid sequence comprises the template strand, wherein said plurality of thymine nucleotides comprises at least, greater than, equal to, or any number in between 20, 30, 40, 50, 60, 70, 80, 90, 100, 110, 120, 130, 140, 150, 175, 200, 225, 250, 275, 300, 325, 350, 375, 400, 425, 450, 475, 500 or 550 covalently linked thymine nucleotides and wherein the third nucleic acid comprises the restriction endonuclease cleavage site, wherein the restriction endonuclease cleavage site is located within the plurality of thymine nucleotides or within 1, 2, 3, 4, 5, 6, 7, 7, 8, 9, 10, 11, 12, 13, 14, 15, 16, 17, 18, 19 or 20 base pairs away from the most 5' thymine (or 5' terminal thymine) in the plurality of thymine nucleotides and wherein said second nucleic acid is covalently linked to one end of said third nucleic acid sequence, and wherein the said restriction endonuclease recognition site is located within 55 base pairs of the restriction endonuclease cleavage site for the restriction endonuclease and said restriction endonuclease cleavage site is within 1 to 40 base pairs of a most 5' thymine in the plurality of thymine nucleotides. In some alternatives, the polynucleotide further comprises telomeres. In some alternatives, the polynucleotide is a linear cloning vector, wherein the linear cloning vector comprises a left telomere and at least one selectable marker, a right arm comprising a right telomere and at least one selectable marker, and a cloning region located between the left arm and the right arm. In some alternatives, a gene is cloned into the cloning region wherein the gene encodes a nuclease. Without being limiting an endonuclease can include, for example, a CRISPR, a restriction endonuclease, a Type II restriction endonuclease and a Type IIS restriction endonuclease. In some alternatives, the endonuclease is a CRISPR, a restriction endonuclease, a Type II restriction endonuclease or a Type IIS restriction endonuclease. In some alternatives, the endonuclease is a CRISPR, a restriction endonuclease, a Type II restriction endonuclease or a Type IIS restriction endonuclease. In some alternatives, wherein StuI is provided, the endonuclease cleavage site is a StuI cleavage site, AGGCCT (SEQ ID NO: 633), and StuI cleaves between the G and C, leaving a blunt end that terminates in a GG. In some alternatives, the endonuclease cleavage site is AGGCCT (SEQ ID NO: 633). In some alternatives, the endonuclease is StuI. In some alternatives, the plurality of adenines terminates in GG. In some alternatives, the StuI cleavage site is inverted. In some alternatives, the endonuclease recognition site is a BsaI restriction recognition site, and the endonuclease is BSaI. In some alternatives, the BsaI restriction recognition site is inverted. In some alternatives, the endonuclease cleavage site is located 1, 2, 3, 4, 5, 6, 7, 7, 8, 9, 10, 11, 12, 13, 14, 15, 16, 17, 18, 19 or 20 base pairs away from the most 5' thymine (or 5' terminal thymine) in the plurality of thymine nucleotides. In some alternatives, the endonuclease cleavage site is located 1, 2, 3, 4, 5, 6, 7, 7, 8, 9 or 10 base pairs away from the most 5' thymine (or 5' terminal thymine) in the plurality of thymine nucleotides.

In some alternatives, the polynucleotide comprises at least, greater than, equal to, or any number in between 20, 30, 40, 50, 60, 70, 80, 90, 100, 110, 120, 130, 140, 150, 175, 200, 225, 250, 275, 300, 325, 350, 375, 400, 425, 450, 475, 500, 525 or 550 covalently linked thymine residues within the template strand. In some alternatives, the at least one endonuclease recognition site is a Type II restriction endonuclease recognition site, and the endonuclease is a Type II restriction endonuclease. In some alternatives the Type II endonuclease recognition site is a Type IIS restriction endonuclease recognition site and the endonuclease is a Type IIS restriction endonuclease. In some alternatives, the at least one Type IIS restriction endonuclease recognition site is inverted. In some alternatives, the Type IIS restriction endonuclease recognition site is a sequence set forth in Table 1 and is inverted (SEQ ID NOs: 18-632, 634-636). In some alternatives, the at least one Type IIS restriction endonuclease recognition site is a BsaI endonuclease recognition site and endonuclease is BsaI. In some alternatives, the BsaI endonuclease recognition site is inverted. In some alternatives, the polynucleotide is a linear polynucleotide. In some alternatives, the polynucleotide has only one BsaI restriction site. In some alternatives, the polynucleotide has an inverted BsaI restriction site. In some alternatives, the polynucleotide further comprises a gene. In some alternatives the gene is 10-50 kb. In some alternatives, the gene is 10, 20, 30, 40, 50, 60, 70, 80, 90 or 100 kb or any length between any two aforementioned values. In some alternatives, the gene is at least 100 Kb. In some alternatives, the polynucleotide or vector having the plurality of covalently linked thymine residues comprises only one BsaI restriction site such that said BsaI site is unique for a linker domain defined by having 5' and 3' polymers of thymine residues flanking said BsaI site. In some alternatives, the polynucleotide or vector having the plurality of covalently linked thymine residues comprises only one BsaI restriction site, wherein the BsaI restriction site is inverted. In some alternatives, the polynucleotide further comprises telomeres. In some alternatives, the polynucleotide is a linear cloning vector, wherein the linear cloning vector comprises a left telomere and at least one selectable marker, a right arm comprising a right telomere and at least one selectable marker, and a cloning region located between the left arm and the right arm. In some alternatives, the endonuclease cleavage site is located 1, 2, 3, 4, 5, 6, 7, 7, 8, 9, 10, 11, 12, 13, 14, 15, 16, 17, 18, 19 or 20 base pairs away from the most 5' thymine (or 5' terminal thymine) in the plurality of thymine nucleotides. In some alternatives, the endonuclease cleavage site is located 1, 2, 3, 4, 5, 6, 7, 7, 8, 9 or 10 base pairs away from the most 5' thymine (or 5' terminal thymine) in the plurality of thymine nucleotides.

Also described herein are methods of making a polynucleotide comprising a template strand, an endonuclease recognition site and an endonuclease cleavage site for an endonuclease inserted therein, wherein said template strand comprises a plurality of thymine nucleotides, is provided The method of making a polynucleotide comprising a sequence encoding a nuclease, a template strand, an endonuclease recognition site and an endonuclease cleavage site for an endonuclease inserted therein, wherein said template strand comprises a plurality of thymine nucleotides can comprise providing a first nucleic acid sequence encoding a nuclease, providing a second nucleic acid sequence comprising at least one endonuclease recognition site, providing a third nucleic acid sequence, wherein the third nucleic acid sequence comprises the template strand, wherein the template strand comprises a plurality of thymine nucleotides, wherein said plurality of thymine nucleotides comprises at least, greater than, equal to, or any number in between 20, 30, 40, 50, 60, 70, 80, 90, 100, 110, 120, 130, 140, 150, 175, 200, 225, 250, 275, 300, 325, 350, 375, 400, 425, 450, 475, 500 or 550 covalently linked thymine nucleotides and wherein the third nucleic acid comprises the endonuclease cleavage site, wherein the endonuclease cleavage site is located within the plurality of thymine nucleotides or within 1, 2, 3, 4, 5, 6, 7, 7, 8, 9, 10, 11, 12, 13, 14, 15, 16, 17, 18, 19 or 20 base pairs away from the most 5' thymine (or 5' terminal thymine) in the plurality of thymine nucleotides, joining said first nucleic acid to one end of the second nucleic acid sequence and joining said third nucleic acid sequence to one end of the second nucleic acid sequence, wherein said second nucleic acid is covalently linked to one end of said third nucleic acid sequence, and wherein the said endonuclease recognition site is located within 55 base pairs of the endonuclease cleavage site for the endonuclease and said endonuclease cleavage site is within 1 to 40 base pairs of a most 5' thymine in the plurality of thymine nucleotides. In some alternatives, the plurality of thymine nucleotides comprises at least, greater than, equal to, or any number in between 20, 30, 40, 50, 60, 70, 80, 90, 100, 110, 120, 130, 140, 150, 175, 200, 225, 250, 275, 300, 325, 350, 375, 400, 425, 450, 475, 500 or 550 covalently linked thymines or any number of thymines between any two aforementioned values. In some alternatives, the plurality of thymine nucleotides comprises at least one guanine, cytosine, or an adenine. In some alternatives, the endonuclease cleavage site comprises at least one guanine, cytosine, or an adenine. In some alternatives, wherein the endonuclease cleavage site comprises at least one guanine, cytosine, or an adenine, the endonuclease cleaves between a thymine and the at least one guanine, cytosine or adenine, resulting in a plurality of thymine residues that can terminate in a guanine, cytosine or adenine. In some alternatives, the at least one endonuclease recognition site is a Type II restriction endonuclease recognition site, and the endonuclease is a Type II restriction endonuclease. In some alternatives, the at least one endonuclease recognition site is a Type IIS restriction endonuclease recognition site, and the endonuclease is a Type IIS restriction endonuclease. In some alternatives, the at least one Type IIS restriction endonuclease recognition site is a BsaI restriction endonuclease recognition site, and the endonuclease is BsaI. In some alternatives, the Type IIS restriction endonuclease recognition site is inverted. In some alternatives, the Type IIS restriction endonuclease site is an inverted BsaI restriction endonuclease restriction site. In some alternatives, the endonuclease recognition site comprises an endonuclease recognition site sequence set forth in Table 1 (SEQ ID NOs: 18-632, 634-636). In some alternatives, the at least one Type II restriction endonuclease recognition site is a BsaI restriction endonuclease recognition site and the endonuclease is BsaI. In some alternatives, the at least one Type II restriction endonuclease recognition site is an inverted BsaI restriction endonuclease recognition site. In some alternatives, the polynucleotide is a linear polynucleotide. In some alternatives, the polynucleotide has only one BsaI restriction site. In some alternatives, the polynucleotide further comprises a gene. In some alternatives, the gene comprises at least, greater than, equal to, or any number in between 1, 5, 10, 20, 30, 40 or 50 Kb or any number between any two aforementioned values. In some alternatives, the gene is at least 100 Kb. In some alternatives the gene is 1-50 kb. In some alternatives, the polynucleotide or vector having the plurality of covalently linked thymine residues comprises only one BsaI restriction site, wherein the BsaI restriction site is inverted. In some alternatives, the polynucleotide further comprises telomeres. In some alternatives, the polynucleotide is a linear cloning vector, wherein the linear cloning vector comprises a left telomere and at least one selectable marker, a right arm comprising a right telomere and at least one selectable marker, and a cloning region located between the left arm and the right arm. Without being limiting an endonuclease can include, for example, a CRISPR, a restriction endonuclease, a Type II restriction endonuclease and a Type IIS restriction endonuclease. In some alternatives, the endonuclease is a CRISPR, a restriction endonuclease, a Type II restriction endonuclease or a Type IIS restriction endonuclease. In some alternatives, the endonuclease is a CRISPR, a restriction endonuclease, a Type II restriction endonuclease or a Type IIS restriction endonuclease. In some alternatives, wherein StuI is provided, the endonuclease cleavage site is a StuI cleavage site, AGGCCT (SEQ ID NO: 633), and StuI cleaves between the G and C, leaving a blunt end that terminates in a GG. In some alternatives, the endonuclease cleavage site is AGGCCT (SEQ ID NO: 633). In some alternatives, the endonuclease is StuI. In some alternatives, the plurality of adenines terminates in GG. In some alternatives, the StuI cleavage site is inverted. In some alternatives, the endonuclease recognition site is a BsaI restriction recognition site, and the endonuclease is BsaI. In some alternatives, the BsaI restriction recognition site is inverted. In some alternatives, the endonuclease cleavage site is located 1, 2, 3, 4, 5, 6, 7, 8, 9, 10, 11, 12, 13, 14, 15, 16, 17, 18, 19 or 20 base pairs away from the most 5' thymine (or 5' terminal thymine) in the plurality of thymine nucleotides. In some alternatives, the endonuclease cleavage site is located 1, 2, 3, 4, 5, 6, 7, 7, 8, 9 or 10 base pairs away from the most 5' thymine (or 5' terminal thymine) in the plurality of thymine nucleotides.

PCR Amplification

Polymerase chain reaction (PCR) is a technique used for many biological applications and involves the amplification of a single or several copies of a piece of a polynucleotide in order to generate thousands or millions of copies of a specific nucleic acid. PCR can result in multiple copies of DNA. PCR utilizes thermal cycling in which several cycles of heating and cooling of the reaction results in melting the template polynucleotide for replication, enzymatic replication, and amplification of copies of the polynucleotide resulting in thousands or millions of copies of the polynucleotide. The melting (90° C. to 105° C.), annealing (5° C. below the melting temperature of the primer), and amplification (70° C. to 74° C.) cycle can be repeated 12 to 35 times and is dependent on the stability of the polynucleotide template and primers. PCR can require a heat stable DNA polymerase, complimentary primers, and nucleotides. Nucleotides for PCR can be adenine, cytosine, guanine, thymine and/or uracil. DNA polymerases for PCR can be a thermal stable polymerase that can polymerize DNA at temperatures from 90° C. to 105° C. Thermal stable polymerases can include without limitation, Taq polymerases, fusion Taq polymerases comprising processivity enhancing domains, genetically engineered Taq enzymes for high fidelity and fast extension, as well as other heat stable polymerases known to those skilled in the art.

Fusion PCR can also be used to amplify a nucleic acid from a polynucleotide template. However, fusion PCR is also used to extend the amplified nucleic strand at either the 5' end or the 3' end, or for both ends of the nucleic acid by use of extended primers. Fusion PCR can be performed by using a 5'primer and a 3'primer, in which either the 5'primer, 3'primer or both have an extension of sequences as well as a site that is complimentary to the polynucleotide template for extension. For example, fusion PCR can be used to add an additional plurality of thymine nucleotides at the 3' end of a gene sequence.

Disclosed herein are methods for making a nucleic acid having a plurality of covalently linked thymine nucleotides (a poly(T) tract) and one or more of the aforementioned endonuclease recognition sites inserted therein or attached thereto, as well as, compositions comprising these polynucleotides and methods of use thereof. In some alternatives, the endonuclease recognition sites are inverted. In some alternatives, the endonuclease recognition sites comprise the endonuclease recognition sequences set forth in Table 1 (SEQ ID NOs: 18-632, 634-636). In some alternatives, the endonuclease recognition site is for the endonuclease AciI, MnlI, AlwI, BbvI, BccI, BceAI, BsmAI, BsmFI, BspCNI, BsrI, BtsCI, FokI, HgaI, HphI, HpyAV, MboII, MlyI, PleI, SfaNI, AcuI, BciVI, BfuAI, BmgBI, BmrI, BpmI, BpuEI, BsaI, BseRI, BsgI, BsmI, BspMI, BsrBI, BsrDI, BtgZI, BtsI, EarI, EciI, MmeI, NmeAIII, BbvCI, Bpu10I, BspQI, SapI, BaeI, BsaXI, CspCI, AfaI, AluBI, AspLEI, BscFI, Bsh1236I, BshFI, BshI, BsiSI, BsnI, Bsp143I, BspANI, BspFNI, BssMI, BstENII, BstFNI, BstHHI, BstKTI, BstMBI, BsuRI, CfoI, Csp6I, FaeI, FaiI, FnuDII, FspBI, GlaI, HapII, HinIII, R9529, Hsp92II, HspAI, MaeI, MaeII, MvnI, PalI, RsaNI, SetI, SgeI, Sse9I, Tru1I, Tru9I, TscI, TspEI, TthHB8I, XspI, AflI, AgsI, AspS9I, AsuC2I, AsuI, BcefI, BenI, BisI, BlsI, Bme1390I, Bme18I, BmrFI, BscGI, BseBI, BsiLI, BsiZI, BslFI, BsoMAI, BspNCI, Bst2UI, Bst71I, BstDEI, BstOI,BstSCI, CauII, CdiI, Cfr13I, Eco47I, EcoRII, FaqI, FinI, Fsp4HI, GluI, Hin4II, HpyF3I, ItaI, MaeIII, MspR9I, MvaI, NmuCI, Psp6I, PspPI, SatI, SinI, TscAI, VpaK11BI, AanI, AatI, AauI, Acc113I, Acc16I, AccB1I, AceIII, AcsI, AcvI, AcyI, AhlI, Alw21I, Alw44I, Ama87I, Aor51HI, AsiAI, AsnI, Asp718I, AspHI, AsuII, AsuNHI, AvaIII, AviII, BanIII, BauI, BbeI, BbrPI, BbuI, Bbv12I, BbvII, Bce83I, BeoI, BcuI, BfmI, BfrB1,BfrI, BlnI, BmcAI, BmeT110I, BmiI, BmuI, BmyI, Bpu14I, BpvUI, Bsa29I, BsaOI, BsbI, BscBI, BscCI, Bse118I, BseAI, BseCI, BseDI, BsePI, BseSI, BseX3I, Bsh1285I, BshNI, BshTI, BshVI, BsiCI, BsiHKCI, BsiMI, BsiQI, BsiXI, Bsp106I, Bsp119I, Bsp120I, Bsp13I, Bsp1407I, Bsp143II, Bsp19I, Bsp68I, BspA2I, BspCI, BspGI, BspLU11I, BspMAI, BspMII, BspOI, BspT104I, BspT107I, BspTI, BspXI, BssAI, BssHI, BssNAI, BssNI, BssT1I, Bst1107I, Bst98I, BstACI, BstAFI, BstAUI, Bst-BAI, BstC8I, BstDSI, BstH2I, BstHPI, BstNSI, BstSFI, BstSLI, BstSNI, BstX2I, BstZI, BsuTUI, BtuMI, BveI, CciI, Cfr10I, Cfr42I, Cfr9I, CfrI, Csp45I, CspAI, DinI, DrdII, DsaI, Ec1136II, EclXI, Eco105I, Eco130I, Eco147I, Eco24I, Eco32I, Eco47III, Eco52I, Eco72I, Eco88I, EcoICRI, EcoT14I, EcoT22I, EcoT38I, EgeI, EheI, ErhI, FauNDI, FbaI, FblI, FriOI, FunI, FunII, GdiII, GsaI, HaeI, HgiAI, Hin1I, HindII, Hpy178III, Hpy8I, Hsp92I, Kpn2I, Ksp22I, KspAI, KspI, MflI, MhlI, MlsI, MluNI, Mly113I, Mph1103I, MroI, MroNI, Msp20I, MspCI, MstI, MunI, MvrI, NgoAIV, NsbI, NspIII, NspV, PaeI, PagI, PauI, PceI, Pfl23II, PinAI, Ple19I, PmaCI, PshBI, Psp124BI, Psp1406I, PspAI, PspLI, PspN4I, PsuI, ReaI, SduI, Sfr274I, Sfr303I, SfuI, SgrBI, SlaI, SpaHI, SseBI, SspBI, SstI, SstII, SunI, TatI, Vha464I, VneI, XapI, XhoII, XmaCI, XmaIII, XmaJI, XmiI, ZhoI, Zsp2I, AocI, AxyI, Bpu1102I, Bse21I, Bsp1720I, BstPI, CelII, CpoI, CspI, DraII, Eco065I, Eco81I, Eco91I, EspI, KflI, LguI, MabI, PpuXI, Psp5II, PspEI, Rsr2I, SauI, AbsI, CciNI, FspAI, MauBI, MreI, MssI, RgaI, SdaI, SfaAI, SgfI, SmiI, Sse232I, AdeI, AspI, CaiI, PsyI, TelI, Asp700I, BoxI, Bse8I, BseJI, BsiBI, BsrBRI, BstPAI, CjeNII, MamI, MroXI, OliI, PdmI, RseI, SmiMI, AccB7I, AspEI, BasI, BmeRI, BplI, Bsc4I, BseLI, BsiYI, BstENI, BstMWI, CjeI, CjuI, CjuII, DriI, Eam1105I, EclHKI, FalI, HpyF10VI, NgoAVIII, NruGI, PflBI, UbaF14I, XagI, AasI, BdaI, Bsp24I, CjePI, DseDI, UbaF9I, ArsI, BarI, PcsI or UbaF13I. In some alternatives the Type IIS restriction endonuclease recognition site is inverted and the cleavage site is inverted. Without being limiting an endonuclease can include, for example, a CRISPR, a restriction endonuclease, a Type II restriction endonuclease and a Type IIS restriction endonuclease. In some alternatives, the endonuclease is a CRISPR, a restriction endonuclease, a Type II restriction endonuclease or a Type IIS restriction endonuclease. In some alternatives, the endonuclease is a CRISPR, a restriction endonuclease, a Type II restriction endonuclease or a Type IIS restriction endonuclease. In some alternatives, wherein StuI is provided, the endonuclease cleavage site is a StuI cleavage site, AGGCCT (SEQ ID NO: 633), and StuI cleaves between the G and C, leaving a blunt end that terminates in a GG. In some alternatives, the endonuclease cleavage site is AGGCCT (SEQ ID NO: 633). In some alternatives, the endonuclease is StuI. In some alternatives, the plurality of adenines terminates in GG. In some alternatives, the StuI cleavage site is inverted. In some alternatives, the endonuclease recognition site is a BsaI restriction recognition site, and the endonuclease is BSaI. In some alternatives, the BsaI restriction recognition site is inverted. In some alternatives, the endonuclease cleavage site is located 1, 2, 3, 4, 5, 6, 7, 7, 8, 9, 10, 11, 12, 13, 14, 15, 16, 17, 18, 19 or 20 base pairs away from the most 5' thymine (or 5' terminal thymine) in the plurality of thymine nucleotides. In some alternatives, the endonuclease cleavage site is located 1, 2, 3, 4, 5, 6, 7, 7, 8, 9 or 10 base pairs away from the most 5' thymine (or 5' terminal thymine) in the plurality of thymine nucleotides.

In some alternatives, the poly (T) tract in the nucleic acid can be extended by fusion PCR. In some alternatives, the poly (T) tract in the nucleic acid can be extended at the 5'end of the template strand by fusion PCR. In some alternatives, the poly (T) tract in the nucleic acid can be extended at the 3'end by fusion PCR. In some alternatives, the nucleic acid can be extended at the 5' and the 3'end by fusion PCR. In some alternatives, the nucleic acid can be extended by a plurality of thymine nucleotides at the 3'end by fusion PCR.

In more alternatives, a method of making a nucleic acid is contemplated, wherein said method comprises providing any of the polynucleotides described above, and contacting said polynucleotide with a polymerase in the presence of nucleotides. The method of making a polynucleotide comprising a sequence encoding a nuclease, a template strand, an endonuclease recognition site and an endonuclease cleavage site for an endonuclease inserted therein, wherein said template strand comprises a plurality of thymine nucleotides can comprise providing a first nucleic acid sequence encoding a nuclease, providing a second nucleic acid sequence comprising at least one endonuclease recognition site, providing a third nucleic acid sequence, wherein the third nucleic acid sequence comprises the template strand, wherein the template strand comprises a plurality of thymine nucleotides, wherein said plurality of thymine nucleotides comprises at least, greater than, equal to, or any number in between 20, 30, 40, 50, 60, 70, 80, 90, 100, 110, 120, 130, 140, 150, 175, 200, 225, 250, 275, 300, 325, 350, 375, 400, 425, 450, 475, 500 or 550 covalently linked thymine nucleotides and wherein the third nucleic acid comprises the endonuclease cleavage site, wherein the endonuclease cleavage site is located within the plurality of thymine nucleotides or within 1, 2, 3, 4, 5, 6, 7, 7, 8, 9, 10, 11, 12, 13, 14, 15, 16, 17, 18, 19 or 20 base pairs away from the most 5' thymine (or 5' terminal thymine) in the plurality of thymine nucleotides, joining said first nucleic acid to one end of the second nucleic acid sequence and joining said third nucleic acid sequence to one end of the second nucleic acid sequence, wherein said second nucleic acid is covalently linked to one end of said third nucleic acid sequence, and wherein the said endonuclease recognition site is located within 55 base pairs of the endonuclease cleavage site for the endonuclease and said endonuclease cleavage site is within 1 to 40 base pairs of a most 5' thymine in the plurality of thymine nucleotides. In some alternatives, the polynucleotide further comprises telomeres. In some alternatives, the polynucleotide is a linear cloning vector, wherein the linear cloning vector comprises a left telomere and at least one selectable marker, a right arm comprising a right telomere and at least one selectable marker, and a cloning region located between the left arm and the right Armin some alternatives, the polymerase is a DNA polymerase. In some alternatives, the DNA polymerase is a thermal stable polymerase, such as Taq polymerase. In some alternatives, the nucleotides are adenine, cytosine, guanine, thymine and/or uracil. In some alternatives, the method further comprises providing a set of primers. In some alternatives, the primers can have an extension sequence at the 5' end. In some alternatives, the primers can have an extension sequence at the 3' end. In some alternatives, the nucleic acid is DNA. In some alternatives, the polynucleotide comprises a DNA polymerase. In some alternatives, the polynucleotide further comprises a gene. In some alternatives the gene is 1-50 kb.

In some alternatives, the gene comprises at least, greater than, equal to, or any number in between 1, 5, 10, 20, 30, 40 or 50 Kb. In some alternatives, the mRNA comprises a poly A tail, wherein within said poly A tail there exists a sequence that is complimentary to an endonuclease site (on the single strand), such as StuI or BsaI site. A sequence complimentary to the endonuclease recognition site can reside in the mRNA if an endonuclease is not provided to cleave the polynucleotide before transcription. In some alternatives, the sequence is complimentary to an endonuclease recognition site set forth in Table 1 (SEQ ID NOs: 18-632, 634-636). In some alternatives, an mRNA comprising a plurality of adenine nucleotides is provided, wherein the mRNA comprises a first sequence comprising at least one compliment sequence to an endonuclease recognition site, a second nucleic acid sequence, wherein the second nucleic acid sequence comprises a plurality of adenine nucleotides, and wherein the first sequence is covalently linked to the second nucleic acid sequence at the 3' end of said plurality of adenine nucleotides. In some alternatives, the mRNA further encodes a gene. In some alternatives, the gene is an endonuclease gene, such as Cas9 or a derivative thereof or active fragment thereof, a TALEN, or MegaTAL, see e.g., SEQ ID. Nos. 6-14. In some alternatives, the at least one endonuclease site is inverted, and wherein the sequence encoding an RNA compliment is a compliment to the inverted endonuclease site. In some alternatives, the at least one endonuclease is a Type II restriction endonuclease recognition site. In some alternatives, the at least one endonuclease site is a Type IIS restriction endonuclease recognition site. In some alternatives, the at least one endonuclease site is a BsaI recognition site. In some alternatives, the at least one endonuclease site is a StuI recognition site. In some alternatives, the gene is codon optimized for expression in a mammalian cell, such as a human cell. In some alternatives, the sequence encoding an RNA compliment is a compliment to an endonuclease recognition site set forth in Table 1 (SEQ ID NOs: 18-632, 634-636). In some alternatives, the endonuclease recognition site as set forth in Table 1 (SEQ ID NOs: 18-632, 634-636) is an inverted sequence. In some alternatives, the RNA lacks a 5' and/or 3' UTR or lacks a native 5' and/or 3' UTR and/or lacks one or more sequences required for native polyadenylation such as, a cleavage/polyadenylation specificity factor (CPSF) binding site, a cleavage stimulation factor binding site (CstF), a cleavage factor I binding site (CFI), or a cleavage factor II binding site (CFII). Without being limiting an endonuclease can include, for example, a CRISPR, a restriction endonuclease, a Type II restriction endonuclease and a Type IIS restriction endonuclease. In some alternatives, the endonuclease is a CRISPR, a restriction endonuclease, a Type II restriction endonuclease or a Type IIS restriction endonuclease. In some alternatives, the endonuclease is a CRISPR, a restriction endonuclease, a Type II restriction endonuclease or a Type IIS restriction endonuclease. In some alternatives, wherein StuI is provided, the endonuclease cleavage site is a StuI cleavage site, AGGCCT (SEQ ID NO: 633), and StuI cleaves between the G and C, leaving a blunt end that terminates in a GG. In some alternatives, the endonuclease cleavage site is AGGCCT (SEQ ID NO: 633). In some alternatives, the endonuclease is StuI. In some alternatives, the plurality of adenines terminates in GG. In some alternatives, the StuI cleavage site is inverted. In some alternatives, the endonuclease recognition site is a BsaI restriction recognition site, and the endonuclease is BSaI. In some alternatives, the BsaI restriction recognition site is inverted. In some alternatives, the endonuclease cleavage site is located 1, 2, 3, 4, 5, 6, 7, 7, 8, 9, 10, 11, 12, 13, 14, 15, 16, 17, 18, 19 or 20 base pairs away from the most 5' thymine (or 5' terminal thymine) in the plurality of thymine nucleotides. In some alternatives, the endonuclease cleavage site is located 1, 2, 3, 4, 5, 6, 7, 7, 8, 9 or 10 base pairs away from the most 5' thymine (or 5' terminal thymine) in the plurality of thymine nucleotides.

In Vivo and In Vitro Transcription

In vitro and in vivo transcription can give the ability to synthesize RNA that is critical for many biological techniques. For example in vivo and in vitro transcription can generate radiolabeled and nonisotopically labeled RNA probes that can be used in blot hybridizations, nuclease protection assays, as well as RNA that can be used in translation to generate a specific protein.

In vitro transcription requires a purified linear DNA template containing an RNA polymerase promoter, ribonucleotide triphosphates or nucleotides, a buffer system that includes DTT and magnesium ions, and an appropriate RNA polymerase. The exact conditions used in the transcription reaction depend on the amount of RNA needed for a specific application. Basic laboratory protocols for in vitro transcription, as well as, commercial kits can be used in order to synthesize nucleic acid, for example RNA. Commercial kits for synthesizing RNA can include, for example, MEGAscript Kits (Life Technologies), TranscriptAid T7 High Yield Transcription Kit (Thermo Scientific), HiScribe and MiniV™ In vitro Transcription Kit (Epicentre). Other transcription kits can be used for making RNA and are known to those skilled in the art. The protocol for RNA generation can require linear polynucleotide templates of any length that possesses a RNA promoter region and preferably 1 to about 5 moles of nucleic acid or RNA can be produced per mole of polynucleotide template. RNA polymerases can include SP6 RNA polymerase, T7 RNA polymerase, N4 RNA polymerase II, and T3 RNA polymerases. Transcription of an RNA can be performed at a temperature at least, greater than, equal to, or any temperature in between 30° C., 31° C., 32° C., 33° C., 34° C., 35° C., 36° C. or 37° C. Transcription can also be performed for a time at least, greater than, equal to, or any time in between 0.5, 1, 2, 3, 5, 10, 20, 30, 40, 50, 60, 70, 80, 90, or 100 hours. In some alternatives, the RNA transcripts can be at least, greater than, equal to, or any size between 0.5, 1, 2, 3, 4, or 5 Kb. Use of a linear plasmid can stabilize the gene so that it is easily transcribed, especially if the gene has difficulty in cloning into supercoiled circular plasmids. In some alternatives, the RNA transcription can be stabilized at 30° C.-37° C. for at least 100 hours using the polynucleotide of any of the alternatives described herein for transcription. The RNA transcript or mRNA with an extended poly(A) tract can be used successfully for transfection, in which the mRNA is protected (e.g., capped) and can be sustained for in vivo translation. RNA transcribed from a polynucleotide can comprise a poly(A) tract terminating in a guanine, cytosine, or a uracil. While natural mRNA comprises a polyadenylation sequence in the 5'UTR and/or 3'UTR of every natural mRNA, a portion of which remains in the mRNA, the mRNAs made in accordance with the teachings described herein do not need and do not contain such 5'UTR and/or 3' UTR polyadenylation sequences. Accordingly, the mRNAs made in accordance with the teachings described herein are not naturally occurring mRNAs by virtue of the fact that they lack said 5'UTR and/or 3'UTR polyadenylation sequences. Furthermore, in several alternatives, guanylation or diguanylation is added to the poly(A) sequence, preferably at the terminal ends, which can provide extended stability and duration of expression. Additionally, some alternative mRNAs described herein are codon optimized for expression in humans and the alternative mRNAs described herein contain poly(A) tails that are longer than the naturally occurring mRNAs for the particular sequence. Thus, the mRNAs made in accordance with the teachings described herein are not naturally occurring mRNAs.

In some alternatives, the mRNAs may comprise a gene. In this aspect, many synthetic genes can be designed to increase their protein expression level. The design process of codon optimization can be to alter rare codons to codons known to increase maximum protein expression efficiency. In some embodiments, codon selection is described, wherein codon selection can be performed by using algorithms that are known to those skilled in the art to create synthetic genetic transcripts optimized for high protein yield. Programs containing algorithms for codon optimization are known to those skilled in the art. Programs can include, for example, OptimumGene™, GeneGPS® algorithms, etc.

Described herein are methods for making a nucleic acid having a polymer of covalently linked thymine nucleotides, which can be extended to a desired length by virtue of the presence of an endonuclease site within said polymer of covalently linked thymine nucleotides such that a poly(T) insert of a desired length can be ligated to the nucleic acid having the polymer of covalently linked thymine nucleotides and endonuclease site thereby extending the poly(T) tract to the desired length. Some alternatives include methods of making a polynucleotide having a plurality of thymine nucleotides and an endonuclease recognition site within 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 nucleotides or a number of nucleotides within a range defined by any two of the aforementioned values from the first thymine residue of a poly(T) domain but configured or spaced to permit enzymatic cleavage within the poly(T) domain. After enzymatic cleavage and ligation to a second polymer of thymine nucleotides this resultant nucleic acid can then be transcribed so as to generate an RNA having a poly(A) tract of the desired length, e.g., the length of the poly(T) polymer after ligation with a poly(T) insert. Accordingly, in some alternatives, the methods described herein can include the step of contacting a nucleic acid having a polymer of covalently linked thymine nucleotides, including a poly(T) insert positioned at an endonuclease cleavage site within the polymer of covalently linked thymine nucleotides or within 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 nucleotides or a number of nucleotides within a range defined by any two of the aforementioned values from the first thymine residue of a poly(T) domain with a polymerase in the presence of nucleotides. In some alternatives, said nucleic acid or polynucleotide further comprises a promoter for a DNA or RNA polymerase. In some alternatives, an RNA polymerase is used. In some alternatives, the RNA polymerase is SP6 RNA polymerase, T7 RNA polymerase, N4 RNA polymerase II, or T3 RNA polymerase. In some alternatives, the nucleotides are adenine, cytosine, guanine, thymine, and/or uracil. In some alternatives, the contacting is performed at a temperature at least, greater than, equal to, or any temperature in between 30° C., 31° C., 32° C., 33° C., 34° C., 35° C., 36° C. or 37° C. In some alternatives, the contacting is performed for at least, greater than, equal to, or time in between 1, 5, 10, 20, 30, 40, 50, 60, 70, 80, 90 or 100 hours (e.g., at least, or equal to 1, 5, 10, 20, 30, 40, 50, 60, 70, 80, 90 or 100 hours or within a range defined by any two of the aforementioned times). In some alternatives, the nucleic acid is RNA. In some alternatives, the RNA comprises at least, greater than, equal to, or any number in between 20, 30, 40, 50, 60, 70, 80, 90, 100, 110, 120, 130, 140, 150, 175, 200, 225, 250, 275, 300, 325, 350, 375, 400, 425, 450, 475 or 500 covalently linked adenines. In some alternatives, the RNA lacks a 5' and/or 3' UTR or lacks a native 5' and/or 3' UTR and/or lacks one or more sequences required for native polyadenylation such as, a cleavage/polyadenylation specificity factor (CPSF) binding site, a cleavage stimulation factor binding site (CstF), a cleavage factor I binding site (CFI), or a cleavage factor II binding site (CFII).

Disclosed herein are methods for stabilizing an RNA at 30° C.-37° C. during translation for at least 100 hours (e.g., at least, or equal to 1, 5, 10, 20, 30, 40, 50, 60, 70, 80, 90 or 100 hours or within a range defined by any two of the aforementioned times), the RNA generated from a polynucleotide having a plurality of covalently linked thymine nucleotides (a poly(T) tract) and one or more of the aforementioned endonuclease recognition sites inserted therein or attached thereto, as well as, compositions comprising these polynucleotides. Methods for stabilizing RNA during transcription can be performed for at least, greater than, equal to, or time in between 1, 5, 10, 20, 30, 40, 50, 60, 70, 80, 90 or 100 hours (e.g., at least, or equal to 1, 5, 10, 20, 30, 40, 50, 60, 70, 80, 90 or 100 hours or within a range defined by any two of the aforementioned times). In some alternatives, an mRNA comprises a poly A tail, wherein within said poly A tail there exists a sequence that is complimentary to an endonuclease recognition site (on the single strand), such as StuI or BsaI site. In some alternatives, a sequence that is complimentary to an endonuclease recognition site is an endonuclease recognition site set forth in Table 1 (SEQ ID Nos: 18-632, 634-636). In some alternatives, the recognition site is inverted. In some alternatives, the mRNA comprises a first sequence encoding an RNA compliment to the at least one endonuclease site (on the single strand), wherein the sequence encoding the RNA compliment is covalently linked to a second nucleic acid, wherein the second nucleic acid comprises a plurality of adenine nucleotides, and wherein said first sequence encoding an RNA compliment to at least one endonuclease site of said first nucleic acid is covalently linked to said the said second nucleic acid comprising the plurality of adenine nucleotides at the 3' end of said plurality of adenine nucleotides of said second nucleic acid. In some alternatives, the mRNA further comprises or encodes a gene. In some alternatives, the gene is codon optimized for expression in a mammalian cell, such as a human cell. In some alternatives, the gene is an endonuclease gene, such as Cas9, TALEN, or MegaTAL, see e.g., SEQ ID Nos. 6-14). In some alternatives, the at least one endonuclease site is inverted, and wherein the sequence encoding an RNA compliment is a compliment to the inverted endonuclease site (on the single strand). In some alternatives, the at least one endonuclease is a Type II restriction endonuclease recognition site. In some alternatives, the at least one endonuclease site is a Type IIS restriction endonuclease recognition site. In some alternatives, the at least one endonuclease site is a BsaI recognition site. In some alternatives, the at least one endonuclease recognition site is a StuI recognition site. In some alternatives, the at least one endonuclease recognition site is an endonuclease recognition site for an endonuclease as set forth in Table 1 (SEQ ID Nos: 18-632, 634-636). In some alternatives, the RNA lacks a 5' and/or 3' UTR or lacks a native 5' and/or 3' UTR and/or lacks one or more sequences required for native polyadenylation such as, a cleavage/polyadenylation specificity factor (CPSF) binding site, a cleavage stimulation factor binding site (CstF), a cleavage factor I binding site (CFI), or a cleavage factor II binding site (CFII). Without being limiting an endonuclease can include, for example, a CRISPR, a restriction endonuclease, a Type II restriction endonuclease and a Type IIS restriction endonuclease. In some alternatives, the endonuclease is a CRISPR, a restriction endonuclease, a Type II restriction endonuclease or a Type IIS restriction endonuclease. In some alternatives, the endonuclease is a CRISPR, a restriction endonuclease, a Type II restriction endonuclease or a Type IIS restriction endonuclease. In some alternatives, wherein StuI is provided, the endonuclease cleavage site is a StuI cleavage site, AGGCCT (SEQ ID NO: 633), and StuI cleaves between the G and C, leaving a blunt end that terminates in a GG. In some alternatives, the endonuclease cleavage site is AGGCCT (SEQ ID NO: 633). In some alternatives, the endonuclease is StuI. In some alternatives, the plurality of adenines terminates in GG. In some alternatives, the StuI cleavage site is inverted. In some alternatives, the endonuclease recognition site is a BsaI restriction recognition site, and the endonuclease is BSaI. In some alternatives, the BsaI restriction recognition site is inverted.

The method can comprise providing the polynucleotide of any of the alternatives described herein and contacting said nucleic acid with a ribosome, in the presence of amino acids and tRNAs, wherein said RNA is stable at 30-37 degrees Celsius for at least 100 hours (e.g., at least, or equal to 1, 5, 10, 20, 30, 40, 50, 60, 70, 80, 90 or 100 hours or within a range defined by any two of the aforementioned times). In some alternatives, the polynucleotide further comprises an RNA polymerase promoter. In some alternatives, the contacting is performed at a temperature equal to 37° C. In some alternatives, the contacting is performed for at least, greater than, equal to, or time in between 1, 5, 10, 20, 30, 40, 50, 60, 70, 80, 90 or 100 hours (e.g., at least, or equal to 1, 5, 10, 20, 30, 40, 50, 60, 70, 80, 90 or 100 hours or within a range defined by any two of the aforementioned times). In some alternatives, the RNA comprises at least, greater than, equal to, or any number in between 20, 30, 40, 50, 60, 70, 80, 90, 100, 110, 120, 130, 140, 150, 175, 200, 225, 250, 275, 300, 325, 350, 350, 375, 400, 425, 450, 475 or 500 covalently linked adenines. In some alternatives, the polynucleotide further comprises a gene. In some alternatives the gene is 1-50 kb. In some alternatives, the gene comprises at least, greater than, equal to, or any number in between 1, 5, 10, 20, 30, 40 or 50 Kb. In some alternatives, the mRNA comprises a poly A tail, wherein within said poly A tail there exists a sequence that is complimentary to an endonuclease site (on the single strand) such as StuI or BsaI site. In some alternatives, within said poly A tail there exists a sequence that is complimentary to an endonuclease recognition site as set forth in Table 1 (SEQ ID Nos: 18-632, 634-636). In some alternatives, the sequence that is complimentary to an endonuclease recognition site is complimentary to the inverted endonuclease recognition site. In some alternatives, the mRNA comprises a first sequence encoding an RNA compliment to the at least one endonuclease site (on the single strand), wherein the sequence encoding the RNA compliment is covalently linked to a plurality of adenine nucleotides at the 3' end of said plurality of adenine nucleotides. In some alternatives, the mRNA further comprises or encodes a gene. In some alternatives, the gene is codon optimized for expression in a mammalian cell, such as a human cell. In some alternatives, the gene is an endonuclease gene, such as Cas9 a derivative thereof or active fragment thereof, TALEN, or MegaTAL e.g., SEQ ID NOs. 6-14. In some alternatives, the at least one endonuclease site is inverted, and wherein the sequence encoding an RNA compliment is a compliment to the inverted endonuclease recognition site. In some alternatives, the inverted endonuclease recognition site is an endonuclease recognition site set forth in the sequences in Table 1 (SEQ ID Nos: 18-632, 634-636). In some alternatives, the at least one endonuclease is a Type II restriction endonuclease recognition site. In some alternatives, the at least one endonuclease site is a Type IIS restriction endonuclease recognition site. In some alternatives, the at least one endonuclease site is a BsaI recognition site. In some alternatives, the at least one endonuclease site is a StuI recognition site. In some alternatives, the RNA lacks a 5' and/or 3' UTR or lacks a native 5' and/or 3' UTR and/or lacks one or more sequences required for native polyadenylation such as, a cleavage/polyadenylation specificity factor (CPSF) binding site, a cleavage stimulation factor binding site (CstF), a cleavage factor I binding site (CFI), or a cleavage factor II binding site (CFII). Without being limiting an endonuclease can include, for example, a CRISPR, a restriction endonuclease, a Type II restriction endonuclease and a Type IIS restriction endonuclease. In some alternatives, the endonuclease is a CRISPR, a restriction endonuclease, a Type II restriction endonuclease or a Type IIS restriction endonuclease. In some alternatives, the endonuclease is a CRISPR, a restriction endonuclease, a Type II restriction endonuclease or a Type IIS restriction endonuclease. In some alternatives, wherein StuI is provided, the endonuclease cleavage site is a StuI cleavage site, AGGCCT (SEQ ID NO: 633), and StuI cleaves between the G and C, leaving a blunt end that terminates in a GG. In some alternatives, the endonuclease cleavage site is AGGCCT (SEQ ID NO: 633). In some alternatives, the endonuclease is StuI. In some alternatives, the plurality of adenines terminates in GG. In some alternatives, the StuI cleavage site is inverted. In some alternatives, the endonuclease recognition site is a BsaI restriction recognition site, and the endonuclease is BSaI. In some alternatives, the BsaI restriction recognition site is inverted.

Translation

Synthesis of proteins can be performed in vitro as well as in vivo. For in vivo synthesis, the proteins can be synthesized in prokaryotic or eukaryotic cells. Synthesis of proteins in vivo can be controlled by the length of the poly(A) tail of the mRNA, which can increase the half-life of the mRNA ensuring translation of a higher concentration of protein. An mRNA with a protected 3'end can be sufficient for transfection and sustained in vivo translation. In normal growth conditions, an mRNA with a stably maintained poly(A) tract can be sufficient for translation at 30° C. to 37° C. for at least, greater than, equal to, or time in between 1, 5, 10, 20, 30, 40, 50, 60, 70, 80, 90 or 100 hours (e.g., at least, or equal to 1, 5, 10, 20, 30, 40, 50, 60, 70, 80, 90 or 100 hours or within a range defined by any two of the aforementioned times).

The in vitro synthesis of proteins in cell-free extracts is an important tool for molecular biologists and has a variety of applications, including the rapid identification of gene products, localization of mutations through synthesis of truncated gene products, protein folding studies, and incorporation of modified or unnatural amino acids for functional studies. The use of in vitro translation systems can have advantages over in vivo gene expression when the overexpressed product is toxic to the host cell, when the product is insoluble or forms inclusion bodies, or when the protein undergoes rapid proteolytic degradation by intracellular proteases. In principle, it should be possible to prepare a cell-free extract for in vitro translation of mRNAs from any type of cells. In practice, only a few cell-free systems have been developed for in vitro protein synthesis.

In vitro translation systems can be performed by using treated cellular lysates in which the machinery for translation are used to translate a protein from a purified mRNA, and can include treated bacterial lysate (i.e, E. coli cell free systems), wheat germ extract, rabbit reticulocyte lysate, or even a commercially available lysate treated specifically for in vitro translation, for example. Kits for translation can include, Retic Lysate IVT™ (Life Technologies), 1-Step Human In vitro Translation System (Thermo Scientific), and other kits that are known to those skilled in the art. Additionally, there are also coupled in vitro transcription/translation kits that can be used to produce protein from a starting point of a DNA. Treated cellular lysate for in vitro translation must contain essential components of the cellular translational machinery, such as the ribosomes, initiation and elongation factors, tRNAs and other basic components required for protein synthesis, that are known to those skilled in the art. In some alternatives, the translation is performed with an in vitro system. The in vitro system can comprise ribosomes, initiation and elongation factors, tRNAs and other basic components required for protein synthesis, such as, for example, amino acids. When supplemented with proprietary accessory proteins, ATP, and an energy regenerating system, the treated cellular extracts can sustain synthesis of target proteins from the mRNA templates for up to 6 to 100 hours without the need to remove inhibitory byproducts. The methods for in vitro translation can be performed at temperatures between 30° C. to 37° C. However the efficiency of translation can also depend upon the length of the mRNA, the mRNA cap, as well as the poly(A) tail. Efficiency of translation can depend on the poly(A) tail length in which a poly (A) tail of 75 to 300 covalently linked adenines both in vivo and in vitro.

Disclosed herein are methods for increasing expression of a protein from an mRNA generated from a polynucleotide having a plurality of covalently linked thymine nucleotides (a poly(T) tract) and one or more of the aforementioned endonuclease recognition sites inserted therein or attached thereto, as well as, compositions comprising these polynucleotides. The method comprises generating an mRNA from the polynucleotide of any of the alternatives described herein, and translating said mRNA into a peptide. In some alternatives, the mRNA comprises a poly A tail, wherein within said poly A tail there exists a sequence that is complimentary to an endonuclease site (on the single strand), such as StuI or BsaI site. In some alternatives, the at least one endonuclease recognition site is an endonuclease recognition site for an endonuclease as set forth in Table 1 (SEQ ID Nos: 18-632, 634-636). In some alternatives, the mRNA comprises a first sequence encoding an RNA compliment to the at least one endonuclease site (on the single strand), wherein the sequence encoding the RNA compliment is covalently linked to a plurality of adenine nucleotides at the 3' end of said plurality of adenine nucleotides In some alternatives, the mRNA further comprises a gene. In some alternatives, the gene is codon optimized for expression in a mammalian cell, such as a human cell. In some alternatives, the gene is an endonuclease gene, such as Cas9 a derivative thereof or active fragment thereof, TALEN, or MegaTAL e.g., SEQ ID NOs. 6-14. In some alternatives, the at least one endonuclease site is inverted, and wherein the sequence encoding an RNA compliment is a compliment to the inverted endonuclease site. In some alternatives, the at least one endonuclease is a Type II restriction endonuclease recognition site. In some alternatives, the at least one endonuclease site is a Type IIS restriction endonuclease recognition site. In some alternatives, the at least one endonuclease site is a BsaI recognition site. In some alternatives, the at least one endonuclease site is a StuI recognition site. In some alternatives, the at least one endonuclease recognition site is an endonuclease recognition site for an endonuclease as set forth in Table 1 (SEQ ID Nos: 18-632, 634-636). In some alternatives, the polynucleotide further comprises an RNA polymerase promoter. In some alternatives, the translating is performed at a temperature at least, greater than, equal to, or any temperature in between 30° C., 31° C., 32° C., 33° C., 34° C., 35° C., 36° C. or 37° C. In some alternatives, the translating is performed for at least, greater than, equal to, or time in between 1, 5, 10, 20, 30, 40, 50, 60, 70, 80, 90 or 100 hours (e.g., at least, or equal to 1, 5, 10, 20, 30, 40, 50, 60, 70, 80, 90 or 100 hours or within a range defined by any two of the aforementioned times). In some alternatives, the mRNA comprises at least, greater than, equal to, or any number in between 20, 30, 40, 50, 60, 70, 80, 90, 100, 110, 120, 130, 140, 150, 175, 200, 225, 250, 275, 300, 325, 350, 350, 375, 400, 425, 450, 475 or 500 covalently linked adenines. In some alternatives, the polynucleotide further comprises a gene. In some alternatives the gene is 1-50 kb. In some alternatives, the method is performed in vivo. In some alternatives, the method is performed in vitro. In some alternatives, translation is performed in bacterial cells. In some alternatives, translation is performed in eukaryotic cells. In some alternatives, the translation is performed in mammalian cells. In some alternatives, the translation is performed in human cells. In some alternatives, the translation is performed in human CD34+ hematopoietic cells. In some alternatives, the translation is performed in human primary T-cells. In some alternatives, the endonuclease is a CRISPR, a restriction endonuclease, a Type II restriction endonuclease or a Type IIS restriction endonuclease. In some alternatives, wherein StuI is provided, the endonuclease cleavage site is a StuI cleavage site, AGGCCT (SEQ ID NO: 633), and StuI cleaves between the G and C, leaving a blunt end that terminates in a GG. In some alternatives, the endonuclease cleavage site is AGGCCT (SEQ ID NO: 633). In some alternatives, the endonuclease is StuI. In some alternatives, the plurality of adenines terminates in GG. In some alternatives, the StuI cleavage site is inverted. In some alternatives, the endonuclease recognition site is a BsaI restriction recognition site, and the endonuclease is BSaI. In some alternatives, the BsaI restriction recognition site is inverted.

Therapeutic mRNA

There are many ways of introducing a nucleic acid into a cell. Transfection is a method of introducing a nucleic acid into a cell. A nucleic acid can be introduced into eukaryotic cells by viral and non-viral methods. Genetic material, such as, supercoiled plasmid DNA, siRNA constructs, and mRNA can be used for transfection. Without being limiting, examples of chemical based transfection methods can be performed using Lipfectamine®, cyclodextrin, polymers, liposomes, nanoparticles, calcium phosphate co-precipitation, diethylaminoethyl-dextran, DEAE-dextran, polyethylenimine or cationic lipid-based transfection reagents. Without being limiting, examples of non-chemical methods of transfection can include electroporation, cell squeezing, hydrodynamic delivery, optical transfection, and sonoporation. As such, there are numerous ways for introducing a nucleic acid into a cell, however there are limitations to many of these protocols.

The delivery of naked DNA into a cell can have several drawbacks, such as integration, as well as, being toxic to a cell. The use of viral particles to deliver DNA can also have the disadvantages of integration mutagenesis, as well as, introducing repetitive elements. However the use of RNA for transfection, such as a modified RNA comprising a poly(A) tail of controlled length can have the desired feature of being able to be introduced to a cell for controlled translation of a protein without integrating into the cell genome or having the toxicity effects like DNA. Additionally as the poly(A) tail controls degradation, the mRNA can be used for a controlled duration.

Messenger RNA (mRNA) plays a fundamental and integral role in every living cell as mRNAs are carriers of genetic information and blueprints for proteins during translation. mRNA allows transient protein expression in all cell types and has many advantages especially over DNA for gene transfer and expression of target molecules. mRNA doesn't require nuclear localization or transcription and is therefore a very safe biomolecule. Additionally, mRNA provides enormous flexibility with respect to production and application because any protein with a known sequence can be encoded and expressed.

mRNAs are currently being investigated as a novel class of therapeutic in areas such as cancer vaccines, prophylactic vaccinations for infectious diseases, and as a source of therapeutic gene products and protein replacement therapies.

mRNA can be applied as a gene delivery molecule, or therapeutic mRNA in the field of cancer immunotherapy and stem cell-based biomedical research as an alternative to plasmid DNA. mRNA has several advantages, such as lack of requirement for nuclear entry, which poses a significant barrier to DNA delivery, especially in non-dividing cells. mRNA also does not integrate into the host genome, avoiding aberrant transcription and expression of oncogenes caused by insertional mutagenesis. Delivering DNA into a cell can also be more toxic than the delivery of mRNA.

However naked mRNA molecules in earlier studies were shown to be not efficient in inducing maturation of antigen-presenting cells or in having an increase in translation of a specific gene. However, mRNA that is protected efficiently can prevent or slow down against RNase-mediated degradation. As described, the use of a stabilized mRNA that can be easily produced can be utilized as a therapeutic mRNA for protein production. As a drug, a stabilized mRNA can supply the biological instructions for producing a protein inside cells, particularly for a person having a genetic disorder. Therapeutic mRNA would also be more efficient than DNA-based gene therapy (which would require the cells to make their own mRNA intermediary before producing a protein) and more effective than recombinant protein therapy.

Therapeutic mRNA can be used for expression of endonucleases, end-processing enzymes and fusion proteins having endonuclease and end-processing activity. Nucleases are enzymes capable of cleaving the phosphodiester bonds between the nucleotide subunits of nucleic acids. Examples of nucleases can include but are not limited to Cas9 (e.g., SEQ ID NOs. 6-14), TALEN and MegaTAL. Cas9 (CRISPR associated protein 9) is an RNA-guided DNA endonuclease enzyme associated with the CRISPR (Clustered Regularly Interspersed Palindromic Repeats) adaptive immunity system in bacteria, for example, *Streptococcus pyogenes*, among other bacteria. *S. pyogenes* can utilize Cas9 to memorize and later interrogate and cleave foreign DNA, such as invading bacteriophage DNA or plasmid DNA. Cas9 performs this interrogation by unwinding foreign DNA and checking for if it is complementary to the 20 basepair spacer region of the guide RNA. Transcription activator-like effector nucleases (TALENs) are artificial restriction enzymes generated by fusing a TAL effector DNA-binding domain to a DNA cleavage domain. MegaTAL is a fusion of a meganuclease with a TAL effector, is a new class of DNA targeting endonucleases with higher activity and specificity. Therapeutic mRNA can be introduced into a cell and the cell can be administered directly to a patient for targeted cleavage of a DNA sequence and for therapeutic or prophylactic applications, for example, cancer, ischemia, diabetic retinopathy, macular degeneration, rheumatoid arthritis, psoriasis, HIV infection, sickle cell anemia, Alzheimer's disease, muscular dystrophy, neurodegenerative diseases, vascular disease, cystic fibrosis, stroke, hyper IGE syndrome, or hemophilia. In some alternatives, compositions comprising therapeutic mRNA are provided. In some alternatives, the compositions described herein (e.g., therapeutic mRNA encoding endonucleases, end-processing enzymes and fusion proteins having endonuclease and end-processing activity) can be used in methods of treating, preventing, ameliorating, or inhibiting a disease (e.g., cancer, ischemia, diabetic retinopathy, macular degeneration, rheumatoid arthritis, psoriasis, HIV infection, sickle cell anemia, Alzheimer's disease, muscular dystrophy, neurodegenerative diseases, vascular disease, cystic fibrosis, stroke, hyper IGE syndrome, or hemophilia) or ameliorating a disease condition or symptom associated with a disease, such as, cancer, ischemia, diabetic retinopathy, macular degeneration, rheumatoid arthritis, psoriasis, HIV infection, sickle cell anemia, Alzheimer's disease, muscular dystrophy, neurodegenerative diseases, vascular disease, cystic fibrosis, stroke, hyper IGE syndrome, or hemophilia. In some alternatives, therapeutic mRNA encoding endonucleases, end-processing enzymes or fusion proteins having endonuclease and end-processing activity, are administered to treat, prevent, ameliorate, or inhibit an autosomal dominant disease, such as achondroplasia, pseudoachondroplasia, the multiple epiphyseal dysplasias, chondrodysplasias, osteogenesis imperfecta, Marfan syndrome, polydactyly, hereditary motor sensory neuropathies I and II (Charcot-Marie-Tooth disease), myotonic dystrophy, or neurofibromatosis or ameliorate a disease condition or symptom associated with an autosomal dominant disease, such as achondroplasia, pseudoachondroplasia, the multiple epiphyseal dysplasias, chondrodysplasias, osteogenesis imperfecta, Marfan syndrome, polydactyly, hereditary motor sensory neuropathies I and II (Charcot-Marie-Tooth disease), myotonic dystrophy, or neurofibromatosis. In some alternatives, therapeutic mRNA encoding endonucleases, end-processing enzymes or fusion proteins having endonuclease and end-processing activity, are introduced into cells. In some alternatives, the cells are administered to treat, prevent, ameliorate, or inhibit a disease caused by misregulation of genes. In some alternatives, therapeutic mRNA encoding endonucleases, end-processing enzymes or fusion proteins having endonuclease and end-processing activity, are administered to treat, prevent, or inhibit a cancer, such as BCL-2, Bcl-XI, and FLIP, or ameliorate a disease condition or symptom associated with a cancer, such as BCL-2, Bcl-XI, and FLIP, by, for example, increasing the mutation rate of genes with anti-apoptotic activity.

In some alternatives, a composition is provided, wherein the composition comprises a therapeutic RNA of any of the alternatives described herein and a pharmaceutical vehicle. In some alternatives, a composition is delivered to a subject in need.

In some alternatives, the mRNA comprises a poly A tail, wherein within said poly A tail or juxtaposed thereto there exists a sequence that is complimentary to an endonuclease site (on the single strand), such as StuI or BsaI site. In some alternatives, the at least one endonuclease recognition site is an endonuclease recognition site for an endonuclease as set forth in Table 1 (SEQ ID NOs: 18-632, 634-636). In some alternatives, the mRNA comprises a first sequence encoding an RNA compliment to the at least one endonuclease recognition site (on the single strand), wherein the sequence encoding the RNA compliment is covalently linked to a plurality of adenine nucleotides at the 3' end of said plurality of adenine nucleotides. In some alternatives, the mRNA further comprises a gene. In some alternatives, the gene is codon optimized for expression in a mammalian cell, such as a human cell. In some alternatives, the gene is an endonuclease gene, such as Cas9 or a derivative thereof or active fragment thereof, TALEN, or MegaTAL e.g., SEQ ID NOs. 6-14). In some alternatives, the at least one endonuclease recognition site is inverted, and wherein the sequence encoding an RNA compliment is a compliment to the inverted endonuclease recognition site. In some alternatives, the at least one endonuclease recognition site is an endonuclease recognition site for an endonuclease as set forth in Table 1 (SEQ ID NOs: 18-632, 634-636). In some alternatives, the at least one endonuclease recognition site is an endonuclease recognition site for an endonuclease as set forth in Table 1 (SEQ ID NOs: 18-632, 634-636), and the recognition site is inverted. In some alternatives, the at least one endonuclease is a Type II restriction endonuclease recognition site. In some alternatives, the at least one endonuclease site is a Type IIS restriction endonuclease recognition site. In some alternatives, the at least one endonuclease site is a BsaI recognition site. In some alternatives, the at least one endonuclease site is a StuI recognition site. Without being limiting an endonuclease can include, for example, a CRISPR, a restriction endonuclease, a Type II restriction endonuclease and a Type IIS restriction endonuclease. In some alternatives, the endonuclease is a CRISPR, a restriction endonuclease, a Type II restriction endonuclease or a Type IIS restriction endonuclease. In some alternatives, the endonuclease is a CRISPR, a restriction endonuclease, a Type II restriction endonuclease or a Type IIS restriction endonuclease. In some alternatives, wherein StuI is provided, the endonuclease cleavage site is a StuI cleavage site, AGGCCT (SEQ ID NO: 633), and StuI cleaves between the G and C, leaving a blunt end that terminates in a GG. In some alternatives, the endonuclease cleavage site is AGGCCT (SEQ ID NO: 633). In some alternatives, the endonuclease is StuI. In some alternatives, the plurality of adenines terminates in GG. In some alternatives, the StuI cleavage site is inverted. In some alternatives, the endonuclease recognition site is a BsaI restriction recognition site, and the endonuclease is BSaI. In some alternatives, the BsaI restriction recognition site is inverted.

Disclosed herein are methods for making an nucleic acid for therapy, the nucleic acid generated from a polynucleotide having a plurality of covalently linked thymine nucleotides (a poly(T) tract) and one or more of the aforementioned endonuclease recognition sites inserted therein or attached thereto, as well as, compositions comprising these polynucleotides are alternatives. In some alternatives, the nucleic acid is suitable or configured for therapy and such constructs are administered to a subject in need. In some alternatives, the nucleic acid comprises a gene. In some alternatives, the gene encodes a protein having therapeutic efficacy. In some alternatives, the subject suffers from a genetic disorder or is in need of a vaccine. In some alternatives, the subject suffers from cancer or a viral disease. In some alternatives, the nucleic acid is administered by a gene delivery molecule, such as a viral plasmid, electroporation or both. In some alternatives, the nucleic acid is mRNA or a DNA vaccine. In some alternatives, the mRNA is a therapeutic mRNA for therapy. In some alternatives, the mRNA comprises a poly A tail, wherein within said poly A tail there exists a sequence that is complimentary to an endonuclease recognition site (on the single strand) such as StuI or BsaI site. In some alternatives, the sequence that is complimentary to an endonuclease recognition site is an endonuclease recognition site for an endonuclease as set forth in Table 1 (SEQ ID NOs: 18-632, 634-636). In some alternatives, the sequence that is complimentary to an endonuclease recognition site is an endonuclease recognition site for an endonuclease as set forth in Table 1 (SEQ ID NOs: 18-632, 634-636) and is inverted. In some alternatives, the endonuclease is a CRISPR, a restriction endonuclease, a Type II restriction endonuclease or a Type IIS restriction endonuclease. In some alternatives, wherein StuI is provided, the endonuclease cleavage site is a StuI cleavage site, AGGCCT (SEQ ID NO: 633), and StuI cleaves between the G and C, leaving a blunt end that terminates in a GG. In some alternatives, the endonuclease cleavage site is AGGCCT (SEQ ID NO: 633). In some alternatives, the endonuclease is StuI. In some alternatives, the plurality of adenines terminates in GG. In some alternatives, the StuI cleavage site is inverted. In some alternatives, the endonuclease recognition site is a BsaI restriction recognition site, and the endonuclease is BSaI. In some alternatives, the BsaI restriction recognition site is inverted.

In some alternatives, the mRNA comprises a plurality of adenine nucleotides, wherein the mRNA comprises a first sequence comprising at least one compliment sequence to an endonuclease recognition site covalently linked to a plurality of adenine nucleotides at the 3' end of said plurality of adenine nucleotides. In some alternatives, the mRNA further encodes a gene. In some alternatives, the gene is an endonuclease gene, such as Cas9, a derivative thereof or active fragment thereof, TALEN, or MegaTAL e.g., SEQ ID NOs. 6-14. In some alternatives, the at least one endonuclease site is inverted, and wherein the sequence encoding an RNA compliment is a compliment to the inverted endonuclease site. In some alternatives, the sequence that is complimentary to an endonuclease recognition site is an endonuclease recognition site for an endonuclease as set forth in Table 1 (SEQ ID NOs: 18-632, 634-636). In some alternatives, the sequence that is complimentary to an endonuclease recognition site is an endonuclease recognition site for an endonuclease as set forth in Table 1 (SEQ ID NOs: 18-632, 634-636) and is inverted. In some alternatives, the at least one endonuclease recognition site is a Type II endonuclease recognition site. In some alternatives, the at least one endonuclease recognition site is a Type IIS restriction endonuclease recognition site. In some alternatives, the at least one endonuclease recognition site is a BsaI recognition site. In some alternatives, the at least one endonuclease recognition site is a StuI recognition site. In some alternatives, the gene is codon optimized for expression in a mammalian cell, such as a human cell. In some alternatives, the endonuclease is a CRISPR, a restriction endonuclease, a Type II restriction endonuclease or a Type IIS restriction endonuclease. In some alternatives, wherein StuI is provided, the endonuclease cleavage site is a StuI cleavage site, AGGCCT (SEQ ID NO: 633), and StuI cleaves between the G and C, leaving a blunt end that terminates in a GG. In some alternatives, the endonuclease cleavage site is AGGCCT (SEQ ID NO: 633). In some alternatives, the endonuclease is StuI. In some alternatives, the plurality of adenines terminates in GG. In some alternatives, the StuI cleavage site is inverted. In some alternatives, the endonuclease recognition site is a BsaI restriction recognition site, and the endonuclease is BSaI. In some alternatives, the BsaI restriction recognition site is inverted.

Additional alternatives include a polynucleotide comprising a template strand, an endonuclease recognition site and an endonuclease cleavage site for an endonuclease inserted therein. The polynucleotide can comprise a first nucleic acid sequence encoding a nuclease, a second nucleic acid sequence comprising at least one restriction endonuclease recognition site and a third nucleic acid sequence, wherein the third nucleic acid sequence comprises the template strand, wherein said plurality of thymine nucleotides comprises at least, greater than, equal to, or any number in between 20, 30, 40, 50, 60, 70, 80, 90, 100, 110, 120, 130, 140, 150, 175, 200, 225, 250, 275, 300, 325, 350, 375, 400, 425, 450, 475, 500 or 550 covalently linked thymine nucleotides and wherein the third nucleic acid comprises the restriction endonuclease cleavage site, wherein the restriction endonuclease cleavage site is located within the plurality of thymine nucleotides or within 1, 2, 3, 4, 5, 6, 7, 7, 8, 9, 10, 11, 12, 13, 14, 15, 16, 17, 18, 19 or 20 base pairs away from the most 5' thymine (or 5' terminal thymine) in the plurality of thymine nucleotides and wherein said second nucleic acid is covalently linked to one end of said third nucleic acid sequence, and wherein the said restriction endonuclease recognition site is located within 55 base pairs of the restriction endonuclease cleavage site for the restriction endonuclease and said restriction endonuclease cleavage site is within 1 to 40 base pairs of a most 5' thymine in the plurality of thymine nucleotides. In some alternatives, the polynucleotide further comprises telomeres. In some alternatives, the polynucleotide comprises a left arm wherein the left arm comprises a left telomere, a right arm wherein the right arm comprises a right telomere and a cloning region located between the left arm and the right arm. In some alternatives, the polynucleotide further comprises a fifth nucleic acid, wherein the fifth nucleic acid comprises a gene. In some alternatives, the gene encodes a protein for therapy. In some alternatives, the gene encodes a nuclease. In some alternatives, the nuclease is an endonuclease. In some alternatives, the nuclease comprises an amino acid sequence set forth in SEQ ID NO. 6 or is encoded by a nucleic acid sequence set forth in SEQ ID NO: 7-14. In some alternatives, the polynucleotide plurality of thymine nucleotides comprises at least, greater than, equal to, or any number in between 20, 30, 40, 50, 60, 70, 80, 90, 100, 110, 120, 130, 140, 150, 175, 200, 225, 250, 275, 300, 325, 350, 375, 400, 425, 450, 475, or 500 covalently linked thymines. In some alternatives, the number of covalently linked thymines is greater than 120. In some alternatives, the number of covalently linked thymines is greater than 200. In some alternatives, the number of covalently linked thymines is greater than 300. In some alternatives, the at least one endonuclease recognition site is a Type II restriction endonuclease recognition site, and the endonuclease is a Type II restriction endonuclease. In some alternatives, the at least one endonuclease recognition site is a Type IIS restriction endonuclease recognition site and wherein the endonuclease is a Type IIS restriction endonuclease. In some alternatives, the at least one Type II endonuclease recognition site is a BsaI restriction endonuclease recognition site or a StuI restriction endonuclease recognition site, and wherein the endonuclease is BsaI or StuI. In some alternatives, the endonuclease recognition site is inverted. In some alternatives, the polynucleotide is a linear polynucleotide. In some alternatives, the polynucleotide has only one BsaI restriction endonuclease recognition site. In some alternatives, the polynucleotide further comprises a DNA polymerase promoter region. In some alternatives, the polynucleotide further comprises an RNA polymerase promoter region. In some alternatives, the plurality of thymine nucleotides comprises at least one covalently linked guanine, cytosine, or an adenine, wherein the at least one covalently linked guanine, cytosine or adenine is optionally joined to the most 5' thymine (or 5' terminal thymine) in the plurality of thymine nucleotides. In some alternatives, the endonuclease cleavage site comprises at least one guanine, cytosine, or an adenine, wherein the endonuclease cleaves between a thymine and the at least one guanine, cytosine or an adenine. In some alternatives, the polynucleotide further comprises at least one palindromic sequence, wherein the at least one palindromic sequence can form a hairpin. In some alternatives, the polynucleotide further comprises a sixth sequence, wherein the sixth sequence is capable of forming a tertiary structure such as a hairpin. Without being limiting an endonuclease can include, for example, a CRISPR, a restriction endonuclease, a Type II restriction endonuclease and a Type IIS restriction endonuclease. In some alternatives, the endonuclease is a CRISPR, a restriction endonuclease, a Type II restriction endonuclease or a Type IIS restriction endonuclease. In some alternatives, the endonuclease is a CRISPR, a restriction endonuclease, a Type II restriction endonuclease or a Type IIS restriction endonuclease. In some alternatives, wherein StuI is provided, the endonuclease cleavage site is a StuI cleavage site, AGGCCT (SEQ ID NO: 633), and StuI cleaves between the G and C, leaving a blunt end that terminates in a GG. In some alternatives, the endonuclease cleavage site is AGGCCT (SEQ ID NO: 633). In some alternatives, the endonuclease is StuI. In some alternatives, the plurality of adenines terminates in GG. In some alternatives, the StuI cleavage site is inverted. In some alternatives, the endonuclease recognition site is a BsaI restriction recognition site, and the endonuclease is BSaI. In some alternatives, the BsaI restriction recognition site is inverted. In some alternatives, the endonuclease recognition site is located 1, 2, 3, 4, 5, 6, 7, 7, 8, 9, 10, 11, 12, 13, 14, 15, 16, 17, 18, 19 or 20 base pairs from the endonuclease cleavage site of from the most 5' thymine (or 5' terminal thymine) in the plurality of thymine nucleotides. In some alternatives, the endonuclease recognition site is located 1, 2, 3, 4, 5, 6, 7, 7, 8, 9 or 10 base pairs from the endonuclease cleavage site of from the most 5' thymine (or 5' terminal thymine) in the plurality of thymine nucleotides. In some alternatives, the endonuclease cleavage site is located 1, 2, 3, 4, 5, 6, 7, 7, 8, 9, 10, 11, 12, 13, 14, 15, 16, 17, 18, 19 or 20 base pairs away from the most 5' thymine (or 5' terminal thymine) in the plurality of thymine nucleotides. In some alternatives, the endonuclease cleavage site is located 1, 2, 3, 4, 5, 6, 7, 7, 8, 9 or 10 base pairs away from the most 5' thymine (or 5' terminal thymine) in the plurality of thymine nucleotides.

In some alternatives, a method of making a polynucleotide having a template strand, an endonuclease recognition site and an endonuclease cleavage site for an endonuclease inserted therein, and wherein said template strand comprises a plurality of thymine nucleotides is provided. The method of making a polynucleotide comprising a sequence encoding a nuclease, a template strand, an endonuclease recognition site and an endonuclease cleavage site for an endonuclease inserted therein, wherein said template strand comprises a plurality of thymine nucleotides can comprise providing a first nucleic acid sequence encoding a nuclease, providing a second nucleic acid sequence comprising at least one endonuclease recognition site, providing a third nucleic acid sequence, wherein the third nucleic acid sequence comprises the template strand, wherein the template strand comprises a plurality of thymine nucleotides, wherein said plurality of thymine nucleotides comprises at least, greater than, equal to, or any number in between 20, 30, 40, 50, 60, 70, 80, 90, 100, 110, 120, 130, 140, 150, 175, 200, 225, 250, 275, 300, 325, 350, 375, 400, 425, 450, 475, 500 or 550 covalently linked thymine nucleotides and wherein the third nucleic acid comprises the endonuclease cleavage site, wherein the endonuclease cleavage site is located within the plurality of thymine nucleotides or within 1, 2, 3, 4, 5, 6, 7, 7, 8, 9, 10, 11, 12, 13, 14, 15, 16, 17, 18, 19 or 20 base pairs away from the most 5' thymine (or 5' terminal thymine) in the plurality of thymine nucleotides, joining said first nucleic acid to one end of the second nucleic acid sequence and joining said third nucleic acid sequence to one end of the second nucleic acid sequence, wherein said second nucleic acid is covalently linked to one end of said third nucleic acid sequence, and wherein the said endonuclease recognition site is located within 55 base pairs of the endonuclease cleavage site for the endonuclease and said endonuclease cleavage site is within 1 to 40 base pairs of a most 5' thymine in the plurality of thymine nucleotides. In some alternatives, the polynucleotide further comprises telomeres. In some alternatives, the polynucleotide comprises a left arm wherein the left arm comprises a left telomere, a right arm wherein the right arm comprises a right telomere and a cloning region located between the left arm and the right arm. In some alternatives, the polynucleotide further comprises a fifth nucleic acid, wherein the fifth nucleic acid comprises a gene. In some alternatives, the gene encodes a protein for therapy. In some alternatives, the gene encodes a nuclease. In some alternatives, the nuclease is an endonuclease. In some alternatives, the nuclease comprises an amino acid sequence set forth in SEQ ID NO. 6 or is encoded by a nucleic acid sequence set forth in SEQ ID NO: 7-14. In some alternatives, the plurality of thymine nucleotides comprises at least, greater than, equal to, or any number in between 20, 30, 40, 50, 60, 70, 80, 90, 100, 110, 120, 130, 140, 150, 175, 200, 225, 250, 275, 300, 325, 350, 375, 400, 425, 450, 475, or 500 covalently linked thymines. In some alternatives, the number of covalently linked thymines is greater than 120. In some alternatives, the number of covalently linked thymines is greater than 200. In some alternatives, the number of covalently linked thymines is greater than 300. In some alternatives, the at least one endonuclease recognition site is a Type II restriction endonuclease recognition site, and the endonuclease is a Type II restriction endonuclease. In some alternatives, the at least one endonuclease recognition site is a Type IIS restriction endonuclease recognition site, and wherein the endonuclease is a Type IIS restriction endonuclease. In some alternatives, the at least one endonuclease recognition site is a BsaI restriction endonuclease recognition site or a StuI restriction endonuclease recognition site, and wherein the endonuclease is BsaI or StuI. In some alternatives, the endonuclease recognition site is inverted. In some alternatives, the polynucleotide is a linear polynucleotide. In some alternatives, the polynucleotide has only one endonuclease recognition site. In some alternatives, the polynucleotide further comprises a DNA polymerase promoter. In some alternatives, the polynucleotide further comprises a RNA polymerase promoter. In some alternatives, the plurality of thymine nucleotide comprises at least one guanine, cytosine, or an adenine. In some alternatives, the endonuclease cleavage site comprises at least one guanine, cytosine, or an adenine, wherein the endonuclease cleaves between a thymine and the at least one guanine, cytosine or adenine. In some alternatives, the polynucleotide further comprises at least one palindromic sequence, wherein the at least one palindromic sequence can form a hairpin. In some alternatives, the polynucleotide further comprises a sixth sequence, wherein the sixth sequence is capable of forming a tertiary structure such as a hairpin. In some alternatives, the RNA lacks a 5' and/or 3' UTR or lacks a native 5' and/or 3' UTR and/or lacks one or more sequences required for native polyadenylation such as, a cleavage/polyadenylation specificity factor (CPSF) binding site, a cleavage stimulation factor binding site (CstF), a cleavage factor I binding site (CFI), or a cleavage factor II binding site (CFII). In some alternatives, the endonuclease is a CRISPR, a restriction endonuclease, a Type II restriction endonuclease or a Type IIS restriction endonuclease. In some alternatives, the endonuclease is a CRISPR, a restriction endonuclease, a Type II restriction endonuclease or a Type IIS restriction endonuclease. In some alternatives, wherein StuI is provided, the endonuclease cleavage site is a StuI cleavage site, AGGCCT (SEQ ID NO: 633), and StuI cleaves between the G and C, leaving a blunt end that terminates in a GG. In some alternatives, the endonuclease cleavage site is AGGCCT (SEQ ID NO: 633). In some alternatives, the endonuclease is StuI. In some alternatives, the plurality of adenines terminates in GG. In some alternatives, the StuI cleavage site is inverted. In some alternatives, the endonuclease recognition site is a BsaI restriction recognition site, and the endonuclease is BSaI. In some alternatives, the BsaI restriction recognition site is inverted. In some alternatives, the endonuclease cleavage site is located 1, 2, 3, 4, 5, 6, 7, 7, 8, 9, 10, 11, 12, 13, 14, 15, 16, 17, 18, 19 or 20 base pairs away from the most 5' thymine (or 5' terminal thymine) in the plurality of thymine nucleotides. In some alternatives, the endonuclease cleavage site is located 1, 2, 3, 4, 5, 6, 7, 7, 8, 9 or 10 base pairs away from the most 5' thymine (or 5' terminal thymine) in the plurality of thymine nucleotides.

In some alternatives, a method of making a polynucleotide having a template strand, an endonuclease recognition site and an endonuclease cleavage site for an endonuclease inserted therein, and wherein said template strand comprises a plurality of thymine nucleotides is provided. The method of making a polynucleotide comprising a sequence encoding a nuclease, a template strand, an endonuclease recognition site and an endonuclease cleavage site for an endonuclease inserted therein, wherein said template strand comprises a plurality of thymine nucleotides can comprise providing a first nucleic acid sequence encoding a nuclease, providing a second nucleic acid sequence comprising at least one endonuclease recognition site, providing a third nucleic acid sequence, wherein the third nucleic acid sequence comprises the template strand, wherein the template strand comprises a plurality of thymine nucleotides, wherein said plurality of thymine nucleotides comprises at least, greater than, equal to, or any number in between 20, 30, 40, 50, 60, 70, 80, 90, 100, 110, 120, 130, 140, 150, 175, 200, 225, 250, 275, 300, 325, 350, 375, 400, 425, 450, 475, 500 or 550 covalently linked thymine nucleotides and wherein the third nucleic acid comprises the endonuclease cleavage site, wherein the endonuclease cleavage site is located within the plurality of thymine nucleotides or within 1, 2, 3, 4, 5, 6, 7, 7, 8, 9, 10, 11, 12, 13, 14, 15, 16, 17, 18, 19 or 20 base pairs away from the most 5' thymine (or 5' terminal thymine) in the plurality of thymine nucleotides, joining said first nucleic acid to one end of the second nucleic acid sequence and joining said third nucleic acid sequence to one end of the second nucleic acid sequence, wherein said second nucleic acid is covalently linked to one end of said third nucleic acid sequence, and wherein the said endonuclease recognition site is located within 55 base pairs of the endonuclease cleavage site for the endonuclease and said endonuclease cleavage site is within 1 to 40 base pairs of a most 5' thymine in the plurality of thymine nucleotides. In some alternatives, the polynucleotide further comprises telomeres. In some alternatives, the polynucleotide comprises a left arm wherein the left arm comprises a left telomere, a right arm wherein the right arm comprises a right telomere and a cloning region located between the left arm and the right arm. In some alternatives, the polynucleotide further comprises a fifth nucleic acid, wherein the fifth nucleic acid comprises a gene. In some alternatives, the gene encodes a protein for therapy. In some alternatives, the gene encodes a nuclease. In some alternatives, the nuclease is an endonuclease. In some alternatives, the nuclease comprises an amino acid sequence set forth in SEQ ID NO. 6 or is encoded by a nucleic acid sequence set forth in SEQ ID NO: 7-14. In some alternatives, the plurality of thymine nucleotides comprises at least, greater than, equal to, or any number in between 20, 30, 40, 50, 60, 70, 80, 90, 100, 110, 120, 130, 140, 150, 175, 200, 225, 250, 275, 300, 325, 350, 375, 400, 425, 450, 475, or 500 covalently linked thymines. In some alternatives, the number of covalently linked thymines is greater than 120. In some alternatives, the number of covalently linked thymines is greater than 200. In some alternatives, the number of covalently linked thymines is greater than 300. In some alternatives, the at least one endonuclease recognition site is a Type II restriction endonuclease recognition site, and the endonuclease is a Type II restriction endonuclease. In some alternatives, the at least one endonuclease recognition site is a Type IIS restriction endonuclease recognition site, and wherein the endonuclease is a Type IIS restriction endonuclease. In some alternatives, the at least one endonuclease recognition site is a BsaI restriction endonuclease recognition site or a StuI restriction endonuclease recognition site, and wherein the endonuclease is BsaI or StuI. In some alternatives, the endonuclease recognition site is inverted. In some alternatives, the polynucleotide is a linear polynucleotide. In some alternatives, the polynucleotide has only one endonuclease recognition site. In some alternatives, the polynucleotide further comprises a DNA polymerase promoter. In some alternatives, the polynucleotide further comprises a RNA polymerase promoter. In some alternatives, the plurality of thymine nucleotide comprises at least one guanine, cytosine, or an adenine. In some alternatives, the endonuclease cleavage site comprises at least one guanine, cytosine, or an adenine, wherein the endonuclease cleaves between a thymine and the at least one guanine, cytosine or adenine. In some alternatives, the polynucleotide further comprises at least one palindromic sequence, wherein the at least one palindromic sequence can form a hairpin. In some alternatives, the polynucleotide further comprises a sixth sequence, wherein the sixth sequence is capable of forming a tertiary structure such as a hairpin. In some alternatives, the RNA lacks a 5' and/or 3' UTR or lacks a native 5' and/or 3' UTR and/or lacks one or more sequences required for native polyadenylation such as, a cleavage/polyadenylation specificity factor (CPSF) binding site, a cleavage stimulation factor binding site (CstF), a cleavage factor I binding site (CFI), or a cleavage factor II binding site (CFII). In some alternatives, the endonuclease is a CRISPR, a restriction endonuclease, a Type II restriction endonuclease or a Type IIS restriction endonuclease. In some alternatives, the endonuclease is a CRISPR, a restriction endonuclease, a Type II restriction endonuclease or a Type IIS restriction endonuclease. In some alternatives, wherein StuI is provided, the endonuclease cleavage site is a StuI cleavage site, AGGCCT (SEQ ID NO: 633), and StuI cleaves between the G and C, leaving a blunt end that terminates in a GG. In some alternatives, the endonuclease cleavage site is AGGCCT (SEQ ID NO: 633). In some alternatives, the endonuclease is StuI. In some alternatives, the plurality of adenines terminates in GG. In some alternatives, the StuI cleavage site is inverted. In some alternatives, the endonuclease recognition site is a BsaI restriction recognition site, and the endonuclease is BSaI. In some alternatives, the BsaI restriction recognition site is inverted. In some alternatives, the endonuclease cleavage site is located 1, 2, 3, 4, 5, 6, 7, 7, 8, 9, 10, 11, 12, 13, 14, 15, 16, 17, 18, 19 or 20 base pairs away from the most 5' thymine (or 5' terminal thymine) in the plurality of thymine nucleotides. In some alternatives, the endonuclease cleavage site is located 1, 2, 3, 4, 5, 6, 7, 7, 8, 9 or 10 base pairs away from the most 5' thymine (or 5' terminal thymine) in the plurality of thymine nucleotides.

A method of making a nucleic acid comprising providing the polynucleotide of any one of the alternatives described herein and contacting said polynucleotide with a polymerase in the presence of nucleotides. In some alternatives, the endonuclease cleavage site is located 1, 2, 3, 4, 5, 6, 7, 7, 8, 9, 10, 11, 12, 13, 14, 15, 16, 17, 18, 19 or 20 base pairs away from the most 5' thymine (or 5' terminal thymine) in the plurality of thymine nucleotides. In some alternatives, the endonuclease cleavage site is located 1, 2, 3, 4, 5, 6, 7, 7, 8, 9 or 10 base pairs away from the most 5' thymine (or 5' terminal thymine) in the plurality of thymine nucleotides. In some alternatives, a method of making a nucleic acid is provided, wherein the nucleic acid comprises providing the polynucleotide of any one of the alternatives described herein, or the polynucleotide manufactured by of any one of the alternatives described herein and contacting said polynucleotide with a polymerase in the presence of nucleotides. The method of making a polynucleotide comprising a sequence encoding a nuclease, a template strand, an endonuclease recognition site and an endonuclease cleavage site for an endonuclease inserted therein, wherein said template strand comprises a plurality of thymine nucleotides can comprise providing a first nucleic acid sequence encoding a nuclease, providing a second nucleic acid sequence comprising at least one endonuclease recognition site, providing a third nucleic acid sequence, wherein the third nucleic acid sequence comprises the template strand, wherein the template strand comprises a plurality of thymine nucleotides, wherein said plurality of thymine nucleotides comprises at least, greater than, equal to, or any number in between 20, 30, 40, 50, 60, 70, 80, 90, 100, 110, 120, 130, 140, 150, 175, 200, 225, 250, 275, 300, 325, 350, 375, 400, 425, 450, 475, 500 or 550 covalently linked thymine nucleotides and wherein the third nucleic acid comprises the endonuclease cleavage site, wherein the endonuclease cleavage site is located within the plurality of thymine nucleotides or within 1, 2, 3, 4, 5, 6, 7, 7, 8, 9, 10, 11, 12, 13, 14, 15, 16, 17, 18, 19 or 20 base pairs away from the most 5' thymine (or 5' terminal thymine) in the plurality of thymine nucleotides, joining said first nucleic acid to one end of the second nucleic acid sequence and joining said third nucleic acid sequence to one end of the second nucleic acid sequence, wherein said second nucleic acid is covalently linked to one end of said third nucleic acid sequence, and wherein the said endonuclease recognition site is located within 55 base pairs of the endonuclease cleavage site for the endonuclease and said endonuclease cleavage site is within 1 to 40 base pairs of a most 5' thymine in the plurality of thymine nucleotides. In some alternatives, the polynucleotide further comprises a promoter for a DNA or RNA polymerase. In some alternatives, the polymerase is a DNA polymerase. In some alternatives, the DNA polymerase is a thermal stable polymerase, such as Taq polymerase. In some alternatives, the nucleotides are adenine, cytosine, guanine, thymine and/or uracil. In some alternatives, the method further comprises providing a set of primers. In some alternatives, the nucleic acid is DNA. In some alternatives, an RNA polymerase is used. In some alternatives, the contacting is performed at a temperature at least, greater than, equal to, or any temperature in between 30° C., 31° C., 32° C., 33° C., 34° C., 35° C., 36° C. or 37° C. In some alternatives, the contacting is performed for at least, greater than, equal to, or time in between 1, 5, 10, 20, 30, 40, 50, 60, 70, 80, 90 or 100 hours (e.g., at least, or equal to 1, 5, 10, 20, 30, 40, 50, 60, 70, 80, 90 or 100 hours or within a range defined by any two of the aforementioned times). In some alternatives, the nucleic acid is RNA. In some alternatives, the RNA comprises a plurality of adenine nucleotides, wherein the plurality of adenine nucleotides comprises at least, greater than, equal to, or any number in between 20, 30, 40, 50, 60, 70, 80, 90, 100, 110, 120, 130, 140, 150, 175, 200, 225, 250, 275, 300, 325, 350, 375, 400, 425, 450, 475, or 500 covalently linked adenines. In some alternatives, the number of covalently linked adenines is greater than 120. In some alternatives, the number of covalently linked adenines is greater than 200. In some alternatives, the number of covalently linked adenines is greater than 300. In some alternatives, the RNA further comprises a gene. In some alternatives, the gene encodes a protein for therapy. In some alternatives, the gene encodes a nuclease. In some alternatives, the gene encodes an endonuclease. In some alternatives, the nuclease comprises an amino acid sequence set forth in SEQ ID NO. 6 or is encoded by a nucleic acid sequence set forth in SEQ ID NO: 7-14. In some alternatives, the plurality of adenine nucleotides further comprises a guanine, cytosine or a uracil, and wherein the number of covalently linked adenines terminates with a guanine, cytosine or a uracil. In some alternatives, the nucleic acid further comprises at least one palindromic sequence, wherein the at least one palindromic sequence can form a hairpin. In some alternatives, the nucleic acid further comprises a sequence capable of forming a tertiary structure such as a hairpin. In some alternatives, the method further comprises providing an endonuclease. In some alternatives, the endonuclease is a Type II restriction endonuclease. In some alternatives, the endonuclease is a Type IIS restriction endonuclease. In some alternatives, the endonuclease is BsaI or StuI. In some alternatives, the RNA lacks a 5' and/or 3' UTR or lacks a native 5' and/or 3' UTR and/or lacks one or more sequences required for native polyadenylation such as, a cleavage/polyadenylation specificity factor (CPSF) binding site, a cleavage stimulation factor binding site (CstF), a cleavage factor I binding site (CFI), or a cleavage factor II binding site (CFII). Without being limiting an endonuclease can include, for example, a CRISPR, a restriction endonuclease, a Type II restriction endonuclease and a Type IIS restriction endonuclease. In some alternatives, the endonuclease is a CRISPR, a restriction endonuclease, a Type II restriction endonuclease or a Type IIS restriction endonuclease. In some alternatives, the endonuclease is a CRISPR, a restriction endonuclease, a Type II restriction endonuclease or a Type IIS restriction endonuclease. In some alternatives, wherein StuI is provided, the endonuclease cleavage site is a StuI cleavage site, AGGCCT (SEQ ID NO: 633), and StuI cleaves between the G and C, leaving a blunt end that terminates in a GG. In some alternatives, the endonuclease cleavage site is AGGCCT (SEQ ID NO: 633). In some alternatives, the endonuclease is StuI. In some alternatives, the plurality of adenines terminates in GG. In some alternatives, the StuI cleavage site is inverted. In some alternatives, the endonuclease recognition site is a BsaI restriction recognition site, and the endonuclease is BSaI. In some alternatives, the BsaI restriction recognition site is inverted. In some alternatives, the endonuclease cleavage site is located 1, 2, 3, 4, 5, 6, 7, 7, 8, 9, 10, 11, 12, 13, 14, 15, 16, 17, 18, 19 or 20 base pairs away from the most 5' thymine (or 5' terminal thymine) in the plurality of thymine nucleotides. In some alternatives, the endonuclease cleavage site is located 1, 2, 3, 4, 5, 6, 7, 7, 8, 9 or 10 base pairs away from the most 5' thymine (or 5' terminal thymine) in the plurality of thymine nucleotides.

In some alternatives, a nucleic acid manufactured by a method of any one of the alternatives herein is provided. In some alternatives the nucleic acid is a DNA. In some alternatives the nucleic acid is a RNA. In some alternatives the RNA comprises a plurality of adenine nucleotides, wherein the plurality of adenine nucleotides comprises at least, greater than, equal to, or any number in between 20, 30, 40, 50, 60, 70, 80, 90, 100, 110, 120, 130, 140, 150, 175, 200, 225, 250, 275, 300, 325, 350, 375, 400, 425, 450, 475, or 500 covalently linked adenines. In some alternatives the number of covalently linked adenines is greater than 120. In some alternatives the number of covalently linked adenines is greater than 200. In some alternatives the number of covalently linked adenines is greater than 300. In some alternatives the nucleic acid further comprises a gene. In some alternatives the gene encodes a protein for therapy. In some alternatives the gene encodes a nuclease. In some alternatives the gene encodes an endonuclease. In some alternatives the nuclease comprises an amino acid sequence set forth in SEQ ID NO. 6 or is encoded by a nucleic acid sequence set forth in SEQ ID NO: 7-14. In some alternatives the covalently linked adenines terminates with a guanine, cytosine, thymine, or a uracil. In some alternatives the nucleic acid further comprises at least one palindromic sequence, wherein the at least one palindromic sequence can form a hairpin. In some alternatives the nucleic acid further comprises a sequence capable of forming a tertiary structure such as a hairpin. Without being limiting an endonuclease can include, for example, a CRISPR, a restriction endonuclease, a Type II restriction endonuclease and a Type IIS restriction endonuclease. In some alternatives, the endonuclease is a CRISPR, a restriction endonuclease, a Type II restriction endonuclease or a Type IIS restriction endonuclease. In some alternatives, the endonuclease is a CRISPR, a restriction endonuclease, a Type II restriction endonuclease or a Type IIS restriction endonuclease. In some alternatives, wherein StuI is provided, the endonuclease cleavage site is a StuI cleavage site, AGGCCT (SEQ ID NO: 633), and StuI cleaves between the G and C, leaving a blunt end that terminates in a GG. In some alternatives, the endonuclease cleavage site is AGGCCT (SEQ ID NO: 633). In some alternatives, the endonuclease is StuI. In some alternatives, the plurality of adenines terminates in GG. In some alternatives, the StuI cleavage site is inverted. In some alternatives, the endonuclease recognition site is a BsaI restriction recognition site, and the endonuclease is BSaI. In some alternatives, the BsaI restriction recognition site is inverted. In some alternatives, the endonuclease cleavage site is located 1, 2, 3, 4, 5, 6, 7, 7, 8, 9, 10, 11, 12, 13, 14, 15, 16, 17, 18, 19 or 20 base pairs away from the most 5' thymine (or 5' terminal thymine) in the plurality of thymine nucleotides. In some alternatives, the endonuclease cleavage site is located 1, 2, 3, 4, 5, 6, 7, 7, 8, 9 or 10 base pairs away from the most 5' thymine (or 5' terminal thymine) in the plurality of thymine nucleotides.

A method of enhancing transcription of a gene comprising providing the polynucleotide of any one of the alternatives described herein, wherein said polynucleotide further comprises a gene, and contacting said polynucleotide with a RNA polymerase in the presence of nucleotides. In some alternatives, a method of enhancing transcription of a gene is provided, wherein the method comprises providing the polynucleotide of any one of the alternatives provided herein, or the polynucleotide manufactured by any one of the alternatives described herein and contacting said polynucleotide with a RNA polymerase in the presence of nucleotides. In some alternatives, the method further comprises providing a Type II restriction endonuclease. In some alternatives, the method further comprises providing a Type IIS restriction endonuclease. In some alternatives, the endonuclease is BsaI or StuI. In some alternatives, the polynucleotide further comprises an RNA polymerase promoter. In some alternatives, the contacting is performed at a temperature at least, greater than, equal to, or any temperature in between 30° C., 31° C., 32° C., 33° C., 34° C., 35° C., 36° C. or 37° C. In some alternatives, the method is performed for at least, greater than, equal to, or time in between 1, 5, 10, 20, 30, 40, 50, 60, 70, 80, 90 or 100 hours (e.g., at least, or equal to 1, 5, 10, 20, 30, 40, 50, 60, 70, 80, 90 or 100 hours or within a range defined by any two of the aforementioned times). Without being limiting an endonuclease can include, for example, a CRISPR, a restriction endonuclease, a Type II restriction endonuclease and a Type IIS restriction endonuclease. In some alternatives, the endonuclease is a CRISPR, a restriction endonuclease, a Type II restriction endonuclease or a Type IIS restriction endonuclease. In some alternatives, the endonuclease is a CRISPR, a restriction endonuclease, a Type II restriction endonuclease or a Type IIS restriction endonuclease. In some alternatives, wherein StuI is provided, the endonuclease cleavage site is a StuI cleavage site, AGGCCT (SEQ ID NO: 633), and StuI cleaves between the G and C, leaving a blunt end that terminates in a GG. In some alternatives, the endonuclease cleavage site is AGGCCT (SEQ ID NO: 633). In some alternatives, the endonuclease is StuI. In some alternatives, the plurality of adenines terminates in GG. In some alternatives, the StuI cleavage site is inverted. In some alternatives, the endonuclease recognition site is a BsaI restriction recognition site, and the endonuclease is BSaI. In some alternatives, the endonuclease cleavage site is located 1, 2, 3, 4, 5, 6, 7, 7, 8, 9, 10, 11, 12, 13, 14, 15, 16, 17, 18, 19 or 20 base pairs away from the most 5' thymine (or 5' terminal thymine) in the plurality of thymine nucleotides. In some alternatives, the endonuclease cleavage site is located 1, 2, 3, 4, 5, 6, 7, 7, 8, 9 or 10 base pairs away from the most 5' thymine (or 5' terminal thymine) in the plurality of thymine nucleotides.

Also contemplated is a method of stabilizing an RNA during translation at 30° C.-37° C. for at least 100 hours (e.g., at least, or equal to 1, 5, 10, 20, 30, 40, 50, 60, 70, 80, 90 or 100 hours or within a range defined by any two of the aforementioned times), wherein the method comprises providing the polynucleotide of any one of the alternatives described herein, and contacting said nucleic acid with a ribosome, in the presence of amino acids and tRNAs, wherein said RNA is stable at 30-37 degrees Celsius for at least 100 hours (e.g., at least, or equal to 1, 5, 10, 20, 30, 40, 50, 60, 70, 80, 90 or 100 hours or within a range defined by any two of the aforementioned times). In some alternatives, a method of stabilizing an RNA during in vitro translation at 30-37 degrees Celsius for at least 100 hours (e.g., at least, or equal to 1, 5, 10, 20, 30, 40, 50, 60, 70, 80, 90 or 100 hours or within a range defined by any two of the aforementioned times) is provided, wherein the method comprises providing the nucleic acid of any one of the alternatives provided herein or a nucleic acid manufactured by a method of any of the alternatives described herein and contacting said nucleic acid with a ribosome, in the presence of amino acids and tRNAs, wherein said RNA is stable at 30-37 degrees Celsius for at least 100 hours (e.g., at least, or equal to 1, 5, 10, 20, 30, 40, 50, 60, 70, 80, 90 or 100 hours or within a range defined by any two of the aforementioned times). In some alternatives, the nucleic acid is an RNA. In some alternatives, the RNA further comprises an RNA polymerase promoter. In some alternatives, the contacting is performed at a temperature equal to 37° C. In some alternatives, the contacting is performed for at least, greater than, equal to, or time in between 1, 5, 10, 20, 30, 40, 50, 60, 70, 80, 90 or 100 hours (e.g., at least, or equal to 1, 5, 10, 20, 30, 40, 50, 60, 70, 80, 90 or 100 hours or within a range defined by any two of the aforementioned times). In some alternatives, the RNA comprises a plurality of adenine nucleotides, wherein the plurality of adenine nucleotides comprises at least, greater than, equal to, or any number in between 20, 30, 40, 50, 60, 70, 80, 90, 100, 110, 120, 130, 140, 150, 175, 200, 225, 250, 275, 300, 325, 350, 375, 400, 425, 450, 475, or 500 covalently linked adenines. In some alternatives, the number of covalently linked adenines is greater than 120. In some alternatives, the number of covalently linked adenines is greater than 200. In some alternatives, the number of covalently linked adenines is greater than 300. In some alternatives, the RNA further comprises a gene. In some alternatives, the gene encodes a protein for therapy. In some alternatives, the gene encodes an endonuclease. In some alternatives, the gene encodes a nuclease. In some alternatives, the nuclease comprises an amino acid sequence set forth in SEQ ID NO. 6 or is encoded by a nucleic acid sequence set forth in SEQ ID NO: 7-14. In some alternatives, the covalently linked adenines terminates with a guanine, cytosine, thymine, or a uracil. In some alternatives, the nucleic acid further comprises at least one palindromic sequence, wherein the at least one palindromic sequence can form a hairpin. In some alternatives, the RNA lacks a 5' and/or 3' UTR or lacks a native 5' and/or 3' UTR and/or lacks one or more sequences required for native polyadenylation such as, a cleavage/polyadenylation specificity factor (CPSF) binding site, a cleavage stimulation factor binding site (CstF), a cleavage factor I binding site (CFI), or a cleavage factor II binding site (CFII). Without being limiting an endonuclease can include, for example, a CRISPR, a restriction endonuclease, a Type II restriction endonuclease and a Type IIS restriction endonuclease. In some alternatives, the endonuclease is a CRISPR, a restriction endonuclease, a Type II restriction endonuclease or a Type IIS restriction endonuclease. In some alternatives, the endonuclease is a CRISPR, a restriction endonuclease, a Type II restriction endonuclease or a Type IIS restriction endonuclease. In some alternatives, wherein StuI is provided, the endonuclease cleavage site is a StuI cleavage site, AGGCCT (SEQ ID NO: 633), and StuI cleaves between the G and C, leaving a blunt end that terminates in a GG. In some alternatives, the endonuclease cleavage site is AGGCCT (SEQ ID NO: 633). In some alternatives, the endonuclease is StuI. In some alternatives, the plurality of adenines terminates in GG. In some alternatives, the StuI cleavage site is inverted. In some alternatives, the endonuclease recognition site is a BsaI restriction recognition site, and the endonuclease is BSaI. In some alternatives, the BsaI restriction recognition site is inverted. In some alternatives, the endonuclease cleavage site is located 1, 2, 3, 4, 5, 6, 7, 7, 8, 9, 10, 11, 12, 13, 14, 15, 16, 17, 18, 19 or 20 base pairs away from the most 5' thymine (or 5' terminal thymine) in the plurality of thymine nucleotides. In some alternatives, the endonuclease cleavage site is located 1, 2, 3, 4, 5, 6, 7, 7, 8, 9 or 10 base pairs away from the most 5' thymine (or 5' terminal thymine) in the plurality of thymine nucleotides.

Also contemplated is a method of stabilizing an RNA during in vivo translation at 30-37 degrees Celsius for at least 100 hours (e.g., at least, or equal to 1, 5, 10, 20, 30, 40, 50, 60, 70, 80, 90 or 100 hours or within a range defined by any two of the aforementioned times) in a cell. The method can comprise transfecting into a cell the nucleic acid of any one of the alternatives described herein or a nucleic acid manufactured by a method of any one of the alternatives described herein placing the cell into a culture vessel with media, supplying the cell with nutrients and amino acids for translation and incubating the cell for at least 100 hours (e.g., at least, or equal to 1, 5, 10, 20, 30, 40, 50, 60, 70, 80, 90 or 100 hours or within a range defined by any two of the aforementioned times) so as to allow translation. In some alternatives, the mRNA lacks a 5' and/or 3' UTR or lacks a native 5' and/or 3' UTR and/or lacks one or more sequences required for native polyadenylation such as, a cleavage/polyadenylation specificity factor (CPSF) binding site, a cleavage stimulation factor binding site (CstF), a cleavage factor I binding site (CFI), or a cleavage factor II binding site (CFII). Without being limiting an endonuclease can include, for example, a CRISPR, a restriction endonuclease, a Type II restriction endonuclease and a Type IIS restriction endonuclease. In some alternatives, the endonuclease is a CRISPR, a restriction endonuclease, a Type II restriction endonuclease or a Type IIS restriction endonuclease. In some alternatives, the endonuclease is a CRISPR, a restriction endonuclease, a Type II restriction endonuclease or a Type IIS restriction endonuclease. In some alternatives, wherein StuI is provided, the endonuclease cleavage site is a StuI cleavage site, AGGCCT (SEQ ID NO: 633), and StuI cleaves between the G and C, leaving a blunt end that terminates in a GG. In some alternatives, the endonuclease cleavage site is AGGCCT (SEQ ID NO: 633). In some alternatives, the endonuclease is StuI. In some alternatives, the plurality of adenines terminates in GG. In some alternatives, the StuI cleavage site is inverted. In some alternatives, the endonuclease recognition site is a BsaI restriction recognition site, and the endonuclease is BSaI. In some alternatives, the BsaI restriction recognition site is inverted. In some alternatives, the endonuclease cleavage site is located 1, 2, 3, 4, 5, 6, 7, 7, 8, 9, 10, 11, 12, 13, 14, 15, 16, 17, 18, 19 or 20 base pairs away from the most 5' thymine (or 5' terminal thymine) in the plurality of thymine nucleotides. In some alternatives, the endonuclease cleavage site is located 1, 2, 3, 4, 5, 6, 7, 7, 8, 9 or 10 base pairs away from the most 5' thymine (or 5' terminal thymine) in the plurality of thymine nucleotides.

Also contemplated are methods of increasing expression of a protein comprising generating an mRNA from the polynucleotide of any one of the alternatives described herein or from a polynucleotide manufactured by a method of any of the alternatives described herein and translating said mRNA into a peptide. The polynucleotide can comprise a first nucleic acid sequence encoding a nuclease, a second nucleic acid sequence comprising at least one restriction endonuclease recognition site and a third nucleic acid sequence, wherein the third nucleic acid sequence comprises the template strand, wherein said plurality of thymine nucleotides comprises at least, greater than, equal to, or any number in between 20, 30, 40, 50, 60, 70, 80, 90, 100, 110, 120, 130, 140, 150, 175, 200, 225, 250, 275, 300, 325, 350, 375, 400, 425, 450, 475, 500 or 550 covalently linked thymine nucleotides and wherein the third nucleic acid comprises the restriction endonuclease cleavage site, wherein the restriction endonuclease cleavage site is located within the plurality of thymine nucleotides or within 1, 2, 3, 4, 5, 6, 7, 7, 8, 9, 10, 11, 12, 13, 14, 15, 16, 17, 18, 19 or 20 base pairs away from the most 5' thymine (or 5' terminal thymine) in the plurality of thymine nucleotides and wherein said second nucleic acid is covalently linked to one end of said third nucleic acid sequence, and wherein the said restriction endonuclease recognition site is located within 55 base pairs of the restriction endonuclease cleavage site for the restriction endonuclease and said restriction endonuclease cleavage site is within 1 to 40 base pairs of a most 5' thymine in the plurality of thymine nucleotides. In some alternatives, the translating step further comprises providing an RNA polymerase. In some alternatives, the method further comprises providing a Type II restriction endonuclease. In some alternatives, the method further comprises providing a Type IIS restriction endonuclease. In some alternatives, the Type IIS restriction endonuclease is BsaI or StuI. In some alternatives, the polynucleotide further comprises an RNA polymerase promoter. In some alternatives, the translating is performed at a temperature at least, greater than, equal to, or any temperature in between 30° C., 31° C., 32° C., 33° C., 34° C., 35° C., 36° C. or 37° C. In some alternatives, the translating is performed for at least, greater than, equal to, or time in between 1, 5, 10, 20, 30, 40, 50, 60, 70, 80, 90 or 100 hours (e.g., at least, or equal to 1, 5, 10, 20, 30, 40, 50, 60, 70, 80, 90 or 100 hours or within a range defined by any two of the aforementioned times). In some alternatives, the RNA comprises a plurality of adenine nucleotides, wherein the plurality of adenine nucleotides comprises at least, greater than, equal to, or any number in between 20, 30, 40, 50, 60, 70, 80, 90, 100, 110, 120, 130, 140, 150, 175, 200, 225, 250, 275, 300, 325, 350, 375, 400, 425, 450, 475, or 500 covalently linked adenines. In some alternatives, the number of covalently linked adenines is greater than 120. In some alternatives, the number of covalently linked adenines is greater than 200. In some alternatives, the number of covalently linked adenines is greater than 300. In some alternatives, the RNA further comprises a gene encoding a protein. In some alternatives, the protein is a protein for therapy. In some alternatives, the gene encodes a nuclease. In some alternatives, the gene encodes an endonuclease. In some alternatives, the nuclease comprises an amino acid sequence set forth in SEQ ID NO. 6 or is encoded by a nucleic acid sequence set forth in SEQ ID NO: 7-14. In some alternatives, the plurality of adenine nucleotides further comprises a guanine, cytosine or a uracil, and wherein the number of covalently linked adenines terminates with a guanine, cytosine or a uracil. In some alternatives, the polynucleotide further comprises at least one palindromic sequence, wherein the at least one palindromic sequence can form a hairpin. In some alternatives, the polynucleotide further comprises a sequence capable of forming a tertiary structure such as a hairpin. In some alternatives, the polynucleotide further comprises an RNA polymerase promoter. In some alternatives, the translating is performed at a temperature at least, greater than, equal to, or any temperature in between 30° C., 31° C., 32° C., 33° C., 34° C., 35° C., 36° C. or 37° C. In some alternatives, the translating is performed for at least, greater than, equal to, or time in between 1, 5, 10, 20, 30, 40, 50, 60, 70, 80, 90 or 100 hours (e.g., at least, or equal to 1, 5, 10, 20, 30, 40, 50, 60, 70, 80, 90 or 100 hours or within a range defined by any two of the aforementioned times). In some alternatives, the mRNA comprises at least, greater than, equal to, or any number in between 20, 30, 40, 50, 60, 70, 80, 90, 100, 110, 120, 130, 140, 150, 175, 200, 225, 250, 275, 300, 325, 350, 350, 375, 400, 425, 450, 475 or 500 covalently linked adenines. In some alternatives, the mRNA lacks a 5' and/or 3' UTR or lacks a native 5' and/or 3' UTR and/or lacks one or more sequences required for native polyadenylation such as, a cleavage/polyadenylation specificity factor (CPSF) binding site, a cleavage stimulation factor binding site (CstF), a cleavage factor I binding site (CFI), or a cleavage factor II binding site (CFII). Without being limiting an endonuclease can include, for example, a CRISPR, a restriction endonuclease, a Type II restriction endonuclease and a Type IIS restriction endonuclease. In some alternatives, the endonuclease is a CRISPR, a restriction endonuclease, a Type II restriction endonuclease or a Type IIS restriction endonuclease. In some alternatives, the endonuclease is a CRISPR, a restriction endonuclease, a Type II restriction endonuclease or a Type IIS restriction endonuclease. In some alternatives, wherein StuI is provided, the endonuclease cleavage site is a StuI cleavage site, AGGCCT (SEQ ID NO: 633), and StuI cleaves between the G and C, leaving a blunt end that terminates in a GG. In some alternatives, the endonuclease cleavage site is AGGCCT (SEQ ID NO: 633). In some alternatives, the endonuclease is StuI. In some alternatives, the plurality of adenines terminates in GG. In some alternatives, the StuI cleavage site is inverted. In some alternatives, the endonuclease recognition site is a BsaI restriction recognition site, and the endonuclease is BSaI. In some alternatives, the BsaI restriction recognition site is inverted. In some alternatives, the endonuclease cleavage site is located 1, 2, 3, 4, 5, 6, 7, 7, 8, 9, 10, 11, 12, 13, 14, 15, 16, 17, 18, 19 or 20 base pairs away from the most 5' thymine (or 5' terminal thymine) in the plurality of thymine nucleotides. In some alternatives, the endonuclease cleavage site is located 1, 2, 3, 4, 5, 6, 7, 7, 8, 9 or 10 base pairs away from the most 5' thymine (or 5' terminal thymine) in the plurality of thymine nucleotides.

In some alternatives, a method of enhancing stability of a replicating gene is provided, wherein the method comprises providing the polynucleotide of any one of the alternatives described herein or a polynucleotide manufactured by any method of any of the alternatives described herein, wherein said polynucleotide further comprises a gene, transforming a cell with said polynucleotide and propagating the cell, wherein the polynucleotide is replicated. In some alternatives, the cell is propagated for 1 day, 2 days, 4 days, 6 days, 8 days, 10 days, 12 days, 14 days, or any other times between these values. The polynucleotide can comprise a first nucleic acid sequence encoding a nuclease, a second nucleic acid sequence comprising at least one restriction endonuclease recognition site and a third nucleic acid sequence, wherein the third nucleic acid sequence comprises the template strand, wherein said plurality of thymine nucleotides comprises at least, greater than, equal to, or any number in between 20, 30, 40, 50, 60, 70, 80, 90, 100, 110, 120, 130, 140, 150, 175, 200, 225, 250, 275, 300, 325, 350, 375, 400, 425, 450, 475, 500 or 550 covalently linked thymine nucleotides and wherein the third nucleic acid comprises the restriction endonuclease cleavage site, wherein the restriction endonuclease cleavage site is located within the plurality of thymine nucleotides or within 1, 2, 3, 4, 5, 6, 7, 7, 8, 9, 10, 11, 12, 13, 14, 15, 16, 17, 18, 19 or 20 base pairs away from the most 5' thymine (or 5' terminal thymine) in the plurality of thymine nucleotides and wherein said second nucleic acid is covalently linked to one end of said third nucleic acid sequence, and wherein the said restriction endonuclease recognition site is located within 55 base pairs of the restriction endonuclease cleavage site for the restriction endonuclease and said restriction endonuclease cleavage site is within 1 to 40 base pairs of a most 5' thymine in the plurality of thymine nucleotides. In some alternatives, the cell is propagated at 30° C., 31° C., 32° C., 33° C., 34° C., 35° C., 36° C., 37° C. or any other temperature between any these values. Without being limiting an endonuclease can include, for example, a CRISPR, a restriction endonuclease, a Type II restriction endonuclease and a Type IIS restriction endonuclease. In some alternatives, the endonuclease is a CRISPR, a restriction endonuclease, a Type II restriction endonuclease or a Type IIS restriction endonuclease. In some alternatives, the endonuclease is a CRISPR, a restriction endonuclease, a Type II restriction endonuclease or a Type IIS restriction endonuclease. In some alternatives, wherein StuI is provided, the endonuclease cleavage site is a StuI cleavage site, AGGCCT (SEQ ID NO: 633), and StuI cleaves between the G and C, leaving a blunt end that terminates in a GG. In some alternatives, the endonuclease cleavage site is AGGCCT (SEQ ID NO: 633). In some alternatives, the endonuclease is StuI. In some alternatives, the plurality of adenines terminates in GG. In some alternatives, the StuI cleavage site is inverted. In some alternatives, the endonuclease recognition site is a BsaI restriction recognition site, and the endonuclease is BSaI. In some alternatives, the BsaI restriction recognition site is inverted. In some alternatives, the endonuclease recognition site is located 1, 2, 3, 4, 5, 6, 7, 7, 8, 9, 10, 11, 12, 13, 14, 15, 16, 17, 18, 19 or 20 base pairs away from the most 5' thymine (or 5' terminal thymine) in the plurality of thymine nucleotides. In some alternatives, the endonuclease recognition site is located 1, 2, 3, 4, 5, 6, 7, 7, 8, 9 or 10 base pairs away from the most 5' thymine (or 5' terminal thymine) in the plurality of thymine nucleotides.

In some alternatives, a polynucleotide comprising a sequence encoding a nuclease, a template strand, an endonuclease recognition site and an endonuclease cleavage site for an endonuclease inserted therein, wherein said template strand comprises a plurality of thymine nucleotides is provided. The polynucleotide can comprise a first nucleic acid sequence encoding a nuclease, a second nucleic acid sequence comprising at least one restriction endonuclease recognition site and a third nucleic acid sequence, wherein the third nucleic acid sequence comprises the template strand, wherein said plurality of thymine nucleotides comprises at least, greater than, equal to, or any number in between 20, 30, 40, 50, 60, 70, 80, 90, 100, 110, 120, 130, 140, 150, 175, 200, 225, 250, 275, 300, 325, 350, 375, 400, 425, 450, 475, 500 or 550 covalently linked thymine nucleotides and wherein the third nucleic acid comprises the restriction endonuclease cleavage site, wherein the restriction endonuclease cleavage site is located within the plurality of thymine nucleotides or within 1, 2, 3, 4, 5, 6, 7, 7, 8, 9, 10, 11, 12, 13, 14, 15, 16, 17, 18, 19 or 20 base pairs away from the most 5' thymine (or 5' terminal thymine) in the plurality of thymine nucleotides and wherein said second nucleic acid is covalently linked to one end of said third nucleic acid sequence, and wherein the said restriction endonuclease recognition site is located within 55 base pairs of the restriction endonuclease cleavage site for the restriction endonuclease and said restriction endonuclease cleavage site is within 1 to 40 base pairs of a most 5' thymine in the plurality of thymine nucleotides. In some alternatives, the polynucleotide comprises a left arm wherein the left arm comprises a left telomere, a right arm wherein the right arm comprises a right telomere and a cloning region located between the left arm and the right arm. In some alternatives, the nuclease comprises an amino acid sequence set forth in SEQ ID NO. 6 or is encoded by a nucleic acid sequence set forth in SEQ ID NO: 7-14. In some alternatives, the plurality of thymine nucleotides comprises at least, greater than, equal to, or any number in between 20, 30, 40, 50, 60, 70, 80, 90, 100, 110, 120, 130, 140, 150, 175, 200, 225, 250, 275, 300, 325, 350, 375, 400, 425, 450, 475, or 500 covalently linked thymines. In some alternatives, the number of covalently linked thymines is greater than 120. In some alternatives, the number of covalently linked thymines is greater than 200. In some alternatives, the number of covalently linked thymines is greater than 300. In some alternatives, the at least one endonuclease recognition site is a Type II restriction endonuclease recognition site, and the endonuclease is a Type II restriction endonuclease. In some alternatives, the at least one endonuclease recognition site is a Type IIS restriction endonuclease recognition site and wherein the endonuclease is a Type IIS restriction endonuclease. In some alternatives, the at least one Type IIS restriction endonuclease recognition site is a BsaI restriction endonuclease recognition site or a StuI restriction endonuclease recognition site, and wherein the endonuclease is BsaI or StuI. In some alternatives, the endonuclease recognition site is inverted. In some alternatives, the polynucleotide is a linear polynucleotide. In some alternatives, the polynucleotide has only one endonuclease recognition site. In some alternatives, the polynucleotide further comprises a DNA polymerase promoter. In some alternatives, the polynucleotide further comprises an RNA polymerase promoter. In some alternatives, the plurality of thymine nucleotides comprises at least one covalently linked guanine, cytosine, or an adenine, wherein the at least one covalently linked guanine, cytosine or adenine is optionally at the most 5' thymine (or 5' terminal thymine) in the plurality of thymine nucleotides. In some alternatives, the endonuclease cleavage site comprises at least one guanine, cytosine, or an adenine, wherein the endonuclease cleaves between a thymine and the at least one guanine, cytosine or adenine. In some alternatives, the polynucleotide further comprises at least one palindromic sequence, wherein the at least one palindromic sequence can form a hairpin. In some alternatives, the polynucleotide further comprises a seventh sequence, wherein the seventh sequence is capable of forming a tertiary structure such as a hairpin. Without being limiting an endonuclease can include, for example, a CRISPR, a restriction endonuclease, a Type II restriction endonuclease and a Type IIS restriction endonuclease. In some alternatives, the endonuclease is a CRISPR, a restriction endonuclease, a Type II restriction endonuclease or a Type IIS restriction endonuclease. In some alternatives, the endonuclease is a CRISPR, a restriction endonuclease, a Type II restriction endonuclease or a Type IIS restriction endonuclease. In some alternatives, wherein StuI is provided, the endonuclease cleavage site is a StuI cleavage site, AGGCCT (SEQ ID NO: 633), and StuI cleaves between the G and C, leaving a blunt end that terminates in a GG. In some alternatives, the endonuclease cleavage site is AGGCCT (SEQ ID NO: 633). In some alternatives, the endonuclease is StuI. In some alternatives, the plurality of adenines terminates in GG. In some alternatives, the StuI cleavage site is inverted. In some alternatives, the endonuclease recognition site is a BsaI restriction recognition site, and the endonuclease is BSaI. In some alternatives, the BsaI restriction recognition site is inverted. In some alternatives, the endonuclease cleavage site is located 1, 2, 3, 4, 5, 6, 7, 7, 8, 9, 10, 11, 12, 13, 14, 15, 16, 17, 18, 19 or 20 base pairs away from the most 5' thymine (or 5' terminal thymine) in the plurality of thymine nucleotides. In some alternatives, the endonuclease cleavage site is located 1, 2, 3, 4, 5, 6, 7, 7, 8, 9 or 10 base pairs away the endonuclease cleavage site of from the most 5' thymine (or 5' terminal thymine) in the plurality of thymine nucleotides.

In some alternatives, a method of making polynucleotide comprising a sequence encoding a nuclease, a template strand, an endonuclease recognition site and an endonuclease cleavage site for an endonuclease inserted therein, wherein said template strand comprises a plurality of thymine nucleotides, is provided. The method of making a polynucleotide comprising a sequence encoding a nuclease, a template strand, an endonuclease recognition site and an endonuclease cleavage site for an endonuclease inserted therein, wherein said template strand comprises a plurality of thymine nucleotides can comprise providing a first nucleic acid sequence encoding a nuclease, providing a second nucleic acid sequence comprising at least one endonuclease recognition site, providing a third nucleic acid sequence, wherein the third nucleic acid sequence comprises the template strand, wherein the template strand comprises a plurality of thymine nucleotides, wherein said plurality of thymine nucleotides comprises at least, greater than, equal to, or any number in between 20, 30, 40, 50, 60, 70, 80, 90, 100, 110, 120, 130, 140, 150, 175, 200, 225, 250, 275, 300, 325, 350, 375, 400, 425, 450, 475, 500 or 550 covalently linked thymine nucleotides and wherein the third nucleic acid comprises the endonuclease cleavage site, wherein the endonuclease cleavage site is located within the plurality of thymine nucleotides or within 1, 2, 3, 4, 5, 6, 7, 7, 8, 9, 10, 11, 12, 13, 14, 15, 16, 17, 18, 19 or 20 base pairs away from the most 5' thymine (or 5' terminal thymine) in the plurality of thymine nucleotides, joining said first nucleic acid to one end of the second nucleic acid sequence and joining said third nucleic acid sequence to one end of the second nucleic acid sequence, wherein said second nucleic acid is covalently linked to one end of said third nucleic acid sequence, and wherein the said endonuclease recognition site is located within 55 base pairs of the endonuclease cleavage site for the endonuclease and said endonuclease cleavage site is within 1 to 40 base pairs of a most 5' thymine in the plurality of thymine nucleotides. In some alternatives, the plurality of thymine nucleotides of said third nucleic acid comprises at least, greater than, equal to, or any number in between 20, 30, 40, 50, 60, 70, 80, 90, 100, 110, 120, 130, 140, 150, 175, 200, 225, 250, 275, 300, 325, 350, 375, 400, 425, 450, 475, or 500 covalently linked thymines. In some alternatives, the number of covalently linked thymines is greater than 120. In some alternatives, the number of covalently linked thymines is greater than 200. In some alternatives, the number of covalently linked thymines is greater than 300. In some alternatives, the at least one endonuclease recognition site is a Type II restriction endonuclease recognition site and the endonuclease is a Type II restriction endonuclease. In some alternatives, the at least one endonuclease recognition site is a Type IIS restriction endonuclease recognition site and the endonuclease is a Type IIS restriction endonuclease. In some alternatives, the at least one endonuclease recognition site is a BsaI restriction endonuclease recognition site or a StuI restriction endonuclease recognition site, and wherein the endonuclease is BsaI or StuI. In some alternatives, the endonuclease recognition site is inverted. In some alternatives, the polynucleotide is a linear polynucleotide. In some alternatives, the polynucleotide has only one endonuclease recognition site. In some alternatives, wherein the plurality of thymine nucleotides comprises at least one covalently linked guanine, cytosine, or an adenine, wherein the at least one covalently linked guanine, cytosine or adenine is optionally at the most 5' thymine (or 5' terminal thymine) in the plurality of thymine nucleotides. In some alternatives, the endonuclease cleavage site comprises at least one guanine, cytosine, or an adenine, wherein the endonuclease cleaves between a thymine and the at least one guanine, cytosine or adenine. In some alternatives, the nuclease comprises an amino acid sequence set forth in SEQ ID NO. 6 or is encoded by a nucleic acid sequence set forth in SEQ ID NO: 7-14. Without being limiting an endonuclease can include, for example, a CRISPR, a restriction endonuclease, a Type II restriction endonuclease and a Type IIS restriction endonuclease. In some alternatives, the endonuclease is a CRISPR, a restriction endonuclease, a Type II restriction endonuclease or a Type IIS restriction endonuclease. In some alternatives, the endonuclease is a CRISPR, a restriction endonuclease, a Type II restriction endonuclease or a Type IIS restriction endonuclease. In some alternatives, wherein StuI is provided, the endonuclease cleavage site is a StuI cleavage site, AGGCCT (SEQ ID NO: 633), and StuI cleaves between the G and C, leaving a blunt end that terminates in a GG. In some alternatives, the endonuclease cleavage site is AGGCCT (SEQ ID NO: 633). In some alternatives, the endonuclease is StuI. In some alternatives, the plurality of adenines terminates in GG. In some alternatives, the StuI cleavage site is inverted. In some alternatives, the endonuclease recognition site is a BsaI restriction recognition site, and the endonuclease is BSaI. In some alternatives, the BsaI restriction recognition site is inverted. In some alternatives, the endonuclease cleavage site is located 1, 2, 3, 4, 5, 6, 7, 7, 8, 9, 10, 11, 12, 13, 14, 15, 16, 17, 18, 19 or 20 base pairs away from the most 5' thymine (or 5' terminal thymine) in the plurality of thymine nucleotides. In some alternatives, the endonuclease cleavage site is located 1, 2, 3, 4, 5, 6, 7, 7, 8, 9 or 10 base pairs away from the most 5' thymine (or 5' terminal thymine) in the plurality of thymine nucleotides.

In some alternatives, a method of making a nucleic acid encoding a nuclease is provided, the method comprising providing the polynucleotide of any of the alternatives described herein or a polynucleotide manufactured by a method of any one of the alternatives described herein and contacting said polynucleotide with a polymerase in the presence of nucleotides. The polynucleotide can comprise a first nucleic acid sequence encoding a nuclease, a second nucleic acid sequence comprising at least one restriction endonuclease recognition site and a third nucleic acid sequence, wherein the third nucleic acid sequence comprises the template strand, wherein said plurality of thymine nucleotides comprises at least, greater than, equal to, or any number in between 20, 30, 40, 50, 60, 70, 80, 90, 100, 110, 120, 130, 140, 150, 175, 200, 225, 250, 275, 300, 325, 350, 375, 400, 425, 450, 475, 500 or 550 covalently linked thymine nucleotides and wherein the third nucleic acid comprises the restriction endonuclease cleavage site, wherein the restriction endonuclease cleavage site is located within the plurality of thymine nucleotides or within 1, 2, 3, 4, 5, 6, 7, 7, 8, 9, 10, 11, 12, 13, 14, 15, 16, 17, 18, 19 or 20 base pairs away from the most 5' thymine (or 5' terminal thymine) in the plurality of thymine nucleotides and wherein said second nucleic acid is covalently linked to one end of said third nucleic acid sequence, and wherein the said restriction endonuclease recognition site is located within 55 base pairs of the restriction endonuclease cleavage site for the restriction endonuclease and said restriction endonuclease cleavage site is within 1 to 40 base pairs of a most 5' thymine in the plurality of thymine nucleotides. In some alternatives, the polynucleotide further comprises a promoter for a DNA or RNA polymerase. In some alternatives, the polymerase is a DNA polymerase. In some alternatives, the DNA polymerase is a thermal stable polymerase, such as Taq polymerase. In some alternatives, the nucleotides are adenine, cytosine, guanine, thymine and/or uracil. In some alternatives, the method further comprises providing a set of primers. In some alternatives, the nucleic acid is DNA. In some alternatives, an RNA polymerase is used. In some alternatives, the contacting is performed at a temperature at least, greater than, equal to, or any temperature in between 30° C., 31° C., 32° C., 33° C., 34° C., 35° C., 36° C. or 37° C. In some alternatives, the contacting is performed for at least 100 hours (e.g., at least, or equal to 1, 5, 10, 20, 30, 40, 50, 60, 70, 80, 90 or 100 hours or within a range defined by any two of the aforementioned times). In some alternatives, the nucleic acid is RNA. In some alternatives, the RNA comprises a plurality of adenine nucleotides, wherein the plurality of adenine nucleotides comprises at least, greater than, equal to, or any number in between 20, 30, 40, 50, 60, 70, 80, 90, 100, 110, 120, 130, 140, 150, 175, 200, 225, 250, 275, 300, 325, 350, 375, 400, 425, 450, 475, or 500 covalently linked adenines. In some alternatives, the number of covalently linked adenines is greater than 120. In some alternatives, the number of covalently linked adenines is greater than 200. In some alternatives, the number of covalently linked adenines is greater than 300. In some alternatives, the nuclease comprises an amino acid sequence set forth in SEQ ID NO. 6 or is encoded by a nucleic acid sequence set forth in SEQ ID NO: 7-14. In some alternatives, the plurality of adenine nucleotides further comprises a guanine, cytosine or a uracil, and wherein the number of covalently linked adenines terminates with a guanine, cytosine or a uracil. In some alternatives, the nucleic acid further comprises at least one palindromic sequence, wherein the at least one palindromic sequence can form a hairpin. In some alternatives, the nucleic acid further comprises a sequence capable of forming a tertiary structure such as a hairpin. In some alternatives, the method further comprises providing an endonuclease. In some alternatives, the endonuclease is a Type II restriction endonuclease. In some alternatives, the endonuclease is a Type IIS restriction endonuclease. In some alternatives, the endonuclease is BsaI or StuI. Without being limiting an endonuclease can include, for example, a CRISPR, a restriction endonuclease, a Type II restriction endonuclease and a Type IIS restriction endonuclease. In some alternatives, the endonuclease is a CRISPR, a restriction endonuclease, a Type II restriction endonuclease or a Type IIS restriction endonuclease. In some alternatives, the endonuclease is a CRISPR, a restriction endonuclease, a Type II restriction endonuclease or a Type IIS restriction endonuclease. In some alternatives, wherein StuI is provided, the endonuclease cleavage site is a StuI cleavage site, AGGCCT (SEQ ID NO: 633), and StuI cleaves between the G and C, leaving a blunt end that terminates in a GG. In some alternatives, the endonuclease cleavage site is AGGCCT (SEQ ID NO: 633). In some alternatives, the endonuclease is StuI. In some alternatives, the plurality of adenines terminates in GG. In some alternatives, the StuI cleavage site is inverted. In some alternatives, the endonuclease recognition site is a BsaI restriction recognition site, and the endonuclease is BSaI. In some alternatives, the BsaI restriction recognition site is inverted. In some alternatives, the endonuclease cleavage site is located 1, 2, 3, 4, 5, 6, 7, 7, 8, 9, 10, 11, 12, 13, 14, 15, 16, 17, 18, 19 or 20 base pairs away from the most 5' thymine (or 5' terminal thymine) in the plurality of thymine nucleotides. In some alternatives, the endonuclease cleavage site is located 1, 2, 3, 4, 5, 6, 7, 7, 8, 9 or 10 base pairs away from the most 5' thymine (or 5' terminal thymine) in the plurality of thymine nucleotides.

In some alternatives, a method of enhancing transcription of a gene encoding a nuclease is provided, the method comprising providing polynucleotide of any one of the alternatives provided herein or a polynucleotide manufactured by a method any one of the alternatives provided herein and contacting said polynucleotide with a RNA polymerase in the presence of nucleotides. The polynucleotide can comprise a first nucleic acid sequence encoding a nuclease, a second nucleic acid sequence comprising at least one restriction endonuclease recognition site and a third nucleic acid sequence, wherein the third nucleic acid sequence comprises the template strand, wherein said plurality of thymine nucleotides comprises at least, greater than, equal to, or any number in between 20, 30, 40, 50, 60, 70, 80, 90, 100, 110, 120, 130, 140, 150, 175, 200, 225, 250, 275, 300, 325, 350, 375, 400, 425, 450, 475, 500 or 550 covalently linked thymine nucleotides and wherein the third nucleic acid comprises the restriction endonuclease cleavage site, wherein the restriction endonuclease cleavage site is located within the plurality of thymine nucleotides or within 1, 2, 3, 4, 5, 6, 7, 7, 8, 9, 10, 11, 12, 13, 14, 15, 16, 17, 18, 19 or 20 base pairs away from the most 5' thymine (or 5' terminal thymine) in the plurality of thymine nucleotides and wherein said second nucleic acid is covalently linked to one end of said third nucleic acid sequence, and wherein the said restriction endonuclease recognition site is located within 55 base pairs of the restriction endonuclease cleavage site for the restriction endonuclease and said restriction endonuclease cleavage site is within 1 to 40 base pairs of a most 5' thymine in the plurality of thymine nucleotides. In some alternatives, the polynucleotide further comprises an RNA polymerase promoter. In some alternatives, the method further comprises providing an endonuclease. In some alternatives, the endonuclease is a Type II restriction endonuclease. In some alternatives, the endonuclease is a Type IIS restriction endonuclease. In some alternatives, the endonuclease is BsaI or StuI. In some alternatives, the contacting is performed at a temperature at least, greater than, equal to, or any temperature in between 30° C., 31° C., 32° C., 33° C., 34° C., 35° C., 36° C. or 37° C. In some alternatives, the method is performed for at least, greater than, equal to, or time in between 1, 5, 10, 20, 30, 40, 50, 60, 70, 80, 90 or 100 hours (e.g., at least, or equal to 1, 5, 10, 20, 30, 40, 50, 60, 70, 80, 90 or 100 hours or within a range defined by any two of the aforementioned times). Without being limiting an endonuclease can include, for example, a CRISPR, a restriction endonuclease, a Type II restriction endonuclease and a Type IIS restriction endonuclease. In some alternatives, the endonuclease is a CRISPR, a restriction endonuclease, a Type II restriction endonuclease or a Type IIS restriction endonuclease. In some alternatives, the endonuclease is a CRISPR, a restriction endonuclease, a Type II restriction endonuclease or a Type IIS restriction endonuclease. In some alternatives, wherein StuI is provided, the endonuclease cleavage site is a StuI cleavage site, AGGCCT (SEQ ID NO: 633), and StuI cleaves between the G and C, leaving a blunt end that terminates in a GG. In some alternatives, the endonuclease cleavage site is AGGCCT (SEQ ID NO: 633). In some alternatives, the endonuclease is StuI. In some alternatives, the plurality of adenines terminates in GG. In some alternatives, the StuI cleavage site is inverted. In some alternatives, the endonuclease recognition site is a BsaI restriction recognition site, and the endonuclease is BSaI. In some alternatives, the BsaI restriction recognition site is inverted. In some alternatives, the endonuclease recognition site is located 1, 2, 3, 4, 5, 6, 7, 7, 8, 9, 10, 11, 12, 13, 14, 15, 16, 17, 18, 19 or 20 base pairs from the endonuclease cleavage site of from the most 5' thymine (or 5' terminal thymine) in the plurality of thymine nucleotides. In some alternatives, the endonuclease cleavage site is located 1, 2, 3, 4, 5, 6, 7, 7, 8, 9, 10, 11, 12, 13, 14, 15, 16, 17, 18, 19 or 20 base pairs away from the most 5' thymine (or 5' terminal thymine) in the plurality of thymine nucleotides. In some alternatives, the endonuclease cleavage site is located 1, 2, 3, 4, 5, 6, 7, 7, 8, 9 or 10 base pairs away from the most 5' thymine (or 5' terminal thymine) in the plurality of thymine nucleotides.

In some alternatives, a nucleic acid encoding a nuclease manufactured by any one of the methods of any one of the alternatives is provided.

In some alternatives, a method of stabilizing translation of an RNA encoding a nuclease at 30-37 degrees Celsius for at least 100 hours (e.g., at least, or equal to 1, 5, 10, 20, 30, 40, 50, 60, 70, 80, 90 or 100 hours or within a range defined by any two of the aforementioned times) is provided, wherein the method comprises providing the nucleic acid of any one of the alternatives provided herein or a nucleic acid manufactured by any one of the alternatives provided herein and contacting said nucleic acid with a ribosome, in the presence of amino acids and tRNAs, wherein said RNA is stable at 30-37 degrees Celsius for at least 100 hours (e.g., at least, or equal to 1, 5, 10, 20, 30, 40, 50, 60, 70, 80, 90 or 100 hours or within a range defined by any two of the aforementioned times). In some alternatives, the nucleic acid further comprises an RNA polymerase promoter. In some alternatives, the contacting is performed at a temperature equal to 37° C. In some alternatives, the contacting is performed for at least, greater than, equal to, or time in between 1, 5, 10, 20, 30, 40, 50, 60, 70, 80, 90 or 100 hours (e.g., at least, or equal to 1, 5, 10, 20, 30, 40, 50, 60, 70, 80, 90 or 100 hours or within a range defined by any two of the aforementioned times). In some alternatives, the nucleic acid comprises a plurality of adenines, wherein the plurality of adenines comprises at least, greater than, equal to, or any number in between 20, 30, 40, 50, 60, 70, 80, 90, 100, 110, 120, 130, 140, 150, 175, 200, 225, 250, 275, 300, 325, 350, 375, 400, 425, 450, 475, or 500 covalently linked adenines. In some alternatives, the number of covalently linked adenines is greater than 120. In some alternatives, the number of covalently linked adenines is greater than 200. In some alternatives, the number of covalently linked adenines is greater than 300. In some alternatives, the nucleic acid is an RNA. In some alternatives, the RNA lacks a 5' and/or 3' UTR or lacks a native 5' and/or 3' UTR and/or lacks one or more sequences required for native polyadenylation such as, a cleavage/polyadenylation specificity factor (CPSF) binding site, a cleavage stimulation factor binding site (CstF), a cleavage factor I binding site (CFI), or a cleavage factor II binding site (CFII),In some alternatives, the nuclease comprises an amino acid sequence set forth in SEQ ID NO. 6 or is encoded by a nucleic acid sequence set forth in SEQ ID NO: 7-14. In some alternatives, the plurality of adenine nucleotides further comprises a guanine, cytosine or a uracil, and wherein the number of covalently linked adenines terminates with a guanine, cytosine or a uracil. In some alternatives, the nucleic acid further comprises at least one palindromic sequence, wherein the at least one palindromic sequence can form a hairpin. In some alternatives, the nucleic acid further comprises a sequence capable of forming a tertiary structure such as a hairpin. Without being limiting an endonuclease can include, for example, a CRISPR, a restriction endonuclease, a Type II restriction endonuclease and a Type IIS restriction endonuclease. In some alternatives, the endonuclease is a CRISPR, a restriction endonuclease, a Type II restriction endonuclease or a Type IIS restriction endonuclease. In some alternatives, the endonuclease is a CRISPR, a restriction endonuclease, a Type II restriction endonuclease or a Type IIS restriction endonuclease. In some alternatives, wherein StuI is provided, the endonuclease cleavage site is a StuI cleavage site, AGGCCT (SEQ ID NO: 633), and StuI cleaves between the G and C, leaving a blunt end that terminates in a GG. In some alternatives, the endonuclease cleavage site is AGGCCT (SEQ ID NO: 633). In some alternatives, the endonuclease is StuI. In some alternatives, the plurality of adenines terminates in GG. In some alternatives, the StuI cleavage site is inverted. In some alternatives, the endonuclease recognition site is a BsaI restriction recognition site, and the endonuclease is BSaI. In some alternatives, the BsaI restriction recognition site is inverted. In some alternatives, the endonuclease cleavage site is located 1, 2, 3, 4, 5, 6, 7, 7, 8, 9, 10, 11, 12, 13, 14, 15, 16, 17, 18, 19 or 20 base pairs away from the most 5' thymine (or 5' terminal thymine) in the plurality of thymine nucleotides. In some alternatives, the endonuclease cleavage site is located 1, 2, 3, 4, 5, 6, 7, 7, 8, 9 or 10 base pairs away from the most 5' thymine (or 5' terminal thymine) in the plurality of thymine nucleotides.

In some alternatives, a method of expression of a nuclease or increasing expression of a nuclease is provided, wherein the method comprises generating an mRNA from the polynucleotide of any one of the alternatives described herein or a polynucleotide manufactured by a method any one of the alternatives described herein and translating said mRNA into a peptide. In some alternatives, the polynucleotide further comprises an RNA polymerase promoter. In some alternatives, the method further comprises providing an endonuclease. In some alternatives, the endonuclease is a Type II restriction endonuclease. In some alternatives, the endonuclease is a Type IIS restriction endonuclease. In some alternatives, the endonuclease is BsaI or StuI. In some alternatives, the translating is performed at a temperature at least, greater than, equal to, or any temperature in between 30° C., 31° C., 32° C., 33° C., 34° C., 35° C., 36° C. or 37° C. In some alternatives, the translating is performed for at least, greater than, equal to, or time in between 1, 5, 10, 20, 30, 40, 50, 60, 70, 80, 90 or 100 hours (e.g., at least, or equal to 1, 5, 10, 20, 30, 40, 50, 60, 70, 80, 90 or 100 hours or within a range defined by any two of the aforementioned times). In some alternatives, the mRNA comprises a plurality of adenines, wherein the plurality of adenines comprises at least, greater than, equal to, or any number in between 20, 30, 40, 50, 60, 70, 80, 90, 100, 110, 120, 130, 140, 150, 175, 200, 225, 250, 275, 300, 325, 350, 375, 400, 425, 450, 475, or 500 covalently linked adenines. Without being limiting an endonuclease can include, for example, a CRISPR, a restriction endonuclease, a Type II restriction endonuclease and a Type IIS restriction endonuclease. In some alternatives, the endonuclease is a CRISPR, a restriction endonuclease, a Type II restriction endonuclease or a Type IIS restriction endonuclease. In some alternatives, the endonuclease is a CRISPR, a restriction endonuclease, a Type II restriction endonuclease or a Type IIS restriction endonuclease. In some alternatives, wherein StuI is provided, the endonuclease cleavage site is a StuI cleavage site, AGGCCT (SEQ ID NO: 633), and StuI cleaves between the G and C, leaving a blunt end that terminates in a GG. In some alternatives, the endonuclease cleavage site is AGGCCT (SEQ ID NO: 633). In some alternatives, the endonuclease is StuI. In some alternatives, the plurality of adenines terminates in GG. In some alternatives, the StuI cleavage site is inverted. In some alternatives, the endonuclease recognition site is a BsaI restriction recognition site, and the endonuclease is BSaI. In some alternatives, the BsaI restriction recognition site is inverted. In some alternatives, the endonuclease cleavage site is located 1, 2, 3, 4, 5, 6, 7, 7, 8, 9, 10, 11, 12, 13, 14, 15, 16, 17, 18, 19 or 20 base pairs away from the most 5' thymine (or 5' terminal thymine) in the plurality of thymine nucleotides. In some alternatives, the endonuclease cleavage site is located 1, 2, 3, 4, 5, 6, 7, 7, 8, 9 or 10 base pairs away from the most 5' thymine (or 5' terminal thymine) in the plurality of thymine nucleotides.

In some alternatives, a method of replicating a gene comprising a nuclease or enhancing stability of a replicating gene comprising a nuclease is provided, the method comprising providing the polynucleotide of any one of the alternatives provided herein or a polynucleotide manufactured by a method of any one of the alternatives provided herein, wherein said polynucleotide comprises a gene encoding a nuclease transforming a cell with said polynucleotide and propagating the cell, wherein the polynucleotide is replicated. In some alternatives, the cell is propagated for 1 day, 2 days, 4 days, 6 days, 8 days, 10 days, 12 days, or 14 days, or any other times between these values. In some alternatives, the cell is propagated at 30° C., 31° C., 32° C., 33° C., 34° C., 35° C., 36° C., or 37° C. or any other temperature between any these values. In some alternatives, the nuclease comprises an amino acid sequence set forth in SEQ ID NO. 6 or is encoded by a nucleic acid sequence set forth in SEQ ID NO: 7-14.

In some alternatives, an RNA having a plurality of adenine nucleotides is provided, the RNA comprising a first sequence comprising at least one compliment sequence to an endonuclease recognition site covalently linked to a plurality of adenine nucleotides at the 3' end of said plurality of adenine nucleotides a second sequence that comprises a plurality of adenine nucleotides, wherein the plurality of adenines comprises at least, greater than, equal to, or any number in between 20, 30, 40, 50, 60, 70, 80, 90, 100, 110, 120, 130, 140, 150, 175, 200, 225, 250, 275, 300, 325, 350, 375, 400, 425, 450, 475, or 500 covalently linked adenines and wherein said compliment sequence to an endonuclease recognition site of said first nucleic acid is covalently linked to said plurality of adenine nucleotides of said second nucleic acid at the 3' end of said plurality of adenine nucleotides of said second nucleic acid. In some alternatives, the mRNA further encodes a gene. In some alternatives, the gene is an endonuclease gene. In some alternatives, the at least one endonuclease site is inverted, and wherein the sequence encoding an RNA compliment is a compliment to the inverted endonuclease site. In some alternatives, the at least one endonuclease is a Type II restriction endonuclease recognition site. In some alternatives, the at least one endonuclease site is a Type IIS restriction endonuclease recognition site. In some alternatives, the at least one endonuclease site is a BsaI recognition site or a StuI recognition site. In some alternatives, the RNA lacks a 5' and/or 3' UTR or lacks a native 5' and/or 3' UTR and/or lacks one or more sequences required for native polyadenylation such as, a cleavage/polyadenylation specificity factor (CPSF) binding site, a cleavage stimulation factor binding site (CstF), a cleavage factor I binding site (CFI), or a cleavage factor II binding site (CFII). Without being limiting an endonuclease can include, for example, a CRISPR, a restriction endonuclease, a Type II restriction endonuclease and a Type IIS restriction endonuclease. In some alternatives, the endonuclease is a CRISPR, a restriction endonuclease, a Type II restriction endonuclease or a Type IIS restriction endonuclease. In some alternatives, the endonuclease is a CRISPR, a restriction endonuclease, a Type II restriction endonuclease or a Type IIS restriction endonuclease. In some alternatives, wherein StuI is provided, the endonuclease cleavage site is a StuI cleavage site, AGGCCT (SEQ ID NO: 633), and StuI cleaves between the G and C, leaving a blunt end that terminates in a GG. In some alternatives, the endonuclease cleavage site is AGGCCT (SEQ ID NO: 633). In some alternatives, the endonuclease is StuI. In some alternatives, the plurality of adenines terminates in GG. In some alternatives, the StuI cleavage site is inverted. In some alternatives, the endonuclease recognition site is a BsaI restriction recognition site, and the endonuclease is BSaI. In some alternatives, the BsaI restriction recognition site is inverted. In some alternatives, the endonuclease cleavage site is located 1, 2, 3, 4, 5, 6, 7, 7, 8, 9, 10, 11, 12, 13, 14, 15, 16, 17, 18, 19 or 20 base pairs away from the most 5' thymine (or 5' terminal thymine) in the plurality of thymine nucleotides. In some alternatives, the endonuclease cleavage site is located 1, 2, 3, 4, 5, 6, 7, 7, 8, 9 or 10 base pairs away from the most 5' thymine (or 5' terminal thymine) in the plurality of thymine nucleotides.

In some alternatives, a cell manufactured by the methods of any one of any of the alternatives described herein is provided.

In some alternatives, a pharmaceutical composition is provided wherein the composition comprises a pharmaceutical vehicle and a nucleic acid of any one of the alternatives provided herein or mRNA of any one of the alternatives described herein.

In some alternatives, a method of treating, ameliorating, or a inhibiting disease in a subject is provided, wherein the method comprises introducing into a cell the nucleic acid of any one of the alternatives described herein or the mRNA of any one of the alternatives described herein and delivering the cell to the subject. In some alternatives, the cell is a T-cell or a primary cell. In some alternatives, the introducing is performed by electroporation. In some alternatives, the cell is a human cell.

In some alternatives, a method of treating, ameliorating, or a inhibiting disease in a subject comprising: delivering the pharmaceutical composition of any of the alternatives described herein to the subject.

In some alternatives, a method of treating, ameliorating, or a inhibiting disease in a subject is provided, wherein the method comprises introducing into a cell the mRNA of any of the alternatives described herein and delivering the cell to the subject. In some alternatives, the cell is a T-cell or a primary cell. In some alternatives, the introducing is performed by electroporation. In some alternatives, the cell is a human cell.

In some alternatives, a pharmaceutical composition is provided, wherein the composition comprises a pharmaceutical vehicle and the mRNA of any of the alternatives described herein. In some alternatives, the mRNA lacks a 5' and/or 3' UTR or lacks a native 5' and/or 3' UTR and/or lacks one or more sequences required for native polyadenylation such as, a cleavage/polyadenylation specificity factor (CPSF) binding site, a cleavage stimulation factor binding site (CstF), a cleavage factor I binding site (CFI), or a cleavage factor II binding site (CFII).

In some alternatives, a method of treating, ameliorating, or a inhibiting disease in a subject is provided, wherein the method comprises delivering the pharmaceutical composition of any of the alternatives described herein. to the subject.

In some alternatives, a method of treating, ameliorating, or a inhibiting a disease in a subject is provided, wherein the method comprises delivering the cell of any of the alternatives described herein to the subject.

In some alternatives, polynucleotide that encodes a protein, such as a nuclease, for example SEQ ID NOs. 6-14, wherein said polynucleotide comprises an endonuclease site at the 3' end of said polynucleotide, preferably outside of the coding region for said protein, and said endonuclease site is joined to at least 7, 8, 9, 10, 11, 12, 13, 14, 15, 16, 17, 18, 19, 20, 25, 30, 35, 40, 45, 50, 60, 70, 80, 90, 100, 150, 200, 250, 300, 400, or 500 covalently linked thymine residues or an amount of covalently linked thymine residues that is within a range defined by any two of the aforementioned values, is provided.

In some alternatives, an mRNA that encodes a protein, such as a nuclease, for example SEQ ID NOs. 6-14, wherein said mRNA comprises a poly(A) tail that is at least 7, 8, 9, 10, 11, 12, 13, 14, 15, 16, 17, 18, 19, 20, 25, 30, 35, 40, 45, 50, 60, 70, 80, 90, 100, 150, 200, 250, 300, 400, or 500 residues in length or a length that is within a range defined by any two of the aforementioned lengths and, wherein said mRNA lacks a 5' and/or 3' UTR or lacks a native 5' and/or 3' UTR and/or lacks one or more sequences required for native polyadenylation such as, a cleavage/polyadenylation specificity factor (CPSF) binding site, a cleavage stimulation factor binding site (CstF), a cleavage factor I binding site (CFI), or a cleavage factor II binding site (CFII) is provided.

In some alternatives, a method of treating, ameliorating, or a inhibiting disease in a subject is provided, wherein the method comprises introducing into a cell any one or more of the polynucleotides or nucleic acids set forth in any of the aforementioned claims; and delivering the cell to the subject. In some alternatives, the cell is a T-cell or a primary cell. In some alternatives, said disease is cancer, ischemia, diabetic retinopathy, macular degeneration, rheumatoid arthritis, psoriasis, HIV infection, sickle cell anemia, Alzheimer's disease, muscular dystrophy, neurodegenerative diseases, vascular disease, cystic fibrosis, stroke, hyper IGE syndrome, hemophilia.

In some alternatives, a method of treating, ameliorating, or a inhibiting disease in a subject is provided, wherein the method comprises administering any one or more of the polynucleotides or nucleic acids set forth in any of the aforementioned claims to a subject. In some alternatives, said disease is cancer, ischemia, diabetic retinopathy, macular degeneration, rheumatoid arthritis, psoriasis, HIV infection, sickle cell anemia, Alzheimer's disease, muscular dystrophy, neurodegenerative diseases, vascular disease, cystic fibrosis, stroke, hyper IGE syndrome, hemophilia.

In some alternatives, a method of increasing and/or stabilizing expression of a protein is provided, wherein the method comprises generating an mRNA from any one or more of the polynucleotides of any one or more of the aforementioned claims and translating said mRNA into a peptide.

In some alternatives, a method of enhancing transcription or expression of a gene is provided, wherein the method comprises providing any one or more of the polynucleotides or nucleic acids of any one or more of the aforementioned claims, wherein said polynucleotide further comprises a gene, such as a nuclease gene, for example SEQ ID NOs. 6-14; and contacting said polynucleotide or nucleic acid with a RNA polymerase in the presence of nucleotides.

In some alternatives, a system for editing at least one target gene in a cell is provided, wherein the system comprises a nucleic acid encoding an endonuclease protein that targets at least one sequence in a cell, and at least one nucleic acid encoding at least one protein which alone or together with other proteins modifies the substrate specificity of at least one ubiquitin ligase enzyme or enzyme complex in the cell and, optionally, a vector that comprises a nucleic acid template for homologous gene targeting.

In some alternatives, a method of editing at least one target gene in a cell is provided, wherein the method comprises introducing into a cell a nucleic acid sequence encoding an endonuclease, introducing into said cell at least one nucleic acid sequence encoding a ubiquitin ligase enzyme/enzyme complex substrate specificity modifying protein and optionally, introducing into said cell a vector that comprises a nucleic acid template capable of homologous gene targeting of at least one genomic sequence in the cell.

In some alternatives, a polynucleotide comprising a template strand, an endonuclease recognition site and an endonuclease cleavage site for an endonuclease inserted therein, wherein said template strand comprises a plurality of thymine nucleotides, is provided. The polynucleotide can comprise a first nucleic acid sequence encoding a nuclease, a second nucleic acid sequence comprising at least one restriction endonuclease recognition site and a third nucleic acid sequence, wherein the third nucleic acid sequence comprises the template strand, wherein said plurality of thymine nucleotides comprises at least, greater than, equal to, or any number in between 20, 30, 40, 50, 60, 70, 80, 90, 100, 110, 120, 130, 140, 150, 175, 200, 225, 250, 275, 300, 325, 350, 375, 400, 425, 450, 475, 500 or 550 covalently linked thymine nucleotides and wherein the third nucleic acid comprises the restriction endonuclease cleavage site, wherein the restriction endonuclease cleavage site is located within the plurality of thymine nucleotides or within 1, 2, 3, 4, 5, 6, 7, 7, 8, 9, 10, 11, 12, 13, 14, 15, 16, 17, 18, 19 or 20 base pairs away from the most 5' thymine (or 5' terminal thymine) in the plurality of thymine nucleotides and wherein said second nucleic acid is covalently linked to one end of said third nucleic acid sequence, and wherein the said restriction endonuclease recognition site is located within 55 base pairs of the restriction endonuclease cleavage site for the restriction endonuclease and said restriction endonuclease cleavage site is within 1 to 40 base pairs of a most 5' thymine in the plurality of thymine nucleotides. In some alternatives, the at least one endonuclease recognition site is a Type II restriction endonuclease recognition site. In some alternatives, the at least one endonuclease recognition site is a Type IIS restriction endonuclease recognition site. In some alternatives, the at least one Type II restriction endonuclease recognition site is a BsaI restriction endonuclease recognition site. In some alternatives, the at least one Type II restriction endonuclease recognition site is a StuI restriction endonuclease recognition site. In some alternatives, the polynucleotide is a linear polynucleotide. In some alternatives, the endonuclease recognition site is inverted. Without being limiting an endonuclease can include, for example, a CRISPR, a restriction endonuclease, a Type II restriction endonuclease and a Type IIS restriction endonuclease. In some alternatives, the endonuclease is a CRISPR, a restriction endonuclease, a Type II restriction endonuclease or a Type IIS restriction endonuclease. In some alternatives, the endonuclease is a CRISPR, a restriction endonuclease, a Type II restriction endonuclease or a Type IIS restriction endonuclease. In some alternatives, wherein StuI is provided, the endonuclease cleavage site is a StuI cleavage site, AGGCCT (SEQ ID NO: 633), and StuI cleaves between the G and C, leaving a blunt end that terminates in a GG. In some alternatives, the endonuclease cleavage site is AGGCCT (SEQ ID NO: 633). In some alternatives, the endonuclease is StuI. In some alternatives, the plurality of adenines terminates in GG. In some alternatives, the StuI cleavage site is inverted. In some alternatives, the endonuclease recognition site is a BsaI restriction recognition site, and the endonuclease is BSaI. In some alternatives, the BsaI restriction recognition site is inverted. In some alternatives, the endonuclease cleavage site is located 1, 2, 3, 4, 5, 6, 7, 7, 8, 9, 10, 11, 12, 13, 14, 15, 16, 17, 18, 19 or 20 base pairs away from the most 5' thymine (or 5' terminal thymine) in the plurality of thymine nucleotides. In some alternatives, the endonuclease cleavage site is located 1, 2, 3, 4, 5, 6, 7, 7, 8, 9 or 10 base pairs away from the most 5' thymine (or 5' terminal thymine) in the plurality of thymine nucleotides.

In some alternatives, an mRNA having a plurality of adenine nucleotides is provided, wherein the mRNA comprises a first sequence comprising at least one compliment sequence to an endonuclease recognition site covalently linked to a second sequence, wherein the second sequence comprises a plurality of adenine nucleotides, and wherein said compliment sequence to an endonuclease recognition site of said first nucleic acid is covalently linked to said plurality of adenine nucleotides of said second nucleic acid at the 5' end of said plurality of adenine nucleotides of said second nucleic acid. In some alternatives, the mRNA further encodes a gene. In some alternatives, the gene is an endonuclease gene, such as Cas9, a derivative thereof or active fragment thereof, TALEN, or MegaTAL. In some alternatives, the at least one endonuclease site is inverted, and wherein the sequence encoding an RNA compliment is a compliment to the inverted endonuclease site. In some alternatives, the at least one endonuclease is a Type II restriction endonuclease recognition site. In some alternatives, the at least one endonuclease site is a Type IIS restriction endonuclease recognition site. In some alternatives, the at least one endonuclease site is a BsaI recognition site. In some alternatives, the at least one endonuclease site is a StuI recognition site. In some alternatives, the gene is codon optimized for expression in a mammalian cell, such as a human cell. In some alternatives, the mRNA lacks a 5' and/or 3' UTR or lacks a native 5' and/or 3' UTR and/or lacks one or more sequences required for native polyadenylation such as, a cleavage/polyadenylation specificity factor (CPSF) binding site, a cleavage stimulation factor binding site (CstF), a cleavage factor I binding site (CFI), or a cleavage factor II binding site (CFII). Without being limiting an endonuclease can include, for example, a CRISPR, a restriction endonuclease, a Type II restriction endonuclease and a Type IIS restriction endonuclease. In some alternatives, the endonuclease is a CRISPR, a restriction endonuclease, a Type II restriction endonuclease or a Type IIS restriction endonuclease. In some alternatives, the endonuclease is a CRISPR, a restriction endonuclease, a Type II restriction endonuclease or a Type IIS restriction endonuclease. In some alternatives, wherein StuI is provided, the endonuclease cleavage site is a StuI cleavage site, AGGCCT (SEQ ID NO: 633), and StuI cleaves between the G and C, leaving a blunt end that terminates in a GG. In some alternatives, the endonuclease cleavage site is AGGCCT (SEQ ID NO: 633). In some alternatives, the endonuclease is StuI. In some alternatives, the plurality of adenines terminates in GG. In some alternatives, the StuI cleavage site is inverted. In some alternatives, the endonuclease recognition site is a BsaI restriction recognition site, and the endonuclease is BSaI. In some alternatives, the BsaI restriction recognition site is inverted. In some alternatives, the endonuclease cleavage site is located 1, 2, 3, 4, 5, 6, 7, 7, 8, 9, 10, 11, 12, 13, 14, 15, 16, 17, 18, 19 or 20 base pairs away from the most 5' thymine (or 5' terminal thymine) in the plurality of thymine nucleotides. In some alternatives, the endonuclease cleavage site is located 1, 2, 3, 4, 5, 6, 7, 7, 8, 9 or 10 base pairs away from the most 5' thymine (or 5' terminal thymine) in the plurality of thymine nucleotides.

In some alternatives, a cell is provided, wherein the cell is manufactured by any of the methods provided herein. The method can comprise providing the polynucleotide of any of the alternatives described herein, wherein said polynucleotide further comprises a gene, transforming a cell with said polynucleotide and propagating the cell, wherein the polynucleotide is replicated. The polynucleotide can comprise a first nucleic acid sequence encoding a nuclease, a second nucleic acid sequence comprising at least one restriction endonuclease recognition site and a third nucleic acid sequence, wherein the third nucleic acid sequence comprises the template strand, wherein said plurality of thymine nucleotides comprises at least, greater than, equal to, or any number in between 20, 30, 40, 50, 60, 70, 80, 90, 100, 110, 120, 130, 140, 150, 175, 200, 225, 250, 275, 300, 325, 350, 375, 400, 425, 450, 475, 500 or 550 covalently linked thymine nucleotides and wherein the third nucleic acid comprises the restriction endonuclease cleavage site, wherein the restriction endonuclease cleavage site is located within the plurality of thymine nucleotides or within 1, 2, 3, 4, 5, 6, 7, 7, 8, 9, 10, 11, 12, 13, 14, 15, 16, 17, 18, 19 or 20 base pairs away from the most 5' thymine (or 5' terminal thymine) in the plurality of thymine nucleotides and wherein said second nucleic acid is covalently linked to one end of said third nucleic acid sequence, and wherein the said restriction endonuclease recognition site is located within 55 base pairs of the restriction endonuclease cleavage site for the restriction endonuclease and said restriction endonuclease cleavage site is within 1 to 40 base pairs of a most 5' thymine in the plurality of thymine nucleotides. In some alternatives, the polynucleotide comprises at least, greater than, equal to, or any number in between 20, 30, 40, 50, 60, 70, 80, 90, 100, 110, 120, 130, 140, 150, 175, 200, 225, 250, 275, 300, 325, 350, 375, 400, 425, 450, 475, 500 or 550 covalently linked thymines. In some alternatives, the at least one endonuclease recognition site is a Type II restriction endonuclease recognition site. In some alternatives, the at least one endonuclease recognition site is a Type IIS restriction endonuclease recognition site. In some alternatives, the at least one Type II restriction endonuclease recognition site is a BsaI restriction endonuclease recognition site. In some alternatives, the at least one Type II restriction endonuclease recognition site is a StuI restriction endonuclease recognition site. In some alternatives, the polynucleotide is a linear polynucleotide. In some alternatives, the endonuclease recognition site is inverted. In some alternatives, the polynucleotide further comprises an RNA polymerase promoter. In some alternatives, the cell is propagated for 1 day, 2 days, 4 days, 6 days, 8 days, 10 days, 12 days, 14 days, or any other times between these values. In some alternatives, the cell is propagated at 30° C., 31° C., 32° C., 33° C., 34° C., 35° C., 36° C., 37° C. or any other temperature between any these values. In some alternatives, the cell is a human cell. In some alternatives, the gene is codon optimized for expression in a mammalian cell, such as a human cell. Without being limiting an endonuclease can include, for example, a CRISPR, a restriction endonuclease, a Type II restriction endonuclease and a Type IIS restriction endonuclease. In some alternatives, the endonuclease is a CRISPR, a restriction endonuclease, a Type II restriction endonuclease or a Type IIS restriction endonuclease. In some alternatives, the endonuclease is a CRISPR, a restriction endonuclease, a Type II restriction endonuclease or a Type IIS restriction endonuclease. In some alternatives, wherein StuI is provided, the endonuclease cleavage site is a StuI cleavage site, AGGCCT (SEQ ID NO: 633), and StuI cleaves between the G and C, leaving a blunt end that terminates in a GG. In some alternatives, the endonuclease cleavage site is AGGCCT (SEQ ID NO: 633). In some alternatives, the endonuclease is StuI. In some alternatives, the plurality of adenines terminates in GG. In some alternatives, the StuI cleavage site is inverted. In some alternatives, the endonuclease recognition site is a BsaI restriction recognition site, and the endonuclease is BSaI. In some alternatives, the BsaI restriction recognition site is inverted. In some alternatives, the endonuclease cleavage site is located 1, 2, 3, 4, 5, 6, 7, 7, 8, 9, 10, 11, 12, 13, 14, 15, 16, 17, 18, 19 or 20 base pairs away from the most 5' thymine (or 5' terminal thymine) in the plurality of thymine nucleotides. In some alternatives, the endonuclease cleavage site is located 1, 2, 3, 4, 5, 6, 7, 7, 8, 9 or 10 base pairs away from the most 5' thymine (or 5' terminal thymine) in the plurality of thymine nucleotides.

In some alternatives, a method of treating, ameliorating, or a inhibiting a disease in a subject is provided, wherein the method comprises introducing into a cell a polynucleotide and delivering the cell to the subject. In some alternatives the disease is sickle cell disease, hypercholesterolemia, cancer, autoimmune disease, inherited disorder of metabolism, or immunodeficiency. In some alternatives, the disease is cancer, ischemia, diabetic retinopathy, macular degeneration, rheumatoid arthritis, psoriasis, HIV infection, sickle cell anemia, Alzheimer's disease, muscular dystrophy, neurodegenerative diseases, vascular disease, cystic fibrosis, stroke, hyper IGE syndrome, hemophilia. In some alternatives, the disease is cancer, ischemia, diabetic retinopathy, macular degeneration, rheumatoid arthritis, psoriasis, HIV infection, sickle cell anemia, Alzheimer's disease, muscular dystrophy, neurodegenerative diseases, vascular disease, cystic fibrosis, stroke, hyper IGE syndrome or hemophilia. The polynucleotide can comprise a first nucleic acid sequence encoding a nuclease, a second nucleic acid sequence comprising at least one restriction endonuclease recognition site and a third nucleic acid sequence, wherein the third nucleic acid sequence comprises the template strand, wherein said plurality of thymine nucleotides comprises at least, greater than, equal to, or any number in between 20, 30, 40, 50, 60, 70, 80, 90, 100, 110, 120, 130, 140, 150, 175, 200, 225, 250, 275, 300, 325, 350, 375, 400, 425, 450, 475, 500 or 550 covalently linked thymine nucleotides and wherein the third nucleic acid comprises the restriction endonuclease cleavage site, wherein the restriction endonuclease cleavage site is located within the plurality of thymine nucleotides or within 1, 2, 3, 4, 5, 6, 7, 7, 8, 9, 10, 11, 12, 13, 14, 15, 16, 17, 18, 19 or 20 base pairs away from the most 5' thymine (or 5' terminal thymine) in the plurality of thymine nucleotides and wherein said second nucleic acid is covalently linked to one end of said third nucleic acid sequence, and wherein the said restriction endonuclease recognition site is located within 55 base pairs of the restriction endonuclease cleavage site for the restriction endonuclease and said restriction endonuclease cleavage site is within 1 to 40 base pairs of a most 5' thymine in the plurality of thymine nucleotides. In some alternatives, the polynucleotide comprises at least, greater than, equal to, or any number in between 20, 30, 40, 50, 60, 70, 80, 90, 100, 110, 120, 130, 140, 150, 175, 200, 225, 250, 275, 300, 325, 350, 375, 400, 425, 450, 475, 500 or 550 covalently linked thymines. In some alternatives, the at least one endonuclease recognition site is a Type II restriction endonuclease recognition site. In some alternatives, the at least one endonuclease recognition site is a Type IIS restriction endonuclease recognition site. In some alternatives, the at least one Type II restriction endonuclease recognition site is a BsaI restriction endonuclease recognition site. In some alternatives, the at least one Type II restriction endonuclease recognition site is a StuI restriction endonuclease recognition site. In some alternatives, the polynucleotide is a linear polynucleotide. In some alternatives, the endonuclease recognition site is inverted. In some alternatives, the polynucleotide further comprises an RNA polymerase promoter. In some alternatives, the cell is a T-cell or a primary cell. In some alternatives, the introducing is performed by electroporation. In some alternatives, the cell is a human cell. Without being limiting an endonuclease can include, for example, a CRISPR, a restriction endonuclease, a Type II restriction endonuclease and a Type IIS restriction endonuclease. In some alternatives, the endonuclease is a CRISPR, a restriction endonuclease, a Type II restriction endonuclease or a Type IIS restriction endonuclease. In some alternatives, the endonuclease is a CRISPR, a restriction endonuclease, a Type II restriction endonuclease or a Type IIS restriction endonuclease. In some alternatives, wherein StuI is provided, the endonuclease cleavage site is a StuI cleavage site, AGGCCT (SEQ ID NO: 633), and StuI cleaves between the G and C, leaving a blunt end that terminates in a GG. In some alternatives, the endonuclease cleavage site is AGGCCT (SEQ ID NO: 633). In some alternatives, the endonuclease is StuI. In some alternatives, the plurality of adenines terminates in GG. In some alternatives, the StuI cleavage site is inverted. In some alternatives, the endonuclease recognition site is a BsaI restriction recognition site, and the endonuclease is BSaI. In some alternatives, the BsaI restriction recognition site is inverted. In some alternatives, the endonuclease cleavage site is located 1, 2, 3, 4, 5, 6, 7, 7, 8, 9, 10, 11, 12, 13, 14, 15, 16, 17, 18, 19 or 20 base pairs away from the most 5' thymine (or 5' terminal thymine) in the plurality of thymine nucleotides. In some alternatives, the endonuclease cleavage site is located 1, 2, 3, 4, 5, 6, 7, 7, 8, 9 or 10 base pairs away from the most 5' thymine (or 5' terminal thymine) in the plurality of thymine nucleotides.

In some alternatives, a method of treating, ameliorating, or a inhibiting disease in a subject is provided, wherein the method comprises introducing into a cell an mRNA of any and delivering the cell to the subject. In some alternatives, the mRNA further encodes a gene. In some alternatives, the gene is an endonuclease gene, such as Cas9, a derivative thereof or active fragment thereof, TALEN, or MegaTAL. In some alternatives, the at least one endonuclease site is inverted, and wherein the sequence encoding an RNA compliment is a compliment to the inverted endonuclease site. In some alternatives, the at least one endonuclease is a Type II restriction endonuclease recognition site. In some alternatives, the at least one endonuclease site is a Type IIS restriction endonuclease recognition site. In some alternatives, the at least one endonuclease site is a BsaI recognition site. In some alternatives, the at least one endonuclease site is a StuI recognition site. In some alternatives, the cell is a T-cell or a primary cell. In some alternatives, the introducing is performed by electroporation. In some alternatives, the cell is a human cell. In some alternatives, the gene is codon optimized for expression in a mammalian cell, such as a human cell. Without being limiting an endonuclease can include, for example, a CRISPR, a restriction endonuclease, a Type II restriction endonuclease and a Type IIS restriction endonuclease. In some alternatives, the endonuclease is a CRISPR, a restriction endonuclease, a Type II restriction endonuclease or a Type IIS restriction endonuclease. In some alternatives, the endonuclease is a CRISPR, a restriction endonuclease, a Type II restriction endonuclease or a Type IIS restriction endonuclease. In some alternatives, wherein StuI is provided, the endonuclease cleavage site is a StuI cleavage site, AGGCCT (SEQ ID NO: 633), and StuI cleaves between the G and C, leaving a blunt end that terminates in a GG. In some alternatives, the endonuclease cleavage site is AGGCCT (SEQ ID NO: 633). In some alternatives, the endonuclease is StuI. In some alternatives, the plurality of adenines terminates in GG. In some alternatives, the StuI cleavage site is inverted. In some alternatives, the endonuclease recognition site is a BsaI restriction recognition site, and the endonuclease is BSaI. In some alternatives, the BsaI restriction recognition site is inverted. In some alternatives, the endonuclease cleavage site is located 1, 2, 3, 4, 5, 6, 7, 7, 8, 9, 10, 11, 12, 13, 14, 15, 16, 17, 18, 19 or 20 base pairs away from the most 5' thymine (or 5' terminal thymine) in the plurality of thymine nucleotides. In some alternatives, the endonuclease cleavage site is located 1, 2, 3, 4, 5, 6, 7, 7, 8, 9 or 10 base pairs away from the most 5' thymine (or 5' terminal thymine) in the plurality of thymine nucleotides.

In some alternatives, a method of treating, ameliorating, or a inhibiting a disease in a subject is provided, wherein the method comprises delivering a cell to the subject. In some alternatives, the cell is manufactured by any of the methods provided herein. The method can comprise providing the polynucleotide of any of the alternatives described herein, wherein said polynucleotide further comprises a gene, transforming a cell with said polynucleotide and propagating the cell, wherein the polynucleotide is replicated. The polynucleotide can comprise a first nucleic acid sequence encoding a nuclease, a second nucleic acid sequence comprising at least one restriction endonuclease recognition site and a third nucleic acid sequence, wherein the third nucleic acid sequence comprises the template strand, wherein said plurality of thymine nucleotides comprises at least, greater than, equal to, or any number in between 20, 30, 40, 50, 60, 70, 80, 90, 100, 110, 120, 130, 140, 150, 175, 200, 225, 250, 275, 300, 325, 350, 375, 400, 425, 450, 475, 500 or 550 covalently linked thymine nucleotides and wherein the third nucleic acid comprises the restriction endonuclease cleavage site, wherein the restriction endonuclease cleavage site is located within the plurality of thymine nucleotides or within 1, 2, 3, 4, 5, 6, 7, 7, 8, 9, 10, 11, 12, 13, 14, 15, 16, 17, 18, 19 or 20 base pairs away from the most 5' thymine (or 5' terminal thymine) in the plurality of thymine nucleotides and wherein said second nucleic acid is covalently linked to one end of said third nucleic acid sequence, and wherein the said restriction endonuclease recognition site is located within 55 base pairs of the restriction endonuclease cleavage site for the restriction endonuclease and said restriction endonuclease cleavage site is within 1 to 40 base pairs of a most 5' thymine in the plurality of thymine nucleotides. In some alternatives, the cell is propagated for 1 day, 2 days, 4 days, 6 days, 8 days, 10 days, 12 days, 14 days, or any other times between these values. In some alternatives, the cell is propagated at 30° C., 31° C., 32° C., 33° C., 34° C., 35° C., 36° C., 37° C. or any other temperature between any these values. In some alternatives, the cell is a human cell. In some alternatives, the polynucleotide comprises at least, greater than, equal to, or any number in between 20, 30, 40, 50, 60, 70, 80, 90, 100, 110, 120, 130, 140, 150, 175, 200, 225, 250, 275, 300, 325, 350, 375, 400, 425, 450, 475, 500 or 550 covalently linked thymines. In some alternatives, the at least one endonuclease recognition site is a Type II restriction endonuclease recognition site. In some alternatives, the at least one endonuclease recognition site is a Type IIS restriction endonuclease recognition site. In some alternatives, the at least one Type II restriction endonuclease recognition site is a BsaI restriction endonuclease recognition site. In some alternatives, the at least one endonuclease recognition site is a StuI restriction endonuclease recognition site. In some alternatives, the polynucleotide is a linear polynucleotide. In some alternatives, the endonuclease recognition site is inverted. In some alternatives, the polynucleotide further comprises an RNA polymerase promoter. In some alternatives, the polynucleotide further comprises an RNA polymerase promoter. In some alternatives, the gene is codon optimized for expression in a mammalian cell, such as a human cell. In some alternatives, the gene encodes an endonuclease protein that targets at least one sequence in a cell. In some alternatives, the cell is a mammalian cell. In some alternatives, is a human cell. In some alternatives, is a primary cell. In some alternatives, the cell is not a transformed cell. In some alternatives, the cell is a primary lymphocyte or a CD34+ stem cell. In some alternatives, the cell is a hepatocyte. In some alternatives, the cell is a cardiomyocyte. In some alternatives, the gene encodes Cas9, a derivative thereof or active fragment thereof, TALEN or MegaTAL. In some alternatives, the gene is codon optimized for expression in a eukaryotic cell, such as a human cell. In some alternatives, the gene encodes ubiquitin ligase enzyme/enzyme complex substrate specificity modifying proteins. In some alternatives, the gene encodes the adenoviral protein E4ORF6 of any adenoviral serotype. In some alternatives, the gene encodes E1B55k of any adenovirus serotype. In some alternatives, the gene encodes a meganuclease, a TALEN, a zinc finger nuclease, or a MegaTAL. In some alternatives, the gene encodes a nuclease. In some alternatives, the adenoviral proteins comprise a sequence set forth in SEQ ID NOs: 1-5. Without being limiting an endonuclease can include, for example, a CRISPR, a restriction endonuclease, a Type II restriction endonuclease and a Type IIS restriction endonuclease. In some alternatives, the endonuclease is a CRISPR, a restriction endonuclease, a Type II restriction endonuclease or a Type IIS restriction endonuclease. In some alternatives, the endonuclease is a CRISPR, a restriction endonuclease, a Type II restriction endonuclease or a Type IIS restriction endonuclease. In some alternatives, wherein StuI is provided, the endonuclease cleavage site is a StuI cleavage site, AGGCCT (SEQ ID NO: 633), and StuI cleaves between the G and C, leaving a blunt end that terminates in a GG. In some alternatives, the endonuclease cleavage site is AGGCCT (SEQ ID NO: 633). In some alternatives, the endonuclease is StuI. In some alternatives, the plurality of adenines terminates in GG. In some alternatives, the StuI cleavage site is inverted. In some alternatives, the endonuclease recognition site is a BsaI restriction recognition site, and the endonuclease is BSaI. In some alternatives, the BsaI restriction recognition site is inverted. In some alternatives, the endonuclease recognition site is located 1, 2, 3, 4, 5, 6, 7, 7, 8, 9, 10, 11, 12, 13, 14, 15, 16, 17, 18, 19 or 20 base pairs from the endonuclease cleavage site of from the most 5' thymine (or 5' terminal thymine) in the plurality of thymine nucleotides. In some alternatives, the endonuclease recognition site is located 1, 2, 3, 4, 5, 6, 7, 7, 8, 9 or 10 base pairs from the endonuclease cleavage site of from the most 5' thymine (or 5' terminal thymine) in the plurality of thymine nucleotides. In some alternatives, the endonuclease cleavage site is located 1, 2, 3, 4, 5, 6, 7, 7, 8, 9, 10, 11, 12, 13, 14, 15, 16, 17, 18, 19 or 20 base pairs away from the most 5' thymine (or 5' terminal thymine) in the plurality of thymine nucleotides. In some alternatives, the endonuclease cleavage site is located 1, 2, 3, 4, 5, 6, 7, 7, 8, 9 or 10 base pairs away from the most 5' thymine (or 5' terminal thymine) in the plurality of thymine nucleotides.

In some alternatives of treating, ameliorating, or inhibiting disease in a subject, the disease is sickle cell disease, hypercholesterolemia, cancer, autoimmune disease, inherited disorder of metabolism, or immunodeficiency.

In some alternatives, a method of making a polynucleotide comprising a gene encoding a protein one desires to express is provided, wherein the polynucleotide comprises a plurality of thymine nucleotides and an endonuclease recognition site inserted therein. The method of making a polynucleotide comprising a sequence encoding a nuclease, a template strand, an endonuclease recognition site and an endonuclease cleavage site for an endonuclease inserted therein, wherein said template strand comprises a plurality of thymine nucleotides can comprise providing a first nucleic acid sequence encoding a nuclease, providing a second nucleic acid sequence comprising at least one endonuclease recognition site, providing a third nucleic acid sequence, wherein the third nucleic acid sequence comprises the template strand, wherein the template strand comprises a plurality of thymine nucleotides, wherein said plurality of thymine nucleotides comprises at least, greater than, equal to, or any number in between 20, 30, 40, 50, 60, 70, 80, 90, 100, 110, 120, 130, 140, 150, 175, 200, 225, 250, 275, 300, 325, 350, 375, 400, 425, 450, 475, 500 or 550 covalently linked thymine nucleotides and wherein the third nucleic acid comprises the endonuclease cleavage site, wherein the endonuclease cleavage site is located within the plurality of thymine nucleotides or within 1, 2, 3, 4, 5, 6, 7, 7, 8, 9, 10, 11, 12, 13, 14, 15, 16, 17, 18, 19 or 20 base pairs away from the most 5' thymine (or 5' terminal thymine) in the plurality of thymine nucleotides, joining said first nucleic acid to one end of the second nucleic acid sequence and joining said third nucleic acid sequence to one end of the second nucleic acid sequence, wherein said second nucleic acid is covalently linked to one end of said third nucleic acid sequence, and wherein the said endonuclease recognition site is located within 55 base pairs of the endonuclease cleavage site for the endonuclease and said endonuclease cleavage site is within 1 to 40 base pairs of a most 5' thymine in the plurality of thymine nucleotides. Without being limiting an endonuclease can include, for example, a CRISPR, a restriction endonuclease, a Type II restriction endonuclease and a Type IIS restriction endonuclease. In some alternatives, the endonuclease is a CRISPR, a restriction endonuclease, a Type II restriction endonuclease or a Type IIS restriction endonuclease. In some alternatives, the endonuclease is a CRISPR, a restriction endonuclease, a Type II restriction endonuclease or a Type IIS restriction endonuclease. In some alternatives, wherein StuI is provided, the endonuclease cleavage site is a StuI cleavage site, AGGCCT (SEQ ID NO: 633), and StuI cleaves between the G and C, leaving a blunt end that terminates in a GG. In some alternatives, the endonuclease cleavage site is AGGCCT (SEQ ID NO: 633). In some alternatives, the endonuclease is StuI. In some alternatives, the plurality of adenines terminates in GG. In some alternatives, the StuI cleavage site is inverted. In some alternatives, the endonuclease recognition site is a BsaI restriction recognition site, and the endonuclease is BSaI. In some alternatives, the BsaI restriction recognition site is inverted. In some alternatives, the endonuclease cleavage site is located 1, 2, 3, 4, 5, 6, 7, 7, 8, 9, 10, 11, 12, 13, 14, 15, 16, 17, 18, 19 or 20 base pairs away from the most 5' thymine (or 5' terminal thymine) in the plurality of thymine nucleotides. In some alternatives, the endonuclease cleavage site is located 1, 2, 3, 4, 5, 6, 7, 7, 8, 9 or 10 base pairs away from the most 5' thymine (or 5' terminal thymine) in the plurality of thymine nucleotides.

In some alternatives, an mRNA generated by the methods described herein is used as a therapeutic mRNA for treating disease by directly delivering the mRNA into a human, either alone or in conjunction with an encapsulating substance that promotes its deliver to inside a cell. In some alternatives, the mRNA is introduced into a cell. In some alternatives, the cell is a primary cell. In some alternatives, the cell is delivered to a subject in need. In some alternatives the subject is a human.

In some alternatives of the polynucleotide, the polynucleotide comprises a Type IIS endonuclease recognition site downstream from the intended cut site, thereby creating a Type IIS endonuclease cleavage site upstream from the Type IIS endonuclease recognition site. In some alternatives, the Type IIS restriction is inverted. In some alternatives, the Type IIS endonuclease cleavage site is at a distance of 1-30 bases away from the Type IIS endonuclease recognition site. In some alternatives, the endonuclease cleavage site is located 1, 2, 3, 4, 5, 6, 7, 7, 8, 9, 10, 11, 12, 13, 14, 15, 16, 17, 18, 19 or 20 base pairs away from the most 5' thymine (or 5' terminal thymine) in the plurality of thymine nucleotides. In some alternatives, the endonuclease cleavage site is located 1, 2, 3, 4, 5, 6, 7, 7, 8, 9 or 10 base pairs away from the most 5' thymine (or 5' terminal thymine) in the plurality of thymine nucleotides.

In some alternatives, a polynucleotide having a plurality of thymine nucleotides and an endonuclease recognition site inserted therein is provided. The polynucleotide can comprise a first nucleic acid sequence encoding a nuclease, a second nucleic acid sequence comprising at least one restriction endonuclease recognition site and a third nucleic acid sequence, wherein the third nucleic acid sequence comprises the template strand, wherein said plurality of thymine nucleotides comprises at least, greater than, equal to, or any number in between 20, 30, 40, 50, 60, 70, 80, 90, 100, 110, 120, 130, 140, 150, 175, 200, 225, 250, 275, 300, 325, 350, 375, 400, 425, 450, 475, 500 or 550 covalently linked thymine nucleotides and wherein the third nucleic acid comprises the restriction endonuclease cleavage site, wherein the restriction endonuclease cleavage site is located within the plurality of thymine nucleotides or within 1, 2, 3, 4, 5, 6, 7, 7, 8, 9, 10, 11, 12, 13, 14, 15, 16, 17, 18, 19 or 20 base pairs away from the most 5' thymine (or 5' terminal thymine) in the plurality of thymine nucleotides and wherein said second nucleic acid is covalently linked to one end of said third nucleic acid sequence, and wherein the said restriction endonuclease recognition site is located within 55 base pairs of the restriction endonuclease cleavage site for the restriction endonuclease and said restriction endonuclease cleavage site is within 1 to 40 base pairs of a most 5' thymine in the plurality of thymine nucleotides. In some alternatives, the at least one endonuclease recognition site is a Type II restriction endonuclease recognition site. In some alternatives, the at least endonuclease recognition site is a BsaI or a StuI restriction endonuclease recognition site. In some alternatives, the endonuclease cleavage site is between 1-5 nucleotides upstream from the endonuclease recognition site. In some alternatives, the polynucleotide further comprises a gene. In some alternatives, the gene is an endonuclease gene e.g., SEQ ID NOs. 6-14. Without being limiting an endonuclease can include, for example, a CRISPR, a restriction endonuclease, a Type II restriction endonuclease and a Type IIS restriction endonuclease. In some alternatives, the endonuclease is a CRISPR, a restriction endonuclease, a Type II restriction endonuclease or a Type IIS restriction endonuclease. In some alternatives, the endonuclease is a CRISPR, a restriction endonuclease, a Type II restriction endonuclease or a Type IIS restriction endonuclease. In some alternatives, wherein StuI is provided, the endonuclease cleavage site is a StuI cleavage site, AGGCCT (SEQ ID NO: 633), and StuI cleaves between the G and C, leaving a blunt end that terminates in a GG. In some alternatives, the endonuclease cleavage site is AGGCCT (SEQ ID NO: 633). In some alternatives, the endonuclease is StuI. In some alternatives, the plurality of adenines terminates in GG. In some alternatives, the StuI cleavage site is inverted. In some alternatives, the endonuclease recognition site is a BsaI restriction recognition site, and the endonuclease is BSaI. In some alternatives, the BsaI restriction recognition site is inverted. In some alternatives, the endonuclease cleavage site is located 1, 2, 3, 4, 5, 6, 7, 7, 8, 9, 10, 11, 12, 13, 14, 15, 16, 17, 18, 19 or 20 base pairs away from the most 5' thymine (or 5' terminal thymine) in the plurality of thymine nucleotides. In some alternatives, the endonuclease cleavage site is located 1, 2, 3, 4, 5, 6, 7, 7, 8, 9 or 10 base pairs away from the most 5' thymine (or 5' terminal thymine) in the plurality of thymine nucleotides. In some alternatives, a method of making a polynucleotide having a plurality of thymine nucleotides and an endonuclease recognition site inserted therein is provided. The method of making a polynucleotide comprising a sequence encoding a nuclease, a template strand, an endonuclease recognition site and an endonuclease cleavage site for an endonuclease inserted therein, wherein said template strand comprises a plurality of thymine nucleotides can comprise providing a first nucleic acid sequence encoding a nuclease, providing a second nucleic acid sequence comprising at least one endonuclease recognition site, providing a third nucleic acid sequence, wherein the third nucleic acid sequence comprises the template strand, wherein the template strand comprises a plurality of thymine nucleotides, wherein said plurality of thymine nucleotides comprises at least, greater than, equal to, or any number in between 20, 30, 40, 50, 60, 70, 80, 90, 100, 110, 120, 130, 140, 150, 175, 200, 225, 250, 275, 300, 325, 350, 375, 400, 425, 450, 475, 500 or 550 covalently linked thymine nucleotides and wherein the third nucleic acid comprises the endonuclease cleavage site, wherein the endonuclease cleavage site is located within the plurality of thymine nucleotides or within 1, 2, 3, 4, 5, 6, 7, 7, 8, 9, 10, 11, 12, 13, 14, 15, 16, 17, 18, 19 or 20 base pairs away from the most 5' thymine (or 5' terminal thymine) in the plurality of thymine nucleotides, joining said first nucleic acid to one end of the second nucleic acid sequence and joining said third nucleic acid sequence to one end of the second nucleic acid sequence, wherein said second nucleic acid is covalently linked to one end of said third nucleic acid sequence, and wherein the said endonuclease recognition site is located within 55 base pairs of the endonuclease cleavage site for the endonuclease and said endonuclease cleavage site is within 1 to 40 base pairs of a most 5' thymine in the plurality of thymine nucleotides. In some alternatives, the polynucleotide comprises at least, greater than, equal to, or any number in between 20, 30, 40, 50, 60, 70, 80, 90, 100, 110, 120, 130, 140, 150, 175, 200, 225, 250, 275, 300, 325, 350, 375, 400, 425, 450, 475, 500 or 550 covalently linked thymines. In some alternatives, the at least one endonuclease recognition site is a Type II restriction endonuclease recognition site. In some alternatives, the at least one endonuclease recognition site is a Type IIS restriction endonuclease recognition site. In some alternatives, the at least one Type II restriction endonuclease recognition site is a BsaI or a StuI restriction endonuclease recognition site. In some alternatives, the endonuclease cleavage site is between 1-5 nucleotides from the endonuclease recognition site. In some alternatives, the polynucleotide further comprises a gene. In some alternatives, the gene is an endonuclease gene e.g., SEQ ID NOs. 6-14. Without being limiting an endonuclease can include, for example, a CRISPR, a restriction endonuclease, a Type II restriction endonuclease and a Type IIS restriction endonuclease. In some alternatives, the endonuclease is a CRISPR, a restriction endonuclease, a Type II restriction endonuclease or a Type IIS restriction endonuclease. In some alternatives, the endonuclease is a CRISPR, a restriction endonuclease, a Type II restriction endonuclease or a Type IIS restriction endonuclease. In some alternatives, wherein StuI is provided, the endonuclease cleavage site is a StuI cleavage site, AGGCCT (SEQ ID NO: 633), and StuI cleaves between the G and C, leaving a blunt end that terminates in a GG. In some alternatives, the endonuclease cleavage site is AGGCCT (SEQ ID NO: 633). In some alternatives, the endonuclease is StuI. In some alternatives, the plurality of adenines terminates in GG. In some alternatives, the StuI cleavage site is inverted. In some alternatives, the endonuclease recognition site is a BsaI restriction recognition site, and the endonuclease is BSaI. In some alternatives, the BsaI restriction recognition site is inverted. In some alternatives, the endonuclease cleavage site is located 1, 2, 3, 4, 5, 6, 7, 7, 8, 9, 10, 11, 12, 13, 14, 15, 16, 17, 18, 19 or 20 base pairs away from the most 5' thymine (or 5' terminal thymine) in the plurality of thymine nucleotides. In some alternatives, the endonuclease cleavage site is located 1, 2, 3, 4, 5, 6, 7, 7, 8, 9 or 10 base pairs away from the most 5' thymine (or 5' terminal thymine) in the plurality of thymine nucleotides.

In some alternatives, a method of making a polynucleotide having a plurality of thymine nucleotides and an endonuclease recognition site inserted therein is provided. The method of making a polynucleotide comprising a sequence encoding a nuclease, a template strand, an endonuclease recognition site and an endonuclease cleavage site for an endonuclease inserted therein, wherein said template strand comprises a plurality of thymine nucleotides can comprise providing a first nucleic acid sequence encoding a nuclease, providing a second nucleic acid sequence comprising at least one endonuclease recognition site, providing a third nucleic acid sequence, wherein the third nucleic acid sequence comprises the template strand, wherein the template strand comprises a plurality of thymine nucleotides, wherein said plurality of thymine nucleotides comprises at least, greater than, equal to, or any number in between 20, 30, 40, 50, 60, 70, 80, 90, 100, 110, 120, 130, 140, 150, 175, 200, 225, 250, 275, 300, 325, 350, 375, 400, 425, 450, 475, 500 or 550 covalently linked thymine nucleotides and wherein the third nucleic acid comprises the endonuclease cleavage site, wherein the endonuclease cleavage site is located within the plurality of thymine nucleotides or within 1, 2, 3, 4, 5, 6, 7, 7, 8, 9, 10, 11, 12, 13, 14, 15, 16, 17, 18, 19 or 20 base pairs away from the most 5' thymine (or 5' terminal thymine) in the plurality of thymine nucleotides, joining said first nucleic acid to one end of the second nucleic acid sequence and joining said third nucleic acid sequence to one end of the second nucleic acid sequence, wherein said second nucleic acid is covalently linked to one end of said third nucleic acid sequence, and wherein the said endonuclease recognition site is located within 55 base pairs of the endonuclease cleavage site for the endonuclease and said endonuclease cleavage site is within 1 to 40 base pairs of a most 5' thymine in the plurality of thymine nucleotides. In some alternatives, the polynucleotide comprises at least, greater than, equal to, or any number in between 20, 30, 40, 50, 60, 70, 80, 90, 100, 110, 120, 130, 140, 150, 175, 200, 225, 250, 275, 300, 325, 350, 375, 400, 425, 450, 475, 500 or 550 covalently linked thymines. In some alternatives, the at least one endonuclease recognition site is a Type II restriction endonuclease recognition site. In some alternatives, the at least one endonuclease recognition site is a Type IIS restriction endonuclease recognition site. In some alternatives, the at least one Type II restriction endonuclease recognition site is a BsaI or a StuI restriction endonuclease recognition site. In some alternatives, the endonuclease cleavage site is between 1-5 nucleotides from the endonuclease recognition site. In some alternatives, the polynucleotide further comprises a gene. In some alternatives, the gene is an endonuclease gene e.g., SEQ ID NOs. 6-14. Without being limiting an endonuclease can include, for example, a CRISPR, a restriction endonuclease, a Type II restriction endonuclease and a Type IIS restriction endonuclease. In some alternatives, the endonuclease is a CRISPR, a restriction endonuclease, a Type II restriction endonuclease or a Type IIS restriction endonuclease. In some alternatives, the endonuclease is a CRISPR, a restriction endonuclease, a Type II restriction endonuclease or a Type IIS restriction endonuclease. In some alternatives, wherein StuI is provided, the endonuclease cleavage site is a StuI cleavage site, AGGCCT (SEQ ID NO: 633), and StuI cleaves between the G and C, leaving a blunt end that terminates in a GG. In some alternatives, the endonuclease cleavage site is AGGCCT (SEQ ID NO: 633). In some alternatives, the endonuclease is StuI. In some alternatives, the plurality of adenines terminates in GG. In some alternatives, the StuI cleavage site is inverted. In some alternatives, the endonuclease recognition site is a BsaI restriction recognition site, and the endonuclease is BSaI. In some alternatives, the BsaI restriction recognition site is inverted. In some alternatives, the endonuclease cleavage site is located 1, 2, 3, 4, 5, 6, 7, 7, 8, 9, 10, 11, 12, 13, 14, 15, 16, 17, 18, 19 or 20 base pairs away from the most 5' thymine (or 5' terminal thymine) in the plurality of thymine nucleotides. In some alternatives, the endonuclease cleavage site is located 1, 2, 3, 4, 5, 6, 7, 7, 8, 9 or 10 base pairs away from the most 5' thymine (or 5' terminal thymine) in the plurality of thymine nucleotides.

Creation of Linear Plasmid-OK-MCS-pA-100, -200, and -300.

To prepare linear plasmid-OK blunt (Lucigen) for insertion of the polyA tail, an MCS comprising multiple blunt and sticky-ended RE sites as well as a terminal BsaI site [DraIII-FspI-BsiWI-NheI-BsaI] was ligated into linear plasmid-OK blunt to create linear plasmid-OK-MCS. linear plasmid-OK-MCS was digested with NheI, blunted, and dephosphorylated with CIP. To create a long poly(A) tail, oligos of 200 T's and 50 A's were annealed at an equimolar ratio. The annealed oligos were treated with T4 polymerase, Klenow fragment, and T4 PNK to trim flaps, fill gaps, and create blunt, phosphorylated ends. The resulting mixture was run on a 3% agarose gel and fragments in the range of c.a. 200-800 bp were gel extracted. After purification, these fragments were ligated into the previously prepared linear plasmid—OK MCS with T4 DNA ligase at room temperature for 2 hours. Resulting colonies were screened for tail insert length by colony PCR using primers that flank the MCS/tail insertion site, and then colonies with inserts of appropriate length were sequenced to confirm correct orientation of the insert. This resulted in the successful identification of tail lengths of 70, 172, and 325 bp. These constructs were named linear plasmid-OK-MCS-pA-100, -200, and -300, respectively.

Creation of Linear Plasmid-OK-MCS-ΔBsaI.

To create longer tails, it was necessary to mutate the 4 BsaI sites native to linear plasmid-OK to allow for digestion only at the BsaI site in the inserted MCS. One site was removed by Gibson assembly. The remaining 3 sites were removed by restriction digest of a fragment containing the BsaI site to be mutated as well as a pair of flanking RE sites, blunting and ligation of this fragment into pUC57 digested with EcoRV, site-directed mutagenesis of the BsaI site, and then sub-cloning the mutated fragment back into linear plasmid-OK MCS using the included flanking RE sites. This plasmid was designated linear plasmid-OK-MCS-ΔBsaI.

Creation of pEVL Series Plasmids.

Once all native BsaI sites were removed, the fragment containing the polyA tail from linear plasmid-OK-MCS-pA-100, -200, and -300 was cloned into linear plasmid-OK-MCS-ΔBsaI, creating pEVL-100, -200, and -300. pEVL-300 was then digested with BsaI, blunted with Klenow, dephosphorylated with CIP, and ligated with additional blunt double stranded poly(A) fragment prepared as above. Screening as above resulted in plasmids with 425 and 525 bp p(A) tails. These were designated pEVL-400 and pEVL-500.

Cloning of CRISPR Associated Protein 9 (Cas9) and TCRa Guides.

Cas9 expression construct was obtained from Addgene (plasmid #41815). To ensure nuclear expression of Cas9 in primary human T-cells, Nuclear Localization Signals (NLS's) at both 5' and 3' ends (2X-NLS). To track transfection efficiency, Cas9 was fused in-frame with T2A-mCherry and cloned into an in-house modified version of pUC57 with a T7 promoter called pWNY2.0 to obtain pWNY2.0-2X-NLS-Cas9-T2A-mCherry. Subsequently, 2X-NLS-Cas9-T2A-mCherry was spliced from pWNY2.0 and cloned into pEVL200.

Guides targeting the constant region of TCR alpha were designed using an online CRISPR design tool. Guides were designed with a U6 promoter and ordered as gblocks (IDT). Subsequently, the gblock comprising U6 promoter and sgRNA (crRNA+tracrRNA) was cloned into a self-complementary (sc) AAV2 vector backbone, and checked for maintenance of intact ITR's. Four different G-block-guide constructs generated in this way were used for AAV6 synthesis, and following a series of pilot experiments, a best-performing guide was chosen further comparative analyses.

Production of IVT mRNA.

For BFP and TALEN constructs, inserts containing a T7 promoter and Kozak sequence were cloned into pEVL-100 through pEVL-500. These constructs were digested with BsaI to create a free poly(A) tail as well as a RE site upstream of the T7 (typically XbaI or SpeI) for ease of purification. The digested DNA was purified by silica column and eluted in water or 10 mM Tris. IVT with ARCA capping was carried out using the mMessage mMachine T7 Ultra kit (Ambion) per the manufacturer's directions with 200-500 ng of the T7 to polyA template fragment. IVT reactions were routinely extended to 150 min. The DNAse step was altered either in time or DNAse amount to account for the total amount of template DNA in the reaction. For pEVL constructs, after DNAse treatment, the reaction was cleaned up using the RNeasy Mini kit (Qiagen) following the manufacturer's directions. For pWNY constructs, the enzymatic tailing step of the mMes sage mMachine T7 Ultra kit was carried out according to the manufacturer's instructions before RNA clean-up. RNA purity was determined by NanoDrop spectrophotometry and gel analysis with the FlashGel RNA system (Lonza).

For Cas9 mRNA production, pWNY2.0-2X-NLS-Cas9-T2A-mCherry construct was linearized using AdeI (DraIII) and Pfl23II (BsiWI) (Fermentas FastDigest) and pEVL200-2X-NLS-Cas9-T2A-mCherry was digested with BsaI and SpeI. Both constructs were checked for completeness of digestion on 1% agarose gels, column purified, and RNA was transcribed in-vitro using the mMessage mMachine T7 ULTRA Transcription kit (Life Technologies) with slight modifications from the manufacturer's protocol. Briefly, the IVT reaction was done for 2.5 hrs, DNase treatment for 1 hour. Poly (A) tailing for the pWNY-2.0 construct was performed for 1 hour, and mRNA was subsequently purified using the RNeasy kit (Qiagen), aliquoted and frozen at −80° C.

BFP and TALEN mRNA Electroporation of Primary Human T-Cells.

Freshly isolated primary human T-cells were stimmed with anti-CD3/anti-CD28 microbeads (Dynal) in RPMI with 10% FBS, 2.5% HEPES, and 1% L-glut with 5 ng/mL IL-2 and 1 ng/mL IL-15. After 2-3 days, the stim beads were removed, and the T-cells were resuspended at $3 \times 10^7$ cells/mL in Neon Electroporation system Buffer T (Invitrogen) with 0.25-2 μg mRNA per 300,000 cells. Electroporation was carried out on the Neon electroporation system at 1400V, 10 ms, and 3 pulses. Immediately following electroporation, cells were resuspended in complete T-cell media with IL-2 and IL-15 (as above). Cells were either placed in a 37° C. incubator or in a 30° C. incubator for 24 hrs and then moved to a 37° C. incubator, as a cold-shock step of this nature has been observed to increase the amount of protein per cell for the period when the mRNA is present (Doyon Y. et al. Transient cold-shock enhances zinc-finger nuclease-mediated gene disruption. Nature Methods 7, 459-460 (2010), herein incorporated by reference in its entirety). Expression of the encoded protein was assayed by flow cytometry. For TCR knockout by TALEN or CRISPR, loss of TCR expression was assayed at 72 hr-7 days after electroporation by staining with anti-CD3 (clone HIT3a, direct FITC or PerCP-Cy5.5 conjugate).

Cas9 mRNA Comparison (pWNY2.0 Versus pEVL) in Primary Human T-Cells Using TCRa-KO as a Readout.

Frozen CD4+ T cells isolated from a donor were stimulated with human T-activator CD3/CD28 Dynabeads (Life Technologies) for 48 hours in antibiotic-free RPMI media with 20% FBS, 100 mM HEPES, 2 mM Glutamax, 55 uM b-ME and cytokines (Il-2=50 ng/ml, Il-7=5 ng/ul and Il-15=5 ng/ul), hereafter referred to as 'RPMI media'. Beads were magnetically removed 48 hours post-stim and cells were rested in RPMI media for 5 hours before prepping them for mRNA transfection. RNA transcribed in-vitro from both pWNY2.0-2X-NLS-Cas9-T2A-mCherry and pEVL200-2X-NLS-Cas9-T2A-mCherry was electroporated into $4.5 \times 10^5$ cells using a 10 ul tip at two different concentrations −3 ug and 1.5 ug (Neon transfection system; Life technologies) at 1400V, 10 ms width, pulses=3, after which cells were rested for 3 hours followed by AAV transduction at constant 10% culture volume.

Flow Cytometry.

Cells were acquired for Cas9-mCherry expression on a LSRII flow cytometer (BD Biosciences) at 24, 48, 72 and 168 hours, respectively. Analysis of TCRa was performed using an anti-CD3 directly conjugated to Alexa 488 (BioLegend) and data was analyzed using FlowJo software (Treestar). Cells were gated on live cells based on the forward and side scatter for downstream analysis of the TCR-Knockout (KO).

Evaluation of Transformation-Associated Tail Shortening.

BFP-pEVL100, 200, and 300 were digested with DraIII (cuts 5' of BFP) and SwaI (cuts in pEVL backbone ~75 bp 3' of tail/BsaI site). This fragment was gel purified and ligated back into pEVL digested with DraIII and SwaI and CIP'd as well as pWNY digested with DraIII and SmaI and CIP'd. Following ligation, the ligase was heat-killed and all ligation products were transformed by electroporation into BigEasyTSA electrocompetent cells (Lucigen) for pEVL or Top10 electrocompetent cells (Invitrogen) for pWNY. After recovery at 30° C. for 1 hr in SOC, aliquots of each transformation were plated in triplicate on Kan plates and grown at 25° C. (72 hrs), 30° C. (24 hrs), or 37° C. (20 hrs). Colonies were screened for tail length by colony PCR with primers that bind in BFP (5'-cgcaaacgctaaaactacc-3') and 3' of the tail (5'-tcagttctatgtaccagcaagg-3'). For ligations of the 325 bp tail into pWNY, recovery of any clones with full-length tail was not possible, so this was excluded from further analysis. For ligations of 70 bp and 172 bp tails into pWNY, 2 clones of each that screened as full-length by colony PCR were grown overnight in 1 ml of TB with carbenicillin in triplicate, with 1 aliquot at 25° C., 1 at 30° C., and one at 37° C. After 24 hours, 1 ul of each culture was seeded into a fresh 1 ml aliquot of TB+carb. The remaining culture was spun down and the pellet frozen for minipreping at a later date. This was repeated for a total of 7 full days. At this time, all of the frozen pellets were miniprepped. For each miniprep, 3 ug of DNA was digested with BsiWI and BsaI to isolate the tail fragment and the digested product was run on a 3% agarose gel and then stained with GelStar Nucleic acid stain (Lonza). Because there is a BsiWI site in the tail fragment that was inserted into pWNY2.0 as well as one that is present in the pWNY2.0 backbone, there is an additional band of ~95 bp on these gels that can be used as a DNA loading control.

Evaluation of Propagation-Associated Tail Shortening.

Freshly transformed colonies of pEVL-200 to -500 were screened for tail length by colony PCR and colonies with the correct tail lengths were seeded into 4 aliquots of 1 ml TB+Kan and grown overnight, 2 at 30° C. and 2 at 37° C. At each temperature, 1 aliquot was grown under arabinose induction and 1 without. After 24 hours, 1 ul of each culture without arabinose was seeded into another 1 ml of TC+Kan without induction. This was carried out for 2 weeks. At the time of seeding each day, another 1 ul was seeded into a 1 ml culture of TB+Kan+arabinose. Each induced culture was spun down and the pellet frozen after 24 hours of growth. At the end of 2 weeks, all of these frozen pellets were miniprepped and digested with BsaI and BsiWI to isolate the tail fragment. These fragments were run on a 3% agarose gel and stained with GelStar Nucleic Acid stain.

Generation of a Linear Polynucleotide Comprising a Plurality of Covalently Linked Thymine Nucleotides and an Endonuclease Recognition Site Inserted within.

A polynucleotide comprising a plurality of covalently linked thymine nucleotides (poly(T) tract) and an endonuclease recognition site inserted within the poly(T) tract was constructed in multiple cloning steps. Reference is made to FIG. 1A, which illustrates the structure of the linear polynucleotide, pEVL, which results from the insertion of the BsaI containing multicloning site (MCS), the removal of the plurality of BsaI sties and the addition of the poly(A) encoding region.

In order to create a linear polynucleotide comprising a plurality of covalently linked thymine nucleotides and an endonuclease recognition site inserted within, the BsaI sites were located and using site directed PCR mutagenesis and primers for mutations, single base substitutions were made within all four BsaI sites, to result in silent mutations. The unique restriction sites flanking the modifications were used to excise the fragment and clone it into a standard cloning vector (pUC57). Site-directed mutagenesis was used on a pUC57 vector to alter a base in the BsaI site, and the unique restriction sites were used to move the fragment back into cloning vector. This was repeated stepwise for each of the four BsaI sites.

Figure 1B:
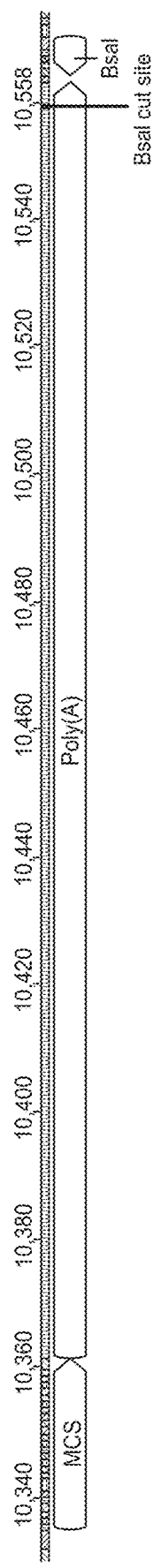

With the plurality of BsaI sites removed, a new multicloning region, including a now-unique BsaI site, was constructed and used to clone into the linear vector along with a poly(A) sequence. First, a new multicloning site (MCS) was introduced with restriction sites that would support cloning in a Transcription activator-like effector nuclease (TALEN) upstream of a now-unique BsaI site "facing" into where the short poly(A) would be introduced (annotated "MCS" and "BsaI" on the map, respectively, FIG. 1B). The BsaI site was designed to "face" the poly(A) such that the cut site (annotated "BsaI Cut" on the map, FIGS. 1A and 1B) would be within the poly(A) sequence, 4 bases upstream of the poly(A) terminus on the coding strand. In this way, RNA transcripts created using this vector as a template would terminate in a poly(A) without any additional bases beyond it. Second, the poly(A) was cloned in directly upstream of the BsaI site and then lengthened to the desired lengths. Synthetic poly(T) and poly(A) oligonucleotides were phosphorylated and annealed to create double stranded poly(A/T) concatamers of various lengths. This mixture was ligated in directly upstream of the BsaI site and clones were selected which had a poly(A)s of desired lengths in the correct orientation. The longest clone obtained from screening had a poly(A) of approximately 300 adenine bases in length, and was designated pEVL300. A variant with a ~100 base poly(A), and another with a ~200 base poly(A) were also saved and designated pEVL100 and pEVL200, respectively. In order to extend the poly(A) beyond 300 bases in length, pEVL300 was digested with BsaI and the same poly(A/T) concatamers used in the previous step were again ligated into the vector. Screening yielded clones with ~400 and ~500 base poly(A)s, designated pEVL400 and pEVL500, respectively. FIG. 1A shows a final map of the resultant linear vector comprising telomeric ends, a telN open reading frame (ORF1), ORF6, ORF3, ORF5, Poly(A) tract coding region, Kan2 resistance gene, 4 disrupted BsaI sites, and an ORF4 sequence. Reference is made to FIG. 1B, which shows a zoomed in version of the site of interest comprising the poly(A) encoding tract along with the inverted BsaI restriction site.

Assay to Determine the Poly(A) Tail Stability

Polynucleotide vectors comprising a plurality of covalently linked thymine nucleotides and an endonuclease recognition site inserted within were created with the protocol previously described. Four vectors were used to determine Poly(A) tail stability which had 100, 200, 300, or 500 covalently linked thymines for transcribing an mRNA comprising 100, 200, 300, and 500 covalently adenosines (pEVL100, pEVL200, pEVL300, and pEVL500). Once the pEVL vectors were generated, the stability of the mRNA comprising the poly(A) tracts were tested for their dependency on temperature.

Poly(A) stability in standard cloning vectors for generating a transcript with a poly (A) tail (e.g. pUC57) is extremely limited, shortening to 30-60 bases during overnight propagation, even in chemically competent host cells that are purported to increase stability (e.g. STBL3™). In order to test the stability of the pEVL poly(A) tracts, *E. coli* were grown continuously in liquid culture for a two week period at either 30° C. or 37° C. Cultures were split off and induced to produce high copy plasmids for preparation at 1, 6 and 14 days. The plasmids were isolated and digested with BsaI at the terminus of the poly(A), and XbaI upstream of the poly(A) by 151 base pairs. Bands corresponding to the poly(A) tracts were resolved on a 3% agarose gel and run next to size standards.

Figure 2:
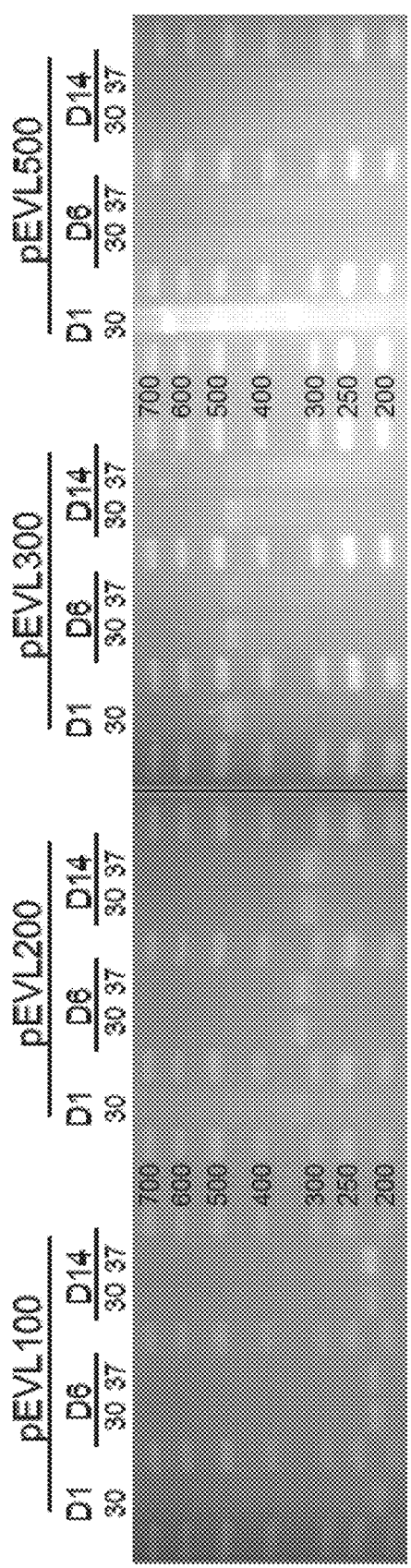
FIG. 2 is a series of 3% agarose gel separations demonstrating the fidelity of DNA replication of the poly(A) encoding region of the plasmids that encode for poly(A) tracts of 100, 200, 300, or 500 covalently linked adenines. The plasmids encoding for the poly(A) tracts were generated from the linear vector shown in FIGS. 1A and 1B. After replication, the plasmids from the bacteria were cut on either side of the poly(A) encoding tract and the product was run on the 3% gel to examine the sizes of the poly(A) tract after replication.

As shown in FIG. 2, the poly(A) tract of pEVL100 and pEVL200 appear to be stable when grown at 30° C. or 37° C. for at least two weeks; no shortening was detectable. As shown in the gels at day 6 and day 14, the bands remain sharp at one length for the corresponding mRNA at the temperatures of 30° C. or 37° C. The poly(A) tract of pEVL300 was less stable when grown at 37° C., with minimal shortening observed at day 6, but notable shortening observed at day 14, in which a smear of mRNA product is shown below the marker of 500 bases. This shortening was largely avoided in cultures grown at 30° C., even at 14 days. Although pEVL500's poly(A) was maintained during a single day of growth at 30° C., the poly(A) tract was significantly unstable with considerable shortening by day 6, even at 30° C. pEVL500 was unstable at 37° C. and had shortened in cultures from both days 6 and 14. Any long-term work done with pEVL500 would require poly(A) length screening and validation at each point. However, an end-point pEVL500 plasmid could still be easily maintained in an *E. coli* frozen stock, grown overnight, and purified if required.

Accordingly from the data it is contemplated that the poly(A) length can dictate the poly(A) tract stability, and is susceptible to shortening at long tract lengths, but the stability is greater than previously achievable by an order of magnitude (30 bases from Promega versus 300 bases). Poly(A) tract lengths that are stable in this system (e.g. pEVL100, pEVL200, pEVL300) are capable of producing mRNA that can be used in vivo directly. This is in contrast to the short encoded poly(A) tracts in plasmids currently available which support only the generation of mRNA to be used for in vitro translation or would require further enzymatic polyadenylation to be used in vivo.

Figure 3:
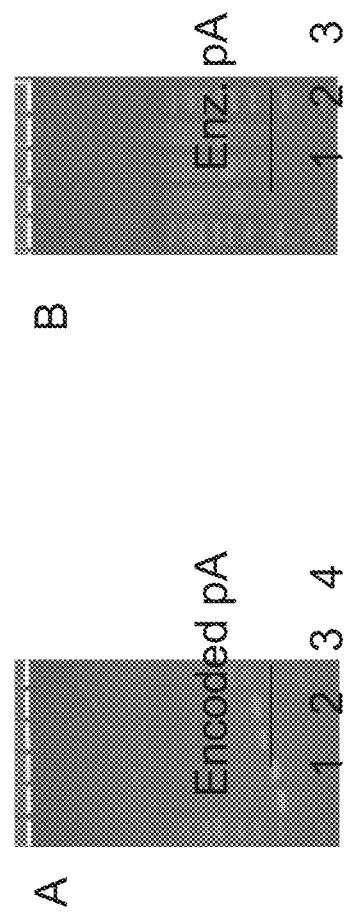
FIG. 3A and FIG. 3B are a series of Lonza FlashGels (Lonza) of 1.2% agarose gel, where separations of mRNA were run to illustrate the use of a pEVL linear vector as a template to produce highly homogenous mRNA. The pEVL linear template comprised a site encoding a poly(A) tail in which a BsaI endonuclease cleavage site is within the poly(A) tail and is compared to a standard method of adding a poly(A) tract by a transcription vector and a polyadenylation enzyme. The linear vectors used for transcribing the mRNA are derived from a linear vector, as shown in FIGS. 1A and 1B.

Homogeneous RNA Length.

mRNA production using the pEVL vector, in which the method of creating the pEVL vector was described, as a template produces highly homogenous mRNA, as intended. Reference is made to FIG. 3A, which show mRNA from a typical pEVL transcription on a Lonza Flashgel (1.2% agarose) while mRNA from a typical standard transcription and enzymatic polyadenylation is shown in FIG. 3B. To create this mRNA, pEVL200 (lanes 1 & 2) and pEVL300

(lanes 3 & 4) plasmids with inserts were digested with BsaI, column purified, and used as a template for transcription using Ambion's mMessage mMachine kit. The resulting mRNA was purified using Qiagen's Rneasy columns, resulting in transfection-ready mRNA. The transfection-ready mRNA was validated by running it on a Lonza FlashGel with a size marker. The mRNA shown in FIG. 3B was made using a standard commercial transcription vector as a template followed by enzymatically polyadenylation and then purification using Qiagen's Rneasy columns.

As shown in FIG. 3A, a homogeneous poly(A) tail length would result in a single tight band of mRNA on the gel, since all mRNA products would be the same length. FIG. 3A illustrates the bands of mRNA that were transcribed from pEVL200 and pEV300 as clean sharp bands. The mRNA produced from the pEVL encoded poly(A) vector was highly homogeneous with only a slight smear below the primary band, indicating minimal byproducts of primarily smaller size (FIG. 3B). The mRNA produced using enzymatic polyadenylation was significantly more varied. Not only did the smear extend above and below the primary band, it was also more pronounced and extended to a far larger range. This is likely due to the Gaussian distribution of the extent of acetylation performed by the enzyme, and is supported by the lower concentration (dimmer) primary band. Accordingly from the data shown, it is contemplated that the mRNA produced using the encoded poly(A) of pEVL is markedly more homogenous than that produced using enzymatic polyadenylation and is more stable.

Expression of Blue Fluorescent Protein (BFP) from a Poly (A) Encoding Linear Vector.

mRNA produced from the encoded poly(A) linear plasmid was at least as effective as mRNA produced by traditional enzymatic polyadenylation. To test the linear plasmid's effectiveness, linear plasmids comprising a plurality of covalently linked thymine nucleotides (poly(T) tract) and an endonuclease recognition site inserted within the poly(T) tract was made with the protocol previously described. The plasmid further comprised a gene encoding for blue fluorescent protein (BFP), as the reporter protein. The five linear plasmids with the BFP reporter had 100, 200, 300, 400, and 500 poly(T) tracts for transcribing an mRNA transcript with 100, 200, 300, 400, and 500 poly(A) tracts, respectively. The plasmids were used to transfect a constant 1 microgram of different BFP-encoding mRNAs into primary human T-cells and the cells were analyzed 24 hours later by flow cytometry.

mRNA encoding BFP from two different types of plasmids were produced. The first type of plasmid used was a control plasmid comprising a standard circular cloning vector with a T7 RNA promoter, a ribosome binding site (Kozak sequence), the mTagBFP2 protein coding sequence, and a BsiWI restriction site for linearization (pWNY). The second type of plasmid was the previously described encoded poly(A) vector, either pEVL100, pEVL200, pEVL300, pEVL400, or pEVL500, with the gene encoding BPA cloned directly upstream of the encoded poly(A). Three of the pEVL plasmids in this particular experiment also had a 150 base pair untranslated region after the coding sequence but before the poly(A), noted by 'a', this sequence to have little to no effect on BFP expression. The pWNY plasmids were linearized and purified, transcribed, enzymatically polyadenylated, and purified according to a standard Ambion protocol, known to those skilled in the art. The pEVL plasmids were linearized and purified, transcribed, and purified, skipping the enzymatic polyadenylation step.

Figure 4:
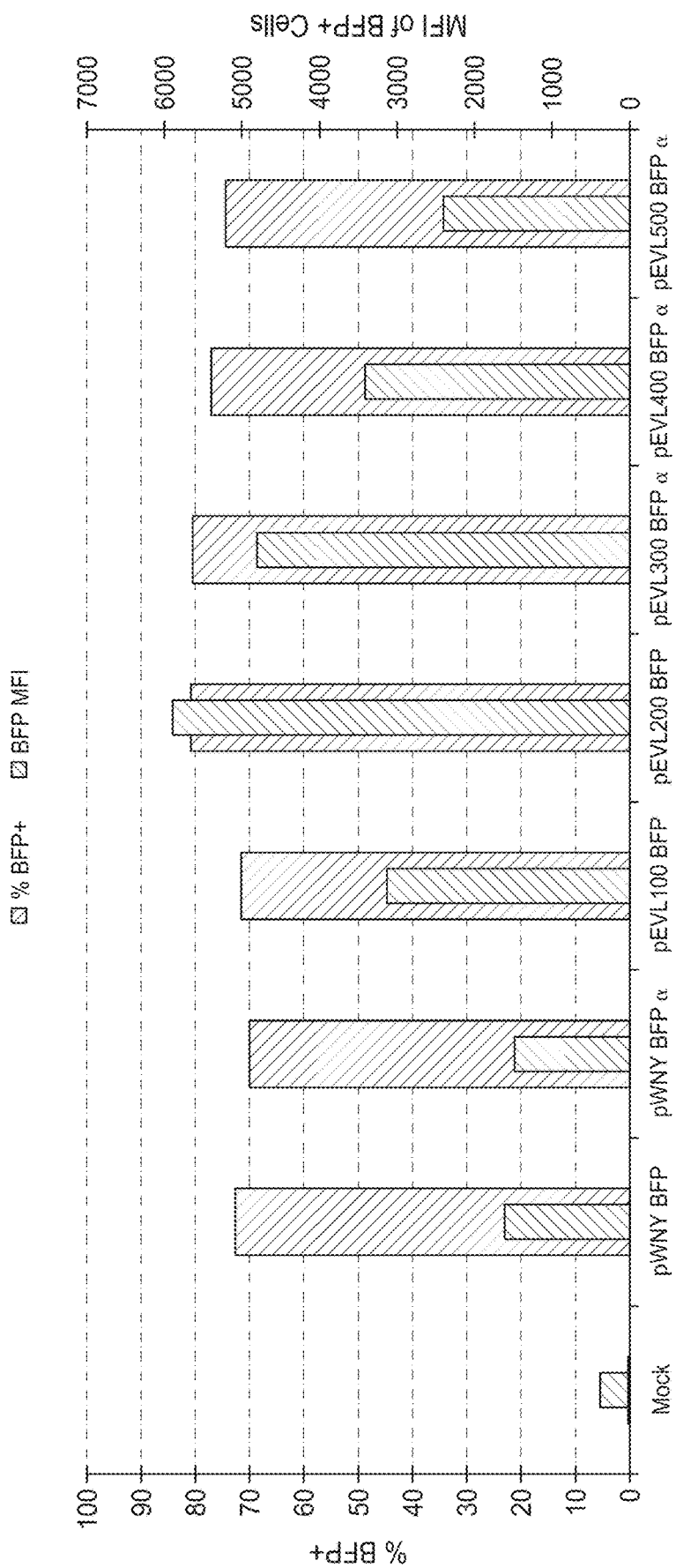
FIG. 4 is a bar graph illustrating the expression of blue fluorescent protein (BFP) from the use of an mRNA comprising a poly(A) tail that was transcribed from a linear vector encoding a poly(A) tract in which a BsaI endonuclease cleavage site resides within the poly (A) encoding region for the translation of a reporter protein (BFP) (FIGS. 1A and 1B) at 30° C. in human primary T cells. The mRNA produced from a plasmid comprising a poly(A)tract encoding region was compared to an mRNA produced from a standard method of adding a poly(A) tract by a transcription vector and a polyadenylation enzyme. In order to determine the efficiency of the transcript mRNA for translation for both methods, BFP was used as the reporter protein. As shown in the figure, the shaded region is the % BFP+ and the hatched regions are the BFP MFI.

Reference is made to FIG. 4, in which the data shows that the mRNA from pEVL plasmids transfects at least as efficiently as, and is translated as well or better than, enzymatically encoded poly(A) mRNA. The number of BFP positive cells (left Y-axis) in the pEVL samples were on par with or slightly higher than the pWNY samples, especially for poly(A) tail lengths greater than 100 bases. Translation experiments were performed at 30° C. The level of translation, inferred from the intensity of the blue signal (mean fluorescence intensity, MFI, right Y-axis), was higher in the samples transfected with the mRNA produced from the encoded poly(A) plasmids. Overall, the mRNA produced from the pEVL200 and pEVL300 appeared to give the best results, especially compared to the enzymatically encoded mRNAs. This may be due to the fact that enzymatic polyadenylation only adds approximately 60-100 bases according to the manufacturer. It should however be noted that since a constant 1 microgram of mRNA was transfected, a lower molar amount of the longer poly(A) mRNAs were transfected compared to the shorter poly(A) mRNAs. Accordingly from the data shown, it is contemplated that a poly (A) tail produced from the pEVL200 and pEVL300 can give better results indicating the stability of mRNA with 200 or 300 adenines in the poly(A) tail, and thus can be used for a longer amount of time (24 hours) for translation of a protein. As such, reference is also made to FIGS. 3A and 3B, which indicates the stability of the mRNA which can be used for translation.

Translation of RNAs Generated by Enzymatic Polyadenylation and Linear Vectors at 30° C. and 37° C.

Translational efficiency is the rate of mRNA translation into proteins that are within the cells. It can be measured in the amounts of protein per mRNA per hour. As previously described, RNA was generated from a standard method of adding a poly(A) tract by a transcription vector and a polyadenylation enzyme. The previously described linear vector, pEVL, was also transcribed to generate an RNA for translation. The RNAs generated from both methods encoded a BFP reporter for determining translational efficiency. The RNAs were transfected into human primary T-cells.

Figure 5:
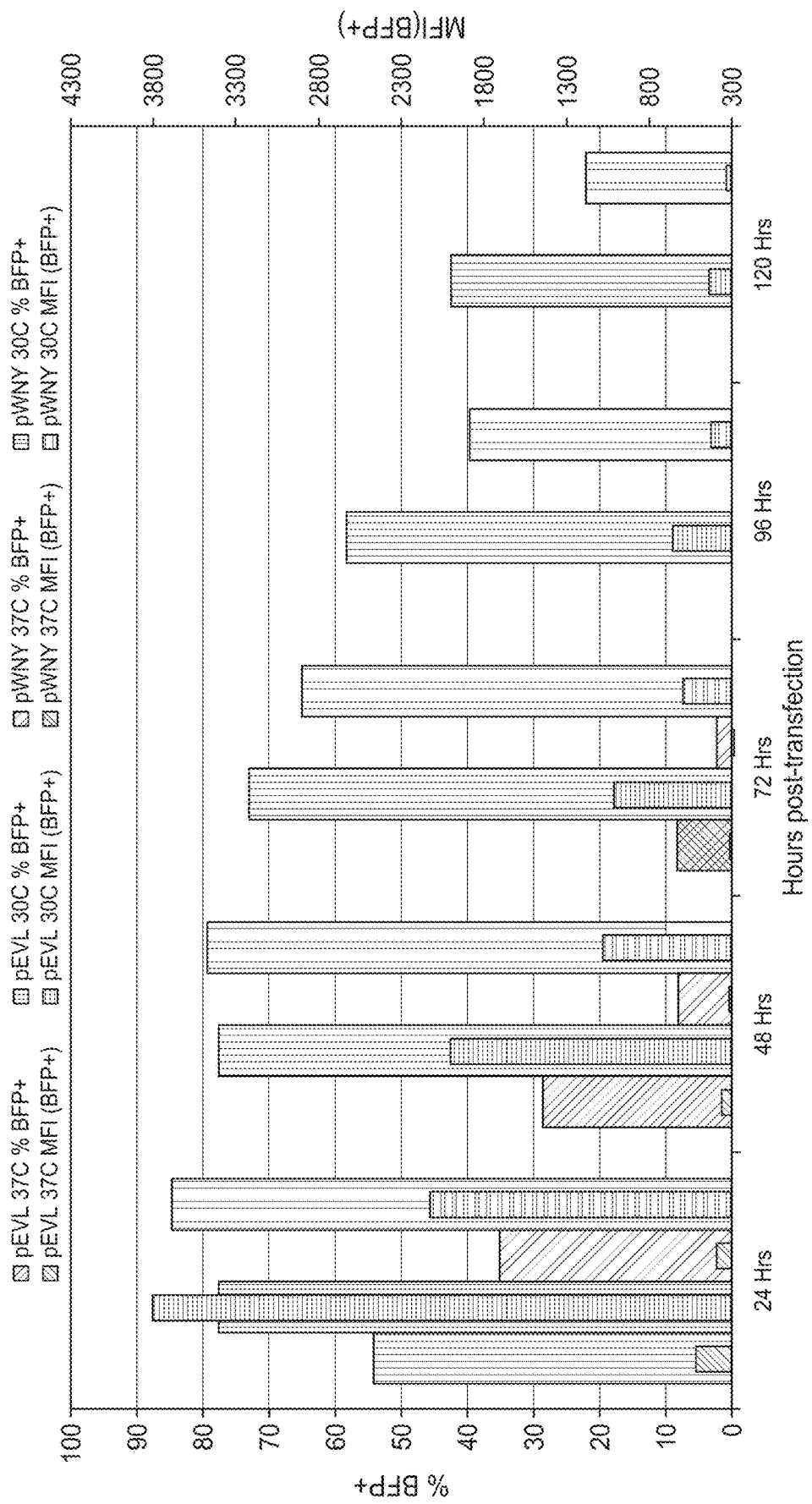
FIG. 5 is a bar graph that illustrates the expression of blue fluorescent protein (BFP) from the use of an mRNA comprising a poly(A) tail that was transcribed from a linear vector encoding a poly(A) tract in which a BsaI endonuclease cleavage site resides within the poly (A) encoding region for the translation of a reporter protein (BFP). RNA was generated from a linear vector encoding a poly(A) tract in which a BsaI endonuclease cleavage site resides within the poly (A) encoding region for the translation of a reporter protein (BFP) and the RNA was used to transfect human primary T cells. The RNA generated from pEVL300 (300 polyA encoded tail) and pWNY (enzymatic tailing) transfected into cells were assayed by looking at % BFP+ cells and the brightness (MFI) of those BFP+ cells over time, with and without the 30° C. 24 hour incubation and were then compared.

Attention is drawn to FIG. 5, which shows the translational efficiency of the RNAs from enzymatic polyadenylation and the linear vector over time in human primary T-cells. The RNA generated from pEVL300 (300 pA encoded tail) and pWNY (enzymatic polyadenylation) transfected into primary T-cells cells were compared by quantifying the percent BFP positive cells and the mean fluorescence intensity (MFI) of the BFP positive cells over time, with and without the 30° C. incubation.

It was discovered that although a 24 hour 30° C. incubation post-transfection has been found to increase accumulation of the translated protein, some cell types do not tolerate abnormal culturing for such an extended period of time (for example, CD34+ hematopoietic stem cells fall into this category). It was discovered that mRNA coding for BFP created using the encoded polyA plasmid as a template was more potent compared to mRNA created using standard enzymatic polyadenylation. The cells transfected with pEVL-derived mRNA (pEVL300) had higher percentages of BFP+ cells over time, and the BFP+ cells were significantly brighter (higher MFI, striped bars). Although this effect was seen to some extent when the cells were incubated at 30° C. for 24 hours post-transfection (dark bars), the effect was more pronounced when this incubation was removed and the cells were grown continuously at 37° C. (light bars). This effect can be due to the fact that the tests were approaching the maximum transfection efficiency when performing the 30° C. incubation, and therefore a significant difference due to a reduced experimental dynamic range was not observed.
mRNA Production.

DNA template was linearized/cut with specific restriction enzymes (backbone—pWNY2.0 or pEVL 200) and linearized plasmids were purified using the QiaQuick PCR purification kit (Qiagen). mRNA was made using a kit (mMessage mMachine T7 Ultra; Ambion) with slight modifications from the manufacturer's protocol. Briefly, the in vitro translation (IVT) reaction was done for 2.5 hrs, DNase treatment for 1 hour. Poly(A) tailing, if required, was done for 1 hour and mRNA was cleaned up using the RNeasy kit (Qiagen), was aliquoted and frozen at −80° C.
Transfection and Transduction.

Primary CD4+ T cells isolated from a donor were stimulated with CD3/CD28 Dynabeads (Life technologies) in the presence of cytokines (IL-2, IL-7 and IL-15) for 60 hours in antibiotic free media. Next, beads were magnetically removed and cells were allowed to rest in fresh media with cytokines for 2.5-5 hours before electroporation. Primary cells were washed with PBS and resuspended in Buffer T (Life Technologies) at $4.5 \times 10^5$ cells/10 ul and mixed with requisite concentrations of mRNA. Neon (Life Technologies) was used for electroporating mRNA (1400V, 10 ms width, pulses=3) using either the 10 ul/100 ul tip after which the cells were rested for 1-3 hours followed by AAV transduction. AAV was added either based on titer or by volume (not exceeding 20%).
Flow Cytometry.

Analysis of TCRa was performed using the LSRII flow cytometer (BD Biosciences) and data was analyzed using the FlowJo software (Treestar). Briefly, the cells were labeled with a CD3 antibody directly conjugated to Alexa 488 or PerCP-Cy5.5, washed and acquired on LSRII. Cells were gated on live cells based on the forward and side scatter for downstream analysis of the TCR-Knockout (KO).
T7 Endonuclease I (T7EI) Assay.

The cutting efficiency of Cas9 and sgRNA was estimated using the T7EI assay for both TCRa and CCR5 loci. Targeted genomic loci were PCR amplified using specific oligos/primers using either Accuprime Pfx or Hifi Platinum Taq DNA polymerase (Life Technologies). PCR products were checked on gel and cleaned using the QiaQuick PCR purification kit. The DNA concentration of the PCR products was measured and 400 ng of the purified product was denatured, subjected to T7EI digestion for 30 mins and analyzed on gel.
Cas9 Construction into a pEVL Vector for Generation of an mRNA Encoding Cas9 with a Poly(A) Tail.

Cas9 was obtained from Addgene (plasmid #41815), PCR amplified and cloned into a pEVL200 (linear construct) with a T7 promoter and two Nuclear Localization Signals (NLS)—one at both N and C-termini. mCherry was linked to Cas9 with a T2A peptide at 3' end of Cas9. A mCherry only control with a T7 promoter and a single NLS at the 5' end of mCherry was also generated. Generation of a pEVL vector encoding Cas9 was also performed in which an mCherry sequences was not added to the construct. The lengths of the poly(T) region encoding the poly(A) tail can range from 20, 30, 40, 50, 60, 70, 80, 90, 100, 200, 300, 400 or 500 covalently linked thymines. In some alternatives, the poly(T) region encoding the poly(A) tail can range from 20, 30, 40, 50, 60, 70, 80, 90, 100, 200, 300, 400 or 500 covalently linked thymines or any length in between any two aforementioned lengths described herein.

In some alternatives the poly(A) tail is comprises at least 200 covalently linked thymines.
Expression of Talen Under the Control of a pEVL Vector.

Figure 6A:
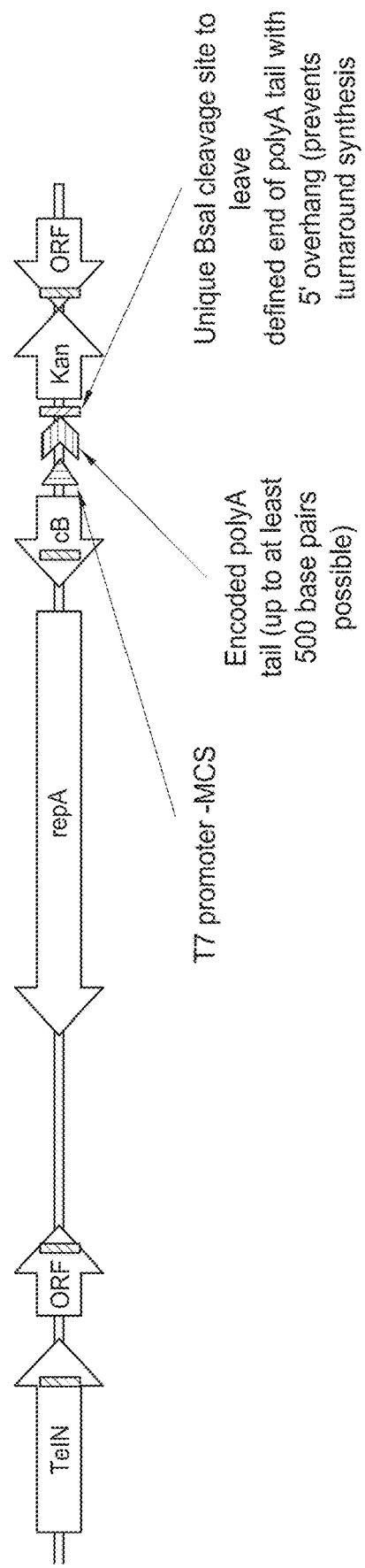
FIGS. 6A and 6B shows the schematic of pEVL (extended variable length) vector (FIG. 6A) and the quantification of TCRa knockout using pEVL and other vectors encoding a T7 promoter that were enzymatically poly-adenylated (FIG. 6B). This vector encodes a T7 promoter, necessary for RNA polymerase, an MCS for ease-of-cloning, an encoded poly-A tail of multiple lengths, ranging from 60 bp (pEVL 100) to 500 bp (pEVL 500), and a unique cleavage site, BsaI, to define the end of the polyA tail and terminate transcription.
Figure 6B:
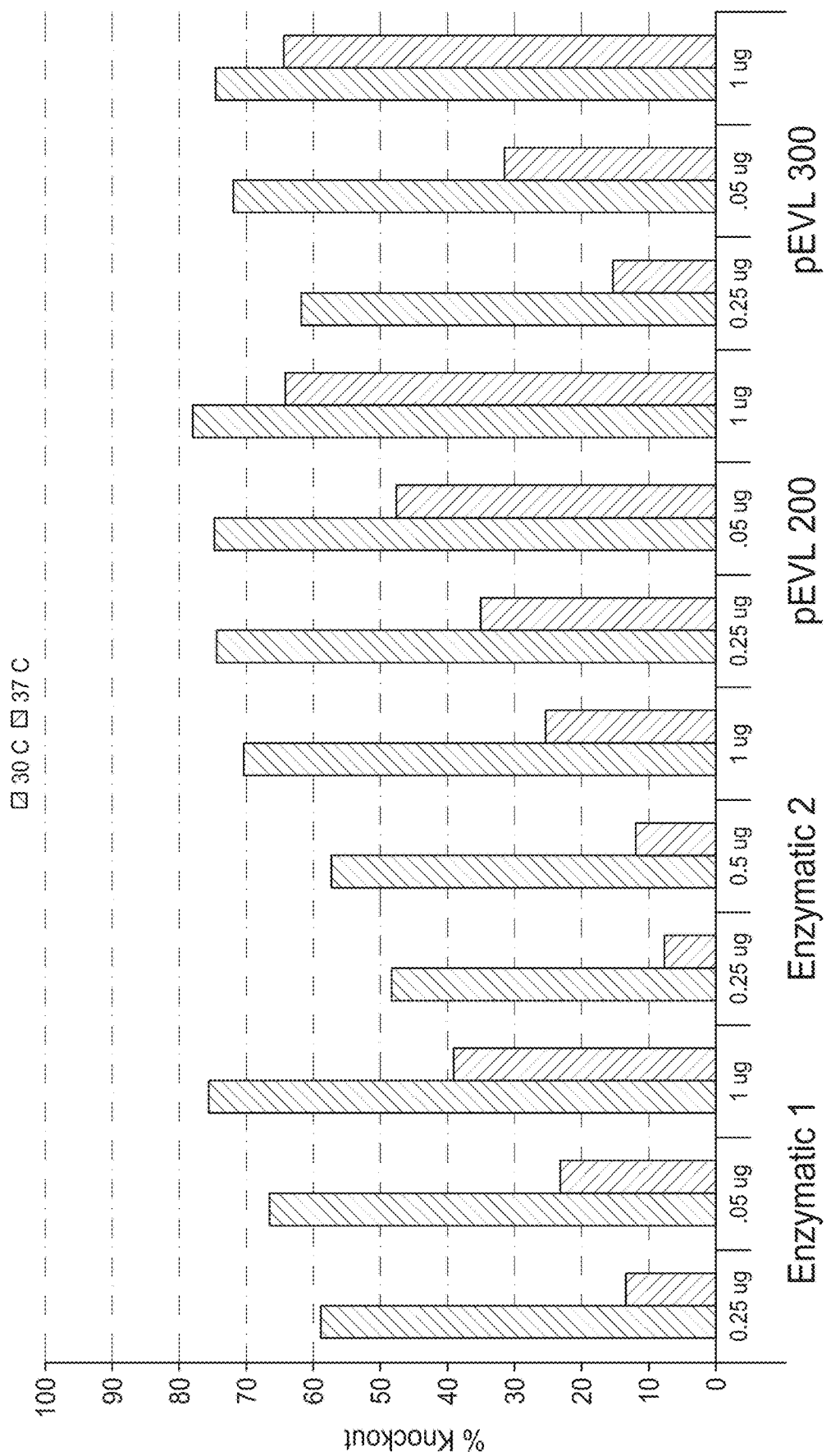

As shown in FIG. 6B, is a schematic of the pEVL (extended variable length) vector. This vector encodes a T7 promoter, necessary for RNA polymerase, an MCS for ease-of-cloning, an encoded poly-A tail of multiple lengths, ranging from 60 bp (pEVL 100) to 500 bp (pEVL 500), and a unique cleavage site, BsaI, to define the end of the polyA tail and terminate transcription. The gene encoding TALEN was subcloned using standard cloning techniques to incorporate the TALEN gene into the pEVL vector. Quantification of TCRa knockout using pEVL and other vectors encoding a T7 promoter that were enzymatically poly-adenylated was then performed (FIG. 6B). TCRa knockout was achieved using TALEN, in which primary human CD4+ T cells were electroporated using the amount of RNA as indicated in the FIG. 6B, (0.25 µg, 0.25 µg and 1 µg). As shown, pEVL constructs are able to achieve 90% knockout when cells are cultured at 37 C, and when incubated at 30 C for 24 hours following electroporation, the lowest dose of TALEN provided by pEVL performs better than both enzymatically tailed mRNA.
TCRα CRISPR Guide #4 Generates the Highest TCRα-KO when Used with a Cas9 Expressed from a Linear Vector for Generation of a Polyadenylated mRNA.

Primary human CD4+ T-cells were thawed from a frozen isolate, stimulated with CD3/CD28 Dynabeads (Life Technologies) in the presence of cytokines (IL-2, IL-7 and IL-15) for 60 hours in antibiotic free media. Next, beads were removed and 4.5×10^5 cells per condition were electroporated using a 10 uL Neon tip ($3 \times 10^5$ cells post electroporation) and AAV was added 3 hours post electroporation. Cas9 mRNA expressed from the pEVL construct was used at 1.5 ug/sample (1 ug post electroporation) and guide-specific AAV's were added at an MOI of 1.33E+04/sample. Post electroporation, cells were plated in a 96 well plate in 200 ul media with cytokines and left in a 30° C. in a $CO_2$ incubator for 24 hours, after which cells were moved to a 37° C. $CO_2$ incubator. (See FIG. 7).

Figure 8:
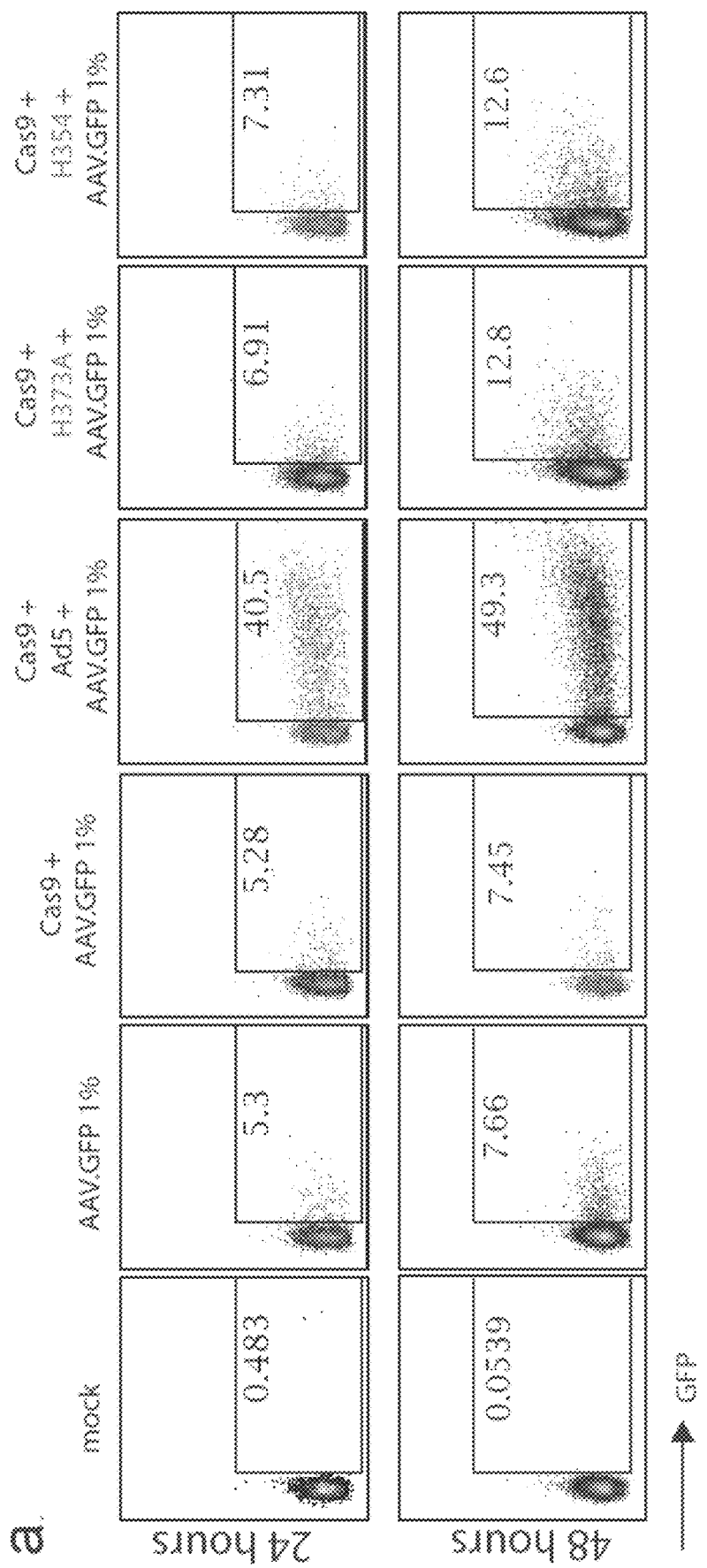
FIG. 8 shows GFP fluorescence of primary human T cells measured by a BD LSRII 24 or 48 hours following mRNA electroporation of mRNAs comprising poly(A) tails generated from a pEVL vector and AAV transduction of primary human T cells.

At 24 hours post electroporation, cells were checked for Cas9-mCherry expression and subsequently at 72, 96 and 168 hours for both mCherry and TCR-KO with CD3-Alexa488 antibody (Biolegend) using BD LSRII. Voltages were kept same throughout the duration of the experiment. (See FIG. 8).
Transient Expression of Ad5$^{wt}$ Proteins and Cas9 Expressed from a pEVL Vector to Increase AAV Transduction in Human T Cells.

Figure 9B:
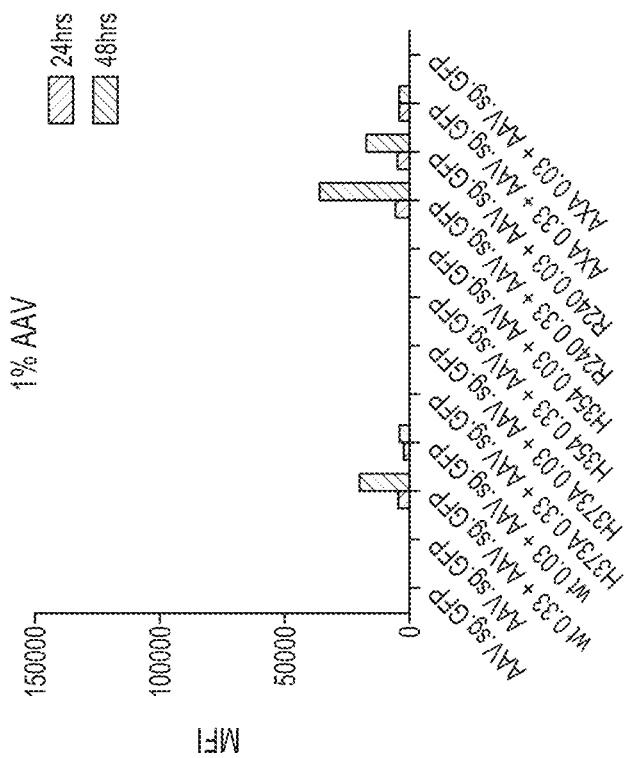
FIGS. 9A and 9B shows GFP mean fluorescence intensity (MFI) in primary human T cells 24 or 48 hours following mRNA electroporation of Cas9 and Ad5 proteins (wildtype or mutants, as indicated, see e.g., SEQ ID NOs: 1-4) and transduction of AAV. mRNA from Cas9 was generated from a pEVL construct for generating a poly(A) tail of 200 covalently linked adenosines.
Figure 9A:
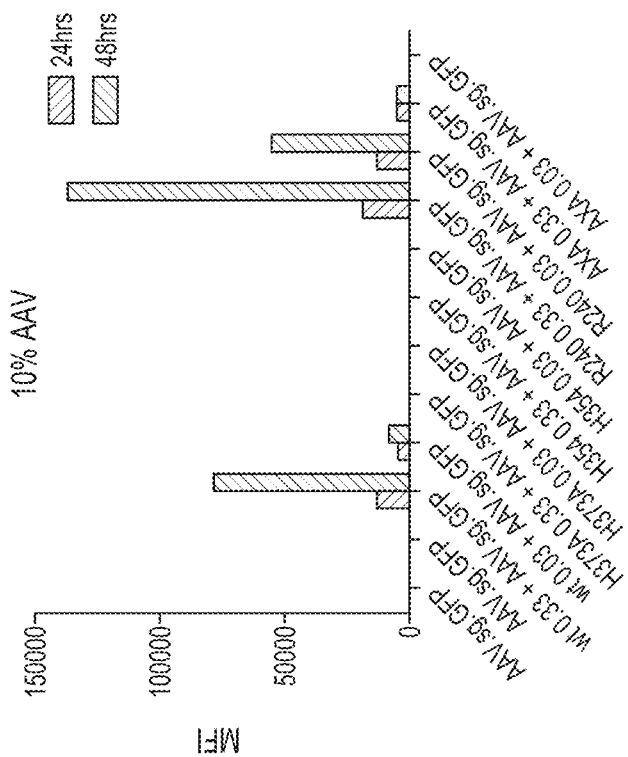

GFP fluorescence of primary human T cells was measured by a BD LSRII 24 or 48 hours following mRNA electroporation of Cas9 generated from a pEVL vector, and AAV transduction of primary human T cells. Cells were treated with 1% culture volume of AAV (2 uL equivalent), 1 ug Cas9 mRNA, and 0.03 ug of each Ad5 protein. AAV was added 4 hours following electroporation, and cells were incubated at 30° C. for 24 hours following electroporation, and left at 37° C. thereafter. 'Ad5' refers to the combination of E4ORF6 and Elb55k proteins, wildtype or the Elb55k mutants H373A or H354 as indicated. As indicated, the mRNA was generated from a pEVL construct in order to incorporated a poly(A) tail for stability of the mRNA in the experiment. As shown in FIG. 9, is the GFP mean fluorescence intensity (MFI) in primary human T cells 24 or 48 hours following mRNA electroporation of Cas9 and Ad5 proteins (wildtype or mutants, as indicated) and transduction of AAV. Cas9 mRNA was generated from a pEVL construct in order to obtain a poly(A) tail for stability of the Cas9 mRNA. Cells were treated with 10% or 1% culture volume of AAV, 1 ug Cas9 mRNA, and 0.03 ug of each Ad5 protein. AAV was added 4 hours following electroporation, and cells were incubated at 30° C. for 24 hours following electroporation, and left at 37° C. thereafter. As such, mRNA generated from the pEVL vector for an increased poly(A) tail can be used for nuclease technologies.

Homopolymeric Poly(A) Tracts 200 Base Pair or Longer are Extremely Unstable in Circular Plasmids.

BFP followed by poly(A) tract inserts of 70, 172, and 325 base pairs bounded by restriction enzyme sites DraIII and SwaI were generated via excision with DraIII and SwaI from the linear plasmid cloning vectors BFP-pEVL-100, BFP-pEVL-200, and BFP-pEVL-300. The inserts were transformed with circular cloning vector pWNY that had been digested with DraIII and SmaI, and transformed into *E. coli* using standard methods. Transformed bacteria were plated onto agarose under ampicillin selection, and grown at 25 degrees. Individual colonies were amplified by PCR using primers flanking the poly(A) tract, and the length of the poly(A) tract was determined based on the resulting band size. Typically, a band was obtained at the expected size, or a smaller size, reflecting shortening of the poly(A) tract during transformation. Colonies were scored for whether the poly(A) tract fragment was approximately of the expected size (open circle, "larger insert"), or was substantially shortened (closed circle) (FIG. 10).

Figure 10:
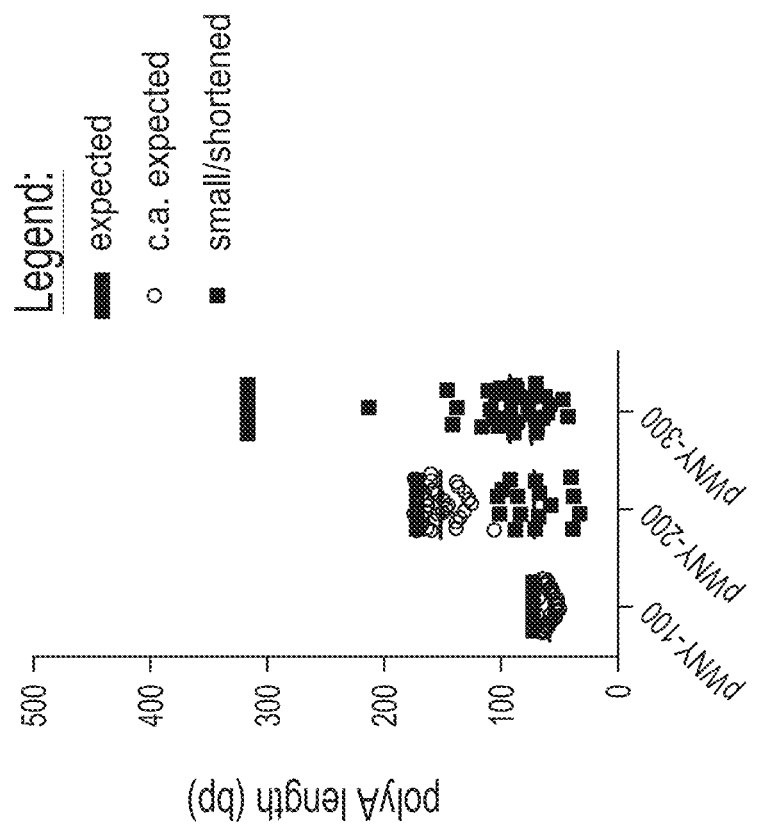
FIG. 10 shows the shortening of poly(A) tracts upon cloning into standard circular plasmid cloning vector at 25° C.

To illustrate the difficulties in cloning and propagating extended homopolymeric tracts, we attempted to ligate inserts containing 70, 172, and 325 base pair homopolymeric poly(A) tracts respectively into a standard circular cloning vector plasmid (designated pWNY) (FIG. 10). To assess the stability of the inserts at 25° C. following transformation and overnight plating onto selective media, PCR across the inserts using DNA isolated from individual bacterial colonies was performed. On analysis by gel electrophoresis, the resulting PCR products resolved primarily into bands of two different sizes (FIG. 10), those products reflecting expected insert sizes are represented by open circles, and products representing substantially shortened sizes are represented by closed circles. As can be seen, poly(A) tracts longer than approximately 100 base pairs are extremely unstable even over the short term process of ligation/transformation into a standard plasmid, with substantial shortening of the tract occurring at a high frequency.

Homopolymeric Poly(A) Tracts of at Least 500 Base Pairs can be Stably Propagated in Linear Plasmid.

DraIII and SwaI were generated via excision with DraIII and SwaI from the linear plasmid cloning vectors pEVL-100, pEVL-200, and pEVL-300. The inserts were ligated into the circular cloning vector pWNY that had been digested with DraIII and SmaI, and transformed into *E. coli* using standard electroporation methods, or alternatively were subcloned into pEVL and transformed into electrocompetent Big Easy cells (Lucigen, Madison, Wis.). Transformed bacteria were plated onto agarose under ampicillin (pWNY) or kanamycin (pEVL) selection, and grown at 30 degrees. Individual colonies were amplified by PCR using primers flanking the poly(A) tract, and the length of the poly(A) tract was determined based on the resulting band size as in FIG. 10. Typically, a band was obtained at the expected size, or a smaller size, reflecting shortening of the poly(A) tract during transformation. Colonies were scored for whether the poly(A) tract fragment was approximately of the expected size (open circle, "larger insert"), or was substantially shortened (closed circle). D) Stability of the encoded poly(A) tracts following overnight induction of pEVL for template preparation. BFP-pEVL-200 through 500 and BFP-pEVL-300-U, G, UU, and GG were grown overnight with induction at 30 C in TB+Kan+arabinose media and then maxi-prepped using the NucleoBond Xtra Maxi kit (Macherey-Nagel), using the manufacturer's instructions for low-copy plasmids (differs from the standard protocol namely in using 8-12 mL resuspension, lysis, and neutralization buffers per gram of pellet weight). For each maxi-prepped sample, 2 ug of DNA was digested overnight with BsiWI and BsaI to release the poly(A) tail fragment from the rest of the plasmid. The digest was run on a 3% agarose gel and post-stained with GelStar Nucleic Acid stain (Lonza). GeneRuler 50 bp ladder (ThermoScientific) was used to determine poly(A) tail length. E) Stability of encoded poly(A) tracts under extended propagation conditions To test the stability of the poly(A) tail under stringent propagation conditions, pEVL 100 through 500 were grown for 2 weeks at 30 C and 37 C in TB+Kan media. Every 24 hours, 1 ul of each sample was seeded into a fresh 1 ml aliquot of TB+Kan media. At days 0, 6, and 13, 1 ul of each sample at each temperature was seeded into 1 ml of TB+Kan+arabinose media and grown overnight before being mini-prepped. After mini-prep, 2 ug of DNA from each sample was digested overnight with BsiWI and BsaI to release the poly(A) tail fragment from the rest of the plasmid. The digest was run on a 3% agarose gel and post-stained with GelStar Nucleic Acid stain (Lonza). GeneRuler 50 bp ladder (ThermoScientific) was used to determine poly(A) tail length.

Figure 11A:
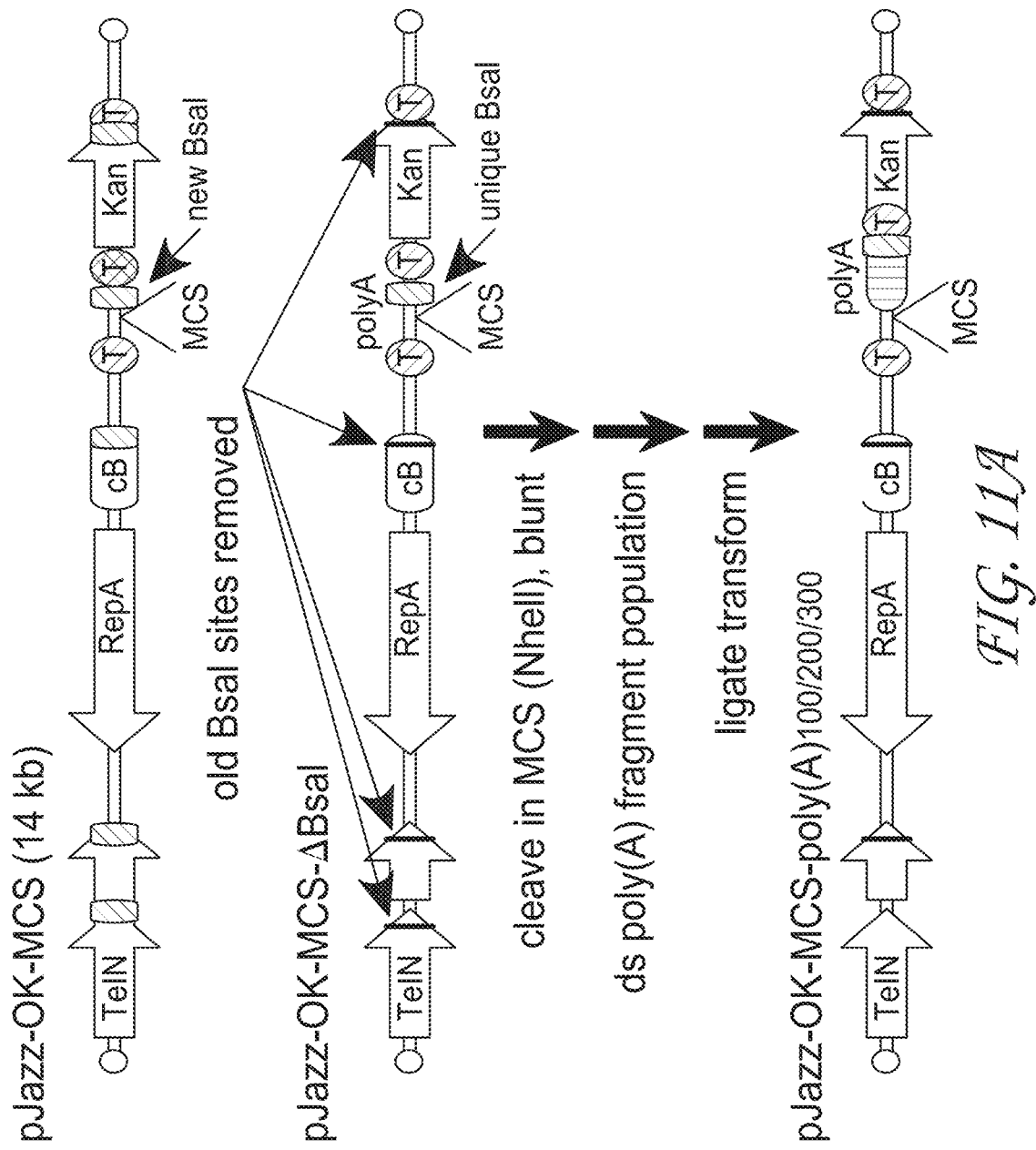
FIGS. 11A, 11B, 11C, 11D and 11E shows the generation and characterization of pEVL: a linear plasmid vector for generation of mRNA with extended encoded polyA tracts. 11A) Schematic of linear plasmid and conversion to pEVL 11B) Schematic of pEVL and method used for generation of extended poly(A) tracts in pEVL 11C) Shortening of poly (A) tracts upon cloning into standard circular or linear plasmid cloning vectors at 30° C. BFP followed by Poly(A) tracts inserts of 72, 164, and 325 base pairs bounded by restriction enzyme sites.
Figure 11B:
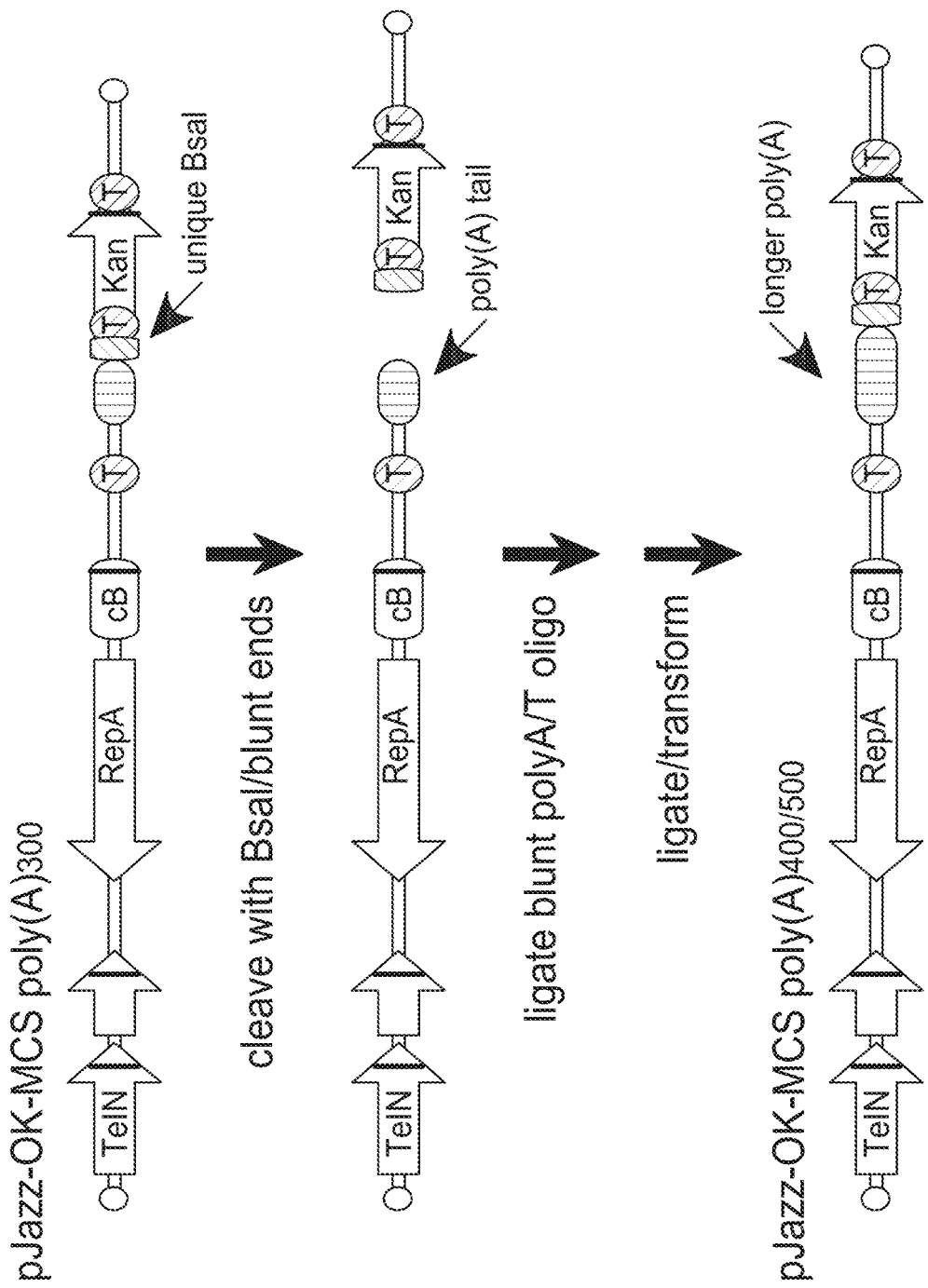

The linear plasmid used was a bacteriophage N15-based linear plasmid system that facilitates propagation of genomic DNA from organisms with highly repetitive genomes, but has not been previously reported to support the cloning or propagation of homopolymeric polynucleotide tracts. To determine whether the linear plasmid was capable of cloning or propagating poly(A) tracts, an in vitro ligation of chemically synthesized oligonucleotides to generate a population of annealed double stranded poly(A) polynucleotides of varied lengths was performed, they were then gel purified where the polynucleotides had lengths between approximately 100 to 850 base pairs, and it was attempted to ligate this population of oligonucleotide into a derivative of linear plasmid with a custom MCS (FIG. 11A). This ligation reaction led to the isolation of the linear plasmid-derivatives containing c.a. 70 base pair, c.a. 170 base pair, and c.a. 325 base pair poly(A) tracts (FIG. 11A, bottom; sizes were assessed by gel electrophoresis e.g. as in FIG. 11D, left panel). To determine the potential for the linear plasmid to stably propagate further extended poly(A) tracts, a method was developed for generation of extended poly(A) tracts of arbitrary length (FIG. 11B). This method required modification of the linear plasmid to position a unique type IIS restriction enzyme just downstream from an encoded poly(A) tract such that it was able to cleave within the poly(A) tract. To achieve this, all internal BsaI sites from the linear plasmid were removed to produce linear plasmid that lacked original BsaI sites (FIG. 11A, middle panel). Cloning of previously generated 70, 172, and 325 base pair tracts into the linear plasmid generated pEVL-100, pEVL-200 and pEVL-300 respectively, and subsequent cloning of a similarly generated blunt ended poly(A) polynucleotide population into BsaI digested/blunted pEVL-300 resulted in incorporation of additional 100 and 200 base pair tracts of poly(A) at the end of the pEVL-300 poly(A) tract, thus allowing the isolation of pEVL-400 and pEVL-500 (FIG. 11D, left panel).

Figure 11C:
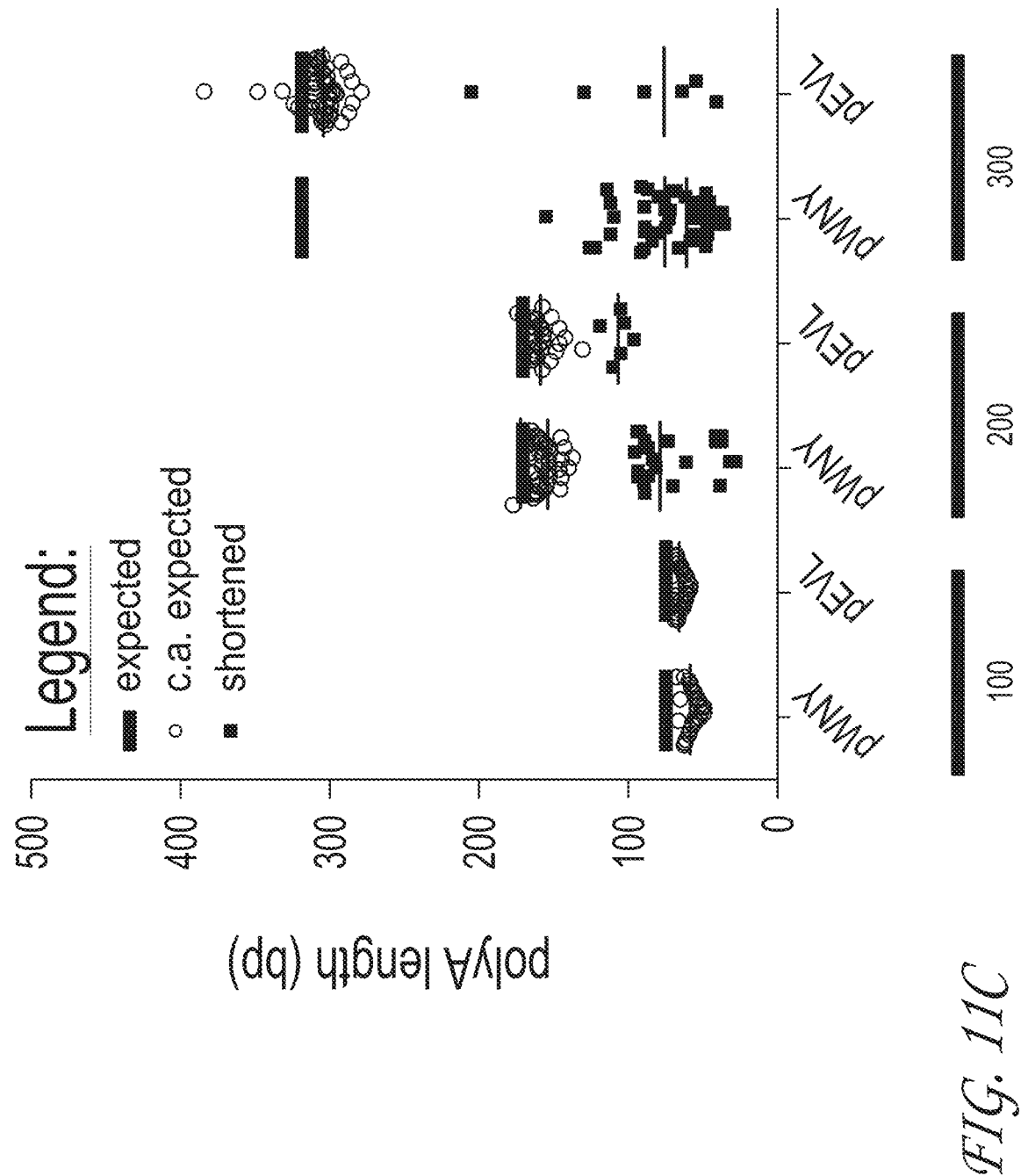
Figure 11D:
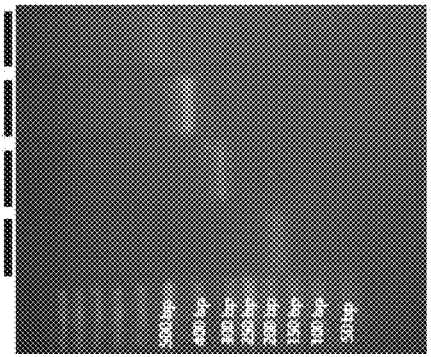
Figure 11E:
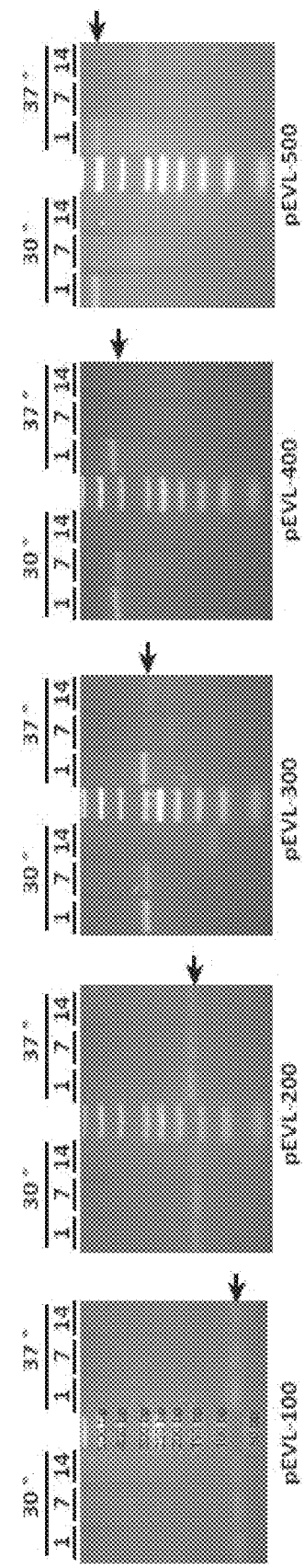
Figure 14A:
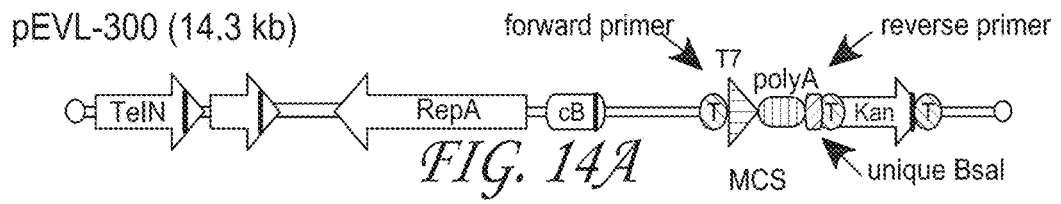
FIGS. 14A, 14B and 14C) show sequencing electropherograms covering the poly(A) tract in pEVL-300 Forward and reverse sequencing electropherograms generated using standard sanger sequencing chemistry over the poly(A) template in pEVL-300, demonstrating the existence of a homopolymeric tract of at least 300 base pairs.
Figure 14B:
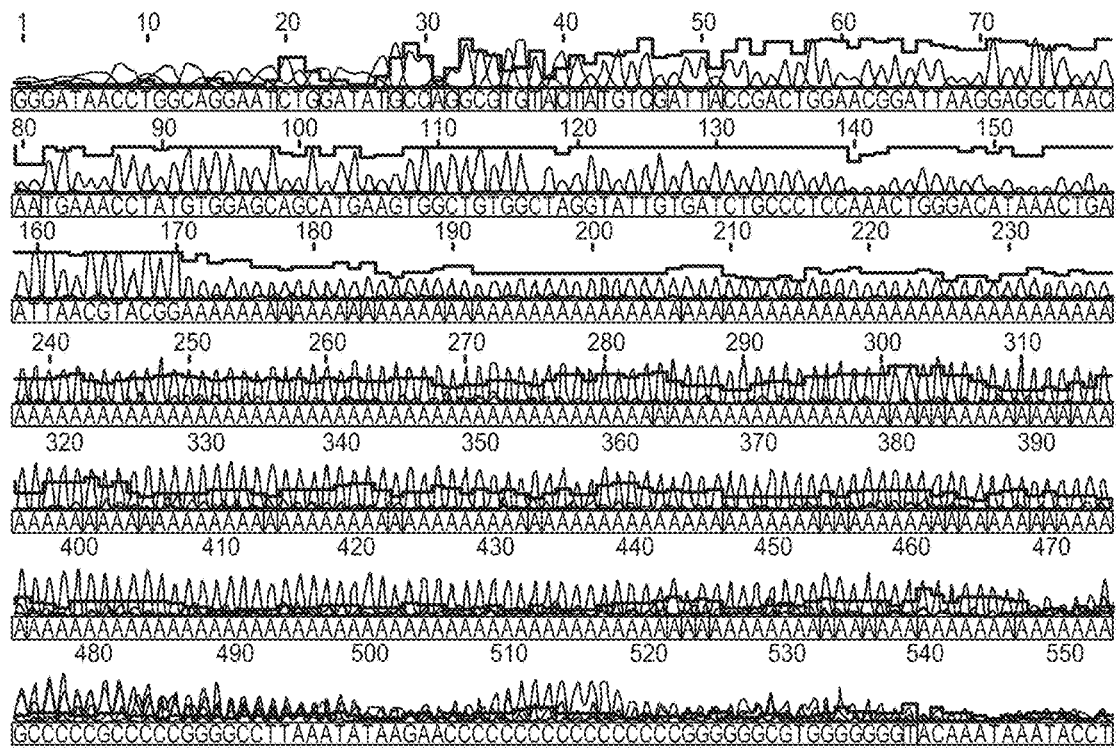
Figure 14C:
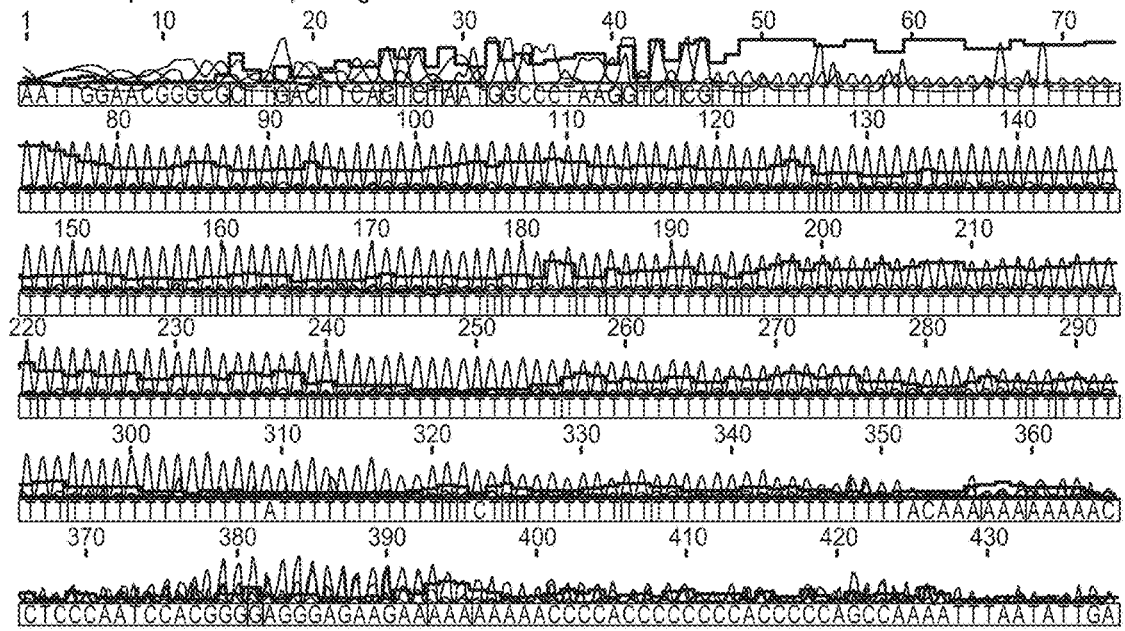

Practically, it was found that inserts possessing up to 300 base pair poly(A) sequences are easily subcloned into pEVL (FIG. 11C, FIG. 11D). These tracts are also highly stable during extended propagation through a two week course of serial liquid culture (FIG. 11E, also supported by DNA sequencing in both directions across the pEVL300 poly(A) tail following expansion, freezing to a glycerol stock, and re-expansion—see FIGS. 14A, 14B and 14C, with forward and reverse primer electropherograms demonstrating that the pEVL-300 poly(A) tract extends at least 300 base pairs). In contrast, it is noted that there is a tendency for the pEVL-500 poly(A) tract to shorten during cloning, although it is always possible to identify clones possessing inserts with a poly(A) tract of the original c.a. 500 base pair size. Similarly, extended propagation of pEVL-500 also shows a tendency for the poly(A) tract to shorten (FIG. 11E), and periodic re-isolation of colonies bearing full length tails is necessary to maintain the poly(A) tract at the desired length. mRNA Incorporating Extended polyA Tails Generated from pEVL Templates Exhibits Superior Translation Properties.

Figure 12A:
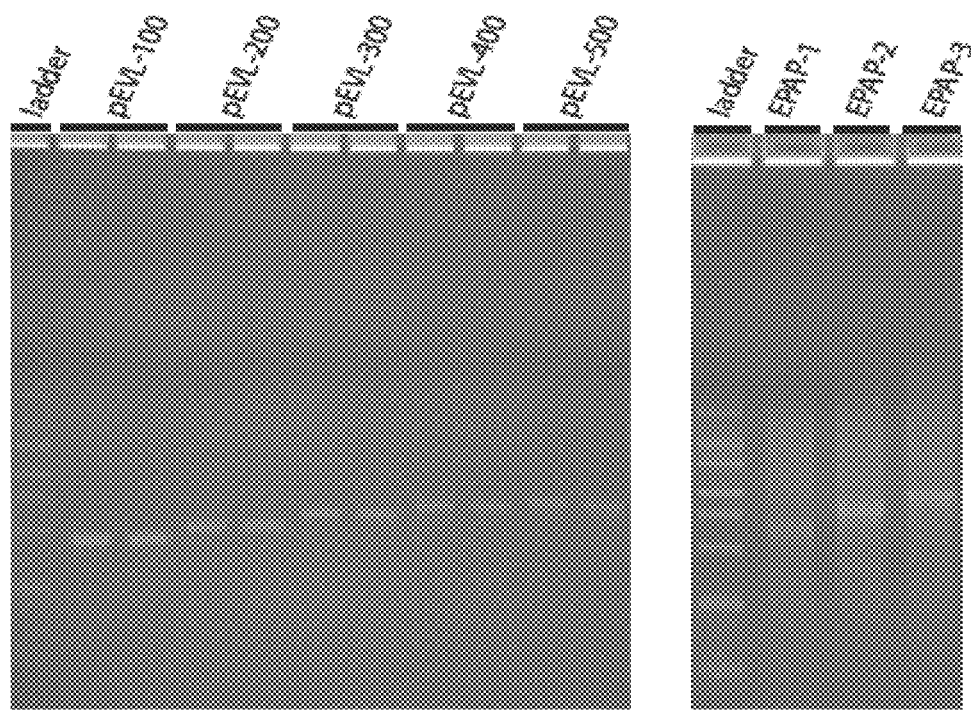
Figure 12C:
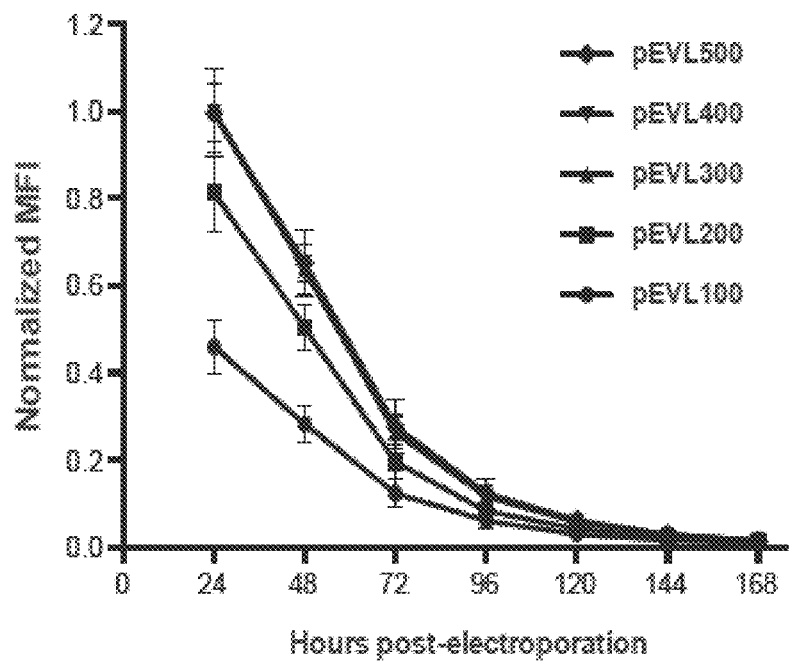
Figure 12B:
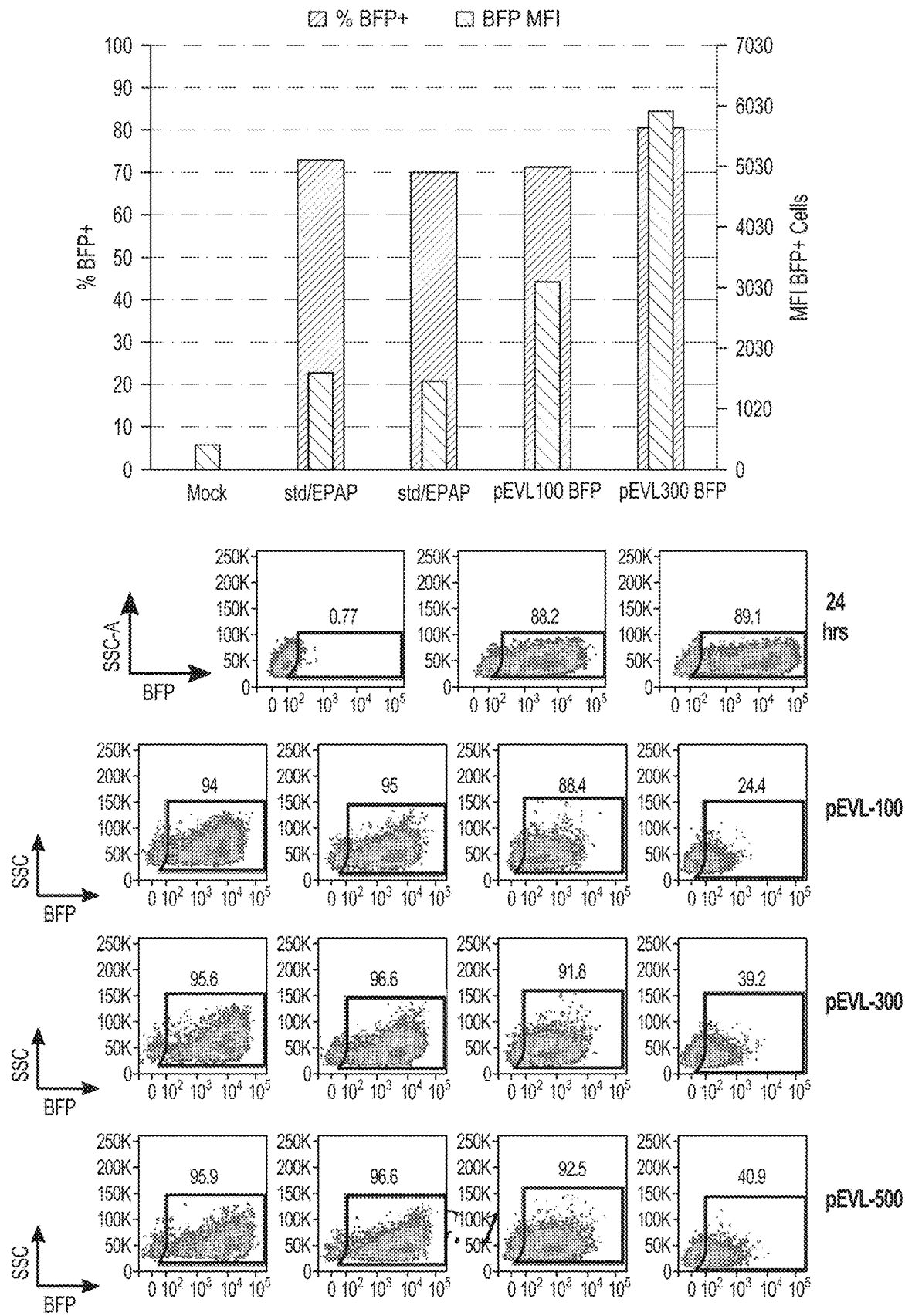

The capacity of pEVL to generate IVT mRNA was validated by cloning blue fluorescent protein (BFP) IVT cassettes upstream from the poly(A) tracts in pEVL-100/200/300/400/500. Using the respective BsaI-cleaved pEVL derivatives as the IVT mRNA templates, IVT mRNA was generated using ARCA capping chemistry from BFP-pEVL-100 through BFP-pEVL-500 (FIG. 12A, left panel). The resulting mRNA's were of predicted size for each pEVL derivative and highly uniform in comparison to enzymatically polyadenylated RNAs (FIG. 12A, right panel, shown are examples of typical ARCA capped $E.$ $coli$ poly(A) polymerase (EPAP) enzymatically polyadenylated mRNAs). The potency of the mRNA produced from pEVL was validated by comparing BFP expression following electroporation of mRNAs generated through enzymatic polyadenylation and from pEVL-100 and pEVL-300 into primary human T-cells, followed by analysis by flow cytometry (FIGS. 12B and 12D). A striking enhancement of potency was observed, as assessed by peak BFP mean fluorescence intensity at 24 hours post-electroporation, for mRNA generated from pEVL-300 vs. pEVL-100 or enzymatically polyadenylated mRNA. Importantly it was typically observed that pEVL-encoded mRNA produced a cell population with a tighter distribution of BFP fluorescence vs. enzymatically poly-adenylated mRNA (e.g. compare flow plots in FIG. 12B). Analyses comparing BFP expression driven by mRNA generated from pEVL-100 through pEVL-500 over a period of 7 days (FIG. 12C) confirmed the above observations pEVL-100 and pEVL-200 derived mRNA possessing poly(A) tail lengths of 72 base pairs and 165 base pairs respectively exhibited reduced potency vs mRNA's derived from pEVL-300, pEVL-400, or pEVL-500 (poly(A) tails of lengths of approximately 325, 420 and 500 base pairs (lengths are approximate and inferred from gel electrophoresis comparisons with MW standards in FIG. 11E). Significant potency differences among pEVL-derived mRNAs possessing encoded poly(A) tracts of 300 was not detected.

Figure 15A:
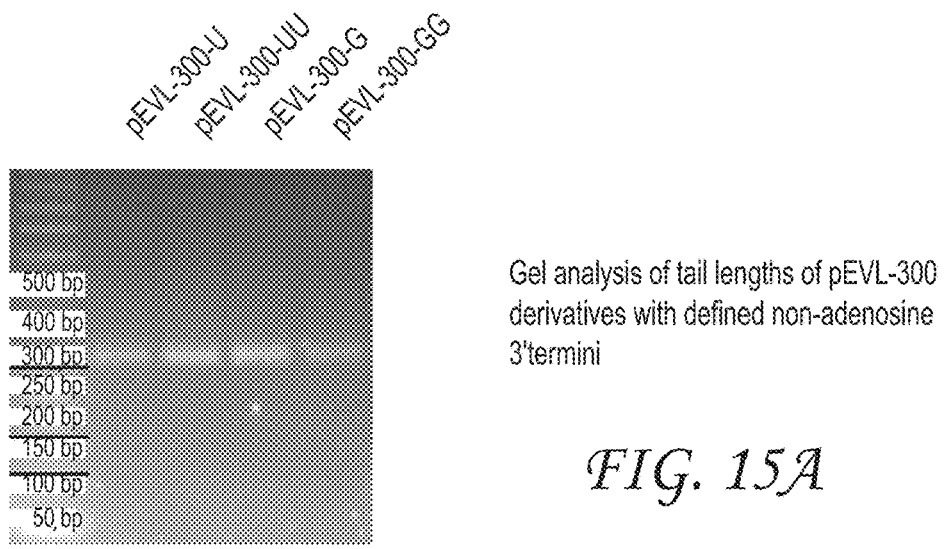
FIGS. 15A, 15B and 15C show the potency of mRNA generated from pEVL-300 variants with encoded terminal U, -UU, G-, -GG residues BFP-pEVL variants were generated for which the mRNA poly(A) tract was terminated by -U, -UU, -G, or -GG residues following BsaI digestion. mRNA was generated from these pEVL variants, and 0.5 microgram was transfected into primary human T-cells. BFP fluorescence was monitored by flow cytometry over a 7 day period. Plots represent relative MFI vs. time for each variant mRNA.
Figure 15B:
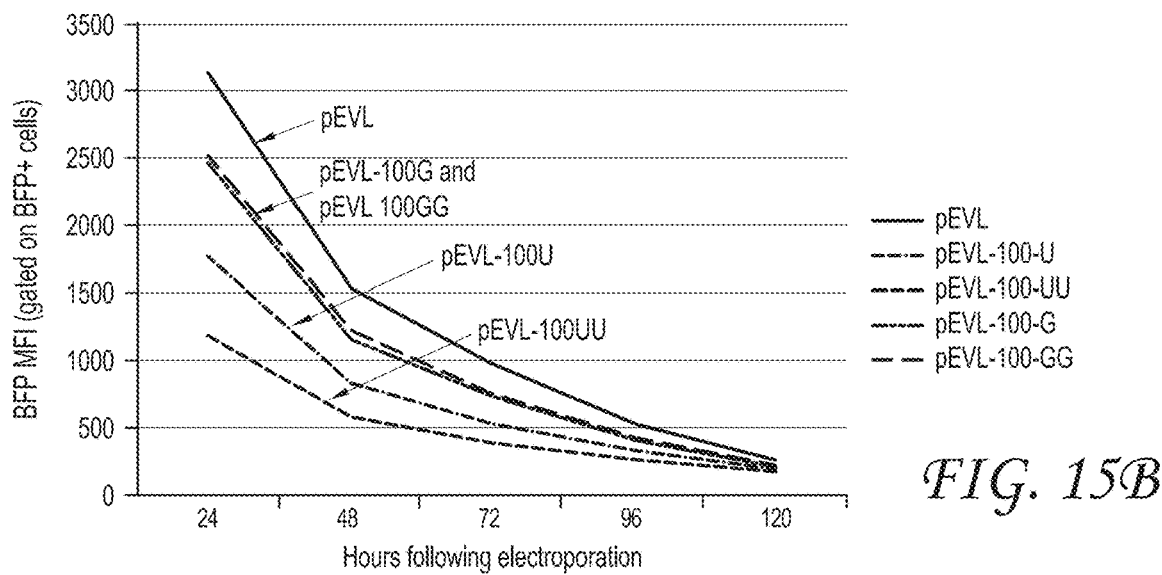
Figure 15C:
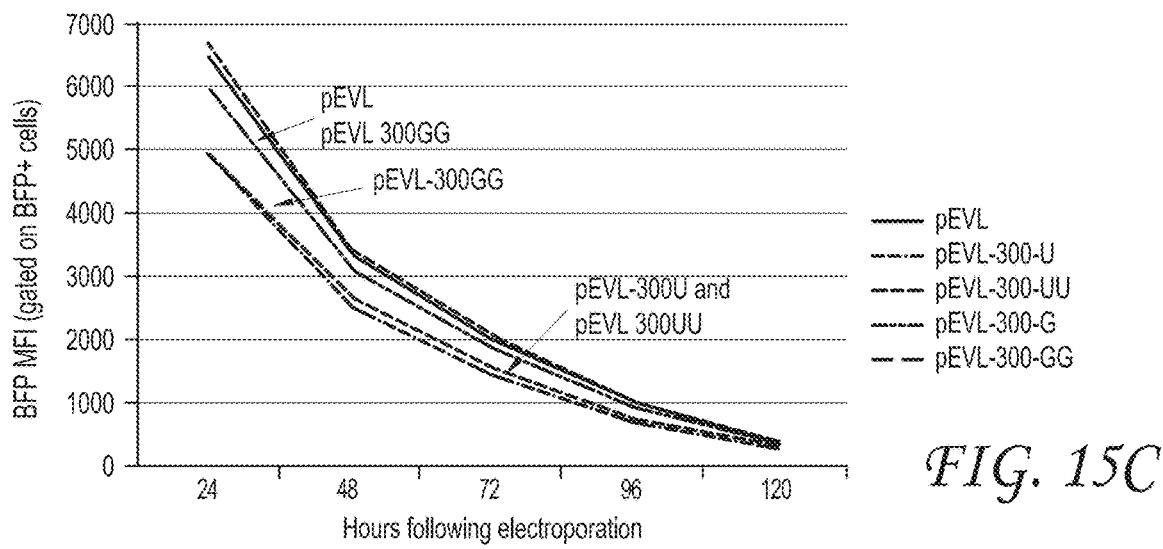

Based on evidence from sequencing of cellular RNAs, which has identified correlations between RNA length and the presence of single or double uridine or guanine residues on mRNA 3' termini 24-26, the pEVL-300 system to generate mRNA's with defined termini consisting of single or double uridine or guanine bases was further used, and their capacity to support fluorescent protein expression following transfection into primary human T-cells was evaluated (FIGS. 15B and 15C). Consistently, it was observed that mRNA's possessing 3' uridine termini (U or UU) exhibited reduced potency (both reduced total magnitude and duration of expression) relative to a standard poly(A) tail of identical length, while those bearing 3' guanine termini (G or GG) drove BFP expression that was indistinguishable from comparable length standard poly(A) tails.

Figures 13A, 13B, 13C, 13D:
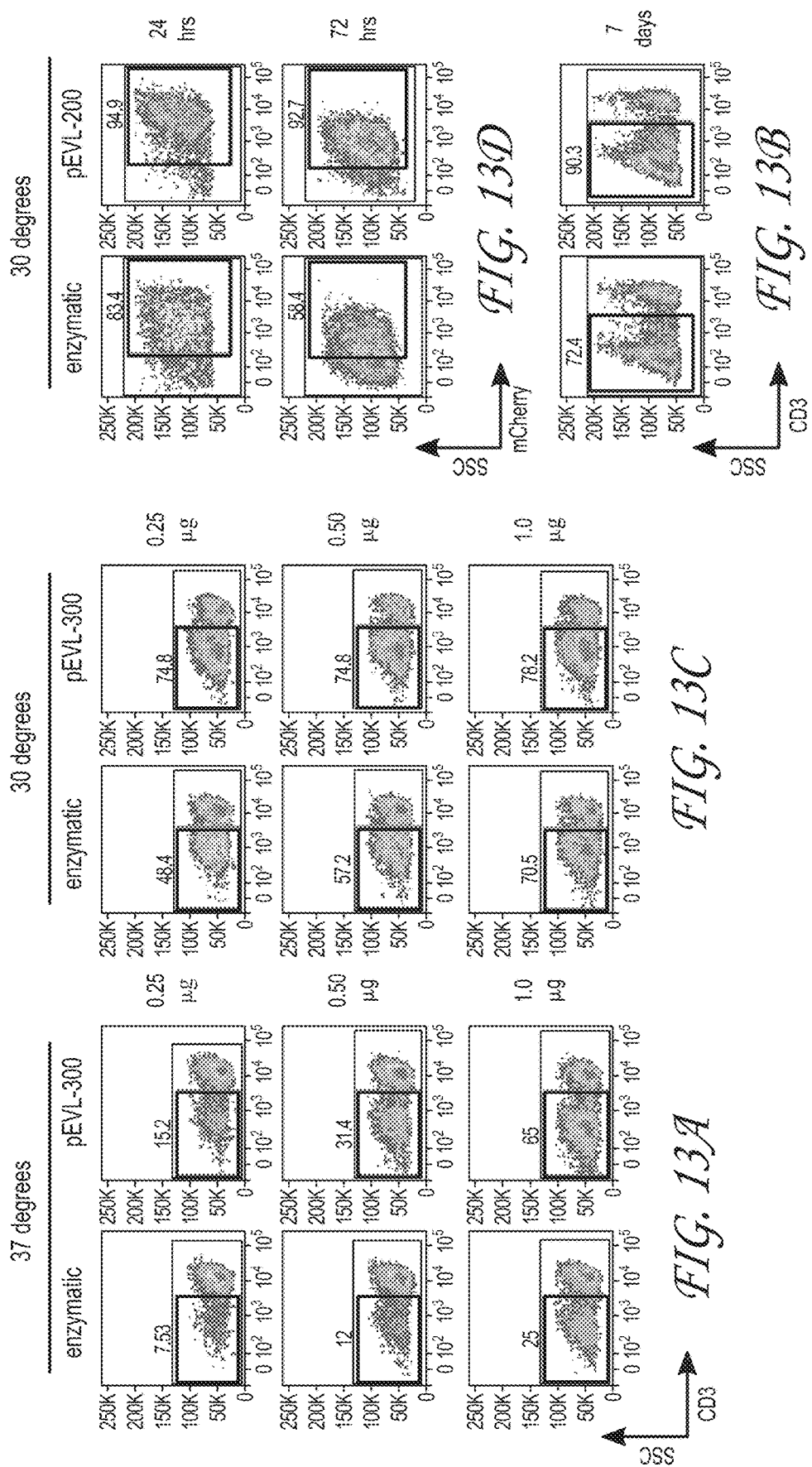
FIGS. 13A, 13B, 13C and 13D show the application of pEVL-encoded mRNA for gene editing in primary human T-cells. 13A and 13C) pEVL-mediated editing of the TCRa locus with TALENs in primary human T-cells A TALEN pair targeting the constant region of the TCRa locus was cloned into pEVL-300. After IVT mRNA production, the indicated amounts of each TALEN half were electroporated into pre-stimulated primary human T-cells. After 72 hours, successful TCR knockout was assayed by flow cytometry for a lack of CD3 expression. 13D) pEVL-mediated editing of the TCRa locus with CRISPR/Cas9 in primary human T-cells A Cas9-T2A-mCherry construct was cloned into pEVL-200. After IVT mRNA production, Cas9 was electroporated into pre-stimulated primary human T-cells. 4 hr post-electroporation, a CRISPR guide targeting the TCRa constant region was delivered via AAV6 transduction. At 24 and 72 hr post-electroporation, Cas9 electroporation efficiency was determined by FACS analysis of mCherry fluorescence. 13B) After 7 days, successful TCR knockout was assayed by flow cytometry for a lack of CD3 expression.

Finally, the performance of pEVL-derived IVT mRNA in a gene editing application was evaluated: disruption of the TCRα locus in primary human T-cells (FIGS. 13A, 13B, 13C and 13D). For this purpose, ORFs encoding TALENs targeting the TCRα locus were cloned into pEVL-300 and used for IVT mRNA production in parallel with production of TALEN mRNA from a standard circular plasmid. Following electroporation of pEVL-derived TALEN mRNA into primary human T-cells, it was observed that rates of CD3 loss, which occur following disruption of the TCRα gene due to the necessity for TCR α/β holoreceptor/CD3 interaction to support surface expression of CD3, were consistently higher than equal weights of enzymatically polyadenylated mRNA generated in parallel (FIGS. 13A and 13C). This was interpreted as being consistent with the general observation that increased expression of gene editing nucleases results in higher rates of target site modification. As a second evaluation of the performance of pEVL-derived mRNA for gene editing applications, the Cas9 nuclease fused through a 2A linker to mCherry was cloned into either a circular plasmid vector or pEVL-200, and used mRNA's derived from these vectors to express Cas9 and mcherry in primary human T-cells, whilst simultaneously expressing a guide RNA targeting the TCRα constant region using an AAV (FIGS. 13B and 13D). In the case of expression of Cas9-2A-mCherry using either enzymatically polyadenylated vs. pEVL-200 derived mRNA, it was again observed that pEVL-derived mRNA produced populations with a tighter distribution of fluorescence, as well as higher average fluorescence, and that this correlated with an enhanced efficiency of CRISPR-mediated gene editing (top panel). Collectively, these data support the concept that level and duration of nuclease expression are important determinants of the cleavage activity observed for a nuclease at a genomic target site in a living cell 27, and that use of mRNAs with >250 base pair poly(A) tails to express gene editing nucleases will support higher gene editing efficiencies vs. use of mRNA with shorter poly(A) tails.

H9 T-Cell Line Growth after Transfection with pEVL Encoded mRNA.

Figure 16:
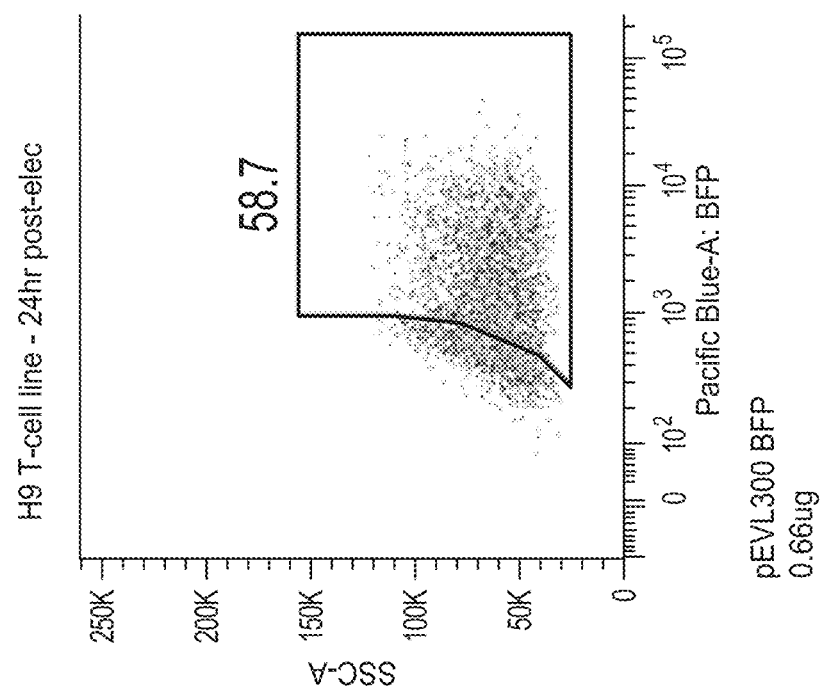
FIG. 16 shows H9 T-cell line growth after transfection with pEVL encoded mRNA.

H9 T-cells were grown in culture, and 1×10$^6$ cells were resuspended in neon electroporation buffer. 0.66 ug of BFP mRNA generated by in vitro transcription from the pEVL-300 vector was added to the electroporation cuvette, and cells were electroporated at 1000 volts×2 pulses, followed by transfer to and culture at 37° C. degrees Celsius in regular culture media. 24 hours following transfection, BFP fluorescence was analyzed by flow cytometry, demonstrating that nearly 60% of the cells expressed BFP, indicative of highly efficient transfection with the pEVL-encoded mRNA. (FIG. 16).

K562 Cells Line Growth after Transfection with pEVL Encoded mRNA.

Figure 17:
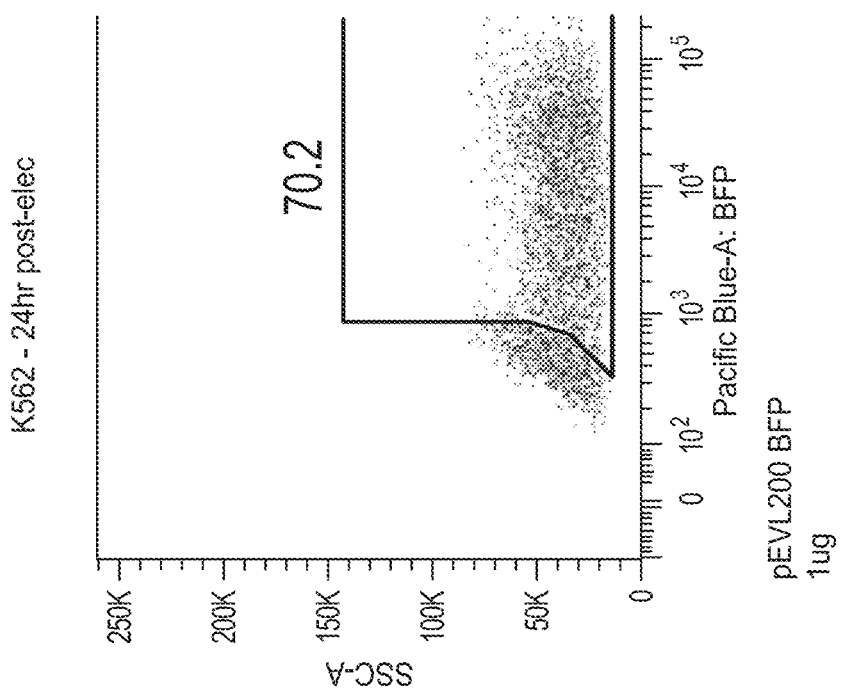
FIG. 17 shows K562 cells line growth after transfection with pEVL encoded mRNA.

K562 T-cells were grown in culture, and 1×10$^6$ cells were resuspended in neon electroporation buffer. 1.0 ug of BFP mRNA generated by in vitro transcription from the pEVL-300 vector was added to the electroporation cuvette, and cells were electroporated at 1000 volts×2 pulses, followed by transfer to and culture at 37 degrees Celsius in regular culture media. BFP fluorescence was analyzed by flow cytometry, and demonstrated that 70% of the cells expressed BFP, indicative of highly efficient transfection with the pEVL-encoded mRNA. (FIG. 17).

Jurkat Cells Growth after Transfection with the pEVL-Encoded mRNA.

$1 \times 10e^6$ Jurkat cultured T-cells were mock electroplated, or electroporated with 1.5 micrograms of mRNA encoding a Cas9-2A-mCherry protein. Transfected cells were placed in culture for 24 hours, following which the cells were collected and analyzed for mCherry expression by flow cytometry. As shown in the figure, >75% of cells were demonstrated to be mCherry+, indicative of highly efficient transfection. (FIG. 18B).

HepG2 Liver Cells Growth after Transfection with the pEVL-Encoded mRNA.

Figures 19A, 19B:
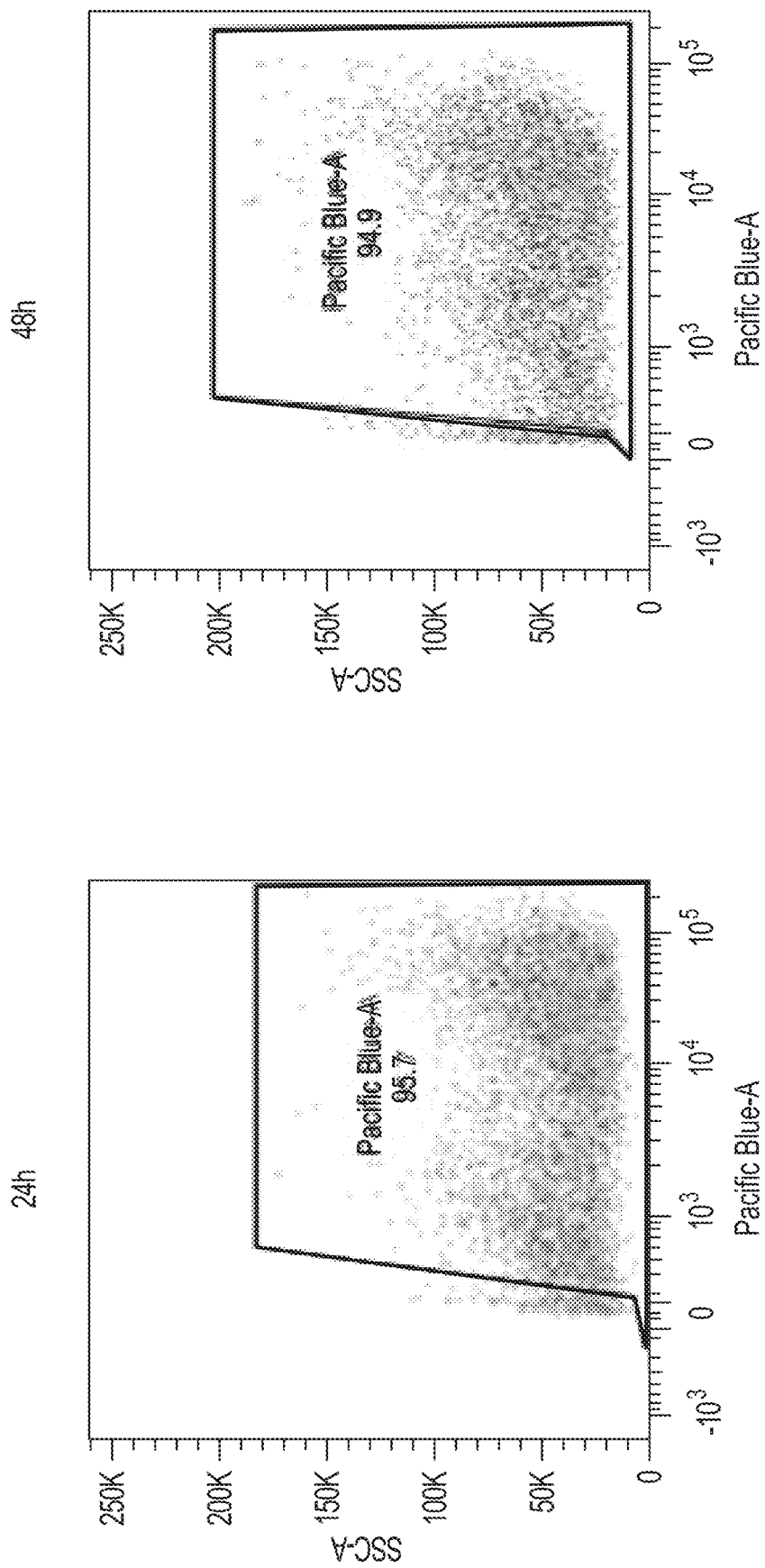
FIGS. 19A and 19B show that HepG2 liver cells growth after transfection with the pEVL-encoded mRNA.

HepG2 cells were grown in culture, and $3 \times 10^5$ cells were resuspended in neon electroporation buffer. 0.25 ug of BFP mRNA generated by in vitro transcription from the pEVL-300 vector was added to the electroporation cuvette, and cells were electroporated at 1295 volts×3 pulses, followed by transfer to and culture at 37 degrees Celsius in regular culture media. 24 and 48 hours following transfection, BFP fluorescence was analyzed by flow cytometry, demonstrating that nearly 95% of the cells expressed BFP by 24 hours and remained highly BFP+ at 48 hours, indicative of highly efficient transfection with the pEVL-encoded mRNA. (FIGS. 19A and 19B).

Human CD34 Cells Transfected with BFP mRNA.

Human CD34 cells were cultured in SCGM culture media supplemented with Flt3-L/SCF/TPO/IL-3 and incubated for 48 hours at 37 degrees Celsius. The cells were then resuspended in Neon electroporation buffer T. 1.5 ug of BFP mRNA, was generated by in vitro transcription from pEVL-300 vectors which prepared by Trilink was added to $0.2 \times 10^6$/ml cells. Cells were electroporated at 1300 volts, 1 pulse, 20 ms, followed by transfer to and culture at 30 degrees for 16 hours, and subsequently at 37 degrees for additional days. Cells were analyzed by flow cytometry at 24, 48, 72, 96 and 120 hr post-electroporation. The BFP mRNA-transfected cells show >80% BFP signals at 24 hr and 48 hr post-electroporation (FIGS. 20A, 20B and 20C). The BFP signals decrease gradually from 80% to 20% at 120 hr post-electroporation. (FIGS. 20D, 20E and 20F).

pELV pEVL can act as a template during RNA synthesis. The template can be made with an encoded polyA tail of a predefined length and does not require PCR for its synthesis. pEVL plasmids can have a multiple cloning site (MCS) directly upstream of a polyA tract of a defined length that terminates in a unique Type IIS restriction enzyme, BsaI. BsaI can be oriented such that the cleavage occurs at the end, and within the polyA tract, thus the recognition site for the enzyme is inverted. Multiple pEVL plasmids can exist with polyA lengths ranging from approximately 100 to 500 bp in length; the naming corresponds to the tail length e.g., pEVL100 and pEVL500, respectively. Cloning a T7 RNA polymerase promoter and gene into the MCS, and then cleaving the purified DNA with BsaI, can generate a template for the generation of polyadenylated RNA. This template can be used to generate RNA with a predefined, homogeneous polyA tail length in as little as one enzymatic step.

The generated pEVL can be kept frozen or at −20° C. when not actively in use. pEVL can also be protected by proteins produced by telN.

E. coli Strain Selection

E. coli can be used with pELV. For example, the strain BigEasy E. coli can be used with the pELV. The plasmid can be propagated in BigEasy cells, to induce higher plasmid copy number.

pEVL plasmids can also be linear plasmid-OK derivatives, and thus the plasmids can be Kanamycin (Kan) resistant. Kan can be used at 50 µg/mL, 40 µg/mL or 30 µg/mL or any other concentration between any two aforementioned values, preferably, 2,000× (10 mg/mL) is used.

Molecular Cloning

During cloning, adapters can be used or other variable recognition sites.

Exemplary recognition sites include DraIII-BsiWI or DraIII sites.

Digesting the Plasmid

Digestion of the plasmid can be performed by the appropriate endonuclease and is dependent on the endonuclease recognition site in the plasmid.

Ligations and Transformations

Ligation of a polyT tract into the plasmid can be performed by standard molecular cloning procedures and standard trouble shooting. The plasmids can be transformed into bacterial cells grown on standard media plates, for example LB agar plates. These procedures are known to those skilled in the art.

The linear plasmids can also be screened to check for the insert and polyA length maintenance. Without being limiting PCR, colony PCR, sequencing and other methods known to one skilled in the art, can be used to look for polyA shortening.

Growing Cells with pEVL

Cells harboring the linear plasmids can be grown in a nutritional media such as TB and an appropriate selection antibiotic. Cells such as E. coli, BigEasy E. coli strains, can be used, for example. Examples of selective antibiotics can include but are not limited to Kanamycin, Ampicillin, Penicillin, and chloramphenicol. If there is an operon or promoter region, a molecule to induce induction can be used. For example, if there is an arabinose operon, arabinose can be used for induction.

Cells containing plasmids can be frozen down for later use, such as glycerol stocks, for example.

Growth for DNA Preps

If the pEVL construct made is a low copy plasmid, the pEVL can require a larger mass of bacteria in order to obtain standard amounts of plasmid from a commercial preparation, (e.g., Macherey Nagel Nucleobond Xtra Maxi). The bacteria can be grown in the presence of an antibiotic, depending on the antibiotic resistance.

Plasmid DNA and RNA Preps

DNA plasmid preps can be made from techniques known to skilled in the art, as well as from commercially available kits, for example (for example, Qiagen Maxi and MiniPrep kits and Invitrogens Maxi kit). Commercially available kits are known to those skilled in the art and the kits can have RNase, lysis buffers, for example. Kits can also be used to retrieve RNA and to avoid RNA contamination and to avoid low yields.

RNA Transcription Using pEVL

The pEVL construct can be digested with the proper endonuclease, for example, when the restriction recognition site is BsaI, BsaI can be used. The amount of enzyme required depends on the size of the insert, since larger inserts (and therefore larger plasmids) will have a lower number of sites per µg of DNA, and would therefore require less enzyme, for example.

After digestion, purification of the reaction can be performed. Purification can be performed by standard purification techniques known to those skilled in the art, or by a commercially available kit, such as Qiagen PCR purification columns for example.

Transcription Reaction

After purification of the template, the template can be used for the transcription reaction.

Here the development and application of a linear plasmid vector system, (plasmid-Extended Variable Length (pEVL)) is described, which allows for generation of IVT mRNA with poly(A) tracts possessing defined 3' ends of up to at least 500 base pairs. Furthermore, it is shown that IVT mRNA's generated with pEVL have high potency when used in conjunction with electroporation of primary human T-cells, and that the observed potency is highest for transcripts possessing 3' poly(A) tracts greater than approximately 300 base pairs and either adenine or guanine residues at their 3' terminus.

pEVL using the framework of a linear plasmid was built, in which the linear plasmid was developed for cloning of highly repetitive DNA from bacterial genomes. As schematized in FIG. 11B, adaptation of the linear plasmid for facile generation of extended poly(A) tracts required its modification such that it possessed a unique target site for the type IIS restriction enzyme BsaI, as the BsaI site 3' to the poly(A) tract is central to the method developed for iterative cloning of blunt end poly (A) oligonucleotides in order to extend the encoded poly(A) tract to a length greater than 300 base pairs. The BsaI site or another restriction site or endonuclease site may also be used for generation of arbitrary alternative terminal residues on the 3' end of the mRNA, that, as it is shown in FIGS. 15A, 15B and 15C, may include one or two terminal guanines following the homo-polymeric poly(A) stretch while still yielding mRNA with potency indistinguishable from a homopolymeric poly(A) tract, at least in primary T-cells.

One of the most important uses of pEVL will be for large scale generation of mRNA for therapeutic applications. pEVL is easily scaled up for large scale GMP plasmid production using kanamycin selection, and allows for generation of uniform size capped and polyadenylated mRNAs in a single reaction using standard T7 RNA polymerase chemistry. As validating examples for the utility of pEVL at scale, pEVL-200 and pEVL-300 can be used and shown to generate extremely high quality and high potency mRNAs encoding TALENs, BFP, Sleeping Beauty transposase, and Cas9-2A-mCherry at 10 mg scale using standard mRNA IVT methods.

pEVL also represents a new tool for investigators interested in mRNA biology. By providing a method for generation of transcripts that possess poly(A) tails of a desired length and terminal residues, pEVL allows detailed studies of the relationship between mRNA architecture and translational efficiency over a wider range of poly(A) tail lengths.

The development of a linear plasmid vector pEVL that enables generation of templates encoding mRNA's bearing extended encoded poly(A) tracts up to at least 500 base pairs in length is provided herein. pEVL is a significant advance toward simple, efficient, and consistent large scale synthesis of highly potent mRNA's for therapeutic application, as well as a new tool for the study of the architecture and function of mRNAs possessing defined poly(A) tracts in the physiologic (>200 base pair) range.

More Alternatives

As provided herein are novel methods for the generation of extended poly(A) tracts using a previously described linear plasmid system. It is found that the linear plasmid linear plasmid is able to stably propagate poly(A) tracts up to at least 500 base pairs in length. To facilitate generation of IVT mRNA with precisely defined encoded poly(A) tracts and 3'termini, alternatives are provided with modified linear plasmid, by removing extraneous restriction sites, adding a T7 promoter sequence upstream from an extended MCS, and adding a unique type IIS restriction site downstream from the position of the encoded poly(A) tract. The resulting plasmid, designated p(Extended Variable Length) (pEVL), can be used to generate IVT mRNA with consistent, defined lengths and terminal residue(s).

Some alternatives relate to a polynucleotide comprising a template strand, an endonuclease recognition site and an endonuclease cleavage site for an endonuclease inserted therein, wherein said template strand comprises a plurality of thymine nucleotides. Some polynucleotides comprise a first nucleic acid sequence comprising at least one restriction endonuclease recognition site and a second nucleic acid sequence, wherein the second nucleic acid sequence comprises the template strand, wherein the template strand comprises a plurality of thymine nucleotides, wherein said plurality of thymine nucleotides comprises at least, greater than, equal to, or any number in between 20, 30, 40, 50, 60, 70, 80, 90, 100, 110, 120, 130, 140, 150, 175, 200, 225, 250, 275, 300, 325, 350, 375, 400, 425, 450, 475, 500 or 550 covalently linked thymine nucleotides, wherein the second nucleic acid comprises the restriction endonuclease cleavage site, and wherein the restriction endonuclease cleavage site is within the plurality of thymine nucleotides or within 1, 2, 3, 4, 5, 6, 7, 7, 8, 9, 10, 11, 12, 13, 14, 15, 16, 17, 18, 19 or 20 base pairs away from the most 5' thymine (or 5' terminal thymine) in the plurality of thymine nucleotides and wherein said first nucleic acid is covalently linked to said second nucleic acid at one end of said second nucleic acid, and wherein the said restriction endonuclease recognition site is located within 1-55 base pairs such as, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54 or 55 base pairs, of the restriction endonuclease cleavage site for the restriction endonuclease and said restriction endonuclease cleavage site is within 1 to 40 base pairs, such as 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 base pairs, of a most 5' thymine (or 5' terminal thymine) in the plurality of thymine nucleotides. In some alternatives, the polynucleotide further comprises telomeres. In some alternatives, the polynucleotide comprises a left arm wherein the left arm comprises a left telomere, a right arm wherein the right arm comprises a right telomere and a cloning region located between the left arm and the right arm. In some alternatives, the polynucleotide further comprises a third nucleic acid, wherein the third nucleic acid comprises a gene. In some alternatives, the gene encodes a protein for therapy. In some alternatives, the gene encodes a nuclease. In some alternatives, the nuclease is an endonuclease. In some alternatives, the nuclease comprises an amino acid sequence set forth in SEQ ID NO. 6 or is encoded by a nucleic acid sequence set forth in SEQ ID NO: 7-14. In some alternatives, the number of covalently linked thymines is greater than 120. In some alternatives, the number of covalently linked thymines is greater than 200. In some alternatives, the number of covalently linked thymines is greater than 300. In some alternatives, the at least one endonuclease recognition site is a Type II restriction endonuclease recognition site, and the endonuclease is a Type II restriction endonuclease. In some alternatives, the at least one endonuclease recognition site is a Type IIS restriction endonuclease recognition site and wherein the endonuclease is a Type IIS restriction endonuclease. In some alternatives, the at least one endonuclease recognition site is a BsaI restriction endonuclease recognition site or a StuI restriction endonuclease recognition site, and wherein the endonuclease is BsaI or StuI. In some alternatives, the endonuclease recognition site is inverted. In some alternatives, the polynucleotide is a linear polynucleotide. In some alternatives, the polynucleotide has only one endonuclease recognition site. In some alternatives, the polynucleotide further comprises a polymerase promoter region. In some alternatives, the plurality of thymine nucleotides comprises at least one covalently linked guanine, cytosine, or an adenine, wherein the at least one covalently linked guanine, cytosine or adenine is optionally joined to the most 5' thymine (or 5' terminal thymine) in the plurality of thymine nucleotides. In some alternatives, the endonuclease cleavage site comprises at least one guanine, cytosine, or an adenine, wherein the endonuclease cleaves between a thymine and the at least one guanine, cytosine or adenine. In some alternatives, the polynucleotide further comprises at least one palindromic sequence, wherein the at least one palindromic sequence can form a hairpin. In some alternatives, the polynucleotide further comprises a third sequence, wherein the third sequence is capable of forming a tertiary structure such as a hairpin. In some alternatives, the gene is codon optimized for expression in human cells. In some alternatives, the endonuclease cleavage site is located 1, 2, 3, 4, 5, 6, 7, 7, 8, 9, 10, 11, 12, 13, 14, 15, 16, 17, 18, 19 or 20 base pairs away from the most 5' thymine (or 5' terminal thymine) in the plurality of thymine nucleotides. In some alternatives, the endonuclease cleavage site is located 1, 2, 3, 4, 5, 6, 7, 7, 8, 9 or 10 base pairs away from the most 5' thymine (or 5' terminal thymine) in the plurality of thymine nucleotides.

In some alternatives, a method of making a polynucleotide having a template strand, an endonuclease recognition site and an endonuclease cleavage site for an endonuclease inserted therein, and wherein said template strand comprises a plurality of thymine nucleotides, is provided. Some methods can comprise providing a first nucleic acid sequence comprising at least one endonuclease recognition site, providing a second nucleic acid sequence, wherein said plurality of thymine nucleotides comprises at least, greater than, equal to, or any number in between 20, 30, 40, 50, 60, 70, 80, 90, 100, 110, 120, 130, 140, 150, 175, 200, 225, 250, 275, 300, 325, 350, 375, 400, 425, 450, 475, 500 or 550 covalently linked thymine nucleotides and wherein the second nucleic acid comprises the endonuclease cleavage site, wherein the endonuclease cleavage site is within the plurality of thymine nucleotides or within 1, 2, 3, 4, 5, 6, 7, 7, 8, 9, 10, 11, 12, 13, 14, 15, 16, 17, 18, 19 or 20 base pairs away from the most 5' thymine (or 5' terminal thymine) in the plurality of thymine nucleotides and joining said first nucleic acid sequence to said second nucleic acid sequence, wherein said first nucleic acid is covalently linked to said second nucleic acid at one end, and wherein the said endonuclease recognition site is located within 1 to 55 base pairs, such as 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54 or 55 base pairs, of the endonuclease cleavage site for the endonuclease and said endonuclease cleavage site is within 1 to 40 base pairs such as, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 base pairs, of a most 5' thymine or 5' terminal thymine in the plurality of thymine nucleotides or within 1, 2, 3, 4, 5, 6, 7, 7, 8, 9, 10, 11, 12, 13, 14, 15, 16, 17, 18, 19 or 20 base pairs away from the most 5' thymine (or 5' terminal thymine) in the plurality of thymine nucleotides. In some alternatives, the polynucleotide further comprises telomeres. In some alternatives, the polynucleotide comprises a left arm wherein the left arm comprises a left telomere, a right arm wherein the right arm comprises a right telomere and a cloning region located between the left arm and the right arm. In some alternatives, the polynucleotide further comprises a third nucleic acid, wherein the third nucleic acid comprises a gene. In some alternatives, the gene encodes a protein for therapy. In some alternatives, the gene encodes a nuclease. In some alternatives, the nuclease is an endonuclease. In some alternatives, the nuclease comprises an amino acid sequence set forth in SEQ ID NO. 6 or is encoded by a nucleic acid sequence set forth in SEQ ID NO: 7-14. In some alternatives, the number of covalently linked thymines is greater than 120. In some alternatives, the number of covalently linked thymines is greater than 200. In some alternatives, the number of covalently linked thymines is greater than 300. In some alternatives, the at least one endonuclease recognition site is a Type II restriction endonuclease recognition site, and the endonuclease is a Type II restriction endonuclease. In some alternatives, the at least one endonuclease recognition site is a Type IIS restriction endonuclease recognition site, and wherein the endonuclease is a Type IIS restriction endonuclease. In some alternatives, the at least one endonuclease recognition site is a BsaI restriction endonuclease recognition site or a StuI restriction endonuclease recognition site, and wherein the endonuclease is BsaI or StuI. In some alternatives, the endonuclease recognition site is inverted. In some alternatives, the polynucleotide is a linear polynucleotide. In some alternatives, the polynucleotide has only one endonuclease recognition site. In some alternatives, the polynucleotide further comprises a polymerase promoter. In some alternatives, the plurality of thymine nucleotides comprises at least one covalently linked guanine, cytosine, or an adenine, wherein the at least one covalently linked guanine, cytosine or adenine is optionally joined to the most 5' thymine (or 5' terminal thymine) in the plurality of thymine nucleotides. In some alternatives, the endonuclease cleavage site comprises at least one guanine, cytosine, or an adenine, wherein the endonuclease cleaves between a thymine and the at least one guanine, cytosine or adenine. In some alternatives, the polynucleotide further comprises at least one palindromic sequence, wherein the at least one palindromic sequence can form a hairpin. In some alternatives, the polynucleotide further comprises a fourth sequence, wherein the fourth sequence is capable of forming a tertiary structure such as a hairpin. In some alternatives, the gene is codon optimized for expression in human cells. In some alternatives, the endonuclease cleavage site is located 1, 2, 3, 4, 5, 6, 7, 7, 8, 9, 10, 11, 12, 13, 14, 15, 16, 17, 18, 19 or 20 base pairs away from the most 5' thymine (or 5' terminal thymine) in the plurality of thymine nucleotides. In some alternatives, the endonuclease cleavage site is located 1, 2, 3, 4, 5, 6, 7, 7, 8, 9 or 10 base pairs away from the most 5' thymine (or 5' terminal thymine) in the plurality of thymine nucleotides.

In some alternatives, a method of making a nucleic acid is provided. The method can comprise providing the polynucleotide of any one of the alternatives provided herein, or the polynucleotide manufactured by any one of the alternatives provided herein and contacting said polynucleotide with a polymerase in the presence of nucleotides. Some methods can comprise providing a first nucleic acid sequence comprising at least one endonuclease recognition site, providing a second nucleic acid sequence, wherein said plurality of thymine nucleotides comprises at least, greater than, equal to, or any number in between 20, 30, 40, 50, 60, 70, 80, 90, 100, 110, 120, 130, 140, 150, 175, 200, 225, 250, 275, 300, 325, 350, 375, 400, 425, 450, 475, 500 or 550 covalently linked thymine nucleotides and wherein the second nucleic acid comprises the endonuclease cleavage site, wherein the endonuclease cleavage site is within the plurality of thymine nucleotides or within 1, 2, 3, 4, 5, 6, 7, 7, 8, 9, 10, 11, 12, 13, 14, 15, 16, 17, 18, 19 or 20 base pairs away from the most 5' thymine (or 5' terminal thymine) in the plurality of thymine nucleotides and joining said first nucleic acid sequence to said second nucleic acid sequence, wherein said first nucleic acid is covalently linked to said second nucleic acid at one end, and wherein the said endonuclease recognition site is located within 1 to 55 base pairs, such as 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54 or 55 base pairs, of the endonuclease cleavage site for the endonuclease and said endonuclease cleavage site is within 1 to 40 base pairs such as, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 base pairs, of a most 5' thymine or 5' terminal thymine in the plurality of thymine nucleotides or within 1, 2, 3, 4, 5, 6, 7, 7, 8, 9, 10, 11, 12, 13, 14, 15, 16, 17, 18, 19 or 20 base pairs away from the most 5' thymine (or 5' terminal thymine) in the plurality of thymine nucleotides. In some alternatives, the polynucleotide further comprises telomeres. In some alternatives, the polynucleotide comprises a left arm wherein the left arm comprises a left telomere, a right arm wherein the right arm comprises a right telomere and a cloning region located between the left arm and the right arm. In some alternatives, the polynucleotide further comprises a third nucleic acid, wherein the third nucleic acid comprises a gene. In some alternatives, the gene encodes a protein for therapy. In some alternatives, the gene encodes a nuclease. In some alternatives, the nuclease is an endonuclease. In some alternatives, the nuclease comprises an amino acid sequence set forth in SEQ ID NO. 6 or is encoded by a nucleic acid sequence set forth in SEQ ID NO: 7-14. In some alternatives, the number of covalently linked thymines is greater than 120. In some alternatives, the number of covalently linked thymines is greater than 200. In some alternatives, the number of covalently linked thymines is greater than 300. In some alternatives, the at least one endonuclease recognition site is a Type II restriction endonuclease recognition site, and the endonuclease is a Type II restriction endonuclease. In some alternatives, the at least one endonuclease recognition site is a Type IIS restriction endonuclease recognition site, and wherein the endonuclease is a Type IIS restriction endonuclease. In some alternatives, the at least one endonuclease recognition site is a BsaI restriction endonuclease recognition site or a StuI restriction endonuclease recognition site, and wherein the endonuclease is BsaI or StuI. In some alternatives, the endonuclease recognition site is inverted. In some alternatives, the polynucleotide is a linear polynucleotide. In some alternatives, the polynucleotide has only one endonuclease recognition site. In some alternatives, the polynucleotide further comprises a polymerase promoter. In some alternatives, the plurality of thymine nucleotides comprises at least one covalently linked guanine, cytosine, or an adenine, wherein the at least one covalently linked guanine, cytosine or adenine is optionally at the most 5' thymine (or 5' terminal thymine) in the plurality of thymine nucleotides. In some alternatives, the endonuclease cleavage site comprises at least one guanine, cytosine, or an adenine, wherein the endonuclease cleaves between a thymine and the at least one guanine, cytosine or adenine. In some alternatives, the polynucleotide further comprises at least one palindromic sequence, wherein the at least one palindromic sequence can form a hairpin. In some alternatives, the polynucleotide further comprises a fourth sequence, wherein the fourth sequence is capable of forming a tertiary structure such as a hairpin. In some alternatives, the gene is codon optimized for expression in human cells. The polynucleotide can comprise a first nucleic acid sequence comprising at least one endonuclease recognition site and a second nucleic acid sequence, wherein the second nucleic acid sequence comprises the template strand, wherein the template strand comprises a plurality of thymine nucleotides, wherein said plurality of thymine nucleotides comprises at least, greater than, equal to, or any number in between 20, 30, 40, 50, 60, 70, 80, 90, 100, 110, 120, 130, 140, 150, 175, 200, 225, 250, 275, 300, 325, 350, 375, 400, 425, 450, 475, 500 or 550 covalently linked thymine nucleotides, wherein the second nucleic acid comprises the endonuclease cleavage site, and wherein the endonuclease cleavage site is within the plurality of thymine nucleotides and wherein said first nucleic acid is covalently linked to said second nucleic acid at one end of said second nucleic acid, and wherein the said endonuclease recognition site is located within 1-55 base pairs such as, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54 or 55 base pairs, of the endonuclease cleavage site for the endonuclease and said endonuclease cleavage site is within 1 to 40 base pairs, such as 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 base pairs, of a most 5' thymine (or 5' terminal thymine) in the plurality of thymine nucleotides. In some alternatives, the polynucleotide further comprises telomeres. In some alternatives, the polynucleotide comprises a left arm wherein the left arm comprises a left telomere, a right arm wherein the right arm comprises a right telomere and a cloning region located between the left arm and the right arm. In some alternatives, the polynucleotide further comprises a third nucleic acid, wherein the third nucleic acid comprises a gene. In some alternatives, the gene encodes a protein for therapy. In some alternatives, the gene encodes a nuclease. In some alternatives, the nuclease is an endonuclease. In some alternatives, the nuclease comprises an amino acid sequence set forth in SEQ ID NO. 6 or is encoded by a nucleic acid sequence set forth in SEQ ID NO: 7-14. In some alternatives, the number of covalently linked thymines is greater than 120. In some alternatives, the number of covalently linked thymines is greater than 200. In some alternatives, the number of covalently linked thymines is greater than 300. In some alternatives, the at least one endonuclease recognition site is a Type II restriction endonuclease recognition site, and the endonuclease is a Type II restriction endonuclease. In some alternatives, the at least one endonuclease recognition site is a Type IIS restriction endonuclease recognition site and wherein the endonuclease is a Type IIS restriction endonuclease. In some alternatives, the at least one endonuclease recognition site is a BsaI restriction endonuclease recognition site or a StuI restriction endonuclease recognition site, and wherein the endonuclease is BsaI or StuI. In some alternatives, the endonuclease recognition site is inverted. In some alternatives, the polynucleotide is a linear polynucleotide. In some alternatives, the polynucleotide has only one endonuclease recognition site. In some alternatives, the polynucleotide further comprises a polymerase promoter region. In some alternatives, the plurality of thymine nucleotides comprises at least one covalently linked guanine, cytosine, or an adenine, wherein the at least one covalently linked guanine, cytosine or adenine is optionally joined to the most 5' thymine (or 5' terminal thymine) in the plurality of thymine nucleotides. In some alternatives, the endonuclease cleavage site comprises at least one guanine, cytosine, or an adenine, wherein the endonuclease cleaves between a thymine and the at least one guanine, cytosine or adenine. In some alternatives, the polynucleotide further comprises at least one palindromic sequence, wherein the at least one palindromic sequence can form a hairpin. In some alternatives, the polynucleotide further comprises a third sequence, wherein the third sequence is capable of forming a tertiary structure such as a hairpin. In some alternatives, the gene is codon optimized for expression in human cells. In some alternatives, the polynucleotide further comprises a promoter for a polymerase. In some alternatives, the polymerase is a DNA polymerase. In some alternatives, the DNA polymerase is a thermal stable polymerase, such as Taq polymerase. In some alternatives, the nucleotides are adenine, cytosine, guanine, thymine and/or uracil. In some alternatives, the method further comprises providing a set of primers. In some alternatives, the nucleic acid is DNA. In some alternatives, an RNA polymerase is used. In some alternatives, contacting is performed at a temperature at least, greater than, equal to, or any temperature in between 30° C., 31° C., 32° C., 33° C., 34° C., 35° C., 36° C. or 37° C. In some alternatives, the contacting is performed for at least, greater than, equal to, or time in between 1, 5, 10, 20, 30, 40, 50, 60, 70, 80, 90 or 100 hours (e.g., at least, or equal to 1, 5, 10, 20, 30, 40, 50, 60, 70, 80, 90 or 100 hours or within a range defined by any two of the aforementioned times). In some alternatives, the nucleic acid is RNA. In some alternatives, the RNA comprises a plurality of adenine nucleotides, wherein the plurality of adenine nucleotides comprises at least, greater than, equal to, or any number in between 20, 30, 40, 50, 60, 70, 80, 90, 100, 110, 120, 130, 140, 150, 175, 200, 225, 250, 275, 300, 325, 350, 375, 400, 425, 450, 475, or 500 covalently linked adenines. In some alternatives, the number of covalently linked adenines is greater than 120. In some alternatives, the number of covalently linked adenines is greater than 200. In some alternatives, the number of covalently linked adenines is greater than 300. In some alternatives, the RNA further comprises a gene. In some alternatives, the gene encodes a protein for therapy. In some alternatives, the gene encodes a nuclease. In some alternatives, the gene encodes an endonuclease. In some alternatives, the nuclease comprises an amino acid sequence set forth in SEQ ID NO. 6 or is encoded by a nucleic acid sequence set forth in SEQ ID NO: 7-14. In some alternatives, the plurality of adenine nucleotides further comprises a guanine, cytosine or a uracil, and wherein the number of covalently linked adenines terminates with a guanine, cytosine or a uracil. In some alternatives, the nucleic acid further comprises at least one palindromic sequence, wherein the at least one palindromic sequence can form a hairpin. In some alternatives, the nucleic acid further comprises a sequence capable of forming a tertiary structure such as a hairpin. In some alternatives, the method further comprises providing an endonuclease. In some alternatives, the endonuclease is a Type II restriction endonuclease. In some alternatives, the endonuclease is a Type IIS restriction endonuclease. In some alternatives, the endonuclease is BsaI or StuI. In some alternatives, the gene is codon optimized for expression in human cells. In some alternatives, the endonuclease cleavage site is located 1, 2, 3, 4, 5, 6, 7, 7, 8, 9, 10, 11, 12, 13, 14, 15, 16, 17, 18, 19 or 20 base pairs away from the most 5' thymine (or 5' terminal thymine) in the plurality of thymine nucleotides. In some alternatives, the endonuclease cleavage site is located 1, 2, 3, 4, 5, 6, 7, 7, 8, 9 or 10 base pairs away from the most 5' thymine (or 5' terminal thymine) in the plurality of thymine nucleotides.

In some alternatives, a nucleic acid is provided. The nucleic acid can be manufactured by a method of any of the alternatives described herein. The method of making a nucleic acid can comprise providing the polynucleotide of any one of the alternatives provided herein, or the polynucleotide manufactured by any one of the alternatives provided herein and contacting said polynucleotide with a polymerase in the presence of nucleotides. Some methods can comprise providing a first nucleic acid sequence comprising at least one endonuclease recognition site, providing a second nucleic acid sequence, wherein said plurality of thymine nucleotides comprises at least, greater than, equal to, or any number in between 20, 30, 40, 50, 60, 70, 80, 90, 100, 110, 120, 130, 140, 150, 175, 200, 225, 250, 275, 300, 325, 350, 375, 400, 425, 450, 475, 500 or 550 covalently linked thymine nucleotides and wherein the second nucleic acid comprises the endonuclease cleavage site, wherein the endonuclease cleavage site is within the plurality of thymine nucleotides or within 1, 2, 3, 4, 5, 6, 7, 7, 8, 9, 10, 11, 12, 13, 14, 15, 16, 17, 18, 19 or 20 base pairs away from the most 5' thymine (or 5' terminal thymine) in the plurality of thymine nucleotides and joining said first nucleic acid sequence to said second nucleic acid sequence, wherein said first nucleic acid is covalently linked to said second nucleic acid at one end, and wherein the said endonuclease recognition site is located within 1 to 55 base pairs, such as 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54 or 55 base pairs, of the endonuclease cleavage site for the endonuclease and said endonuclease cleavage site is within 1 to 40 base pairs such as, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 base pairs, of a most 5' thymine or 5' terminal thymine in the plurality of thymine nucleotides or within 1, 2, 3, 4, 5, 6, 7, 7, 8, 9, 10, 11, 12, 13, 14, 15, 16, 17, 18, 19 or 20 base pairs away from the most 5' thymine (or 5' terminal thymine) in the plurality of thymine nucleotides. In some alternatives, the polynucleotide further comprises telomeres. In some alternatives, the polynucleotide comprises a left arm wherein the left arm comprises a left telomere, a right arm wherein the right arm comprises a right telomere and a cloning region located between the left arm and the right arm. In some alternatives, the polynucleotide further comprises a third nucleic acid, wherein the third nucleic acid comprises a gene. In some alternatives, the gene encodes a protein for therapy. In some alternatives, the gene encodes a nuclease. In some alternatives, the nuclease is an endonuclease. In some alternatives, the nuclease comprises an amino acid sequence set forth in SEQ ID NO. 6 or is encoded by a nucleic acid sequence set forth in SEQ ID NO: 7-14. In some alternatives, the number of covalently linked thymines is greater than 120. In some alternatives, the number of covalently linked thymines is greater than 200. In some alternatives, the number of covalently linked thymines is greater than 300. In some alternatives, the at least one endonuclease recognition site is a Type II restriction endonuclease recognition site, and the endonuclease is a Type II restriction endonuclease. In some alternatives, the at least one endonuclease recognition site is a Type IIS restriction endonuclease recognition site, and wherein the endonuclease is a Type IIS restriction endonuclease. In some alternatives, the at least one endonuclease recognition site is a BsaI restriction endonuclease recognition site or a StuI restriction endonuclease recognition site, and wherein the endonuclease is BsaI or StuI. In some alternatives, the endonuclease recognition site is inverted. In some alternatives, the polynucleotide is a linear polynucleotide. In some alternatives, the polynucleotide has only one endonuclease recognition site. In some alternatives, the polynucleotide further comprises a polymerase promoter. In some alternatives, the plurality of thymine nucleotides comprises at least one covalently linked guanine, cytosine, or an adenine, wherein the at least one covalently linked guanine, cytosine or adenine is optionally at the most 5' thymine (or 5' terminal thymine) in the plurality of thymine nucleotides. In some alternatives, the endonuclease cleavage site comprises at least one guanine, cytosine, or an adenine, wherein the endonuclease cleaves between a thymine and the at least one guanine, cytosine or adenine. In some alternatives, the polynucleotide further comprises at least one palindromic sequence, wherein the at least one palindromic sequence can form a hairpin. In some alternatives, the polynucleotide further comprises a fourth sequence, wherein the fourth sequence is capable of forming a tertiary structure such as a hairpin. In some alternatives, the gene is codon optimized for expression in human cells. Some polynucleotides can comprise a first nucleic acid sequence comprising at least one restriction endonuclease recognition site and a second nucleic acid sequence, wherein the second nucleic acid sequence comprises the template strand, wherein the template strand comprises a plurality of thymine nucleotides, wherein said plurality of thymine nucleotides comprises at least, greater than, equal to, or any number in between 20, 30, 40, 50, 60, 70, 80, 90, 100, 110, 120, 130, 140, 150, 175, 200, 225, 250, 275, 300, 325, 350, 375, 400, 425, 450, 475, 500 or 550 covalently linked thymine nucleotides, wherein the second nucleic acid comprises the restriction endonuclease cleavage site, and wherein the restriction endonuclease cleavage site is within the plurality of thymine nucleotides or within 1, 2, 3, 4, 5, 6, 7, 7, 8, 9, 10, 11, 12, 13, 14, 15, 16, 17, 18, 19 or 20 base pairs away from the most 5' thymine (or 5' terminal thymine) in the plurality of thymine nucleotides and wherein said first nucleic acid is covalently linked to said second nucleic acid at one end of said second nucleic acid, and wherein the said restriction endonuclease recognition site is located within 1-55 base pairs such as, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54 or 55 base pairs, of the restriction endonuclease cleavage site for the restriction endonuclease and said restriction endonuclease cleavage site is within 1 to 40 base pairs, such as 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 base pairs, of a most 5' thymine (or 5' terminal thymine) in the plurality of thymine nucleotides. In some alternatives, the polynucleotide further comprises telomeres. In some alternatives, the polynucleotide comprises a left arm wherein the left arm comprises a left telomere, a right arm wherein the right arm comprises a right telomere and a cloning region located between the left arm and the right arm. In some alternatives, the polynucleotide further comprises a third nucleic acid, wherein the third nucleic acid comprises a gene. In some alternatives, the gene encodes a protein for therapy. In some alternatives, the gene encodes a nuclease. In some alternatives, the nuclease is an endonuclease. In some alternatives, the nuclease comprises an amino acid sequence set forth in SEQ ID NO. 6 or is encoded by a nucleic acid sequence set forth in SEQ ID NO: 7-14. In some alternatives, the number of covalently linked thymines is greater than 120. In some alternatives, the number of covalently linked thymines is greater than 200. In some alternatives, the number of covalently linked thymines is greater than 300. In some alternatives, the at least one endonuclease recognition site is a Type II restriction endonuclease recognition site, and the endonuclease is a Type II restriction endonuclease. In some alternatives, the at least one endonuclease recognition site is a Type IIS restriction endonuclease recognition site and wherein the endonuclease is a Type IIS restriction endonuclease. In some alternatives, the at least one endonuclease recognition site is a BsaI restriction endonuclease recognition site or a StuI restriction endonuclease recognition site, and wherein the endonuclease is BsaI or StuI. In some alternatives, the endonuclease recognition site is inverted. In some alternatives, the polynucleotide is a linear polynucleotide. In some alternatives, the polynucleotide has only one endonuclease recognition site. In some alternatives, the polynucleotide further comprises a polymerase promoter region. In some alternatives, the plurality of thymine nucleotides comprises at least one covalently linked guanine, cytosine, or an adenine, wherein the at least one covalently linked guanine, cytosine or adenine is optionally joined to the most 5' thymine (or 5' terminal thymine) in the plurality of thymine nucleotides. In some alternatives, the endonuclease cleavage site comprises at least one guanine, cytosine, or an adenine, wherein the endonuclease cleaves between a thymine and the at least one guanine, cytosine or adenine. In some alternatives, the polynucleotide further comprises at least one palindromic sequence, wherein the at least one palindromic sequence can form a hairpin. In some alternatives, the polynucleotide further comprises a third sequence, wherein the third sequence is capable of forming a tertiary structure such as a hairpin. In some alternatives, the gene is codon optimized for expression in human cells. In some alternatives, the polynucleotide further comprises a promoter for a polymerase. In some alternatives, the polymerase is a DNA polymerase. In some alternatives, the DNA polymerase is a thermal stable polymerase, such as Taq polymerase. In some alternatives, the nucleotides are adenine, cytosine, guanine, thymine and/or uracil. In some alternatives, the method further comprises providing a set of primers. In some alternatives, the nucleic acid is DNA. In some alternatives, an RNA polymerase is used. In some alternatives, contacting is performed at a temperature at least, greater than, equal to, or any temperature in between 30° C., 31° C., 32° C., 33° C., 34° C., 35° C., 36° C. or 37° C. In some alternatives, the contacting is performed for at least, greater than, equal to, or time in between 1, 5, 10, 20, 30, 40, 50, 60, 70, 80, 90 or 100 hours (e.g., at least, or equal to 1, 5, 10, 20, 30, 40, 50, 60, 70, 80, 90 or 100 hours or within a range defined by any two of the aforementioned times). In some alternatives, the nucleic acid is RNA. In some alternatives, the RNA comprises a plurality of adenine nucleotides, wherein the plurality of adenine nucleotides comprises at least, greater than, equal to, or any number in between 20, 30, 40, 50, 60, 70, 80, 90, 100, 110, 120, 130, 140, 150, 175, 200, 225, 250, 275, 300, 325, 350, 375, 400, 425, 450, 475, or 500 covalently linked adenines. In some alternatives, the number of covalently linked adenines is greater than 120. In some alternatives, the number of covalently linked adenines is greater than 200. In some alternatives, the number of covalently linked adenines is greater than 300. In some alternatives, the RNA further comprises a gene. In some alternatives, the gene encodes a protein for therapy. In some alternatives, the gene encodes a nuclease. In some alternatives, the gene encodes an endonuclease. In some alternatives, the nuclease comprises an amino acid sequence set forth in SEQ ID NO. 6 or is encoded by a nucleic acid sequence set forth in SEQ ID NO: 7-14. In some alternatives, the plurality of adenine nucleotides further comprises a guanine, cytosine or a uracil, and wherein the number of covalently linked adenines terminates with a guanine, cytosine or a uracil. In some alternatives, the nucleic acid further comprises at least one palindromic sequence, wherein the at least one palindromic sequence can form a hairpin. In some alternatives, the nucleic acid further comprises a sequence capable of forming a tertiary structure such as a hairpin. In some alternatives, the method further comprises providing an endonuclease. In some alternatives, the endonuclease is a Type II restriction endonuclease. In some alternatives, the endonuclease is a Type IIS restriction endonuclease. In some alternatives, the endonuclease is BsaI or StuI. In some alternatives, the gene is codon optimized for expression in human cells. In some alternatives, the nucleic acid is a DNA. In some alternatives, the nucleic acid is a RNA. In some alternatives, the RNA comprises a plurality of adenine nucleotides, wherein the plurality of adenine nucleotides comprises at least, greater than, equal to, or any number in between 20, 30, 40, 50, 60, 70, 80, 90, 100, 110, 120, 130, 140, 150, 175, 200, 225, 250, 275, 300, 325, 350, 375, 400, 425, 450, 475, or 500 covalently linked adenines. In some alternatives, the number of covalently linked adenines is greater than 120. In some alternatives, the number of covalently linked adenines is greater than 200. In some alternatives, the number of covalently linked adenines is greater than 300. In some alternatives, the nucleic acid further comprises a gene. In some alternatives, the gene encodes a protein for therapy. In some alternatives, the gene encodes a nuclease. In some alternatives, the gene encodes an endonuclease. In some alternatives, the nuclease comprises an amino acid sequence set forth in SEQ ID NO. 6 or is encoded by a nucleic acid sequence set forth in SEQ ID NO: 7-14. In some alternatives, the covalently linked adenines terminates with a guanine, cytosine, thymine, or a uracil. In some alternatives, the nucleic acid further comprises at least one palindromic sequence, wherein the at least one palindromic sequence can form a hairpin. In some alternatives, the nucleic acid further comprises a sequence capable of forming a tertiary structure such as a hairpin. In some alternatives, the gene is codon optimized for expression in human cells. In some alternatives, the endonuclease cleavage site is located 1, 2, 3, 4, 5, 6, 7, 7, 8, 9, 10, 11, 12, 13, 14, 15, 16, 17, 18, 19 or 20 base pairs away from the most 5' thymine (or 5' terminal thymine) in the plurality of thymine nucleotides. In some alternatives, the endonuclease cleavage site is located 1, 2, 3, 4, 5, 6, 7, 7, 8, 9 or 10 base pairs away from the most 5' thymine (or 5' terminal thymine) in the plurality of thymine nucleotides.

In some alternatives, a method of enhancing transcription of a gene is provided. The method can comprise providing the polynucleotide of any one of the alternatives provided herein, or the polynucleotide manufactured by any one of any one of the alternatives provided herein and contacting said polynucleotide with a RNA polymerase in the presence of nucleotides. Some polynucleotides comprise a first nucleic acid sequence comprising at least one restriction endonuclease recognition site and a second nucleic acid sequence, wherein the second nucleic acid sequence comprises the template strand, wherein the template strand comprises a plurality of thymine nucleotides, wherein said plurality of thymine nucleotides comprises at least, greater than, equal to, or any number in between 20, 30, 40, 50, 60, 70, 80, 90, 100, 110, 120, 130, 140, 150, 175, 200, 225, 250, 275, 300, 325, 350, 375, 400, 425, 450, 475, 500 or 550 covalently linked thymine nucleotides, wherein the second nucleic acid comprises the restriction endonuclease cleavage site, and wherein the restriction endonuclease cleavage site is within the plurality of thymine nucleotides or within 1, 2, 3, 4, 5, 6, 7, 7, 8, 9, 10, 11, 12, 13, 14, 15, 16, 17, 18, 19 or 20 base pairs away from the most 5' thymine (or 5' terminal thymine) in the plurality of thymine nucleotides and wherein said first nucleic acid is covalently linked to said second nucleic acid at one end of said second nucleic acid, and wherein the said restriction endonuclease recognition site is located within 1-55 base pairs such as, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54 or 55 base pairs, of the restriction endonuclease cleavage site for the restriction endonuclease and said restriction endonuclease cleavage site is within 1 to 40 base pairs, such as 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 base pairs, of a most 5' thymine (or 5' terminal thymine) in the plurality of thymine nucleotides. In some alternatives, the polynucleotide further comprises telomeres. In some alternatives, the polynucleotide comprises a left arm wherein the left arm comprises a left telomere, a right arm wherein the right arm comprises a right telomere and a cloning region located between the left arm and the right arm. In some alternatives, the polynucleotide further comprises a third nucleic acid, wherein the third nucleic acid comprises a gene. In some alternatives, the gene encodes a protein for therapy. In some alternatives, the gene encodes a nuclease. In some alternatives, the nuclease is an endonuclease. In some alternatives, the nuclease comprises an amino acid sequence set forth in SEQ ID NO. 6 or is encoded by a nucleic acid sequence set forth in SEQ ID NO: 7-14. In some alternatives, the number of covalently linked thymines is greater than 120. In some alternatives, the number of covalently linked thymines is greater than 200. In some alternatives, the number of covalently linked thymines is greater than 300. In some alternatives, the at least one endonuclease recognition site is a Type II restriction endonuclease recognition site, and the endonuclease is a Type II restriction endonuclease. In some alternatives, the at least one endonuclease recognition site is a Type IIS restriction endonuclease recognition site and wherein the endonuclease is a Type IIS restriction endonuclease. In some alternatives, the at least one endonuclease recognition site is a BsaI restriction endonuclease recognition site or a StuI restriction endonuclease recognition site, and wherein the endonuclease is BsaI or StuI. In some alternatives, the endonuclease recognition site is inverted. In some alternatives, the polynucleotide is a linear polynucleotide. In some alternatives, the polynucleotide has only one endonuclease recognition site. In some alternatives, the polynucleotide further comprises a polymerase promoter region. In some alternatives, the plurality of thymine nucleotides comprises at least one covalently linked guanine, cytosine, or an adenine, wherein the at least one covalently linked guanine, cytosine or adenine is optionally joined to the most 5' thymine (or 5' terminal thymine) in the plurality of thymine nucleotides. In some alternatives, the endonuclease cleavage site comprises at least one guanine, cytosine, or an adenine, wherein the endonuclease cleaves between a thymine and the at least one guanine, cytosine or adenine. In some alternatives, the polynucleotide further comprises at least one palindromic sequence, wherein the at least one palindromic sequence can form a hairpin. In some alternatives, the polynucleotide further comprises a third sequence, wherein the third sequence is capable of forming a tertiary structure such as a hairpin. In some alternatives, the gene is codon optimized for expression in human cells. Some methods can comprise providing a first nucleic acid sequence comprising at least one endonuclease recognition site, providing a second nucleic acid sequence, wherein said plurality of thymine nucleotides comprises at least, greater than, equal to, or any number in between 20, 30, 40, 50, 60, 70, 80, 90, 100, 110, 120, 130, 140, 150, 175, 200, 225, 250, 275, 300, 325, 350, 375, 400, 425, 450, 475, 500 or 550 covalently linked thymine nucleotides and wherein the second nucleic acid comprises the endonuclease cleavage site, wherein the endonuclease cleavage site is within the plurality of thymine nucleotides or within 1, 2, 3, 4, 5, 6, 7, 7, 8, 9, 10, 11, 12, 13, 14, 15, 16, 17, 18, 19 or 20 base pairs away from the most 5' thymine (or 5' terminal thymine) in the plurality of thymine nucleotides and joining said first nucleic acid sequence to said second nucleic acid sequence, wherein said first nucleic acid is covalently linked to said second nucleic acid at one end, and wherein the said endonuclease recognition site is located within 1 to 55 base pairs, such as 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54 or 55 base pairs, of the endonuclease cleavage site for the endonuclease and said endonuclease cleavage site is within 1 to 40 base pairs such as, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 base pairs, of a most 5' thymine or 5' terminal thymine in the plurality of thymine nucleotides or within 1, 2, 3, 4, 5, 6, 7, 7, 8, 9, 10, 11, 12, 13, 14, 15, 16, 17, 18, 19 or 20 base pairs away from the most 5' thymine (or 5' terminal thymine) in the plurality of thymine nucleotides. In some alternatives, the polynucleotide further comprises telomeres. In some alternatives, the polynucleotide comprises a left arm wherein the left arm comprises a left telomere, a right arm wherein the right arm comprises a right telomere and a cloning region located between the left arm and the right arm. In some alternatives, the polynucleotide further comprises a third nucleic acid, wherein the third nucleic acid comprises a gene. In some alternatives, the gene encodes a protein for therapy. In some alternatives, the gene encodes a nuclease. In some alternatives, the nuclease is an endonuclease. In some alternatives, the nuclease comprises an amino acid sequence set forth in SEQ ID NO. 6 or is encoded by a nucleic acid sequence set forth in SEQ ID NO: 7-14. In some alternatives, the number of covalently linked thymines is greater than 120. In some alternatives, the number of covalently linked thymines is greater than 200. In some alternatives, the number of covalently linked thymines is greater than 300. In some alternatives, the at least one endonuclease recognition site is a Type II restriction endonuclease recognition site, and the endonuclease is a Type II restriction endonuclease. In some alternatives, the at least one endonuclease recognition site is a Type IIS restriction endonuclease recognition site, and wherein the endonuclease is a Type IIS restriction endonuclease. In some alternatives, the at least one endonuclease recognition site is a BsaI restriction endonuclease recognition site or a StuI restriction endonuclease recognition site, and wherein the endonuclease is BsaI or StuI. In some alternatives, the endonuclease recognition site is inverted. In some alternatives, the polynucleotide is a linear polynucleotide. In some alternatives, the polynucleotide has only one endonuclease recognition site. In some alternatives, the polynucleotide further comprises a polymerase promoter. In some alternatives, the plurality of thymine nucleotides comprises at least one covalently linked guanine, cytosine, or an adenine, wherein the at least one covalently linked guanine, cytosine or adenine is optionally at the most 5' thymine (or 5' terminal thymine) in the plurality of thymine nucleotides. In some alternatives, the endonuclease cleavage site comprises at least one guanine, cytosine, or an adenine, wherein the endonuclease cleaves between a thymine and the at least one guanine, cytosine or adenine. In some alternatives, the polynucleotide further comprises at least one palindromic sequence, wherein the at least one palindromic sequence can form a hairpin. In some alternatives, the polynucleotide further comprises a fourth sequence, wherein the fourth sequence is capable of forming a tertiary structure such as a hairpin. In some alternatives, the gene is codon optimized for expression in human cells. In some alternatives, the method further comprises providing an endonuclease. In some alternatives, the endonuclease is a Type II restriction endonuclease or a Type IIS restriction endonuclease. In some alternatives, the endonuclease is BsaI or StuI. In some alternatives, the polynucleotide further comprises an RNA polymerase promoter. In some alternatives, the contacting is performed at a temperature at least, greater than, equal to, or any temperature in between 30° C., 31° C., 32° C., 33° C., 34° C., 35° C., 36° C. or 37° C. In some alternatives, the method is performed for at least, greater than, equal to, or time in between 1, 5, 10, 20, 30, 40, 50, 60, 70, 80, 90 or 100 hours (e.g., at least, or equal to 1, 5, 10, 20, 30, 40, 50, 60, 70, 80, 90 or 100 hours or within a range defined by any two of the aforementioned times). In some alternatives, the gene is codon optimized for expression in human cells. In some alternatives, the endonuclease cleavage site is located 1, 2, 3, 4, 5, 6, 7, 7, 8, 9, 10, 11, 12, 13, 14, 15, 16, 17, 18, 19 or 20 base pairs away from the most 5' thymine (or 5' terminal thymine) in the plurality of thymine nucleotides. In some alternatives, the endonuclease cleavage site is located 1, 2, 3, 4, 5, 6, 7, 7, 8, 9 or 10 base pairs away from the most 5' thymine (or 5' terminal thymine) in the plurality of thymine nucleotides.

In some alternatives, a method of stabilizing an RNA during in vitro translation at 30-37 degrees Celsius for at least 100 hours (e.g., at least, or equal to 1, 5, 10, 20, 30, 40, 50, 60, 70, 80, 90 or 100 hours or within a range defined by any two of the aforementioned times) is provided. The method can comprise providing the nucleic acid of any one of the alternatives herein or a nucleic acid manufactured by a method of any one of the alternatives herein and contacting said nucleic acid with a ribosome, in the presence of amino acids and tRNAs, wherein said RNA is stable at 30-37 degrees Celsius for at least 100 hours (e.g., at least, or equal to 1, 5, 10, 20, 30, 40, 50, 60, 70, 80, 90 or 100 hours or within a range defined by any two of the aforementioned times). The method can of making the nucleic acid can comprise providing the polynucleotide of any one of the alternatives provided herein, or the polynucleotide manufactured by any one of the alternatives provided herein and contacting said polynucleotide with a polymerase in the presence of nucleotides. Some methods can comprise providing a first nucleic acid sequence comprising at least one endonuclease recognition site, providing a second nucleic acid sequence, wherein said plurality of thymine nucleotides comprises at least, greater than, equal to, or any number in between 20, 30, 40, 50, 60, 70, 80, 90, 100, 110, 120, 130, 140, 150, 175, 200, 225, 250, 275, 300, 325, 350, 375, 400, 425, 450, 475, 500 or 550 covalently linked thymine nucleotides and wherein the second nucleic acid comprises the endonuclease cleavage site, wherein the endonuclease cleavage site is within the plurality of thymine nucleotides or within 1, 2, 3, 4, 5, 6, 7, 7, 8, 9, 10, 11, 12, 13, 14, 15, 16, 17, 18, 19 or 20 base pairs away from the most 5' thymine (or 5' terminal thymine) in the plurality of thymine nucleotides and joining said first nucleic acid sequence to said second nucleic acid sequence, wherein said first nucleic acid is covalently linked to said second nucleic acid at one end, and wherein the said endonuclease recognition site is located within 1 to 55 base pairs, such as 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54 or 55 base pairs, of the endonuclease cleavage site for the endonuclease and said endonuclease cleavage site is within 1 to 40 base pairs such as, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 base pairs, of a most 5' thymine or 5' terminal thymine in the plurality of thymine nucleotides or within 1, 2, 3, 4, 5, 6, 7, 7, 8, 9, 10, 11, 12, 13, 14, 15, 16, 17, 18, 19 or 20 base pairs away from the most 5' thymine (or 5' terminal thymine) in the plurality of thymine nucleotides. In some alternatives, the polynucleotide further comprises telomeres. In some alternatives, the polynucleotide comprises a left arm wherein the left arm comprises a left telomere, a right arm wherein the right arm comprises a right telomere and a cloning region located between the left arm and the right arm. In some alternatives, the polynucleotide further comprises a third nucleic acid, wherein the third nucleic acid comprises a gene. In some alternatives, the gene encodes a protein for therapy. In some alternatives, the gene encodes a nuclease. In some alternatives, the nuclease is an endonuclease. In some alternatives, the nuclease comprises an amino acid sequence set forth in SEQ ID NO. 6 or is encoded by a nucleic acid sequence set forth in SEQ ID NO: 7-14. In some alternatives, the number of covalently linked thymines is greater than 120. In some alternatives, the number of covalently linked thymines is greater than 200. In some alternatives, the number of covalently linked thymines is greater than 300. In some alternatives, the at least one endonuclease recognition site is a Type II restriction endonuclease recognition site, and the endonuclease is a Type II restriction endonuclease. In some alternatives, the at least one endonuclease recognition site is a Type IIS restriction endonuclease recognition site, and wherein the endonuclease is a Type IIS restriction endonuclease. In some alternatives, the at least one endonuclease recognition site is a BsaI restriction endonuclease recognition site or a StuI restriction endonuclease recognition site, and wherein the endonuclease is BsaI or StuI. In some alternatives, the endonuclease recognition site is inverted. In some alternatives, the polynucleotide is a linear polynucleotide. In some alternatives, the polynucleotide has only one endonuclease recognition site. In some alternatives, the polynucleotide further comprises a polymerase promoter. In some alternatives, the plurality of thymine nucleotides comprises at least one covalently linked guanine, cytosine, or an adenine, wherein the at least one covalently linked guanine, cytosine or adenine is optionally at the most 5' thymine (or 5' terminal thymine) in the plurality of thymine nucleotides. In some alternatives, the endonuclease cleavage site comprises at least one guanine, cytosine, or an adenine, wherein the endonuclease cleaves between a thymine and the at least one guanine, cytosine or adenine. In some alternatives, the polynucleotide further comprises at least one palindromic sequence, wherein the at least one palindromic sequence can form a hairpin. In some alternatives, the polynucleotide further comprises a fourth sequence, wherein the fourth sequence is capable of forming a tertiary structure such as a hairpin. In some alternatives, the gene is codon optimized for expression in human cells. Some polynucleotides a first nucleic acid sequence comprising at least one restriction endonuclease recognition site and a second nucleic acid sequence, wherein the second nucleic acid sequence comprises the template strand, wherein the template strand comprises a plurality of thymine nucleotides, wherein said plurality of thymine nucleotides comprises at least, greater than, equal to, or any number in between 20, 30, 40, 50, 60, 70, 80, 90, 100, 110, 120, 130, 140, 150, 175, 200, 225, 250, 275, 300, 325, 350, 375, 400, 425, 450, 475, 500 or 550 covalently linked thymine nucleotides, wherein the second nucleic acid comprises the restriction endonuclease cleavage site, and wherein the restriction endonuclease cleavage site is within the plurality of thymine nucleotides or within 1, 2, 3, 4, 5, 6, 7, 7, 8, 9, 10, 11, 12, 13, 14, 15, 16, 17, 18, 19 or 20 base pairs away from the most 5' thymine (or 5' terminal thymine) in the plurality of thymine nucleotides and wherein said first nucleic acid is covalently linked to said second nucleic acid at one end of said second nucleic acid, and wherein the said restriction endonuclease recognition site is located within 1-55 base pairs such as, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54 or 55 base pairs, of the restriction endonuclease cleavage site for the restriction endonuclease and said restriction endonuclease cleavage site is within 1 to 40 base pairs, such as 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 base pairs, of a most 5' thymine (or 5' terminal thymine) in the plurality of thymine nucleotides. In some alternatives, the polynucleotide further comprises telomeres. In some alternatives, the polynucleotide comprises a left arm wherein the left arm comprises a left telomere, a right arm wherein the right arm comprises a right telomere and a cloning region located between the left arm and the right arm. In some alternatives, the polynucleotide further comprises a third nucleic acid, wherein the third nucleic acid comprises a gene. In some alternatives, the gene encodes a protein for therapy. In some alternatives, the gene encodes a nuclease. In some alternatives, the nuclease is an endonuclease. In some alternatives, the nuclease comprises an amino acid sequence set forth in SEQ ID NO. 6 or is encoded by a nucleic acid sequence set forth in SEQ ID NO: 7-14. In some alternatives, the number of covalently linked thymines is greater than 120. In some alternatives, the number of covalently linked thymines is greater than 200. In some alternatives, the number of covalently linked thymines is greater than 300. In some alternatives, the at least one endonuclease recognition site is a Type II endonuclease recognition site, and the endonuclease is a Type II restriction endonuclease. In some alternatives, the at least one endonuclease recognition site is a Type IIS restriction endonuclease recognition site and wherein the endonuclease is a Type IIS restriction endonuclease. In some alternatives, the at least one endonuclease recognition site is a BsaI restriction endonuclease recognition site or a StuI restriction endonuclease recognition site, and wherein the endonuclease is BsaI or StuI. In some alternatives, the endonuclease recognition site is inverted. In some alternatives, the polynucleotide is a linear polynucleotide. In some alternatives, the polynucleotide has only one endonuclease recognition site. In some alternatives, the polynucleotide further comprises a polymerase promoter region. In some alternatives, the plurality of thymine nucleotides comprises at least one covalently linked guanine, cytosine, or an adenine, wherein the at least one covalently linked guanine, cytosine or adenine is optionally at the most 5' thymine (or 5' terminal thymine) in the plurality of thymine nucleotides. In some alternatives, the endonuclease cleavage site comprises at least one guanine, cytosine, or an adenine, wherein the endonuclease cleaves between a thymine and the at least one guanine, cytosine or adenine. In some alternatives, the polynucleotide further comprises at least one palindromic sequence, wherein the at least one palindromic sequence can form a hairpin. In some alternatives, the polynucleotide further comprises a third sequence, wherein the third sequence is capable of forming a tertiary structure such as a hairpin. In some alternatives, the gene is codon optimized for expression in human cells. In some alternatives, the polynucleotide further comprises a promoter for a polymerase. In some alternatives, the polymerase is a DNA polymerase. In some alternatives, the DNA polymerase is a thermal stable polymerase, such as Taq polymerase. In some alternatives, the nucleotides are adenine, cytosine, guanine, thymine and/or uracil. In some alternatives, the method further comprises providing a set of primers. In some alternatives, the nucleic acid is DNA. In some alternatives, an RNA polymerase is used. In some alternatives, contacting is performed at a temperature at least, greater than, equal to, or any temperature in between 30° C., 31° C., 32° C., 33° C., 34° C., 35° C., 36° C. or 37° C. In some alternatives, the contacting is performed for at least, greater than, equal to, or time in between 1, 5, 10, 20, 30, 40, 50, 60, 70, 80, 90 or 100 hours (e.g., at least, or equal to 1, 5, 10, 20, 30, 40, 50, 60, 70, 80, 90 or 100 hours or within a range defined by any two of the aforementioned times). In some alternatives, the nucleic acid is RNA. In some alternatives, the RNA comprises a plurality of adenine nucleotides, wherein the plurality of adenine nucleotides comprises at least, greater than, equal to, or any number in between 20, 30, 40, 50, 60, 70, 80, 90, 100, 110, 120, 130, 140, 150, 175, 200, 225, 250, 275, 300, 325, 350, 375, 400, 425, 450, 475, or 500 covalently linked adenines. In some alternatives, the number of covalently linked adenines is greater than 120. In some alternatives, the number of covalently linked adenines is greater than 200. In some alternatives, the number of covalently linked adenines is greater than 300. In some alternatives, the RNA further comprises a gene. In some alternatives, the gene encodes a protein for therapy. In some alternatives, the gene encodes a nuclease. In some alternatives, the gene encodes an endonuclease. In some alternatives, the nuclease comprises an amino acid sequence set forth in SEQ ID NO. 6 or is encoded by a nucleic acid sequence set forth in SEQ ID NO: 7-14. In some alternatives, the plurality of adenine nucleotides further comprises a guanine, cytosine or a uracil, and wherein the number of covalently linked adenines terminates with a guanine, cytosine or a uracil. In some alternatives, the nucleic acid further comprises at least one palindromic sequence, wherein the at least one palindromic sequence can form a hairpin. In some alternatives, the nucleic acid further comprises a sequence capable of forming a tertiary structure such as a hairpin. In some alternatives, the method further comprises providing an endonuclease. In some alternatives, the endonuclease is a Type II restriction endonuclease. In some alternatives, the endonuclease is a Type IIS restriction endonuclease. In some alternatives, the endonuclease is BsaI or StuI. In some alternatives, the gene is codon optimized for expression in human cells. In some alternatives, the nucleic acid is DNA. In some alternatives, an RNA polymerase is used. In some alternatives, contacting is performed at a temperature at least, greater than, equal to, or any temperature in between 30° C., 31° C., 32° C., 33° C., 34° C., 35° C., 36° C. or 37° C. In some alternatives, the contacting is performed for at least, greater than, equal to, or time in between 1, 5, 10, 20, 30, 40, 50, 60, 70, 80, 90 or 100 hours (e.g., at least, or equal to 1, 5, 10, 20, 30, 40, 50, 60, 70, 80, 90 or 100 hours or within a range defined by any two of the aforementioned times). In some alternatives, the nucleic acid is RNA. In some alternatives, the RNA comprises a plurality of adenine nucleotides, wherein the plurality of adenine nucleotides comprises at least, greater than, equal to, or any number in between 20, 30, 40, 50, 60, 70, 80, 90, 100, 110, 120, 130, 140, 150, 175, 200, 225, 250, 275, 300, 325, 350, 375, 400, 425, 450, 475, or 500 covalently linked adenines. In some alternatives, the number of covalently linked adenines is greater than 120. In some alternatives, the number of covalently linked adenines is greater than 200. In some alternatives, the number of covalently linked adenines is greater than 300. In some alternatives, the nucleic acid further comprises a gene. In some alternatives, the gene encodes a protein for therapy. In some alternatives, the gene encodes a nuclease. In some alternatives, the gene encodes an endonuclease. In some alternatives, the nuclease comprises an amino acid sequence set forth in SEQ ID NO. 6 or is encoded by a nucleic acid sequence set forth in SEQ ID NO: 7-14. In some alternatives, the covalently linked adenines terminate with a guanine, cytosine, thymine, or a uracil. In some alternatives, the nucleic acid further comprises at least one palindromic sequence, wherein the at least one palindromic sequence can form a hairpin. In some alternatives, the nucleic acid further comprises a sequence capable of forming a tertiary structure such as a hairpin. In some alternatives, the gene is codon optimized for expression in human cells. In some alternatives, the nucleic acid is a RNA. In some alternatives, the contacting is performed at a temperature equal to 37° C. In some alternatives, the contacting is performed for at least, greater than, equal to, or time in between 1, 5, 10, 20, 30, 40, 50, 60, 70, 80, 90 or 100 hours (e.g., at least, or equal to 1, 5, 10, 20, 30, 40, 50, 60, 70, 80, 90 or 100 hours or within a range defined by any two of the aforementioned times). In some alternatives, the RNA comprises a plurality of adenine nucleotides, wherein the plurality of adenine nucleotides comprises at least, greater than, equal to, or any number in between 20, 30, 40, 50, 60, 70, 80, 90, 100, 110, 120, 130, 140, 150, 175, 200, 225, 250, 275, 300, 325, 350, 375, 400, 425, 450, 475, or 500 covalently linked adenines. In some alternatives, the number of covalently linked adenines is greater than 120. In some alternatives, the number of covalently linked adenines is greater than 200. In some alternatives, the number of covalently linked adenines is greater than 300. In some alternatives, the RNA further comprises a gene. In some alternatives, the gene encodes a protein for therapy. In some alternatives, the gene encodes an endonuclease. In some alternatives, the gene encodes a nuclease. In some alternatives, the nuclease comprises an amino acid sequence set forth in SEQ ID NO. 6 or is encoded by a nucleic acid sequence set forth in SEQ ID NO: 7-14. In some alternatives, the covalently linked adenines terminate with a guanine, cytosine, thymine, or a uracil. In some alternatives, the nucleic acid further comprises at least one palindromic sequence, wherein the at least one palindromic sequence can form a hairpin. In some alternatives, the gene is codon optimized for expression in human cells. In some alternatives, the endonuclease cleavage site is located 1, 2, 3, 4, 5, 6, 7, 7, 8, 9, 10, 11, 12, 13, 14, 15, 16, 17, 18, 19 or 20 base pairs away from the most 5' thymine (or 5' terminal thymine) in the plurality of thymine nucleotides. In some alternatives, the endonuclease cleavage site is located 1, 2, 3, 4, 5, 6, 7, 7, 8, 9 or 10 base pairs away from the most 5' thymine (or 5' terminal thymine) in the plurality of thymine nucleotides.

In some alternatives, a method of stabilizing RNA during in vivo translation at 30-37 degrees Celsius for at least 100 hours (e.g., at least, or equal to 1, 5, 10, 20, 30, 40, 50, 60, 70, 80, 90 or 100 hours or within a range defined by any two of the aforementioned times) in a cell, is provided. The method can comprise transfecting into a cell the nucleic acid of any one of the alternatives herein or a nucleic acid manufactured by a method of any one of the alternatives herein, placing the cell into a culture vessel with media, supplying the cell with nutrients and amino acids for translation and incubating the cell for at at least, greater than, equal to, or time in between 1, 5, 10, 20, 30, 40, 50, 60, 70, 80, 90 or 100 hours (e.g., at least, or equal to 1, 5, 10, 20, 30, 40, 50, 60, 70, 80, 90 or 100 hours or within a range defined by any two of the aforementioned times) so as to allow for translation. In some alternatives, the method of making the nucleic acid or RNA comprise providing the polynucleotide of any one of the alternatives provided herein, or the polynucleotide manufactured by any one of the alternatives provided herein and contacting said polynucleotide with a polymerase in the presence of nucleotides. Some methods can comprise providing a first nucleic acid sequence comprising at least one endonuclease recognition site, providing a second nucleic acid sequence, wherein said plurality of thymine nucleotides comprises at least, greater than, equal to, or any number in between 20, 30, 40, 50, 60, 70, 80, 90, 100, 110, 120, 130, 140, 150, 175, 200, 225, 250, 275, 300, 325, 350, 375, 400, 425, 450, 475, 500 or 550 covalently linked thymine nucleotides and wherein the second nucleic acid comprises the endonuclease cleavage site, wherein the endonuclease cleavage site is within the plurality of thymine nucleotides or within 1, 2, 3, 4, 5, 6, 7, 7, 8, 9, 10, 11, 12, 13, 14, 15, 16, 17, 18, 19 or 20 base pairs away from the most 5' thymine (or 5' terminal thymine) in the plurality of thymine nucleotides and joining said first nucleic acid sequence to said second nucleic acid sequence, wherein said first nucleic acid is covalently linked to said second nucleic acid at one end, and wherein the said endonuclease recognition site is located within 1 to 55 base pairs, such as 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54 or 55 base pairs, of the endonuclease cleavage site for the endonuclease and said endonuclease cleavage site is within 1 to 40 base pairs such as, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 base pairs, of a most 5' thymine or 5' terminal thymine in the plurality of thymine nucleotides or within 1, 2, 3, 4, 5, 6, 7, 7, 8, 9, 10, 11, 12, 13, 14, 15, 16, 17, 18, 19 or 20 base pairs away from the most 5' thymine (or 5' terminal thymine) in the plurality of thymine nucleotides. In some alternatives, the polynucleotide further comprises telomeres. In some alternatives, the polynucleotide comprises a left arm wherein the left arm comprises a left telomere, a right arm wherein the right arm comprises a right telomere and a cloning region located between the left arm and the right arm. In some alternatives, the polynucleotide further comprises a third nucleic acid, wherein the third nucleic acid comprises a gene. In some alternatives, the gene encodes a protein for therapy. In some alternatives, the gene encodes a nuclease. In some alternatives, the nuclease is an endonuclease. In some alternatives, the nuclease comprises an amino acid sequence set forth in SEQ ID NO. 6 or is encoded by a nucleic acid sequence set forth in SEQ ID NO: 7-14. In some alternatives, the number of covalently linked thymines is greater than 120. In some alternatives, the number of covalently linked thymines is greater than 200. In some alternatives, the number of covalently linked thymines is greater than 300. In some alternatives, the at least one endonuclease recognition site is a Type II restriction endonuclease recognition site, and the endonuclease is a Type II restriction endonuclease. In some alternatives, the at least one endonuclease recognition site is a Type IIS restriction endonuclease recognition site, and wherein the endonuclease is a Type IIS restriction endonuclease. In some alternatives, the at least one endonuclease recognition site is a BsaI restriction endonuclease recognition site or a StuI restriction endonuclease recognition site, and wherein the endonuclease is BsaI or StuI. In some alternatives, the endonuclease recognition site is inverted. In some alternatives, the polynucleotide is a linear polynucleotide. In some alternatives, the polynucleotide has only one endonuclease recognition site. In some alternatives, the polynucleotide further comprises a polymerase promoter. In some alternatives, the plurality of thymine nucleotides comprises at least one covalently linked guanine, cytosine, or an adenine, wherein the at least one covalently linked guanine, cytosine or adenine is optionally at the most 5' thymine (or 5' terminal thymine) in the plurality of thymine nucleotides. In some alternatives, the endonuclease cleavage site comprises at least one guanine, cytosine, or an adenine, wherein the endonuclease cleaves between a thymine and the at least one guanine, cytosine or adenine. In some alternatives, the polynucleotide further comprises at least one palindromic sequence, wherein the at least one palindromic sequence can form a hairpin. In some alternatives, the polynucleotide further comprises a fourth sequence, wherein the fourth sequence is capable of forming a tertiary structure such as a hairpin. In some alternatives, the gene is codon optimized for expression in human cells. Some polynucleotides comprise a first nucleic acid sequence comprising at least one restriction endonuclease recognition site and a second nucleic acid sequence, wherein the second nucleic acid sequence comprises the template strand, wherein the template strand comprises a plurality of thymine nucleotides, wherein said plurality of thymine nucleotides comprises at least, greater than, equal to, or any number in between 20, 30, 40, 50, 60, 70, 80, 90, 100, 110, 120, 130, 140, 150, 175, 200, 225, 250, 275, 300, 325, 350, 375, 400, 425, 450, 475, 500 or 550 covalently linked thymine nucleotides, wherein the second nucleic acid comprises the restriction endonuclease cleavage site, and wherein the restriction endonuclease cleavage site is within the plurality of thymine nucleotides or within 1, 2, 3, 4, 5, 6, 7, 7, 8, 9, 10, 11, 12, 13, 14, 15, 16, 17, 18, 19 or 20 base pairs away from the most 5' thymine (or 5' terminal thymine) in the plurality of thymine nucleotides and wherein said first nucleic acid is covalently linked to said second nucleic acid at one end of said second nucleic acid, and wherein the said restriction endonuclease recognition site is located within 1-55 base pairs such as, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54 or 55 base pairs, of the restriction endonuclease cleavage site for the restriction endonuclease and said restriction endonuclease cleavage site is within 1 to 40 base pairs, such as 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 base pairs, of a most 5' thymine (or 5' terminal thymine) in the plurality of thymine nucleotides. In some alternatives, the polynucleotide comprises a left arm wherein the left arm comprises a left telomere, a right arm wherein the right arm comprises a right telomere and a cloning region located between the left arm and the right arm. In some alternatives, the polynucleotide further comprises a third nucleic acid, wherein the third nucleic acid comprises a gene. In some alternatives, the gene encodes a protein for therapy. In some alternatives, the gene encodes a nuclease. In some alternatives, the nuclease is an endonuclease. In some alternatives, the nuclease comprises an amino acid sequence set forth in SEQ ID NO. 6 or is encoded by a nucleic acid sequence set forth in SEQ ID NO: 7-14. In some alternatives, the number of covalently linked thymines is greater than 120. In some alternatives, the number of covalently linked thymines is greater than 200. In some alternatives, the number of covalently linked thymines is greater than 300. In some alternatives, the at least one endonuclease recognition site is a Type II restriction endonuclease recognition site, and the endonuclease is a Type II restriction endonuclease. In some alternatives, the at least one endonuclease recognition site is a Type IIS restriction endonuclease recognition site and wherein the endonuclease is a Type IIS restriction endonuclease. In some alternatives, the at least one endonuclease recognition site is a BsaI restriction endonuclease recognition site or a StuI restriction endonuclease recognition site, and wherein the endonuclease is BsaI or StuI. In some alternatives, the endonuclease recognition site is inverted. In some alternatives, the polynucleotide is a linear polynucleotide. In some alternatives, the polynucleotide has only one endonuclease recognition site. In some alternatives, the polynucleotide further comprises a polymerase promoter region. In some alternatives, the plurality of thymine nucleotides comprises at least one covalently linked guanine, cytosine, or an adenine, wherein the at least one covalently linked guanine, cytosine or adenine is optionally at the most 5' thymine (or 5' terminal thymine) in the plurality of thymine nucleotides. In some alternatives, the endonuclease cleavage site comprises at least one guanine, cytosine, or an adenine, wherein the endonuclease cleaves between a thymine and the at least one guanine, cytosine or adenine. In some alternatives, the polynucleotide further comprises at least one palindromic sequence, wherein the at least one palindromic sequence can form a hairpin. In some alternatives, the polynucleotide further comprises a third sequence, wherein the third sequence is capable of forming a tertiary structure such as a hairpin. In some alternatives, the gene is codon optimized for expression in human cells. In some alternatives, the polynucleotide further comprises a promoter for a polymerase. In some alternatives, the polymerase is a DNA polymerase. In some alternatives, the DNA polymerase is a thermal stable polymerase, such as Taq polymerase. In some alternatives, the nucleotides are adenine, cytosine, guanine, thymine and/or uracil. In some alternatives, the method further comprises providing a set of primers. In some alternatives, the nucleic acid is DNA. In some alternatives, an RNA polymerase is used. In some alternatives, contacting is performed at a temperature at least, greater than, equal to, or any temperature in between 30° C., 31° C., 32° C., 33° C., 34° C., 35° C., 36° C. or 37° C. In some alternatives, the contacting is performed for at least, greater than, equal to, or time in between 1, 5, 10, 20, 30, 40, 50, 60, 70, 80, 90 or 100 hours (e.g., at least, or equal to 1, 5, 10, 20, 30, 40, 50, 60, 70, 80, 90 or 100 hours or within a range defined by any two of the aforementioned times). In some alternatives, the nucleic acid is RNA. In some alternatives, the RNA comprises a plurality of adenine nucleotides, wherein the plurality of adenine nucleotides comprises at least, greater than, equal to, or any number in between 20, 30, 40, 50, 60, 70, 80, 90, 100, 110, 120, 130, 140, 150, 175, 200, 225, 250, 275, 300, 325, 350, 375, 400, 425, 450, 475, or 500 covalently linked adenines. In some alternatives, the number of covalently linked adenines is greater than 120. In some alternatives, the number of covalently linked adenines is greater than 200. In some alternatives, the number of covalently linked adenines is greater than 300. In some alternatives, the RNA further comprises a gene. In some alternatives, the gene encodes a protein for therapy. In some alternatives, the gene encodes a nuclease. In some alternatives, the gene encodes an endonuclease. In some alternatives, the nuclease comprises an amino acid sequence set forth in SEQ ID NO. 6 or is encoded by a nucleic acid sequence set forth in SEQ ID NO: 7-14. In some alternatives, the plurality of adenine nucleotides further comprises a guanine, cytosine or a uracil, and wherein the number of covalently linked adenines terminates with a guanine, cytosine or a uracil. In some alternatives, the nucleic acid further comprises at least one palindromic sequence, wherein the at least one palindromic sequence can form a hairpin. In some alternatives, the nucleic acid further comprises a sequence capable of forming a tertiary structure such as a hairpin. In some alternatives, the method further comprises providing an endonuclease. In some alternatives, the endonuclease is a Type II restriction endonuclease. In some alternatives, the endonuclease is a Type IIS restriction endonuclease. In some alternatives, the endonuclease is BsaI or StuI. In some alternatives, the gene is codon optimized for expression in human cells. In some alternatives, the cell is a human cell. In some alternatives, the cell is selected from a group consisting of primary cells, human primary T cells, CD4+ cells and CD8+ cells. In some alternatives, the endonuclease cleavage site is located 1, 2, 3, 4, 5, 6, 7, 7, 8, 9, 10, 11, 12, 13, 14, 15, 16, 17, 18, 19 or 20 base pairs away from the most 5' thymine (or 5' terminal thymine) in the plurality of thymine nucleotides. In some alternatives, the endonuclease cleavage site is located 1, 2, 3, 4, 5, 6, 7, 7, 8, 9 or 10 base pairs away from the most 5' thymine (or 5' terminal thymine) in the plurality of thymine nucleotides.

In some alternatives, a method of increasing and/or stabilizing expression of a protein is provided. The method can comprise generating RNA from the polynucleotide of any one of the alternatives herein or a polynucleotide manufactured by a method of any one of the alternatives herein and translating said RNA into a peptide. Some polynucleotides comprise a first nucleic acid sequence comprising at least one restriction endonuclease recognition site and a second nucleic acid sequence, wherein the second nucleic acid sequence comprises the template strand, wherein the template strand comprises a plurality of thymine nucleotides, wherein said plurality of thymine nucleotides comprises at least, greater than, equal to, or any number in between 20, 30, 40, 50, 60, 70, 80, 90, 100, 110, 120, 130, 140, 150, 175, 200, 225, 250, 275, 300, 325, 350, 375, 400, 425, 450, 475, 500 or 550 covalently linked thymine nucleotides, wherein the second nucleic acid comprises the restriction endonuclease cleavage site, and wherein the restriction endonuclease cleavage site is within the plurality of thymine nucleotides or within 1, 2, 3, 4, 5, 6, 7, 7, 8, 9, 10, 11, 12, 13, 14, 15, 16, 17, 18, 19 or 20 base pairs away from the most 5' thymine (or 5' terminal thymine) in the plurality of thymine nucleotides and wherein said first nucleic acid is covalently linked to said second nucleic acid at one end of said second nucleic acid, and wherein the said restriction endonuclease recognition site is located within 1-55 base pairs such as, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54 or 55 base pairs, of the restriction endonuclease cleavage site for the restriction endonuclease and said restriction endonuclease cleavage site is within 1 to 40 base pairs, such as 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 base pairs, of a most 5' thymine (or 5' terminal thymine) in the plurality of thymine nucleotides. In some alternatives, the polynucleotide further comprises telomeres. In some alternatives, the polynucleotide comprises a left arm wherein the left arm comprises a left telomere, a right arm wherein the right arm comprises a right telomere and a cloning region located between the left arm and the right arm. In some alternatives, the polynucleotide further comprises a third nucleic acid, wherein the third nucleic acid comprises a gene. In some alternatives, the gene encodes a protein for therapy. In some alternatives, the gene encodes a nuclease. In some alternatives, the nuclease is an endonuclease. In some alternatives, the nuclease comprises an amino acid sequence set forth in SEQ ID NO. 6 or is encoded by a nucleic acid sequence set forth in SEQ ID NO: 7-14. In some alternatives, the number of covalently linked thymines is greater than 120. In some alternatives, the number of covalently linked thymines is greater than 200. In some alternatives, the number of covalently linked thymines is greater than 300. In some alternatives, the at least one endonuclease recognition site is a Type II restriction endonuclease recognition site, and the endonuclease is a Type II restriction endonuclease. In some alternatives, the at least one endonuclease recognition site is a Type IIS restriction endonuclease recognition site and wherein the endonuclease is a Type IIS restriction endonuclease. In some alternatives, the at least one endonuclease recognition site is a BsaI restriction endonuclease recognition site or a StuI restriction endonuclease recognition site, and wherein the endonuclease is BsaI or StuI. In some alternatives, the endonuclease recognition site is inverted. In some alternatives, the polynucleotide is a linear polynucleotide. In some alternatives, the polynucleotide has only one endonuclease recognition site. In some alternatives, the polynucleotide further comprises a polymerase promoter region. In some alternatives, the plurality of thymine nucleotides comprises at least one covalently linked guanine, cytosine, or an adenine, wherein the at least one covalently linked guanine, cytosine or adenine is optionally at the most 5' thymine (or 5' terminal thymine) in the plurality of thymine nucleotides. In some alternatives, the endonuclease cleavage site comprises at least one guanine, cytosine, or an adenine, wherein the endonuclease cleaves between a thymine and the at least one guanine, cytosine or adenine. In some alternatives, the polynucleotide further comprises at least one palindromic sequence, wherein the at least one palindromic sequence can form a hairpin. In some alternatives, the polynucleotide further comprises a third sequence, wherein the third sequence is capable of forming a tertiary structure such as a hairpin. In some alternatives, the gene is codon optimized for expression in human cells. In some alternatives, the method of making the polynucleotide can comprise providing a first nucleic acid sequence comprising at least one endonuclease recognition site, providing a second nucleic acid sequence, wherein said plurality of thymine nucleotides comprises at least, greater than, equal to, or any number in between 20, 30, 40, 50, 60, 70, 80, 90, 100, 110, 120, 130, 140, 150, 175, 200, 225, 250, 275, 300, 325, 350, 375, 400, 425, 450, 475, 500 or 550 covalently linked thymine nucleotides and wherein the second nucleic acid comprises the endonuclease cleavage site, wherein the endonuclease cleavage site is within the plurality of thymine nucleotides or within 1, 2, 3, 4, 5, 6, 7, 7, 8, 9, 10, 11, 12, 13, 14, 15, 16, 17, 18, 19 or 20 base pairs away from the most 5' thymine (or 5' terminal thymine) in the plurality of thymine nucleotides and joining said first nucleic acid sequence to said second nucleic acid sequence, wherein said first nucleic acid is covalently linked to said second nucleic acid at one end, and wherein the said endonuclease recognition site is located within 1 to 55 base pairs, such as 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54 or 55 base pairs, of the endonuclease cleavage site for the endonuclease and said endonuclease cleavage site is within 1 to 40 base pairs such as, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 base pairs, of a most 5' thymine (or 5' terminal thymine) in the plurality of thymine nucleotides or within 1, 2, 3, 4, 5, 6, 7, 7, 8, 9, 10, 11, 12, 13, 14, 15, 16, 17, 18, 19 or 20 base pairs away from the most 5' thymine (or 5' terminal thymine) in the plurality of thymine nucleotides. In some alternatives, the polynucleotide further comprises telomeres. In some alternatives, the polynucleotide comprises a left arm wherein the left arm comprises a left telomere, a right arm wherein the right arm comprises a right telomere and a cloning region located between the left arm and the right arm. In some alternatives, the polynucleotide further comprises a third nucleic acid, wherein the third nucleic acid comprises a gene. In some alternatives, the gene encodes a protein for therapy. In some alternatives, the gene encodes a nuclease. In some alternatives, the nuclease is an endonuclease. In some alternatives, the nuclease comprises an amino acid sequence set forth in SEQ ID NO. 6 or is encoded by a nucleic acid sequence set forth in SEQ ID NO: 7-14. In some alternatives, the number of covalently linked thymines is greater than 120. In some alternatives, the number of covalently linked thymines is greater than 200. In some alternatives, the number of covalently linked thymines is greater than 300. In some alternatives, the at least one endonuclease recognition site is a Type II restriction endonuclease recognition site, and the restriction endonuclease is a Type II restriction endonuclease. In some alternatives, the at least one endonuclease recognition site is a Type IIS restriction endonuclease recognition site, and wherein the endonuclease is a Type IIS restriction endonuclease. In some alternatives, the at least one endonuclease recognition site is a BsaI restriction endonuclease recognition site or a StuI restriction endonuclease recognition site, and wherein the endonuclease is BsaI or StuI. In some alternatives, the endonuclease recognition site is inverted. In some alternatives, the polynucleotide is a linear polynucleotide. In some alternatives, the polynucleotide has only one endonuclease recognition site. In some alternatives, the polynucleotide further comprises a polymerase promoter. In some alternatives, the plurality of thymine nucleotides comprises at least one covalently linked guanine, cytosine, or an adenine, wherein the at least one covalently linked guanine, cytosine or adenine is optionally joined to the most 5' thymine (or 5' terminal thymine) in the plurality of thymine nucleotides. In some alternatives, the endonuclease cleavage site comprises at least one guanine, cytosine, or an adenine, wherein the endonuclease cleaves between a thymine and the at least one guanine, cytosine or adenine. In some alternatives, the polynucleotide further comprises at least one palindromic sequence, wherein the at least one palindromic sequence can form a hairpin. In some alternatives, the polynucleotide further comprises a fourth sequence, wherein the fourth sequence is capable of forming a tertiary structure such as a hairpin. In some alternatives, the gene is codon optimized for expression in human cells. In some alternatives, the translating step further comprises providing ribosomes, tRNA and amino acids. In some alternatives, the endonuclease is BsaI or StuI. In some alternatives, the method further comprises providing an endonuclease. In some alternatives, the endonuclease is a Type II restriction endonuclease or a Type IIS restriction endonuclease. In some alternatives, the polynucleotide further comprises a polymerase promoter. In some alternatives, the translating is performed at a temperature at least, greater than, equal to, or any temperature in between 30° C., 31° C., 32° C., 33° C., 34° C., 35° C., 36° C. or 37° C. In some alternatives, the translating is performed for at least, greater than, equal to, or time in between 1, 5, 10, 20, 30, 40, 50, 60, 70, 80, 90 or 100 hours (e.g., at least, or equal to 1, 5, 10, 20, 30, 40, 50, 60, 70, 80, 90 or 100 hours or within a range defined by any two of the aforementioned times). In some alternatives, the RNA comprises a plurality of adenine nucleotides, wherein the plurality of adenine nucleotides comprises at least, greater than, equal to, or any number in between 20, 30, 40, 50, 60, 70, 80, 90, 100, 110, 120, 130, 140, 150, 175, 200, 225, 250, 275, 300, 325, 350, 375, 400, 425, 450, 475, or 500 covalently linked adenines. In some alternatives, the number of covalently linked adenines is greater than 120. In some alternatives, the number of covalently linked adenines is greater than 200. In some alternatives, the number of covalently linked adenines is greater than 300. In some alternatives, the RNA further comprises a gene encoding a protein. In some alternatives, the protein is a protein for therapy. In some alternatives, the gene encodes a nuclease. In some alternatives, the gene encodes an endonuclease. In some alternatives, the nuclease comprises an amino acid sequence set forth in SEQ ID NO. 6 or is encoded by a nucleic acid sequence set forth in SEQ ID NO: 7-14. In some alternatives, the plurality of adenine nucleotides further comprises a guanine, cytosine or a uracil, and wherein the number of covalently linked adenines terminates with a guanine, cytosine or a uracil. In some alternatives, the polynucleotide further comprises at least one palindromic sequence, wherein the at least one palindromic sequence can form a hairpin. In some alternatives, the polynucleotide further comprises a sequence capable of forming a tertiary structure such as a hairpin. In some alternatives, the gene is codon optimized for expression in human cells. In some alternatives, the endonuclease cleavage site is located 1, 2, 3, 4, 5, 6, 7, 7, 8, 9, 10, 11, 12, 13, 14, 15, 16, 17, 18, 19 or 20 base pairs away from the most 5' thymine (or 5' terminal thymine) in the plurality of thymine nucleotides. In some alternatives, the endonuclease cleavage site is located 1, 2, 3, 4, 5, 6, 7, 7, 8, 9 or 10 base pairs away from the most 5' thymine (or 5' terminal thymine) in the plurality of thymine nucleotides.

In some alternatives, a method of enhancing stability of a replicating gene is provided, wherein the method comprises providing the polynucleotide of any one of the alternatives herein or a polynucleotide manufactured by any method any one of the alternatives herein, wherein said polynucleotide further comprises a gene transforming a cell with said polynucleotide; and propagating the cell, wherein the polynucleotide is replicated. Some polynucleotides comprise a first nucleic acid sequence comprising at least one restriction endonuclease recognition site and a second nucleic acid sequence, wherein the second nucleic acid sequence comprises the template strand, wherein the template strand comprises a plurality of thymine nucleotides, wherein said plurality of thymine nucleotides comprises at least, greater than, equal to, or any number in between 20, 30, 40, 50, 60, 70, 80, 90, 100, 110, 120, 130, 140, 150, 175, 200, 225, 250, 275, 300, 325, 350, 375, 400, 425, 450, 475, 500 or 550 covalently linked thymine nucleotides, wherein the second nucleic acid comprises the restriction endonuclease cleavage site, and wherein the restriction endonuclease cleavage site is within the plurality of thymine nucleotides or within 1, 2, 3, 4, 5, 6, 7, 7, 8, 9, 10, 11, 12, 13, 14, 15, 16, 17, 18, 19 or 20 base pairs away from the most 5' thymine (or 5' terminal thymine) in the plurality of thymine nucleotides and wherein said first nucleic acid is covalently linked to said second nucleic acid at one end of said second nucleic acid, and wherein the said restriction endonuclease recognition site is located within 1-55 base pairs such as, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54 or 55 base pairs, of the restriction endonuclease cleavage site for the restriction endonuclease and said restriction endonuclease cleavage site is within 1 to 40 base pairs, such as 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 base pairs, of a most 5' thymine (or 5' terminal thymine) in the plurality of thymine nucleotides. In some alternatives, the polynucleotide further comprises telomeres. In some alternatives, the polynucleotide comprises a left arm wherein the left arm comprises a left telomere, a right arm wherein the right arm comprises a right telomere and a cloning region located between the left arm and the right arm. In some alternatives, the polynucleotide further comprises a third nucleic acid, wherein the third nucleic acid comprises a gene. In some alternatives, the gene encodes a protein for therapy. In some alternatives, the gene encodes a nuclease. In some alternatives, the nuclease is an endonuclease. In some alternatives, the nuclease comprises an amino acid sequence set forth in SEQ ID NO. 6 or is encoded by a nucleic acid sequence set forth in SEQ ID NO: 7-14. In some alternatives, the number of covalently linked thymines is greater than 120. In some alternatives, the number of covalently linked thymines is greater than 200. In some alternatives, the number of covalently linked thymines is greater than 300. In some alternatives, the at least one endonuclease recognition site is a Type II restriction endonuclease recognition site, and the endonuclease is a Type II restriction endonuclease. In some alternatives, the at least one endonuclease recognition site is a Type IIS restriction endonuclease recognition site and the endonuclease is a Type IIS restriction endonuclease. In some alternatives, the at least one endonuclease recognition site is a BsaI restriction endonuclease recognition site or a StuI restriction endonuclease recognition site, and wherein the r endonuclease is BsaI or StuI. In some alternatives, the endonuclease recognition site is inverted. In some alternatives, the polynucleotide is a linear polynucleotide. In some alternatives, the polynucleotide has only one endonuclease recognition site. In some alternatives, the polynucleotide further comprises a polymerase promoter region. In some alternatives, the plurality of thymine nucleotides comprises at least one covalently linked guanine, cytosine, or an adenine, wherein the at least one covalently linked guanine, cytosine or adenine is optionally at the most 5' thymine (or 5' terminal thymine) in the plurality of thymine nucleotides. In some alternatives, the endonuclease cleavage site comprises at least one guanine, cytosine, or an adenine, wherein the endonuclease cleaves between a thymine and the at least one guanine, cytosine or adenine. In some alternatives, the polynucleotide further comprises at least one palindromic sequence, wherein the at least one palindromic sequence can form a hairpin. In some alternatives, the polynucleotide further comprises a third sequence, wherein the third sequence is capable of forming a tertiary structure such as a hairpin. In some alternatives, the gene is codon optimized for expression in human cells. In some alternatives, the method of making a polynucleotide having a template strand, an endonuclease recognition site and an endonuclease cleavage site for an endonuclease inserted therein, and wherein said template strand comprises a plurality of thymine nucleotides, is provided. The method for making the polynucleotide can comprise providing a first nucleic acid sequence comprising at least one endonuclease recognition site, providing a second nucleic acid sequence, wherein said plurality of thymine nucleotides comprises at least, greater than, equal to, or any number in between 20, 30, 40, 50, 60, 70, 80, 90, 100, 110, 120, 130, 140, 150, 175, 200, 225, 250, 275, 300, 325, 350, 375, 400, 425, 450, 475, 500 or 550 covalently linked thymine nucleotides and wherein the second nucleic acid comprises the endonuclease cleavage site, wherein the endonuclease cleavage site is within the plurality of thymine nucleotides or within 1, 2, 3, 4, 5, 6, 7, 7, 8, 9, 10, 11, 12, 13, 14, 15, 16, 17, 18, 19 or 20 base pairs away from the most 5' thymine (or 5' terminal thymine) in the plurality of thymine nucleotides and joining said first nucleic acid sequence to said second nucleic acid sequence, wherein said first nucleic acid is covalently linked to said second nucleic acid at one end, and wherein the said endonuclease recognition site is located within 1 to 55 base pairs, such as 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54 or 55 base pairs, of the endonuclease cleavage site for the endonuclease and said endonuclease cleavage site is within 1 to 40 base pairs such as, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 base pairs, of a most 5' thymine or 5' terminal thymine in the plurality of thymine nucleotides or within 1, 2, 3, 4, 5, 6, 7, 7, 8, 9, 10, 11, 12, 13, 14, 15, 16, 17, 18, 19 or 20 base pairs away from the most 5' thymine (or 5' terminal thymine) in the plurality of thymine nucleotides. In some alternatives, the polynucleotide further comprises telomeres. In some alternatives, the polynucleotide comprises a left arm wherein the left arm comprises a left telomere, a right arm wherein the right arm comprises a right telomere and a cloning region located between the left arm and the right arm. In some alternatives, the polynucleotide further comprises a third nucleic acid, wherein the third nucleic acid comprises a gene. In some alternatives, the gene encodes a protein for therapy. In some alternatives, the gene encodes a nuclease. In some alternatives, the nuclease is an endonuclease. In some alternatives, the nuclease comprises an amino acid sequence set forth in SEQ ID NO. 6 or is encoded by a nucleic acid sequence set forth in SEQ ID NO: 7-14. In some alternatives, the number of covalently linked thymines is greater than 120. In some alternatives, the number of covalently linked thymines is greater than 200. In some alternatives, the number of covalently linked thymines is greater than 300. In some alternatives, the at least one endonuclease recognition site is a Type II restriction endonuclease recognition site, and the endonuclease is a Type II restriction endonuclease. In some alternatives, the at least one endonuclease recognition site is a Type IIS restriction endonuclease recognition site, and wherein the endonuclease is a Type IIS restriction endonuclease. In some alternatives, the at least one endonuclease recognition site is a BsaI restriction endonuclease recognition site or a StuI restriction endonuclease recognition site, and wherein the endonuclease is BsaI or StuI. In some alternatives, the endonuclease recognition site is inverted. In some alternatives, the polynucleotide is a linear polynucleotide. In some alternatives, the polynucleotide has only one endonuclease recognition site. In some alternatives, the polynucleotide further comprises a polymerase promoter. In some alternatives, the plurality of thymine nucleotides comprises at least one covalently linked guanine, cytosine, or an adenine, wherein the at least one covalently linked guanine, cytosine or adenine is optionally joined to the most 5' thymine (or 5' terminal thymine) in the plurality of thymine nucleotides. In some alternatives, the endonuclease cleavage site comprises at least one guanine, cytosine, or an adenine, wherein the endonuclease cleaves between a thymine and the at least one guanine, cytosine or adenine. In some alternatives, the polynucleotide further comprises at least one palindromic sequence, wherein the at least one palindromic sequence can form a hairpin. In some alternatives, the polynucleotide further comprises a fourth sequence, wherein the fourth sequence is capable of forming a tertiary structure such as a hairpin. In some alternatives, the gene is codon optimized for expression in human cells. In some alternatives, the cell is propagated for 1 day, 2 days, 4 days, 6 days, 8 days, 10 days, 12 days, 14 days, or any other times between these values. In some alternatives, the cell is propagated at 30° C., 31° C., 32° C., 33° C., 34° C., 35° C., 36° C., 37° C. or any other temperature between any these values. In some alternatives, the cell is a human cell. In some alternatives, the cell is selected from a group consisting of primary cells, human primary T cells, CD4+ cells and CD8+ cells. In some alternatives, the endonuclease cleavage site is located 1, 2, 3, 4, 5, 6, 7, 7, 8, 9, 10, 11, 12, 13, 14, 15, 16, 17, 18, 19 or 20 base pairs away from the most 5' thymine (or 5' terminal thymine) in the plurality of thymine nucleotides. In some alternatives, the endonuclease cleavage site is located 1, 2, 3, 4, 5, 6, 7, 7, 8, 9 or 10 base pairs away from the most 5' thymine (or 5' terminal thymine) in the plurality of thymine nucleotides.

In some alternatives, a polynucleotide comprising a sequence encoding a nuclease, a template strand, an endonuclease recognition site and an endonuclease cleavage site for an endonuclease inserted therein, wherein said template strand comprises a plurality of thymine nucleotides, is provided. The polynucleotide can comprise a first nucleic acid sequence encoding a nuclease, a second nucleic acid sequence comprising at least one restriction endonuclease recognition site and a third nucleic acid sequence, wherein the third nucleic acid sequence comprises the template strand, wherein said plurality of thymine nucleotides comprises at least, greater than, equal to, or any number in between 20, 30, 40, 50, 60, 70, 80, 90, 100, 110, 120, 130, 140, 150, 175, 200, 225, 250, 275, 300, 325, 350, 375, 400, 425, 450, 475, 500 or 550 covalently linked thymine nucleotides and wherein the third nucleic acid comprises the restriction endonuclease cleavage site, wherein the restriction endonuclease cleavage site is located within the plurality of thymine nucleotides or within 1, 2, 3, 4, 5, 6, 7, 7, 8, 9, 10, 11, 12, 13, 14, 15, 16, 17, 18, 19 or 20 base pairs away from the most 5' thymine (or 5' terminal thymine) in the plurality of thymine nucleotides and wherein said second nucleic acid is covalently linked to one end of said third nucleic acid sequence, and wherein the said restriction endonuclease recognition site is located within 55 base pairs of the restriction endonuclease cleavage site for the restriction endonuclease and said restriction endonuclease cleavage site is within 1 to 40 base pairs of a most 5' thymine in the plurality of thymine nucleotides. In some alternatives, the polynucleotide further comprises telomeres. In some alternatives, the polynucleotide comprises a left arm wherein the left arm comprises a left telomere, a right arm wherein the right arm comprises a right telomere and a cloning region located between the left arm and the right arm. In some alternatives, the nuclease comprises an amino acid sequence set forth in SEQ ID NO. 6 or is encoded by a nucleic acid sequence set forth in SEQ ID NO: 7-14. In some alternatives, the number of covalently linked thymines is greater than 120. In some alternatives, the number of covalently linked thymines is greater than 200. In some alternatives, the number of covalently linked thymines is greater than 300. In some alternatives, the at least one endonuclease recognition site is a Type II restriction endonuclease recognition site, and the endonuclease is a Type II restriction endonuclease. In some alternatives, the at least one endonuclease recognition site is a Type IIS restriction endonuclease recognition site and wherein the endonuclease is a Type IIS restriction endonuclease. In some alternatives, the at least one endonuclease recognition site is a BsaI restriction endonuclease recognition site or a StuI restriction endonuclease recognition site, and wherein the endonuclease is BsaI or StuI. In some alternatives, the endonuclease recognition site is inverted. In some alternatives, the polynucleotide is a linear polynucleotide. In some alternatives, the polynucleotide has only one endonuclease recognition site. In some alternatives, the polynucleotide further comprises a polymerase promoter. In some alternatives, the plurality of thymine nucleotides comprises at least one covalently linked guanine, cytosine, or an adenine, wherein the at least one covalently linked guanine, cytosine or adenine is optionally joined to the most 5' thymine (or 5' terminal thymine) in the plurality of thymine nucleotides. In some alternatives, the endonuclease cleavage site comprises at least one guanine, cytosine, or an adenine, wherein the endonuclease cleaves between a thymine and the at least one guanine, cytosine or adenine. In some alternatives, the polynucleotide further comprises at least one palindromic sequence, wherein the at least one palindromic sequence can form a hairpin. In some alternatives, the polynucleotide further comprises a seventh sequence, wherein the seventh sequence is capable of forming a tertiary structure such as a hairpin. In some alternatives, the sequence encoding the nuclease is optimized for expression in human cells. In some alternatives, the endonuclease cleavage site is located 1, 2, 3, 4, 5, 6, 7, 7, 8, 9, 10, 11, 12, 13, 14, 15, 16, 17, 18, 19 or 20 base pairs away from the most 5' thymine (or 5' terminal thymine) in the plurality of thymine nucleotides. In some alternatives, the endonuclease cleavage site is located 1, 2, 3, 4, 5, 6, 7, 7, 8, 9 or 10 base pairs away from the most 5' thymine (or 5' terminal thymine) in the plurality of thymine nucleotides.

In some alternatives, a method of making polynucleotide comprising a sequence encoding a nuclease, a template strand, an endonuclease recognition site and an endonuclease cleavage site for an endonuclease inserted therein, wherein said template strand comprises a plurality of thymine nucleotides, is provided. The method can comprise providing a first nucleic acid sequence encoding a nuclease, providing a second nucleic acid sequence comprising at least one endonuclease recognition site, providing a third nucleic acid sequence, wherein the third nucleic acid sequence comprises the template strand, wherein the template strand comprises a plurality of thymine nucleotides, wherein said plurality of thymine nucleotides comprises at least, greater than, equal to, or any number in between 20, 30, 40, 50, 60, 70, 80, 90, 100, 110, 120, 130, 140, 150, 175, 200, 225, 250, 275, 300, 325, 350, 375, 400, 425, 450, 475, 500 or 550 covalently linked thymine nucleotides and wherein the third nucleic acid comprises the endonuclease cleavage site, wherein the endonuclease cleavage site is located within the plurality of thymine nucleotides or within 1, 2, 3, 4, 5, 6, 7, 7, 8, 9, 10, 11, 12, 13, 14, 15, 16, 17, 18, 19 or 20 base pairs away from the most 5' thymine (or 5' terminal thymine) in the plurality of thymine nucleotides, joining said first nucleic acid to one end of the second nucleic acid sequence and joining said third nucleic acid sequence to one end of the second nucleic acid sequence, wherein said second nucleic acid is covalently linked to one end of said third nucleic acid sequence, and wherein the said endonuclease recognition site is located within 55 base pairs of the endonuclease cleavage site for the endonuclease and said endonuclease cleavage site is within 1 to 40 base pairs of a most 5' thymine in the plurality of thymine nucleotides. In some alternatives, the number of covalently linked thymines is greater than 120. In some alternatives, the number of covalently linked thymines is greater than 200. In some alternatives, the number of covalently linked thymines is greater than 300. In some alternatives, the at least one endonuclease recognition site is a Type II restriction endonuclease recognition site and the endonuclease is a Type II restriction endonuclease. In some alternatives, the at least one endonuclease recognition site is a Type IIS restriction endonuclease recognition site and the endonuclease is a Type IIS restriction endonuclease. In some alternatives, the at least one endonuclease recognition site is a BsaI restriction endonuclease recognition site or a StuI restriction endonuclease recognition site, and wherein the endonuclease is BsaI or StuI. In some alternatives, the endonuclease recognition site is inverted. In some alternatives, the polynucleotide is a linear polynucleotide. In some alternatives, the polynucleotide has only one endonuclease recognition site. In some alternatives, the plurality of thymine nucleotides comprises at least one covalently linked guanine, cytosine, or an adenine, wherein the at least one covalently linked guanine, cytosine or adenine is optionally joined to the most 5' thymine (or 5' terminal thymine) in the plurality of thymine nucleotides. In some alternatives, the endonuclease cleavage site comprises at least one guanine, cytosine, or an adenine, wherein the endonuclease cleaves between a thymine and the at least one guanine, cytosine or adenine. In some alternatives, the nuclease comprises an amino acid sequence set forth in SEQ ID NO. 6 or is encoded by a nucleic acid sequence set forth in SEQ ID NO: 7-14. In some alternatives, the first nucleic acid sequence encoding the nuclease is codon optimized for expression in human cells. In some alternatives, the endonuclease cleavage site is located 1, 2, 3, 4, 5, 6, 7, 7, 8, 9, 10, 11, 12, 13, 14, 15, 16, 17, 18, 19 or 20 base pairs away from the most 5' thymine (or 5' terminal thymine) in the plurality of thymine nucleotides. In some alternatives, the endonuclease cleavage site is located 1, 2, 3, 4, 5, 6, 7, 7, 8, 9 or 10 base pairs away from the most 5' thymine (or 5' terminal thymine) in the plurality of thymine nucleotides.

In some alternatives, a method of making a nucleic acid encoding a nuclease, s provided, wherein the method comprises providing the polynucleotide of any one of the alternatives herein or a polynucleotide manufactured by a method of any one of the alternatives herein and contacting said polynucleotide with a polymerase in the presence of nucleotides. The polynucleotide can comprise a first nucleic acid sequence encoding a nuclease, a second nucleic acid sequence comprising at least one restriction endonuclease recognition site and a third nucleic acid sequence, wherein the third nucleic acid sequence comprises the template strand, wherein said plurality of thymine nucleotides comprises at least, greater than, equal to, or any number in between 20, 30, 40, 50, 60, 70, 80, 90, 100, 110, 120, 130, 140, 150, 175, 200, 225, 250, 275, 300, 325, 350, 375, 400, 425, 450, 475, 500 or 550 covalently linked thymine nucleotides and wherein the third nucleic acid comprises the restriction endonuclease cleavage site, wherein the restriction endonuclease cleavage site is located within the plurality of thymine nucleotides or within 1, 2, 3, 4, 5, 6, 7, 7, 8, 9, 10, 11, 12, 13, 14, 15, 16, 17, 18, 19 or 20 base pairs away from the most 5' thymine (or 5' terminal thymine) in the plurality of thymine nucleotides and wherein said second nucleic acid is covalently linked to one end of said third nucleic acid sequence, and wherein the said restriction endonuclease recognition site is located within 55 base pairs of the restriction endonuclease cleavage site for the restriction endonuclease and said restriction endonuclease cleavage site is within 1 to 40 base pairs of a most 5' thymine in the plurality of thymine nucleotides. In some alternatives, the polynucleotide further comprises telomeres. In some alternatives, the polynucleotide comprises a left arm wherein the left arm comprises a left telomere, a right arm wherein the right arm comprises a right telomere and a cloning region located between the left arm and the right arm. In some alternatives, the nuclease comprises an amino acid sequence set forth in SEQ ID NO. 6 or is encoded by a nucleic acid sequence set forth in SEQ ID NO: 7-14. In some alternatives, the number of covalently linked thymines is greater than 120. In some alternatives, the number of covalently linked thymines is greater than 200. In some alternatives, the number of covalently linked thymines is greater than 300. In some alternatives, the at least one endonuclease recognition site is a Type II restriction endonuclease recognition site, and the endonuclease is a Type II restriction endonuclease. In some alternatives, the at least one endonuclease recognition site is a Type IIS restriction endonuclease recognition site and wherein the endonuclease is a Type IIS restriction endonuclease. In some alternatives, the at least one endonuclease recognition site is a BsaI restriction endonuclease recognition site or a StuI restriction endonuclease recognition site, and wherein the endonuclease is BsaI or StuI. In some alternatives, the endonuclease recognition site is inverted. In some alternatives, the polynucleotide is a linear polynucleotide. In some alternatives, the polynucleotide has only one endonuclease recognition site. In some alternatives, the polynucleotide further comprises a polymerase promoter. In some alternatives, the plurality of thymine nucleotides comprises at least one covalently linked guanine, cytosine, or an adenine, wherein the at least one covalently linked guanine, cytosine or adenine is optionally at the most 5' thymine (or 5' terminal thymine) in the plurality of thymine nucleotides. In some alternatives, the endonuclease cleavage site comprises at least one guanine, cytosine, or an adenine, wherein the endonuclease cleaves between a thymine and the at least one guanine, cytosine or adenine. In some alternatives, the polynucleotide further comprises at least one palindromic sequence, wherein the at least one palindromic sequence can form a hairpin. In some alternatives, the polynucleotide further comprises a seventh sequence, wherein the seventh sequence is capable of forming a tertiary structure such as a hairpin. In some alternatives, the sequence encoding the nuclease is optimized for expression in human cells. The method of making a polynucleotide comprising a sequence encoding a nuclease, a template strand, an endonuclease recognition site and an endonuclease cleavage site for an endonuclease inserted therein, wherein said template strand comprises a plurality of thymine nucleotides can comprise providing a first nucleic acid sequence encoding a nuclease, providing a second nucleic acid sequence comprising at least one endonuclease recognition site, providing a third nucleic acid sequence, wherein the third nucleic acid sequence comprises the template strand, wherein the template strand comprises a plurality of thymine nucleotides, wherein said plurality of thymine nucleotides comprises at least, greater than, equal to, or any number in between 20, 30, 40, 50, 60, 70, 80, 90, 100, 110, 120, 130, 140, 150, 175, 200, 225, 250, 275, 300, 325, 350, 375, 400, 425, 450, 475, 500 or 550 covalently linked thymine nucleotides and wherein the third nucleic acid comprises the endonuclease cleavage site, wherein the endonuclease cleavage site is located within the plurality of thymine nucleotides or within 1, 2, 3, 4, 5, 6, 7, 7, 8, 9, 10, 11, 12, 13, 14, 15, 16, 17, 18, 19 or 20 base pairs away from the most 5' thymine (or 5' terminal thymine) in the plurality of thymine nucleotides, joining said first nucleic acid to one end of the second nucleic acid sequence and joining said third nucleic acid sequence to one end of the second nucleic acid sequence, wherein said second nucleic acid is covalently linked to one end of said third nucleic acid sequence, and wherein the said endonuclease recognition site is located within 55 base pairs of the endonuclease cleavage site for the endonuclease and said endonuclease cleavage site is within 1 to 40 base pairs of a most 5' thymine in the plurality of thymine nucleotides. In some alternatives, the number of covalently linked thymines is greater than 120. In some alternatives, the number of covalently linked thymines is greater than 200. In some alternatives, the number of covalently linked thymines is greater than 300. In some alternatives, the at least one endonuclease recognition site is a Type II restriction endonuclease recognition site and the endonuclease is a Type II restriction endonuclease. In some alternatives, the at least one endonuclease recognition site is a Type IIS restriction endonuclease recognition site and the endonuclease is a Type IIS restriction endonuclease. In some alternatives, the at least one endonuclease recognition site is a BsaI restriction endonuclease recognition site or a StuI restriction endonuclease recognition site, and wherein the endonuclease is BsaI or StuI. In some alternatives, the endonuclease recognition site is inverted. In some alternatives, the polynucleotide is a linear polynucleotide. In some alternatives, the polynucleotide has only one endonuclease recognition site. In some alternatives, the plurality of thymine nucleotides comprises at least one covalently linked guanine, cytosine, or an adenine, wherein the at least one covalently linked guanine, cytosine or adenine is optionally at the most 5' thymine (or 5' terminal thymine) in the plurality of thymine nucleotides. In some alternatives, the endonuclease cleavage site comprises at least one guanine, cytosine, or an adenine, wherein the endonuclease cleaves between a thymine and the at least one guanine, cytosine or adenine. In some alternatives, the nuclease comprises an amino acid sequence set forth in SEQ ID NO. 6 or is encoded by a nucleic acid sequence set forth in SEQ ID NO: 7-14. In some alternatives, the first nucleic acid sequence encoding the nuclease is codon optimized for expression in human cells. In some alternatives, the polynucleotide further comprises a promoter for a polymerase. In some alternatives, the polymerase is a DNA polymerase. In some alternatives, the DNA polymerase is a thermal stable polymerase, such as Taq polymerase. In some alternatives, the nucleotides are adenine, cytosine, guanine, thymine and/or uracil. In some alternatives, the method further comprises providing a set of primers. In some alternatives, the nucleic acid is DNA. In some alternatives, an RNA polymerase is used. In some alternatives, the contacting is performed at a temperature at least, greater than, equal to, or any temperature in between 30° C., 31° C., 32° C., 33° C., 34° C., 35° C., 36° C. or 37° C. In some alternatives, the contacting is performed for at least, greater than, equal to, or time in between 1, 5, 10, 20, 30, 40, 50, 60, 70, 80, 90 or 100 hours (e.g., at least, or equal to 1, 5, 10, 20, 30, 40, 50, 60, 70, 80, 90 or 100 hours or within a range defined by any two of the aforementioned times). In some alternatives, the nucleic acid is RNA. In some alternatives, the RNA comprises a plurality of adenine nucleotides, wherein the plurality of adenine nucleotides comprises at least, greater than, equal to, or any number in between 20, 30, 40, 50, 60, 70, 80, 90, 100, 110, 120, 130, 140, 150, 175, 200, 225, 250, 275, 300, 325, 350, 375, 400, 425, 450, 475, or 500 covalently linked adenines. In some alternatives, the number of covalently linked adenines is greater than 120. In some alternatives, the number of covalently linked adenines is greater than 200. In some alternatives, the number of covalently linked adenines is greater than 300. In some alternatives, the nuclease comprises an amino acid sequence set forth in SEQ ID NO. 6 or is encoded by a nucleic acid sequence set forth in SEQ ID NO: 7-14. In some alternatives, the plurality of adenine nucleotides further comprises a guanine, cytosine or a uracil, and wherein the number of covalently linked adenines terminates with a guanine, cytosine or a uracil. In some alternatives, the nucleic acid further comprises at least one palindromic sequence, wherein the at least one palindromic sequence can form a hairpin. In some alternatives, the nucleic acid further comprises a sequence capable of forming a tertiary structure such as a hairpin. In some alternatives, the method further comprises providing an endonuclease. In some alternatives, the endonuclease is a Type II restriction endonuclease. In some alternatives, the endonuclease is a Type IIS restriction endonuclease. In some alternatives, the endonuclease is BsaI or StuI. In some alternatives, the endonuclease cleavage site is located 1, 2, 3, 4, 5, 6, 7, 7, 8, 9, 10, 11, 12, 13, 14, 15, 16, 17, 18, 19 or 20 base pairs away from the most 5' thymine (or 5' terminal thymine) in the plurality of thymine nucleotides. In some alternatives, the endonuclease cleavage site is located 1, 2, 3, 4, 5, 6, 7, 7, 8, 9 or 10 base pairs away from the most 5' thymine (or 5' terminal thymine) in the plurality of thymine nucleotides.

In some alternatives, a method of enhancing transcription of a gene encoding a nuclease, is provided. The method can comprise providing polynucleotide of any one of alternatives herein, or a polynucleotide manufactured by a method of any one of alternatives herein and contacting said polynucleotide with a RNA polymerase in the presence of nucleotides. The polynucleotide can comprise a first nucleic acid sequence encoding a nuclease, a second nucleic acid sequence comprising at least one restriction endonuclease recognition site and a third nucleic acid sequence, wherein the third nucleic acid sequence comprises the template strand, wherein said plurality of thymine nucleotides comprises at least, greater than, equal to, or any number in between 20, 30, 40, 50, 60, 70, 80, 90, 100, 110, 120, 130, 140, 150, 175, 200, 225, 250, 275, 300, 325, 350, 375, 400, 425, 450, 475, 500 or 550 covalently linked thymine nucleotides and wherein the third nucleic acid comprises the restriction endonuclease cleavage site, wherein the restriction endonuclease cleavage site is located within the plurality of thymine nucleotides or within 1, 2, 3, 4, 5, 6, 7, 7, 8, 9, 10, 11, 12, 13, 14, 15, 16, 17, 18, 19 or 20 base pairs away from the most 5' thymine (or 5' terminal thymine) in the plurality of thymine nucleotides and wherein said second nucleic acid is covalently linked to one end of said third nucleic acid sequence, and wherein the said restriction endonuclease recognition site is located within 55 base pairs of the restriction endonuclease cleavage site for the restriction endonuclease and said restriction endonuclease cleavage site is within 1 to 40 base pairs of a most 5' thymine in the plurality of thymine nucleotides. In some alternatives, the polynucleotide further comprises telomeres. In some alternatives, the polynucleotide comprises a left arm wherein the left arm comprises a left telomere, a right arm wherein the right arm comprises a right telomere and a cloning region located between the left arm and the right arm. In some alternatives, the nuclease comprises an amino acid sequence set forth in SEQ ID NO. 6 or is encoded by a nucleic acid sequence set forth in SEQ ID NO: 7-14. In some alternatives, the number of covalently linked thymines is greater than 120. In some alternatives, the number of covalently linked thymines is greater than 200. In some alternatives, the number of covalently linked thymines is greater than 300. In some alternatives, the at least one endonuclease recognition site is a Type II restriction endonuclease recognition site, and the endonuclease is a Type II restriction endonuclease. In some alternatives, the at least one endonuclease recognition site is a Type IIS endonuclease recognition site and wherein the endonuclease is a Type IIS restriction endonuclease. In some alternatives, the at least one Type IIS restriction endonuclease recognition site is a BsaI restriction endonuclease recognition site or a StuI restriction endonuclease recognition site, and wherein the endonuclease is BsaI or StuI. In some alternatives, the endonuclease recognition site is inverted. In some alternatives, the polynucleotide is a linear polynucleotide. In some alternatives, the polynucleotide has only one endonuclease recognition site. In some alternatives, the polynucleotide further comprises a polymerase promoter. In some alternatives, the plurality of thymine nucleotides comprises at least one covalently linked guanine, cytosine, or an adenine, wherein the at least one covalently linked guanine, cytosine or adenine is optionally at the most 5' thymine (or 5' terminal thymine) in the plurality of thymine nucleotides. In some alternatives, the endonuclease cleavage site comprises at least one guanine, cytosine, or an adenine, wherein the endonuclease cleaves between a thymine and the at least one guanine, cytosine or adenine. In some alternatives, the polynucleotide further comprises at least one palindromic sequence, wherein the at least one palindromic sequence can form a hairpin. In some alternatives, the polynucleotide further comprises a seventh sequence, wherein the seventh sequence is capable of forming a tertiary structure such as a hairpin. In some alternatives, the sequence encoding the nuclease is optimized for expression in human cells. The method of making a polynucleotide comprising a sequence encoding a nuclease, a template strand, an endonuclease recognition site and an endonuclease cleavage site for an endonuclease inserted therein, wherein said template strand comprises a plurality of thymine nucleotides can comprise providing a first nucleic acid sequence encoding a nuclease, providing a second nucleic acid sequence comprising at least one endonuclease recognition site, providing a third nucleic acid sequence, wherein the third nucleic acid sequence comprises the template strand, wherein the template strand comprises a plurality of thymine nucleotides, wherein said plurality of thymine nucleotides comprises at least, greater than, equal to, or any number in between 20, 30, 40, 50, 60, 70, 80, 90, 100, 110, 120, 130, 140, 150, 175, 200, 225, 250, 275, 300, 325, 350, 375, 400, 425, 450, 475, 500 or 550 covalently linked thymine nucleotides and wherein the third nucleic acid comprises the endonuclease cleavage site, wherein the endonuclease cleavage site is located within the plurality of thymine nucleotides or within 1, 2, 3, 4, 5, 6, 7, 7, 8, 9, 10, 11, 12, 13, 14, 15, 16, 17, 18, 19 or 20 base pairs away from the most 5' thymine (or 5' terminal thymine) in the plurality of thymine nucleotides, joining said first nucleic acid to one end of the second nucleic acid sequence and joining said third nucleic acid sequence to one end of the second nucleic acid sequence, wherein said second nucleic acid is covalently linked to one end of said third nucleic acid sequence, and wherein the said endonuclease recognition site is located within 55 base pairs of the endonuclease cleavage site for the endonuclease and said endonuclease cleavage site is within 1 to 40 base pairs of a most 5' thymine in the plurality of thymine nucleotides. In some alternatives, the number of covalently linked thymines is greater than 120. In some alternatives, the number of covalently linked thymines is greater than 200. In some alternatives, the number of covalently linked thymines is greater than 300. In some alternatives, the at least one endonuclease recognition site is a Type II restriction endonuclease recognition site and the endonuclease is a Type II restriction endonuclease. In some alternatives, the at least one endonuclease recognition site is a Type IIS restriction endonuclease recognition site and the endonuclease is a Type IIS restriction endonuclease. In some alternatives, the at least one endonuclease recognition site is a BsaI restriction endonuclease recognition site or a StuI restriction endonuclease recognition site, and wherein the endonuclease is BsaI or StuI. In some alternatives, the endonuclease recognition site is inverted. In some alternatives, the polynucleotide is a linear polynucleotide. In some alternatives, the polynucleotide has only one endonuclease recognition site. In some alternatives, the plurality of thymine nucleotides comprises at least one covalently linked guanine, cytosine, or an adenine, wherein the at least one covalently linked guanine, cytosine or adenine is optionally joined to the most 5' thymine (or 5' terminal thymine) in the plurality of thymine nucleotides. In some alternatives, the endonuclease cleavage site comprises at least one guanine, cytosine, or an adenine, wherein the endonuclease cleaves between a thymine and the at least one guanine, cytosine or adenine. In some alternatives, the nuclease comprises an amino acid sequence set forth in SEQ ID NO. 6 or is encoded by a nucleic acid sequence set forth in SEQ ID NO: 7-14. In some alternatives, the first nucleic acid sequence encoding the nuclease is codon optimized for expression in human cells. In some alternatives, the polynucleotide further comprises an RNA polymerase promoter. In some alternatives, the method further comprises providing an endonuclease. In some alternatives, the endonuclease is a Type II restriction endonuclease. In some alternatives, the endonuclease is a Type IIS restriction endonuclease. In some alternatives, the endonuclease is BsaI or StuI. In some alternatives, the contacting is performed at a temperature at least, greater than, equal to, or any temperature in between 30° C., 31° C., 32° C., 33° C., 34° C., 35° C., 36° C. or 37° C. In some alternatives, the method is performed for at least, greater than, equal to, or time in between 1, 5, 10, 20, 30, 40, 50, 60, 70, 80, 90 or 100 hours (e.g., at least, or equal to 1, 5, 10, 20, 30, 40, 50, 60, 70, 80, 90 or 100 hours or within a range defined by any two of the aforementioned times). In some alternatives, the endonuclease cleavage site is located 1, 2, 3, 4, 5, 6, 7, 7, 8, 9, 10, 11, 12, 13, 14, 15, 16, 17, 18, 19 or 20 base pairs away from the most 5' thymine (or 5' terminal thymine) in the plurality of thymine nucleotides. In some alternatives, the endonuclease cleavage site is located 1, 2, 3, 4, 5, 6, 7, 7, 8, 9 or 10 base pairs away from the most 5' thymine (or 5' terminal thymine) in the plurality of thymine nucleotides.

In some alternatives, a nucleic acid encoding a nuclease manufactured by any one of the methods of any of the alternatives herein, is provided. The method for manufacturing the nucleic acid comprises providing the polynucleotide of any one of the alternatives herein or a polynucleotide manufactured by a method of any one of the alternatives herein and contacting said polynucleotide with a polymerase in the presence of nucleotides. The polynucleotide can comprise a first nucleic acid sequence encoding a nuclease, a second nucleic acid sequence comprising at least one restriction endonuclease recognition site and a third nucleic acid sequence, wherein the third nucleic acid sequence comprises the template strand, wherein said plurality of thymine nucleotides comprises at least, greater than, equal to, or any number in between 20, 30, 40, 50, 60, 70, 80, 90, 100, 110, 120, 130, 140, 150, 175, 200, 225, 250, 275, 300, 325, 350, 375, 400, 425, 450, 475, 500 or 550 covalently linked thymine nucleotides and wherein the third nucleic acid comprises the restriction endonuclease cleavage site, wherein the restriction endonuclease cleavage site is located within the plurality of thymine nucleotides or within 1, 2, 3, 4, 5, 6, 7, 7, 8, 9, 10, 11, 12, 13, 14, 15, 16, 17, 18, 19 or 20 base pairs away from the most 5' thymine (or 5' terminal thymine) in the plurality of thymine nucleotides and wherein said second nucleic acid is covalently linked to one end of said third nucleic acid sequence, and wherein the said restriction endonuclease recognition site is located within 55 base pairs of the restriction endonuclease cleavage site for the restriction endonuclease and said restriction endonuclease cleavage site is within 1 to 40 base pairs of a most 5' thymine in the plurality of thymine nucleotides. In some alternatives, the polynucleotide further comprises telomeres. In some alternatives, the polynucleotide comprises a left arm wherein the left arm comprises a left telomere, a right arm wherein the right arm comprises a right telomere and a cloning region located between the left arm and the right arm. In some alternatives, the nuclease comprises an amino acid sequence set forth in SEQ ID NO. 6 or is encoded by a nucleic acid sequence set forth in SEQ ID NO: 7-14. In some alternatives, the number of covalently linked thymines is greater than 120. In some alternatives, the number of covalently linked thymines is greater than 200. In some alternatives, the number of covalently linked thymines is greater than 300. In some alternatives, the at least one endonuclease recognition site is a Type II restriction endonuclease recognition site, and the endonuclease is a Type II restriction endonuclease. In some alternatives, the at least one endonuclease recognition site is a Type IIS restriction endonuclease recognition site and wherein the endonuclease is a Type IIS restriction endonuclease. In some alternatives, the at least one endonuclease recognition site is a BsaI restriction endonuclease recognition site or a StuI restriction endonuclease recognition site, and wherein the endonuclease is BsaI or StuI. In some alternatives, the endonuclease recognition site is inverted. In some alternatives, the polynucleotide is a linear polynucleotide. In some alternatives, the polynucleotide has only one endonuclease recognition site. In some alternatives, the polynucleotide further comprises a polymerase promoter. In some alternatives, the plurality of thymine nucleotides comprises at least one covalently linked guanine, cytosine, or an adenine, wherein the at least one covalently linked guanine, cytosine or adenine is optionally at the most 5' thymine (or 5' terminal thymine) in the plurality of thymine nucleotides. In some alternatives, the endonuclease cleavage site comprises at least one guanine, cytosine, or an adenine, wherein the endonuclease cleaves between a thymine and the at least one guanine, cytosine or adenine. In some alternatives, the polynucleotide further comprises at least one palindromic sequence, wherein the at least one palindromic sequence can form a hairpin. In some alternatives, the polynucleotide further comprises a seventh sequence, wherein the seventh sequence is capable of forming a tertiary structure such as a hairpin. In some alternatives, the sequence encoding the nuclease is optimized for expression in human cells. The method of making a polynucleotide comprising a sequence encoding a nuclease, a template strand, an endonuclease recognition site and an endonuclease cleavage site for an endonuclease inserted therein, wherein said template strand comprises a plurality of thymine nucleotides can comprise providing a first nucleic acid sequence encoding a nuclease, providing a second nucleic acid sequence comprising at least one endonuclease recognition site, providing a third nucleic acid sequence, wherein the third nucleic acid sequence comprises the template strand, wherein the template strand comprises a plurality of thymine nucleotides, wherein said plurality of thymine nucleotides comprises at least, greater than, equal to, or any number in between 20, 30, 40, 50, 60, 70, 80, 90, 100, 110, 120, 130, 140, 150, 175, 200, 225, 250, 275, 300, 325, 350, 375, 400, 425, 450, 475, 500 or 550 covalently linked thymine nucleotides and wherein the third nucleic acid comprises the endonuclease cleavage site, wherein the endonuclease cleavage site is located within the plurality of thymine nucleotides or within 1, 2, 3, 4, 5, 6, 7, 7, 8, 9, 10, 11, 12, 13, 14, 15, 16, 17, 18, 19 or 20 base pairs away from the most 5' thymine (or 5' terminal thymine) in the plurality of thymine nucleotides, joining said first nucleic acid to one end of the second nucleic acid sequence and joining said third nucleic acid sequence to one end of the second nucleic acid sequence, wherein said second nucleic acid is covalently linked to one end of said third nucleic acid sequence, and wherein the said endonuclease recognition site is located within 55 base pairs of the endonuclease cleavage site for the endonuclease and said endonuclease cleavage site is within 1 to 40 base pairs of a most 5' thymine in the plurality of thymine nucleotides. In some alternatives, the number of covalently linked thymines is greater than 120. In some alternatives, the number of covalently linked thymines is greater than 200. In some alternatives, the number of covalently linked thymines is greater than 300. In some alternatives, the at least one endonuclease recognition site is a Type II restriction endonuclease recognition site and the endonuclease is a Type II restriction endonuclease. In some alternatives, the at least one endonuclease recognition site is a Type IIS restriction endonuclease recognition site and the endonuclease is a Type IIS restriction endonuclease. In some alternatives, the at least one endonuclease recognition site is a BsaI restriction endonuclease recognition site or a StuI restriction endonuclease recognition site, and wherein the endonuclease is BsaI or StuI. In some alternatives, the endonuclease recognition site is inverted. In some alternatives, the polynucleotide is a linear polynucleotide. In some alternatives, the polynucleotide has only one endonuclease recognition site. In some alternatives, the plurality of covalently linked thymines comprises at least one guanine, cytosine, or an adenine. In some alternatives, the endonuclease cleavage site comprises at least one guanine, cytosine, or an adenine, wherein the endonuclease cleaves between a thymine and the at least one guanine, cytosine or adenine. In some alternatives, the nuclease comprises an amino acid sequence set forth in SEQ ID NO. 6 or is encoded by a nucleic acid sequence set forth in SEQ ID NO: 7-14. In some alternatives, the first nucleic acid sequence encoding the nuclease is codon optimized for expression in human cells. In some alternatives, the polynucleotide further comprises a promoter for a polymerase. In some alternatives, the polymerase is a DNA polymerase. In some alternatives, the DNA polymerase is a thermal stable polymerase, such as Taq polymerase. In some alternatives, the nucleotides are adenine, cytosine, guanine, thymine and/or uracil. In some alternatives, the method further comprises providing a set of primers. In some alternatives, the nucleic acid is DNA. In some alternatives, an RNA polymerase is used. In some alternatives, the contacting is performed at a temperature at least, greater than, equal to, or any temperature in between 30° C., 31° C., 32° C., 33° C., 34° C., 35° C., 36° C. or 37° C. In some alternatives, the contacting is performed for at least, greater than, equal to, or time in between 1, 5, 10, 20, 30, 40, 50, 60, 70, 80, 90 or 100 hours (e.g., at least, or equal to 1, 5, 10, 20, 30, 40, 50, 60, 70, 80, 90 or 100 hours or within a range defined by any two of the aforementioned times). In some alternatives, the nucleic acid is RNA. In some alternatives, the RNA comprises a plurality of adenine nucleotides, wherein the plurality of adenine nucleotides comprises at least, greater than, equal to, or any number in between 20, 30, 40, 50, 60, 70, 80, 90, 100, 110, 120, 130, 140, 150, 175, 200, 225, 250, 275, 300, 325, 350, 375, 400, 425, 450, 475, or 500 covalently linked adenines. In some alternatives, the number of covalently linked adenines is greater than 120. In some alternatives, the number of covalently linked adenines is greater than 200. In some alternatives, the number of covalently linked adenines is greater than 300. In some alternatives, the nuclease comprises an amino acid sequence set forth in SEQ ID NO. 6 or is encoded by a nucleic acid sequence set forth in SEQ ID NO: 7-14. In some alternatives, the plurality of adenine nucleotides further comprises a guanine, cytosine or a uracil, and wherein the number of covalently linked adenines terminates with a guanine, cytosine or a uracil. In some alternatives, the nucleic acid further comprises at least one palindromic sequence, wherein the at least one palindromic sequence can form a hairpin. In some alternatives, the nucleic acid further comprises a sequence capable of forming a tertiary structure such as a hairpin. In some alternatives, the method further comprises providing an endonuclease. In some alternatives, the endonuclease is a Type II restriction endonuclease. In some alternatives, the endonuclease is a Type IIS restriction endonuclease. In some alternatives, the endonuclease is BsaI or StuI. In some alternatives, the endonuclease cleavage site is located 1, 2, 3, 4, 5, 6, 7, 7, 8, 9, 10, 11, 12, 13, 14, 15, 16, 17, 18, 19 or 20 base pairs away from the most 5' thymine (or 5' terminal thymine) in the plurality of thymine nucleotides. In some alternatives, the endonuclease cleavage site is located 1, 2, 3, 4, 5, 6, 7, 7, 8, 9 or 10 base pairs away from the most 5' thymine (or 5' terminal thymine) in the plurality of thymine nucleotides.

In some alternatives, a method of stabilizing translation of an RNA encoding a nuclease during in vitro translation at 30-37 degrees Celsius for at least 100 hours (e.g., at least, or equal to 1, 5, 10, 20, 30, 40, 50, 60, 70, 80, 90 or 100 hours or within a range defined by any two of the aforementioned times) is provided. The method can comprise providing the nucleic acid of any of the alternatives herein or a nucleic acid manufactured by a method of any one of the alternatives herein and contacting said nucleic acid with a ribosome and tRNAs in the presence of amino acids, wherein said RNA is stable at 30-37 degrees Celsius for at least 100 hours (e.g., at least, or equal to 1, 5, 10, 20, 30, 40, 50, 60, 70, 80, 90 or 100 hours or within a range defined by any two of the aforementioned times). The method of making the nucleic acid can comprise providing the polynucleotide of any one of the alternatives herein or a polynucleotide manufactured by a method of any one of the alternatives herein and contacting said nucleic acid with a ribosome, in the presence of amino acids and tRNAs, wherein said RNA is stable at 30-37 degrees Celsius for at least 100 hours (e.g., at least, or equal to 1, 5, 10, 20, 30, 40, 50, 60, 70, 80, 90 or 100 hours or within a range defined by any two of the aforementioned times). The polynucleotide can comprise a first nucleic acid sequence encoding a nuclease, a second nucleic acid sequence comprising at least one restriction endonuclease recognition site and a third nucleic acid sequence, wherein the third nucleic acid sequence comprises the template strand, wherein said plurality of thymine nucleotides comprises at least, greater than, equal to, or any number in between 20, 30, 40, 50, 60, 70, 80, 90, 100, 110, 120, 130, 140, 150, 175, 200, 225, 250, 275, 300, 325, 350, 375, 400, 425, 450, 475, 500 or 550 covalently linked thymine nucleotides and wherein the third nucleic acid comprises the restriction endonuclease cleavage site, wherein the restriction endonuclease cleavage site is located within the plurality of thymine nucleotides or within 1, 2, 3, 4, 5, 6, 7, 7, 8, 9, 10, 11, 12, 13, 14, 15, 16, 17, 18, 19 or 20 base pairs away from the most 5' thymine (or 5' terminal thymine) in the plurality of thymine nucleotides and wherein said second nucleic acid is covalently linked to one end of said third nucleic acid sequence, and wherein the said restriction endonuclease recognition site is located within 55 base pairs of the restriction endonuclease cleavage site for the restriction endonuclease and said restriction endonuclease cleavage site is within 1 to 40 base pairs of a most 5' thymine in the plurality of thymine nucleotides. Some polynucleotides comprise a first nucleic acid sequence comprising at least one restriction endonuclease recognition site and a second nucleic acid sequence, wherein the second nucleic acid sequence comprises the template strand, wherein the template strand comprises a plurality of thymine nucleotides, wherein said plurality of thymine nucleotides comprises at least, greater than, equal to, or any number in between 20, 30, 40, 50, 60, 70, 80, 90, 100, 110, 120, 130, 140, 150, 175, 200, 225, 250, 275, 300, 325, 350, 375, 400, 425, 450, 475, 500 or 550 covalently linked thymine nucleotides, wherein the second nucleic acid comprises the restriction endonuclease cleavage site, and wherein the restriction endonuclease cleavage site is within the plurality of thymine nucleotides or within 1, 2, 3, 4, 5, 6, 7, 7, 8, 9, 10, 11, 12, 13, 14, 15, 16, 17, 18, 19 or 20 base pairs away from the most 5' thymine (or 5' terminal thymine) in the plurality of thymine nucleotides and wherein said first nucleic acid is covalently linked to said second nucleic acid at one end of said second nucleic acid, and wherein the said restriction endonuclease recognition site is located within 1-55 base pairs such as, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54 or 55 base pairs, of the restriction endonuclease cleavage site for the restriction endonuclease and said restriction endonuclease cleavage site is within 1 to 40 base pairs, such as 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 base pairs, of a most 5' thymine (or 5' terminal thymine) in the plurality of thymine nucleotides. In some alternatives, the polynucleotide further comprises telomeres. In some alternatives, the polynucleotide comprises a left arm wherein the left arm comprises a left telomere, a right arm wherein the right arm comprises a right telomere and a cloning region located between the left arm and the right arm. In some alternatives, the nuclease comprises an amino acid sequence set forth in SEQ ID NO. 6 or is encoded by a nucleic acid sequence set forth in SEQ ID NO: 7-14. In some alternatives, the number of covalently linked thymines is greater than 120. In some alternatives, the number of covalently linked thymines is greater than 200. In some alternatives, the number of covalently linked thymines is greater than 300. In some alternatives, the at least one endonuclease recognition site is a Type II restriction endonuclease recognition site, and the endonuclease is a Type II restriction endonuclease. In some alternatives, the at least one endonuclease recognition site is a Type IIS restriction endonuclease recognition site and wherein the endonuclease is a Type IIS restriction endonuclease. In some alternatives, the at least one endonuclease recognition site is a BsaI restriction endonuclease recognition site or a StuI restriction endonuclease recognition site, and wherein the endonuclease is BsaI or StuI. In some alternatives, the endonuclease recognition site is inverted. In some alternatives, the polynucleotide is a linear polynucleotide. In some alternatives, the polynucleotide has only one endonuclease recognition site. In some alternatives, the polynucleotide further comprises a polymerase promoter. In some alternatives, the plurality of thymine nucleotides comprises at least one covalently linked guanine, cytosine, or an adenine, wherein the at least one covalently linked guanine, cytosine or adenine is optionally joined to the most 5' thymine (or 5' terminal thymine) in the plurality of thymine nucleotides. In some alternatives, the endonuclease cleavage site comprises at least one guanine, cytosine, or an adenine, wherein the endonuclease cleaves between a thymine and the at least one guanine, cytosine or adenine. In some alternatives, the polynucleotide further comprises at least one palindromic sequence, wherein the at least one palindromic sequence can form a hairpin. In some alternatives, the polynucleotide further comprises a seventh sequence, wherein the seventh sequence is capable of forming a tertiary structure such as a hairpin. In some alternatives, the sequence encoding the nuclease is optimized for expression in human cells. The method of making a polynucleotide comprising a sequence encoding a nuclease, a template strand, an endonuclease recognition site and an endonuclease cleavage site for an endonuclease inserted therein, wherein said template strand comprises a plurality of thymine nucleotides can comprise providing a first nucleic acid sequence encoding a nuclease, providing a second nucleic acid sequence comprising at least one endonuclease recognition site, providing a third nucleic acid sequence, wherein the third nucleic acid sequence comprises the template strand, wherein the template strand comprises a plurality of thymine nucleotides, wherein said plurality of thymine nucleotides comprises at least, greater than, equal to, or any number in between 20, 30, 40, 50, 60, 70, 80, 90, 100, 110, 120, 130, 140, 150, 175, 200, 225, 250, 275, 300, 325, 350, 375, 400, 425, 450, 475, 500 or 550 covalently linked thymine nucleotides and wherein the third nucleic acid comprises the endonuclease cleavage site, wherein the endonuclease cleavage site is located within the plurality of thymine nucleotides or within 1, 2, 3, 4, 5, 6, 7, 7, 8, 9, 10, 11, 12, 13, 14, 15, 16, 17, 18, 19 or 20 base pairs away from the most 5' thymine (or 5' terminal thymine) in the plurality of thymine nucleotides, joining said first nucleic acid to one end of the second nucleic acid sequence and joining said third nucleic acid sequence to one end of the second nucleic acid sequence, wherein said second nucleic acid is covalently linked to one end of said third nucleic acid sequence, and wherein the said endonuclease recognition site is located within 55 base pairs of the endonuclease cleavage site for the endonuclease and said endonuclease cleavage site is within 1 to 40 base pairs of a most 5' thymine in the plurality of thymine nucleotides. Some methods of making a polynucleotide can comprise providing a first nucleic acid sequence comprising at least one endonuclease recognition site, providing a second nucleic acid sequence, wherein said plurality of thymine nucleotides comprises at least, greater than, equal to, or any number in between 20, 30, 40, 50, 60, 70, 80, 90, 100, 110, 120, 130, 140, 150, 175, 200, 225, 250, 275, 300, 325, 350, 375, 400, 425, 450, 475, 500 or 550 covalently linked thymine nucleotides and wherein the second nucleic acid comprises the endonuclease cleavage site, wherein the endonuclease cleavage site is within the plurality of thymine nucleotides or within 1, 2, 3, 4, 5, 6, 7, 7, 8, 9, 10, 11, 12, 13, 14, 15, 16, 17, 18, 19 or 20 base pairs away from the most 5' thymine (or 5' terminal thymine) in the plurality of thymine nucleotides and joining said first nucleic acid sequence to said second nucleic acid sequence, wherein said first nucleic acid is covalently linked to said second nucleic acid at one end, and wherein the said endonuclease recognition site is located within 1 to 55 base pairs, such as 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54 or 55 base pairs, of the endonuclease cleavage site for the endonuclease and said endonuclease cleavage site is within 1 to 40 base pairs such as, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 base pairs, of a most 5' thymine or 5' terminal thymine in the plurality of thymine nucleotides or within 1, 2, 3, 4, 5, 6, 7, 7, 8, 9, 10, 11, 12, 13, 14, 15, 16, 17, 18, 19 or 20 base pairs away from the most 5' thymine (or 5' terminal thymine) in the plurality of thymine nucleotides. In some alternatives, the number of covalently linked thymines is greater than 120. In some alternatives, the number of covalently linked thymines is greater than 200. In some alternatives, the number of covalently linked thymines is greater than 300. In some alternatives, the at least one endonuclease recognition site is a Type II restriction endonuclease recognition site and the endonuclease is a Type II restriction endonuclease. In some alternatives, the at least one endonuclease recognition site is a Type IIS restriction endonuclease recognition site and the endonuclease is a Type IIS restriction endonuclease. In some alternatives, the at least one endonuclease recognition site is a BsaI restriction endonuclease recognition site or a StuI restriction endonuclease recognition site, and wherein the endonuclease is BsaI or StuI. In some alternatives, the endonuclease recognition site is inverted. In some alternatives, the polynucleotide is a linear polynucleotide. In some alternatives, the polynucleotide has only one endonuclease recognition site. In some alternatives, the plurality of covalently linked thymines comprises at least one guanine, cytosine, or an adenine. In some alternatives, the endonuclease cleavage site comprises at least one guanine, cytosine, or an adenine, wherein the endonuclease cleaves between a thymine and the at least one guanine, cytosine or adenine. In some alternatives, the nuclease comprises an amino acid sequence set forth in SEQ ID NO. 6 or is encoded by a nucleic acid sequence set forth in SEQ ID NO: 7-14. In some alternatives, the first nucleic acid sequence encoding the nuclease is codon optimized for expression in human cells. In some alternatives, the polynucleotide further comprises a promoter for a polymerase. In some alternatives, the polymerase is a DNA polymerase. In some alternatives, the DNA polymerase is a thermal stable polymerase, such as Taq polymerase. In some alternatives, the nucleotides are adenine, cytosine, guanine, thymine and/or uracil. In some alternatives, the method further comprises providing a set of primers. In some alternatives, the nucleic acid is DNA. In some alternatives, an RNA polymerase is used. In some alternatives, the contacting is performed at a temperature at least, greater than, equal to, or any temperature in between 30° C., 31° C., 32° C., 33° C., 34° C., 35° C., 36° C. or 37° C. In some alternatives, the contacting is performed for at least, greater than, equal to, or time in between 1, 5, 10, 20, 30, 40, 50, 60, 70, 80, 90 or 100 hours (e.g., at least, or equal to 1, 5, 10, 20, 30, 40, 50, 60, 70, 80, 90 or 100 hours or within a range defined by any two of the aforementioned times). In some alternatives, the nucleic acid is RNA. In some alternatives, the RNA comprises a plurality of adenine nucleotides, wherein the plurality of adenine nucleotides comprises at least, greater than, equal to, or any number in between 20, 30, 40, 50, 60, 70, 80, 90, 100, 110, 120, 130, 140, 150, 175, 200, 225, 250, 275, 300, 325, 350, 375, 400, 425, 450, 475, or 500 covalently linked adenines. In some alternatives, the number of covalently linked adenines is greater than 120. In some alternatives, the number of covalently linked adenines is greater than 200. In some alternatives, the number of covalently linked adenines is greater than 300. In some alternatives, the nuclease comprises an amino acid sequence set forth in SEQ ID NO. 6 or is encoded by a nucleic acid sequence set forth in SEQ ID NO: 7-14. In some alternatives, the plurality of adenine nucleotides further comprises a guanine, cytosine or a uracil, and wherein the number of covalently linked adenines terminates with a guanine, cytosine or a uracil. In some alternatives, the nucleic acid further comprises at least one palindromic sequence, wherein the at least one palindromic sequence can form a hairpin. In some alternatives, the nucleic acid further comprises a sequence capable of forming a tertiary structure such as a hairpin. In some alternatives, the method further comprises providing an endonuclease. In some alternatives, the endonuclease is a Type II restriction endonuclease. In some alternatives, the endonuclease is a Type IIS restriction endonuclease. In some alternatives, the endonuclease is BsaI or StuI. In some alternatives, the nucleic acid further comprises an RNA polymerase promoter. In some alternatives, the contacting is performed at a temperature equal to 37° C. In some alternatives, the contacting is performed for at least, greater than, equal to, or time in between 1, 5, 10, 20, 30, 40, 50, 60, 70, 80, 90 or 100 hours. In some alternatives, the nucleic acid comprises a plurality of adenines, wherein the plurality of adenines comprises at least, greater than, equal to, or any number in between 20, 30, 40, 50, 60, 70, 80, 90, 100, 110, 120, 130, 140, 150, 175, 200, 225, 250, 275, 300, 325, 350, 375, 400, 425, 450, 475, or 500 covalently linked adenines. In some alternatives, the number of covalently linked adenines is greater than 120. In some alternatives, the number of covalently linked adenines is greater than 200. In some alternatives, the number of covalently linked adenines is greater than 300. In some alternatives, the nuclease comprises an amino acid sequence set forth in SEQ ID NO. 6 or is encoded by a nucleic acid sequence set forth in SEQ ID NO: 7-14. In some alternatives, the plurality of adenine nucleotides further comprises a guanine, cytosine or a uracil, and wherein the number of covalently linked adenines terminates with a guanine, cytosine or a uracil. In some alternatives, the nucleic acid further comprises at least one palindromic sequence, wherein the at least one palindromic sequence can form a hairpin. In some alternatives, the nucleic acid further comprises a sequence capable of forming a tertiary structure such as a hairpin. In some alternatives, the endonuclease cleavage site is located 1, 2, 3, 4, 5, 6, 7, 7, 8, 9, 10, 11, 12, 13, 14, 15, 16, 17, 18, 19 or 20 base pairs away from the most 5' thymine (or 5' terminal thymine) in the plurality of thymine nucleotides. In some alternatives, the endonuclease cleavage site is located 1, 2, 3, 4, 5, 6, 7, 7, 8, 9 or 10 base pairs away from the most 5' thymine (or 5' terminal thymine) in the plurality of thymine nucleotides.

In some alternatives, a method of stabilizing translation of an RNA encoding a nuclease during in vivo translation at 30-37 degrees Celsius for at least 100 hours (e.g., at least, or equal to 1, 5, 10, 20, 30, 40, 50, 60, 70, 80, 90 or 100 hours or within a range defined by any two of the aforementioned times) is provided. The method can comprise transfecting into a cell the nucleic acid of any of the alternatives herein or a nucleic acid manufactured by a method of any of the alternatives herein, placing the cell into a culture vessel with media, supplying the cell with nutrients and amino acids for translation and incubating the cell for at least, greater than, equal to, or time in between 1, 5, 10, 20, 30, 40, 50, 60, 70, 80, 90 or 100 hours (e.g., at least, or equal to 1, 5, 10, 20, 30, 40, 50, 60, 70, 80, 90 or 100 hours or within a range defined by any two of the aforementioned times) to allow translation. The method for manufacturing the nucleic acid comprises providing the polynucleotide of any one of the alternatives herein or a polynucleotide manufactured by a method of any one of the alternatives herein and contacting said polynucleotide with a polymerase in the presence of nucleotides. The polynucleotide can comprise a first nucleic acid sequence encoding a nuclease, a second nucleic acid sequence comprising at least one restriction endonuclease recognition site and a third nucleic acid sequence, wherein the third nucleic acid sequence comprises the template strand, wherein said plurality of thymine nucleotides comprises at least, greater than, equal to, or any number in between 20, 30, 40, 50, 60, 70, 80, 90, 100, 110, 120, 130, 140, 150, 175, 200, 225, 250, 275, 300, 325, 350, 375, 400, 425, 450, 475, 500 or 550 covalently linked thymine nucleotides and wherein the third nucleic acid comprises the restriction endonuclease cleavage site, wherein the restriction endonuclease cleavage site is located within the plurality of thymine nucleotides or within 1, 2, 3, 4, 5, 6, 7, 7, 8, 9, 10, 11, 12, 13, 14, 15, 16, 17, 18, 19 or 20 base pairs away from the most 5' thymine (or 5' terminal thymine) in the plurality of thymine nucleotides and wherein said second nucleic acid is covalently linked to one end of said third nucleic acid sequence, and wherein the said restriction endonuclease recognition site is located within 55 base pairs of the restriction endonuclease cleavage site for the restriction endonuclease and said restriction endonuclease cleavage site is within 1 to 40 base pairs of a most 5' thymine in the plurality of thymine nucleotides. Some polynucleotides comprise a first nucleic acid sequence comprising at least one restriction endonuclease recognition site and a second nucleic acid sequence, wherein the second nucleic acid sequence comprises the template strand, wherein the template strand comprises a plurality of thymine nucleotides, wherein said plurality of thymine nucleotides comprises at least, greater than, equal to, or any number in between 20, 30, 40, 50, 60, 70, 80, 90, 100, 110, 120, 130, 140, 150, 175, 200, 225, 250, 275, 300, 325, 350, 375, 400, 425, 450, 475, 500 or 550 covalently linked thymine nucleotides, wherein the second nucleic acid comprises the restriction endonuclease cleavage site, and wherein the restriction endonuclease cleavage site is within the plurality of thymine nucleotides or within 1, 2, 3, 4, 5, 6, 7, 7, 8, 9, 10, 11, 12, 13, 14, 15, 16, 17, 18, 19 or 20 base pairs away from the most 5' thymine (or 5' terminal thymine) in the plurality of thymine nucleotides and wherein said first nucleic acid is covalently linked to said second nucleic acid at one end of said second nucleic acid, and wherein the said restriction endonuclease recognition site is located within 1-55 base pairs such as, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54 or 55 base pairs, of the restriction endonuclease cleavage site for the restriction endonuclease and said restriction endonuclease cleavage site is within 1 to 40 base pairs, such as 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 base pairs, of a most 5' thymine (or 5' terminal thymine) in the plurality of thymine nucleotides. In some alternatives, the polynucleotide further comprises telomeres. In some alternatives, the polynucleotide comprises a left arm wherein the left arm comprises a left telomere, a right arm wherein the right arm comprises a right telomere and a cloning region located between the left arm and the right arm. In some alternatives, the nuclease comprises an amino acid sequence set forth in SEQ ID NO. 6 or is encoded by a nucleic acid sequence set forth in SEQ ID NO: 7-14. In some alternatives, the number of covalently linked thymines is greater than 120. In some alternatives, the number of covalently linked thymines is greater than 200. In some alternatives, the number of covalently linked thymines is greater than 300. In some alternatives, the at least one endonuclease recognition site is a Type II restriction endonuclease recognition site, and the endonuclease is a Type II restriction endonuclease. In some alternatives, the at least one endonuclease recognition site is a Type IIS restriction endonuclease recognition site and wherein the endonuclease is a Type IIS restriction endonuclease. In some alternatives, the at least one endonuclease recognition site is a BsaI restriction endonuclease recognition site or a StuI restriction endonuclease recognition site, and wherein the endonuclease is BsaI or StuI. In some alternatives, the endonuclease recognition site is inverted. In some alternatives, the polynucleotide is a linear polynucleotide. In some alternatives, the polynucleotide has only one endonuclease recognition site. In some alternatives, the polynucleotide further comprises a polymerase promoter. In some alternatives, the plurality of thymine nucleotides comprises at least one covalently linked guanine, cytosine, or an adenine, wherein the at least one covalently linked guanine, cytosine or adenine is optionally at the most 5' thymine (or 5' terminal thymine) in the plurality of thymine nucleotides. In some alternatives, the endonuclease cleavage site comprises at least one guanine, cytosine, or an adenine, wherein the endonuclease cleaves between a thymine and the at least one guanine, cytosine or adenine. In some alternatives, the polynucleotide further comprises at least one palindromic sequence, wherein the at least one palindromic sequence can form a hairpin. In some alternatives, the polynucleotide further comprises a seventh sequence, wherein the seventh sequence is capable of forming a tertiary structure such as a hairpin. In some alternatives, the sequence encoding the nuclease is optimized for expression in human cells. The method of making a polynucleotide comprising a sequence encoding a nuclease, a template strand, an endonuclease recognition site and an endonuclease cleavage site for an endonuclease inserted therein, wherein said template strand comprises a plurality of thymine nucleotides can comprise providing a first nucleic acid sequence encoding a nuclease, providing a second nucleic acid sequence comprising at least one endonuclease recognition site, providing a third nucleic acid sequence, wherein the third nucleic acid sequence comprises the template strand, wherein the template strand comprises a plurality of thymine nucleotides, wherein said plurality of thymine nucleotides comprises at least, greater than, equal to, or any number in between 20, 30, 40, 50, 60, 70, 80, 90, 100, 110, 120, 130, 140, 150, 175, 200, 225, 250, 275, 300, 325, 350, 375, 400, 425, 450, 475, 500 or 550 covalently linked thymine nucleotides and wherein the third nucleic acid comprises the endonuclease cleavage site, wherein the endonuclease cleavage site is located within the plurality of thymine nucleotides or within 1, 2, 3, 4, 5, 6, 7, 7, 8, 9, 10, 11, 12, 13, 14, 15, 16, 17, 18, 19 or 20 base pairs away from the most 5' thymine (or 5' terminal thymine) in the plurality of thymine nucleotides, joining said first nucleic acid to one end of the second nucleic acid sequence and joining said third nucleic acid sequence to one end of the second nucleic acid sequence, wherein said second nucleic acid is covalently linked to one end of said third nucleic acid sequence, and wherein the said endonuclease recognition site is located within 55 base pairs of the endonuclease cleavage site for the endonuclease and said endonuclease cleavage site is within 1 to 40 base pairs of a most 5' thymine in the plurality of thymine nucleotides. Some methods of making a polynucleotide can comprise providing a first nucleic acid sequence comprising at least one endonuclease recognition site, providing a second nucleic acid sequence, wherein said plurality of thymine nucleotides comprises at least, greater than, equal to, or any number in between 20, 30, 40, 50, 60, 70, 80, 90, 100, 110, 120, 130, 140, 150, 175, 200, 225, 250, 275, 300, 325, 350, 375, 400, 425, 450, 475, 500 or 550 covalently linked thymine nucleotides and wherein the second nucleic acid comprises the endonuclease cleavage site, wherein the endonuclease cleavage site is within the plurality of thymine nucleotides or within 1, 2, 3, 4, 5, 6, 7, 7, 8, 9, 10, 11, 12, 13, 14, 15, 16, 17, 18, 19 or 20 base pairs away from the most 5' thymine (or 5' terminal thymine) in the plurality of thymine nucleotides and joining said first nucleic acid sequence to said second nucleic acid sequence, wherein said first nucleic acid is covalently linked to said second nucleic acid at one end, and wherein the said endonuclease recognition site is located within 1 to 55 base pairs, such as 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54 or 55 base pairs, of the endonuclease cleavage site for the endonuclease and said endonuclease cleavage site is within 1 to 40 base pairs such as, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 base pairs, of a most 5' thymine (or 5' terminal thymine) in the plurality of thymine nucleotides or within 1, 2, 3, 4, 5, 6, 7, 7, 8, 9, 10, 11, 12, 13, 14, 15, 16, 17, 18, 19 or 20 base pairs away from the most 5' thymine (or 5' terminal thymine) in the plurality of thymine nucleotides. In some alternatives, the number of covalently linked thymines is greater than 120. In some alternatives, the number of covalently linked thymines is greater than 200. In some alternatives, the number of covalently linked thymines is greater than 300. In some alternatives, the at least one endonuclease recognition site is a Type II restriction endonuclease recognition site and the endonuclease is a Type II restriction endonuclease. In some alternatives, the at least one endonuclease recognition site is a Type IIS restriction endonuclease recognition site and the endonuclease is a Type IIS restriction endonuclease. In some alternatives, the at least one endonuclease recognition site is a BsaI restriction endonuclease recognition site or a StuI restriction endonuclease recognition site, and wherein the endonuclease is BsaI or StuI. In some alternatives, the endonuclease recognition site is inverted. In some alternatives, the polynucleotide is a linear polynucleotide. In some alternatives, the polynucleotide has only one endonuclease recognition site. In some alternatives, the plurality of covalently linked thymines comprises at least one guanine, cytosine, or an adenine. In some alternatives, the endonuclease cleavage site comprises at least one guanine, cytosine, or an adenine, wherein the endonuclease cleaves between a thymine and the at least one guanine, cytosine or adenine. In some alternatives, the nuclease comprises an amino acid sequence set forth in SEQ ID NO. 6 or is encoded by a nucleic acid sequence set forth in SEQ ID NO: 7-14. In some alternatives, the first nucleic acid sequence encoding the nuclease is codon optimized for expression in human cells. In some alternatives, the polynucleotide further comprises a promoter for a polymerase. In some alternatives, the polymerase is a DNA polymerase. In some alternatives, the DNA polymerase is a thermal stable polymerase, such as Taq polymerase. In some alternatives, the nucleotides are adenine, cytosine, guanine, thymine and/or uracil. In some alternatives, the method further comprises providing a set of primers. In some alternatives, the nucleic acid is DNA. In some alternatives, an RNA polymerase is used. In some alternatives, the contacting is performed at a temperature at least, greater than, equal to, or any temperature in between 30° C., 31° C., 32° C., 33° C., 34° C., 35° C., 36° C. or 37° C. In some alternatives, the contacting is performed for at least, greater than, equal to, or time in between 1, 5, 10, 20, 30, 40, 50, 60, 70, 80, 90 or 100 hours (e.g., at least, or equal to 1, 5, 10, 20, 30, 40, 50, 60, 70, 80, 90 or 100 hours or within a range defined by any two of the aforementioned times). In some alternatives, the nucleic acid is RNA. In some alternatives, the RNA comprises a plurality of adenine nucleotides, wherein the plurality of adenine nucleotides comprises at least, greater than, equal to, or any number in between 20, 30, 40, 50, 60, 70, 80, 90, 100, 110, 120, 130, 140, 150, 175, 200, 225, 250, 275, 300, 325, 350, 375, 400, 425, 450, 475, or 500 covalently linked adenines. In some alternatives, the number of covalently linked adenines is greater than 120. In some alternatives, the number of covalently linked adenines is greater than 200. In some alternatives, the number of covalently linked adenines is greater than 300. In some alternatives, the nuclease comprises an amino acid sequence set forth in SEQ ID NO. 6 or is encoded by a nucleic acid sequence set forth in SEQ ID NO: 7-14. In some alternatives, the plurality of adenine nucleotides further comprises a guanine, cytosine or a uracil, and wherein the number of covalently linked adenines terminates with a guanine, cytosine or a uracil. In some alternatives, the nucleic acid further comprises at least one palindromic sequence, wherein the at least one palindromic sequence can form a hairpin. In some alternatives, the nucleic acid further comprises a sequence capable of forming a tertiary structure such as a hairpin. In some alternatives, the method further comprises providing an endonuclease. In some alternatives, the endonuclease is a Type II restriction endonuclease. In some alternatives, the endonuclease is a Type IIS restriction endonuclease. In some alternatives, the endonuclease is BsaI or StuI. In some alternatives, the cell is a human cell. In some alternatives, the cell is selected from a group consisting of primary cells, human primary T cells, CD4+ cells and CD8+ cells. In some alternatives, the endonuclease cleavage site is located 1, 2, 3, 4, 5, 6, 7, 7, 8, 9, 10, 11, 12, 13, 14, 15, 16, 17, 18, 19 or 20 base pairs away from the most 5' thymine (or 5' terminal thymine) in the plurality of thymine nucleotides. In some alternatives, the endonuclease cleavage site is located 1, 2, 3, 4, 5, 6, 7, 7, 8, 9 or 10 base pairs away from the most 5' thymine (or 5' terminal thymine) in the plurality of thymine nucleotides.

In some alternatives, a method of expression of a nuclease or increasing expression of a nuclease is provided. The method can comprise generating an mRNA from the polynucleotide of any one of the alternatives herein or a polynucleotide manufactured by a method of any one of any one of the alternatives herein and translating said mRNA into a peptide. The polynucleotide can comprise a first nucleic acid sequence encoding a nuclease, a second nucleic acid sequence comprising at least one restriction endonuclease recognition site and a third nucleic acid sequence, wherein the third nucleic acid sequence comprises the template strand, wherein said plurality of thymine nucleotides comprises at least, greater than, equal to, or any number in between 20, 30, 40, 50, 60, 70, 80, 90, 100, 110, 120, 130, 140, 150, 175, 200, 225, 250, 275, 300, 325, 350, 375, 400, 425, 450, 475, 500 or 550 covalently linked thymine nucleotides and wherein the third nucleic acid comprises the restriction endonuclease cleavage site, wherein the restriction endonuclease cleavage site is located within the plurality of thymine nucleotides or within 1, 2, 3, 4, 5, 6, 7, 7, 8, 9, 10, 11, 12, 13, 14, 15, 16, 17, 18, 19 or 20 base pairs away from the most 5' thymine (or 5' terminal thymine) in the plurality of thymine nucleotides and wherein said second nucleic acid is covalently linked to one end of said third nucleic acid sequence, and wherein the said restriction endonuclease recognition site is located within 55 base pairs of the restriction endonuclease cleavage site for the restriction endonuclease and said restriction endonuclease cleavage site is within 1 to 40 base pairs of a most 5' thymine in the plurality of thymine nucleotides. Some polynucleotides comprise a first nucleic acid sequence comprising at least one restriction endonuclease recognition site and a second nucleic acid sequence, wherein the second nucleic acid sequence comprises the template strand, wherein the template strand comprises a plurality of thymine nucleotides, wherein said plurality of thymine nucleotides comprises at least, greater than, equal to, or any number in between 20, 30, 40, 50, 60, 70, 80, 90, 100, 110, 120, 130, 140, 150, 175, 200, 225, 250, 275, 300, 325, 350, 375, 400, 425, 450, 475, 500 or 550 covalently linked thymine nucleotides, wherein the second nucleic acid comprises the restriction endonuclease cleavage site, and wherein the restriction endonuclease cleavage site is within the plurality of thymine nucleotides or within 1, 2, 3, 4, 5, 6, 7, 7, 8, 9, 10, 11, 12, 13, 14, 15, 16, 17, 18, 19 or 20 base pairs away from the most 5' thymine (or 5' terminal thymine) in the plurality of thymine nucleotides and wherein said first nucleic acid is covalently linked to said second nucleic acid at one end of said second nucleic acid, and wherein the said restriction endonuclease recognition site is located within 1-55 base pairs such as, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54 or 55 base pairs, of the restriction endonuclease cleavage site for the restriction endonuclease and said restriction endonuclease cleavage site is within 1 to 40 base pairs, such as 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 base pairs, of a most 5' thymine (or 5' terminal thymine) in the plurality of thymine nucleotides. In some alternatives, the polynucleotide further comprises telomeres. In some alternatives, the polynucleotide comprises a left arm wherein the left arm comprises a left telomere, a right arm wherein the right arm comprises a right telomere and a cloning region located between the left arm and the right arm. In some alternatives, the nuclease comprises an amino acid sequence set forth in SEQ ID NO. 6 or is encoded by a nucleic acid sequence set forth in SEQ ID NO: 7-14. In some alternatives, the number of covalently linked thymines is greater than 120. In some alternatives, the number of covalently linked thymines is greater than 200. In some alternatives, the number of covalently linked thymines is greater than 300. In some alternatives, the at least one endonuclease recognition site is a Type II restriction endonuclease recognition site, and the endonuclease is a Type II restriction endonuclease. In some alternatives, the at least one endonuclease recognition site is a Type IIS restriction endonuclease recognition site and wherein the endonuclease is a Type IIS restriction endonuclease. In some alternatives, the at least one endonuclease recognition site is a BsaI restriction endonuclease recognition site or a StuI restriction endonuclease recognition site, and wherein the endonuclease is BsaI or StuI. In some alternatives, the endonuclease recognition site is inverted. In some alternatives, the polynucleotide is a linear polynucleotide. In some alternatives, the polynucleotide has only one endonuclease recognition site. In some alternatives, the polynucleotide further comprises a polymerase promoter. In some alternatives, the plurality of thymine nucleotides comprises at least one covalently linked guanine, cytosine, or an adenine, wherein the at least one covalently linked guanine, cytosine or adenine is optionally at the most 5' thymine (or 5' terminal thymine) in the plurality of thymine nucleotides. In some alternatives, the endonuclease cleavage site comprises at least one guanine, cytosine, or an adenine, wherein the endonuclease cleaves between a thymine and the at least one guanine, cytosine or adenine. In some alternatives, the polynucleotide further comprises at least one palindromic sequence, wherein the at least one palindromic sequence can form a hairpin. In some alternatives, the polynucleotide further comprises a seventh sequence, wherein the seventh sequence is capable of forming a tertiary structure such as a hairpin. In some alternatives, the sequence encoding the nuclease is optimized for expression in human cells. The method of making a polynucleotide comprising a sequence encoding a nuclease, a template strand, an endonuclease recognition site and an endonuclease cleavage site for an endonuclease inserted therein, wherein said template strand comprises a plurality of thymine nucleotides can comprise providing a first nucleic acid sequence encoding a nuclease, providing a second nucleic acid sequence comprising at least one endonuclease recognition site, providing a third nucleic acid sequence, wherein the third nucleic acid sequence comprises the template strand, wherein the template strand comprises a plurality of thymine nucleotides, wherein said plurality of thymine nucleotides comprises at least, greater than, equal to, or any number in between 20, 30, 40, 50, 60, 70, 80, 90, 100, 110, 120, 130, 140, 150, 175, 200, 225, 250, 275, 300, 325, 350, 375, 400, 425, 450, 475, 500 or 550 covalently linked thymine nucleotides and wherein the third nucleic acid comprises the endonuclease cleavage site, wherein the endonuclease cleavage site is located within the plurality of thymine nucleotides or within 1, 2, 3, 4, 5, 6, 7, 7, 8, 9, 10, 11, 12, 13, 14, 15, 16, 17, 18, 19 or 20 base pairs away from the most 5' thymine (or 5' terminal thymine) in the plurality of thymine nucleotides, joining said first nucleic acid to one end of the second nucleic acid sequence and joining said third nucleic acid sequence to one end of the second nucleic acid sequence, wherein said second nucleic acid is covalently linked to one end of said third nucleic acid sequence, and wherein the said endonuclease recognition site is located within 55 base pairs of the endonuclease cleavage site for the endonuclease and said endonuclease cleavage site is within 1 to 40 base pairs of a most 5' thymine in the plurality of thymine nucleotides. In some alternatives, the number of covalently linked thymines is greater than 120. In some alternatives, the number of covalently linked thymines is greater than 200. In some alternatives, the number of covalently linked thymines is greater than 300. In some alternatives, the at least one endonuclease recognition site is a Type II restriction endonuclease recognition site and the endonuclease is a Type II restriction endonuclease. In some alternatives, the at least one endonuclease recognition site is a Type IIS restriction endonuclease recognition site and the endonuclease is a Type IIS restriction endonuclease.

In some alternatives, the at least one endonuclease recognition site is a BsaI restriction endonuclease recognition site or a StuI restriction endonuclease recognition site, and wherein the endonuclease is BsaI or StuI. In some alternatives, the endonuclease recognition site is inverted. In some alternatives, the polynucleotide is a linear polynucleotide. In some alternatives, the polynucleotide has only one endonuclease recognition site. In some alternatives, the plurality of covalently linked thymines comprises at least one guanine, cytosine, or an adenine. In some alternatives, the endonuclease cleavage site comprises at least one guanine, cytosine, or an adenine, wherein the endonuclease cleaves between a thymine and the at least one guanine, cytosine or adenine. In some alternatives, the nuclease comprises an amino acid sequence set forth in SEQ ID NO. 6 or is encoded by a nucleic acid sequence set forth in SEQ ID NO: 7-14. In some alternatives, the first nucleic acid sequence encoding the nuclease is codon optimized for expression in human cells. In some alternatives, the polynucleotide further comprises a promoter for a polymerase. In some alternatives, the polymerase is a DNA polymerase. In some alternatives, the DNA polymerase is a thermal stable polymerase, such as Taq polymerase. In some alternatives, the nucleotides are adenine, cytosine, guanine, thymine and/or uracil. In some alternatives, the method further comprises providing a set of primers. In some alternatives, the nucleic acid is DNA. In some alternatives, an RNA polymerase is used. In some alternatives, the contacting is performed at a temperature at least, greater than, equal to, or any temperature in between 30° C., 31° C., 32° C., 33° C., 34° C., 35° C., 36° C. or 37° C. In some alternatives, the contacting is performed for at least, greater than, equal to, or time in between 1, 5, 10, 20, 30, 40, 50, 60, 70, 80, 90 or 100 hours (e.g., at least, or equal to 1, 5, 10, 20, 30, 40, 50, 60, 70, 80, 90 or 100 hours or within a range defined by any two of the aforementioned times). In some alternatives, the nucleic acid is RNA. In some alternatives, the RNA comprises a plurality of adenine nucleotides, wherein the plurality of adenine nucleotides comprises at least, greater than, equal to, or any number in between 20, 30, 40, 50, 60, 70, 80, 90, 100, 110, 120, 130, 140, 150, 175, 200, 225, 250, 275, 300, 325, 350, 375, 400, 425, 450, 475, or 500 covalently linked adenines. In some alternatives, the number of covalently linked adenines is greater than 120. In some alternatives, the number of covalently linked adenines is greater than 200. In some alternatives, the number of covalently linked adenines is greater than 300. In some alternatives, the nuclease comprises an amino acid sequence set forth in SEQ ID NO. 6 or is encoded by a nucleic acid sequence set forth in SEQ ID NO: 7-14. In some alternatives, the plurality of adenine nucleotides further comprises a guanine, cytosine or a uracil, and wherein the number of covalently linked adenines terminates with a guanine, cytosine or a uracil. In some alternatives, the nucleic acid further comprises at least one palindromic sequence, wherein the at least one palindromic sequence can form a hairpin. In some alternatives, the nucleic acid further comprises a sequence capable of forming a tertiary structure such as a hairpin. In some alternatives, the method further comprises providing an endonuclease. In some alternatives, the endonuclease is a Type II restriction endonuclease. In some alternatives, the endonuclease is a Type IIS restriction endonuclease. In some alternatives, the endonuclease is BsaI or StuI. In some alternatives, the polynucleotide further comprises an RNA polymerase promoter. In some alternatives, the method further comprises providing an endonuclease. In some alternatives, the endonuclease is a Type II restriction endonuclease. In some alternatives, the endonuclease is a Type IIS restriction endonuclease. In some alternatives, the endonuclease is BsaI or StuI. In some alternatives, the translating is performed at a temperature at least, greater than, equal to, or any temperature in between 30° C., 31° C., 32° C., 33° C., 34° C., 35° C., 36° C. or 37° C. In some alternatives, the translating is performed for at least, greater than, equal to, or time in between 1, 5, 10, 20, 30, 40, 50, 60, 70, 80, 90 or 100 hours (e.g., at least, or equal to 1, 5, 10, 20, 30, 40, 50, 60, 70, 80, 90 or 100 hours or within a range defined by any two of the aforementioned times). In some alternatives, the mRNA comprises a plurality of adenines, wherein the plurality of adenines comprises at least, greater than, equal to, or any number in between 20, 30, 40, 50, 60, 70, 80, 90, 100, 110, 120, 130, 140, 150, 175, 200, 225, 250, 275, 300, 325, 350, 375, 400, 425, 450, 475, or 500 covalently linked adenines. In some alternatives, the endonuclease cleavage site is located 1, 2, 3, 4, 5, 6, 7, 7, 8, 9, 10, 11, 12, 13, 14, 15, 16, 17, 18, 19 or 20 base pairs away from the most 5' thymine (or 5' terminal thymine) in the plurality of thymine nucleotides. In some alternatives, the endonuclease cleavage site is located 1, 2, 3, 4, 5, 6, 7, 7, 8, 9 or 10 base pairs away from the most 5' thymine (or 5' terminal thymine) in the plurality of thymine nucleotides.

In some alternatives, a method of replicating a gene comprising a nuclease or enhancing stability of a replicating gene comprising a nuclease, is provided. The method can comprise providing the polynucleotide of any one of the alternatives herein or a polynucleotide manufactured by a method of any one of the alternatives herein, wherein said polynucleotide comprises a gene encoding a nuclease, transforming a cell with said polynucleotide and propagating the cell, wherein the polynucleotide is replicated. The polynucleotide can comprise a first nucleic acid sequence encoding a nuclease, a second nucleic acid sequence comprising at least one restriction endonuclease recognition site and a third nucleic acid sequence, wherein the third nucleic acid sequence comprises the template strand, wherein said plurality of thymine nucleotides comprises at least, greater than, equal to, or any number in between 20, 30, 40, 50, 60, 70, 80, 90, 100, 110, 120, 130, 140, 150, 175, 200, 225, 250, 275, 300, 325, 350, 375, 400, 425, 450, 475, 500 or 550 covalently linked thymine nucleotides and wherein the third nucleic acid comprises the restriction endonuclease cleavage site, wherein the restriction endonuclease cleavage site is located within the plurality of thymine nucleotides or within 1, 2, 3, 4, 5, 6, 7, 7, 8, 9, 10, 11, 12, 13, 14, 15, 16, 17, 18, 19 or 20 base pairs away from the most 5' thymine (or 5' terminal thymine) in the plurality of thymine nucleotides and wherein said second nucleic acid is covalently linked to one end of said third nucleic acid sequence, and wherein the said restriction endonuclease recognition site is located within 55 base pairs of the restriction endonuclease cleavage site for the restriction endonuclease and said restriction endonuclease cleavage site is within 1 to 40 base pairs of a most 5' thymine (or 5' terminal thymine) in the plurality of thymine nucleotides. Some polynucleotides comprise a first nucleic acid sequence comprising at least one restriction endonuclease recognition site and a second nucleic acid sequence, wherein the second nucleic acid sequence comprises the template strand, wherein the template strand comprises a plurality of thymine nucleotides, wherein said plurality of thymine nucleotides comprises at least, greater than, equal to, or any number in between 20, 30, 40, 50, 60, 70, 80, 90, 100, 110, 120, 130, 140, 150, 175, 200, 225, 250, 275, 300, 325, 350, 375, 400, 425, 450, 475, 500 or 550 covalently linked thymine nucleotides, wherein the second nucleic acid comprises the restriction endonuclease cleavage site, and wherein the restriction endonuclease cleavage site is within the plurality of thymine nucleotides or within 1, 2, 3, 4, 5, 6, 7, 7, 8, 9, 10, 11, 12, 13, 14, 15, 16, 17, 18, 19 or 20 base pairs away from the most 5' thymine (or 5' terminal thymine) in the plurality of thymine nucleotides and wherein said first nucleic acid is covalently linked to said second nucleic acid at one end of said second nucleic acid, and wherein the said restriction endonuclease recognition site is located within 1-55 base pairs such as, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54 or 55 base pairs, of the restriction endonuclease cleavage site for the restriction endonuclease and said restriction endonuclease cleavage site is within 1 to 40 base pairs, such as 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 base pairs, of a most 5' thymine (or 5' terminal thymine) in the plurality of thymine nucleotides. In some alternatives, the polynucleotide further comprises telomeres. In some alternatives, the polynucleotide comprises a left arm wherein the left arm comprises a left telomere, a right arm wherein the right arm comprises a right telomere and a cloning region located between the left arm and the right arm. In some alternatives, the nuclease comprises an amino acid sequence set forth in SEQ ID NO. 6 or is encoded by a nucleic acid sequence set forth in SEQ ID NO: 7-14. In some alternatives, the number of covalently linked thymines is greater than 120. In some alternatives, the number of covalently linked thymines is greater than 200. In some alternatives, the number of covalently linked thymines is greater than 300. In some alternatives, the at least one endonuclease recognition site is a Type II restriction endonuclease recognition site, and the endonuclease is a Type II restriction endonuclease. In some alternatives, the at least one endonuclease recognition site is a Type IIS restriction endonuclease recognition site and wherein the endonuclease is a Type IIS restriction endonuclease. In some alternatives, the at least one endonuclease recognition site is a BsaI restriction endonuclease recognition site or a StuI restriction endonuclease recognition site, and wherein the endonuclease is BsaI or StuI. In some alternatives, the endonuclease recognition site is inverted. In some alternatives, the polynucleotide is a linear polynucleotide. In some alternatives, the polynucleotide has only one endonuclease recognition site. In some alternatives, the polynucleotide further comprises a polymerase promoter. In some alternatives, the plurality of thymine nucleotides comprises at least one covalently linked guanine, cytosine, or an adenine, wherein the at least one covalently linked guanine, cytosine or adenine is optionally at the most 5' thymine (or 5' terminal thymine) in the plurality of thymine nucleotides. In some alternatives, the endonuclease cleavage site comprises at least one guanine, cytosine, or an adenine, wherein the endonuclease cleaves between a thymine and the at least one guanine, cytosine or adenine. In some alternatives, the polynucleotide further comprises at least one palindromic sequence, wherein the at least one palindromic sequence can form a hairpin. In some alternatives, the polynucleotide further comprises a seventh sequence, wherein the seventh sequence is capable of forming a tertiary structure such as a hairpin. In some alternatives, the sequence encoding the nuclease is optimized for expression in human cells. The method of making a polynucleotide comprising a sequence encoding a nuclease, a template strand, an endonuclease recognition site and an endonuclease cleavage site for an endonuclease inserted therein, wherein said template strand comprises a plurality of thymine nucleotides can comprise providing a first nucleic acid sequence encoding a nuclease, providing a second nucleic acid sequence comprising at least one endonuclease recognition site, providing a third nucleic acid sequence, wherein the third nucleic acid sequence comprises the template strand, wherein the template strand comprises a plurality of thymine nucleotides, wherein said plurality of thymine nucleotides comprises at least, greater than, equal to, or any number in between 20, 30, 40, 50, 60, 70, 80, 90, 100, 110, 120, 130, 140, 150, 175, 200, 225, 250, 275, 300, 325, 350, 375, 400, 425, 450, 475, 500 or 550 covalently linked thymine nucleotides and wherein the third nucleic acid comprises the endonuclease cleavage site, wherein the endonuclease cleavage site is located within the plurality of thymine nucleotides or within 1, 2, 3, 4, 5, 6, 7, 7, 8, 9, 10, 11, 12, 13, 14, 15, 16, 17, 18, 19 or 20 base pairs away from the most 5' thymine (or 5' terminal thymine) in the plurality of thymine nucleotides, joining said first nucleic acid to one end of the second nucleic acid sequence and joining said third nucleic acid sequence to one end of the second nucleic acid sequence, wherein said second nucleic acid is covalently linked to one end of said third nucleic acid sequence, and wherein the said endonuclease recognition site is located within 55 base pairs of the endonuclease cleavage site for the endonuclease and said endonuclease cleavage site is within 1 to 40 base pairs of a most 5' thymine in the plurality of thymine nucleotides. In some alternatives, the number of covalently linked thymines is greater than 120. In some alternatives, the number of covalently linked thymines is greater than 200. In some alternatives, the number of covalently linked thymines is greater than 300. In some alternatives, the at least one endonuclease recognition site is a Type II restriction endonuclease recognition site and the endonuclease is a Type II restriction endonuclease. In some alternatives, the at least one endonuclease recognition site is a Type IIS restriction endonuclease recognition site and the endonuclease is a Type IIS restriction endonuclease. In some alternatives, the at least one endonuclease recognition site is a BsaI restriction endonuclease recognition site or a StuI restriction endonuclease recognition site, and wherein the endonuclease is BsaI or StuI. In some alternatives, the endonuclease recognition site is inverted. In some alternatives, the polynucleotide is a linear polynucleotide. In some alternatives, the polynucleotide has only one endonuclease recognition site. In some alternatives, the plurality of covalently linked thymines comprises at least one guanine, cytosine, or an adenine. In some alternatives, the endonuclease cleavage site comprises at least one guanine, cytosine, or an adenine, wherein the endonuclease cleaves between a thymine and the at least one guanine, cytosine or adenine. In some alternatives, the nuclease comprises an amino acid sequence set forth in SEQ ID NO. 6 or is encoded by a nucleic acid sequence set forth in SEQ ID NO: 7-14. In some alternatives, the first nucleic acid sequence encoding the nuclease is codon optimized for expression in human cells. In some alternatives, the polynucleotide further comprises a promoter for a polymerase. In some alternatives, the polymerase is a DNA polymerase. In some alternatives, the DNA polymerase is a thermal stable polymerase, such as Taq polymerase. In some alternatives, the nucleotides are adenine, cytosine, guanine, thymine and/or uracil. In some alternatives, the method further comprises providing a set of primers. In some alternatives, the nucleic acid is DNA. In some alternatives, an RNA polymerase is used. In some alternatives, the contacting is performed at a temperature at least, greater than, equal to, or any temperature in between 30° C., 31° C., 32° C., 33° C., 34° C., 35° C., 36° C. or 37° C. In some alternatives, the contacting is performed for at least, greater than, equal to, or time in between 1, 5, 10, 20, 30, 40, 50, 60, 70, 80, 90 or 100 hours (e.g., at least, or equal to 1, 5, 10, 20, 30, 40, 50, 60, 70, 80, 90 or 100 hours or within a range defined by any two of the aforementioned times). In some alternatives, the nucleic acid is RNA. In some alternatives, the RNA comprises a plurality of adenine nucleotides, wherein the plurality of adenine nucleotides comprises at least, greater than, equal to, or any number in between 20, 30, 40, 50, 60, 70, 80, 90, 100, 110, 120, 130, 140, 150, 175, 200, 225, 250, 275, 300, 325, 350, 375, 400, 425, 450, 475, or 500 covalently linked adenines. In some alternatives, the number of covalently linked adenines is greater than 120. In some alternatives, the number of covalently linked adenines is greater than 200. In some alternatives, the number of covalently linked adenines is greater than 300. In some alternatives, the nuclease comprises an amino acid sequence set forth in SEQ ID NO. 6 or is encoded by a nucleic acid sequence set forth in SEQ ID NO: 7-14. In some alternatives, the plurality of adenine nucleotides further comprises a guanine, cytosine or a uracil, and wherein the number of covalently linked adenines terminates with a guanine, cytosine or a uracil. In some alternatives, the nucleic acid further comprises at least one palindromic sequence, wherein the at least one palindromic sequence can form a hairpin. In some alternatives, the nucleic acid further comprises a sequence capable of forming a tertiary structure such as a hairpin. In some alternatives, the method further comprises providing an endonuclease. In some alternatives, the endonuclease is a Type II restriction endonuclease. In some alternatives, the endonuclease is a Type IIS restriction endonuclease. In some alternatives, the endonuclease is BsaI or StuI. In some alternatives, the cell is propagated for 1 day, 2 days, 4 days, 6 days, 8 days, 10 days, 12 days, or 14 days, or any other times between these values. In some alternatives, the cell is propagated at 30° C., 31° C., 32° C., 33° C., 34° C., 35° C., 36° C., or 37° C. or any other temperature between any these values. In some alternatives, the nuclease comprises an amino acid sequence set forth in SEQ ID NO. 6 or is encoded by a nucleic acid sequence set forth in SEQ ID NO: 7-14. In some alternatives, the cell is a human cell. In some alternatives, the cell is selected from a group consisting of primary cells, human primary T cells, CD4+ cells and CD8+ cells. In some alternatives, the endonuclease cleavage site is located 1, 2, 3, 4, 5, 6, 7, 7, 8, 9, 10, 11, 12, 13, 14, 15, 16, 17, 18, 19 or 20 base pairs away from the most 5' thymine (or 5' terminal thymine) in the plurality of thymine nucleotides. In some alternatives, the endonuclease cleavage site is located 1, 2, 3, 4, 5, 6, 7, 7, 8, 9 or 10 base pairs away from the most 5' thymine (or 5' terminal thymine) in the plurality of thymine nucleotides.

In some alternatives, an RNA having a plurality of adenine nucleotides, is provided. The RNA can comprise a first sequence comprising at least one compliment sequence to an endonuclease recognition site covalently linked to a plurality of adenine nucleotides at the 3' end of said plurality of adenine nucleotides, a second sequence that comprises a plurality of adenine nucleotides, wherein the plurality of adenines comprises at least, greater than, equal to, or any number in between 20, 30, 40, 50, 60, 70, 80, 90, 100, 110, 120, 130, 140, 150, 175, 200, 225, 250, 275, 300, 325, 350, 375, 400, 425, 450, 475, or 500 covalently linked adenines and wherein said compliment sequence to an endonuclease recognition site of said first nucleic acid is covalently linked to said plurality of adenine nucleotides of said second nucleic acid at the 3' end of said plurality of adenine nucleotides of said second nucleic acid. In some alternatives, the mRNA further encodes a gene. In some alternatives, the gene is an endonuclease gene. In some alternatives, the at least one endonuclease site is inverted, and wherein the sequence encoding an RNA compliment is a compliment to the inverted endonuclease site. In some alternatives, the at least one endonuclease is a Type II restriction endonuclease recognition site. In some alternatives, the at least one endonuclease site is a Type IIS restriction endonuclease recognition site. In some alternatives, the at least one endonuclease site is a BsaI recognition site or a StuI recognition site. In some alternatives, the gene is codon optimized for expression in a human cell. In some alternatives, the endonuclease cleavage site is located 1, 2, 3, 4, 5, 6, 7, 7, 8, 9, 10, 11, 12, 13, 14, 15, 16, 17, 18, 19 or 20 base pairs away from the most 5' thymine (or 5' terminal thymine) in the plurality of thymine nucleotides. In some alternatives, the endonuclease cleavage site is located 1, 2, 3, 4, 5, 6, 7, 7, 8, 9 or 10 base pairs away from the most 5' thymine (or 5' terminal thymine) in the plurality of thymine nucleotides.

In some alternative, a cell manufactured by the methods of any one of the alternatives herein is provided. The method can comprise transfecting into a cell the nucleic acid of any of the alternatives herein or a nucleic acid manufactured by a method of any of the alternatives herein, placing the cell into a culture vessel with media, supplying the cell with nutrients and amino acids for translation and incubating the cell for at least, greater than, equal to, or time in between 1, 5, 10, 20, 30, 40, 50, 60, 70, 80, 90 or 100 hours to allow translation. The method for manufacturing the nucleic acid comprises providing the polynucleotide of any one of the alternatives herein or a polynucleotide manufactured by a method of any one of the alternatives herein and contacting said polynucleotide with a polymerase in the presence of nucleotides. The polynucleotide can comprise a first nucleic acid sequence encoding a nuclease, a second nucleic acid sequence comprising at least one restriction endonuclease recognition site and a third nucleic acid sequence, wherein the third nucleic acid sequence comprises the template strand, wherein said plurality of thymine nucleotides comprises at least, greater than, equal to, or any number in between 20, 30, 40, 50, 60, 70, 80, 90, 100, 110, 120, 130, 140, 150, 175, 200, 225, 250, 275, 300, 325, 350, 375, 400, 425, 450, 475, 500 or 550 covalently linked thymine nucleotides and wherein the third nucleic acid comprises the restriction endonuclease cleavage site, wherein the restriction endonuclease cleavage site is located within the plurality of thymine nucleotides or within 1, 2, 3, 4, 5, 6, 7, 7, 8, 9, 10, 11, 12, 13, 14, 15, 16, 17, 18, 19 or 20 base pairs away from the most 5' thymine (or 5' terminal thymine) in the plurality of thymine nucleotides and wherein said second nucleic acid is covalently linked to one end of said third nucleic acid sequence, and wherein the said restriction endonuclease recognition site is located within 55 base pairs of the restriction endonuclease cleavage site for the restriction endonuclease and said restriction endonuclease cleavage site is within 1 to 40 base pairs of a most 5' thymine in the plurality of thymine nucleotides. Some polynucleotides comprise a first nucleic acid sequence comprising at least one restriction endonuclease recognition site and a second nucleic acid sequence, wherein the second nucleic acid sequence comprises the template strand, wherein the template strand comprises a plurality of thymine nucleotides, wherein said plurality of thymine nucleotides comprises at least, greater than, equal to, or any number in between 20, 30, 40, 50, 60, 70, 80, 90, 100, 110, 120, 130, 140, 150, 175, 200, 225, 250, 275, 300, 325, 350, 375, 400, 425, 450, 475, 500 or 550 covalently linked thymine nucleotides, wherein the second nucleic acid comprises the restriction endonuclease cleavage site, and wherein the restriction endonuclease cleavage site is within the plurality of thymine nucleotides or within 1, 2, 3, 4, 5, 6, 7, 7, 8, 9, 10, 11, 12, 13, 14, 15, 16, 17, 18, 19 or 20 base pairs away from the most 5' thymine (or 5' terminal thymine) in the plurality of thymine nucleotides and wherein said first nucleic acid is covalently linked to said second nucleic acid at one end of said second nucleic acid, and wherein the said restriction endonuclease recognition site is located within 1-55 base pairs such as, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54 or 55 base pairs, of the restriction endonuclease cleavage site for the restriction endonuclease and said restriction endonuclease cleavage site is within 1 to 40 base pairs, such as 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 base pairs, of a most 5' thymine (or 5' terminal thymine) in the plurality of thymine nucleotides. In some alternatives, the polynucleotide further comprises telomeres. In some alternatives, the polynucleotide comprises a left arm wherein the left arm comprises a left telomere, a right arm wherein the right arm comprises a right telomere and a cloning region located between the left arm and the right arm. In some alternatives, the nuclease comprises an amino acid sequence set forth in SEQ ID NO. 6 or is encoded by a nucleic acid sequence set forth in SEQ ID NO: 7-14. In some alternatives, the number of covalently linked thymines is greater than 120. In some alternatives, the number of covalently linked thymines is greater than 200. In some alternatives, the number of covalently linked thymines is greater than 300. In some alternatives, the at least one endonuclease recognition site is a Type II restriction endonuclease recognition site, and the endonuclease is a Type II restriction endonuclease. In some alternatives, the at least one endonuclease recognition site is a Type IIS restriction endonuclease recognition site and wherein the endonuclease is a Type IIS restriction endonuclease. In some alternatives, the at least one Type IIS restriction endonuclease recognition site is a BsaI restriction endonuclease recognition site or a StuI restriction endonuclease recognition site, and wherein the endonuclease is BsaI or StuI. In some alternatives, the restriction endonuclease recognition site is inverted. In some alternatives, the polynucleotide is a linear polynucleotide. In some alternatives, the polynucleotide has only one endonuclease recognition site. In some alternatives, the polynucleotide further comprises a polymerase promoter. In some alternatives, the plurality of thymine nucleotides comprises at least one covalently linked guanine, cytosine, or an adenine, wherein the at least one covalently linked guanine, cytosine or adenine is optionally joined to the most 5' thymine (or 5' terminal thymine) in the plurality of thymine nucleotides. In some alternatives, the endonuclease cleavage site comprises at least one guanine, cytosine, or an adenine, wherein the endonuclease cleaves between a thymine and the at least one guanine, cytosine or adenine. In some alternatives, the polynucleotide further comprises at least one palindromic sequence, wherein the at least one palindromic sequence can form a hairpin. In some alternatives, the polynucleotide further comprises a seventh sequence, wherein the seventh sequence is capable of forming a tertiary structure such as a hairpin. In some alternatives, the sequence encoding the nuclease is optimized for expression in human cells. The method of making a polynucleotide comprising a sequence encoding a nuclease, a template strand, an endonuclease recognition site and an endonuclease cleavage site for an endonuclease inserted therein, wherein said template strand comprises a plurality of thymine nucleotides can comprise providing a first nucleic acid sequence encoding a nuclease, providing a second nucleic acid sequence comprising at least one endonuclease recognition site, providing a third nucleic acid sequence, wherein the third nucleic acid sequence comprises the template strand, wherein the template strand comprises a plurality of thymine nucleotides, wherein said plurality of thymine nucleotides comprises at least, greater than, equal to, or any number in between 20, 30, 40, 50, 60, 70, 80, 90, 100, 110, 120, 130, 140, 150, 175, 200, 225, 250, 275, 300, 325, 350, 375, 400, 425, 450, 475, 500 or 550 covalently linked thymine nucleotides and wherein the third nucleic acid comprises the endonuclease cleavage site, wherein the endonuclease cleavage site is located within the plurality of thymine nucleotides or within 1, 2, 3, 4, 5, 6, 7, 7, 8, 9, 10, 11, 12, 13, 14, 15, 16, 17, 18, 19 or 20 base pairs away from the most 5' thymine (or 5' terminal thymine) in the plurality of thymine nucleotides, joining said first nucleic acid to one end of the second nucleic acid sequence and joining said third nucleic acid sequence to one end of the second nucleic acid sequence, wherein said second nucleic acid is covalently linked to one end of said third nucleic acid sequence, and wherein the said endonuclease recognition site is located within 55 base pairs of the endonuclease cleavage site for the endonuclease and said endonuclease cleavage site is within 1 to 40 base pairs of a most 5' thymine (or 5' terminal thymine) in the plurality of thymine nucleotides. In some alternatives, the number of covalently linked thymines is greater than 120. In some alternatives, the number of covalently linked thymines is greater than 200. In some alternatives, the number of covalently linked thymines is greater than 300. In some alternatives, the at least one endonuclease recognition site is a Type II restriction endonuclease recognition site and the endonuclease is a Type II restriction endonuclease. In some alternatives, the at least one endonuclease recognition site is a Type IIS restriction endonuclease recognition site and the endonuclease is a Type IIS restriction endonuclease. In some alternatives, the at least one endonuclease recognition site is a BsaI restriction endonuclease recognition site or a StuI restriction endonuclease recognition site, and wherein the endonuclease is BsaI or StuI. In some alternatives, the endonuclease recognition site is inverted. In some alternatives, the polynucleotide is a linear polynucleotide. In some alternatives, the polynucleotide has only one endonuclease recognition site. In some alternatives, the plurality of covalently linked thymines comprises at least one guanine, cytosine, or an adenine. In some alternatives, the endonuclease cleavage site comprises at least one guanine, cytosine, or an adenine, wherein the endonuclease cleaves between a thymine and the at least one guanine, cytosine or adenine. In some alternatives, the nuclease comprises an amino acid sequence set forth in SEQ ID NO. 6 or is encoded by a nucleic acid sequence set forth in SEQ ID NO: 7-14. In some alternatives, the first nucleic acid sequence encoding the nuclease is codon optimized for expression in human cells. In some alternatives, the polynucleotide further comprises a promoter for a polymerase. In some alternatives, the polymerase is a DNA polymerase. In some alternatives, the DNA polymerase is a thermal stable polymerase, such as Taq polymerase. In some alternatives, the nucleotides are adenine, cytosine, guanine, thymine and/or uracil. In some alternatives, the method further comprises providing a set of primers. In some alternatives, the nucleic acid is DNA. In some alternatives, an RNA polymerase is used. In some alternatives, the contacting is performed at a temperature at least, greater than, equal to, or any temperature in between 30° C., 31° C., 32° C., 33° C., 34° C., 35° C., 36° C. or 37° C. In some alternatives, the contacting is performed for at least, greater than, equal to, or time in between 1, 5, 10, 20, 30, 40, 50, 60, 70, 80, 90 or 100 hours (e.g., at least, or equal to 1, 5, 10, 20, 30, 40, 50, 60, 70, 80, 90 or 100 hours or within a range defined by any two of the aforementioned times). In some alternatives, the nucleic acid is RNA. In some alternatives, the RNA comprises a plurality of adenine nucleotides, wherein the plurality of adenine nucleotides comprises at least, greater than, equal to, or any number in between 20, 30, 40, 50, 60, 70, 80, 90, 100, 110, 120, 130, 140, 150, 175, 200, 225, 250, 275, 300, 325, 350, 375, 400, 425, 450, 475, or 500 covalently linked adenines. In some alternatives, the number of covalently linked adenines is greater than 120. In some alternatives, the number of covalently linked adenines is greater than 200. In some alternatives, the number of covalently linked adenines is greater than 300. In some alternatives, the nuclease comprises an amino acid sequence set forth in SEQ ID NO. 6 or is encoded by a nucleic acid sequence set forth in SEQ ID NO: 7-14. In some alternatives, the plurality of adenine nucleotides further comprises a guanine, cytosine or a uracil, and wherein the number of covalently linked adenines terminates with a guanine, cytosine or a uracil. In some alternatives, the nucleic acid further comprises at least one palindromic sequence, wherein the at least one palindromic sequence can form a hairpin. In some alternatives, the nucleic acid further comprises a sequence capable of forming a tertiary structure such as a hairpin. In some alternatives, the method further comprises providing an endonuclease. In some alternatives, the endonuclease is a Type II restriction endonuclease. In some alternatives, the endonuclease is a Type IIS restriction endonuclease. In some alternatives, the endonuclease is BsaI or StuI. In some alternatives, the cell is a human cell. In some alternatives, the cell is selected from a group consisting of primary cells, human primary T cells, CD4+ cells and CD8+ cells. In some alternatives, the method comprises providing the polynucleotide of any one of the alternatives herein or a polynucleotide manufactured by any method any one of the alternatives herein, wherein said polynucleotide further comprises a gene transforming a cell with said polynucleotide; and propagating the cell, wherein the polynucleotide is replicated. The polynucleotide can comprise a first nucleic acid sequence encoding a nuclease, a second nucleic acid sequence comprising at least one restriction endonuclease recognition site and a third nucleic acid sequence, wherein the third nucleic acid sequence comprises the template strand, wherein said plurality of thymine nucleotides comprises at least, greater than, equal to, or any number in between 20, 30, 40, 50, 60, 70, 80, 90, 100, 110, 120, 130, 140, 150, 175, 200, 225, 250, 275, 300, 325, 350, 375, 400, 425, 450, 475, 500 or 550 covalently linked thymine nucleotides and wherein the third nucleic acid comprises the restriction endonuclease cleavage site, wherein the restriction endonuclease cleavage site is located within the plurality of thymine nucleotides or within 1, 2, 3, 4, 5, 6, 7, 7, 8, 9, 10, 11, 12, 13, 14, 15, 16, 17, 18, 19 or 20 base pairs away from the most 5' thymine (or 5' terminal thymine) in the plurality of thymine nucleotides and wherein said second nucleic acid is covalently linked to one end of said third nucleic acid sequence, and wherein the said restriction endonuclease recognition site is located within 55 base pairs of the restriction endonuclease cleavage site for the restriction endonuclease and said restriction endonuclease cleavage site is within 1 to 40 base pairs of a most 5' thymine in the plurality of thymine nucleotides. Some polynucleotides comprise a first nucleic acid sequence comprising at least one restriction endonuclease recognition site and a second nucleic acid sequence, wherein the second nucleic acid sequence comprises the template strand, wherein the template strand comprises a plurality of thymine nucleotides, wherein said plurality of thymine nucleotides comprises at least, greater than, equal to, or any number in between 20, 30, 40, 50, 60, 70, 80, 90, 100, 110, 120, 130, 140, 150, 175, 200, 225, 250, 275, 300, 325, 350, 375, 400, 425, 450, 475, 500 or 550 covalently linked thymine nucleotides, wherein the second nucleic acid comprises the restriction endonuclease cleavage site, and wherein the restriction endonuclease cleavage site is within the plurality of thymine nucleotides or within 1, 2, 3, 4, 5, 6, 7, 7, 8, 9, 10, 11, 12, 13, 14, 15, 16, 17, 18, 19 or 20 base pairs away from the most 5' thymine (or 5' terminal thymine) in the plurality of thymine nucleotides and wherein said first nucleic acid is covalently linked to said second nucleic acid at one end of said second nucleic acid, and wherein the said restriction endonuclease recognition site is located within 1-55 base pairs such as, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54 or 55 base pairs, of the restriction endonuclease cleavage site for the restriction endonuclease and said restriction endonuclease cleavage site is within 1 to 40 base pairs, such as 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 base pairs, of a most 5' thymine (or 5' terminal thymine) in the plurality of thymine nucleotides. In some alternatives, the polynucleotide further comprises telomeres. In some alternatives, the polynucleotide comprises a left arm wherein the left arm comprises a left telomere, a right arm wherein the right arm comprises a right telomere and a cloning region located between the left arm and the right arm. In some alternatives, the polynucleotide further comprises a third nucleic acid, wherein the third nucleic acid comprises a gene. In some alternatives, the gene encodes a protein for therapy. In some alternatives, the gene encodes a nuclease. In some alternatives, the nuclease is an endonuclease. In some alternatives, the nuclease comprises an amino acid sequence set forth in SEQ ID NO. 6 or is encoded by a nucleic acid sequence set forth in SEQ ID NO: 7-14. In some alternatives, the number of covalently linked thymines is greater than 120. In some alternatives, the number of covalently linked thymines is greater than 200. In some alternatives, the number of covalently linked thymines is greater than 300. In some alternatives, the at least one endonuclease recognition site is a Type II restriction endonuclease recognition site, and the endonuclease is a Type II restriction endonuclease. In some alternatives, the at least one endonuclease recognition site is a Type IIS restriction endonuclease recognition site and wherein the endonuclease is a Type IIS restriction endonuclease. In some alternatives, the at least one endonuclease recognition site is a BsaI restriction endonuclease recognition site or a StuI restriction endonuclease recognition site, and wherein the endonuclease is BsaI or StuI. In some alternatives, the endonuclease recognition site is inverted. In some alternatives, the polynucleotide is a linear polynucleotide. In some alternatives, the polynucleotide has only one endonuclease recognition site. In some alternatives, the polynucleotide further comprises a polymerase promoter region. In some alternatives, the plurality of thymine nucleotides comprises at least one covalently linked guanine, cytosine, or an adenine, wherein the at least one covalently linked guanine, cytosine or adenine is optionally at the most 5' thymine (or 5' terminal thymine) in the plurality of thymine nucleotides. In some alternatives, the endonuclease cleavage site comprises at least one guanine, cytosine, or an adenine, wherein the endonuclease cleaves between a thymine and the at least one guanine, cytosine or adenine. In some alternatives, the polynucleotide further comprises at least one palindromic sequence, wherein the at least one palindromic sequence can form a hairpin. In some alternatives, the polynucleotide further comprises a third sequence, wherein the third sequence is capable of forming a tertiary structure such as a hairpin. In some alternatives, the gene is codon optimized for expression in human cells. The method of making a polynucleotide comprising a sequence encoding a nuclease, a template strand, an endonuclease recognition site and an endonuclease cleavage site for an endonuclease inserted therein, wherein said template strand comprises a plurality of thymine nucleotides can comprise providing a first nucleic acid sequence encoding a nuclease, providing a second nucleic acid sequence comprising at least one endonuclease recognition site, providing a third nucleic acid sequence, wherein the third nucleic acid sequence comprises the template strand, wherein the template strand comprises a plurality of thymine nucleotides, wherein said plurality of thymine nucleotides comprises at least, greater than, equal to, or any number in between 20, 30, 40, 50, 60, 70, 80, 90, 100, 110, 120, 130, 140, 150, 175, 200, 225, 250, 275, 300, 325, 350, 375, 400, 425, 450, 475, 500 or 550 covalently linked thymine nucleotides and wherein the third nucleic acid comprises the endonuclease cleavage site, wherein the endonuclease cleavage site is located within the plurality of thymine nucleotides or within 1, 2, 3, 4, 5, 6, 7, 7, 8, 9, 10, 11, 12, 13, 14, 15, 16, 17, 18, 19 or 20 base pairs away from the most 5' thymine (or 5' terminal thymine) in the plurality of thymine nucleotides, joining said first nucleic acid to one end of the second nucleic acid sequence and joining said third nucleic acid sequence to one end of the second nucleic acid sequence, wherein said second nucleic acid is covalently linked to one end of said third nucleic acid sequence, and wherein the said endonuclease recognition site is located within 55 base pairs of the endonuclease cleavage site for the endonuclease and said endonuclease cleavage site is within 1 to 40 base pairs of a most 5' thymine in the plurality of thymine nucleotides. Some methods of making a polynucleotide can comprise providing a first nucleic acid sequence comprising at least one endonuclease recognition site, providing a second nucleic acid sequence, wherein said plurality of thymine nucleotides comprises at least, greater than, equal to, or any number in between 20, 30, 40, 50, 60, 70, 80, 90, 100, 110, 120, 130, 140, 150, 175, 200, 225, 250, 275, 300, 325, 350, 375, 400, 425, 450, 475, 500 or 550 covalently linked thymine nucleotides and wherein the second nucleic acid comprises the endonuclease cleavage site, wherein the endonuclease cleavage site is within the plurality of thymine nucleotides or within 1, 2, 3, 4, 5, 6, 7, 7, 8, 9, 10, 11, 12, 13, 14, 15, 16, 17, 18, 19 or 20 base pairs away from the most 5' thymine (or 5' terminal thymine) in the plurality of thymine nucleotides and joining said first nucleic acid sequence to said second nucleic acid sequence, wherein said first nucleic acid is covalently linked to said second nucleic acid at one end, and wherein the said endonuclease recognition site is located within 1 to 55 base pairs, such as 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54 or 55 base pairs, of the endonuclease cleavage site for the endonuclease and said endonuclease cleavage site is within 1 to 40 base pairs such as, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 base pairs, of a most 5' thymine or 5' terminal thymine in the plurality of thymine nucleotides or within 1, 2, 3, 4, 5, 6, 7, 7, 8, 9, 10, 11, 12, 13, 14, 15, 16, 17, 18, 19 or 20 base pairs away from the most 5' thymine (or 5' terminal thymine) in the plurality of thymine nucleotides. In some alternatives, the polynucleotide further comprises telomeres. In some alternatives, the polynucleotide comprises a left arm wherein the left arm comprises a left telomere, a right arm wherein the right arm comprises a right telomere and a cloning region located between the left arm and the right arm. In some alternatives, the polynucleotide further comprises a third nucleic acid, wherein the third nucleic acid comprises a gene. In some alternatives, the gene encodes a protein for therapy. In some alternatives, the gene encodes a nuclease. In some alternatives, the nuclease is an endonuclease. In some alternatives, the nuclease comprises an amino acid sequence set forth in SEQ ID NO. 6 or is encoded by a nucleic acid sequence set forth in SEQ ID NO: 7-14. In some alternatives, the number of covalently linked thymines is greater than 120. In some alternatives, the number of covalently linked thymines is greater than 200. In some alternatives, the number of covalently linked thymines is greater than 300. In some alternatives, the at least one endonuclease recognition site is a Type II restriction endonuclease recognition site, and the endonuclease is a Type II restriction endonuclease. In some alternatives, the at least one endonuclease recognition site is a Type IIS restriction endonuclease recognition site, and wherein the endonuclease is a Type IIS restriction endonuclease. In some alternatives, the at least one Type II restriction endonuclease recognition site is a BsaI restriction endonuclease recognition site or a StuI restriction endonuclease recognition site, and wherein the endonuclease is BsaI or StuI. In some alternatives, the endonuclease recognition site is inverted. In some alternatives, the polynucleotide is a linear polynucleotide. In some alternatives, the polynucleotide has only one endonuclease recognition site. In some alternatives, the polynucleotide further comprises a polymerase promoter. In some alternatives, the plurality of thymine nucleotide comprises at least one guanine, cytosine, or an adenine. In some alternatives, the endonuclease cleavage site comprises at least one guanine, cytosine, or an adenine, wherein the endonuclease cleaves between a thymine and the at least one guanine, cytosine or adenine. In some alternatives, the polynucleotide further comprises at least one palindromic sequence, wherein the at least one palindromic sequence can form a hairpin. In some alternatives, the polynucleotide further comprises a fourth sequence, wherein the fourth sequence is capable of forming a tertiary structure such as a hairpin. In some alternatives, the gene is codon optimized for expression in human cells. In some alternatives, the cell is propagated for 1 day, 2 days, 4 days, 6 days, 8 days, 10 days, 12 days, 14 days, or any other times between these values. In some alternatives, the cell is propagated at 30° C., 31° C., 32° C., 33° C., 34° C., 35° C., 36° C., 37° C. or any other temperature between any these values. In some alternatives, the cell is a human cell. In some alternatives, the cell is selected from a group consisting of primary cells, human primary T cells, CD4+ cells and CD8+ cells. The method can comprise providing the polynucleotide of any one of the alternatives herein or a polynucleotide manufactured by a method of any one of the alternatives herein, wherein said polynucleotide comprises a gene encoding a nuclease, transforming a cell with said polynucleotide and propagating the cell, wherein the polynucleotide is replicated. The polynucleotide can comprise a first nucleic acid sequence encoding a nuclease, a second nucleic acid sequence comprising at least one restriction endonuclease recognition site and a third nucleic acid sequence, wherein the third nucleic acid sequence comprises the template strand, wherein said plurality of thymine nucleotides comprises at least, greater than, equal to, or any number in between 20, 30, 40, 50, 60, 70, 80, 90, 100, 110, 120, 130, 140, 150, 175, 200, 225, 250, 275, 300, 325, 350, 375, 400, 425, 450, 475, 500 or 550 covalently linked thymine nucleotides and wherein the third nucleic acid comprises the restriction endonuclease cleavage site, wherein the restriction endonuclease cleavage site is located within the plurality of thymine nucleotides or within 1, 2, 3, 4, 5, 6, 7, 7, 8, 9, 10, 11, 12, 13, 14, 15, 16, 17, 18, 19 or 20 base pairs away from the most 5' thymine (or 5' terminal thymine) in the plurality of thymine nucleotides and wherein said second nucleic acid is covalently linked to one end of said third nucleic acid sequence, and wherein the said restriction endonuclease recognition site is located within 55 base pairs of the restriction endonuclease cleavage site for the restriction endonuclease and said restriction endonuclease cleavage site is within 1 to 40 base pairs of a most 5' thymine in the plurality of thymine nucleotides. Some polynucleotides comprise a first nucleic acid sequence comprising at least one restriction endonuclease recognition site and a second nucleic acid sequence, wherein the second nucleic acid sequence comprises the template strand, wherein the template strand comprises a plurality of thymine nucleotides, wherein said plurality of thymine nucleotides comprises at least, greater than, equal to, or any number in between 20, 30, 40, 50, 60, 70, 80, 90, 100, 110, 120, 130, 140, 150, 175, 200, 225, 250, 275, 300, 325, 350, 375, 400, 425, 450, 475, 500 or 550 covalently linked thymine nucleotides, wherein the second nucleic acid comprises the restriction endonuclease cleavage site, and wherein the restriction endonuclease cleavage site is within the plurality of thymine nucleotides or within 1, 2, 3, 4, 5, 6, 7, 7, 8, 9, 10, 11, 12, 13, 14, 15, 16, 17, 18, 19 or 20 base pairs away from the most 5' thymine (or 5' terminal thymine) in the plurality of thymine nucleotides and wherein said first nucleic acid is covalently linked to said second nucleic acid at one end of said second nucleic acid, and wherein the said restriction endonuclease recognition site is located within 1-55 base pairs such as, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54 or 55 base pairs, of the restriction endonuclease cleavage site for the restriction endonuclease and said restriction endonuclease cleavage site is within 1 to 40 base pairs, such as 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 base pairs, of a most 5' thymine (or 5' terminal thymine) in the plurality of thymine nucleotides. In some alternatives, the polynucleotide further comprises telomeres. In some alternatives, the polynucleotide comprises a left arm wherein the left arm comprises a left telomere, a right arm wherein the right arm comprises a right telomere and a cloning region located between the left arm and the right arm. In some alternatives, the nuclease comprises an amino acid sequence set forth in SEQ ID NO. 6 or is encoded by a nucleic acid sequence set forth in SEQ ID NO: 7-14. In some alternatives, the number of covalently linked thymines is greater than 120. In some alternatives, the number of covalently linked thymines is greater than 200. In some alternatives, the number of covalently linked thymines is greater than 300. In some alternatives, the at least one endonuclease recognition site is a Type II restriction endonuclease recognition site, and the endonuclease is a Type II restriction endonuclease. In some alternatives, the at least one endonuclease recognition site is a Type IIS restriction endonuclease recognition site and wherein the endonuclease is a Type IIS restriction endonuclease. In some alternatives, the at least one Type IIS restriction endonuclease recognition site is a BsaI restriction endonuclease recognition site or a StuI restriction endonuclease recognition site, and wherein the endonuclease is BsaI or StuI. In some alternatives, the endonuclease recognition site is inverted. In some alternatives, the polynucleotide is a linear polynucleotide. In some alternatives, the polynucleotide has only one endonuclease recognition site. In some alternatives, the polynucleotide further comprises a polymerase promoter. In some alternatives, the plurality of thymine nucleotides comprises at least one covalently linked guanine, cytosine, or an adenine, wherein the at least one covalently linked guanine, cytosine or adenine is optionally at the most 5' thymine (or 5' terminal thymine) in the plurality of thymine nucleotides. In some alternatives, the endonuclease cleavage site comprises at least one guanine, cytosine, or an adenine, wherein the endonuclease cleaves between a thymine and the at least one guanine, cytosine or adenine. In some alternatives, the polynucleotide further comprises at least one palindromic sequence, wherein the at least one palindromic sequence can form a hairpin. In some alternatives, the polynucleotide further comprises a seventh sequence, wherein the seventh sequence is capable of forming a tertiary structure such as a hairpin. In some alternatives, the sequence encoding the nuclease is optimized for expression in human cells. The method of making a polynucleotide comprising a sequence encoding a nuclease, a template strand, an endonuclease recognition site and an endonuclease cleavage site for an endonuclease inserted therein, wherein said template strand comprises a plurality of thymine nucleotides can comprise providing a first nucleic acid sequence encoding a nuclease, providing a second nucleic acid sequence comprising at least one endonuclease recognition site, providing a third nucleic acid sequence, wherein the third nucleic acid sequence comprises the template strand, wherein the template strand comprises a plurality of thymine nucleotides, wherein said plurality of thymine nucleotides comprises at least, greater than, equal to, or any number in between 20, 30, 40, 50, 60, 70, 80, 90, 100, 110, 120, 130, 140, 150, 175, 200, 225, 250, 275, 300, 325, 350, 375, 400, 425, 450, 475, 500 or 550 covalently linked thymine nucleotides and wherein the third nucleic acid comprises the endonuclease cleavage site, wherein the endonuclease cleavage site is located within the plurality of thymine nucleotides or within 1, 2, 3, 4, 5, 6, 7, 7, 8, 9, 10, 11, 12, 13, 14, 15, 16, 17, 18, 19 or 20 base pairs away from the most 5' thymine (or 5' terminal thymine) in the plurality of thymine nucleotides, joining said first nucleic acid to one end of the second nucleic acid sequence and joining said third nucleic acid sequence to one end of the second nucleic acid sequence, wherein said second nucleic acid is covalently linked to one end of said third nucleic acid sequence, and wherein the said endonuclease recognition site is located within 55 base pairs of the endonuclease cleavage site for the endonuclease and said endonuclease cleavage site is within 1 to 40 base pairs of a most 5' thymine in the plurality of thymine nucleotides. In some alternatives, the number of covalently linked thymines is greater than 120. In some alternatives, the number of covalently linked thymines is greater than 200. In some alternatives, the number of covalently linked thymines is greater than 300. In some alternatives, the at least one endonuclease recognition site is a Type II restriction endonuclease recognition site and the endonuclease is a Type II restriction endonuclease. In some alternatives, the at least one endonuclease recognition site is a Type IIS restriction endonuclease recognition site and the endonuclease is a Type IIS restriction endonuclease. In some alternatives, the at least one endonuclease recognition site is a BsaI restriction endonuclease recognition site or a StuI restriction endonuclease recognition site, and wherein the endonuclease is BsaI or StuI. In some alternatives, the endonuclease recognition site is inverted. In some alternatives, the polynucleotide is a linear polynucleotide. In some alternatives, the polynucleotide has only one endonuclease recognition site. In some alternatives, the plurality of covalently linked thymines comprises at least one guanine, cytosine, or an adenine. In some alternatives, the endonuclease cleavage site comprises at least one guanine, cytosine, or an adenine, wherein the endonuclease cleaves between a thymine and the at least one guanine, cytosine or adenine. In some alternatives, the nuclease comprises an amino acid sequence set forth in SEQ ID NO. 6 or is encoded by a nucleic acid sequence set forth in SEQ ID NO: 7-14. In some alternatives, the first nucleic acid sequence encoding the nuclease is codon optimized for expression in human cells. In some alternatives, the polynucleotide further comprises a promoter for a polymerase. In some alternatives, the polymerase is a DNA polymerase. In some alternatives, the DNA polymerase is a thermal stable polymerase, such as Taq polymerase. In some alternatives, the nucleotides are adenine, cytosine, guanine, thymine and/or uracil. In some alternatives, the method further comprises providing a set of primers. In some alternatives, the nucleic acid is DNA. In some alternatives, an RNA polymerase is used. In some alternatives, the contacting is performed at a temperature at least, greater than, equal to, or any temperature in between 30° C., 31° C., 32° C., 33° C., 34° C., 35° C., 36° C. or 37° C. In some alternatives, the contacting is performed for at least, greater than, equal to, or time in between 1, 5, 10, 20, 30, 40, 50, 60, 70, 80, 90 or 100 hours (e.g., at least, or equal to 1, 5, 10, 20, 30, 40, 50, 60, 70, 80, 90 or 100 hours or within a range defined by any two of the aforementioned times). In some alternatives, the nucleic acid is RNA. In some alternatives, the RNA comprises a plurality of adenine nucleotides, wherein the plurality of adenine nucleotides comprises at least, greater than, equal to, or any number in between 20, 30, 40, 50, 60, 70, 80, 90, 100, 110, 120, 130, 140, 150, 175, 200, 225, 250, 275, 300, 325, 350, 375, 400, 425, 450, 475, or 500 covalently linked adenines. In some alternatives, the number of covalently linked adenines is greater than 120. In some alternatives, the number of covalently linked adenines is greater than 200. In some alternatives, the number of covalently linked adenines is greater than 300. In some alternatives, the nuclease comprises an amino acid sequence set forth in SEQ ID NO. 6 or is encoded by a nucleic acid sequence set forth in SEQ ID NO: 7-14. In some alternatives, the plurality of adenine nucleotides further comprises a guanine, cytosine or a uracil, and wherein the number of covalently linked adenines terminates with a guanine, cytosine or a uracil. In some alternatives, the nucleic acid further comprises at least one palindromic sequence, wherein the at least one palindromic sequence can form a hairpin. In some alternatives, the nucleic acid further comprises a sequence capable of forming a tertiary structure such as a hairpin. In some alternatives, the method further comprises providing an endonuclease. In some alternatives, the endonuclease is a Type II restriction endonuclease. In some alternatives, the endonuclease is a Type IIS restriction endonuclease. In some alternatives, the endonuclease is BsaI or StuI. In some alternatives, the cell is propagated for 1 day, 2 days, 4 days, 6 days, 8 days, 10 days, 12 days, or 14 days, or any other times between these values. In some alternatives, the cell is propagated at 30° C., 31° C., 32° C., 33° C., 34° C., 35° C., 36° C., or 37° C. or any other temperature between any these values. In some alternatives, the nuclease comprises an amino acid sequence set forth in SEQ ID NO. 6 or is encoded by a nucleic acid sequence set forth in SEQ ID NO: 7-14. In some alternatives, the cell is a human cell. In some alternatives, the cell is selected from a group consisting of primary cells, human primary T cells, CD4+ cells and CD8+ cells. In some alternatives, the endonuclease cleavage site is located 1, 2, 3, 4, 5, 6, 7, 7, 8, 9, 10, 11, 12, 13, 14, 15, 16, 17, 18, 19 or 20 base pairs away from the most 5' thymine (or 5' terminal thymine) in the plurality of thymine nucleotides. In some alternatives, the endonuclease cleavage site is located 1, 2, 3, 4, 5, 6, 7, 7, 8, 9 or 10 base pairs away from the most 5' thymine (or 5' terminal thymine) in the plurality of thymine nucleotides.

In some alternatives, a pharmaceutical composition is provided. The pharmaceutical composition can comprise a pharmaceutical vehicle and a nucleic acid of any one of the alternatives herein or mRNA of any one of the alternatives herein. The nucleic acid can manufactured by a method of any one of the alternatives described herein. In some alternatives, the method comprises providing the polynucleotide of any one of the alternatives provided herein, or the polynucleotide manufactured by any one of the alternatives provided herein and contacting said polynucleotide with a polymerase in the presence of nucleotides. The polynucleotide can comprise a first nucleic acid sequence encoding a nuclease, a second nucleic acid sequence comprising at least one restriction endonuclease recognition site and a third nucleic acid sequence, wherein the third nucleic acid sequence comprises the template strand, wherein said plurality of thymine nucleotides comprises at least, greater than, equal to, or any number in between 20, 30, 40, 50, 60, 70, 80, 90, 100, 110, 120, 130, 140, 150, 175, 200, 225, 250, 275, 300, 325, 350, 375, 400, 425, 450, 475, 500 or 550 covalently linked thymine nucleotides and wherein the third nucleic acid comprises the restriction endonuclease cleavage site, wherein the restriction endonuclease cleavage site is located within the plurality of thymine nucleotides or within 1, 2, 3, 4, 5, 6, 7, 7, 8, 9, 10, 11, 12, 13, 14, 15, 16, 17, 18, 19 or 20 base pairs away from the most 5' thymine (or 5' terminal thymine) in the plurality of thymine nucleotides and wherein said second nucleic acid is covalently linked to one end of said third nucleic acid sequence, and wherein the said restriction endonuclease recognition site is located within 55 base pairs of the restriction endonuclease cleavage site for the restriction endonuclease and said restriction endonuclease cleavage site is within 1 to 40 base pairs of a most 5' thymine (or 5' terminal thymine) in the plurality of thymine nucleotides. Some polynucleotides comprise a first nucleic acid sequence comprising at least one restriction endonuclease recognition site and a second nucleic acid sequence, wherein the second nucleic acid sequence comprises the template strand, wherein the template strand comprises a plurality of thymine nucleotides, wherein said plurality of thymine nucleotides comprises at least, greater than, equal to, or any number in between 20, 30, 40, 50, 60, 70, 80, 90, 100, 110, 120, 130, 140, 150, 175, 200, 225, 250, 275, 300, 325, 350, 375, 400, 425, 450, 475, 500 or 550 covalently linked thymine nucleotides, wherein the second nucleic acid comprises the restriction endonuclease cleavage site, and wherein the restriction endonuclease cleavage site is within the plurality of thymine nucleotides or within 1, 2, 3, 4, 5, 6, 7, 7, 8, 9, 10, 11, 12, 13, 14, 15, 16, 17, 18, 19 or 20 base pairs away from the most 5' thymine (or 5' terminal thymine) in the plurality of thymine nucleotides and wherein said first nucleic acid is covalently linked to said second nucleic acid at one end of said second nucleic acid, and wherein the said restriction endonuclease recognition site is located within 1-55 base pairs such as, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54 or 55 base pairs, of the restriction endonuclease cleavage site for the restriction endonuclease and said restriction endonuclease cleavage site is within 1 to 40 base pairs, such as 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 base pairs, of a most 5' thymine (or 5' terminal thymine) in the plurality of thymine nucleotides. In some alternatives, the polynucleotide further comprises telomeres. In some alternatives, the polynucleotide comprises a left arm wherein the left arm comprises a left telomere, a right arm wherein the right arm comprises a right telomere and a cloning region located between the left arm and the right arm. In some alternatives, the polynucleotide further comprises a third nucleic acid, wherein the third nucleic acid comprises a gene. In some alternatives, the gene encodes a protein for therapy. In some alternatives, the gene encodes a nuclease. In some alternatives, the nuclease is an endonuclease. In some alternatives, the nuclease comprises an amino acid sequence set forth in SEQ ID NO. 6 or is encoded by a nucleic acid sequence set forth in SEQ ID NO: 7-14. In some alternatives, the number of covalently linked thymines is greater than 120. In some alternatives, the number of covalently linked thymines is greater than 200. In some alternatives, the number of covalently linked thymines is greater than 300. In some alternatives, the at least one endonuclease recognition site is a Type II restriction endonuclease recognition site, and the endonuclease is a Type II restriction endonuclease. In some alternatives, the at least one endonuclease recognition site is a Type IIS restriction endonuclease recognition site and wherein the endonuclease is a Type IIS restriction endonuclease. In some alternatives, the at least one endonuclease recognition site is a BsaI restriction endonuclease recognition site or a StuI restriction endonuclease recognition site, and wherein the endonuclease is BsaI or StuI. In some alternatives, the endonuclease recognition site is inverted. In some alternatives, the polynucleotide is a linear polynucleotide. In some alternatives, the polynucleotide has only one endonuclease recognition site. In some alternatives, the polynucleotide further comprises a polymerase promoter region. In some alternatives, the plurality of thymine nucleotides comprises at least one covalently linked guanine, cytosine, or an adenine, wherein the at least one covalently linked guanine, cytosine or adenine is optionally joined to the most 5' thymine (or 5' terminal thymine) in the plurality of thymine nucleotides. In some alternatives, the endonuclease cleavage site comprises at least one guanine, cytosine, or an adenine, wherein the endonuclease cleaves between a thymine and the at least one guanine, cytosine or adenine. In some alternatives, the polynucleotide further comprises at least one palindromic sequence, wherein the at least one palindromic sequence can form a hairpin. In some alternatives, the polynucleotide further comprises a third sequence, wherein the third sequence is capable of forming a tertiary structure such as a hairpin. In some alternatives, the gene is codon optimized for expression in human cells. The method of making a polynucleotide comprising a sequence encoding a nuclease, a template strand, an endonuclease recognition site and an endonuclease cleavage site for an endonuclease inserted therein, wherein said template strand comprises a plurality of thymine nucleotides can comprise providing a first nucleic acid sequence encoding a nuclease, providing a second nucleic acid sequence comprising at least one endonuclease recognition site, providing a third nucleic acid sequence, wherein the third nucleic acid sequence comprises the template strand, wherein the template strand comprises a plurality of thymine nucleotides, wherein said plurality of thymine nucleotides comprises at least, greater than, equal to, or any number in between 20, 30, 40, 50, 60, 70, 80, 90, 100, 110, 120, 130, 140, 150, 175, 200, 225, 250, 275, 300, 325, 350, 375, 400, 425, 450, 475, 500 or 550 covalently linked thymine nucleotides and wherein the third nucleic acid comprises the endonuclease cleavage site, wherein the endonuclease cleavage site is located within the plurality of thymine nucleotides or within 1, 2, 3, 4, 5, 6, 7, 7, 8, 9, 10, 11, 12, 13, 14, 15, 16, 17, 18, 19 or 20 base pairs away from the most 5' thymine (or 5' terminal thymine) in the plurality of thymine nucleotides, joining said first nucleic acid to one end of the second nucleic acid sequence and joining said third nucleic acid sequence to one end of the second nucleic acid sequence, wherein said second nucleic acid is covalently linked to one end of said third nucleic acid sequence, and wherein the said endonuclease recognition site is located within 55 base pairs of the endonuclease cleavage site for the endonuclease and said endonuclease cleavage site is within 1 to 40 base pairs of a most 5' thymine in the plurality of thymine nucleotides. In some alternatives, the polynucleotide further comprises telomeres. In some alternatives, the polynucleotide comprises a left arm wherein the left arm comprises a left telomere, a right arm wherein the right arm comprises a right telomere and a cloning region located between the left arm and the right arm. In some alternatives, the polynucleotide further comprises a third nucleic acid, wherein the third nucleic acid comprises a gene. In some alternatives, the gene encodes a protein for therapy. In some alternatives, the gene encodes a nuclease. In some alternatives, the nuclease is an endonuclease. In some alternatives, the nuclease comprises an amino acid sequence set forth in SEQ ID NO. 6 or is encoded by a nucleic acid sequence set forth in SEQ ID NO: 7-14. In some alternatives, the number of covalently linked thymines is greater than 120. In some alternatives, the number of covalently linked thymines is greater than 200. In some alternatives, the number of covalently linked thymines is greater than 300. In some alternatives, the at least one endonuclease recognition site is a Type II restriction endonuclease recognition site, and the endonuclease is a Type II restriction endonuclease. In some alternatives, the at least one endonuclease recognition site is a Type IIS restriction endonuclease recognition site, and wherein the endonuclease is a Type IIS restriction endonuclease. In some alternatives, the at least one Type II restriction endonuclease recognition site is a BsaI restriction endonuclease recognition site or a StuI restriction endonuclease recognition site, and wherein the endonuclease is BsaI or StuI. In some alternatives, the endonuclease recognition site is inverted. In some alternatives, the polynucleotide is a linear polynucleotide. In some alternatives, the polynucleotide has only one endonuclease recognition site. In some alternatives, the polynucleotide further comprises a polymerase promoter. In some alternatives, the plurality of thymine nucleotide comprises at least one guanine, cytosine, or an adenine. In some alternatives, the endonuclease cleavage site comprises at least one guanine, cytosine, or an adenine, wherein the endonuclease cleaves between a thymine and the at least one guanine, cytosine or adenine. In some alternatives, the polynucleotide further comprises at least one palindromic sequence, wherein the at least one palindromic sequence can form a hairpin. In some alternatives, the polynucleotide further comprises a fourth sequence, wherein the fourth sequence is capable of forming a tertiary structure such as a hairpin. In some alternatives, the gene is codon optimized for expression in human cells. In some alternatives, the polynucleotide further comprises a promoter for a polymerase. In some alternatives, polymerase is a DNA polymerase. In some alternatives, the DNA polymerase is a thermal stable polymerase, such as Taq polymerase. In some alternatives, the nucleotides are adenine, cytosine, guanine, thymine and/or uracil. In some alternatives, the method further comprises providing a set of primers. In some alternatives, the nucleic acid is DNA. In some alternatives, an RNA polymerase is used. In some alternatives, the contacting is performed at a temperature at least, greater than, equal to, or any temperature in between 30° C., 31° C., 32° C., 33° C., 34° C., 35° C., 36° C. or 37° C. In some alternatives, the contacting is performed for at least, greater than, equal to, or time in between 1, 5, 10, 20, 30, 40, 50, 60, 70, 80, 90 or 100 hours (e.g., at least, or equal to 1, 5, 10, 20, 30, 40, 50, 60, 70, 80, 90 or 100 hours or within a range defined by any two of the aforementioned times). In some alternatives, the nucleic acid is RNA. In some alternatives, the RNA comprises a plurality of adenine nucleotides, wherein the plurality of adenine nucleotides comprises at least, greater than, equal to, or any number in between 20, 30, 40, 50, 60, 70, 80, 90, 100, 110, 120, 130, 140, 150, 175, 200, 225, 250, 275, 300, 325, 350, 375, 400, 425, 450, 475, or 500 covalently linked adenines. In some alternatives, the number of covalently linked adenines is greater than 120. In some alternatives, the number of covalently linked adenines is greater than 200. In some alternatives, the number of covalently linked adenines is greater than 300. In some alternatives, the RNA further comprises a gene. In some alternatives, the gene encodes a protein for therapy. In some alternatives, the gene encodes a nuclease. In some alternatives, the gene encodes an endonuclease. In some alternatives, the nuclease comprises an amino acid sequence set forth in SEQ ID NO. 6 or is encoded by a nucleic acid sequence set forth in SEQ ID NO: 7-14. In some alternatives, the plurality of adenine nucleotides further comprises a guanine, cytosine or a uracil, and wherein the number of covalently linked adenines terminates with a guanine, cytosine or a uracil. In some alternatives, the nucleic acid further comprises at least one palindromic sequence, wherein the at least one palindromic sequence can form a hairpin. In some alternatives, the nucleic acid further comprises a sequence capable of forming a tertiary structure such as a hairpin. In some alternatives, the method further comprises providing an endonuclease. In some alternatives, the endonuclease is a Type II restriction endonuclease. In some alternatives, the endonuclease is a Type IIS restriction endonuclease. In some alternatives, the endonuclease is BsaI or StuI. In some alternatives, the gene is codon optimized for expression in human cells. In some alternatives, the nucleic acid is a DNA. In some alternatives, the nucleic acid is RNA. In some alternatives, the RNA comprises a plurality of adenine nucleotides, wherein the plurality of adenine nucleotides comprises at least, greater than, equal to, or any number in between 20, 30, 40, 50, 60, 70, 80, 90, 100, 110, 120, 130, 140, 150, 175, 200, 225, 250, 275, 300, 325, 350, 375, 400, 425, 450, 475, or 500 covalently linked adenines. In some alternatives, the number of covalently linked adenines is greater than 120. In some alternatives, the number of covalently linked adenines is greater than 200. In some alternatives, the number of covalently linked adenines is greater than 300. In some alternatives, the nucleic acid further comprises a gene. In some alternatives, the gene encodes a protein for therapy. In some alternatives, the gene encodes a nuclease. In some alternatives, the gene encodes an endonuclease. In some alternatives, the nuclease comprises an amino acid sequence set forth in SEQ ID NO. 6 or is encoded by a nucleic acid sequence set forth in SEQ ID NO: 7-14. In some alternatives, the covalently linked adenines terminate with a guanine, cytosine, thymine, or a uracil. In some alternatives, the nucleic acid further comprises at least one palindromic sequence, wherein the at least one palindromic sequence can form a hairpin. In some alternatives, the nucleic acid further comprises a sequence capable of forming a tertiary structure such as a hairpin. In some alternatives, the gene is codon optimized for expression in human cells. The method for manufacturing the nucleic acid comprising a nuclease can also be provided. The method comprises providing the polynucleotide of any one of the alternatives herein or a polynucleotide manufactured by a method of any one of the alternatives herein and contacting said polynucleotide with a polymerase in the presence of nucleotides. The polynucleotide can comprise a first nucleic acid sequence encoding a nuclease, a second nucleic acid sequence comprising at least one restriction endonuclease recognition site and a third nucleic acid sequence, wherein the third nucleic acid sequence comprises the template strand, wherein said plurality of thymine nucleotides comprises at least, greater than, equal to, or any number in between 20, 30, 40, 50, 60, 70, 80, 90, 100, 110, 120, 130, 140, 150, 175, 200, 225, 250, 275, 300, 325, 350, 375, 400, 425, 450, 475, 500 or 550 covalently linked thymine nucleotides and wherein the third nucleic acid comprises the restriction endonuclease cleavage site, wherein the restriction endonuclease cleavage site is located within the plurality of thymine nucleotides or within 1, 2, 3, 4, 5, 6, 7, 7, 8, 9, 10, 11, 12, 13, 14, 15, 16, 17, 18, 19 or 20 base pairs away from the most 5' thymine (or 5' terminal thymine) in the plurality of thymine nucleotides and wherein said second nucleic acid is covalently linked to one end of said third nucleic acid sequence, and wherein the said restriction endonuclease recognition site is located within 55 base pairs of the restriction endonuclease cleavage site for the restriction endonuclease and said restriction endonuclease cleavage site is within 1 to 40 base pairs of a most 5' thymine in the plurality of thymine nucleotides. Some polynucleotides comprise a first nucleic acid sequence comprising at least one restriction endonuclease recognition site and a second nucleic acid sequence, wherein the second nucleic acid sequence comprises the template strand, wherein the template strand comprises a plurality of thymine nucleotides, wherein said plurality of thymine nucleotides comprises at least, greater than, equal to, or any number in between 20, 30, 40, 50, 60, 70, 80, 90, 100, 110, 120, 130, 140, 150, 175, 200, 225, 250, 275, 300, 325, 350, 375, 400, 425, 450, 475, 500 or 550 covalently linked thymine nucleotides, wherein the second nucleic acid comprises the restriction endonuclease cleavage site, and wherein the restriction endonuclease cleavage site is within the plurality of thymine nucleotides or within 1, 2, 3, 4, 5, 6, 7, 7, 8, 9, 10, 11, 12, 13, 14, 15, 16, 17, 18, 19 or 20 base pairs away from the most 5' thymine (or 5' terminal thymine) in the plurality of thymine nucleotides and wherein said first nucleic acid is covalently linked to said second nucleic acid at one end of said second nucleic acid, and wherein the said restriction endonuclease recognition site is located within 1-55 base pairs such as, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54 or 55 base pairs, of the restriction endonuclease cleavage site for the restriction endonuclease and said restriction endonuclease cleavage site is within 1 to 40 base pairs, such as 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 base pairs, of a most 5' thymine (or 5' terminal thymine) in the plurality of thymine nucleotides. In some alternatives, the polynucleotide further comprises telomeres. In some alternatives, the polynucleotide comprises a left arm wherein the left arm comprises a left telomere, a right arm wherein the right arm comprises a right telomere and a cloning region located between the left arm and the right arm. In some alternatives, the nuclease comprises an amino acid sequence set forth in SEQ ID NO. 6 or is encoded by a nucleic acid sequence set forth in SEQ ID NO: 7-14. In some alternatives, the number of covalently linked thymines is greater than 120. In some alternatives, the number of covalently linked thymines is greater than 200. In some alternatives, the number of covalently linked thymines is greater than 300. In some alternatives, the at least one endonuclease recognition site is a Type II restriction endonuclease recognition site, and the endonuclease is a Type II restriction endonuclease. In some alternatives, the at least one endonuclease recognition site is a Type IIS restriction endonuclease recognition site and wherein the endonuclease is a Type IIS restriction endonuclease. In some alternatives, the at least one Type IIS restriction endonuclease recognition site is a BsaI restriction endonuclease recognition site or a StuI restriction endonuclease recognition site, and wherein the endonuclease is BsaI or StuI. In some alternatives, the endonuclease recognition site is inverted. In some alternatives, the polynucleotide is a linear polynucleotide. In some alternatives, the polynucleotide has only one endonuclease recognition site. In some alternatives, the polynucleotide further comprises a polymerase promoter. In some alternatives, the plurality of thymine nucleotides comprises at least one covalently linked guanine, cytosine, or an adenine, wherein the at least one covalently linked guanine, cytosine or adenine is optionally joined to the most 5' thymine (or 5' terminal thymine) in the plurality of thymine nucleotides. In some alternatives, the endonuclease cleavage site comprises at least one guanine, cytosine, or an adenine, wherein the endonuclease cleaves between a thymine and the at least one guanine, cytosine or adenine. In some alternatives, the polynucleotide further comprises at least one palindromic sequence, wherein the at least one palindromic sequence can form a hairpin. In some alternatives, the polynucleotide further comprises a seventh sequence, wherein the seventh sequence is capable of forming a tertiary structure such as a hairpin. In some alternatives, the sequence encoding the nuclease is optimized for expression in human cells. The method of making a polynucleotide comprising a sequence encoding a nuclease, a template strand, an endonuclease recognition site and an endonuclease cleavage site for an endonuclease inserted therein, wherein said template strand comprises a plurality of thymine nucleotides can comprise providing a first nucleic acid sequence encoding a nuclease, providing a second nucleic acid sequence comprising at least one endonuclease recognition site, providing a third nucleic acid sequence, wherein the third nucleic acid sequence comprises the template strand, wherein the template strand comprises a plurality of thymine nucleotides, wherein said plurality of thymine nucleotides comprises at least, greater than, equal to, or any number in between 20, 30, 40, 50, 60, 70, 80, 90, 100, 110, 120, 130, 140, 150, 175, 200, 225, 250, 275, 300, 325, 350, 375, 400, 425, 450, 475, 500 or 550 covalently linked thymine nucleotides and wherein the third nucleic acid comprises the endonuclease cleavage site, wherein the endonuclease cleavage site is located within the plurality of thymine nucleotides or within 1, 2, 3, 4, 5, 6, 7, 7, 8, 9, 10, 11, 12, 13, 14, 15, 16, 17, 18, 19 or 20 base pairs away from the most 5' thymine (or 5' terminal thymine) in the plurality of thymine nucleotides, joining said first nucleic acid to one end of the second nucleic acid sequence and joining said third nucleic acid sequence to one end of the second nucleic acid sequence, wherein said second nucleic acid is covalently linked to one end of said third nucleic acid sequence, and wherein the said endonuclease recognition site is located within 55 base pairs of the endonuclease cleavage site for the endonuclease and said endonuclease cleavage site is within 1 to 40 base pairs of a most 5' thymine in the plurality of thymine nucleotides. In some alternatives, the number of covalently linked thymines is greater than 120. In some alternatives, the number of covalently linked thymines is greater than 200. In some alternatives, the number of covalently linked thymines is greater than 300. In some alternatives, the at least one endonuclease recognition site is a Type II restriction endonuclease recognition site and the endonuclease is a Type II restriction endonuclease. In some alternatives, the at least one endonuclease recognition site is a Type IIS restriction endonuclease recognition site and the endonuclease is a Type IIS restriction endonuclease. In some alternatives, the at least one Type II restriction endonuclease recognition site is a BsaI restriction endonuclease recognition site or a StuI restriction endonuclease recognition site, and wherein the endonuclease is BsaI or StuI. In some alternatives, the endonuclease recognition site is inverted. In some alternatives, the polynucleotide is a linear polynucleotide. In some alternatives, the polynucleotide has only one endonuclease recognition site. In some alternatives, the plurality of covalently linked thymines comprises at least one guanine, cytosine, or an adenine. In some alternatives, the endonuclease cleavage site comprises at least one guanine, cytosine, or an adenine, wherein the endonuclease cleaves between a thymine and the at least one guanine, cytosine or adenine. In some alternatives, the nuclease comprises an amino acid sequence set forth in SEQ ID NO. 6 or is encoded by a nucleic acid sequence set forth in SEQ ID NO: 7-14. In some alternatives, the first nucleic acid sequence encoding the nuclease is codon optimized for expression in human cells. In some alternatives, the polynucleotide further comprises a promoter for a polymerase. In some alternatives, the polymerase is a DNA polymerase. In some alternatives, the DNA polymerase is a thermal stable polymerase, such as Taq polymerase. In some alternatives, the nucleotides are adenine, cytosine, guanine, thymine and/or uracil. In some alternatives, the method further comprises providing a set of primers. In some alternatives, the nucleic acid is DNA. In some alternatives, an RNA polymerase is used. In some alternatives, the contacting is performed at a temperature at least, greater than, equal to, or any temperature in between 30° C., 31° C., 32° C., 33° C., 34° C., 35° C., 36° C. or 37° C. In some alternatives, the contacting is performed for at least, greater than, equal to, or time in between 1, 5, 10, 20, 30, 40, 50, 60, 70, 80, 90 or 100 hours (e.g., at least, or equal to 1, 5, 10, 20, 30, 40, 50, 60, 70, 80, 90 or 100 hours or within a range defined by any two of the aforementioned times). In some alternatives, the nucleic acid is RNA. In some alternatives, the RNA comprises a plurality of adenine nucleotides, wherein the plurality of adenine nucleotides comprises at least, greater than, equal to, or any number in between 20, 30, 40, 50, 60, 70, 80, 90, 100, 110, 120, 130, 140, 150, 175, 200, 225, 250, 275, 300, 325, 350, 375, 400, 425, 450, 475, or 500 covalently linked adenines. In some alternatives, the number of covalently linked adenines is greater than 120. In some alternatives, the number of covalently linked adenines is greater than 200. In some alternatives, the number of covalently linked adenines is greater than 300. In some alternatives, the nuclease comprises an amino acid sequence set forth in SEQ ID NO. 6 or is encoded by a nucleic acid sequence set forth in SEQ ID NO: 7-14. In some alternatives, the plurality of adenine nucleotides further comprises a guanine, cytosine or a uracil, and wherein the number of covalently linked adenines terminates with a guanine, cytosine or a uracil. In some alternatives, the nucleic acid further comprises at least one palindromic sequence, wherein the at least one palindromic sequence can form a hairpin. In some alternatives, the nucleic acid further comprises a sequence capable of forming a tertiary structure such as a hairpin. In some alternatives, the method further comprises providing an endonuclease. In some alternatives, the endonuclease is a Type II restriction endonuclease. In some alternatives, the endonuclease is a Type IIS restriction endonuclease. In some alternatives, the endonuclease is BsaI or StuI. The RNA can comprise a first sequence comprising at least one compliment sequence to an endonuclease recognition site covalently linked to a plurality of adenine nucleotides at the 3' end of said plurality of adenine nucleotides, a second sequence that comprises a plurality of adenine nucleotides, wherein the plurality of adenines comprises at least, greater than, equal to, or any number in between 20, 30, 40, 50, 60, 70, 80, 90, 100, 110, 120, 130, 140, 150, 175, 200, 225, 250, 275, 300, 325, 350, 375, 400, 425, 450, 475, or 500 covalently linked adenines and wherein said compliment sequence to an endonuclease recognition site of said first nucleic acid is covalently linked to said plurality of adenine nucleotides of said second nucleic acid at the 3' end of said plurality of adenine nucleotides of said second nucleic acid. In some alternatives, the mRNA further encodes a gene. In some alternatives, the gene is an endonuclease gene. In some alternatives, the at least one endonuclease site is inverted, and wherein the sequence encoding an RNA compliment is a compliment to the inverted endonuclease site. In some alternatives, the at least one endonuclease is a Type II restriction endonuclease recognition site. In some alternatives, the at least one endonuclease site is a Type IIS restriction endonuclease recognition site. In some alternatives, the at least one endonuclease site is a BsaI recognition site or a StuI recognition site. In some alternatives, the gene is codon optimized for expression in a human cell. In some alternatives, the endonuclease cleavage site is located 1, 2, 3, 4, 5, 6, 7, 7, 8, 9, 10, 11, 12, 13, 14, 15, 16, 17, 18, 19 or 20 base pairs away from the most 5' thymine (or 5' terminal thymine) in the plurality of thymine nucleotides. In some alternatives, the endonuclease cleavage site is located 1, 2, 3, 4, 5, 6, 7, 7, 8, 9 or 10 base pairs away from the most 5' thymine (or 5' terminal thymine) in the plurality of thymine nucleotides.

In some alternatives, a method of treating, ameliorating, or inhibiting disease in a subject is provided. The method can comprise introducing into a cell the nucleic acid of any one of the alternatives herein or the mRNA of any one of the alternatives herein and delivering the cell to the subject. The nucleic acid can manufactured by a method of any one of the alternatives described herein. In some alternatives, the method comprises providing the polynucleotide of any one of the alternatives provided herein, or the polynucleotide manufactured by any one of the alternatives provided herein and contacting said polynucleotide with a polymerase in the presence of nucleotides. The polynucleotide can comprise a first nucleic acid sequence encoding a nuclease, a second nucleic acid sequence comprising at least one restriction endonuclease recognition site and a third nucleic acid sequence, wherein the third nucleic acid sequence comprises the template strand, wherein said plurality of thymine nucleotides comprises at least, greater than, equal to, or any number in between 20, 30, 40, 50, 60, 70, 80, 90, 100, 110, 120, 130, 140, 150, 175, 200, 225, 250, 275, 300, 325, 350, 375, 400, 425, 450, 475, 500 or 550 covalently linked thymine nucleotides and wherein the third nucleic acid comprises the restriction endonuclease cleavage site, wherein the restriction endonuclease cleavage site is located within the plurality of thymine nucleotides or within 1, 2, 3, 4, 5, 6, 7, 7, 8, 9, 10, 11, 12, 13, 14, 15, 16, 17, 18, 19 or 20 base pairs away from the most 5' thymine (or 5' terminal thymine) in the plurality of thymine nucleotides and wherein said second nucleic acid is covalently linked to one end of said third nucleic acid sequence, and wherein the said restriction endonuclease recognition site is located within 55 base pairs of the restriction endonuclease cleavage site for the restriction endonuclease and said restriction endonuclease cleavage site is within 1 to 40 base pairs of a most 5' thymine in the plurality of thymine nucleotides. Some polynucleotides comprise a first nucleic acid sequence comprising at least one restriction endonuclease recognition site and a second nucleic acid sequence, wherein the second nucleic acid sequence comprises the template strand, wherein the template strand comprises a plurality of thymine nucleotides, wherein said plurality of thymine nucleotides comprises at least, greater than, equal to, or any number in between 20, 30, 40, 50, 60, 70, 80, 90, 100, 110, 120, 130, 140, 150, 175, 200, 225, 250, 275, 300, 325, 350, 375, 400, 425, 450, 475, 500 or 550 covalently linked thymine nucleotides, wherein the second nucleic acid comprises the restriction endonuclease cleavage site, and wherein the restriction endonuclease cleavage site is within the plurality of thymine nucleotides or within 1, 2, 3, 4, 5, 6, 7, 7, 8, 9, 10, 11, 12, 13, 14, 15, 16, 17, 18, 19 or 20 base pairs away from the most 5' thymine (or 5' terminal thymine) in the plurality of thymine nucleotides and wherein said first nucleic acid is covalently linked to said second nucleic acid at one end of said second nucleic acid, and wherein the said restriction endonuclease recognition site is located within 1-55 base pairs such as, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54 or 55 base pairs, of the restriction endonuclease cleavage site for the restriction endonuclease and said restriction endonuclease cleavage site is within 1 to 40 base pairs, such as 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 base pairs, of a most 5' thymine (or 5' terminal thymine) in the plurality of thymine nucleotides. In some alternatives, the polynucleotide further comprises telomeres. In some alternatives, the polynucleotide comprises a left arm wherein the left arm comprises a left telomere, a right arm wherein the right arm comprises a right telomere and a cloning region located between the left arm and the right arm. In some alternatives, the polynucleotide further comprises a third nucleic acid, wherein the third nucleic acid comprises a gene. In some alternatives, the gene encodes a protein for therapy. In some alternatives, the gene encodes a nuclease. In some alternatives, the nuclease is an endonuclease. In some alternatives, the nuclease comprises an amino acid sequence set forth in SEQ ID NO. 6 or is encoded by a nucleic acid sequence set forth in SEQ ID NO: 7-14. In some alternatives, the number of covalently linked thymines is greater than 120. In some alternatives, the number of covalently linked thymines is greater than 200. In some alternatives, the number of covalently linked thymines is greater than 300. In some alternatives, the at least one endonuclease recognition site is a Type II restriction endonuclease recognition site, and the endonuclease is a Type II restriction endonuclease. In some alternatives, the at least one endonuclease recognition site is a Type IIS restriction endonuclease recognition site and wherein the endonuclease is a Type IIS restriction endonuclease. In some alternatives, the at least one Type II restriction endonuclease recognition site is a BsaI restriction endonuclease recognition site or a StuI restriction endonuclease recognition site, and wherein the endonuclease is BsaI or StuI. In some alternatives, the endonuclease recognition site is inverted. In some alternatives, the polynucleotide is a linear polynucleotide. In some alternatives, the polynucleotide has only one endonuclease recognition site. In some alternatives, the polynucleotide further comprises a polymerase promoter region. In some alternatives, the plurality of thymine nucleotides comprises at least one covalently linked guanine, cytosine, or an adenine, wherein the at least one covalently linked guanine, cytosine or adenine is optionally joined to the most 5' thymine (or 5' terminal thymine) in the plurality of thymine nucleotides. In some alternatives, the endonuclease cleavage site comprises at least one guanine, cytosine, or an adenine, wherein the endonuclease cleaves between a thymine and the at least one guanine, cytosine or adenine. In some alternatives, the polynucleotide further comprises at least one palindromic sequence, wherein the at least one palindromic sequence can form a hairpin. In some alternatives, the polynucleotide further comprises a third sequence, wherein the third sequence is capable of forming a tertiary structure such as a hairpin. In some alternatives, the gene is codon optimized for expression in human cells. The method of making a polynucleotide comprising a sequence encoding a nuclease, a template strand, an endonuclease recognition site and an endonuclease cleavage site for an endonuclease inserted therein, wherein said template strand comprises a plurality of thymine nucleotides can comprise providing a first nucleic acid sequence encoding a nuclease, providing a second nucleic acid sequence comprising at least one endonuclease recognition site, providing a third nucleic acid sequence, wherein the third nucleic acid sequence comprises the template strand, wherein the template strand comprises a plurality of thymine nucleotides, wherein said plurality of thymine nucleotides comprises at least, greater than, equal to, or any number in between 20, 30, 40, 50, 60, 70, 80, 90, 100, 110, 120, 130, 140, 150, 175, 200, 225, 250, 275, 300, 325, 350, 375, 400, 425, 450, 475, 500 or 550 covalently linked thymine nucleotides and wherein the third nucleic acid comprises the endonuclease cleavage site, wherein the endonuclease cleavage site is located within the plurality of thymine nucleotides or within 1, 2, 3, 4, 5, 6, 7, 7, 8, 9, 10, 11, 12, 13, 14, 15, 16, 17, 18, 19 or 20 base pairs away from the most 5' thymine (or 5' terminal thymine) in the plurality of thymine nucleotides, joining said first nucleic acid to one end of the second nucleic acid sequence and joining said third nucleic acid sequence to one end of the second nucleic acid sequence, wherein said second nucleic acid is covalently linked to one end of said third nucleic acid sequence, and wherein the said endonuclease recognition site is located within 55 base pairs of the endonuclease cleavage site for the endonuclease and said endonuclease cleavage site is within 1 to 40 base pairs of a most 5' thymine (or 5' terminal thymine) in the plurality of thymine nucleotides. In some alternatives, the polynucleotide further comprises telomeres. In some alternatives, the polynucleotide comprises a left arm wherein the left arm comprises a left telomere, a right arm wherein the right arm comprises a right telomere and a cloning region located between the left arm and the right arm. In some alternatives, the polynucleotide further comprises a third nucleic acid, wherein the third nucleic acid comprises a gene. In some alternatives, the gene encodes a protein for therapy. In some alternatives, the gene encodes a nuclease. In some alternatives, the nuclease is an endonuclease. In some alternatives, the nuclease comprises an amino acid sequence set forth in SEQ ID NO. 6 or is encoded by a nucleic acid sequence set forth in SEQ ID NO: 7-14. In some alternatives, the number of covalently linked thymines is greater than 120. In some alternatives, the number of covalently linked thymines is greater than 200. In some alternatives, the number of covalently linked thymines is greater than 300. In some alternatives, the at least one endonuclease recognition site is a Type II restriction endonuclease recognition site, and the endonuclease is a Type II restriction endonuclease. In some alternatives, the at least one endonuclease recognition site is a Type IIS restriction endonuclease recognition site, and wherein the endonuclease is a Type IIS restriction endonuclease. In some alternatives, the at least one Type II restriction endonuclease recognition site is a BsaI restriction endonuclease recognition site or a StuI restriction endonuclease recognition site, and wherein the endonuclease is BsaI or StuI. In some alternatives, the endonuclease recognition site is inverted. In some alternatives, the polynucleotide is a linear polynucleotide. In some alternatives, the polynucleotide has only one endonuclease recognition site. In some alternatives, the polynucleotide further comprises a polymerase promoter. In some alternatives, the plurality of thymine nucleotide comprises at least one guanine, cytosine, or an adenine. In some alternatives, the endonuclease cleavage site comprises at least one guanine, cytosine, or an adenine, wherein the endonuclease cleaves between a thymine and the at least one guanine, cytosine or adenine. In some alternatives, the polynucleotide further comprises at least one palindromic sequence, wherein the at least one palindromic sequence can form a hairpin. In some alternatives, the polynucleotide further comprises a fourth sequence, wherein the fourth sequence is capable of forming a tertiary structure such as a hairpin. In some alternatives, the gene is codon optimized for expression in human cells. In some alternatives, the polynucleotide further comprises a promoter for a polymerase. In some alternatives, polymerase is a DNA polymerase. In some alternatives, the DNA polymerase is a thermal stable polymerase, such as Taq polymerase. In some alternatives, the nucleotides are adenine, cytosine, guanine, thymine and/or uracil. In some alternatives, the method further comprises providing a set of primers. In some alternatives, the nucleic acid is DNA. In some alternatives, an RNA polymerase is used. In some alternatives, the contacting is performed at a temperature at least, greater than, equal to, or any temperature in between 30° C., 31° C., 32° C., 33° C., 34° C., 35° C., 36° C. or 37° C. In some alternatives, the contacting is performed for at least, greater than, equal to, or time in between 1, 5, 10, 20, 30, 40, 50, 60, 70, 80, 90 or 100 hours (e.g., at least, or equal to 1, 5, 10, 20, 30, 40, 50, 60, 70, 80, 90 or 100 hours or within a range defined by any two of the aforementioned times). In some alternatives, the nucleic acid is RNA. In some alternatives, the RNA comprises a plurality of adenine nucleotides, wherein the plurality of adenine nucleotides comprises at least, greater than, equal to, or any number in between 20, 30, 40, 50, 60, 70, 80, 90, 100, 110, 120, 130, 140, 150, 175, 200, 225, 250, 275, 300, 325, 350, 375, 400, 425, 450, 475, or 500 covalently linked adenines. In some alternatives, the number of covalently linked adenines is greater than 120. In some alternatives, the number of covalently linked adenines is greater than 200. In some alternatives, the number of covalently linked adenines is greater than 300. In some alternatives, the RNA further comprises a gene. In some alternatives, the gene encodes a protein for therapy. In some alternatives, the gene encodes a nuclease. In some alternatives, the gene encodes an endonuclease. In some alternatives, the nuclease comprises an amino acid sequence set forth in SEQ ID NO. 6 or is encoded by a nucleic acid sequence set forth in SEQ ID NO: 7-14. In some alternatives, the plurality of adenine nucleotides further comprises a guanine, cytosine or a uracil, and wherein the number of covalently linked adenines terminates with a guanine, cytosine or a uracil. In some alternatives, the nucleic acid further comprises at least one palindromic sequence, wherein the at least one palindromic sequence can form a hairpin. In some alternatives, the nucleic acid further comprises a sequence capable of forming a tertiary structure such as a hairpin. In some alternatives, the method further comprises providing an endonuclease. In some alternatives, the endonuclease is a Type II restriction endonuclease. In some alternatives, the endonuclease is a Type IIS restriction endonuclease. In some alternatives, the endonuclease is BsaI or StuI. In some alternatives, the gene is codon optimized for expression in human cells. In some alternatives, the nucleic acid is a DNA. In some alternatives, the nucleic acid is RNA. In some alternatives, the RNA comprises a plurality of adenine nucleotides, wherein the plurality of adenine nucleotides comprises at least, greater than, equal to, or any number in between 20, 30, 40, 50, 60, 70, 80, 90, 100, 110, 120, 130, 140, 150, 175, 200, 225, 250, 275, 300, 325, 350, 375, 400, 425, 450, 475, or 500 covalently linked adenines. In some alternatives, the number of covalently linked adenines is greater than 120. In some alternatives, the number of covalently linked adenines is greater than 200. In some alternatives, the number of covalently linked adenines is greater than 300. In some alternatives, the nucleic acid further comprises a gene. In some alternatives, the gene encodes a protein for therapy. In some alternatives, the gene encodes a nuclease. In some alternatives, the gene encodes an endonuclease. In some alternatives, the nuclease comprises an amino acid sequence set forth in SEQ ID NO. 6 or is encoded by a nucleic acid sequence set forth in SEQ ID NO: 7-14. In some alternatives, the covalently linked adenines terminate with a guanine, cytosine, thymine, or a uracil. In some alternatives, the nucleic acid further comprises at least one palindromic sequence, wherein the at least one palindromic sequence can form a hairpin. In some alternatives, the nucleic acid further comprises a sequence capable of forming a tertiary structure such as a hairpin. In some alternatives, the gene is codon optimized for expression in human cells. The method for manufacturing the nucleic acid comprising a nuclease can also be provided. The method comprises providing the polynucleotide of any one of the alternatives herein or a polynucleotide manufactured by a method of any one of the alternatives herein and contacting said polynucleotide with a polymerase in the presence of nucleotides. The polynucleotide can comprise a first nucleic acid sequence encoding a nuclease, a second nucleic acid sequence comprising at least one restriction endonuclease recognition site and a third nucleic acid sequence, wherein the third nucleic acid sequence comprises the template strand, wherein said plurality of thymine nucleotides comprises at least, greater than, equal to, or any number in between 20, 30, 40, 50, 60, 70, 80, 90, 100, 110, 120, 130, 140, 150, 175, 200, 225, 250, 275, 300, 325, 350, 375, 400, 425, 450, 475, 500 or 550 covalently linked thymine nucleotides and wherein the third nucleic acid comprises the restriction endonuclease cleavage site, wherein the restriction endonuclease cleavage site is located within the plurality of thymine nucleotides or within 1, 2, 3, 4, 5, 6, 7, 7, 8, 9, 10, 11, 12, 13, 14, 15, 16, 17, 18, 19 or 20 base pairs away from the most 5' thymine (or 5' terminal thymine) in the plurality of thymine nucleotides and wherein said second nucleic acid is covalently linked to one end of said third nucleic acid sequence, and wherein the said restriction endonuclease recognition site is located within 55 base pairs of the restriction endonuclease cleavage site for the restriction endonuclease and said restriction endonuclease cleavage site is within 1 to 40 base pairs of a most 5' thymine in the plurality of thymine nucleotides. Some polynucleotides comprise a first nucleic acid sequence comprising at least one restriction endonuclease recognition site and a second nucleic acid sequence, wherein the second nucleic acid sequence comprises the template strand, wherein the template strand comprises a plurality of thymine nucleotides, wherein said plurality of thymine nucleotides comprises at least, greater than, equal to, or any number in between 20, 30, 40, 50, 60, 70, 80, 90, 100, 110, 120, 130, 140, 150, 175, 200, 225, 250, 275, 300, 325, 350, 375, 400, 425, 450, 475, 500 or 550 covalently linked thymine nucleotides, wherein the second nucleic acid comprises the restriction endonuclease cleavage site, and wherein the restriction endonuclease cleavage site is within the plurality of thymine nucleotides or within 1, 2, 3, 4, 5, 6, 7, 7, 8, 9, 10, 11, 12, 13, 14, 15, 16, 17, 18, 19 or 20 base pairs away from the most 5' thymine (or 5' terminal thymine) in the plurality of thymine nucleotides and wherein said first nucleic acid is covalently linked to said second nucleic acid at one end of said second nucleic acid, and wherein the said restriction endonuclease recognition site is located within 1-55 base pairs such as, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54 or 55 base pairs, of the restriction endonuclease cleavage site for the restriction endonuclease and said restriction endonuclease cleavage site is within 1 to 40 base pairs, such as 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 base pairs, of a most 5' thymine (or 5' terminal thymine) in the plurality of thymine nucleotides. In some alternatives, the polynucleotide further comprises telomeres. In some alternatives, the polynucleotide comprises a left arm wherein the left arm comprises a left telomere, a right arm wherein the right arm comprises a right telomere and a cloning region located between the left arm and the right arm. In some alternatives, the nuclease comprises an amino acid sequence set forth in SEQ ID NO. 6 or is encoded by a nucleic acid sequence set forth in SEQ ID NO: 7-14. In some alternatives, the number of covalently linked thymines is greater than 120. In some alternatives, the number of covalently linked thymines is greater than 200. In some alternatives, the number of covalently linked thymines is greater than 300. In some alternatives, the at least one endonuclease recognition site is a Type II restriction endonuclease recognition site, and the endonuclease is a Type II restriction endonuclease. In some alternatives, the at least one endonuclease recognition site is a Type IIS restriction endonuclease recognition site and wherein the endonuclease is a Type IIS restriction endonuclease. In some alternatives, the at least one endonuclease recognition site is a BsaI restriction endonuclease recognition site or a StuI restriction endonuclease recognition site, and wherein the endonuclease is BsaI or StuI. In some alternatives, the endonuclease recognition site is inverted. In some alternatives, the polynucleotide is a linear polynucleotide. In some alternatives, the polynucleotide has only one endonuclease recognition site. In some alternatives, the polynucleotide further comprises a polymerase promoter. In some alternatives, the plurality of thymine nucleotides comprises at least one covalently linked guanine, cytosine, or an adenine, wherein the at least one covalently linked guanine, cytosine or adenine is optionally at the most 5' thymine (or 5' terminal thymine) in the plurality of thymine nucleotides. In some alternatives, the endonuclease cleavage site comprises at least one guanine, cytosine, or an adenine, wherein the endonuclease cleaves between a thymine and the at least one guanine, cytosine or adenine. In some alternatives, the polynucleotide further comprises at least one palindromic sequence, wherein the at least one palindromic sequence can form a hairpin. In some alternatives, the polynucleotide further comprises a seventh sequence, wherein the seventh sequence is capable of forming a tertiary structure such as a hairpin. In some alternatives, the sequence encoding the nuclease is optimized for expression in human cells. The method of making a polynucleotide comprising a sequence encoding a nuclease, a template strand, an endonuclease recognition site and an endonuclease cleavage site for an endonuclease inserted therein, wherein said template strand comprises a plurality of thymine nucleotides can comprise providing a first nucleic acid sequence encoding a nuclease, providing a second nucleic acid sequence comprising at least one endonuclease recognition site, providing a third nucleic acid sequence, wherein the third nucleic acid sequence comprises the template strand, wherein the template strand comprises a plurality of thymine nucleotides, wherein said plurality of thymine nucleotides comprises at least, greater than, equal to, or any number in between 20, 30, 40, 50, 60, 70, 80, 90, 100, 110, 120, 130, 140, 150, 175, 200, 225, 250, 275, 300, 325, 350, 375, 400, 425, 450, 475, 500 or 550 covalently linked thymine nucleotides and wherein the third nucleic acid comprises the endonuclease cleavage site, wherein the endonuclease cleavage site is located within the plurality of thymine nucleotides or within 1, 2, 3, 4, 5, 6, 7, 7, 8, 9, 10, 11, 12, 13, 14, 15, 16, 17, 18, 19 or 20 base pairs away from the most 5' thymine (or 5' terminal thymine) in the plurality of thymine nucleotides, joining said first nucleic acid to one end of the second nucleic acid sequence and joining said third nucleic acid sequence to one end of the second nucleic acid sequence, wherein said second nucleic acid is covalently linked to one end of said third nucleic acid sequence, and wherein the said endonuclease recognition site is located within 55 base pairs of the endonuclease cleavage site for the endonuclease and said endonuclease cleavage site is within 1 to 40 base pairs of a most 5' thymine in the plurality of thymine nucleotides. In some alternatives, the number of covalently linked thymines is greater than 120. In some alternatives, the number of covalently linked thymines is greater than 200. In some alternatives, the number of covalently linked thymines is greater than 300. In some alternatives, the at least one endonuclease recognition site is a Type II restriction endonuclease recognition site and the endonuclease is a Type II restriction endonuclease. In some alternatives, the at least one endonuclease recognition site is a Type IIS restriction endonuclease recognition site and the endonuclease is a Type IIS restriction endonuclease. In some alternatives, the at least one endonuclease recognition site is a BsaI restriction endonuclease recognition site or a StuI restriction endonuclease recognition site, and wherein the endonuclease is BsaI or StuI. In some alternatives, the endonuclease recognition site is inverted. In some alternatives, the polynucleotide is a linear polynucleotide. In some alternatives, the polynucleotide has only one endonuclease recognition site. In some alternatives, the plurality of covalently linked thymines comprises at least one guanine, cytosine, or an adenine. In some alternatives, the endonuclease cleavage site comprises at least one guanine, cytosine, or an adenine, wherein the endonuclease cleaves between a thymine and the at least one guanine, cytosine or adenine. In some alternatives, the nuclease comprises an amino acid sequence set forth in SEQ ID NO. 6 or is encoded by a nucleic acid sequence set forth in SEQ ID NO: 7-14. In some alternatives, the first nucleic acid sequence encoding the nuclease is codon optimized for expression in human cells. In some alternatives, the polynucleotide further comprises a promoter for a polymerase. In some alternatives, the polymerase is a DNA polymerase. In some alternatives, the DNA polymerase is a thermal stable polymerase, such as Taq polymerase. In some alternatives, the nucleotides are adenine, cytosine, guanine, thymine and/or uracil. In some alternatives, the method further comprises providing a set of primers. In some alternatives, the nucleic acid is DNA. In some alternatives, an RNA polymerase is used. In some alternatives, the contacting is performed at a temperature at least, greater than, equal to, or any temperature in between 30° C., 31° C., 32° C., 33° C., 34° C., 35° C., 36° C. or 37° C. In some alternatives, the contacting is performed for at least, greater than, equal to, or time in between 1, 5, 10, 20, 30, 40, 50, 60, 70, 80, 90 or 100 hours (e.g., at least, or equal to 1, 5, 10, 20, 30, 40, 50, 60, 70, 80, 90 or 100 hours or within a range defined by any two of the aforementioned times). In some alternatives, the nucleic acid is RNA. In some alternatives, the RNA comprises a plurality of adenine nucleotides, wherein the plurality of adenine nucleotides comprises at least, greater than, equal to, or any number in between 20, 30, 40, 50, 60, 70, 80, 90, 100, 110, 120, 130, 140, 150, 175, 200, 225, 250, 275, 300, 325, 350, 375, 400, 425, 450, 475, or 500 covalently linked adenines. In some alternatives, the number of covalently linked adenines is greater than 120. In some alternatives, the number of covalently linked adenines is greater than 200. In some alternatives, the number of covalently linked adenines is greater than 300. In some alternatives, the nuclease comprises an amino acid sequence set forth in SEQ ID NO. 6 or is encoded by a nucleic acid sequence set forth in SEQ ID NO: 7-14. In some alternatives, the plurality of adenine nucleotides further comprises a guanine, cytosine or a uracil, and wherein the number of covalently linked adenines terminates with a guanine, cytosine or a uracil. In some alternatives, the nucleic acid further comprises at least one palindromic sequence, wherein the at least one palindromic sequence can form a hairpin. In some alternatives, the nucleic acid further comprises a sequence capable of forming a tertiary structure such as a hairpin. In some alternatives, the method further comprises providing an endonuclease. In some alternatives, the endonuclease is a Type II restriction endonuclease. In some alternatives, the endonuclease is a Type IIS restriction endonuclease. In some alternatives, the endonuclease is BsaI or StuI. The RNA can comprise a first sequence comprising at least one compliment sequence to an endonuclease recognition site covalently linked to a plurality of adenine nucleotides at the 3' end of said plurality of adenine nucleotides, a second sequence that comprises a plurality of adenine nucleotides, wherein the plurality of adenines comprises at least, greater than, equal to, or any number in between 20, 30, 40, 50, 60, 70, 80, 90, 100, 110, 120, 130, 140, 150, 175, 200, 225, 250, 275, 300, 325, 350, 375, 400, 425, 450, 475, or 500 covalently linked adenines and wherein said compliment sequence to an endonuclease recognition site of said first nucleic acid is covalently linked to said plurality of adenine nucleotides of said second nucleic acid at the 3' end of said plurality of adenine nucleotides of said second nucleic acid. In some alternatives, the mRNA further encodes a gene. In some alternatives, the gene is an endonuclease gene. In some alternatives, the at least one endonuclease site is inverted, and wherein the sequence encoding an RNA compliment is a compliment to the inverted endonuclease site. In some alternatives, the at least one endonuclease is a Type II restriction endonuclease recognition site. In some alternatives, the at least one endonuclease site is a Type IIS restriction endonuclease recognition site. In some alternatives, the at least one endonuclease site is a BsaI recognition site or a StuI recognition site. In some alternatives, the gene is codon optimized for expression in a human cell. In some alternatives, the cell is a T-cell or a primary cell. In some alternatives, the introducing is performed by electroporation. In some alternatives, the cell is a human cell. In some alternatives, the endonuclease cleavage site is located 1, 2, 3, 4, 5, 6, 7, 7, 8, 9, 10, 11, 12, 13, 14, 15, 16, 17, 18, 19 or 20 base pairs away from the most 5' thymine (or 5' terminal thymine) in the plurality of thymine nucleotides. In some alternatives, the endonuclease cleavage site is located 1, 2, 3, 4, 5, 6, 7, 7, 8, 9 or 10 base pairs away from the most 5' thymine (or 5' terminal thymine) in the plurality of thymine nucleotides.

In some alternatives, a method of treating, ameliorating, or inhibiting disease in a subject is provided, wherein the method comprises delivering the pharmaceutical composition of any of the alternatives herein, to the subject. The pharmaceutical composition can comprise a pharmaceutical vehicle and a nucleic acid of any one of the alternatives herein or mRNA of any one of the alternatives herein. The nucleic acid can manufactured by a method of any one of the alternatives described herein. In some alternatives, the method comprises providing the polynucleotide of any one of the alternatives provided herein, or the polynucleotide manufactured by any one of the alternatives provided herein and contacting said polynucleotide with a polymerase in the presence of nucleotides. The polynucleotide can comprise a first nucleic acid sequence encoding a nuclease, a second nucleic acid sequence comprising at least one restriction endonuclease recognition site and a third nucleic acid sequence, wherein the third nucleic acid sequence comprises the template strand, wherein said plurality of thymine nucleotides comprises at least, greater than, equal to, or any number in between 20, 30, 40, 50, 60, 70, 80, 90, 100, 110, 120, 130, 140, 150, 175, 200, 225, 250, 275, 300, 325, 350, 375, 400, 425, 450, 475, 500 or 550 covalently linked thymine nucleotides and wherein the third nucleic acid comprises the restriction endonuclease cleavage site, wherein the restriction endonuclease cleavage site is located within the plurality of thymine nucleotides or within 1, 2, 3, 4, 5, 6, 7, 7, 8, 9, 10, 11, 12, 13, 14, 15, 16, 17, 18, 19 or 20 base pairs away from the most 5' thymine (or 5' terminal thymine) in the plurality of thymine nucleotides and wherein said second nucleic acid is covalently linked to one end of said third nucleic acid sequence, and wherein the said restriction endonuclease recognition site is located within 55 base pairs of the restriction endonuclease cleavage site for the restriction endonuclease and said restriction endonuclease cleavage site is within 1 to 40 base pairs of a most 5' thymine (or 5' terminal thymine) in the plurality of thymine nucleotides. Some polynucleotides comprise a first nucleic acid sequence comprising at least one restriction endonuclease recognition site and a second nucleic acid sequence, wherein the second nucleic acid sequence comprises the template strand, wherein the template strand comprises a plurality of thymine nucleotides, wherein said plurality of thymine nucleotides comprises at least, greater than, equal to, or any number in between 20, 30, 40, 50, 60, 70, 80, 90, 100, 110, 120, 130, 140, 150, 175, 200, 225, 250, 275, 300, 325, 350, 375, 400, 425, 450, 475, 500 or 550 covalently linked thymine nucleotides, wherein the second nucleic acid comprises the restriction endonuclease cleavage site, and wherein the restriction endonuclease cleavage site is within the plurality of thymine nucleotides or within 1, 2, 3, 4, 5, 6, 7, 7, 8, 9, 10, 11, 12, 13, 14, 15, 16, 17, 18, 19 or 20 base pairs away from the most 5' thymine (or 5' terminal thymine) in the plurality of thymine nucleotides and wherein said first nucleic acid is covalently linked to said second nucleic acid at one end of said second nucleic acid, and wherein the said restriction endonuclease recognition site is located within 1-55 base pairs such as, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54 or 55 base pairs, of the restriction endonuclease cleavage site for the restriction endonuclease and said restriction endonuclease cleavage site is within 1 to 40 base pairs, such as 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 base pairs, of a most 5' thymine (or 5' terminal thymine) in the plurality of thymine nucleotides. In some alternatives, the polynucleotide further comprises telomeres. In some alternatives, the polynucleotide comprises a left arm wherein the left arm comprises a left telomere, a right arm wherein the right arm comprises a right telomere and a cloning region located between the left arm and the right arm. In some alternatives, the polynucleotide further comprises a third nucleic acid, wherein the third nucleic acid comprises a gene. In some alternatives, the gene encodes a protein for therapy. In some alternatives, the gene encodes a nuclease. In some alternatives, the nuclease is an endonuclease. In some alternatives, the nuclease comprises an amino acid sequence set forth in SEQ ID NO. 6 or is encoded by a nucleic acid sequence set forth in SEQ ID NO: 7-14. In some alternatives, the number of covalently linked thymines is greater than 120. In some alternatives, the number of covalently linked thymines is greater than 200. In some alternatives, the number of covalently linked thymines is greater than 300. In some alternatives, the at least one endonuclease recognition site is a Type II restriction endonuclease recognition site, and the endonuclease is a Type II restriction endonuclease. In some alternatives, the at least one endonuclease recognition site is a Type IIS restriction endonuclease recognition site and wherein the endonuclease is a Type IIS restriction endonuclease. In some alternatives, the at least one endonuclease recognition site is a BsaI restriction endonuclease recognition site or a StuI restriction endonuclease recognition site, and wherein the endonuclease is BsaI or StuI. In some alternatives, the endonuclease recognition site is inverted. In some alternatives, the polynucleotide is a linear polynucleotide. In some alternatives, the polynucleotide has only one endonuclease recognition site. In some alternatives, the polynucleotide further comprises a polymerase promoter region. In some alternatives, the plurality of thymine nucleotides comprises at least one covalently linked guanine, cytosine, or an adenine, wherein the at least one covalently linked guanine, cytosine or adenine is optionally joined to the most 5' thymine (or 5' terminal thymine) in the plurality of thymine nucleotides. In some alternatives, the endonuclease cleavage site comprises at least one guanine, cytosine, or an adenine, wherein the endonuclease cleaves between a thymine and the at least one guanine, cytosine or adenine. In some alternatives, the polynucleotide further comprises at least one palindromic sequence, wherein the at least one palindromic sequence can form a hairpin. In some alternatives, the polynucleotide further comprises a third sequence, wherein the third sequence is capable of forming a tertiary structure such as a hairpin. In some alternatives, the gene is codon optimized for expression in human cells. The method of making a polynucleotide comprising a sequence encoding a nuclease, a template strand, an endonuclease recognition site and an endonuclease cleavage site for an endonuclease inserted therein, wherein said template strand comprises a plurality of thymine nucleotides can comprise providing a first nucleic acid sequence encoding a nuclease, providing a second nucleic acid sequence comprising at least one endonuclease recognition site, providing a third nucleic acid sequence, wherein the third nucleic acid sequence comprises the template strand, wherein the template strand comprises a plurality of thymine nucleotides, wherein said plurality of thymine nucleotides comprises at least, greater than, equal to, or any number in between 20, 30, 40, 50, 60, 70, 80, 90, 100, 110, 120, 130, 140, 150, 175, 200, 225, 250, 275, 300, 325, 350, 375, 400, 425, 450, 475, 500 or 550 covalently linked thymine nucleotides and wherein the third nucleic acid comprises the endonuclease cleavage site, wherein the endonuclease cleavage site is located within the plurality of thymine nucleotides or within 1, 2, 3, 4, 5, 6, 7, 7, 8, 9, 10, 11, 12, 13, 14, 15, 16, 17, 18, 19 or 20 base pairs away from the most 5' thymine (or 5' terminal thymine) in the plurality of thymine nucleotides, joining said first nucleic acid to one end of the second nucleic acid sequence and joining said third nucleic acid sequence to one end of the second nucleic acid sequence, wherein said second nucleic acid is covalently linked to one end of said third nucleic acid sequence, and wherein the said endonuclease recognition site is located within 55 base pairs of the endonuclease cleavage site for the endonuclease and said endonuclease cleavage site is within 1 to 40 base pairs of a most 5' thymine in the plurality of thymine nucleotides. In some alternatives, the polynucleotide further comprises telomeres. In some alternatives, the polynucleotide comprises a left arm wherein the left arm comprises a left telomere, a right arm wherein the right arm comprises a right telomere and a cloning region located between the left arm and the right arm. In some alternatives, the polynucleotide further comprises a third nucleic acid, wherein the third nucleic acid comprises a gene. In some alternatives, the gene encodes a protein for therapy. In some alternatives, the gene encodes a nuclease. In some alternatives, the nuclease is an endonuclease. In some alternatives, the nuclease comprises an amino acid sequence set forth in SEQ ID NO. 6 or is encoded by a nucleic acid sequence set forth in SEQ ID NO: 7-14. In some alternatives, the number of covalently linked thymines is greater than 120. In some alternatives, the number of covalently linked thymines is greater than 200. In some alternatives, the number of covalently linked thymines is greater than 300. In some alternatives, the at least one endonuclease recognition site is a Type II restriction endonuclease recognition site, and the endonuclease is a Type II restriction endonuclease. In some alternatives, the at least one endonuclease recognition site is a Type IIS restriction endonuclease recognition site, and wherein the endonuclease is a Type IIS restriction endonuclease. In some alternatives, the at least one endonuclease recognition site is a BsaI restriction endonuclease recognition site or a StuI restriction endonuclease recognition site, and wherein the endonuclease is BsaI or StuI. In some alternatives, the endonuclease recognition site is inverted. In some alternatives, the polynucleotide is a linear polynucleotide. In some alternatives, the polynucleotide has only one endonuclease recognition site. In some alternatives, the polynucleotide further comprises a polymerase promoter. In some alternatives, the plurality of thymine nucleotides comprises at least one covalently linked guanine, cytosine, or an adenine, wherein the at least one covalently linked guanine, cytosine or adenine is optionally joined to the most 5' thymine (or 5' terminal thymine) in the plurality of thymine nucleotides. In some alternatives, the endonuclease cleavage site comprises at least one guanine, cytosine, or an adenine, wherein the endonuclease cleaves between a thymine and the at least one guanine, cytosine or adenine. In some alternatives, the polynucleotide further comprises at least one palindromic sequence, wherein the at least one palindromic sequence can form a hairpin. In some alternatives, the polynucleotide further comprises a fourth sequence, wherein the fourth sequence is capable of forming a tertiary structure such as a hairpin. In some alternatives, the gene is codon optimized for expression in human cells. In some alternatives, the polynucleotide further comprises a promoter for a polymerase. In some alternatives, polymerase is a DNA polymerase. In some alternatives, the DNA polymerase is a thermal stable polymerase, such as Taq polymerase. In some alternatives, the nucleotides are adenine, cytosine, guanine, thymine and/or uracil. In some alternatives, the method further comprises providing a set of primers. In some alternatives, the nucleic acid is DNA. In some alternatives, an RNA polymerase is used. In some alternatives, the contacting is performed at a temperature at least, greater than, equal to, or any temperature in between 30° C., 31° C., 32° C., 33° C., 34° C., 35° C., 36° C. or 37° C. In some alternatives, the contacting is performed for at least, greater than, equal to, or time in between 1, 5, 10, 20, 30, 40, 50, 60, 70, 80, 90 or 100 hours (e.g., at least, or equal to 1, 5, 10, 20, 30, 40, 50, 60, 70, 80, 90 or 100 hours or within a range defined by any two of the aforementioned times). In some alternatives, the nucleic acid is RNA. In some alternatives, the RNA comprises a plurality of adenine nucleotides, wherein the plurality of adenine nucleotides comprises at least, greater than, equal to, or any number in between 20, 30, 40, 50, 60, 70, 80, 90, 100, 110, 120, 130, 140, 150, 175, 200, 225, 250, 275, 300, 325, 350, 375, 400, 425, 450, 475, or 500 covalently linked adenines. In some alternatives, the number of covalently linked adenines is greater than 120. In some alternatives, the number of covalently linked adenines is greater than 200. In some alternatives, the number of covalently linked adenines is greater than 300. In some alternatives, the RNA further comprises a gene. In some alternatives, the gene encodes a protein for therapy. In some alternatives, the gene encodes a nuclease.

In some alternatives, the gene encodes an endonuclease. In some alternatives, the nuclease comprises an amino acid sequence set forth in SEQ ID NO. 6 or is encoded by a nucleic acid sequence set forth in SEQ ID NO: 7-14. In some alternatives, the plurality of adenine nucleotides further comprises a guanine, cytosine or a uracil, and wherein the number of covalently linked adenines terminates with a guanine, cytosine or a uracil. In some alternatives, the nucleic acid further comprises at least one palindromic sequence, wherein the at least one palindromic sequence can form a hairpin. In some alternatives, the nucleic acid further comprises a sequence capable of forming a tertiary structure such as a hairpin. In some alternatives, the method further comprises providing an endonuclease. In some alternatives, the endonuclease is a Type II restriction endonuclease. In some alternatives, the endonuclease is a Type IIS restriction endonuclease. In some alternatives, the endonuclease is BsaI or StuI. In some alternatives, the gene is codon optimized for expression in human cells. In some alternatives, the nucleic acid is a DNA. In some alternatives, the nucleic acid is RNA. In some alternatives, the RNA comprises a plurality of adenine nucleotides, wherein the plurality of adenine nucleotides comprises at least, greater than, equal to, or any number in between 20, 30, 40, 50, 60, 70, 80, 90, 100, 110, 120, 130, 140, 150, 175, 200, 225, 250, 275, 300, 325, 350, 375, 400, 425, 450, 475, or 500 covalently linked adenines. In some alternatives, the number of covalently linked adenines is greater than 120. In some alternatives, the number of covalently linked adenines is greater than 200. In some alternatives, the number of covalently linked adenines is greater than 300. In some alternatives, the nucleic acid further comprises a gene. In some alternatives, the gene encodes a protein for therapy. In some alternatives, the gene encodes a nuclease. In some alternatives, the gene encodes an endonuclease. In some alternatives, the nuclease comprises an amino acid sequence set forth in SEQ ID NO. 6 or is encoded by a nucleic acid sequence set forth in SEQ ID NO: 7-14. In some alternatives, the covalently linked adenines terminate with a guanine, cytosine, thymine, or a uracil. In some alternatives, the nucleic acid further comprises at least one palindromic sequence, wherein the at least one palindromic sequence can form a hairpin. In some alternatives, the nucleic acid further comprises a sequence capable of forming a tertiary structure such as a hairpin. In some alternatives, the gene is codon optimized for expression in human cells. The method for manufacturing the nucleic acid comprising a nuclease can also be provided. The method comprises providing the polynucleotide of any one of the alternatives herein or a polynucleotide manufactured by a method of any one of the alternatives herein and contacting said polynucleotide with a polymerase in the presence of nucleotides. The polynucleotide can comprise a first nucleic acid sequence encoding a nuclease, a second nucleic acid sequence comprising at least one restriction endonuclease recognition site and a third nucleic acid sequence, wherein the third nucleic acid sequence comprises the template strand, wherein said plurality of thymine nucleotides comprises at least, greater than, equal to, or any number in between 20, 30, 40, 50, 60, 70, 80, 90, 100, 110, 120, 130, 140, 150, 175, 200, 225, 250, 275, 300, 325, 350, 375, 400, 425, 450, 475, 500 or 550 covalently linked thymine nucleotides and wherein the third nucleic acid comprises the restriction endonuclease cleavage site, wherein the restriction endonuclease cleavage site is located within the plurality of thymine nucleotides or within 1, 2, 3, 4, 5, 6, 7, 7, 8, 9, 10, 11, 12, 13, 14, 15, 16, 17, 18, 19 or 20 base pairs away from the most 5' thymine (or 5' terminal thymine) in the plurality of thymine nucleotides and wherein said second nucleic acid is covalently linked to one end of said third nucleic acid sequence, and wherein the said restriction endonuclease recognition site is located within 55 base pairs of the restriction endonuclease cleavage site for the restriction endonuclease and said restriction endonuclease cleavage site is within 1 to 40 base pairs of a most 5' thymine in the plurality of thymine nucleotides. Some polynucleotides comprise a first nucleic acid sequence comprising at least one restriction endonuclease recognition site and a second nucleic acid sequence, wherein the second nucleic acid sequence comprises the template strand, wherein the template strand comprises a plurality of thymine nucleotides, wherein said plurality of thymine nucleotides comprises at least, greater than, equal to, or any number in between 20, 30, 40, 50, 60, 70, 80, 90, 100, 110, 120, 130, 140, 150, 175, 200, 225, 250, 275, 300, 325, 350, 375, 400, 425, 450, 475, 500 or 550 covalently linked thymine nucleotides, wherein the second nucleic acid comprises the restriction endonuclease cleavage site, and wherein the restriction endonuclease cleavage site is within the plurality of thymine nucleotides or within 1, 2, 3, 4, 5, 6, 7, 7, 8, 9, 10, 11, 12, 13, 14, 15, 16, 17, 18, 19 or 20 base pairs away from the most 5' thymine (or 5' terminal thymine) in the plurality of thymine nucleotides and wherein said first nucleic acid is covalently linked to said second nucleic acid at one end of said second nucleic acid, and wherein the said restriction endonuclease recognition site is located within 1-55 base pairs such as, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54 or 55 base pairs, of the restriction endonuclease cleavage site for the restriction endonuclease and said restriction endonuclease cleavage site is within 1 to 40 base pairs, such as 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 base pairs, of a most 5' thymine (or 5' terminal thymine) in the plurality of thymine nucleotides. In some alternatives, the polynucleotide further comprises telomeres. In some alternatives, the polynucleotide comprises a left arm wherein the left arm comprises a left telomere, a right arm wherein the right arm comprises a right telomere and a cloning region located between the left arm and the right arm. In some alternatives, the nuclease comprises an amino acid sequence set forth in SEQ ID NO. 6 or is encoded by a nucleic acid sequence set forth in SEQ ID NO: 7-14. In some alternatives, the number of covalently linked thymines is greater than 120. In some alternatives, the number of covalently linked thymines is greater than 200. In some alternatives, the number of covalently linked thymines is greater than 300. In some alternatives, the at least one endonuclease recognition site is a Type II restriction endonuclease recognition site, and the endonuclease is a Type II restriction endonuclease. In some alternatives, the at least one endonuclease recognition site is a Type IIS restriction endonuclease recognition site and wherein the endonuclease is a Type IIS restriction endonuclease. In some alternatives, the at least one endonuclease recognition site is a BsaI restriction endonuclease recognition site or a StuI restriction endonuclease recognition site, and wherein the endonuclease is BsaI or StuI. In some alternatives, the endonuclease recognition site is inverted. In some alternatives, the polynucleotide is a linear polynucleotide. In some alternatives, the polynucleotide has only one endonuclease recognition site. In some alternatives, the polynucleotide further comprises a polymerase promoter. In some alternatives, the plurality of thymine nucleotides comprises at least one covalently linked guanine, cytosine, or an adenine, wherein the at least one covalently linked guanine, cytosine or adenine is optionally joined to the most 5' thymine (or 5' terminal thymine) in the plurality of thymine nucleotides. In some alternatives, the endonuclease cleavage site comprises at least one guanine, cytosine, or an adenine, wherein the endonuclease cleaves between a thymine and the at least one guanine, cytosine or adenine. In some alternatives, the polynucleotide further comprises at least one palindromic sequence, wherein the at least one palindromic sequence can form a hairpin. In some alternatives, the polynucleotide further comprises a seventh sequence, wherein the seventh sequence is capable of forming a tertiary structure such as a hairpin. In some alternatives, the sequence encoding the nuclease is optimized for expression in human cells. The method of making a polynucleotide comprising a sequence encoding a nuclease, a template strand, an endonuclease recognition site and an endonuclease cleavage site for an endonuclease inserted therein, wherein said template strand comprises a plurality of thymine nucleotides can comprise providing a first nucleic acid sequence encoding a nuclease, providing a second nucleic acid sequence comprising at least one endonuclease recognition site, providing a third nucleic acid sequence, wherein the third nucleic acid sequence comprises the template strand, wherein the template strand comprises a plurality of thymine nucleotides, wherein said plurality of thymine nucleotides comprises at least, greater than, equal to, or any number in between 20, 30, 40, 50, 60, 70, 80, 90, 100, 110, 120, 130, 140, 150, 175, 200, 225, 250, 275, 300, 325, 350, 375, 400, 425, 450, 475, 500 or 550 covalently linked thymine nucleotides and wherein the third nucleic acid comprises the endonuclease cleavage site, wherein the endonuclease cleavage site is located within the plurality of thymine nucleotides or within 1, 2, 3, 4, 5, 6, 7, 7, 8, 9, 10, 11, 12, 13, 14, 15, 16, 17, 18, 19 or 20 base pairs away from the most 5' thymine (or 5' terminal thymine) in the plurality of thymine nucleotides, joining said first nucleic acid to one end of the second nucleic acid sequence and joining said third nucleic acid sequence to one end of the second nucleic acid sequence, wherein said second nucleic acid is covalently linked to one end of said third nucleic acid sequence, and wherein the said endonuclease recognition site is located within 55 base pairs of the endonuclease cleavage site for the endonuclease and said endonuclease cleavage site is within 1 to 40 base pairs of a most 5' thymine in the plurality of thymine nucleotides. In some alternatives, the number of covalently linked thymines is greater than 120. In some alternatives, the number of covalently linked thymines is greater than 200. In some alternatives, the number of covalently linked thymines is greater than 300. In some alternatives, the at least one endonuclease recognition site is a Type II restriction endonuclease recognition site and the endonuclease is a Type II restriction endonuclease. In some alternatives, the at least one endonuclease recognition site is a Type IIS restriction endonuclease recognition site and the endonuclease is a Type IIS restriction endonuclease. In some alternatives, the at least one Type II restriction endonuclease recognition site is a BsaI restriction endonuclease recognition site or a StuI restriction endonuclease recognition site, and wherein the endonuclease is BsaI or StuI. In some alternatives, the endonuclease recognition site is inverted. In some alternatives, the polynucleotide is a linear polynucleotide. In some alternatives, the polynucleotide has only one endonuclease recognition site. In some alternatives, the plurality of thymine nucleotides comprises at least one covalently linked guanine, cytosine, or an adenine, wherein the at least one covalently linked guanine, cytosine or adenine is optionally joined to the most 5' thymine (or 5' terminal thymine) in the plurality of thymine nucleotides. In some alternatives, the endonuclease cleavage site comprises at least one guanine, cytosine, or an adenine, wherein the endonuclease cleaves between a thymine and the at least one guanine, cytosine or adenine. In some alternatives, the nuclease comprises an amino acid sequence set forth in SEQ ID NO. 6 or is encoded by a nucleic acid sequence set forth in SEQ ID NO: 7-14. In some alternatives, the first nucleic acid sequence encoding the nuclease is codon optimized for expression in human cells. In some alternatives, the polynucleotide further comprises a promoter for a polymerase. In some alternatives, the polymerase is a DNA polymerase. In some alternatives, the DNA polymerase is a thermal stable polymerase, such as Taq polymerase. In some alternatives, the nucleotides are adenine, cytosine, guanine, thymine and/or uracil. In some alternatives, the method further comprises providing a set of primers. In some alternatives, the nucleic acid is DNA. In some alternatives, an RNA polymerase is used. In some alternatives, the contacting is performed at a temperature at least, greater than, equal to, or any temperature in between 30° C., 31° C., 32° C., 33° C., 34° C., 35° C., 36° C. or 37° C. In some alternatives, the contacting is performed for at least, greater than, equal to, or time in between 1, 5, 10, 20, 30, 40, 50, 60, 70, 80, 90 or 100 hours (e.g., at least, or equal to 1, 5, 10, 20, 30, 40, 50, 60, 70, 80, 90 or 100 hours or within a range defined by any two of the aforementioned times). In some alternatives, the nucleic acid is RNA. In some alternatives, the RNA comprises a plurality of adenine nucleotides, wherein the plurality of adenine nucleotides comprises at least, greater than, equal to, or any number in between 20, 30, 40, 50, 60, 70, 80, 90, 100, 110, 120, 130, 140, 150, 175, 200, 225, 250, 275, 300, 325, 350, 375, 400, 425, 450, 475, or 500 covalently linked adenines. In some alternatives, the number of covalently linked adenines is greater than 120. In some alternatives, the number of covalently linked adenines is greater than 200. In some alternatives, the number of covalently linked adenines is greater than 300. In some alternatives, the nuclease comprises an amino acid sequence set forth in SEQ ID NO. 6 or is encoded by a nucleic acid sequence set forth in SEQ ID NO: 7-14. In some alternatives, the plurality of adenine nucleotides further comprises a guanine, cytosine or a uracil, and wherein the number of covalently linked adenines terminates with a guanine, cytosine or a uracil. In some alternatives, the nucleic acid further comprises at least one palindromic sequence, wherein the at least one palindromic sequence can form a hairpin. In some alternatives, the nucleic acid further comprises a sequence capable of forming a tertiary structure such as a hairpin. In some alternatives, the method further comprises providing an endonuclease. In some alternatives, the endonuclease is a Type II restriction endonuclease. In some alternatives, the endonuclease is a Type IIS restriction endonuclease. In some alternatives, the endonuclease is BsaI or StuI. The RNA can comprise a first sequence comprising at least one compliment sequence to an endonuclease recognition site covalently linked to a plurality of adenine nucleotides at the 3' end of said plurality of adenine nucleotides, a second sequence that comprises a plurality of adenine nucleotides, wherein the plurality of adenines comprises at least, greater than, or any number in between 20, 30, 40, 50, 60, 70, 80, 90, 100, 110, 120, 130, 140, 150, 175, 200, 225, 250, 275, 300, 325, 350, 375, 400, 425, 450, 475, or 500 covalently linked adenines and wherein said compliment sequence to an endonuclease recognition site of said first nucleic acid is covalently linked to said plurality of adenine nucleotides of said second nucleic acid at the 3' end of said plurality of adenine nucleotides of said second nucleic acid. In some alternatives, the mRNA further encodes a gene. In some alternatives, the gene is an endonuclease gene. In some alternatives, the at least one endonuclease site is inverted, and wherein the sequence encoding an RNA compliment is a compliment to the inverted endonuclease site. In some alternatives, the at least one endonuclease is a Type II restriction endonuclease recognition site. In some alternatives, the at least one endonuclease site is a Type IIS restriction endonuclease recognition site. In some alternatives, the at least one endonuclease site is a BsaI recognition site or a StuI recognition site. In some alternatives, the gene is codon optimized for expression in a human cell. In some alternatives, the endonuclease cleavage site is located 1, 2, 3, 4, 5, 6, 7, 7, 8, 9, 10, 11, 12, 13, 14, 15, 16, 17, 18, 19 or 20 base pairs away from the most 5' thymine (or 5' terminal thymine) in the plurality of thymine nucleotides. In some alternatives, the endonuclease cleavage site is located 1, 2, 3, 4, 5, 6, 7, 7, 8, 9 or 10 base pairs away from the most 5' thymine (or 5' terminal thymine) in the plurality of thymine nucleotides.

In some alternatives, a method of treating, ameliorating, or inhibiting disease in a subject is provided, the method can comprise introducing into a cell the mRNA or RNA of any one of the alternatives herein and delivering the cell to the subject. In some alternatives, the RNA comprises a plurality of adenine nucleotides, wherein the plurality of adenine nucleotides comprises at least, greater than, equal to, or any number in between 20, 30, 40, 50, 60, 70, 80, 90, 100, 110, 120, 130, 140, 150, 175, 200, 225, 250, 275, 300, 325, 350, 375, 400, 425, 450, 475, or 500 covalently linked adenines. In some alternatives, the number of covalently linked adenines is greater than 120. In some alternatives, the number of covalently linked adenines is greater than 200. In some alternatives, the number of covalently linked adenines is greater than 300. In some alternatives, the RNA further comprises a gene. In some alternatives, the gene encodes a protein for therapy. In some alternatives, the gene encodes a nuclease. In some alternatives, the gene encodes an endonuclease. In some alternatives, the nuclease comprises an amino acid sequence set forth in SEQ ID NO. 6 or is encoded by a nucleic acid sequence set forth in SEQ ID NO: 7-14. In some alternatives, the plurality of adenine nucleotides further comprises a guanine, cytosine or a uracil, and wherein the number of covalently linked adenines terminates with a guanine, cytosine or a uracil. In some alternatives, the nucleic acid further comprises at least one palindromic sequence, wherein the at least one palindromic sequence can form a hairpin. In some alternatives, the nucleic acid further comprises a sequence capable of forming a tertiary structure such as a hairpin. In some alternatives, the method further comprises providing an endonuclease. In some alternatives, the endonuclease is a Type II restriction endonuclease. In some alternatives, the endonuclease is a Type IIS restriction endonuclease. In some alternatives, the endonuclease is BsaI or StuI. In some alternatives, the gene is codon optimized for expression in human cells. In some alternatives, the nucleic acid is a DNA. In some alternatives, the nucleic acid is RNA. In some alternatives, the RNA comprises a plurality of adenine nucleotides, wherein the plurality of adenine nucleotides comprises at least, greater than, equal to, or any number in between 20, 30, 40, 50, 60, 70, 80, 90, 100, 110, 120, 130, 140, 150, 175, 200, 225, 250, 275, 300, 325, 350, 375, 400, 425, 450, 475, or 500 covalently linked adenines. In some alternatives, the number of covalently linked adenines is greater than 120. In some alternatives, the number of covalently linked adenines is greater than 200. In some alternatives, the number of covalently linked adenines is greater than 300. In some alternatives, the nucleic acid further comprises a gene. In some alternatives, the gene encodes a protein for therapy. In some alternatives, the gene encodes a nuclease. In some alternatives, the gene encodes an endonuclease. In some alternatives, the nuclease comprises an amino acid sequence set forth in SEQ ID NO. 6 or is encoded by a nucleic acid sequence set forth in SEQ ID NO: 7-14. In some alternatives, the covalently linked adenines terminate with a guanine, cytosine, thymine, or a uracil. In some alternatives, the nucleic acid further comprises at least one palindromic sequence, wherein the at least one palindromic sequence can form a hairpin. In some alternatives, the nucleic acid further comprises a sequence capable of forming a tertiary structure such as a hairpin. In some alternatives, the gene is codon optimized for expression in human cells. In some alternatives, the mRNA encodes a protein, such as a nuclease, for example SEQ ID NOs. 6-14, wherein said mRNA comprises a poly(A) tail that is at least 7, 8, 9, 10, 11, 12, 13, 14, 15, 16, 17, 18, 19, 20, 25, 30, 35, 40, 45, 50, 60, 70, 80, 90, 100, 150, 200, 250, 300, 400, or 500 residues in length or a length that is within a range defined by any two of the aforementioned lengths and, wherein said mRNA lacks a 5' and/or 3' UTR or lacks a native 5' and/or 3' UTR and/or lacks one or more sequences required for native polyadenylation such as, a cleavage/polyadenylation specificity factor (CPSF) binding site, a cleavage stimulation factor binding site (CstF), a cleavage factor I binding site (CFI), or a cleavage factor II binding site (CFII),In some alternatives, the cell is a T-cell or a primary cell. In some alternatives, the introducing is performed by electroporation. In some alternatives, the cell is a human cell. In some alternatives, the endonuclease cleavage site is located 1, 2, 3, 4, 5, 6, 7, 7, 8, 9, 10, 11, 12, 13, 14, 15, 16, 17, 18, 19 or 20 base pairs away from the most 5' thymine (or 5' terminal thymine) in the plurality of thymine nucleotides. In some alternatives, the endonuclease cleavage site is located 1, 2, 3, 4, 5, 6, 7, 7, 8, 9 or 10 base pairs away from the most 5' thymine (or 5' terminal thymine) in the plurality of thymine nucleotides.

In some alternatives, a pharmaceutical composition is provided, wherein the composition comprises a pharmaceutical vehicle and the mRNA of any one of the alternatives herein. In some alternatives, the RNA comprises a plurality of adenine nucleotides, wherein the plurality of adenine nucleotides comprises at least, greater than, equal to, or any number in between 20, 30, 40, 50, 60, 70, 80, 90, 100, 110, 120, 130, 140, 150, 175, 200, 225, 250, 275, 300, 325, 350, 375, 400, 425, 450, 475, or 500 covalently linked adenines. In some alternatives, the number of covalently linked adenines is greater than 120. In some alternatives, the number of covalently linked adenines is greater than 200. In some alternatives, the number of covalently linked adenines is greater than 300. In some alternatives, the RNA further comprises a gene. In some alternatives, the gene encodes a protein for therapy. In some alternatives, the gene encodes a nuclease. In some alternatives, the gene encodes an endonuclease. In some alternatives, the nuclease comprises an amino acid sequence set forth in SEQ ID NO. 6 or is encoded by a nucleic acid sequence set forth in SEQ ID NO: 7-14. In some alternatives, the plurality of adenine nucleotides further comprises a guanine, cytosine or a uracil, and wherein the number of covalently linked adenines terminates with a guanine, cytosine or a uracil. In some alternatives, the nucleic acid further comprises at least one palindromic sequence, wherein the at least one palindromic sequence can form a hairpin. In some alternatives, the nucleic acid further comprises a sequence capable of forming a tertiary structure such as a hairpin. In some alternatives, the method further comprises providing an endonuclease. In some alternatives, the endonuclease is a Type II restriction endonuclease. In some alternatives, the endonuclease is a Type IIS restriction endonuclease. In some alternatives, the endonuclease is BsaI or StuI. In some alternatives, the gene is codon optimized for expression in human cells. In some alternatives, the nucleic acid is a DNA. In some alternatives, the nucleic acid is RNA. In some alternatives, the RNA comprises a plurality of adenine nucleotides, wherein the plurality of adenine nucleotides comprises at least, greater than, equal to, or any number in between 20, 30, 40, 50, 60, 70, 80, 90, 100, 110, 120, 130, 140, 150, 175, 200, 225, 250, 275, 300, 325, 350, 375, 400, 425, 450, 475, or 500 covalently linked adenines. In some alternatives, the number of covalently linked adenines is greater than 120. In some alternatives, the number of covalently linked adenines is greater than 200. In some alternatives, the number of covalently linked adenines is greater than 300. In some alternatives, the nucleic acid further comprises a gene. In some alternatives, the gene encodes a protein for therapy. In some alternatives, the gene encodes a nuclease. In some alternatives, the gene encodes an endonuclease. In some alternatives, the nuclease comprises an amino acid sequence set forth in SEQ ID NO. 6 or is encoded by a nucleic acid sequence set forth in SEQ ID NO: 7-14. In some alternatives, the covalently linked adenines terminate with a guanine, cytosine, thymine, or a uracil. In some alternatives, the nucleic acid further comprises at least one palindromic sequence, wherein the at least one palindromic sequence can form a hairpin. In some alternatives, the nucleic acid further comprises a sequence capable of forming a tertiary structure such as a hairpin. In some alternatives, the gene is codon optimized for expression in human cells. In some alternatives, the mRNA encodes a protein, such as a nuclease, for example SEQ ID NOs. 6-14, wherein said mRNA comprises a poly(A) tail that is at least 7, 8, 9, 10, 11, 12, 13, 14, 15, 16, 17, 18, 19, 20, 25, 30, 35, 40, 45, 50, 60, 70, 80, 90, 100, 150, 200, 250, 300, 400, or 500 residues in length or a length that is within a range defined by any two of the aforementioned lengths and, wherein said mRNA lacks a 5' and/or 3' UTR or lacks a native 5' and/or 3' UTR and/or lacks one or more sequences required for native polyadenylation such as, a cleavage/polyadenylation specificity factor (CPSF) binding site, a cleavage stimulation factor binding site (CstF), a cleavage factor I binding site (CFI), or a cleavage factor II binding site (CFII). In some alternatives, the RNA lacks a 5' and/or 3' UTR or lacks a native 5' and/or 3' UTR and/or lacks one or more sequences required for native polyadenylation such as, a cleavage/polyadenylation specificity factor (CPSF) binding site, a cleavage stimulation factor binding site (CstF), a cleavage factor I binding site (CFI), or a cleavage factor II binding site (CFII). In some alternatives, the endonuclease cleavage site is located 1, 2, 3, 4, 5, 6, 7, 7, 8, 9, 10, 11, 12, 13, 14, 15, 16, 17, 18, 19 or 20 base pairs away from the most 5' thymine (or 5' terminal thymine) in the plurality of thymine nucleotides. In some alternatives, the endonuclease cleavage site is located 1, 2, 3, 4, 5, 6, 7, 7, 8, 9 or 10 base pairs away from the most 5' thymine (or 5' terminal thymine) in the plurality of thymine nucleotides.

In some alternatives, a method of treating, ameliorating, or an inhibiting disease in a subject is provided wherein the method comprises delivering the pharmaceutical composition of any of the alternatives herein to the subject. In some alternatives, the composition comprises a pharmaceutical vehicle and the mRNA of any one of the alternatives herein. In some alternatives, the RNA comprises a plurality of adenine nucleotides, wherein the plurality of adenine nucleotides comprises at least, greater than, equal to, or any number in between 20, 30, 40, 50, 60, 70, 80, 90, 100, 110, 120, 130, 140, 150, 175, 200, 225, 250, 275, 300, 325, 350, 375, 400, 425, 450, 475, or 500 covalently linked adenines. In some alternatives, the number of covalently linked adenines is greater than 120. In some alternatives, the number of covalently linked adenines is greater than 200. In some alternatives, the number of covalently linked adenines is greater than 300. In some alternatives, the RNA further comprises a gene. In some alternatives, the gene encodes a protein for therapy. In some alternatives, the gene encodes a nuclease. In some alternatives, the gene encodes an endonuclease. In some alternatives, the nuclease comprises an amino acid sequence set forth in SEQ ID NO. 6 or is encoded by a nucleic acid sequence set forth in SEQ ID NO: 7-14. In some alternatives, the plurality of adenine nucleotides further comprises a guanine, cytosine or a uracil, and wherein the number of covalently linked adenines terminates with a guanine, cytosine or a uracil. In some alternatives, the nucleic acid further comprises at least one palindromic sequence, wherein the at least one palindromic sequence can form a hairpin. In some alternatives, the nucleic acid further comprises a sequence capable of forming a tertiary structure such as a hairpin. In some alternatives, the method further comprises providing an endonuclease. In some alternatives, the endonuclease is a Type II restriction endonuclease. In some alternatives, the endonuclease is a Type IIS restriction endonuclease. In some alternatives, the endonuclease is BsaI or StuI. In some alternatives, the gene is codon optimized for expression in human cells. In some alternatives, the nucleic acid is a DNA. In some alternatives, the nucleic acid is RNA. In some alternatives, the RNA comprises a plurality of adenine nucleotides, wherein the plurality of adenine nucleotides comprises at least, greater than, equal to, or any number in between 20, 30, 40, 50, 60, 70, 80, 90, 100, 110, 120, 130, 140, 150, 175, 200, 225, 250, 275, 300, 325, 350, 375, 400, 425, 450, 475, or 500 covalently linked adenines. In some alternatives, the number of covalently linked adenines is greater than 120. In some alternatives, the number of covalently linked adenines is greater than 200. In some alternatives, the number of covalently linked adenines is greater than 300. In some alternatives, the nucleic acid further comprises a gene. In some alternatives, the gene encodes a protein for therapy. In some alternatives, the gene encodes a nuclease. In some alternatives, the gene encodes an endonuclease. In some alternatives, the nuclease comprises an amino acid sequence set forth in SEQ ID NO. 6 or is encoded by a nucleic acid sequence set forth in SEQ ID NO: 7-14. In some alternatives, the covalently linked adenines terminate with a guanine, cytosine, thymine, or a uracil. In some alternatives, the nucleic acid further comprises at least one palindromic sequence, wherein the at least one palindromic sequence can form a hairpin. In some alternatives, the nucleic acid further comprises a sequence capable of forming a tertiary structure such as a hairpin. In some alternatives, the gene is codon optimized for expression in human cells. In some alternatives, the mRNA encodes a protein, such as a nuclease, for example SEQ ID NOs. 6-14, wherein said mRNA comprises a poly(A) tail that is at least 7, 8, 9, 10, 11, 12, 13, 14, 15, 16, 17, 18, 19, 20, 25, 30, 35, 40, 45, 50, 60, 70, 80, 90, 100, 150, 200, 250, 300, 400, or 500 residues in length or a length that is within a range defined by any two of the aforementioned lengths and, wherein said mRNA lacks a 5' and/or 3' UTR or lacks a native 5' and/or 3' UTR and/or lacks one or more sequences required for native polyadenylation such as, a cleavage/polyadenylation specificity factor (CPSF) binding site, a cleavage stimulation factor binding site (CstF), a cleavage factor I binding site (CFI), or a cleavage factor II binding site (CFII). In some alternatives, the RNA lacks a 5' and/or 3' UTR or lacks a native 5' and/or 3' UTR and/or lacks one or more sequences required for native polyadenylation such as, a cleavage/polyadenylation specificity factor (CPSF) binding site, a cleavage stimulation factor binding site (CstF), a cleavage factor I binding site (CFI), or a cleavage factor II binding site (CFII). In some alternatives, the endonuclease cleavage site is located 1, 2, 3, 4, 5, 6, 7, 7, 8, 9, 10, 11, 12, 13, 14, 15, 16, 17, 18, 19 or 20 base pairs away from the most 5' thymine (or 5' terminal thymine) in the plurality of thymine nucleotides. In some alternatives, the endonuclease cleavage site is located 1, 2, 3, 4, 5, 6, 7, 7, 8, 9 or 10 base pairs away from the most 5' thymine (or 5' terminal thymine) in the plurality of thymine nucleotides.

In some alternatives, a method of treating, ameliorating, or a inhibiting a disease in a subject is provided, wherein the method comprises delivering the cell of any one of the alternatives, to the subject. In some alternatives, the cell is manufactured by transfecting into a cell the nucleic acid of any one of the alternatives herein or a nucleic acid manufactured by a method of any one of the alternatives herein, placing the cell into a culture vessel with media, supplying the cell with nutrients and amino acids for translation and incubating the cell for at least, greater than, equal to, or time in between 1, 5, 10, 20, 30, 40, 50, 60, 70, 80, 90 or 100 hours (e.g., at least, or equal to 1, 5, 10, 20, 30, 40, 50, 60, 70, 80, 90 or 100 hours or within a range defined by any two of the aforementioned times) so as to allow for translation. In some alternatives, the method of making the nucleic acid or RNA comprises providing the polynucleotide of any one of the alternatives provided herein, or the polynucleotide manufactured by any one of the alternatives provided herein and contacting said polynucleotide with a polymerase in the presence of nucleotides. The polynucleotide can comprise a first nucleic acid sequence encoding a nuclease, a second nucleic acid sequence comprising at least one restriction endonuclease recognition site and a third nucleic acid sequence, wherein the third nucleic acid sequence comprises the template strand, wherein said plurality of thymine nucleotides comprises at least, greater than, equal to, or any number in between 20, 30, 40, 50, 60, 70, 80, 90, 100, 110, 120, 130, 140, 150, 175, 200, 225, 250, 275, 300, 325, 350, 375, 400, 425, 450, 475, 500 or 550 covalently linked thymine nucleotides and wherein the third nucleic acid comprises the restriction endonuclease cleavage site, wherein the restriction endonuclease cleavage site is located within the plurality of thymine nucleotides or within 1, 2, 3, 4, 5, 6, 7, 7, 8, 9, 10, 11, 12, 13, 14, 15, 16, 17, 18, 19 or 20 base pairs away from the most 5' thymine (or 5' terminal thymine) in the plurality of thymine nucleotides and wherein said second nucleic acid is covalently linked to one end of said third nucleic acid sequence, and wherein the said restriction endonuclease recognition site is located within 55 base pairs of the restriction endonuclease cleavage site for the restriction endonuclease and said restriction endonuclease cleavage site is within 1 to 40 base pairs of a most 5' thymine (or 5' terminal thymine) in the plurality of thymine nucleotides. Some polynucleotides comprise a first nucleic acid sequence comprising at least one restriction endonuclease recognition site and a second nucleic acid sequence, wherein the second nucleic acid sequence comprises the template strand, wherein the template strand comprises a plurality of thymine nucleotides, wherein said plurality of thymine nucleotides comprises at least, greater than, equal to, or any number in between 20, 30, 40, 50, 60, 70, 80, 90, 100, 110, 120, 130, 140, 150, 175, 200, 225, 250, 275, 300, 325, 350, 375, 400, 425, 450, 475, 500 or 550 covalently linked thymine nucleotides, wherein the second nucleic acid comprises the restriction endonuclease cleavage site, and wherein the restriction endonuclease cleavage site is within the plurality of thymine nucleotides or within 1, 2, 3, 4, 5, 6, 7, 7, 8, 9, 10, 11, 12, 13, 14, 15, 16, 17, 18, 19 or 20 base pairs away from the most 5' thymine (or 5' terminal thymine) in the plurality of thymine nucleotides and wherein said first nucleic acid is covalently linked to said second nucleic acid at one end of said second nucleic acid, and wherein the said restriction endonuclease recognition site is located within 1-55 base pairs such as, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54 or 55 base pairs, of the restriction endonuclease cleavage site for the restriction endonuclease and said restriction endonuclease cleavage site is within 1 to 40 base pairs, such as 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 base pairs, of a most 5' thymine (or 5' terminal thymine) in the plurality of thymine nucleotides. In some alternatives, the polynucleotide further comprises telomeres. In some alternatives, the polynucleotide comprises a left arm wherein the left arm comprises a left telomere, a right arm wherein the right arm comprises a right telomere and a cloning region located between the left arm and the right arm. In some alternatives, the polynucleotide further comprises a third nucleic acid, wherein the third nucleic acid comprises a gene. In some alternatives, the gene encodes a protein for therapy. In some alternatives, the gene encodes a nuclease. In some alternatives, the nuclease is an endonuclease. In some alternatives, the nuclease comprises an amino acid sequence set forth in SEQ ID NO. 6 or is encoded by a nucleic acid sequence set forth in SEQ ID NO: 7-14. In some alternatives, the number of covalently linked thymines is greater than 120. In some alternatives, the number of covalently linked thymines is greater than 200. In some alternatives, the number of covalently linked thymines is greater than 300. In some alternatives, the at least one endonuclease recognition site is a Type II restriction endonuclease recognition site, and the endonuclease is a Type II restriction endonuclease. In some alternatives, the at least one endonuclease recognition site is a Type IIS restriction endonuclease recognition site and wherein the endonuclease is a Type IIS restriction endonuclease. In some alternatives, the at least one Type II restriction endonuclease recognition site is a BsaI restriction endonuclease recognition site or a StuI restriction endonuclease recognition site, and wherein the endonuclease is BsaI or StuI. In some alternatives, the endonuclease recognition site is inverted. In some alternatives, the polynucleotide is a linear polynucleotide. In some alternatives, the polynucleotide has only one endonuclease recognition site. In some alternatives, the polynucleotide further comprises a polymerase promoter region. In some alternatives, the plurality of thymine nucleotides comprises at least one covalently linked guanine, cytosine, or an adenine, wherein the at least one covalently linked guanine, cytosine or adenine is optionally joined to the most 5' thymine (or 5' terminal thymine) in the plurality of thymine nucleotides. In some alternatives, the endonuclease cleavage site comprises at least one guanine, cytosine, or an adenine, wherein the endonuclease cleaves between a thymine and the at least one guanine, cytosine or adenine. In some alternatives, the polynucleotide further comprises at least one palindromic sequence, wherein the at least one palindromic sequence can form a hairpin. In some alternatives, the polynucleotide further comprises a third sequence, wherein the third sequence is capable of forming a tertiary structure such as a hairpin. In some alternatives, the gene is codon optimized for expression in human cells. The method of making a polynucleotide comprising a sequence encoding a nuclease, a template strand, an endonuclease recognition site and an endonuclease cleavage site for an endonuclease inserted therein, wherein said template strand comprises a plurality of thymine nucleotides can comprise providing a first nucleic acid sequence encoding a nuclease, providing a second nucleic acid sequence comprising at least one endonuclease recognition site, providing a third nucleic acid sequence, wherein the third nucleic acid sequence comprises the template strand, wherein the template strand comprises a plurality of thymine nucleotides, wherein said plurality of thymine nucleotides comprises at least, greater than, equal to, or any number in between 20, 30, 40, 50, 60, 70, 80, 90, 100, 110, 120, 130, 140, 150, 175, 200, 225, 250, 275, 300, 325, 350, 375, 400, 425, 450, 475, 500 or 550 covalently linked thymine nucleotides and wherein the third nucleic acid comprises the endonuclease cleavage site, wherein the endonuclease cleavage site is located within the plurality of thymine nucleotides or within 1, 2, 3, 4, 5, 6, 7, 7, 8, 9, 10, 11, 12, 13, 14, 15, 16, 17, 18, 19 or 20 base pairs away from the most 5' thymine (or 5' terminal thymine) in the plurality of thymine nucleotides, joining said first nucleic acid to one end of the second nucleic acid sequence and joining said third nucleic acid sequence to one end of the second nucleic acid sequence, wherein said second nucleic acid is covalently linked to one end of said third nucleic acid sequence, and wherein the said endonuclease recognition site is located within 55 base pairs of the endonuclease cleavage site for the endonuclease and said endonuclease cleavage site is within 1 to 40 base pairs of a most 5' thymine in the plurality of thymine nucleotides. In some alternatives, the polynucleotide further comprises telomeres. In some alternatives, the polynucleotide comprises a left arm wherein the left arm comprises a left telomere, a right arm wherein the right arm comprises a right telomere and a cloning region located between the left arm and the right arm. In some alternatives, the polynucleotide further comprises a third nucleic acid, wherein the third nucleic acid comprises a gene. In some alternatives, the gene encodes a protein for therapy. In some alternatives, the gene encodes a nuclease. In some alternatives, the nuclease is an endonuclease. In some alternatives, the nuclease comprises an amino acid sequence set forth in SEQ ID NO. 6 or is encoded by a nucleic acid sequence set forth in SEQ ID NO: 7-14. In some alternatives, the number of covalently linked thymines is greater than 120. In some alternatives, the number of covalently linked thymines is greater than 200. In some alternatives, the number of covalently linked thymines is greater than 300. In some alternatives, the at least one endonuclease recognition site is a Type II restriction endonuclease recognition site, and the endonuclease is a Type II restriction endonuclease. In some alternatives, the at least one endonuclease recognition site is a Type IIS restriction endonuclease recognition site, and wherein the endonuclease is a Type IIS restriction endonuclease. In some alternatives, the at least one endonuclease recognition site is a BsaI restriction endonuclease recognition site or a StuI endonuclease recognition site, and wherein the endonuclease is BsaI or StuI. In some alternatives, the endonuclease recognition site is inverted. In some alternatives, the polynucleotide is a linear polynucleotide. In some alternatives, the polynucleotide has only one endonuclease recognition site. In some alternatives, the polynucleotide further comprises a polymerase promoter. In some alternatives, the plurality of thymine nucleotides comprises at least one covalently linked guanine, cytosine, or an adenine, wherein the at least one covalently linked guanine, cytosine or adenine is optionally joined to the most 5' thymine (or 5' terminal thymine) in the plurality of thymine nucleotides. In some alternatives, the endonuclease cleavage site comprises at least one guanine, cytosine, or an adenine, wherein the endonuclease cleaves between a thymine and the at least one guanine, cytosine or adenine. In some alternatives, the polynucleotide further comprises at least one palindromic sequence, wherein the at least one palindromic sequence can form a hairpin. In some alternatives, the polynucleotide further comprises a fourth sequence, wherein the fourth sequence is capable of forming a tertiary structure such as a hairpin. In some alternatives, the gene is codon optimized for expression in human cells. In some alternatives, the cell is a human cell. In some alternatives, the cell is selected from a group consisting of primary cells, human primary T cells, CD4+ cells and CD8+ cells. In some alternatives, the endonuclease cleavage site is located 1, 2, 3, 4, 5, 6, 7, 7, 8, 9, 10, 11, 12, 13, 14, 15, 16, 17, 18, 19 or 20 base pairs away from the most 5' thymine (or 5' terminal thymine) in the plurality of thymine nucleotides. In some alternatives, the endonuclease cleavage site is located 1, 2, 3, 4, 5, 6, 7, 7, 8, 9 or 10 base pairs away from the most 5' thymine (or 5' terminal thymine) in the plurality of thymine nucleotides.

In some alternatives, a polynucleotide that encodes a protein, such as a nuclease, for example SEQ ID NOs. 6-14, wherein said polynucleotide comprises an endonuclease site at the 3' end of said polynucleotide, preferably outside of the coding region for said protein, and said endonuclease site is joined to at least 7, 8, 9, 10, 11, 12, 13, 14, 15, 16, 17, 18, 19, 20, 25, 30, 35, 40, 45, 50, 60, 70, 80, 90, 100, 150, 200, 250, 300, 400, 500 or 550 covalently linked thymine residues or an amount of covalently linked thymine residues that is within a range defined by any two of the aforementioned values, is provided. In some alternatives, the endonuclease cleavage site is located 1, 2, 3, 4, 5, 6, 7, 7, 8, 9, 10, 11, 12, 13, 14, 15, 16, 17, 18, 19 or 20 base pairs away from the most 5' thymine (or 5' terminal thymine) in the plurality of thymine nucleotides. In some alternatives, the endonuclease cleavage site is located 1, 2, 3, 4, 5, 6, 7, 7, 8, 9 or 10 base pairs away from the most 5' thymine (or 5' terminal thymine) in the plurality of thymine nucleotides.

In some alternatives, an mRNA that encodes a protein, such as a nuclease, for example SEQ ID NOs. 6-14, wherein said mRNA comprises a poly(A) tail that is at least 7, 8, 9, 10, 11, 12, 13, 14, 15, 16, 17, 18, 19, 20, 25, 30, 35, 40, 45, 50, 60, 70, 80, 90, 100, 150, 200, 250, 300, 400, or 500 residues in length or a length that is within a range defined by any two of the aforementioned lengths and, wherein said mRNA lacks a 5' and/or 3' UTR or lacks a native 5' and/or 3' UTR and/or lacks one or more sequences required for native polyadenylation such as, a cleavage/polyadenylation specificity factor (CPSF) binding site, a cleavage stimulation factor binding site (CstF), a cleavage factor I binding site (CFI), or a cleavage factor II binding site (CFII). In some alternatives, the composition comprises a pharmaceutical vehicle and the mRNA or mRNA of any one of the alternatives herein. In some alternatives, the RNA comprises a plurality of adenine nucleotides, wherein the plurality of adenine nucleotides comprises at least, greater than, equal to, or any number in between 20, 30, 40, 50, 60, 70, 80, 90, 100, 110, 120, 130, 140, 150, 175, 200, 225, 250, 275, 300, 325, 350, 375, 400, 425, 450, 475, or 500 covalently linked adenines. In some alternatives, the number of covalently linked adenines is greater than 120. In some alternatives, the number of covalently linked adenines is greater than 200. In some alternatives, the number of covalently linked adenines is greater than 300. In some alternatives, the RNA further comprises a gene. In some alternatives, the gene encodes a protein for therapy. In some alternatives, the gene encodes a nuclease. In some alternatives, the gene encodes an endonuclease. In some alternatives, the nuclease comprises an amino acid sequence set forth in SEQ ID NO. 6 or is encoded by a nucleic acid sequence set forth in SEQ ID NO: 7-14. In some alternatives, the plurality of adenine nucleotides further comprises a guanine, cytosine or a uracil, and wherein the number of covalently linked adenines terminates with a guanine, cytosine or a uracil. In some alternatives, the nucleic acid further comprises at least one palindromic sequence, wherein the at least one palindromic sequence can form a hairpin. In some alternatives, the nucleic acid further comprises a sequence capable of forming a tertiary structure such as a hairpin. In some alternatives, the method further comprises providing an endonuclease. In some alternatives, the endonuclease is a Type II restriction endonuclease. In some alternatives, the endonuclease is a Type IIS restriction endonuclease. In some alternatives, the endonuclease is BsaI or StuI. In some alternatives, the gene is codon optimized for expression in human cells. In some alternatives, the nucleic acid is a DNA. In some alternatives, the nucleic acid is RNA. In some alternatives, the RNA comprises a plurality of adenine nucleotides, wherein the plurality of adenine nucleotides comprises at least, greater than, equal to, or any number in between 20, 30, 40, 50, 60, 70, 80, 90, 100, 110, 120, 130, 140, 150, 175, 200, 225, 250, 275, 300, 325, 350, 375, 400, 425, 450, 475, or 500 covalently linked adenines. In some alternatives, the number of covalently linked adenines is greater than 120. In some alternatives, the number of covalently linked adenines is greater than 200. In some alternatives, the number of covalently linked adenines is greater than 300. In some alternatives, the nucleic acid further comprises a gene. In some alternatives, the gene encodes a protein for therapy. In some alternatives, the gene encodes a nuclease. In some alternatives, the gene encodes an endonuclease. In some alternatives, the nuclease comprises an amino acid sequence set forth in SEQ ID NO. 6 or is encoded by a nucleic acid sequence set forth in SEQ ID NO: 7-14. In some alternatives, the covalently linked adenines terminate with a guanine, cytosine, thymine, or a uracil. In some alternatives, the nucleic acid further comprises at least one palindromic sequence, wherein the at least one palindromic sequence can form a hairpin. In some alternatives, the nucleic acid further comprises a sequence capable of forming a tertiary structure such as a hairpin. In some alternatives, the gene is codon optimized for expression in human cells. In some alternatives, the mRNA encodes a protein, such as a nuclease, for example SEQ ID NOs. 6-14, wherein said mRNA comprises a poly(A) tail that is at least 7, 8, 9, 10, 11, 12, 13, 14, 15, 16, 17, 18, 19, 20, 25, 30, 35, 40, 45, 50, 60, 70, 80, 90, 100, 150, 200, 250, 300, 400, or 500 residues in length or a length that is within a range defined by any two of the aforementioned lengths and, wherein said mRNA lacks a 5' and/or 3' UTR or lacks a native 5' and/or 3' UTR and/or lacks one or more sequences required for native polyadenylation such as, a cleavage/polyadenylation specificity factor (CPSF) binding site, a cleavage stimulation factor binding site (CstF), a cleavage factor I binding site (CFI), or a cleavage factor II binding site (CFII). In some alternatives, the endonuclease cleavage site is located 1, 2, 3, 4, 5, 6, 7, 7, 8, 9, 10, 11, 12, 13, 14, 15, 16, 17, 18, 19 or 20 base pairs away from the most 5' thymine (or 5' terminal thymine) in the plurality of thymine nucleotides. In some alternatives, the endonuclease cleavage site is located 1, 2, 3, 4, 5, 6, 7, 7, 8, 9 or 10 base pairs away from the most 5' thymine (or 5' terminal thymine) in the plurality of thymine nucleotides.

In some alternatives, a method of treating, ameliorating, or inhibiting disease in a subject is provided wherein the method comprises introducing into a cell any one or more of the polynucleotides or nucleic acids set forth in any of the aforementioned claims; and delivering the cell to the subject. The polynucleotide can comprise a first nucleic acid sequence encoding a nuclease, a second nucleic acid sequence comprising at least one restriction endonuclease recognition site and a third nucleic acid sequence, wherein the third nucleic acid sequence comprises the template strand, wherein said plurality of thymine nucleotides comprises at least, greater than, equal to, or any number in between 20, 30, 40, 50, 60, 70, 80, 90, 100, 110, 120, 130, 140, 150, 175, 200, 225, 250, 275, 300, 325, 350, 375, 400, 425, 450, 475, 500 or 550 covalently linked thymine nucleotides and wherein the third nucleic acid comprises the restriction endonuclease cleavage site, wherein the restriction endonuclease cleavage site is located within the plurality of thymine nucleotides or within 1, 2, 3, 4, 5, 6, 7, 7, 8, 9, 10, 11, 12, 13, 14, 15, 16, 17, 18, 19 or 20 base pairs away from the most 5' thymine (or 5' terminal thymine) in the plurality of thymine nucleotides and wherein said second nucleic acid is covalently linked to one end of said third nucleic acid sequence, and wherein the said restriction endonuclease recognition site is located within 55 base pairs of the restriction endonuclease cleavage site for the restriction endonuclease and said restriction endonuclease cleavage site is within 1 to 40 base pairs of a most 5' thymine in the plurality of thymine nucleotides. Some polynucleotides comprise a first nucleic acid sequence comprising at least one restriction endonuclease recognition site and a second nucleic acid sequence, wherein the second nucleic acid sequence comprises the template strand, wherein the template strand comprises a plurality of thymine nucleotides, wherein said plurality of thymine nucleotides comprises at least, greater than, equal to, or any number in between 20, 30, 40, 50, 60, 70, 80, 90, 100, 110, 120, 130, 140, 150, 175, 200, 225, 250, 275, 300, 325, 350, 375, 400, 425, 450, 475, 500 or 550 covalently linked thymine nucleotides, wherein the second nucleic acid comprises the restriction endonuclease cleavage site, and wherein the restriction endonuclease cleavage site is within the plurality of thymine nucleotides or within 1, 2, 3, 4, 5, 6, 7, 7, 8, 9, 10, 11, 12, 13, 14, 15, 16, 17, 18, 19 or 20 base pairs away from the most 5' thymine (or 5' terminal thymine) in the plurality of thymine nucleotides and wherein said first nucleic acid is covalently linked to said second nucleic acid at one end of said second nucleic acid, and wherein the said restriction endonuclease recognition site is located within 1-55 base pairs such as, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54 or 55 base pairs, of the restriction endonuclease cleavage site for the restriction endonuclease and said restriction endonuclease cleavage site is within 1 to 40 base pairs, such as 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 base pairs, of a most 5' thymine (or 5' terminal thymine) in the plurality of thymine nucleotides. In some alternatives, the polynucleotide further comprises telomeres. In some alternatives, the polynucleotide comprises a left arm wherein the left arm comprises a left telomere, a right arm wherein the right arm comprises a right telomere and a cloning region located between the left arm and the right arm. In some alternatives, the polynucleotide further comprises a third nucleic acid, wherein the third nucleic acid comprises a gene. In some alternatives, the gene encodes a protein for therapy. In some alternatives, the gene encodes a nuclease. In some alternatives, the nuclease is an endonuclease. In some alternatives, the nuclease comprises an amino acid sequence set forth in SEQ ID NO. 6 or is encoded by a nucleic acid sequence set forth in SEQ ID NO: 7-14. In some alternatives, the number of covalently linked thymines is greater than 120. In some alternatives, the number of covalently linked thymines is greater than 200. In some alternatives, the number of covalently linked thymines is greater than 300. In some alternatives, the at least one endonuclease recognition site is a Type II restriction endonuclease recognition site, and the endonuclease is a Type II restriction endonuclease. In some alternatives, the at least one endonuclease recognition site is a Type IIS restriction endonuclease recognition site and wherein the endonuclease is a Type IIS restriction endonuclease. In some alternatives, the at least one endonuclease recognition site is a BsaI restriction endonuclease recognition site or a StuI restriction endonuclease recognition site, and wherein the endonuclease is BsaI or StuI. In some alternatives, the endonuclease recognition site is inverted. In some alternatives, the polynucleotide is a linear polynucleotide. In some alternatives, the polynucleotide has only one endonuclease recognition site. In some alternatives, the polynucleotide further comprises a polymerase promoter region. In some alternatives, the plurality of thymine nucleotides comprises at least one covalently linked guanine, cytosine, or an adenine, wherein the at least one covalently linked guanine, cytosine or adenine is optionally joined to the most 5' thymine (or 5' terminal thymine) in the plurality of thymine nucleotides. In some alternatives, the endonuclease cleavage site comprises at least one guanine, cytosine, or an adenine, wherein the endonuclease cleaves between a thymine and the at least one guanine, cytosine or adenine. In some alternatives, the polynucleotide further comprises at least one palindromic sequence, wherein the at least one palindromic sequence can form a hairpin. In some alternatives, the polynucleotide further comprises a third sequence, wherein the third sequence is capable of forming a tertiary structure such as a hairpin. In some alternatives, the gene is codon optimized for expression in human cells. In some alternatives the nucleic acid provided, is manufactured by a method of any one of the alternatives described herein is provided. In some alternatives, the method comprises providing the polynucleotide of any one of the alternatives provided herein, or the polynucleotide manufactured by any one of the alternatives provided herein and contacting said polynucleotide with a polymerase in the presence of nucleotides. The polynucleotide can comprise a first nucleic acid sequence encoding a nuclease, a second nucleic acid sequence comprising at least one restriction endonuclease recognition site and a third nucleic acid sequence, wherein the third nucleic acid sequence comprises the template strand, wherein said plurality of thymine nucleotides comprises at least, greater than, equal to, or any number in between 20, 30, 40, 50, 60, 70, 80, 90, 100, 110, 120, 130, 140, 150, 175, 200, 225, 250, 275, 300, 325, 350, 375, 400, 425, 450, 475, 500 or 550 covalently linked thymine nucleotides and wherein the third nucleic acid comprises the restriction endonuclease cleavage site, wherein the restriction endonuclease cleavage site is located within the plurality of thymine nucleotides or within 1, 2, 3, 4, 5, 6, 7, 7, 8, 9, 10, 11, 12, 13, 14, 15, 16, 17, 18, 19 or 20 base pairs away from the most 5' thymine (or 5' terminal thymine) in the plurality of thymine nucleotides and wherein said second nucleic acid is covalently linked to one end of said third nucleic acid sequence, and wherein the said restriction endonuclease recognition site is located within 55 base pairs of the restriction endonuclease cleavage site for the restriction endonuclease and said restriction endonuclease cleavage site is within 1 to 40 base pairs of a most 5' thymine in the plurality of thymine nucleotides. Some polynucleotides comprise a first nucleic acid sequence comprising at least one restriction endonuclease recognition site and a second nucleic acid sequence, wherein the second nucleic acid sequence comprises the template strand, wherein the template strand comprises a plurality of thymine nucleotides, wherein said plurality of thymine nucleotides comprises at least, greater than, equal to, or any number in between 20, 30, 40, 50, 60, 70, 80, 90, 100, 110, 120, 130, 140, 150, 175, 200, 225, 250, 275, 300, 325, 350, 375, 400, 425, 450, 475, 500 or 550 covalently linked thymine nucleotides, wherein the second nucleic acid comprises the restriction endonuclease cleavage site, and wherein the restriction endonuclease cleavage site is within the plurality of thymine nucleotides or within 1, 2, 3, 4, 5, 6, 7, 7, 8, 9, 10, 11, 12, 13, 14, 15, 16, 17, 18, 19 or 20 base pairs away from the most 5' thymine (or 5' terminal thymine) in the plurality of thymine nucleotides and wherein said first nucleic acid is covalently linked to said second nucleic acid at one end of said second nucleic acid, and wherein the said restriction endonuclease recognition site is located within 1-55 base pairs such as, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54 or 55 base pairs, of the restriction endonuclease cleavage site for the restriction endonuclease and said restriction endonuclease cleavage site is within 1 to 40 base pairs, such as 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 base pairs, of a most 5' thymine (or 5' terminal thymine) in the plurality of thymine nucleotides. In some alternatives, the polynucleotide further comprises telomeres. In some alternatives, the polynucleotide comprises a left arm wherein the left arm comprises a left telomere, a right arm wherein the right arm comprises a right telomere and a cloning region located between the left arm and the right arm. In some alternatives, the polynucleotide further comprises a third nucleic acid, wherein the third nucleic acid comprises a gene. In some alternatives, the gene encodes a protein for therapy. In some alternatives, the gene encodes a nuclease. In some alternatives, the nuclease is an endonuclease. In some alternatives, the nuclease comprises an amino acid sequence set forth in SEQ ID NO. 6 or is encoded by a nucleic acid sequence set forth in SEQ ID NO: 7-14. In some alternatives, the number of covalently linked thymines is greater than 120. In some alternatives, the number of covalently linked thymines is greater than 200. In some alternatives, the number of covalently linked thymines is greater than 300. In some alternatives, the at least one endonuclease recognition site is a Type II restriction endonuclease recognition site, and the endonuclease is a Type II restriction endonuclease. In some alternatives, the at least one endonuclease recognition site is a Type IIS restriction endonuclease recognition site and wherein the endonuclease is a Type IIS restriction endonuclease. In some alternatives, the at least one endonuclease recognition site is a BsaI restriction endonuclease recognition site or a StuI restriction endonuclease recognition site, and wherein the endonuclease is BsaI or StuI. In some alternatives, the endonuclease recognition site is inverted. In some alternatives, the polynucleotide is a linear polynucleotide. In some alternatives, the polynucleotide has only one endonuclease recognition site. In some alternatives, the polynucleotide further comprises a polymerase promoter region. In some alternatives, the plurality of thymine nucleotides comprises at least one covalently linked guanine, cytosine, or an adenine, wherein the at least one covalently linked guanine, cytosine or adenine is optionally joined to the most 5' thymine (or 5' terminal thymine) in the plurality of thymine nucleotides. In some alternatives, the endonuclease cleavage site comprises at least one guanine, cytosine, or an adenine, wherein the endonuclease cleaves between a thymine and the at least one guanine, cytosine or adenine. In some alternatives, the polynucleotide further comprises at least one palindromic sequence, wherein the at least one palindromic sequence can form a hairpin. In some alternatives, the polynucleotide further comprises a third sequence, wherein the third sequence is capable of forming a tertiary structure such as a hairpin. In some alternatives, the gene is codon optimized for expression in human cells. The method of making a polynucleotide comprising a sequence encoding a nuclease, a template strand, an endonuclease recognition site and an endonuclease cleavage site for an endonuclease inserted therein, wherein said template strand comprises a plurality of thymine nucleotides can comprise providing a first nucleic acid sequence encoding a nuclease, providing a second nucleic acid sequence comprising at least one endonuclease recognition site, providing a third nucleic acid sequence, wherein the third nucleic acid sequence comprises the template strand, wherein the template strand comprises a plurality of thymine nucleotides, wherein said plurality of thymine nucleotides comprises at least, greater than, equal to, or any number in between 20, 30, 40, 50, 60, 70, 80, 90, 100, 110, 120, 130, 140, 150, 175, 200, 225, 250, 275, 300, 325, 350, 375, 400, 425, 450, 475, 500 or 550 covalently linked thymine nucleotides and wherein the third nucleic acid comprises the endonuclease cleavage site, wherein the endonuclease cleavage site is located within the plurality of thymine nucleotides or within 1, 2, 3, 4, 5, 6, 7, 7, 8, 9, 10, 11, 12, 13, 14, 15, 16, 17, 18, 19 or 20 base pairs away from the most 5' thymine (or 5' terminal thymine) in the plurality of thymine nucleotides, joining said first nucleic acid to one end of the second nucleic acid sequence and joining said third nucleic acid sequence to one end of the second nucleic acid sequence, wherein said second nucleic acid is covalently linked to one end of said third nucleic acid sequence, and wherein the said endonuclease recognition site is located within 55 base pairs of the endonuclease cleavage site for the endonuclease and said endonuclease cleavage site is within 1 to 40 base pairs of a most 5' thymine (or 5' terminal thymine) in the plurality of thymine nucleotides. In some alternatives, the polynucleotide further comprises telomeres. In some alternatives, the polynucleotide comprises a left arm wherein the left arm comprises a left telomere, a right arm wherein the right arm comprises a right telomere and a cloning region located between the left arm and the right arm. In some alternatives, the polynucleotide further comprises a third nucleic acid, wherein the third nucleic acid comprises a gene. In some alternatives, the gene encodes a protein for therapy. In some alternatives, the gene encodes a nuclease. In some alternatives, the nuclease is an endonuclease. In some alternatives, the nuclease comprises an amino acid sequence set forth in SEQ ID NO. 6 or is encoded by a nucleic acid sequence set forth in SEQ ID NO: 7-14. In some alternatives, the number of covalently linked thymines is greater than 120. In some alternatives, the number of covalently linked thymines is greater than 200. In some alternatives, the number of covalently linked thymines is greater than 300. In some alternatives, the at least one endonuclease recognition site is a Type II restriction endonuclease recognition site, and the endonuclease is a Type II restriction endonuclease. In some alternatives, the at least one endonuclease recognition site is a Type IIS restriction endonuclease recognition site, and wherein the endonuclease is a Type IIS restriction endonuclease. In some alternatives, the at least one endonuclease recognition site is a BsaI restriction endonuclease recognition site or a StuI restriction endonuclease recognition site, and wherein the endonuclease is BsaI or StuI. In some alternatives, the endonuclease recognition site is inverted. In some alternatives, the polynucleotide is a linear polynucleotide. In some alternatives, the polynucleotide has only one endonuclease recognition site. In some alternatives, the polynucleotide further comprises a polymerase promoter. In some alternatives, the plurality of thymine nucleotide comprises at least one guanine, cytosine, or an adenine. In some alternatives, the endonuclease cleavage site comprises at least one guanine, cytosine, or an adenine, wherein the endonuclease cleaves between a thymine and the at least one guanine, cytosine or adenine. In some alternatives, the polynucleotide further comprises at least one palindromic sequence, wherein the at least one palindromic sequence can form a hairpin. In some alternatives, the polynucleotide further comprises a fourth sequence, wherein the fourth sequence is capable of forming a tertiary structure such as a hairpin. In some alternatives, the gene is codon optimized for expression in human cells. In some alternatives, the polynucleotide further comprises a promoter for a polymerase. In some alternatives, polymerase is a DNA polymerase. In some alternatives, the DNA polymerase is a thermal stable polymerase, such as Taq polymerase. In some alternatives, the nucleotides are adenine, cytosine, guanine, thymine and/or uracil. In some alternatives, the method further comprises providing a set of primers. In some alternatives, the nucleic acid is DNA. In some alternatives, an RNA polymerase is used. In some alternatives, the contacting is performed at a temperature at least, greater than, equal to, or any temperature in between 30° C., 31° C., 32° C., 33° C., 34° C., 35° C., 36° C. or 37° C. In some alternatives, the contacting is performed for at least, greater than, equal to, or time in between 1, 5, 10, 20, 30, 40, 50, 60, 70, 80, 90 or 100 hours (e.g., at least, or equal to 1, 5, 10, 20, 30, 40, 50, 60, 70, 80, 90 or 100 hours or within a range defined by any two of the aforementioned times). In some alternatives, the nucleic acid is RNA. In some alternatives, the RNA comprises a plurality of adenine nucleotides, wherein the plurality of adenine nucleotides comprises at least, greater than, equal to, or any number in between 20, 30, 40, 50, 60, 70, 80, 90, 100, 110, 120, 130, 140, 150, 175, 200, 225, 250, 275, 300, 325, 350, 375, 400, 425, 450, 475, or 500 covalently linked adenines. In some alternatives, the number of covalently linked adenines is greater than 120. In some alternatives, the number of covalently linked adenines is greater than 200. In some alternatives, the number of covalently linked adenines is greater than 300. In some alternatives, the RNA further comprises a gene. In some alternatives, the gene encodes a protein for therapy. In some alternatives, the gene encodes a nuclease. In some alternatives, the gene encodes an endonuclease. In some alternatives, the nuclease comprises an amino acid sequence set forth in SEQ ID NO. 6 or is encoded by a nucleic acid sequence set forth in SEQ ID NO: 7-14. In some alternatives, the plurality of adenine nucleotides further comprises a guanine, cytosine or a uracil, and wherein the number of covalently linked adenines terminates with a guanine, cytosine or a uracil. In some alternatives, the nucleic acid further comprises at least one palindromic sequence, wherein the at least one palindromic sequence can form a hairpin. In some alternatives, the nucleic acid further comprises a sequence capable of forming a tertiary structure such as a hairpin. In some alternatives, the method further comprises providing an endonuclease. In some alternatives, the endonuclease is a Type II restriction endonuclease. In some alternatives, the endonuclease is a Type IIS restriction endonuclease. In some alternatives, the endonuclease is BsaI or StuI. In some alternatives, the gene is codon optimized for expression in human cells. In some alternatives, the nucleic acid is a DNA. In some alternatives, the nucleic acid is RNA. In some alternatives, the RNA comprises a plurality of adenine nucleotides, wherein the plurality of adenine nucleotides comprises at least, greater than, equal to, or any number in between 20, 30, 40, 50, 60, 70, 80, 90, 100, 110, 120, 130, 140, 150, 175, 200, 225, 250, 275, 300, 325, 350, 375, 400, 425, 450, 475, or 500 covalently linked adenines. In some alternatives, the number of covalently linked adenines is greater than 120. In some alternatives, the number of covalently linked adenines is greater than 200. In some alternatives, the number of covalently linked adenines is greater than 300. In some alternatives, the nucleic acid further comprises a gene. In some alternatives, the gene encodes a protein for therapy. In some alternatives, the gene encodes a nuclease. In some alternatives, the gene encodes an endonuclease. In some alternatives, the nuclease comprises an amino acid sequence set forth in SEQ ID NO. 6 or is encoded by a nucleic acid sequence set forth in SEQ ID NO: 7-14. In some alternatives, the covalently linked adenines terminate with a guanine, cytosine, thymine, or a uracil. In some alternatives, the nucleic acid further comprises at least one palindromic sequence, wherein the at least one palindromic sequence can form a hairpin. In some alternatives, the nucleic acid further comprises a sequence capable of forming a tertiary structure such as a hairpin. In some alternatives, the gene is codon optimized for expression in human cells. The polynucleotide can comprise a first nucleic acid sequence encoding a nuclease, a second nucleic acid sequence comprising at least one restriction endonuclease recognition site and a third nucleic acid sequence, wherein the third nucleic acid sequence comprises the template strand, wherein said plurality of thymine nucleotides comprises at least, greater than, equal to, or any number in between 20, 30, 40, 50, 60, 70, 80, 90, 100, 110, 120, 130, 140, 150, 175, 200, 225, 250, 275, 300, 325, 350, 375, 400, 425, 450, 475, 500 or 550 covalently linked thymine nucleotides and wherein the third nucleic acid comprises the restriction endonuclease cleavage site, wherein the restriction endonuclease cleavage site is located within the plurality of thymine nucleotides or within 1, 2, 3, 4, 5, 6, 7, 7, 8, 9, 10, 11, 12, 13, 14, 15, 16, 17, 18, 19 or 20 base pairs away from the most 5' thymine (or 5' terminal thymine) in the plurality of thymine nucleotides and wherein said second nucleic acid is covalently linked to one end of said third nucleic acid sequence, and wherein the said restriction endonuclease recognition site is located within 55 base pairs of the restriction endonuclease cleavage site for the restriction endonuclease and said restriction endonuclease cleavage site is within 1 to 40 base pairs of a most 5' thymine in the plurality of thymine nucleotides. Some polynucleotides comprise a first nucleic acid sequence comprising at least one restriction endonuclease recognition site and a second nucleic acid sequence, wherein the second nucleic acid sequence comprises the template strand, wherein the template strand comprises a plurality of thymine nucleotides, wherein said plurality of thymine nucleotides comprises at least, greater than, equal to, or any number in between 20, 30, 40, 50, 60, 70, 80, 90, 100, 110, 120, 130, 140, 150, 175, 200, 225, 250, 275, 300, 325, 350, 375, 400, 425, 450, 475, 500 or 550 covalently linked thymine nucleotides, wherein the second nucleic acid comprises the restriction endonuclease cleavage site, and wherein the restriction endonuclease cleavage site is within the plurality of thymine nucleotides or within 1, 2, 3, 4, 5, 6, 7, 7, 8, 9, 10, 11, 12, 13, 14, 15, 16, 17, 18, 19 or 20 base pairs away from the most 5' thymine (or 5' terminal thymine) in the plurality of thymine nucleotides and wherein said first nucleic acid is covalently linked to said second nucleic acid at one end of said second nucleic acid, and wherein the said restriction endonuclease recognition site is located within 1-55 base pairs such as, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54 or 55 base pairs, of the restriction endonuclease cleavage site for the restriction endonuclease and said restriction endonuclease cleavage site is within 1 to 40 base pairs, such as 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 base pairs, of a most 5' thymine (or 5' terminal thymine) in the plurality of thymine nucleotides. In some alternatives, the polynucleotide further comprises telomeres. In some alternatives, the polynucleotide comprises a left arm wherein the left arm comprises a left telomere, a right arm wherein the right arm comprises a right telomere and a cloning region located between the left arm and the right arm. In some alternatives, the nuclease comprises an amino acid sequence set forth in SEQ ID NO. 6 or is encoded by a nucleic acid sequence set forth in SEQ ID NO: 7-14. In some alternatives, the number of covalently linked thymines is greater than 120. In some alternatives, the number of covalently linked thymines is greater than 200. In some alternatives, the number of covalently linked thymines is greater than 300. In some alternatives, the at least one endonuclease recognition site is a Type II restriction endonuclease recognition site, and the endonuclease is a Type II restriction endonuclease. In some alternatives, the at least one endonuclease recognition site is a Type IIS restriction endonuclease recognition site and wherein the endonuclease is a Type IIS restriction endonuclease. In some alternatives, the at least one endonuclease recognition site is a BsaI restriction endonuclease recognition site or a StuI restriction endonuclease recognition site, and wherein the endonuclease is BsaI or StuI. In some alternatives, the endonuclease recognition site is inverted. In some alternatives, the polynucleotide is a linear polynucleotide. In some alternatives, the polynucleotide has only one endonuclease recognition site. In some alternatives, the polynucleotide further comprises a polymerase promoter. In some alternatives, the plurality of thymine nucleotides comprises at least one covalently linked guanine, cytosine, or an adenine, wherein the at least one covalently linked guanine, cytosine or adenine is optionally at the most 5' thymine (or 5' terminal thymine) in the plurality of thymine nucleotides. In some alternatives, the endonuclease cleavage site comprises at least one guanine, cytosine, or an adenine, wherein the endonuclease cleaves between a thymine and the at least one guanine, cytosine or adenine. In some alternatives, the polynucleotide further comprises at least one palindromic sequence, wherein the at least one palindromic sequence can form a hairpin. In some alternatives, the polynucleotide further comprises a seventh sequence, wherein the seventh sequence is capable of forming a tertiary structure such as a hairpin. In some alternatives, the sequence encoding the nuclease is optimized for expression in human cells. In some alternatives, the cell is a T-cell or a primary cell. In some alternatives, said disease is cancer, ischemia, diabetic retinopathy, macular degeneration, rheumatoid arthritis, psoriasis, HIV infection, sickle cell anemia, Alzheimer's disease, muscular dystrophy, neurodegenerative diseases, vascular disease, cystic fibrosis, stroke, hyper IGE syndrome, hemophilia. In some alternatives, the endonuclease cleavage site is located 1, 2, 3, 4, 5, 6, 7, 7, 8, 9, 10, 11, 12, 13, 14, 15, 16, 17, 18, 19 or 20 base pairs away from the most 5' thymine (or 5' terminal thymine) in the plurality of thymine nucleotides. In some alternatives, the endonuclease cleavage site is located 1, 2, 3, 4, 5, 6, 7, 7, 8, 9 or 10 base pairs away from the most 5' thymine (or 5' terminal thymine) in the plurality of thymine nucleotides.

In some alternatives, a method of treating, ameliorating, or inhibiting disease in a subject is provided, wherein the method comprises administering any one or more of the polynucleotides or nucleic acids set forth in any of the aforementioned claims to a subject. The polynucleotide can comprise a first nucleic acid sequence encoding a nuclease, a second nucleic acid sequence comprising at least one restriction endonuclease recognition site and a third nucleic acid sequence, wherein the third nucleic acid sequence comprises the template strand, wherein said plurality of thymine nucleotides comprises at least, greater than, equal to, or any number in between 20, 30, 40, 50, 60, 70, 80, 90, 100, 110, 120, 130, 140, 150, 175, 200, 225, 250, 275, 300, 325, 350, 375, 400, 425, 450, 475, 500 or 550 covalently linked thymine nucleotides and wherein the third nucleic acid comprises the restriction endonuclease cleavage site, wherein the restriction endonuclease cleavage site is located within the plurality of thymine nucleotides or within 1, 2, 3, 4, 5, 6, 7, 7, 8, 9, 10, 11, 12, 13, 14, 15, 16, 17, 18, 19 or 20 base pairs away from the most 5' thymine (or 5' terminal thymine) in the plurality of thymine nucleotides and wherein said second nucleic acid is covalently linked to one end of said third nucleic acid sequence, and wherein the said restriction endonuclease recognition site is located within 55 base pairs of the restriction endonuclease cleavage site for the restriction endonuclease and said restriction endonuclease cleavage site is within 1 to 40 base pairs of a most 5' thymine in the plurality of thymine nucleotides. Some polynucleotides comprise a first nucleic acid sequence comprising at least one restriction endonuclease recognition site and a second nucleic acid sequence, wherein the second nucleic acid sequence comprises the template strand, wherein the template strand comprises a plurality of thymine nucleotides, wherein said plurality of thymine nucleotides comprises at least, greater than, equal to, or any number in between 20, 30, 40, 50, 60, 70, 80, 90, 100, 110, 120, 130, 140, 150, 175, 200, 225, 250, 275, 300, 325, 350, 375, 400, 425, 450, 475, 500 or 550 covalently linked thymine nucleotides, wherein the second nucleic acid comprises the restriction endonuclease cleavage site, and wherein the restriction endonuclease cleavage site is within the plurality of thymine nucleotides or within 1, 2, 3, 4, 5, 6, 7, 7, 8, 9, 10, 11, 12, 13, 14, 15, 16, 17, 18, 19 or 20 base pairs away from the most 5' thymine (or 5' terminal thymine) in the plurality of thymine nucleotides and wherein said first nucleic acid is covalently linked to said second nucleic acid at one end of said second nucleic acid, and wherein the said restriction endonuclease recognition site is located within 1-55 base pairs such as, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54 or 55 base pairs, of the restriction endonuclease cleavage site for the restriction endonuclease and said restriction endonuclease cleavage site is within 1 to 40 base pairs, such as 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 base pairs, of a most 5' thymine (or 5' terminal thymine) in the plurality of thymine nucleotides. In some alternatives, the polynucleotide further comprises telomeres. In some alternatives, the polynucleotide comprises a left arm wherein the left arm comprises a left telomere, a right arm wherein the right arm comprises a right telomere and a cloning region located between the left arm and the right arm. In some alternatives, the polynucleotide further comprises a third nucleic acid, wherein the third nucleic acid comprises a gene. In some alternatives, the gene encodes a protein for therapy. In some alternatives, the gene encodes a nuclease. In some alternatives, the nuclease is an endonuclease. In some alternatives, the nuclease comprises an amino acid sequence set forth in SEQ ID NO. 6 or is encoded by a nucleic acid sequence set forth in SEQ ID NO: 7-14. In some alternatives, the number of covalently linked thymines is greater than 120. In some alternatives, the number of covalently linked thymines is greater than 200. In some alternatives, the number of covalently linked thymines is greater than 300. In some alternatives, the at least one endonuclease recognition site is a Type II restriction endonuclease recognition site, and the endonuclease is a Type II restriction endonuclease. In some alternatives, the at least one endonuclease recognition site is a Type IIS restriction endonuclease recognition site and wherein the endonuclease is a Type IIS restriction endonuclease. In some alternatives, the at least one endonuclease recognition site is a BsaI restriction endonuclease recognition site or a StuI restriction endonuclease recognition site, and wherein the endonuclease is BsaI or StuI. In some alternatives, the endonuclease recognition site is inverted. In some alternatives, the polynucleotide is a linear polynucleotide. In some alternatives, the polynucleotide has only one endonuclease recognition site. In some alternatives, the polynucleotide further comprises a polymerase promoter region. In some alternatives, the plurality of thymine nucleotides comprises at least one covalently linked guanine, cytosine, or an adenine, wherein the at least one covalently linked guanine, cytosine or adenine is optionally joined to the most 5' thymine (or 5' terminal thymine) in the plurality of thymine nucleotides. In some alternatives, the endonuclease cleavage site comprises at least one guanine, cytosine, or an adenine, wherein the endonuclease cleaves between a thymine and the at least one guanine, cytosine or adenine. In some alternatives, the polynucleotide further comprises at least one palindromic sequence, wherein the at least one palindromic sequence can form a hairpin. In some alternatives, the polynucleotide further comprises a third sequence, wherein the third sequence is capable of forming a tertiary structure such as a hairpin. In some alternatives, the gene is codon optimized for expression in human cells. In some alternatives the nucleic acid provided, is manufactured by a method of any one of the alternatives described herein is provided. In some alternatives, the method comprises providing the polynucleotide of any one of the alternatives provided herein, or the polynucleotide manufactured by any one of the alternatives provided herein and contacting said polynucleotide with a polymerase in the presence of nucleotides. The polynucleotide can comprise a first nucleic acid sequence encoding a nuclease, a second nucleic acid sequence comprising at least one restriction endonuclease recognition site and a third nucleic acid sequence, wherein the third nucleic acid sequence comprises the template strand, wherein said plurality of thymine nucleotides comprises at least, greater than, equal to, or any number in between 20, 30, 40, 50, 60, 70, 80, 90, 100, 110, 120, 130, 140, 150, 175, 200, 225, 250, 275, 300, 325, 350, 375, 400, 425, 450, 475, 500 or 550 covalently linked thymine nucleotides and wherein the third nucleic acid comprises the restriction endonuclease cleavage site, wherein the restriction endonuclease cleavage site is located within the plurality of thymine nucleotides or within 1, 2, 3, 4, 5, 6, 7, 7, 8, 9, 10, 11, 12, 13, 14, 15, 16, 17, 18, 19 or 20 base pairs away from the most 5' thymine (or 5' terminal thymine) in the plurality of thymine nucleotides and wherein said second nucleic acid is covalently linked to one end of said third nucleic acid sequence, and wherein the said restriction endonuclease recognition site is located within 55 base pairs of the restriction endonuclease cleavage site for the restriction endonuclease and said restriction endonuclease cleavage site is within 1 to 40 base pairs of a most 5' thymine in the plurality of thymine nucleotides. Some polynucleotides comprise a first nucleic acid sequence comprising at least one restriction endonuclease recognition site and a second nucleic acid sequence, wherein the second nucleic acid sequence comprises the template strand, wherein the template strand comprises a plurality of thymine nucleotides, wherein said plurality of thymine nucleotides comprises at least, greater than, equal to, or any number in between 20, 30, 40, 50, 60, 70, 80, 90, 100, 110, 120, 130, 140, 150, 175, 200, 225, 250, 275, 300, 325, 350, 375, 400, 425, 450, 475, 500 or 550 covalently linked thymine nucleotides, wherein the second nucleic acid comprises the restriction endonuclease cleavage site, and wherein the restriction endonuclease cleavage site is within the plurality of thymine nucleotides or within 1, 2, 3, 4, 5, 6, 7, 7, 8, 9, 10, 11, 12, 13, 14, 15, 16, 17, 18, 19 or 20 base pairs away from the most 5' thymine (or 5' terminal thymine) in the plurality of thymine nucleotides and wherein said first nucleic acid is covalently linked to said second nucleic acid at one end of said second nucleic acid, and wherein the said restriction endonuclease recognition site is located within 1-55 base pairs such as, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54 or 55 base pairs, of the restriction endonuclease cleavage site for the restriction endonuclease and said restriction endonuclease cleavage site is within 1 to 40 base pairs, such as 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 base pairs, of a most 5' thymine (or 5' terminal thymine) in the plurality of thymine nucleotides. In some alternatives, the polynucleotide further comprises telomeres. In some alternatives, the polynucleotide comprises a left arm wherein the left arm comprises a left telomere, a right arm wherein the right arm comprises a right telomere and a cloning region located between the left arm and the right arm. In some alternatives, the polynucleotide further comprises a third nucleic acid, wherein the third nucleic acid comprises a gene. In some alternatives, the gene encodes a protein for therapy. In some alternatives, the gene encodes a nuclease. In some alternatives, the nuclease is an endonuclease. In some alternatives, the nuclease comprises an amino acid sequence set forth in SEQ ID NO. 6 or is encoded by a nucleic acid sequence set forth in SEQ ID NO: 7-14. In some alternatives, the number of covalently linked thymines is greater than 120. In some alternatives, the number of covalently linked thymines is greater than 200. In some alternatives, the number of covalently linked thymines is greater than 300. In some alternatives, the at least one endonuclease recognition site is a Type II restriction endonuclease recognition site, and the endonuclease is a Type II restriction endonuclease. In some alternatives, the at least one endonuclease recognition site is a Type IIS restriction endonuclease recognition site and wherein the endonuclease is a Type IIS restriction endonuclease. In some alternatives, the at least one Type II restriction endonuclease recognition site is a BsaI restriction endonuclease recognition site or a StuI restriction endonuclease recognition site, and wherein the endonuclease is BsaI or StuI. In some alternatives, the endonuclease recognition site is inverted. In some alternatives, the polynucleotide is a linear polynucleotide. In some alternatives, the polynucleotide has only one endonuclease recognition site. In some alternatives, the polynucleotide further comprises a polymerase promoter region. In some alternatives, the plurality of thymine nucleotides comprises at least one covalently linked guanine, cytosine, or an adenine, wherein the at least one covalently linked guanine, cytosine or adenine is optionally joined to the most 5' thymine (or 5' terminal thymine) in the plurality of thymine nucleotides. In some alternatives, the endonuclease cleavage site comprises at least one guanine, cytosine, or an adenine, wherein the endonuclease cleaves between a thymine and the at least one guanine, cytosine or adenine. In some alternatives, the polynucleotide further comprises at least one palindromic sequence, wherein the at least one palindromic sequence can form a hairpin. In some alternatives, the polynucleotide further comprises a third sequence, wherein the third sequence is capable of forming a tertiary structure such as a hairpin. In some alternatives, the gene is codon optimized for expression in human cells. The method of making a polynucleotide comprising a sequence encoding a nuclease, a template strand, an endonuclease recognition site and an endonuclease cleavage site for an endonuclease inserted therein, wherein said template strand comprises a plurality of thymine nucleotides can comprise providing a first nucleic acid sequence encoding a nuclease, providing a second nucleic acid sequence comprising at least one endonuclease recognition site, providing a third nucleic acid sequence, wherein the third nucleic acid sequence comprises the template strand, wherein the template strand comprises a plurality of thymine nucleotides, wherein said plurality of thymine nucleotides comprises at least, greater than, equal to, or any number in between 20, 30, 40, 50, 60, 70, 80, 90, 100, 110, 120, 130, 140, 150, 175, 200, 225, 250, 275, 300, 325, 350, 375, 400, 425, 450, 475, 500 or 550 covalently linked thymine nucleotides and wherein the third nucleic acid comprises the endonuclease cleavage site, wherein the endonuclease cleavage site is located within the plurality of thymine nucleotides or within 1, 2, 3, 4, 5, 6, 7, 7, 8, 9, 10, 11, 12, 13, 14, 15, 16, 17, 18, 19 or 20 base pairs away from the most 5' thymine (or 5' terminal thymine) in the plurality of thymine nucleotides, joining said first nucleic acid to one end of the second nucleic acid sequence and joining said third nucleic acid sequence to one end of the second nucleic acid sequence, wherein said second nucleic acid is covalently linked to one end of said third nucleic acid sequence, and wherein the said endonuclease recognition site is located within 55 base pairs of the endonuclease cleavage site for the endonuclease and said endonuclease cleavage site is within 1 to 40 base pairs of a most 5' thymine (or 5' terminal thymine) in the plurality of thymine nucleotides. In some alternatives, the polynucleotide further comprises telomeres. In some alternatives, the polynucleotide comprises a left arm wherein the left arm comprises a left telomere, a right arm wherein the right arm comprises a right telomere and a cloning region located between the left arm and the right arm. In some alternatives, the polynucleotide further comprises a third nucleic acid, wherein the third nucleic acid comprises a gene. In some alternatives, the gene encodes a protein for therapy. In some alternatives, the gene encodes a nuclease. In some alternatives, the nuclease is an endonuclease. In some alternatives, the nuclease comprises an amino acid sequence set forth in SEQ ID NO. 6 or is encoded by a nucleic acid sequence set forth in SEQ ID NO: 7-14. In some alternatives, the number of covalently linked thymines is greater than 120. In some alternatives, the number of covalently linked thymines is greater than 200. In some alternatives, the number of covalently linked thymines is greater than 300. In some alternatives, the at least one endonuclease recognition site is a Type II restriction endonuclease recognition site, and the endonuclease is a Type II restriction endonuclease. In some alternatives, the at least one endonuclease recognition site is a Type IIS restriction endonuclease recognition site, and wherein the endonuclease is a Type IIS restriction endonuclease. In some alternatives, the at least one endonuclease recognition site is a BsaI restriction endonuclease recognition site or a StuI restriction endonuclease recognition site, and wherein the endonuclease is BsaI or StuI. In some alternatives, the endonuclease recognition site is inverted. In some alternatives, the polynucleotide is a linear polynucleotide. In some alternatives, the polynucleotide has only one endonuclease recognition site. In some alternatives, the polynucleotide further comprises a polymerase promoter. In some alternatives, the plurality of thymine nucleotides comprises at least one covalently linked guanine, cytosine, or an adenine, wherein the at least one covalently linked guanine, cytosine or adenine is optionally joined to the most 5' thymine (or 5' terminal thymine) in the plurality of thymine nucleotides. In some alternatives, the endonuclease cleavage site comprises at least one guanine, cytosine, or an adenine, wherein the endonuclease cleaves between a thymine and the at least one guanine, cytosine or adenine. In some alternatives, the polynucleotide further comprises at least one palindromic sequence, wherein the at least one palindromic sequence can form a hairpin. In some alternatives, the polynucleotide further comprises a fourth sequence, wherein the fourth sequence is capable of forming a tertiary structure such as a hairpin. In some alternatives, the gene is codon optimized for expression in human cells. In some alternatives, the polynucleotide further comprises a promoter for a polymerase. In some alternatives, polymerase is a DNA polymerase. In some alternatives, the DNA polymerase is a thermal stable polymerase, such as Taq polymerase. In some alternatives, the nucleotides are adenine, cytosine, guanine, thymine and/or uracil. In some alternatives, the method further comprises providing a set of primers. In some alternatives, the nucleic acid is DNA. In some alternatives, an RNA polymerase is used. In some alternatives, the contacting is performed at a temperature at least, greater than, equal to, or any temperature in between 30° C., 31° C., 32° C., 33° C., 34° C., 35° C., 36° C. or 37° C. In some alternatives, the contacting is performed for at least, greater than, equal to, or time in between 1, 5, 10, 20, 30, 40, 50, 60, 70, 80, 90 or 100 hours (e.g., at least, or equal to 1, 5, 10, 20, 30, 40, 50, 60, 70, 80, 90 or 100 hours or within a range defined by any two of the aforementioned times). In some alternatives, the nucleic acid is RNA. In some alternatives, the RNA comprises a plurality of adenine nucleotides, wherein the plurality of adenine nucleotides comprises at least, greater than, equal to, or any number in between 20, 30, 40, 50, 60, 70, 80, 90, 100, 110, 120, 130, 140, 150, 175, 200, 225, 250, 275, 300, 325, 350, 375, 400, 425, 450, 475, or 500 covalently linked adenines. In some alternatives, the number of covalently linked adenines is greater than 120. In some alternatives, the number of covalently linked adenines is greater than 200. In some alternatives, the number of covalently linked adenines is greater than 300. In some alternatives, the RNA further comprises a gene. In some alternatives, the gene encodes a protein for therapy. In some alternatives, the gene encodes a nuclease. In some alternatives, the gene encodes an endonuclease. In some alternatives, the nuclease comprises an amino acid sequence set forth in SEQ ID NO. 6 or is encoded by a nucleic acid sequence set forth in SEQ ID NO: 7-14. In some alternatives, the plurality of adenine nucleotides further comprises a guanine, cytosine or a uracil, and wherein the number of covalently linked adenines terminates with a guanine, cytosine or a uracil. In some alternatives, the nucleic acid further comprises at least one palindromic sequence, wherein the at least one palindromic sequence can form a hairpin. In some alternatives, the nucleic acid further comprises a sequence capable of forming a tertiary structure such as a hairpin. In some alternatives, the method further comprises providing an endonuclease. In some alternatives, the endonuclease is a Type II restriction endonuclease. In some alternatives, the endonuclease is a Type IIS restriction endonuclease. In some alternatives, the endonuclease is BsaI or StuI. In some alternatives, the gene is codon optimized for expression in human cells. In some alternatives, the nucleic acid is a DNA. In some alternatives, the nucleic acid is RNA. In some alternatives, the RNA comprises a plurality of adenine nucleotides, wherein the plurality of adenine nucleotides comprises at least, greater than, equal to, or any number in between 20, 30, 40, 50, 60, 70, 80, 90, 100, 110, 120, 130, 140, 150, 175, 200, 225, 250, 275, 300, 325, 350, 375, 400, 425, 450, 475, or 500 covalently linked adenines. In some alternatives, the number of covalently linked adenines is greater than 120. In some alternatives, the number of covalently linked adenines is greater than 200. In some alternatives, the number of covalently linked adenines is greater than 300. In some alternatives, the nucleic acid further comprises a gene. In some alternatives, the gene encodes a protein for therapy. In some alternatives, the gene encodes a nuclease. In some alternatives, the gene encodes an endonuclease. In some alternatives, the nuclease comprises an amino acid sequence set forth in SEQ ID NO. 6 or is encoded by a nucleic acid sequence set forth in SEQ ID NO: 7-14. In some alternatives, the covalently linked adenines terminate with a guanine, cytosine, thymine, or a uracil. In some alternatives, the nucleic acid further comprises at least one palindromic sequence, wherein the at least one palindromic sequence can form a hairpin. In some alternatives, the nucleic acid further comprises a sequence capable of forming a tertiary structure such as a hairpin. In some alternatives, the gene is codon optimized for expression in human cells. The polynucleotide can comprise a first nucleic acid sequence encoding a nuclease, a second nucleic acid sequence comprising at least one restriction endonuclease recognition site and a third nucleic acid sequence, wherein the third nucleic acid sequence comprises the template strand, wherein said plurality of thymine nucleotides comprises at least, greater than, equal to, or any number in between 20, 30, 40, 50, 60, 70, 80, 90, 100, 110, 120, 130, 140, 150, 175, 200, 225, 250, 275, 300, 325, 350, 375, 400, 425, 450, 475, 500 or 550 covalently linked thymine nucleotides and wherein the third nucleic acid comprises the restriction endonuclease cleavage site, wherein the restriction endonuclease cleavage site is located within the plurality of thymine nucleotides or within 1, 2, 3, 4, 5, 6, 7, 7, 8, 9, 10, 11, 12, 13, 14, 15, 16, 17, 18, 19 or 20 base pairs away from the most 5' thymine (or 5' terminal thymine) in the plurality of thymine nucleotides and wherein said second nucleic acid is covalently linked to one end of said third nucleic acid sequence, and wherein the said restriction endonuclease recognition site is located within 55 base pairs of the restriction endonuclease cleavage site for the restriction endonuclease and said restriction endonuclease cleavage site is within 1 to 40 base pairs of a most 5' thymine in the plurality of thymine nucleotides. Some polynucleotides comprise a first nucleic acid sequence comprising at least one restriction endonuclease recognition site and a second nucleic acid sequence, wherein the second nucleic acid sequence comprises the template strand, wherein the template strand comprises a plurality of thymine nucleotides, wherein said plurality of thymine nucleotides comprises at least, greater than, equal to, or any number in between 20, 30, 40, 50, 60, 70, 80, 90, 100, 110, 120, 130, 140, 150, 175, 200, 225, 250, 275, 300, 325, 350, 375, 400, 425, 450, 475, 500 or 550 covalently linked thymine nucleotides, wherein the second nucleic acid comprises the restriction endonuclease cleavage site, and wherein the restriction endonuclease cleavage site is within the plurality of thymine nucleotides or within 1, 2, 3, 4, 5, 6, 7, 7, 8, 9, 10, 11, 12, 13, 14, 15, 16, 17, 18, 19 or 20 base pairs away from the most 5' thymine (or 5' terminal thymine) in the plurality of thymine nucleotides and wherein said first nucleic acid is covalently linked to said second nucleic acid at one end of said second nucleic acid, and wherein the said restriction endonuclease recognition site is located within 1-55 base pairs such as, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54 or 55 base pairs, of the restriction endonuclease cleavage site for the restriction endonuclease and said restriction endonuclease cleavage site is within 1 to 40 base pairs, such as 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 base pairs, of a most 5' thymine (or 5' terminal thymine) in the plurality of thymine nucleotides. In some alternatives, the polynucleotide further comprises telomeres. In some alternatives, the polynucleotide comprises a left arm wherein the left arm comprises a left telomere, a right arm wherein the right arm comprises a right telomere and a cloning region located between the left arm and the right arm. In some alternatives, the nuclease comprises an amino acid sequence set forth in SEQ ID NO. 6 or is encoded by a nucleic acid sequence set forth in SEQ ID NO: 7-14. In some alternatives, the number of covalently linked thymines is greater than 120. In some alternatives, the number of covalently linked thymines is greater than 200. In some alternatives, the number of covalently linked thymines is greater than 300. In some alternatives, the at least one endonuclease recognition site is a Type II restriction endonuclease recognition site, and the endonuclease is a Type II restriction endonuclease. In some alternatives, the at least one endonuclease recognition site is a Type IIS restriction endonuclease recognition site and wherein the endonuclease is a Type IIS restriction endonuclease. In some alternatives, the at least one endonuclease recognition site is a BsaI restriction endonuclease recognition site or a StuI restriction endonuclease recognition site, and wherein the endonuclease is BsaI or StuI. In some alternatives, the endonuclease recognition site is inverted. In some alternatives, the polynucleotide is a linear polynucleotide. In some alternatives, the polynucleotide has only one endonuclease recognition site. In some alternatives, the polynucleotide further comprises a polymerase promoter. In some alternatives, the plurality of thymine nucleotides comprises at least one covalently linked guanine, cytosine, or an adenine, wherein the at least one covalently linked guanine, cytosine or adenine is optionally at the most 5' thymine (or 5' terminal thymine) in the plurality of thymine nucleotides. In some alternatives, the endonuclease cleavage site comprises at least one guanine, cytosine, or an adenine, wherein the endonuclease cleaves between a thymine and the at least one guanine, cytosine or adenine. In some alternatives, the polynucleotide further comprises at least one palindromic sequence, wherein the at least one palindromic sequence can form a hairpin. In some alternatives, the polynucleotide further comprises a seventh sequence, wherein the seventh sequence is capable of forming a tertiary structure such as a hairpin. In some alternatives, the sequence encoding the nuclease is optimized for expression in human cells. In some alternatives, the cell is a T-cell or a primary cell. In some alternatives, said disease is cancer, ischemia, diabetic retinopathy, macular degeneration, rheumatoid arthritis, psoriasis, HIV infection, sickle cell anemia, Alzheimer's disease, muscular dystrophy, neurodegenerative diseases, vascular disease, cystic fibrosis, stroke, hyper IGE syndrome, hemophilia. In some alternatives, said disease is cancer, ischemia, diabetic retinopathy, macular degeneration, rheumatoid arthritis, psoriasis, HIV infection, sickle cell anemia, Alzheimer's disease, muscular dystrophy, neurodegenerative diseases, vascular disease, cystic fibrosis, stroke, hyper IGE syndrome, hemophilia. In some alternatives, the endonuclease cleavage site is located 1, 2, 3, 4, 5, 6, 7, 7, 8, 9, 10, 11, 12, 13, 14, 15, 16, 17, 18, 19 or 20 base pairs away from the most 5' thymine (or 5' terminal thymine) in the plurality of thymine nucleotides. In some alternatives, the endonuclease cleavage site is located 1, 2, 3, 4, 5, 6, 7, 7, 8, 9 or 10 base pairs away from the most 5' thymine (or 5' terminal thymine) in the plurality of thymine nucleotides.

In some alternatives, a method of increasing and/or stabilizing expression of a protein is provided wherein the method comprises generating an mRNA from any one or more of the polynucleotides of any one or more of the aforementioned claims and translating said mRNA into a peptide. The polynucleotide can comprise a first nucleic acid sequence encoding a nuclease, a second nucleic acid sequence comprising at least one restriction endonuclease recognition site and a third nucleic acid sequence, wherein the third nucleic acid sequence comprises the template strand, wherein said plurality of thymine nucleotides comprises at least, greater than, equal to, or any number in between 20, 30, 40, 50, 60, 70, 80, 90, 100, 110, 120, 130, 140, 150, 175, 200, 225, 250, 275, 300, 325, 350, 375, 400, 425, 450, 475, 500 or 550 covalently linked thymine nucleotides and wherein the third nucleic acid comprises the restriction endonuclease cleavage site, wherein the restriction endonuclease cleavage site is located within the plurality of thymine nucleotides or within 1, 2, 3, 4, 5, 6, 7, 7, 8, 9, 10, 11, 12, 13, 14, 15, 16, 17, 18, 19 or 20 base pairs away from the most 5' thymine (or 5' terminal thymine) in the plurality of thymine nucleotides and wherein said second nucleic acid is covalently linked to one end of said third nucleic acid sequence, and wherein the said restriction endonuclease recognition site is located within 55 base pairs of the restriction endonuclease cleavage site for the restriction endonuclease and said restriction endonuclease cleavage site is within 1 to 40 base pairs of a most 5' thymine in the plurality of thymine nucleotides. Some polynucleotides comprise a first nucleic acid sequence comprising at least one restriction endonuclease recognition site and a second nucleic acid sequence, wherein the second nucleic acid sequence comprises the template strand, wherein the template strand comprises a plurality of thymine nucleotides, wherein said plurality of thymine nucleotides comprises at least, greater than, equal to, or any number in between 20, 30, 40, 50, 60, 70, 80, 90, 100, 110, 120, 130, 140, 150, 175, 200, 225, 250, 275, 300, 325, 350, 375, 400, 425, 450, 475, 500 or 550 covalently linked thymine nucleotides, wherein the second nucleic acid comprises the restriction endonuclease cleavage site, and wherein the restriction endonuclease cleavage site is within the plurality of thymine nucleotides or within 1, 2, 3, 4, 5, 6, 7, 7, 8, 9, 10, 11, 12, 13, 14, 15, 16, 17, 18, 19 or 20 base pairs away from the most 5' thymine (or 5' terminal thymine) in the plurality of thymine nucleotides and wherein said first nucleic acid is covalently linked to said second nucleic acid at one end of said second nucleic acid, and wherein the said restriction endonuclease recognition site is located within 1-55 base pairs such as, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54 or 55 base pairs, of the restriction endonuclease cleavage site for the restriction endonuclease and said restriction endonuclease cleavage site is within 1 to 40 base pairs, such as 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 base pairs, of a most 5' thymine (or 5' terminal thymine) in the plurality of thymine nucleotides. In some alternatives, the polynucleotide further comprises telomeres. In some alternatives, the polynucleotide comprises a left arm wherein the left arm comprises a left telomere, a right arm wherein the right arm comprises a right telomere and a cloning region located between the left arm and the right arm. In some alternatives, the polynucleotide further comprises a third nucleic acid, wherein the third nucleic acid comprises a gene. In some alternatives, the gene encodes a protein for therapy. In some alternatives, the gene encodes a nuclease. In some alternatives, the nuclease is an endonuclease. In some alternatives, the nuclease comprises an amino acid sequence set forth in SEQ ID NO. 6 or is encoded by a nucleic acid sequence set forth in SEQ ID NO: 7-14. In some alternatives, the number of covalently linked thymines is greater than 120. In some alternatives, the number of covalently linked thymines is greater than 200. In some alternatives, the number of covalently linked thymines is greater than 300. In some alternatives, the at least one endonuclease recognition site is a Type II restriction endonuclease recognition site, and the endonuclease is a Type II restriction endonuclease. In some alternatives, the at least one endonuclease recognition site is a Type IIS restriction endonuclease recognition site and wherein the endonuclease is a Type IIS restriction endonuclease. In some alternatives, the at least one endonuclease recognition site is a BsaI restriction endonuclease recognition site or a StuI restriction endonuclease recognition site, and wherein the endonuclease is BsaI or StuI. In some alternatives, the endonuclease recognition site is inverted. In some alternatives, the polynucleotide is a linear polynucleotide. In some alternatives, the polynucleotide has only one endonuclease recognition site. In some alternatives, the polynucleotide further comprises a polymerase promoter region. In some alternatives, the plurality of thymine nucleotides comprises at least one covalently linked guanine, cytosine, or an adenine, wherein the at least one covalently linked guanine, cytosine or adenine is optionally at the most 5' thymine (or 5' terminal thymine) in the plurality of thymine nucleotides. In some alternatives, the endonuclease cleavage site comprises at least one guanine, cytosine, or an adenine, wherein the endonuclease cleaves between a thymine and the at least one guanine, cytosine or adenine. In some alternatives, the polynucleotide further comprises at least one palindromic sequence, wherein the at least one palindromic sequence can form a hairpin. In some alternatives, the polynucleotide further comprises a third sequence, wherein the third sequence is capable of forming a tertiary structure such as a hairpin. In some alternatives, the gene is codon optimized for expression in human cells. In some alternatives the nucleic acid provided, is manufactured by a method of any one of the alternatives described herein is provided. In some alternatives, the method comprises providing the polynucleotide of any one of the alternatives provided herein, or the polynucleotide manufactured by any one of the alternatives provided herein and contacting said polynucleotide with a polymerase in the presence of nucleotides. The polynucleotide can comprise a first nucleic acid sequence encoding a nuclease, a second nucleic acid sequence comprising at least one restriction endonuclease recognition site and a third nucleic acid sequence, wherein the third nucleic acid sequence comprises the template strand, wherein said plurality of thymine nucleotides comprises at least, greater than, equal to, or any number in between 20, 30, 40, 50, 60, 70, 80, 90, 100, 110, 120, 130, 140, 150, 175, 200, 225, 250, 275, 300, 325, 350, 375, 400, 425, 450, 475, 500 or 550 covalently linked thymine nucleotides and wherein the third nucleic acid comprises the restriction endonuclease cleavage site, wherein the restriction endonuclease cleavage site is located within the plurality of thymine nucleotides or within 1, 2, 3, 4, 5, 6, 7, 7, 8, 9, 10, 11, 12, 13, 14, 15, 16, 17, 18, 19 or 20 base pairs away from the most 5' thymine (or 5' terminal thymine) in the plurality of thymine nucleotides and wherein said second nucleic acid is covalently linked to one end of said third nucleic acid sequence, and wherein the said restriction endonuclease recognition site is located within 55 base pairs of the restriction endonuclease cleavage site for the restriction endonuclease and said restriction endonuclease cleavage site is within 1 to 40 base pairs of a most 5' thymine in the plurality of thymine nucleotides. Some polynucleotides comprise a first nucleic acid sequence comprising at least one restriction endonuclease recognition site and a second nucleic acid sequence, wherein the second nucleic acid sequence comprises the template strand, wherein the template strand comprises a plurality of thymine nucleotides, wherein said plurality of thymine nucleotides comprises at least, greater than, equal to, or any number in between 20, 30, 40, 50, 60, 70, 80, 90, 100, 110, 120, 130, 140, 150, 175, 200, 225, 250, 275, 300, 325, 350, 375, 400, 425, 450, 475, 500 or 550 covalently linked thymine nucleotides, wherein the second nucleic acid comprises the restriction endonuclease cleavage site, and wherein the restriction endonuclease cleavage site is within the plurality of thymine nucleotides or within 1, 2, 3, 4, 5, 6, 7, 7, 8, 9, 10, 11, 12, 13, 14, 15, 16, 17, 18, 19 or 20 base pairs away from the most 5' thymine (or 5' terminal thymine) in the plurality of thymine nucleotides and wherein said first nucleic acid is covalently linked to said second nucleic acid at one end of said second nucleic acid, and wherein the said restriction endonuclease recognition site is located within 1-55 base pairs such as, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54 or 55 base pairs, of the restriction endonuclease cleavage site for the restriction endonuclease and said restriction endonuclease cleavage site is within 1 to 40 base pairs, such as 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 base pairs, of a most 5' thymine (or 5' terminal thymine) in the plurality of thymine nucleotides. In some alternatives, the polynucleotide further comprises telomeres. In some alternatives, the polynucleotide comprises a left arm wherein the left arm comprises a left telomere, a right arm wherein the right arm comprises a right telomere and a cloning region located between the left arm and the right arm. In some alternatives, the polynucleotide further comprises a third nucleic acid, wherein the third nucleic acid comprises a gene. In some alternatives, the gene encodes a protein for therapy. In some alternatives, the gene encodes a nuclease. In some alternatives, the nuclease is an endonuclease. In some alternatives, the nuclease comprises an amino acid sequence set forth in SEQ ID NO. 6 or is encoded by a nucleic acid sequence set forth in SEQ ID NO: 7-14. In some alternatives, the number of covalently linked thymines is greater than 120. In some alternatives, the number of covalently linked thymines is greater than 200. In some alternatives, the number of covalently linked thymines is greater than 300. In some alternatives, the at least one endonuclease recognition site is a Type II restriction endonuclease recognition site, and the endonuclease is a Type II restriction endonuclease. In some alternatives, the at least one endonuclease recognition site is a Type IIS restriction endonuclease recognition site and wherein the endonuclease is a Type IIS restriction endonuclease. In some alternatives, the at least one endonuclease recognition site is a BsaI restriction endonuclease recognition site or a StuI restriction endonuclease recognition site, and wherein the endonuclease is BsaI or StuI. In some alternatives, the endonuclease recognition site is inverted. In some alternatives, the polynucleotide is a linear polynucleotide. In some alternatives, the polynucleotide has only one endonuclease recognition site. In some alternatives, the polynucleotide further comprises a polymerase promoter region. In some alternatives, the plurality of thymine nucleotides comprises at least one covalently linked guanine, cytosine, or an adenine, wherein the at least one covalently linked guanine, cytosine or adenine is optionally joined to the most 5' thymine (or 5' terminal thymine) in the plurality of thymine nucleotides. In some alternatives, the endonuclease cleavage site comprises at least one guanine, cytosine, or an adenine, wherein the endonuclease cleaves between a thymine and the at least one guanine, cytosine or adenine. In some alternatives, the polynucleotide further comprises at least one palindromic sequence, wherein the at least one palindromic sequence can form a hairpin. In some alternatives, the polynucleotide further comprises a third sequence, wherein the third sequence is capable of forming a tertiary structure such as a hairpin. In some alternatives, the gene is codon optimized for expression in human cells. The method of making a polynucleotide comprising a sequence encoding a nuclease, a template strand, an endonuclease recognition site and an endonuclease cleavage site for an endonuclease inserted therein, wherein said template strand comprises a plurality of thymine nucleotides can comprise providing a first nucleic acid sequence encoding a nuclease, providing a second nucleic acid sequence comprising at least one endonuclease recognition site, providing a third nucleic acid sequence, wherein the third nucleic acid sequence comprises the template strand, wherein the template strand comprises a plurality of thymine nucleotides, wherein said plurality of thymine nucleotides comprises at least, greater than, equal to, or any number in between 20, 30, 40, 50, 60, 70, 80, 90, 100, 110, 120, 130, 140, 150, 175, 200, 225, 250, 275, 300, 325, 350, 375, 400, 425, 450, 475, 500 or 550 covalently linked thymine nucleotides and wherein the third nucleic acid comprises the endonuclease cleavage site, wherein the endonuclease cleavage site is located within the plurality of thymine nucleotides or within 1, 2, 3, 4, 5, 6, 7, 7, 8, 9, 10, 11, 12, 13, 14, 15, 16, 17, 18, 19 or 20 base pairs away from the most 5' thymine (or 5' terminal thymine) in the plurality of thymine nucleotides, joining said first nucleic acid to one end of the second nucleic acid sequence and joining said third nucleic acid sequence to one end of the second nucleic acid sequence, wherein said second nucleic acid is covalently linked to one end of said third nucleic acid sequence, and wherein the said endonuclease recognition site is located within 55 base pairs of the endonuclease cleavage site for the endonuclease and said endonuclease cleavage site is within 1 to 40 base pairs of a most 5' thymine in the plurality of thymine nucleotides. In some alternatives, the polynucleotide further comprises telomeres. In some alternatives, the polynucleotide comprises a left arm wherein the left arm comprises a left telomere, a right arm wherein the right arm comprises a right telomere and a cloning region located between the left arm and the right arm. In some alternatives, the polynucleotide further comprises a third nucleic acid, wherein the third nucleic acid comprises a gene. In some alternatives, the gene encodes a protein for therapy. In some alternatives, the gene encodes a nuclease. In some alternatives, the nuclease is an endonuclease. In some alternatives, the nuclease comprises an amino acid sequence set forth in SEQ ID NO. 6 or is encoded by a nucleic acid sequence set forth in SEQ ID NO: 7-14. In some alternatives, the number of covalently linked thymines is greater than 120. In some alternatives, the number of covalently linked thymines is greater than 200. In some alternatives, the number of covalently linked thymines is greater than 300. In some alternatives, the at least one endonuclease recognition site is a Type II restriction endonuclease recognition site, and the endonuclease is a Type II restriction endonuclease. In some alternatives, the at least one endonuclease recognition site is a Type IIS restriction endonuclease recognition site, and wherein the endonuclease is a Type IIS restriction endonuclease. In some alternatives, the at least one endonuclease recognition site is a BsaI restriction endonuclease recognition site or a StuI restriction endonuclease recognition site, and wherein the endonuclease is BsaI or StuI. In some alternatives, the endonuclease recognition site is inverted. In some alternatives, the polynucleotide is a linear polynucleotide. In some alternatives, the polynucleotide has only one endonuclease recognition site. In some alternatives, the polynucleotide further comprises a polymerase promoter. In some alternatives, the plurality of thymine nucleotides comprises at least one covalently linked guanine, cytosine, or an adenine, wherein the at least one covalently linked guanine, cytosine or adenine is optionally at the most 5' thymine (or 5' terminal thymine) in the plurality of thymine nucleotides.

In some alternatives, the endonuclease cleavage site comprises at least one guanine, cytosine, or an adenine, wherein the endonuclease cleaves between a thymine and the at least one guanine, cytosine or adenine. In some alternatives, the polynucleotide further comprises at least one palindromic sequence, wherein the at least one palindromic sequence can form a hairpin. In some alternatives, the polynucleotide further comprises a fourth sequence, wherein the fourth sequence is capable of forming a tertiary structure such as a hairpin. In some alternatives, the gene is codon optimized for expression in human cells. In some alternatives, the polynucleotide further comprises a promoter for a polymerase. In some alternatives, polymerase is a DNA polymerase. In some alternatives, the DNA polymerase is a thermal stable polymerase, such as Taq polymerase. In some alternatives, the nucleotides are adenine, cytosine, guanine, thymine and/or uracil. In some alternatives, the method further comprises providing a set of primers. In some alternatives, the nucleic acid is DNA. In some alternatives, an RNA polymerase is used. In some alternatives, the contacting is performed at a temperature at least, greater than, equal to, or any temperature in between 30° C., 31° C., 32° C., 33° C., 34° C., 35° C., 36° C. or 37° C. In some alternatives, the contacting is performed for at least, greater than, equal to, or time in between 1, 5, 10, 20, 30, 40, 50, 60, 70, 80, 90 or 100 hours (e.g., at least, or equal to 1, 5, 10, 20, 30, 40, 50, 60, 70, 80, 90 or 100 hours or within a range defined by any two of the aforementioned times). In some alternatives, the nucleic acid is RNA. In some alternatives, the RNA comprises a plurality of adenine nucleotides, wherein the plurality of adenine nucleotides comprises at least, greater than, equal to, or any number in between 20, 30, 40, 50, 60, 70, 80, 90, 100, 110, 120, 130, 140, 150, 175, 200, 225, 250, 275, 300, 325, 350, 375, 400, 425, 450, 475, or 500 covalently linked adenines. In some alternatives, the number of covalently linked adenines is greater than 120. In some alternatives, the number of covalently linked adenines is greater than 200. In some alternatives, the number of covalently linked adenines is greater than 300. In some alternatives, the RNA further comprises a gene. In some alternatives, the gene encodes a protein for therapy. In some alternatives, the gene encodes a nuclease. In some alternatives, the gene encodes an endonuclease. In some alternatives, the nuclease comprises an amino acid sequence set forth in SEQ ID NO. 6 or is encoded by a nucleic acid sequence set forth in SEQ ID NO: 7-14. In some alternatives, the plurality of adenine nucleotides further comprises a guanine, cytosine or a uracil, and wherein the number of covalently linked adenines terminates with a guanine, cytosine or a uracil. In some alternatives, the nucleic acid further comprises at least one palindromic sequence, wherein the at least one palindromic sequence can form a hairpin. In some alternatives, the nucleic acid further comprises a sequence capable of forming a tertiary structure such as a hairpin. In some alternatives, the method further comprises providing an endonuclease. In some alternatives, the endonuclease is a Type II restriction endonuclease. In some alternatives, the endonuclease is a Type IIS restriction endonuclease. In some alternatives, the endonuclease is BsaI or StuI. In some alternatives, the gene is codon optimized for expression in human cells. In some alternatives, the nucleic acid is a DNA. In some alternatives, the nucleic acid is RNA. In some alternatives, the RNA comprises a plurality of adenine nucleotides, wherein the plurality of adenine nucleotides comprises at least, greater than, equal to, or any number in between 20, 30, 40, 50, 60, 70, 80, 90, 100, 110, 120, 130, 140, 150, 175, 200, 225, 250, 275, 300, 325, 350, 375, 400, 425, 450, 475, or 500 covalently linked adenines. In some alternatives, the number of covalently linked adenines is greater than 120. In some alternatives, the number of covalently linked adenines is greater than 200. In some alternatives, the number of covalently linked adenines is greater than 300. In some alternatives, the nucleic acid further comprises a gene. In some alternatives, the gene encodes a protein for therapy. In some alternatives, the gene encodes a nuclease. In some alternatives, the gene encodes an endonuclease. In some alternatives, the nuclease comprises an amino acid sequence set forth in SEQ ID NO. 6 or is encoded by a nucleic acid sequence set forth in SEQ ID NO: 7-14. In some alternatives, the covalently linked adenines terminates with a guanine, cytosine, thymine, or a uracil. In some alternatives, the nucleic acid further comprises at least one palindromic sequence, wherein the at least one palindromic sequence can form a hairpin. In some alternatives, the nucleic acid further comprises a sequence capable of forming a tertiary structure such as a hairpin. In some alternatives, the gene is codon optimized for expression in human cells. The polynucleotide can comprise a first nucleic acid sequence encoding a nuclease, a second nucleic acid sequence comprising at least one restriction endonuclease recognition site and a third nucleic acid sequence, wherein the third nucleic acid sequence comprises the template strand, wherein said plurality of thymine nucleotides comprises at least, greater than, equal to, or any number in between 20, 30, 40, 50, 60, 70, 80, 90, 100, 110, 120, 130, 140, 150, 175, 200, 225, 250, 275, 300, 325, 350, 375, 400, 425, 450, 475, 500 or 550 covalently linked thymine nucleotides and wherein the third nucleic acid comprises the restriction endonuclease cleavage site, wherein the restriction endonuclease cleavage site is located within the plurality of thymine nucleotides or within 1, 2, 3, 4, 5, 6, 7, 7, 8, 9, 10, 11, 12, 13, 14, 15, 16, 17, 18, 19 or 20 base pairs away from the most 5' thymine (or 5' terminal thymine) in the plurality of thymine nucleotides and wherein said second nucleic acid is covalently linked to one end of said third nucleic acid sequence, and wherein the said restriction endonuclease recognition site is located within 55 base pairs of the restriction endonuclease cleavage site for the restriction endonuclease and said restriction endonuclease cleavage site is within 1 to 40 base pairs of a most 5' thymine in the plurality of thymine nucleotides. Some polynucleotides comprise a first nucleic acid sequence comprising at least one restriction endonuclease recognition site and a second nucleic acid sequence, wherein the second nucleic acid sequence comprises the template strand, wherein the template strand comprises a plurality of thymine nucleotides, wherein said plurality of thymine nucleotides comprises at least, greater than, equal to, or any number in between 20, 30, 40, 50, 60, 70, 80, 90, 100, 110, 120, 130, 140, 150, 175, 200, 225, 250, 275, 300, 325, 350, 375, 400, 425, 450, 475, 500 or 550 covalently linked thymine nucleotides, wherein the second nucleic acid comprises the restriction endonuclease cleavage site, and wherein the restriction endonuclease cleavage site is within the plurality of thymine nucleotides or within 1, 2, 3, 4, 5, 6, 7, 7, 8, 9, 10, 11, 12, 13, 14, 15, 16, 17, 18, 19 or 20 base pairs away from the most 5' thymine (or 5' terminal thymine) in the plurality of thymine nucleotides and wherein said first nucleic acid is covalently linked to said second nucleic acid at one end of said second nucleic acid, and wherein the said restriction endonuclease recognition site is located within 1-55 base pairs such as, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54 or 55 base pairs, of the restriction endonuclease cleavage site for the restriction endonuclease and said restriction endonuclease cleavage site is within 1 to 40 base pairs, such as 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 base pairs, of a most 5' thymine (or 5' terminal thymine) in the plurality of thymine nucleotides. In some alternatives, the polynucleotide further comprises telomeres. In some alternatives, the polynucleotide comprises a left arm wherein the left arm comprises a left telomere, a right arm wherein the right arm comprises a right telomere and a cloning region located between the left arm and the right arm. In some alternatives, the nuclease comprises an amino acid sequence set forth in SEQ ID NO. 6 or is encoded by a nucleic acid sequence set forth in SEQ ID NO: 7-14. In some alternatives, the number of covalently linked thymines is greater than 120. In some alternatives, the number of covalently linked thymines is greater than 200. In some alternatives, the number of covalently linked thymines is greater than 300. In some alternatives, the at least one endonuclease recognition site is a Type II restriction endonuclease recognition site, and the endonuclease is a Type II restriction endonuclease. In some alternatives, the at least one endonuclease recognition site is a Type IIS restriction endonuclease recognition site and wherein the endonuclease is a Type IIS restriction endonuclease. In some alternatives, the at least one endonuclease recognition site is a BsaI restriction endonuclease recognition site or a StuI restriction endonuclease recognition site, and wherein the endonuclease is BsaI or StuI. In some alternatives, the endonuclease recognition site is inverted. In some alternatives, the polynucleotide is a linear polynucleotide. In some alternatives, the polynucleotide has only one endonuclease recognition site. In some alternatives, the polynucleotide further comprises a polymerase promoter. In some alternatives, the plurality of thymine nucleotides comprises at least one covalently linked guanine, cytosine, or an adenine, wherein the at least one covalently linked guanine, cytosine or adenine is optionally joined to the most 5' thymine (or 5' terminal thymine) in the plurality of thymine nucleotides. In some alternatives, the endonuclease cleavage site comprises at least one guanine, cytosine, or an adenine, wherein the endonuclease cleaves between a thymine and the at least one guanine, cytosine or adenine. In some alternatives, the polynucleotide further comprises at least one palindromic sequence, wherein the at least one palindromic sequence can form a hairpin. In some alternatives, the polynucleotide further comprises a seventh sequence, wherein the seventh sequence is capable of forming a tertiary structure such as a hairpin. In some alternatives, the sequence encoding the nuclease is optimized for expression in human cells. In some alternatives, the cell is a T-cell or a primary cell. In some alternatives, said disease is cancer, ischemia, diabetic retinopathy, macular degeneration, rheumatoid arthritis, psoriasis, HIV infection, sickle cell anemia, Alzheimer's disease, muscular dystrophy, neurodegenerative diseases, vascular disease, cystic fibrosis, stroke, hyper IGE syndrome, hemophilia. In some alternatives, the RNA lacks a 5' and/or 3' UTR or lacks a native 5' and/or 3' UTR and/or lacks one or more sequences required for native polyadenylation such as, a cleavage/polyadenylation specificity factor (CPSF) binding site, a cleavage stimulation factor binding site (CstF), a cleavage factor I binding site (CFI), or a cleavage factor II binding site (CFII). In some alternatives, the endonuclease cleavage site is located 1, 2, 3, 4, 5, 6, 7, 7, 8, 9, 10, 11, 12, 13, 14, 15, 16, 17, 18, 19 or 20 base pairs away from the most 5' thymine (or 5' terminal thymine) in the plurality of thymine nucleotides. In some alternatives, the endonuclease cleavage site is located 1, 2, 3, 4, 5, 6, 7, 7, 8, 9 or 10 base pairs away from the most 5' thymine (or 5' terminal thymine) in the plurality of thymine nucleotides.

In some alternatives, a method of enhancing transcription or expression of a gene is provided, where the method comprises providing any one or more of the polynucleotides or nucleic acids of any one or more of the aforementioned claims, wherein said polynucleotide further comprises a gene, such as a nuclease gene, for example SEQ ID NOs. 6-14 and contacting said polynucleotide or nucleic acid with a RNA polymerase in the presence of nucleotides. The polynucleotide can comprise a first nucleic acid sequence encoding a nuclease, a second nucleic acid sequence comprising at least one restriction endonuclease recognition site and a third nucleic acid sequence, wherein the third nucleic acid sequence comprises the template strand, wherein said plurality of thymine nucleotides comprises at least, greater than, equal to, or any number in between 20, 30, 40, 50, 60, 70, 80, 90, 100, 110, 120, 130, 140, 150, 175, 200, 225, 250, 275, 300, 325, 350, 375, 400, 425, 450, 475, 500 or 550 covalently linked thymine nucleotides and wherein the third nucleic acid comprises the restriction endonuclease cleavage site, wherein the restriction endonuclease cleavage site is located within the plurality of thymine nucleotides or within 1, 2, 3, 4, 5, 6, 7, 7, 8, 9, 10, 11, 12, 13, 14, 15, 16, 17, 18, 19 or 20 base pairs away from the most 5' thymine (or 5' terminal thymine) in the plurality of thymine nucleotides and wherein said second nucleic acid is covalently linked to one end of said third nucleic acid sequence, and wherein the said restriction endonuclease recognition site is located within 55 base pairs of the restriction endonuclease cleavage site for the restriction endonuclease and said restriction endonuclease cleavage site is within 1 to 40 base pairs of a most 5' thymine in the plurality of thymine nucleotides. Some polynucleotides comprise a first nucleic acid sequence comprising at least one restriction endonuclease recognition site and a second nucleic acid sequence, wherein the second nucleic acid sequence comprises the template strand, wherein the template strand comprises a plurality of thymine nucleotides, wherein said plurality of thymine nucleotides comprises at least, greater than, equal to, or any number in between 20, 30, 40, 50, 60, 70, 80, 90, 100, 110, 120, 130, 140, 150, 175, 200, 225, 250, 275, 300, 325, 350, 375, 400, 425, 450, 475, 500 or 550 covalently linked thymine nucleotides, wherein the second nucleic acid comprises the restriction endonuclease cleavage site, and wherein the restriction endonuclease cleavage site is within the plurality of thymine nucleotides or within 1, 2, 3, 4, 5, 6, 7, 7, 8, 9, 10, 11, 12, 13, 14, 15, 16, 17, 18, 19 or 20 base pairs away from the most 5' thymine (or 5' terminal thymine) in the plurality of thymine nucleotides and wherein said first nucleic acid is covalently linked to said second nucleic acid at one end of said second nucleic acid, and wherein the said restriction endonuclease recognition site is located within 1-55 base pairs such as, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54 or 55 base pairs, of the restriction endonuclease cleavage site for the restriction endonuclease and said restriction endonuclease cleavage site is within 1 to 40 base pairs, such as 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 base pairs, of a most 5' thymine (or 5' terminal thymine) in the plurality of thymine nucleotides. In some alternatives, the polynucleotide further comprises telomeres. In some alternatives, the polynucleotide comprises a left arm wherein the left arm comprises a left telomere, a right arm wherein the right arm comprises a right telomere and a cloning region located between the left arm and the right arm. In some alternatives, the polynucleotide further comprises a third nucleic acid, wherein the third nucleic acid comprises a gene. In some alternatives, the gene encodes a protein for therapy. In some alternatives, the gene encodes a nuclease. In some alternatives, the nuclease is an endonuclease. In some alternatives, the nuclease comprises an amino acid sequence set forth in SEQ ID NO. 6 or is encoded by a nucleic acid sequence set forth in SEQ ID NO: 7-14. In some alternatives, the number of covalently linked thymines is greater than 120. In some alternatives, the number of covalently linked thymines is greater than 200. In some alternatives, the number of covalently linked thymines is greater than 300. In some alternatives, the at least one endonuclease recognition site is a Type II restriction endonuclease recognition site, and the endonuclease is a Type II restriction endonuclease. In some alternatives, the at least one endonuclease recognition site is a Type IIS restriction endonuclease recognition site and wherein the endonuclease is a Type IIS restriction endonuclease. In some alternatives, the at least one endonuclease recognition site is a BsaI restriction endonuclease recognition site or a StuI restriction endonuclease recognition site, and wherein the endonuclease is BsaI or StuI. In some alternatives, the endonuclease recognition site is inverted. In some alternatives, the polynucleotide is a linear polynucleotide. In some alternatives, the polynucleotide has only one endonuclease recognition site. In some alternatives, the polynucleotide further comprises a polymerase promoter region. In some alternatives, the plurality of thymine nucleotides comprises at least one covalently linked guanine, cytosine, or an adenine, wherein the at least one covalently linked guanine, cytosine or adenine is optionally joined to the most 5' thymine (or 5' terminal thymine) in the plurality of thymine nucleotides. In some alternatives, the endonuclease cleavage site comprises at least one guanine, cytosine, or an adenine, wherein the endonuclease cleaves between a thymine and the at least one guanine, cytosine or adenine. In some alternatives, the polynucleotide further comprises at least one palindromic sequence, wherein the at least one palindromic sequence can form a hairpin. In some alternatives, the polynucleotide further comprises a third sequence, wherein the third sequence is capable of forming a tertiary structure such as a hairpin. In some alternatives, the gene is codon optimized for expression in human cells. In some alternatives the nucleic acid provided, is manufactured by a method of any one of the alternatives described herein is provided. In some alternatives, the method comprises providing the polynucleotide of any one of the alternatives provided herein, or the polynucleotide manufactured by any one of the alternatives provided herein and contacting said polynucleotide with a polymerase in the presence of nucleotides. The polynucleotide can comprise a first nucleic acid sequence encoding a nuclease, a second nucleic acid sequence comprising at least one restriction endonuclease recognition site and a third nucleic acid sequence, wherein the third nucleic acid sequence comprises the template strand, wherein said plurality of thymine nucleotides comprises at least, greater than, equal to, or any number in between 20, 30, 40, 50, 60, 70, 80, 90, 100, 110, 120, 130, 140, 150, 175, 200, 225, 250, 275, 300, 325, 350, 375, 400, 425, 450, 475, 500 or 550 covalently linked thymine nucleotides and wherein the third nucleic acid comprises the restriction endonuclease cleavage site, wherein the restriction endonuclease cleavage site is located within the plurality of thymine nucleotides or within 1, 2, 3, 4, 5, 6, 7, 7, 8, 9, 10, 11, 12, 13, 14, 15, 16, 17, 18, 19 or 20 base pairs away from the most 5' thymine (or 5' terminal thymine) in the plurality of thymine nucleotides and wherein said second nucleic acid is covalently linked to one end of said third nucleic acid sequence, and wherein the said restriction endonuclease recognition site is located within 55 base pairs of the restriction endonuclease cleavage site for the restriction endonuclease and said restriction endonuclease cleavage site is within 1 to 40 base pairs of a most 5' thymine in the plurality of thymine nucleotides. Some polynucleotides comprise a first nucleic acid sequence comprising at least one restriction endonuclease recognition site and a second nucleic acid sequence, wherein the second nucleic acid sequence comprises the template strand, wherein the template strand comprises a plurality of thymine nucleotides, wherein said plurality of thymine nucleotides comprises at least, greater than, equal to, or any number in between 20, 30, 40, 50, 60, 70, 80, 90, 100, 110, 120, 130, 140, 150, 175, 200, 225, 250, 275, 300, 325, 350, 375, 400, 425, 450, 475, 500 or 550 covalently linked thymine nucleotides, wherein the second nucleic acid comprises the restriction endonuclease cleavage site, and wherein the restriction endonuclease cleavage site is within the plurality of thymine nucleotides or within 1, 2, 3, 4, 5, 6, 7, 7, 8, 9, 10, 11, 12, 13, 14, 15, 16, 17, 18, 19 or 20 base pairs away from the most 5' thymine (or 5' terminal thymine) in the plurality of thymine nucleotides and wherein said first nucleic acid is covalently linked to said second nucleic acid at one end of said second nucleic acid, and wherein the said restriction endonuclease recognition site is located within 1-55 base pairs such as, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54 or 55 base pairs, of the restriction endonuclease cleavage site for the restriction endonuclease and said restriction endonuclease cleavage site is within 1 to 40 base pairs, such as 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 base pairs, of a most 5' thymine (or 5' terminal thymine) in the plurality of thymine nucleotides. In some alternatives, the polynucleotide further comprises telomeres. In some alternatives, the polynucleotide comprises a left arm wherein the left arm comprises a left telomere, a right arm wherein the right arm comprises a right telomere and a cloning region located between the left arm and the right arm. In some alternatives, the polynucleotide further comprises a third nucleic acid, wherein the third nucleic acid comprises a gene. In some alternatives, the gene encodes a protein for therapy. In some alternatives, the gene encodes a nuclease. In some alternatives, the nuclease is an endonuclease. In some alternatives, the nuclease comprises an amino acid sequence set forth in SEQ ID NO. 6 or is encoded by a nucleic acid sequence set forth in SEQ ID NO: 7-14. In some alternatives, the number of covalently linked thymines is greater than 120. In some alternatives, the number of covalently linked thymines is greater than 200. In some alternatives, the number of covalently linked thymines is greater than 300. In some alternatives, the at least one endonuclease recognition site is a Type II restriction endonuclease recognition site, and the endonuclease is a Type II restriction endonuclease. In some alternatives, the at least one endonuclease recognition site is a Type IIS restriction endonuclease recognition site and wherein the endonuclease is a Type IIS restriction endonuclease. In some alternatives, the at least one endonuclease recognition site is a BsaI restriction endonuclease recognition site or a StuI restriction endonuclease recognition site, and wherein the endonuclease is BsaI or StuI. In some alternatives, the endonuclease recognition site is inverted. In some alternatives, the polynucleotide is a linear polynucleotide. In some alternatives, the polynucleotide has only one endonuclease recognition site. In some alternatives, the polynucleotide further comprises a polymerase promoter region. In some alternatives, the plurality of thymine nucleotides comprises at least one covalently linked guanine, cytosine, or an adenine, wherein the at least one covalently linked guanine, cytosine or adenine is optionally joined to the most 5' thymine (or 5' terminal thymine) in the plurality of thymine nucleotides. In some alternatives, the endonuclease cleavage site comprises at least one guanine, cytosine, or an adenine, wherein the endonuclease cleaves between a thymine and the at least one guanine, cytosine or adenine. In some alternatives, the polynucleotide further comprises at least one palindromic sequence, wherein the at least one palindromic sequence can form a hairpin. In some alternatives, the polynucleotide further comprises a third sequence, wherein the third sequence is capable of forming a tertiary structure such as a hairpin. In some alternatives, the gene is codon optimized for expression in human cells. The method of making a polynucleotide comprising a sequence encoding a nuclease, a template strand, an endonuclease recognition site and an endonuclease cleavage site for an endonuclease inserted therein, wherein said template strand comprises a plurality of thymine nucleotides can comprise providing a first nucleic acid sequence encoding a nuclease, providing a second nucleic acid sequence comprising at least one endonuclease recognition site, providing a third nucleic acid sequence, wherein the third nucleic acid sequence comprises the template strand, wherein the template strand comprises a plurality of thymine nucleotides, wherein said plurality of thymine nucleotides comprises at least, greater than, equal to, or any number in between 20, 30, 40, 50, 60, 70, 80, 90, 100, 110, 120, 130, 140, 150, 175, 200, 225, 250, 275, 300, 325, 350, 375, 400, 425, 450, 475, 500 or 550 covalently linked thymine nucleotides and wherein the third nucleic acid comprises the endonuclease cleavage site, wherein the endonuclease cleavage site is located within the plurality of thymine nucleotides or within 1, 2, 3, 4, 5, 6, 7, 7, 8, 9, 10, 11, 12, 13, 14, 15, 16, 17, 18, 19 or 20 base pairs away from the most 5' thymine (or 5' terminal thymine) in the plurality of thymine nucleotides, joining said first nucleic acid to one end of the second nucleic acid sequence and joining said third nucleic acid sequence to one end of the second nucleic acid sequence, wherein said second nucleic acid is covalently linked to one end of said third nucleic acid sequence, and wherein the said endonuclease recognition site is located within 55 base pairs of the endonuclease cleavage site for the endonuclease and said endonuclease cleavage site is within 1 to 40 base pairs of a most 5' thymine in the plurality of thymine nucleotides. In some alternatives, the polynucleotide further comprises telomeres. In some alternatives, the polynucleotide comprises a left arm wherein the left arm comprises a left telomere, a right arm wherein the right arm comprises a right telomere and a cloning region located between the left arm and the right arm. In some alternatives, the polynucleotide further comprises a third nucleic acid, wherein the third nucleic acid comprises a gene. In some alternatives, the gene encodes a protein for therapy. In some alternatives, the gene encodes a nuclease. In some alternatives, the nuclease is an endonuclease. In some alternatives, the nuclease comprises an amino acid sequence set forth in SEQ ID NO. 6 or is encoded by a nucleic acid sequence set forth in SEQ ID NO: 7-14. In some alternatives, the number of covalently linked thymines is greater than 120. In some alternatives, the number of covalently linked thymines is greater than 200. In some alternatives, the number of covalently linked thymines is greater than 300. In some alternatives, the at least one endonuclease recognition site is a Type II restriction endonuclease recognition site, and the endonuclease is a Type II restriction endonuclease. In some alternatives, the at least one endonuclease recognition site is a Type IIS restriction endonuclease recognition site, and wherein the endonuclease is a Type IIS restriction endonuclease. In some alternatives, the at least one endonuclease recognition site is a BsaI restriction endonuclease recognition site or a StuI restriction endonuclease recognition site, and wherein the endonuclease is BsaI or StuI. In some alternatives, the endonuclease recognition site is inverted. In some alternatives, the polynucleotide is a linear polynucleotide. In some alternatives, the polynucleotide has only one endonuclease recognition site. In some alternatives, the polynucleotide further comprises a polymerase promoter. In some alternatives, the plurality of thymine nucleotides comprises at least one covalently linked guanine, cytosine, or an adenine, wherein the at least one covalently linked guanine, cytosine or adenine is optionally joined to the most 5' thymine (or 5' terminal thymine) in the plurality of thymine nucleotides. In some alternatives, the endonuclease cleavage site comprises at least one guanine, cytosine, or an adenine, wherein the endonuclease cleaves between a thymine and the at least one guanine, cytosine or adenine. In some alternatives, the polynucleotide further comprises at least one palindromic sequence, wherein the at least one palindromic sequence can form a hairpin. In some alternatives, the polynucleotide further comprises a fourth sequence, wherein the fourth sequence is capable of forming a tertiary structure such as a hairpin. In some alternatives, the gene is codon optimized for expression in human cells. In some alternatives, the polynucleotide further comprises a promoter for a polymerase. In some alternatives, polymerase is a DNA polymerase. In some alternatives, the DNA polymerase is a thermal stable polymerase, such as Taq polymerase. In some alternatives, the nucleotides are adenine, cytosine, guanine, thymine and/or uracil. In some alternatives, the method further comprises providing a set of primers. In some alternatives, the nucleic acid is DNA. In some alternatives, an RNA polymerase is used. In some alternatives, the contacting is performed at a temperature at least, greater than, equal to, or any temperature in between 30° C., 31° C., 32° C., 33° C., 34° C., 35° C., 36° C. or 37° C. In some alternatives, the contacting is performed for at least, greater than, equal to, or time in between 1, 5, 10, 20, 30, 40, 50, 60, 70, 80, 90 or 100 hours (e.g., at least, or equal to 1, 5, 10, 20, 30, 40, 50, 60, 70, 80, 90 or 100 hours or within a range defined by any two of the aforementioned times). In some alternatives, the nucleic acid is RNA. In some alternatives, the RNA comprises a plurality of adenine nucleotides, wherein the plurality of adenine nucleotides comprises at least, greater than, equal to, or any number in between 20, 30, 40, 50, 60, 70, 80, 90, 100, 110, 120, 130, 140, 150, 175, 200, 225, 250, 275, 300, 325, 350, 375, 400, 425, 450, 475, or 500 covalently linked adenines. In some alternatives, the number of covalently linked adenines is greater than 120. In some alternatives, the number of covalently linked adenines is greater than 200. In some alternatives, the number of covalently linked adenines is greater than 300. In some alternatives, the RNA further comprises a gene. In some alternatives, the gene encodes a protein for therapy. In some alternatives, the gene encodes a nuclease.

In some alternatives, the gene encodes an endonuclease. In some alternatives, the nuclease comprises an amino acid sequence set forth in SEQ ID NO. 6 or is encoded by a nucleic acid sequence set forth in SEQ ID NO: 7-14. In some alternatives, the plurality of adenine nucleotides further comprises a guanine, cytosine or a uracil, and wherein the number of covalently linked adenines terminates with a guanine, cytosine or a uracil. In some alternatives, the nucleic acid further comprises at least one palindromic sequence, wherein the at least one palindromic sequence can form a hairpin. In some alternatives, the nucleic acid further comprises a sequence capable of forming a tertiary structure such as a hairpin. In some alternatives, the method further comprises providing an endonuclease. In some alternatives, the endonuclease is a Type II restriction endonuclease. In some alternatives, the endonuclease is a Type IIS restriction endonuclease. In some alternatives, the endonuclease is BsaI or StuI. In some alternatives, the gene is codon optimized for expression in human cells. In some alternatives, the nucleic acid is a DNA. In some alternatives, the nucleic acid is RNA. In some alternatives, the RNA comprises a plurality of adenine nucleotides, wherein the plurality of adenine nucleotides comprises at least, greater than, equal to, or any number in between 20, 30, 40, 50, 60, 70, 80, 90, 100, 110, 120, 130, 140, 150, 175, 200, 225, 250, 275, 300, 325, 350, 375, 400, 425, 450, 475, or 500 covalently linked adenines. In some alternatives, the number of covalently linked adenines is greater than 120. In some alternatives, the number of covalently linked adenines is greater than 200. In some alternatives, the number of covalently linked adenines is greater than 300. In some alternatives, the nucleic acid further comprises a gene. In some alternatives, the gene encodes a protein for therapy. In some alternatives, the gene encodes a nuclease. In some alternatives, the gene encodes an endonuclease. In some alternatives, the nuclease comprises an amino acid sequence set forth in SEQ ID NO. 6 or is encoded by a nucleic acid sequence set forth in SEQ ID NO: 7-14. In some alternatives, the covalently linked adenines terminates with a guanine, cytosine, thymine, or a uracil. In some alternatives, the nucleic acid further comprises at least one palindromic sequence, wherein the at least one palindromic sequence can form a hairpin. In some alternatives, the nucleic acid further comprises a sequence capable of forming a tertiary structure such as a hairpin. In some alternatives, the gene is codon optimized for expression in human cells. The polynucleotide can comprise a first nucleic acid sequence encoding a nuclease, a second nucleic acid sequence comprising at least one restriction endonuclease recognition site and a third nucleic acid sequence, wherein the third nucleic acid sequence comprises the template strand, wherein said plurality of thymine nucleotides comprises at least, greater than, equal to, or any number in between 20, 30, 40, 50, 60, 70, 80, 90, 100, 110, 120, 130, 140, 150, 175, 200, 225, 250, 275, 300, 325, 350, 375, 400, 425, 450, 475, 500 or 550 covalently linked thymine nucleotides and wherein the third nucleic acid comprises the restriction endonuclease cleavage site, wherein the restriction endonuclease cleavage site is located within the plurality of thymine nucleotides or within 1, 2, 3, 4, 5, 6, 7, 7, 8, 9, 10, 11, 12, 13, 14, 15, 16, 17, 18, 19 or 20 base pairs away from the most 5' thymine (or 5' terminal thymine) in the plurality of thymine nucleotides and wherein said second nucleic acid is covalently linked to one end of said third nucleic acid sequence, and wherein the said restriction endonuclease recognition site is located within 55 base pairs of the restriction endonuclease cleavage site for the restriction endonuclease and said restriction endonuclease cleavage site is within 1 to 40 base pairs of a most 5' thymine in the plurality of thymine nucleotides. Some polynucleotides comprise a first nucleic acid sequence comprising at least one restriction endonuclease recognition site and a second nucleic acid sequence, wherein the second nucleic acid sequence comprises the template strand, wherein the template strand comprises a plurality of thymine nucleotides, wherein said plurality of thymine nucleotides comprises at least, greater than, equal to, or any number in between 20, 30, 40, 50, 60, 70, 80, 90, 100, 110, 120, 130, 140, 150, 175, 200, 225, 250, 275, 300, 325, 350, 375, 400, 425, 450, 475, 500 or 550 covalently linked thymine nucleotides, wherein the second nucleic acid comprises the restriction endonuclease cleavage site, and wherein the restriction endonuclease cleavage site is within the plurality of thymine nucleotides or within 1, 2, 3, 4, 5, 6, 7, 7, 8, 9, 10, 11, 12, 13, 14, 15, 16, 17, 18, 19 or 20 base pairs away from the most 5' thymine (or 5' terminal thymine) in the plurality of thymine nucleotides and wherein said first nucleic acid is covalently linked to said second nucleic acid at one end of said second nucleic acid, and wherein the said restriction endonuclease recognition site is located within 1-55 base pairs such as, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54 or 55 base pairs, of the restriction endonuclease cleavage site for the restriction endonuclease and said restriction endonuclease cleavage site is within 1 to 40 base pairs, such as 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 base pairs, of a most 5' thymine (or 5' terminal thymine) in the plurality of thymine nucleotides. In some alternatives, the polynucleotide further comprises telomeres. In some alternatives, the polynucleotide comprises a left arm wherein the left arm comprises a left telomere, a right arm wherein the right arm comprises a right telomere and a cloning region located between the left arm and the right arm. In some alternatives, the nuclease comprises an amino acid sequence set forth in SEQ ID NO. 6 or is encoded by a nucleic acid sequence set forth in SEQ ID NO: 7-14. In some alternatives, the number of covalently linked thymines is greater than 120. In some alternatives, the number of covalently linked thymines is greater than 200. In some alternatives, the number of covalently linked thymines is greater than 300. In some alternatives, the at least one endonuclease recognition site is a Type II restriction endonuclease recognition site, and the endonuclease is a Type II restriction endonuclease. In some alternatives, the at least one endonuclease recognition site is a Type IIS restriction endonuclease recognition site and wherein the endonuclease is a Type IIS restriction endonuclease. In some alternatives, the at least one endonuclease recognition site is a BsaI restriction endonuclease recognition site or a StuI restriction endonuclease recognition site, and wherein the endonuclease is BsaI or StuI. In some alternatives, the endonuclease recognition site is inverted. In some alternatives, the polynucleotide is a linear polynucleotide. In some alternatives, the polynucleotide has only one endonuclease recognition site. In some alternatives, the polynucleotide further comprises a polymerase promoter. In some alternatives, the plurality of thymine nucleotides comprises at least one covalently linked guanine, cytosine, or an adenine, wherein the at least one covalently linked guanine, cytosine or adenine is optionally joined to the most 5' thymine (or 5' terminal thymine) in the plurality of thymine nucleotides. In some alternatives, the endonuclease cleavage site comprises at least one guanine, cytosine, or an adenine, wherein the endonuclease cleaves between a thymine and the at least one guanine, cytosine or adenine. In some alternatives, the polynucleotide further comprises at least one palindromic sequence, wherein the at least one palindromic sequence can form a hairpin. In some alternatives, the polynucleotide further comprises a seventh sequence, wherein the seventh sequence is capable of forming a tertiary structure such as a hairpin. In some alternatives, the sequence encoding the nuclease is optimized for expression in human cells. In some alternatives, the cell is a T-cell or a primary cell. In some alternatives, said disease is cancer, ischemia, diabetic retinopathy, macular degeneration, rheumatoid arthritis, psoriasis, HIV infection, sickle cell anemia, Alzheimer's disease, muscular dystrophy, neurodegenerative diseases, vascular disease, cystic fibrosis, stroke, hyper IGE syndrome, hemophilia. In some alternatives, the RNA lacks a 5' and/or 3' UTR or lacks a native 5' and/or 3' UTR and/or lacks one or more sequences required for native polyadenylation such as, a cleavage/polyadenylation specificity factor (CPSF) binding site, a cleavage stimulation factor binding site (CstF), a cleavage factor I binding site (CFI), or a cleavage factor II binding site (CFII). More alternatives concern a polynucleotide comprising a first nucleic acid sequence that comprises at least one endonuclease recognition site; and a second nucleic acid sequence that comprises a plurality of thymine nucleotides, wherein said plurality of thymine nucleotides comprises at least, greater than, equal to, or any number in between 20, 30, 40, 50, 60, 70, 80, 90, 100, 110, 120, 130, 140, 150, 175, 200, 225, 250, 275, 300, 325, 350, 375, 400, 425, 450, 475, 500 or 550 covalently linked thymine nucleotides, wherein the second nucleic acid comprises an endonuclease cleavage site that is within the plurality of thymine nucleotides or within 1, 2, 3, 4, 5, 6, 7, 7, 8, 9, 10, 11, 12, 13, 14, 15, 16, 17, 18, 19 or 20 nucleotides from the 5' terminal thymine in the plurality of thymine nucleotides; and wherein said first nucleic acid is covalently linked to said second nucleic acid at one end of said second nucleic acid and, wherein said endonuclease recognition site is within 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54 or 55 nucleotides of the endonuclease cleavage site and said endonuclease cleavage site is within 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 nucleotides of the 5' terminal thymine in the plurality of thymine nucleotides. Alternatives also include, wherein the polynucleotide above comprises a left arm that comprises a left telomere; a right arm comprising a right telomere; and a cloning region located between the left arm and the right arm. Alternatives also include, wherein the polynucleotide above further comprises a third nucleic acid and, wherein the third nucleic acid comprises a gene. Alternatives also include, wherein the gene above encodes a protein, a nuclease, or an endonuclease. Alternatives also include, wherein the nuclease above comprises an amino acid sequence set forth in SEQ ID NO. 6 or is encoded by a nucleic acid sequence set forth in SEQ ID NO: 7-14. Alternatives also include, wherein the at least one endonuclease recognition site above is a restriction endonuclease recognition site. Alternatives also include, wherein the restriction endonuclease recognition site above is a Type II restriction endonuclease recognition site or a Type IIS restriction endonuclease recognition site. Alternatives also include, wherein the at least one endonuclease recognition site above is a BsaI restriction endonuclease recognition site or a StuI restriction endonuclease recognition site. Alternatives also include, wherein the endonuclease recognition site above is inverted. Alternatives also include, wherein the plurality of thymine nucleotides terminates in an cysteine, adenine, or a guanine. Alternatives also include, wherein the polynucleotide is a linear polynucleotide. More alternatives concern methods of making a nucleic acid, comprising providing a polynucleotide above; and contacting said polynucleotide with a polymerase in the presence of nucleotides. In some alternatives, the nucleic acid is RNA. Alternatives also include, wherein the RNA above comprises a plurality of adenine nucleotides, wherein the plurality of adenine nucleotides comprises at least, greater than, equal to, or any number in between 20, 30, 40, 50, 60, 70, 80, 90, 100, 110, 120, 130, 140, 150, 175, 200, 225, 250, 275, 300, 325, 350, 375, 400, 425, 450, 475, or 500 covalently linked adenines. More alternatives concern methods of stabilizing an RNA during in vitro translation at 30-37 degrees Celsius for at least 100 hours (e.g., at least, or equal to 1, 5, 10, 20, 30, 40, 50, 60, 70, 80, 90 or 100 hours or within a range defined by any two of the aforementioned times) comprising providing the nucleic acid manufactured by the method above; and contacting said nucleic acid with a ribosome, in the presence of amino acids and tRNAs, wherein said RNA is stable at 30-37 degrees Celsius for at least 100 hours (e.g., at least, or equal to 1, 5, 10, 20, 30, 40, 50, 60, 70, 80, 90 or 100 hours or within a range defined by any two of the aforementioned times). The contacting can be performed for at least, greater than, equal to, or time in between 1, 5, 10, 20, 30, 40, 50, 60, 70, 80, 90 or 100 hours (e.g., at least, or equal to 1, 5, 10, 20, 30, 40, 50, 60, 70, 80, 90 or 100 hours or within a range defined by any two of the aforementioned times). In some alternatives, the nucleic acid is an RNA. In some alternatives, the RNA comprises a plurality of adenine nucleotides and, wherein the plurality of adenine nucleotides comprises at least, greater than, equal to, or any number in between 20, 30, 40, 50, 60, 70, 80, 90, 100, 110, 120, 130, 140, 150, 175, 200, 225, 250, 275, 300, 325, 350, 375, 400, 425, 450, 475, or 500 covalently linked adenines. In some alternatives, the RNA further comprises a gene and, wherein the gene encodes, a protein for therapy, an endonuclease or a nuclease. More alternatives involve methods of stabilizing an RNA during in vivo translation at 30-37 degrees Celsius for at least 100 hours (e.g., at least, or equal to 1, 5, 10, 20, 30, 40, 50, 60, 70, 80, 90 or 100 hours or within a range defined by any two of the aforementioned times) in a cell, comprising transfecting into a cell the nucleic acid providing the nucleic acid manufactured by a method above; placing the cell into a culture vessel with media; supplying the cell with nutrients and amino acids for translation; and incubating the cell for at at least, greater than, equal to, or time in between 1, 5, 10, 20, 30, 40, 50, 60, 70, 80, 90 or 100 hours (e.g., at least, or equal to 1, 5, 10, 20, 30, 40, 50, 60, 70, 80, 90 or 100 hours or within a range defined by any two of the aforementioned times) so as to allow for translation. In some alternatives, the cell is a human cell. In some alternatives, the cell is selected from the group consisting of primary cells, human primary T cells, CD4+ cells and CD8+ cells. More alternatives concern methods of increasing and/or stabilizing expression of a protein comprising generating an RNA from the polynucleotide of claim 278; and translating said RNA into a peptide. In some alternatives, the translating further comprises providing an RNA polymerase. In some alternatives, the method further comprises providing an endonuclease. In some alternatives, the endonuclease is a Type II restriction endonuclease or a Type IIS restriction endonuclease and, preferably, the endonuclease is BsaI or StuI. In some alternatives, the RNA comprises a plurality of adenine nucleotides, wherein the plurality of adenine nucleotides comprises at least, greater than, equal to, or any number in between 20, 30, 40, 50, 60, 70, 80, 90, 100, 110, 120, 130, 140, 150, 175, 200, 225, 250, 275, 300, 325, 350, 375, 400, 425, 450, 475, or 500 covalently linked adenines. More alternatives concern methods of treating, ameliorating, or a inhibiting disease in a subject comprising introducing into a cell the RNA manufactured by a method described above; and delivering the cell to the subject. In some alternatives, the introducing is performed by electroporation. In some alternatives, the cell is a T-cell or a primary cell. In some alternatives, the cell is a human cell and preferably, the cell is CD4+ and/or CD8+.

Some alternatives relate to a polynucleotide. Some polynucleotides comprise a first nucleic acid sequence that comprises at least one endonuclease recognition site and a second nucleic acid sequence that comprises a plurality of thymine nucleotides, wherein said plurality of thymine nucleotides comprises at least, greater than, equal to, or any number in between 20, 30, 40, 50, 60, 70, 80, 90, 100, 110, 120, 130, 140, 150, 175, 200, 225, 250, 275, 300, 325, 350, 375, 400, 425, 450, 475, 500 or 550 covalently linked thymine nucleotides, wherein the second nucleic acid comprises an endonuclease cleavage site that is within the plurality of thymine nucleotides or within 1, 2, 3, 4, 5, 6, 7, 7, 8, 9, 10, 11, 12, 13, 14, 15, 16, 17, 18, 19 or 20 nucleotides from the 5' terminal thymine in the plurality of thymine nucleotides and wherein said first nucleic acid is covalently linked to said second nucleic acid at one end of said second nucleic acid and, wherein said endonuclease recognition site is within 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54 or 55 nucleotides of the endonuclease cleavage site and said endonuclease cleavage site is within 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 nucleotides of the 5' terminal thymine in the plurality of thymine nucleotides. In some alternatives, the polynucleotide comprises a left arm that comprises a left telomere; a right arm comprising a right telomere; and a cloning region located between the left arm and the right arm. In some alternatives, the polynucleotide further comprises a third nucleic acid and, wherein the third nucleic acid comprises a gene. In some alternatives, the gene encodes a protein, a nuclease, or an endonuclease. In some alternatives, nuclease comprises an amino acid sequence set forth in SEQ ID NO. 6 or is encoded by a nucleic acid sequence set forth in SEQ ID NO: 7-14. In some alternatives, the at least one endonuclease recognition site is a restriction endonuclease recognition site. In some alternatives, the restriction endonuclease recognition site is a Type II restriction endonuclease recognition site or a Type IIS restriction endonuclease recognition site. In some alternatives, the at least one endonuclease recognition site is a BsaI restriction endonuclease recognition site or a StuI restriction endonuclease recognition site. In some alternatives, the endonuclease recognition site is inverted. In some alternatives, the plurality of thymine nucleotides terminates in an cysteine, adenine, or a guanine. In some alternatives, the polynucleotide is a linear polynucleotide.

Some alternatives relate to a method of making a nucleic acid. Some alternatives of the method comprise providing the polynucleotide of any of the alternatives provided herein and contacting said polynucleotide with a polymerase in the presence of nucleotides. Some polynucleotides comprise a first nucleic acid sequence that comprises at least one endonuclease recognition site and a second nucleic acid sequence that comprises a plurality of thymine nucleotides, wherein said plurality of thymine nucleotides comprises at least, greater than, equal to, or any number in between 20, 30, 40, 50, 60, 70, 80, 90, 100, 110, 120, 130, 140, 150, 175, 200, 225, 250, 275, 300, 325, 350, 375, 400, 425, 450, 475, 500 or 550 covalently linked thymine nucleotides, wherein the second nucleic acid comprises an endonuclease cleavage site that is within the plurality of thymine nucleotides or within 1, 2, 3, 4, 5, 6, 7, 7, 8, 9, 10, 11, 12, 13, 14, 15, 16, 17, 18, 19 or 20 nucleotides from the 5' terminal thymine in the plurality of thymine nucleotides and wherein said first nucleic acid is covalently linked to said second nucleic acid at one end of said second nucleic acid and, wherein said endonuclease recognition site is within 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54 or 55 nucleotides of the endonuclease cleavage site and said endonuclease cleavage site is within 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 nucleotides of the 5' terminal thymine in the plurality of thymine nucleotides. In some alternatives, the polynucleotide comprises a left arm that comprises a left telomere; a right arm comprising a right telomere; and a cloning region located between the left arm and the right arm. In some alternatives, the polynucleotide further comprises a third nucleic acid and, wherein the third nucleic acid comprises a gene. In some alternatives, the gene encodes a protein, a nuclease, or an endonuclease. In some alternatives, nuclease comprises an amino acid sequence set forth in SEQ ID NO. 6 or is encoded by a nucleic acid sequence set forth in SEQ ID NO: 7-14. In some alternatives, the at least one endonuclease recognition site is a restriction endonuclease recognition site. In some alternatives, the restriction endonuclease recognition site is a Type II restriction endonuclease recognition site or a Type IIS restriction endonuclease recognition site. In some alternatives, the at least one endonuclease recognition site is a BsaI restriction endonuclease recognition site or a StuI restriction endonuclease recognition site. In some alternatives, the endonuclease recognition site is inverted. In some alternatives, the plurality of thymine nucleotides terminates in an cysteine, adenine, or a guanine. In some alternatives, the polynucleotide is a linear polynucleotide. In some alternatives, the nucleic acid is RNA. In some alternatives, the RNA comprises a plurality of adenine nucleotides, wherein the plurality of adenine nucleotides comprises at least, greater than, equal to, or any number in between 20, 30, 40, 50, 60, 70, 80, 90, 100, 110, 120, 130, 140, 150, 175, 200, 225, 250, 275, 300, 325, 350, 375, 400, 425, 450, 475, or 500 covalently linked adenines.

Some alternatives provided herein are methods for stabilizing an RNA during in vitro translation at 30-37 degrees Celsius for at least 100 hours (e.g., at least, or equal to 1, 5, 10, 20, 30, 40, 50, 60, 70, 80, 90 or 100 hours or within a range defined by any two of the aforementioned times) comprising providing the nucleic acid manufactured by a method of any of the alternatives herein, and contacting said nucleic acid with a ribosome, in the presence of amino acids and tRNAs, wherein said RNA is stable at 30-37 degrees Celsius for at least 100 hours (e.g., at least, or equal to 1, 5, 10, 20, 30, 40, 50, 60, 70, 80, 90 or 100 hours or within a range defined by any two of the aforementioned times). Contacting can be performed for at least, greater than, equal to, or time in between 1, 5, 10, 20, 30, 40, 50, 60, 70, 80, 90 or 100 hours (e.g., at least, or equal to 1, 5, 10, 20, 30, 40, 50, 60, 70, 80, 90 or 100 hours or within a range defined by any two of the aforementioned times). Some methods of making the nucleic acid comprise providing the polynucleotide of any of the alternatives provided herein and contacting said polynucleotide with a polymerase in the presence of nucleotides. Some polynucleotides comprise a first nucleic acid sequence that comprises at least one endonuclease recognition site and a second nucleic acid sequence that comprises a plurality of thymine nucleotides, wherein said plurality of thymine nucleotides comprises at least, greater than, equal to, or any number in between 20, 30, 40, 50, 60, 70, 80, 90, 100, 110, 120, 130, 140, 150, 175, 200, 225, 250, 275, 300, 325, 350, 375, 400, 425, 450, 475, 500 or 550 covalently linked thymine nucleotides, wherein the second nucleic acid comprises an endonuclease cleavage site that is within the plurality of thymine nucleotides or within 1, 2, 3, 4, 5, 6, 7, 7, 8, 9, 10, 11, 12, 13, 14, 15, 16, 17, 18, 19 or 20 nucleotides from the 5' terminal thymine in the plurality of thymine nucleotides and wherein said first nucleic acid is covalently linked to said second nucleic acid at one end of said second nucleic acid and, wherein said endonuclease recognition site is within 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54 or 55 nucleotides of the endonuclease cleavage site and said endonuclease cleavage site is within 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 nucleotides of the 5' terminal thymine in the plurality of thymine nucleotides. In some alternatives, the polynucleotide comprises a left arm that comprises a left telomere; a right arm comprising a right telomere; and a cloning region located between the left arm and the right arm. In some alternatives, the polynucleotide further comprises a third nucleic acid and, wherein the third nucleic acid comprises a gene. In some alternatives, the gene encodes a protein, a nuclease, or an endonuclease. In some alternatives, nuclease comprises an amino acid sequence set forth in SEQ ID NO. 6 or is encoded by a nucleic acid sequence set forth in SEQ ID NO: 7-14. In some alternatives, the at least one endonuclease recognition site is a restriction endonuclease recognition site. In some alternatives, the restriction endonuclease recognition site is a Type II restriction endonuclease recognition site or a Type IIS restriction endonuclease recognition site. In some alternatives, the at least one endonuclease recognition site is a BsaI restriction endonuclease recognition site or a StuI restriction endonuclease recognition site. In some alternatives, the endonuclease recognition site is inverted. In some alternatives, the plurality of thymine nucleotides terminates in an cysteine, adenine, or a guanine. In some alternatives, the polynucleotide is a linear polynucleotide. In some alternatives, the nucleic acid is RNA. In some alternatives, the RNA comprises a plurality of adenine nucleotides, wherein the plurality of adenine nucleotides comprises at least, greater than, equal to, or any number in between 20, 30, 40, 50, 60, 70, 80, 90, 100, 110, 120, 130, 140, 150, 175, 200, 225, 250, 275, 300, 325, 350, 375, 400, 425, 450, 475, or 500 covalently linked adenines. In some alternatives, the nucleic acid is an RNA. In some alternatives, the RNA comprises a plurality of adenine nucleotides and, wherein the plurality of adenine nucleotides comprises at least, greater than, equal to, or any number in between 20, 30, 40, 50, 60, 70, 80, 90, 100, 110, 120, 130, 140, 150, 175, 200, 225, 250, 275, 300, 325, 350, 375, 400, 425, 450, 475, or 500 covalently linked adenines. In some alternatives, the RNA further comprises a gene and, wherein the gene encodes, a protein for therapy, an endonuclease or a nuclease.

In some alternatives, a method of stabilizing an RNA during in vivo translation at 30-37 degrees Celsius for at least 100 hours (e.g., at least, or equal to 1, 5, 10, 20, 30, 40, 50, 60, 70, 80, 90 or 100 hours or within a range defined by any two of the aforementioned times) in a cell is provided. In some alternatives, the method comprises transfecting into a cell the nucleic acid, providing the nucleic acid manufactured by a method of any of the alternatives provided herein, placing the cell into a culture vessel with media, supplying the cell with nutrients and amino acids for translation; and incubating the cell for at least, greater than, equal to, or time in between 1, 5, 10, 20, 30, 40, 50, 60, 70, 80, 90 or 100 hours (e.g., at least, or equal to 1, 5, 10, 20, 30, 40, 50, 60, 70, 80, 90 or 100 hours or within a range defined by any two of the aforementioned times) so as to allow for translation. Some methods of making the nucleic acid comprise providing the polynucleotide of any of the alternatives provided herein and contacting said polynucleotide with a polymerase in the presence of nucleotides. Some polynucleotides comprise a first nucleic acid sequence that comprises at least one endonuclease recognition site and a second nucleic acid sequence that comprises a plurality of thymine nucleotides, wherein said plurality of thymine nucleotides comprises at least, greater than, equal to, or any number in between 20, 30, 40, 50, 60, 70, 80, 90, 100, 110, 120, 130, 140, 150, 175, 200, 225, 250, 275, 300, 325, 350, 375, 400, 425, 450, 475, 500 or 550 covalently linked thymine nucleotides, wherein the second nucleic acid comprises an endonuclease cleavage site that is within the plurality of thymine nucleotides or within 1, 2, 3, 4, 5, 6, 7, 7, 8, 9, 10, 11, 12, 13, 14, 15, 16, 17, 18, 19 or 20 nucleotides from the 5' terminal thymine in the plurality of thymine nucleotides and wherein said first nucleic acid is covalently linked to said second nucleic acid at one end of said second nucleic acid and, wherein said endonuclease recognition site is within 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54 or 55 nucleotides of the endonuclease cleavage site and said endonuclease cleavage site is within 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 nucleotides of the 5' terminal thymine in the plurality of thymine nucleotides. In some alternatives, the polynucleotide comprises a left arm that comprises a left telomere; a right arm comprising a right telomere; and a cloning region located between the left arm and the right arm. In some alternatives, the polynucleotide further comprises a third nucleic acid and, wherein the third nucleic acid comprises a gene. In some alternatives, the gene encodes a protein, a nuclease, or an endonuclease. In some alternatives, nuclease comprises an amino acid sequence set forth in SEQ ID NO. 6 or is encoded by a nucleic acid sequence set forth in SEQ ID NO: 7-14. In some alternatives, the at least one endonuclease recognition site is a restriction endonuclease recognition site. In some alternatives, the restriction endonuclease recognition site is a Type II restriction endonuclease recognition site or a Type IIS restriction endonuclease recognition site. In some alternatives, the at least one endonuclease recognition site is a BsaI restriction endonuclease recognition site or a StuI restriction endonuclease recognition site. In some alternatives, the endonuclease recognition site is inverted. In some alternatives, the plurality of thymine nucleotides terminates in an cysteine, adenine, or a guanine. In some alternatives, the polynucleotide is a linear polynucleotide. In some alternatives, the nucleic acid is RNA. In some alternatives, the RNA comprises a plurality of adenine nucleotides, wherein the plurality of adenine nucleotides comprises at least, greater than, equal to, or any number in between 20, 30, 40, 50, 60, 70, 80, 90, 100, 110, 120, 130, 140, 150, 175, 200, 225, 250, 275, 300, 325, 350, 375, 400, 425, 450, 475, or 500 covalently linked adenines. In some alternatives, the cell is a human cell. In some alternatives, the cell is selected from the group consisting of primary cells, human primary T cells, CD4+ cells and CD8+ cells.

In some alternatives, a method of increasing and/or stabilizing expression of a protein is provided, wherein the method comprises generating an RNA from the polynucleotide of any of the alternatives herein and translating said RNA into a peptide. Some polynucleotides comprise a first nucleic acid sequence that comprises at least one endonuclease recognition site and a second nucleic acid sequence that comprises a plurality of thymine nucleotides, wherein said plurality of thymine nucleotides comprises at least, greater than, equal to, or any number in between 20, 30, 40, 50, 60, 70, 80, 90, 100, 110, 120, 130, 140, 150, 175, 200, 225, 250, 275, 300, 325, 350, 375, 400, 425, 450, 475, 500 or 550 covalently linked thymine nucleotides, wherein the second nucleic acid comprises an endonuclease cleavage site that is within the plurality of thymine nucleotides or within 1, 2, 3, 4, 5, 6, 7, 7, 8, 9, 10, 11, 12, 13, 14, 15, 16, 17, 18, 19 or 20 nucleotides from the 5' terminal thymine in the plurality of thymine nucleotides and wherein said first nucleic acid is covalently linked to said second nucleic acid at one end of said second nucleic acid and, wherein said endonuclease recognition site is within 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54 or 55 nucleotides of the endonuclease cleavage site and said endonuclease cleavage site is within 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 nucleotides of the 5' terminal thymine in the plurality of thymine nucleotides. In some alternatives, the polynucleotide comprises a left arm that comprises a left telomere; a right arm comprising a right telomere; and a cloning region located between the left arm and the right arm. In some alternatives, the polynucleotide further comprises a third nucleic acid and, wherein the third nucleic acid comprises a gene. In some alternatives, the gene encodes a protein, a nuclease, or an endonuclease. In some alternatives, nuclease comprises an amino acid sequence set forth in SEQ ID NO. 6 or is encoded by a nucleic acid sequence set forth in SEQ ID NO: 7-14. In some alternatives, the at least one endonuclease recognition site is a restriction endonuclease recognition site. In some alternatives, the restriction endonuclease recognition site is a Type II restriction endonuclease recognition site or a Type IIS restriction endonuclease recognition site. In some alternatives, the at least one endonuclease recognition site is a BsaI restriction endonuclease recognition site or a StuI restriction endonuclease recognition site. In some alternatives, the endonuclease recognition site is inverted. In some alternatives, the plurality of thymine nucleotides terminates in a cysteine, adenine, or a guanine. In some alternatives, the polynucleotide is a linear polynucleotide. In some alternatives, the translating further comprises providing an RNA polymerase ribosomes, tRNAs and amino acids. In some alternatives, the method further comprises providing an endonuclease. In some alternatives, the endonuclease is a Type II restriction endonuclease or a Type IIS restriction endonuclease. In some alternatives, the endonuclease is BsaI or StuI.

With respect to the use of substantially any plural and/or singular terms herein, those having skill in the art can translate from the plural to the singular and/or from the singular to plural as is appropriate to the context and/or application. The various singular/plural permutations can be expressly set forth herein for sake of clarity.

It will be understood by those within the art that, in general, terms used herein, and especially in the appended claims (for example, bodies of the appended claims) are generally intended as "open" terms (for example, the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims can contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to alternatives containing only one such recitation, even when the same claim includes the introductory phrases "one or more" or "at least one" and indefinite articles such as "a" or "an" (for example, "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (for example, the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (for example, "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (for example, "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible sub-ranges and combinations of sub-ranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into sub-ranges as discussed above. Finally, as will be understood by one skilled in the art, a range includes each individual member. Thus, for example, a group having 1-3 articles refers to groups having 1, 2, or 3 articles. Similarly, a group having 1-5 articles refers to groups having 1, 2, 3, 4, or 5 articles, and so forth.

While various aspects and alternatives have been disclosed herein, other aspects and alternatives will be apparent to those skilled in the art. The various aspects and alternatives disclosed herein are for purposes of illustration and are not intended to be limiting, with the true scope and spirit being indicated by the following claims.

One skilled in the art will appreciate that, for this and other processes and methods disclosed herein, the functions performed in the processes and methods can be implemented in differing order. Furthermore, the outlined steps and operations are only provided as examples, and some of the steps and operations can be optional, combined into fewer steps and operations, or expanded into additional steps and operations without detracting from the essence of the disclosed alternatives.

One skilled in the art will appreciate that, for this and other processes and methods disclosed herein, the functions performed in the processes and methods can be implemented in differing order. Furthermore, the outlined steps and operations are only provided as examples, and some of the steps and operations can be optional, combined into fewer steps and operations, or expanded into additional steps and operations without detracting from the essence of the disclosed alternatives.

What is claimed is:

1. A method of generating a polynucleotide, comprising:
  (a) preparing a linear vector comprising:
    (i) obtaining a linear plasmid comprising a first telomere and a first nucleic acid comprising an endonuclease recognition site,
    (ii) obtaining a second nucleic acid comprising at least 130 consecutive thymine nucleotides, wherein the second nucleic acid is double-stranded, and
    (iii) inserting the second nucleic acid into the linear plasmid such that said second nucleic acid comprises an endonuclease cleavage site located within the plurality of thymine nucleotides or within 40 consecutive nucleotides from the 5' terminal thymine of the plurality of thymine nucleotides,
    said first nucleic acid is covalently linked to said second nucleic acid at one end of said second nucleic acid, and
    said endonuclease recognition site is within 55 consecutive nucleotides of the endonuclease cleavage site, thereby preparing the linear vector; and
  (b) contacting said linear vector with a polymerase in the presence of nucleotides, thereby generating the polynucleotide.

2. The method of claim 1, wherein the polymerase comprises an RNA polymerase.

3. The method of claim 2, wherein the polynucleotide comprises at least 130 consecutive adenine residues.

4. The method of claim 1, wherein the polynucleotide encodes a therapeutic protein, an endonuclease, or a nuclease.

5. The method of claim 1, wherein the linear vector comprises a left arm comprising the first telomere, and a right arm comprising a second telomere.

6. The method of claim 5, wherein the linear vector comprises a cloning region located between the left arm and the right arm.

7. The method of claim 1, wherein the linear vector comprises a third nucleic acid sequence comprises a transgene.

8. The method of claim 7, wherein the transgene encodes a protein.

9. The method of claim 1, wherein the contacting is performed at a temperature greater than or equal to 30° C.

10. The method of claim 1, wherein the contacting is performed for a period of at least 1 hour.

11. The method of claim 1, wherein the polynucleotide encodes an antigen for a cancer vaccine, an antigen for an infectious disease vaccine, a protein for a replacement protein therapy, or a nuclease.

12. The method of claim 1, wherein step (a)(ii) comprises annealing a plurality of poly(A) oligonucleotides with a plurality of poly(T) oligonucleotides, wherein the plurality of poly(A) oligonucleotides has a different length from the plurality of poly(T) oligonucleotides, thereby obtaining the double-stranded nucleic acid.

13. The method of claim 1, wherein step (a)(iii) further comprises inserting into the linear plasmid an additional double-stranded nucleic acid comprising a plurality of consecutive thymine nucleotides.

14. A method of stabilizing an RNA during in vitro translation comprising:
   performing the method of claim 2, thereby generating an RNA stable at a temperature range from 30° C. to 37° C. and for a period of at least 1 hour; and
   translating said RNA by contacting said RNA with a ribosome in the presence of amino acids and transfer RNAs (tRNAs).

15. The method of claim 14, wherein the period is at least 24 hours.

16. An in vitro of stabilizing an RNA during translation in a cell, the method comprising:
   performing the method of claim 2;
   introducing the polynucleotide into a cell; and
   culturing the cell for a period of at least 1 hour and at a temperature in a range from 30° C. to 37° C.

17. A method of increasing or stabilizing expression of a protein, comprising:
   performing the method of claim 2, thereby generating an RNA; and
   translating said RNA into a polypeptide.

18. A method of generating a polynucleotide, comprising:
   (a) preparing a linear vector comprising:
      (i) obtaining a linear plasmid comprising a telomere,
      (ii) obtaining a double-stranded nucleic acid comprising at least 130 consecutive thymine nucleotides, and
      (iii) inserting the double-stranded nucleic acid into the linear plasmid, thereby preparing the linear vector; and
   (b) contacting the linear vector with a polymerase in the presence of nucleotides, thereby generating the polynucleotide.

19. The method of claim 18, wherein step (a)(ii) comprises annealing a plurality of poly(A) oligonucleotides with a plurality of poly(T) oligonucleotides, wherein the plurality of poly(A) oligonucleotides has a different length from the plurality of poly(T) oligonucleotides, thereby obtaining the double-stranded nucleic acid.

20. The method of claim 18, wherein step (a)(iii) further comprises inserting into the linear plasmid an additional double-stranded nucleic acid comprising a plurality of consecutive thymine nucleotides.

* * * * *

UNITED STATES PATENT AND TRADEMARK OFFICE
CERTIFICATE OF CORRECTION

PATENT NO. : 11,400,169 B2
APPLICATION NO. : 15/950562
DATED : August 2, 2022
INVENTOR(S) : Andrew M. Scharenberg It is certified that error appears in the above-identified patent and that said Letters Patent is hereby corrected as shown below:

On the Title Page

Column 2, Line 10, under Item (56) Other Publications, delete "d(A/T)$_{100}$tail" and insert --d(A/T)$_{100}$ tail--.

On Page 2, Column 1, Line 2, under Item (56) Other Publications, delete "Portein" and insert --Protein--.

On Page 2, Column 1, Line 10, under Item (56) Other Publications, delete "Amercian" and insert --American--.

In the Drawings

Figure 7:
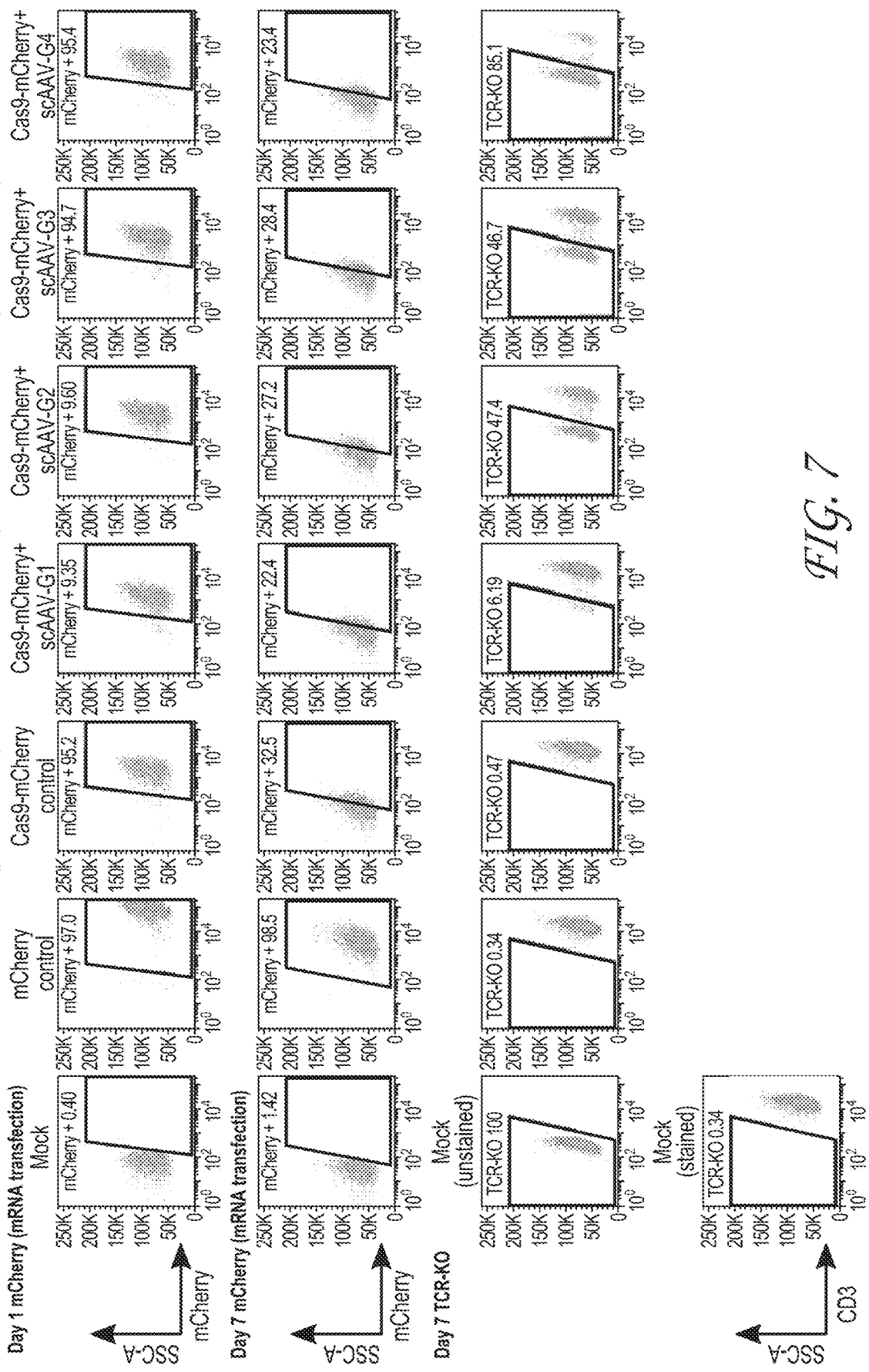
FIG. 7 shows that the TCRα CRISPR guide 4 (SEQ ID NO. 5) generates the highest TCRα-Knock out (KO) when used with a Cas9 protein expressed on a linear vector for a polyadenylated mRNA encoding Cas9.

On Sheet 8 of 25, FIG. 7, Line 1, delete "TCRa" and insert --TCRα--.

On Sheet 8 of 25, FIG. 7, Line 1, delete "TCRa-KO" and insert --TCRα-KO--.

In the Specification

In Column 2, Line 1, delete "homolypolymeric" and insert --homopolymeric--.

In Column 4, Line 57, delete "Celcius" and insert --Celsius--.

In Column 6, Line 6, delete "Celcius" and insert --Celsius--.

In Column 9, Line 15, delete "TCRa" and insert --TCRα--.

In Column 9, Line 22, delete "TCRa" and insert --TCRα--.

In Column 9, Line 24, delete "TCRa" and insert --TCRα--.

Signed and Sealed this
Twenty-third Day of May, 2023

Katherine Kelly Vidal
*Director of the United States Patent and Trademark Office*

In Column 10, Lines 5-6, delete "heterogenous" and insert --heterogeneous--.

In Column 10, Line 19, delete "30 C," and insert --30° C.,--.

In Column 10, Line 24, delete "TCRa" and insert --TCRα--.

In Column 10, Line 26, delete "TCRa" and insert --TCRα--.

In Column 10, Line 32, delete "TCRa" and insert --TCRα--.

In Column 10, Line 36, delete "TCRa" and insert --TCRα--.

In Column 10, Line 42, delete "14C)" and insert --14C--.

In Column 11, Line 2, delete "mRNA.]]" and insert --mRNA.--.

In Column 11, Line 24, delete "a" and insert --A--.

In Column 12, Line 21, delete "phosphoroanilothioate," and insert --phosphoramidothioate,--.

In Column 14, Line 16, delete "BelI," and insert --BclI,--.

In Column 14, Line 25, delete "Earl," and insert --EarI,--.

In Column 14, Line 32, delete "MspAlI," and insert --MspA1I,--.

In Column 14, Line 36, delete "PfMFI" and insert --PflFI--.

In Column 14, Line 48, delete "BegI," and insert --BcgI--.

In Column 14, Line 48, delete "BeoDI," and insert --BcoDI,--.

In Column 14, Line 57, delete "Earl," and insert --EarI,--.

In Column 15, Lines 23-24, delete "include but are not limited to include but are not limited to" and insert --include but are not limited to--.

In Column 15, Line 28, delete "Earl," and insert --EarI,--.

In Column 15, Line 38, delete "BstOI,BstSCI," and insert --BstOI, BstSCI,--.

In Column 15, Line 46, delete "BfrB1,BfrI," and insert --BfrBl, BfrI,--.

In Column 15, Line 58, delete "Ec1136II, EclXI," and insert --Ecl136II, EclXI,--.

In Column 15, Line 63, delete "MisI," and insert --MlsI--.

CERTIFICATE OF CORRECTION (continued)
U.S. Pat. No. 11,400,169 B2

In Column 15, Line 65, delete "Paul," and insert --PauI,--.

In Column 16, Line 8, delete "Tell," and insert --TelI,--.

In Column 16, Line 16, delete "a" and insert --A--.

In Column 16, Line 57, delete "Earl," and insert --EarI,--.

In Column 17, Line 8, delete "BfrB1,BfrI," and insert --BfrBl, BfrI,--.

In Column 17, Line 20, delete "Ec1136II, EcIXI," and insert --Ecl136II, EclXI,--.

In Column 17, Line 27, delete "Paul," and insert --PauI,--.

In Column 17, Line 37, delete "Tell," and insert --TelI,--.

In Column 17, Line 63, delete "Earl," and insert --EarI,--.

In Column 18, Line 10, delete "AesI," and insert --AcsI,--.

In Column 18, Line 11, delete "A1w44I," and insert --Alw44I,--.

In Column 18, Line 13, delete "BeoI," and insert --BcoI,--.

In Column 18, Line 14, delete "BfrB1," and insert --BfrBl,--.

In Column 18, Line 14, delete "BlnI," and insert --BlnI--.

In Column 18, Line 26, delete "Ec1136II, EcIXI," and insert --Ecl136II, EclXI,--.

In Column 18, Line 33, delete "Paul, Peel," and insert --PauI, PceI,--.

In Column 18, Line 43, delete "Tell," and insert --TelI,--.

In Column 19, Line 51, delete "o" and insert --to--.

In Column 28, Line 2, delete "5′terminal" and insert --5′ terminal--.

In Column 29, Line 29, delete "Earl," and insert --EarI,--.

In Column 29, Line 43, delete "AesI," and insert --AcsI,--.

In Column 29, Line 46, delete "BeoI," and insert --BcoI,--.

In Column 29, Line 47, delete "BfrB1,BfrI," and insert --BfrB1, BfrI,--.

CERTIFICATE OF CORRECTION (continued)
U.S. Pat. No. 11,400,169 B2

In Column 29, Line 47, delete "BmeAI," and insert --BmcAI,--.

In Column 29, Line 59, delete "Ec1136II, EcIXI," and insert --Ecl136II, Ec1XI,--.

In Column 29, Line 66, delete "Paul," and insert --PauI,--.

In Column 30, Line 9, delete "Tell," and insert --TelI,--.

In Column 33, Line 29, delete "Bell," and insert --BclI,--.

In Column 33, Line 38, delete "Earl," and insert --EarI,--.

In Column 33, Line 41, delete "HinPlI" and insert --HinP1I,--.

In Column 33, Line 62, delete "Earl," and insert --EarI,--.

In Column 34, Line 9, delete "AesI," and insert --AcsI,--.

In Column 34, Line 10, delete "A1w44I," and insert --Alw44I,--.

In Column 34, Line 12, delete "BeoI," and insert --BcoI,--.

In Column 34, Line 13, delete "BfrB1,BfrI," and insert --BfrBl, BfrI,--.

In Column 34, Line 13, delete "BmeAI," and insert --BmcAI,--.

In Column 34, Line 25, delete "Ec1136II, EcIXI," and insert --Ecl136II, EclXI,--.

In Column 34, Line 32, delete "Paul, Peel," and insert --PauI, PceI,--.

In Column 34, Line 42, delete "Tell," and insert --TelI,--.

In Column 34, Line 56, delete "MnlI" and insert --Mn1I--.

In Column 34, Line 56, delete "MnlI" and insert --Mn1I--.

In Column 35, Line 7, delete "Earl," and insert --EarI,--.

In Column 35, Lines 17-18, delete "BstOI,BstSCI," and insert --BstOI, BstSCI,--.

In Column 35, Line 37, delete "Ec1136II, EcIXI," and insert --Ecl136II, EclXI,--.

In Column 35, Line 44, delete "Paul," and insert --PauI,--.

In Column 36, Line 10, delete "Tell," and insert --TelI,--.

CERTIFICATE OF CORRECTION (continued)
U.S. Pat. No. 11,400,169 B2

In Columns 37-38, Line 21, delete "MboI" and insert --MboII--.

In Columns 37-38, Line 43, delete "157" and insert --157)--.

In Columns 41-42, Line 22, delete "CTAGN" and insert --CTAG--.

In Columns 45-46, Line 11, delete "BslFI" and insert --BslFI--.

In Columns 45-46, Line 27, delete "CauI" and insert --CauII--.

In Columns 47-48, Line 15, delete "SEQ" and insert --(SEQ--.

In Columns 47-48, Line 16, delete "SEQ" and insert --(SEQ--.

In Columns 47-48, Line 17, delete "SEQ" and insert --(SEQ--.

In Columns 47-48, Line 31, delete "AccBI" and insert --AccB1I--.

In Columns 49-50, Line 31, delete "BbvI" and insert --BbvII--.

In Columns 51-52, Line 6, delete "No340)" and insert --No. 340)--.

In Columns 53-54, Line 11, delete "SEQ" and insert --(SEQ--.

In Columns 53-54, Line 12, delete "SEQ" and insert --(SEQ--.

In Columns 53-54, Line 31, delete "SEQ" and insert --(SEQ--.

In Columns 53-54, Line 32, delete "SEQ" and insert --(SEQ--.

In Columns 57-58, Line 9, delete "EcI1361I" and insert --Ecl136II--.

In Columns 57-58, Line 11, delete "EcIXI," and insert --EclXI--.

In Columns 57-88, Line 13, delete "Ecol05I" and insert --Eco105I--.

In Columns 57-58, Line 49, delete "FbiI" and insert --Fb1I--.

In Columns 59-60, Line 19, delete "Hpy17811I" and insert --Hpy178III--.

In Columns 59-60, Line 29, delete "SEQ" and insert --(SEQ--.

In Columns 59-60, Line 30, delete "SEQ" and insert --(SEQ--.

In Columns 59-60, Line 31, delete "SEQ" and insert --(SEQ--.

CERTIFICATE OF CORRECTION (continued)
U.S. Pat. No. 11,400,169 B2

In Columns 59-60, Line 31, delete "SEQ" and insert --(SEQ--.

In Columns 59-60, Line 32, delete "SEQ" and insert --(SEQ--.

In Columns 59-60, Line 35, delete "MhiI" and insert --MhlI--.

In Columns 59-60, Line 45, delete "SEQ" and insert --(SEQ--.

In Columns 59-60, Line 46, delete "SEQ" and insert --(SEQ--.

In Columns 61-62, Line 7, delete "MyrI" and insert --MvrI--.

In Columns 61-62, Line 27, delete "Pf123II" and insert --Pfl23II--.

In Columns 69-70, Line 13, delete "BpiI" and insert --BplI--.

In Columns 71-72, Line 15, delete "BanI" and insert --BarI--.

In Column 72, Line 31, delete "BelI," and insert --BclI,--.

In Column 72, Line 39, delete "BtsIMut1, Cac81," and insert --BtsIMutI, Cac8I,--.

In Column 72, Line 40, delete "Earl," and insert --EarI,--.

In Column 72, Line 43, delete "HinPII," and insert --HinP1I,--.

In Column 72, Line 47, delete "MspAlI," and insert --MspA1I,--.

In Column 72, Line 66, delete "Earl," and insert --EarI,--.

In Column 73, Line 4, delete "HinlII," and insert --Hin1II,--.

In Column 73, Line 5, delete "Pall," and insert --PalI,--.

In Column 73, Line 7, delete "BenI," and insert --BcnI,--.

In Column 73, Line 9, delete "BstOI,BstSCI," and insert --BstOI, BstSCI,--.

In Column 73, Line 13, delete "AesI," and insert --AcsI,--.

In Column 73, Line 16, delete "BeoI," and insert --BcoI,--.

In Column 73, Line 17, delete "BfrB1,BfrI," and insert --BfrBl, BfrI,--.

In Column 73, Line 17, delete "BmeAI," and insert --BmcAI,--.

In Column 73, Line 29, delete "Ec1136II, EcIXI," and insert --Ecl136II, EclXI,--.

In Column 73, Line 34, delete "MisI," and insert --MlsI,--.

In Column 73, Line 36, delete "PauI," and insert --PauI,--.

In Column 73, Line 38, delete "ReaI," and insert --RcaI,--.

In Column 73, Line 46, delete "TelI," and insert --TelI,--.

In Column 74, Line 39, delete "EarI," and insert --EarI,--.

In Column 74, Line 44, delete "HinlII," and insert --Hin1II,--.

In Column 74, Line 53, delete "AesI," and insert --AcsI,--.

In Column 74, Line 56, delete "BeoI," and insert --BcoI,--.

In Column 74, Line 57, delete "BfrB1,BfrI," and insert --BfrBl, BfrI,--.

In Column 74, Line 57, delete "BmeAI," and insert --BmcAI,--.

In Column 74, Line 66, delete "BstC81," and insert --BstC8I,--.

In Column 75, Line 2, delete "Ec1136II, EcIXI," and insert --Ecl136II, Ec1XI,--.

In Column 75, Line 9, delete "PauI," and insert --PauI,--.

In Column 75, Line 11, delete "ReaI," and insert --RcaI,--.

In Column 75, Line 19, delete "TelI," and insert --TelI,--.

In Column 76, Line 56, delete "BelI," and insert --BclI,--.

In Column 76, Line 65, delete "EarI," and insert --EarI,--.

In Column 77, Line 1, delete "HinPII," and insert --HinP1I,--.

In Column 78, Line 38, delete "BelI," and insert --BclI,--.

In Column 78, Line 47, delete "EarI," and insert --EarI,--.

In Column 78, Line 50, delete "HinPII," and insert --HinP1I,--.

In Column 79, Line 15, delete "EarI," and insert --EarI,--.

CERTIFICATE OF CORRECTION (continued)
U.S. Pat. No. 11,400,169 B2

In Column 79, Line 20, delete "HinlII," and insert --Hin1II,--.

In Column 79, Lines 25-26, delete "BstOI,BstSCI," and insert --BstOI, BstSCI,--.

In Column 79, Line 33, delete "BfrB1,BfrI," and insert --BfrBl, BfrI,--.

In Column 79, Line 45, delete "Ec1136II, EcIXI," and insert --Ecl136II, EclXI,--.

In Column 79, Line 52, delete "Paul," and insert --PauI,--.

In Column 79, Line 54, delete "Real," and insert --RcaI,--.

In Column 79, Line 62, delete "Tell," and insert --TelI,--.

In Column 81, Line 66, delete "Earl," and insert --EarI,--.

In Column 82, Line 7, delete "BenI," and insert --BcnI,--.

In Column 82, Line 9, delete "BstOI,BstSCI," and insert --BstOI, BstSCI,--.

In Column 82, Line 13, delete "AesI," and insert --AcsI,--.

In Column 82, Line 14, delete "A1w44I," and insert --Alw44I,--.

In Column 82, Line 16, delete "BeoI," and insert --BcoI,--.

In Column 82, Line 17, delete "BfrB1,BfrI," and insert --BfrBl, BfrI,--.

In Column 82, Line 29, delete "Ec1136II, EcIXI," and insert --Ecl136II, EclXI,--.

In Column 82, Line 36, delete "Paul, Peel," and insert --PauI, PceI,--.

In Column 82, Line 38, delete "Real," and insert --RcaI,--.

In Column 82, Line 46, delete "Tell," and insert --TelI,--.

In Column 82, Line 62, delete "Earl," and insert --EarI,--.

In Column 82, Line 67, delete "HinlII," and insert --Hin1II--.

In Column 83, Line 5, delete "BstOI,BstSCI," and insert --BstOI, BstSCI,--.

In Column 83, Line 13, delete "BfrB1,BfrI," and insert --BfrB1, BfrI,--.

In Column 83, Line 25, delete "Ec1136II," and insert --Ecl136II,--.

In Column 83, Line 32, delete "Paul," and insert --PauI,--.

In Column 83, Line 34, delete "Real," and insert --RcaI,--.

In Column 83, Line 42, delete "Tell," and insert --TelI,--.

In Column 87, Line 5, delete "hairpinends" and insert --hairpin ends--.

In Column 90, Lines 31-32, delete "providedThe" and insert --provided. The--.

In Column 92, Line 63, delete "Earl," and insert --EarI,--.

In Column 93, Line 1, delete "HinlII," and insert --Hin1II,--.

In Column 93, Line 4, delete "BenI," and insert --BcnI,--.

In Column 93, Line 6, delete "BstOI,BstSCI," and insert --BstOI, BstSCI,--.

In Column 93, Line 10, delete "AesI," and insert --AcsI,--.

In Column 93, Line 13, delete "BeoI," and insert --BcoI,--.

In Column 93, Line 14, delete "BfrB1,BfrI," and insert --BfrBl, BfrI,--.

In Column 93, Line 26, delete "Ec1136II, EcIXI," and insert --Ecl136II, EclXI,--.

In Column 93, Line 33, delete "Paul," and insert --PauI,--.

In Column 93, Line 35, delete "Real," and insert --RcaI,--.

In Column 93, Line 43, delete "Tell," and insert --TelI,--.

In Column 93, Line 56, delete "Earl," and insert --EarI,--.

In Column 93, Line 61, delete "HinlII," and insert --Hin1II,--.

In Column 93, Line 66, delete "BstOI,BstSCI," and insert --BstOI, BstSCI,--.

In Column 94, Line 7, delete "BfrB1,BfrI," and insert --BfrBl, BfrI,--.

In Column 94, Line 19, delete "Ec1136II," and insert --Ecl136II,--.

In Column 94, Line 26, delete "Paul," and insert --PauI,--.

In Column 94, Line 28, delete "Real," and insert --RcaI,--.

CERTIFICATE OF CORRECTION (continued)
U.S. Pat. No. 11,400,169 B2

In Column 94, Line 35, delete "Adel," and insert --AdeI,--.

In Column 94, Line 36, delete "Tell," and insert --TelI,--.

In Column 95, Line 55, delete "Armin" and insert --arm. In--.

In Column 102, Line 56, delete "nucleotides" and insert --nucleotides.--.

In Column 103, Line 56, delete "Lipfectamine®," and insert --Lipofectamine®,--.

In Column 127, Line 63, delete "(CFII),In" and insert --(CFII). In--.

In Column 131, Line 8, delete "herein." and insert --herein--.

In Column 143, Line 63, delete "linear" and insert --Linear--.

In Column 144, Line 38, delete "TCRa" and insert --TCRα--.

In Column 145, Line 10, delete "mMes sage" and insert --mMessage--.

In Column 145, Line 55, delete "TCRa-KO" and insert --TCRα-KO--.

In Column 146, Line 8 (Approx.), delete "TCRa" and insert --TCRα--.

In Column 146, Line 49 (Approx.), delete "-95" and insert --~95--.

In Column 147, Line 47, delete "concatamers" and insert --concatemers--.

In Column 147, Line 57, delete "concatamers" and insert --concatemers--.

In Column 151, Line 32, delete "TCRa" and insert --TCRα--.

In Column 151, Line 41, delete "TCRa" and insert --TCRα--.

In Column 152, Line 13, delete "TCRa" and insert --TCRα--.

In Column 152, Line 15, delete "TCRa" and insert --TCRα--.

In Column 152, Line 20, delete "37 C," and insert --37° C.,--.

In Column 152, Line 20, delete "30 C" and insert --30° C.--.

In Column 152, Line 59, delete "ElB55k" and insert --E1B55k--.

In Column 152, Line 59, delete "ElB55k" and insert --E1B55k--.

CERTIFICATE OF CORRECTION (continued)
U.S. Pat. No. 11,400,169 B2

In Column 154, Line 4, delete "30 C" and insert --30° C.--.

In Column 154, Lines 16-17, delete "conditions" and insert --conditions.--.

In Column 154, Line 19, delete "30 C and 37 C" and insert --30° C. and 37° C.--.

In Column 157, Line 45, delete "pELV" and insert --pEVL--.

In Column 158, Line 2, delete "pELV." and insert --pEVL.--.

In Column 158, Line 3, delete "pELV." and insert --pEVL.--.

In Column 247, Line 33, delete "(CFII),In" and insert --(CFII). In--.

In the Claims

In Column 550, Line 6, Claim 16, delete "An in vitro" and insert --An *in vitro* method--

SEQUENCE LISTING

```
<160> NUMBER OF SEQ ID NOS: 638

<210> SEQ ID NO 1
<211> LENGTH: 496
<212> TYPE: PRT
<213> ORGANISM: Artificial Sequence
<220> FEATURE:
<223> OTHER INFORMATION: NruGI
```

```
<220> FEATURE:
<223> OTHER INFORMATION: NruGI

<400> SEQUENCE: 1

Met Glu Arg Arg Asn Pro Ser Glu Arg Gly Val Pro Ala Gly Phe Ser
1               5                   10                  15

Gly His Ala Ser Val Glu Ser Gly Cys Glu Thr Gln Glu Ser Pro Ala
            20                  25                  30

Thr Val Val Phe Arg Pro Pro Gly Asp Asn Thr Asp Gly Gly Ala Ala
        35                  40                  45

Ala Ala Ala Gly Gly Ser Gln Ala Ala Ala Gly Ala Glu Pro Met
50                  55                  60

Glu Pro Glu Ser Arg Pro Gly Pro Ser Gly Met Asn Val Val Gln Val
65                  70                  75                  80

Ala Glu Leu Tyr Pro Glu Leu Arg Arg Ile Leu Thr Ile Thr Glu Asp
                85                  90                  95

Gly Gln Gly Leu Lys Gly Val Lys Arg Glu Arg Gly Ala Cys Glu Ala
            100                 105                 110

Thr Glu Glu Ala Arg Asn Leu Ala Phe Ser Leu Met Thr Arg His Arg
        115                 120                 125

Pro Glu Cys Ile Thr Phe Gln Gln Ile Lys Asp Asn Cys Ala Asn Glu
    130                 135                 140

Leu Asp Leu Leu Ala Gln Lys Tyr Ser Ile Glu Gln Leu Thr Thr Tyr
145                 150                 155                 160

Trp Leu Gln Pro Gly Asp Asp Phe Glu Glu Ala Ile Arg Val Tyr Ala
                165                 170                 175

Lys Val Ala Leu Arg Pro Asp Cys Lys Tyr Lys Ile Ser Lys Leu Val
            180                 185                 190

Asn Ile Arg Asn Cys Cys Tyr Ile Ser Gly Asn Gly Ala Glu Val Glu
        195                 200                 205

Ile Asp Thr Glu Asp Arg Val Ala Phe Arg Cys Ser Met Ile Asn Met
    210                 215                 220

Trp Pro Gly Val Leu Gly Met Asp Gly Val Val Ile Met Asn Val Arg
225                 230                 235                 240

Phe Thr Gly Pro Asn Phe Ser Gly Thr Val Phe Leu Ala Asn Thr Asn
                245                 250                 255

Leu Ile Leu His Gly Val Ser Phe Tyr Gly Phe Asn Asn Thr Cys Val
            260                 265                 270

Glu Ala Trp Thr Asp Val Arg Val Arg Gly Cys Ala Phe Tyr Cys Cys
        275                 280                 285

Trp Lys Gly Val Val Cys Arg Pro Lys Ser Arg Ala Ser Ile Lys Lys
290                 295                 300

Cys Leu Phe Glu Arg Cys Thr Leu Gly Ile Leu Ser Glu Gly Asn Ser
305                 310                 315                 320

Arg Val Arg His Asn Val Ala Ser Asp Cys Gly Cys Phe Met Leu Val
                325                 330                 335

Lys Ser Val Ala Val Ile Lys His Asn Met Val Cys Gly Asn Cys Glu
            340                 345                 350

Asp Arg Ala Ser Gln Met Leu Thr Cys Ser Asp Gly Asn Cys His Leu
        355                 360                 365

Leu Lys Thr Ile His Val Ala Ser His Ser Arg Lys Ala Trp Pro Val
    370                 375                 380

Phe Glu His Asn Ile Leu Thr Arg Cys Ser Leu His Leu Gly Asn Arg
385                 390                 395                 400
```

```
Arg Gly Val Phe Leu Pro Tyr Gln Cys Asn Leu Ser His Thr Lys Ile
                405                 410                 415

Leu Leu Glu Pro Glu Ser Met Ser Lys Val Asn Leu Asn Gly Val Phe
            420                 425                 430

Asp Met Thr Met Lys Ile Trp Lys Val Leu Arg Tyr Asp Glu Thr Arg
                435                 440                 445

Thr Arg Cys Arg Pro Cys Glu Cys Gly Gly Lys His Ile Arg Asn Gln
        450                 455                 460

Pro Val Met Leu Asp Val Thr Glu Glu Leu Arg Pro Asp His Leu Val
465                 470                 475                 480

Leu Ala Cys Thr Arg Ala Glu Phe Gly Ser Ser Asp Glu Asp Thr Asp
                485                 490                 495
```

<210> SEQ ID NO 2
<211> LENGTH: 496
<212> TYPE: PRT
<213> ORGANISM: Artificial Sequence
<220> FEATURE:
<223> OTHER INFORMATION: Mutant adenoviral protein

<400> SEQUENCE: 2

```
Met Glu Arg Arg Asn Pro Ser Glu Arg Gly Val Pro Ala Gly Phe Ser
1               5                   10                  15

Gly His Ala Ser Val Glu Ser Gly Cys Glu Thr Gln Glu Ser Pro Ala
            20                  25                  30

Thr Val Val Phe Arg Pro Pro Gly Asp Asn Thr Asp Gly Gly Ala Ala
                35                  40                  45

Ala Ala Ala Gly Gly Ser Gln Ala Ala Ala Gly Ala Glu Pro Met
        50                  55                  60

Glu Pro Glu Ser Arg Pro Gly Pro Ser Gly Met Asn Val Val Gln Val
65                  70                  75                  80

Ala Glu Leu Tyr Pro Glu Leu Arg Arg Ile Leu Thr Ile Thr Glu Asp
                85                  90                  95

Gly Gln Gly Leu Lys Gly Val Lys Arg Glu Arg Gly Ala Cys Glu Ala
            100                 105                 110

Thr Glu Glu Ala Arg Asn Leu Ala Phe Ser Leu Met Thr Arg His Arg
        115                 120                 125

Pro Glu Cys Ile Thr Phe Gln Gln Ile Lys Asp Asn Cys Ala Asn Glu
    130                 135                 140

Leu Asp Leu Leu Ala Gln Lys Tyr Ser Ile Glu Gln Leu Thr Thr Tyr
145                 150                 155                 160

Trp Leu Gln Pro Gly Asp Asp Phe Glu Glu Ala Ile Arg Val Tyr Ala
                165                 170                 175

Lys Val Ala Leu Arg Pro Asp Cys Lys Tyr Lys Ile Ser Lys Leu Val
            180                 185                 190

Asn Ile Arg Asn Cys Cys Tyr Ile Ser Gly Asn Gly Ala Glu Val Glu
        195                 200                 205

Ile Asp Thr Glu Asp Arg Val Ala Phe Arg Cys Ser Met Ile Asn Met
    210                 215                 220

Trp Pro Gly Val Leu Gly Met Asp Gly Val Val Ile Met Asn Val Arg
225                 230                 235                 240

Phe Thr Gly Pro Asn Phe Ser Gly Thr Val Phe Leu Ala Asn Thr Asn
                245                 250                 255

Leu Ile Leu His Gly Val Ser Phe Tyr Gly Phe Asn Asn Thr Cys Val
            260                 265                 270
```

```
Glu Ala Trp Thr Asp Val Arg Val Arg Gly Cys Ala Phe Tyr Cys Cys
            275                 280                 285

Trp Lys Gly Val Val Cys Arg Pro Lys Ser Arg Ala Ser Ile Lys Lys
        290                 295                 300

Cys Leu Phe Glu Arg Cys Thr Leu Gly Ile Leu Ser Glu Gly Asn Ser
305                 310                 315                 320

Arg Val Arg His Asn Val Ala Ser Asp Cys Gly Cys Phe Met Leu Val
                325                 330                 335

Lys Ser Val Ala Val Ile Lys His Asn Met Val Cys Gly Asn Cys Glu
            340                 345                 350

Asp Arg Ala Ser Gln Met Leu Thr Cys Ser Asp Gly Asn Cys His Leu
        355                 360                 365

Leu Lys Thr Ile Ala Val Ala Ser His Ser Arg Lys Ala Trp Pro Val
    370                 375                 380

Phe Glu His Asn Ile Leu Thr Arg Cys Ser Leu His Leu Gly Asn Arg
385                 390                 395                 400

Arg Gly Val Phe Leu Pro Tyr Gln Cys Asn Leu Ser His Thr Lys Ile
                405                 410                 415

Leu Leu Glu Pro Glu Ser Met Ser Lys Val Asn Leu Asn Gly Val Phe
            420                 425                 430

Asp Met Thr Met Lys Ile Trp Lys Val Leu Arg Tyr Asp Glu Thr Arg
        435                 440                 445

Thr Arg Cys Arg Pro Cys Glu Cys Gly Gly Lys His Ile Arg Asn Gln
    450                 455                 460

Pro Val Met Leu Asp Val Thr Glu Glu Leu Arg Pro Asp His Leu Val
465                 470                 475                 480

Leu Ala Cys Thr Arg Ala Glu Phe Gly Ser Ser Asp Glu Asp Thr Asp
                485                 490                 495

<210> SEQ ID NO 3
<211> LENGTH: 294
<212> TYPE: PRT
<213> ORGANISM: Artificial Sequence
<220> FEATURE:
<223> OTHER INFORMATION: Mutant adenoviral protein

<400> SEQUENCE: 3

Met Thr Thr Ser Gly Val Pro Phe Gly Met Thr Leu Arg Pro Thr Arg
1               5                   10                  15

Ser Arg Leu Ser Arg Arg Thr Pro Tyr Ser Arg Asp Arg Leu Pro Pro
            20                  25                  30

Phe Glu Thr Glu Thr Arg Ala Thr Ile Leu Glu Asp His Pro Leu Leu
        35                  40                  45

Pro Glu Cys Asn Thr Leu Thr Met His Asn Val Ser Tyr Val Arg Gly
    50                  55                  60

Leu Pro Cys Ser Val Gly Phe Thr Leu Ile Gln Glu Trp Val Val Pro
65                  70                  75                  80

Trp Asp Met Val Leu Thr Arg Glu Glu Leu Val Ile Leu Arg Lys Cys
                85                  90                  95

Met His Val Cys Leu Cys Ala Asn Ile Asp Ile Met Thr Ser Met
            100                 105                 110

Met Ile His Gly Tyr Glu Ser Trp Ala Leu His Cys His Cys Ser Ser
        115                 120                 125

Pro Gly Ser Leu Gln Cys Ile Ala Gly Gly Gln Val Leu Ala Ser Trp
    130                 135                 140
```

Phe Arg Met Val Val Asp Gly Ala Met Phe Asn Gln Arg Phe Ile Trp
145                 150                 155                 160

Tyr Arg Glu Val Val Asn Tyr Asn Met Pro Lys Glu Val Met Phe Met
            165                 170                 175

Ser Ser Val Phe Met Arg Gly Arg His Leu Ile Tyr Leu Arg Leu Trp
        180                 185                 190

Tyr Asp Gly His Val Gly Ser Val Pro Ala Met Ser Phe Gly Tyr
    195                 200                 205

Ser Ala Leu His Cys Gly Ile Leu Asn Asn Ile Val Val Leu Cys Cys
210                 215                 220

Ser Tyr Cys Ala Asp Leu Ser Glu Ile Arg Val Arg Cys Cys Ala Arg
225                 230                 235                 240

Arg Thr Arg Arg Leu Met Leu Arg Ala Val Arg Ile Ile Ala Glu Glu
            245                 250                 255

Thr Thr Ala Met Leu Tyr Ser Cys Arg Thr Glu Arg Arg Gln Gln
        260                 265                 270

Phe Ile Arg Ala Leu Leu Gln His Arg Pro Ile Leu Met His Asp
    275                 280                 285

Tyr Asp Ser Thr Pro Met
    290

<210> SEQ ID NO 4
<211> LENGTH: 500
<212> TYPE: PRT
<213> ORGANISM: Artificial Sequence
<220> FEATURE:
<223> OTHER INFORMATION: Mutant adenoviral protein

<400> SEQUENCE: 4

Met Glu Arg Arg Asn Pro Ser Glu Arg Gly Val Pro Ala Gly Phe Ser
1               5                   10                  15

Gly His Ala Ser Val Glu Ser Gly Cys Glu Thr Gln Glu Ser Pro Ala
            20                  25                  30

Thr Val Val Phe Arg Pro Pro Gly Asp Asn Thr Asp Gly Gly Ala Ala
        35                  40                  45

Ala Ala Ala Gly Gly Ser Gln Ala Ala Ala Gly Ala Glu Pro Met
    50                  55                  60

Glu Pro Glu Ser Arg Pro Gly Pro Ser Gly Met Asn Val Val Gln Val
65                  70                  75                  80

Ala Glu Leu Tyr Pro Glu Leu Arg Arg Ile Leu Thr Ile Thr Glu Asp
                85                  90                  95

Gly Gln Gly Leu Lys Gly Val Lys Arg Glu Arg Gly Ala Cys Glu Ala
            100                 105                 110

Thr Glu Glu Ala Arg Asn Leu Ala Phe Ser Leu Met Thr Arg His Arg
        115                 120                 125

Pro Glu Cys Ile Thr Phe Gln Gln Ile Lys Asp Asn Cys Ala Asn Glu
    130                 135                 140

Leu Asp Leu Leu Ala Gln Lys Tyr Ser Ile Glu Gln Leu Thr Thr Tyr
145                 150                 155                 160

Trp Leu Gln Pro Gly Asp Asp Phe Glu Glu Ala Ile Arg Val Tyr Ala
                165                 170                 175

Lys Val Ala Leu Arg Pro Asp Cys Lys Tyr Lys Ile Ser Lys Leu Val
            180                 185                 190

Asn Ile Arg Asn Cys Cys Tyr Ile Ser Gly Asn Gly Ala Glu Val Glu
        195                 200                 205

```
Ile Asp Thr Glu Asp Arg Val Ala Phe Arg Cys Ser Met Ile Asn Met
210                 215                 220

Trp Pro Gly Val Leu Gly Met Asp Gly Val Ile Met Asn Val Arg
225                 230                 235                 240

Phe Thr Gly Pro Asn Phe Ser Gly Thr Val Phe Leu Ala Asn Thr Asn
                245                 250                 255

Leu Ile Leu His Gly Val Ser Phe Tyr Gly Phe Asn Asn Thr Cys Val
                260                 265                 270

Glu Ala Trp Thr Asp Val Arg Val Arg Gly Cys Ala Phe Tyr Cys Cys
            275                 280                 285

Trp Lys Gly Val Val Cys Arg Pro Lys Ser Arg Ala Ser Ile Lys Lys
        290                 295                 300

Cys Leu Phe Glu Arg Cys Thr Leu Gly Ile Leu Ser Glu Gly Asn Ser
305                 310                 315                 320

Arg Val Arg His Asn Val Ala Ser Asp Cys Gly Cys Phe Met Leu Val
                325                 330                 335

Lys Ser Val Ala Val Ile Lys His Asn Met Val Cys Gly Asn Cys Glu
                340                 345                 350

Asp Arg Ala Gly Ile Pro Ala Ser Gln Met Leu Thr Cys Ser Asp Gly
            355                 360                 365

Asn Cys His Leu Leu Lys Thr Ile His Val Ala Ser His Ser Arg Lys
370                 375                 380

Ala Trp Pro Val Phe Glu His Asn Ile Leu Thr Arg Cys Ser Leu His
385                 390                 395                 400

Leu Gly Asn Arg Arg Gly Val Phe Leu Pro Tyr Gln Cys Asn Leu Ser
                405                 410                 415

His Thr Lys Ile Leu Leu Glu Pro Glu Ser Met Ser Lys Val Asn Leu
                420                 425                 430

Asn Gly Val Phe Asp Met Thr Met Lys Ile Trp Lys Val Leu Arg Tyr
            435                 440                 445

Asp Glu Thr Arg Thr Arg Cys Arg Pro Cys Glu Cys Gly Gly Lys His
        450                 455                 460

Ile Arg Asn Gln Pro Val Met Leu Asp Val Thr Glu Glu Leu Arg Pro
465                 470                 475                 480

Asp His Leu Val Leu Ala Cys Thr Arg Ala Glu Phe Gly Ser Ser Asp
                485                 490                 495

Glu Asp Thr Asp
            500

<210> SEQ ID NO 5
<211> LENGTH: 18
<212> TYPE: DNA
<213> ORGANISM: Artificial Sequence
<220> FEATURE:
<223> OTHER INFORMATION: Synthetic guide strand

<400> SEQUENCE: 5
tcaagagcaa cagtgctg                                                  18

<210> SEQ ID NO 6
<211> LENGTH: 1368
<212> TYPE: PRT
<213> ORGANISM: Streptococcus pyogenes

<400> SEQUENCE: 6

Met Asp Lys Lys Tyr Ser Ile Gly Leu Ala Ile Gly Thr Asn Ser Val
```

-continued

```
1               5                   10                  15
Gly Trp Ala Val Ile Thr Asp Glu Tyr Lys Val Pro Ser Lys Lys Phe
                20                  25                  30
Lys Val Leu Gly Asn Thr Asp Arg His Ser Ile Lys Lys Asn Leu Ile
                35                  40                  45
Gly Ala Leu Leu Phe Asp Ser Gly Glu Thr Ala Glu Ala Thr Arg Leu
                50                  55                  60
Lys Arg Thr Ala Arg Arg Arg Tyr Thr Arg Arg Lys Asn Arg Ile Cys
65                  70                  75                  80
Tyr Leu Gln Glu Ile Phe Ser Asn Glu Met Ala Lys Val Asp Asp Ser
                    85                  90                  95
Phe Phe His Arg Leu Glu Glu Ser Phe Leu Val Glu Glu Asp Lys Lys
                    100                 105                 110
His Glu Arg His Pro Ile Phe Gly Asn Ile Val Asp Glu Val Ala Tyr
                    115                 120                 125
His Glu Lys Tyr Pro Thr Ile Tyr His Leu Arg Lys Lys Leu Val Asp
                    130                 135                 140
Ser Thr Asp Lys Ala Asp Leu Arg Leu Ile Tyr Leu Ala Leu Ala His
145                 150                 155                 160
Met Ile Lys Phe Arg Gly His Phe Leu Ile Glu Gly Asp Leu Asn Pro
                    165                 170                 175
Asp Asn Ser Asp Val Asp Lys Leu Phe Ile Gln Leu Val Gln Thr Tyr
                    180                 185                 190
Asn Gln Leu Phe Glu Glu Asn Pro Ile Asn Ala Ser Gly Val Asp Ala
                    195                 200                 205
Lys Ala Ile Leu Ser Ala Arg Leu Ser Lys Ser Arg Arg Leu Glu Asn
                    210                 215                 220
Leu Ile Ala Gln Leu Pro Gly Glu Lys Lys Asn Gly Leu Phe Gly Asn
225                 230                 235                 240
Leu Ile Ala Leu Ser Leu Gly Leu Thr Pro Asn Phe Lys Ser Asn Phe
                    245                 250                 255
Asp Leu Ala Glu Asp Ala Lys Leu Gln Leu Ser Lys Asp Thr Tyr Asp
                    260                 265                 270
Asp Asp Leu Asp Asn Leu Leu Ala Gln Ile Gly Asp Gln Tyr Ala Asp
                    275                 280                 285
Leu Phe Leu Ala Ala Lys Asn Leu Ser Asp Ala Ile Leu Leu Ser Asp
                    290                 295                 300
Ile Leu Arg Val Asn Thr Glu Ile Thr Lys Ala Pro Leu Ser Ala Ser
305                 310                 315                 320
Met Ile Lys Arg Tyr Asp Glu His His Gln Asp Leu Thr Leu Leu Lys
                    325                 330                 335
Ala Leu Val Arg Gln Gln Leu Pro Glu Lys Tyr Lys Glu Ile Phe Phe
                    340                 345                 350
Asp Gln Ser Lys Asn Gly Tyr Ala Gly Tyr Ile Asp Gly Gly Ala Ser
                    355                 360                 365
Gln Glu Glu Phe Tyr Lys Phe Ile Lys Pro Ile Leu Glu Lys Met Asp
                    370                 375                 380
Gly Thr Glu Glu Leu Leu Val Lys Leu Asn Arg Glu Asp Leu Leu Arg
385                 390                 395                 400
Lys Gln Arg Thr Phe Asp Asn Gly Ser Ile Pro His Gln Ile His Leu
                    405                 410                 415
Gly Glu Leu His Ala Ile Leu Arg Arg Gln Glu Asp Phe Tyr Pro Phe
                    420                 425                 430
```

```
Leu Lys Asp Asn Arg Glu Lys Ile Glu Lys Ile Leu Thr Phe Arg Ile
        435                 440                 445

Pro Tyr Tyr Val Gly Pro Leu Ala Arg Gly Asn Ser Arg Phe Ala Trp
    450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser
            500                 505                 510

Leu Leu Tyr Glu Tyr Phe Thr Val Tyr Asn Glu Leu Thr Lys Val Lys
            515                 520                 525

Tyr Val Thr Glu Gly Met Arg Lys Pro Ala Phe Leu Ser Gly Glu Gln
        530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
                565                 570                 575

Ser Val Glu Ile Ser Gly Val Glu Asp Arg Phe Asn Ala Ser Leu Gly
            580                 585                 590

Thr Tyr His Asp Leu Leu Lys Ile Ile Lys Asp Lys Asp Phe Leu Asp
        595                 600                 605

Asn Glu Glu Asn Glu Asp Ile Leu Glu Asp Ile Val Leu Thr Leu Thr
610                 615                 620

Leu Phe Glu Asp Arg Glu Met Ile Glu Glu Arg Leu Lys Thr Tyr Ala
625                 630                 635                 640

His Leu Phe Asp Asp Lys Val Met Lys Gln Leu Lys Arg Arg Arg Tyr
                645                 650                 655

Thr Gly Trp Gly Arg Leu Ser Arg Lys Leu Ile Asn Gly Ile Arg Asp
            660                 665                 670

Lys Gln Ser Gly Lys Thr Ile Leu Asp Phe Leu Lys Ser Asp Gly Phe
        675                 680                 685

Ala Asn Arg Asn Phe Met Gln Leu Ile His Asp Asp Ser Leu Thr Phe
    690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
                725                 730                 735

Ile Leu Gln Thr Val Lys Val Val Asp Glu Leu Val Lys Val Met Gly
            740                 745                 750

Arg His Lys Pro Glu Asn Ile Val Ile Glu Met Ala Arg Glu Asn Gln
        755                 760                 765

Thr Thr Gln Lys Gly Gln Lys Asn Ser Arg Glu Arg Met Lys Arg Ile
    770                 775                 780

Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
                805                 810                 815

Gln Asn Gly Arg Asp Met Tyr Val Asp Gln Glu Leu Asp Ile Asn Arg
            820                 825                 830

Leu Ser Asp Tyr Asp Val Asp Ala Ile Val Pro Gln Ser Phe Leu Lys
        835                 840                 845
```

-continued

Asp Asp Ser Ile Asp Asn Lys Val Leu Thr Arg Ser Asp Lys Asn Arg
        850                 855                 860

Gly Lys Ser Asp Asn Val Pro Ser Glu Val Val Lys Lys Met Lys
865                 870                 875                 880

Asn Tyr Trp Arg Gln Leu Leu Asn Ala Lys Leu Ile Thr Gln Arg Lys
                885                 890                 895

Phe Asp Asn Leu Thr Lys Ala Glu Arg Gly Gly Leu Ser Glu Leu Asp
            900                 905                 910

Lys Ala Gly Phe Ile Lys Arg Gln Leu Val Glu Thr Arg Gln Ile Thr
        915                 920                 925

Lys His Val Ala Gln Ile Leu Asp Ser Arg Met Asn Thr Lys Tyr Asp
    930                 935                 940

Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
                965                 970                 975

Glu Ile Asn Asn Tyr His His Ala His Asp Ala Tyr Leu Asn Ala Val
            980                 985                 990

Val Gly Thr Ala Leu Ile Lys Lys Tyr Pro Lys Leu Glu Ser Glu Phe
        995                 1000                1005

Val Tyr Gly Asp Tyr Lys Val Tyr Asp Val Arg Lys Met Ile Ala Lys
    1010                1015                1020

Ser Glu Gln Glu Ile Gly Lys Ala Thr Ala Lys Tyr Phe Phe Tyr Ser
1025                1030                1035                1040

Asn Ile Met Asn Phe Phe Lys Thr Glu Ile Thr Leu Ala Asn Gly Glu
                1045                1050                1055

Ile Arg Lys Arg Pro Leu Ile Glu Thr Asn Gly Glu Thr Gly Glu Ile
            1060                1065                1070

Val Trp Asp Lys Gly Arg Asp Phe Ala Thr Val Arg Lys Val Leu Ser
        1075                1080                1085

Met Pro Gln Val Asn Ile Val Lys Lys Thr Glu Val Gln Thr Gly Gly
    1090                1095                1100

Phe Ser Lys Glu Ser Ile Leu Pro Lys Arg Asn Ser Asp Lys Leu Ile
1105                1110                1115                1120

Ala Arg Lys Lys Asp Trp Asp Pro Lys Lys Tyr Gly Gly Phe Asp Ser
                1125                1130                1135

Pro Thr Val Ala Tyr Ser Val Leu Val Val Ala Lys Val Glu Lys Gly
            1140                1145                1150

Lys Ser Lys Lys Leu Lys Ser Val Lys Glu Leu Leu Gly Ile Thr Ile
        1155                1160                1165

Met Glu Arg Ser Ser Phe Glu Lys Asn Pro Ile Asp Phe Leu Glu Ala
    1170                1175                1180

Lys Gly Tyr Lys Glu Val Lys Lys Asp Leu Ile Ile Lys Leu Pro Lys
1185                1190                1195                1200

Tyr Ser Leu Phe Glu Leu Glu Asn Gly Arg Lys Arg Met Leu Ala Ser
                1205                1210                1215

Ala Gly Glu Leu Gln Lys Gly Asn Glu Leu Ala Leu Pro Ser Lys Tyr
            1220                1225                1230

Val Asn Phe Leu Tyr Leu Ala Ser His Tyr Glu Lys Leu Lys Gly Ser
        1235                1240                1245

Pro Glu Asp Asn Glu Gln Lys Gln Leu Phe Val Glu Gln His Lys His
    1250                1255                1260

Tyr Leu Asp Glu Ile Ile Glu Gln Ile Ser Glu Phe Ser Lys Arg Val

Ile Leu Ala Asp Ala Asn Leu Asp Lys Val Leu Ser Ala Tyr Asn Lys
1265                1270                1275                1280

His Arg Asp Lys Pro Ile Arg Glu Gln Ala Glu Asn Ile Ile His Leu
            1285                1290                1295

Phe Thr Leu Thr Asn Leu Gly Ala Pro Ala Ala Phe Lys Tyr Phe Asp
    1300                1305                1310

Thr Thr Ile Asp Arg Lys Arg Tyr Thr Ser Lys Glu Val Leu Asp
        1315                1320                1325

Ala Thr Leu Ile His Gln Ser Ile Thr Gly Leu Tyr Glu Thr Arg Ile
1330                1335                1340

Asp Leu Ser Gln Leu Gly Gly Asp
1345                1350                1355                1360

1365

<210> SEQ ID NO 7
<211> LENGTH: 4107
<212> TYPE: DNA
<213> ORGANISM: Streptococcus pyogenes

<400> SEQUENCE: 7
atggataaga aatactcaat aggcttagat atcggcacaa atagcgtcgg atgggcggtg      60
atcactgatg aatataaggt tccgtctaaa aagttcaagg ttctgggaaa tacagaccgc     120
cacagtatca aaaaaaatct tatagggggct cttttatttg acagtggaga cagcggaaa    180 gcgactcgtc tcaaacggac agctcgtaga aggtatacac gtcggaagaa tcgtatttgt     240
tatctacagg agatttttc aaatgagatg gcgaaagtag atgatagttt ctttcatcga     300
cttgaagagt cttttttggt ggaagaagac aagaagcatg aacgtcatcc tatttttgga     360
aatatagtag atgaagttgc ttatcatgag aaatatccaa ctatctatca tctgcgaaaa     420
aaattggtag attctactga taaagcggat tgcgcttaa tctatttggc cttagcgcat     480
atgattaagt ttcgtggtca ttttttgatt gagggagatt taaatcctga taatagtgat     540
gtggacaaac tatttatcca gttggtacaa acctacaatc aattatttga agaaaaccct     600
attaacgcaa gtggagtaga tgctaaagcg attctttctg cacgattgag taaatcaaga     660
cgattagaaa atctcattgc tcagctcccc ggtgagaaga aaatggcttt atttgggaat    720
ctcattgctt tgtcattggg tttgaccccct aattttaaat caattttga tttggcagaa    780 gatgctaaat tacagctttc aaaagatact tacgatgatg atttagataa tttattggcg    840
caaattggag atcaatatgc tgatttgttt ttggcagcta agaatttatc agatgctatt    900
ttactttcag atatcctaag agtaaatact gaaataacta aggctccct atcagcttca    960 atgattaaac gctacgatga acatcatcaa gacttgactc ttttaaaagc tttagttcga    1020
caacaacttc cagaaaagta taaagaaatc ttttttgatc aatcaaaaaa cggatatgca    1080
ggttatattg atgggggagc tagccaagaa gaatttata aatttatcaa accaattta    1140 gaaaaaatgg atggtactga ggaattattg gtgaaactaa atcgtgaaga tttgctgcgc    1200
aagcaacgga cctttgacaa cggctctatt ccccatcaaa ttcacttggg tgagctgcat    1260
gctattttga gaagacaaga agactttat ccatttttaa aagacaatcg tgagaagatt    1320
gaaaaaatct tgacttttcg aattccttat tatgttggtc cattggcgcg tggcaatagt    1380
cgttttgcat ggatgactcg gaagtctgaa gaaacaatta ccccatggaa ttttgaagaa    1440
gttgtcgata aggtgcttc agctcaatca tttattgaac gcatgacaaa ctttgataaa    1500
aatcttccaa atgaaaagt actaccaaaa catagtttgc tttatgagta ttttacggtt    1560

```
tataacgaat tgacaaaggt caaatatgtt actgaaggaa tgcgaaaacc agcatttctt   1620
tcaggtgaac agaagaaagc cattgttgat ttactcttca aaacaaatcg aaaagtaacc   1680
gttaagcaat taaaagaaga ttatttcaaa aaaatagaat gttttgatag tgttgaaatt   1740
tcaggagttg aagatagatt taatgcttca ttaggtacct accatgattt gctaaaaatt   1800
attaaagata aagattttt ggataatgaa gaaaatgaag atatcttaga ggatattgtt   1860
ttaacattga ccttatttga agataggagg atgattgagg aaagacttaa aacatatgct   1920
cacctctttg atgataaggt gatgaaacag cttaaacgtc gccgttatac tggttgggga   1980
cgtttgtctc gaaaattgat taatggtatt agggataagc aatctggcaa aacaatatta   2040
gattttttga aatcagatgg ttttgccaat cgcaatttta tgcagctgat ccatgatgat   2100
agtttgacat ttaagaaga cattcaaaaa gcacaagtgt ctggacaagg cgatagttta   2160
catgaacata ttgcaaattt agctggtagc cctgctatta aaaaggtat tttacagact   2220 gtaaaagttg ttgatgaatt ggtcaaagta atggggcggc ataagccaga aaatatcgtt   2280
attgaaatgg cacgtgaaaa tcagacaact caaaagggcc agaaaaattc gcgagagcgt   2340
atgaaacgaa tcgaagaagg tatcaaagaa ttaggaagtc agattcttaa agagcatcct   2400
gttgaaaata ctcaattgca aaatgaaaag ctctatctct attatctcca aaatggaaga   2460
gacatgtatg tggaccaaga attagatatt aatcgtttaa gtgattatga tgtcgatcac   2520
attgttccac aaagtttcct taaagacgat tcaatagaca ataaggtctt aacgcgttct   2580
gataaaaatc gtggtaaatc ggataacgtt ccaagtgaag aagtagtcaa aaagatgaaa   2640
aactattgga gacaacttct aaacgccaag ttaatcactc aacgtaagtt tgataattta   2700
acgaaagctg aacgtggagg tttgagtgaa cttgataaag ctggttttat caaacgccaa   2760
ttggttgaaa ctcgccaaat cactaagcat gtggcacaaa ttttggatag tcgcatgaat   2820
actaaatacg atgaaaatga taaacttatt cgagaggtta agtgattac cttaaaatct   2880 aaattagttt ctgacttccg aaaagatttc caattctata agtacgtga gattaacaat   2940 taccatcatg cccatgatgc gtatctaaat gccgtcgttg gaactgcttt gattaagaaa   3000
tatccaaaac ttgaatcgga gtttgtctat ggtgattata agtttatga tgttcgtaaa   3060 atgattgcta agtctgagca agaaataggc aaagcaaccg caaaatattt ctttttactct   3120 aatatcatga acttcttcaa aacagaaatt acacttgcaa atggagagat tcgcaaacgc   3180
cctctaatcg aaactaatgg ggaaactgga gaaattgtct gggataaagg gcgagatttt   3240
gccacagtgc gcaaagtatt gtccatgccc caagtcaata ttgtcaagaa aacagaagta   3300
cagacaggcg gattctccaa ggagtcaatt ttaccaaaaa gaaattcgga caagcttatt   3360
gctcgtaaaa aagactggga tccaaaaaaa tatggtggtt ttgatagtcc aacggtagct   3420
tattcagtcc tagtggttgc taaggtggaa aagggaaat cgaagaagtt aaaatccgtt   3480
aaagagttac tagggatcac aattatgaa agaagttcct ttgaaaaaaa tccgattgac   3540
tttttagaag ctaaaggata taaggaagtt aaaaaagact aatcattaa actacctaaa   3600 tatagtcttt ttgagttaga aaacggtcgt aacggatgc tggctagtgc cggagaatta   3660
caaaaaggaa atgagctggc tctgccaagc aaatatgtga ttttttata tttagctagt   3720 cattatgaaa agttgaaggg tagtccagaa gataacgaac aaaaacaatt gtttgtggag   3780
cagcataagc attatttaga tgagattatt gagcaaatca gtgaatttc taagcgtgtt   3840 attttagcag atgccaattt agataaagtt cttagtgcat ataacaaaca tagagacaaa   3900
```

-continued

| | |
|---|---|
| ccaatacgtg aacaagcaga aaatattatt catttattta cgttgacgaa tcttggagct | 3960 |
| cccgctgctt ttaaatattt tgatacaaca attgatcgta aacgatatac gtctacaaaa | 4020 |
| gaagttttag atgccactct tatccatcaa tccatcactg gtctttatga aacacgcatt | 4080 |
| gatttgagtc agctaggagg tgactga | 4107 |

<210> SEQ ID NO 8
<211> LENGTH: 4107
<212> TYPE: DNA
<213> ORGANISM: Streptococcus pyogenes

<400> SEQUENCE: 8

| | |
|---|---|
| atggacaaga agtactccat tgggctcgct atcggcacaa acagcgtcgg ctgggccgtc | 60 |
| attacgacg agtacaaggt gccgagcaaa aaattcaaag ttctgggcaa taccgatcgc | 120 |
| cacagcataa agaagaacct cattggcgcc ctcctgttcg actccgggga cacggccgaa | 180 |
| gccacgcggc tcaaaagaac agcacggcgc agatataccc gcagaaagaa tcggatctgc | 240 |
| tacctgcagg agatctttag taatgagatg gctaaggtgg atgactcttt cttccatagg | 300 |
| ctggaggagt ccttttttggt ggaggaggat aaaaagcacg agcgccaccc aatctttggc | 360 |
| aatatcgtgg acgaggtggc gtaccatgaa aagtacccaa ccatatatca tctgaggaag | 420 |
| aagcttgtag acagtactga taaggctgac ttgcggttga tctatctcgc gctggcgcat | 480 |
| atgatcaaat ttcggggaca cttcctcatc gagggggacc tgaacccaga caacagcgat | 540 |
| gtcgacaaac tctttatcca actggttcag acttacaatc agcttttcga agagaacccg | 600 |
| atcaacgcat ccggagttga cgccaaagca atcctgagcg ctaggctgtc caaatcccgg | 660 |
| cggctcgaaa acctcatcgc acagctccct gggagaagaa gaacggcct gtttggtaat | 720 |
| cttatcgccc tgtcactcgg gctgaccccc aactttaaat ctaacttcga cctggccgaa | 780 |
| gatgccaagc ttcaactgag caaagacacc tacgatgatg atctcgacaa tctgctggcc | 840 |
| cagatcggcg accagtacgc agaccttttt ttggcggcaa agaacctgtc agacgccatt | 900 |
| ctgctgagtg atattctgcg agtgaacacg gagatcacca agctccgct gagcgctagt | 960 |
| atgatcaagc gctatgatga gcaccaccaa gacttgactt tgctgaaggc ccttgtcaga | 1020 |
| cagcaactgc ctgagaagta caaggaaatt ttcttcgatc agtctaaaaa tggctacgcc | 1080 |
| ggatacattg acggcggagc aagccaggag gaattttaca aatttattaa gcccatcttg | 1140 |
| gaaaaaatgg acggcaccga ggagctgctg gtaaagctta acagagaaga tctgttgcgc | 1200 |
| aaacagcgca ctttcgacaa tggaagcatc ccccaccaga ttcacctggg cgaactgcac | 1260 |
| gctatcctca ggcggcaaga ggatttctac cccttttttga agataacag ggaaaagatt | 1320 |
| gagaaaatcc tcacatttcg gatacccdac tatgtaggcc ccctcgcccg ggaaaattcc | 1380 |
| agattcgcgt ggatgactcg caaatcagaa gagaccatca ctccctggaa cttcgaggaa | 1440 |
| gtcgtggata gggggcctc tgcccagtcc ttcatcgaaa ggatgactaa ctttgataaa | 1500 |
| aatctgccta acgaaaaggt gcttcctaaa cactctctgc tgtacgagta cttcacagtt | 1560 |
| tataacgagc tcaccaaggt caaatacgtc acagaaggga tgagaaagcc agcattcctg | 1620 |
| tctggagagc agaagaaagc tatcgtggac ctcctcttca agaccaaccg gaaagttacc | 1680 |
| gtgaaacagc tcaaagaaga ctatttcaaa aagattgaat gtttcgactc tgttgaaatc | 1740 |
| agcggagtgg aggatcgctt caacgcatcc ctgggaacgt atcacgatct cctgaaaatc | 1800 |
| attaaagaca aggacttcct ggacaatgag gagaacgagg acattcttga ggacattgtc | 1860 |
| ctcacccctta cgttgtttga agatagggag atgattgaag aacgcttgaa aacttacgct | 1920 |

```
catctcttcg acgacaaagt catgaaacag ctcaagaggc gccgatatac aggatggggg    1980
cggctgtcaa gaaaactgat caatgggatc cgagacaaga gagtggaaaa gacaatcctg    2040
gattttctta agtccgatgg atttgccaac cggaacttca tgcagttgat ccatgatgac    2100
tctctcacct ttaaggagga catccagaaa gcacaagttt ctggccaggg ggacagtctt    2160
cacgagcaca tcgctaatct tgcaggtagc ccagctatca aaaagggaat actgcagacc    2220
gttaaggtcg tggatgaact cgtcaaagta atgggaaggc ataagcccga gaatatcgtt    2280
atcgagatgg cccgagagaa ccaaactacc cagaagggac agaagaacag tagggaaagg    2340
atgaagagga ttgaagaggg tataaaagaa ctggggtccc aaatccttaa ggaacaccca    2400
gttgaaaaca cccagcttca gaatgagaag ctctacctgt actacctgca gaacggcagg    2460
gacatgtacg tggatcagga actggacatc aatcggctct ccgactacga cgtggctgct    2520
atcgtgcccc agtctttttct caaagatgat tctattgata ataaagtgtt gacaagatcc    2580
gataaagcta gagggaagag tgataacgtc ccctcagaag aagttgtcaa gaaaatgaaa    2640
aattattggc ggcagctgct gaacgccaaa ctgatcacac aacggaagtt cgataatctg    2700
actaaggctg aacgaggtgg cctgtctgag ttggataaag ccggcttcat caaaaggcag    2760
cttgttgaga cacgccagat caccaagcac gtggcccaaa ttctcgattc acgcatgaac    2820
accaagtacg atgaaaatga caaactgatt cgagaggtga agttattac tctgaagtct    2880 aagctggtct cagatttcag aaaggacttt cagtttata aggtgagaga gatcaacaat    2940
taccaccatg cgcatgatgc ctacctgaat gcagtggtag gcactgcact tatcaaaaaa    3000
tatcccaagc ttgaatctga atttgtttac ggagactata agtgtacga tgttaggaaa    3060 atgatcgcaa agtctgagca ggaaataggc aaggccaccg ctaagtactt ctttttacagc    3120 aatattatga attttttcaa gaccgagatt acactggcca atggagagat tcggaagcga    3180
ccacttatcg aaacaaacgg agaaacagga gaaatcgtgt gggacaaggg tagggatttc    3240
gcgacagtcc ggaaggtcct gtccatgccg caggtgaaca tcgttaaaaa gaccgaagta    3300
cagaccggag gcttctccaa ggaaagtatc ctcccgaaaa ggaacagcga caagctgatc    3360
gcacgcaaaa aagattggga ccccaagaaa tacgccggat tcgattctcc tacagtcgct    3420
tacagtgtac tggttgtggc caaagtggag aaggggaagt ctaaaaaact caaaagcgtc    3480
aaggaactgc tgggcatcac aatcatggag cgatcaagct tcgaaaaaaa ccccatcgac    3540
tttctcgagg cgaaaggata taagagggtc aaaaaagacc tcatcattaa gcttcccaag    3600
tactctctct ttgagcttga aaacggccgg aaacgaatgc tcgctagtgc gggcgagctg    3660
cagaaaggta acgagctggc actgccctct aaatacgtta atttcttgta tctggccagc    3720
cactatgaaa agctcaaagg gtctcccgaa gataatgagc agaagcagct gttcgtggaa    3780
caacacaaac actaccttga tgagatcatc gagcaaataa gcgaattctc caaaagagtg    3840
atcctcgccg acgctaacct cgataaggtg ctttctgctt acaataagca cagggataag    3900
cccatcaggg agcaggcaga aaacattatc cacttgttta ctctgaccaa cttgggcgcg    3960
cctgcagcct tcaagtactt cgacaccacc atagacagaa agcggtacac ctctacaaag    4020
gaggtcctgg acgccacact gattcatcag tcaattacgg ggctctatga aacaagaatc    4080
gacctctctc agctcggtgg agactaa                                        4107
```

<210> SEQ ID NO 9
<211> LENGTH: 3366
<212> TYPE: DNA

<213> ORGANISM: Streptococcus thermophilus

<400> SEQUENCE: 9

```
atgagcgacc tggtgctggg cctggacatc ggcatcggca gcgtgggcgt gggcatcctg      60
aacaaggtga ccggcgagat catccacaag aacagtcgca tcttccctgc tgctcaggct     120
gagaacaacc tggtgcgccg caccaaccgc cagggtcgcc ggcttgctcg ccgcaagaag     180
caccggcgcg tgcgcctgaa ccgcctgttc gaggagagcg gcctgatcac cgacttcacc     240
aagatcagca tcaacctgaa ccoctaccag ctgcgcgtga agggcctgac cgacgagctg     300
agcaacgagg agctgttcat cgccctgaag aacatggtga agcaccgcgg catcagctac     360
ctggacgacg ccagcgacga cggcaacagc agcgtgggcg actacgccca gatcgtgaag     420
gagaacagca agcagctgga gaccaagacc cccggccaga tccagctgga gcgctaccag     480
acctacggcc agctgcgcgg cgacttcacc gtggagaagg acggcaagaa gcaccgcctg     540
atcaacgtgt tccccaccag cgcctaccgc agcgaggccc tgcgcatcct gcagacccag     600
caggagttca accoccagat caccgacgag ttcatcaacc gctacctgga gatcctgacc     660
ggcaagcgca gtactacca cggccccggc aacgagaaga ccgcaccga ctacggccgc     720
taccgcacca gcgcgagac cctggacaac atcttcggca tcctgatcgg caagtgcacc     780
ttctaccccg acgagttccg cgccgccaag gccagctaca ccgcccagga gttcaacctg     840
ctgaacgacc tgaacaacct gaccgtgccc accgagacca gaagctgag caaggagcag     900
aagaaccaga tcatcaacta cgtgaagaac gagaaggcca tgggccccgc caagctgttc     960
aagtacatcg ccaagctgct gagctgcgac gtggccgaca tcaagggcta ccgcatcgac    1020
aagagcggca aggccgagat ccacaccttc gaggcctacc gcaagatgaa gacctggag     1080
accctggaca tcgagcagat ggaccgcgag accctggaca gctggccta cgtgctgacc    1140
ctgaacaccg agcgcgaggg catccaggag gccctggagc acgagttcgc cgacggcagc    1200
ttcagccaga gcaggtgga cgagctggtg cagttccgca aggccaacag cagcatcttc    1260
ggcaagggct ggcacaactt cagcgtgaag ctgatgatgg agctgatccc cgagctgtac    1320
gagaccagcg aggagcagat gaccatcctg acccgcctgg gcaagcagaa gaccaccagc    1380
agcagcaaca agaccaagta catcgacgag aagctgctga ccgaggagat ctacaacccc    1440
gtggtggcca gagcgtgcg ccaggccatc aagatcgtga acgccgccat caaggagtac    1500
ggcgacttcg acaacatcgt gatcgagatg gcccgcgaga ccaacgagga cgacgagaag    1560
aaggccatcc agaagatcca gaaggccaac aaggacgaga aggacgccgc catgctgaag    1620
gccgccaacc agtacaacgg caaggccgag ctgccccaca gcgtgttcca cggccacaag    1680
cagctggcca ccaagatccg cctgtggcac cagcagggcg agcgctgcct gtacaccggc    1740
aagaccatca gcatccacga cctgatcaac aacagcaacc agttcgaggt ggaccacatc    1800
ctgcccctga gcatcacctt cgacgacagc ctggccaaca aggtgctggt gtacgccacc    1860
gccaaccagg agaagggcca gcgcaccccc taccaggccc tggacagcat ggacgacgcc    1920
tggagcttcc gcgagctgaa ggccttcgtg cgcgagagca gaccctgag caacaagaag    1980
aaggagtacc tgctgaccga ggaggacatc agcaagttcg acgtgcgcaa gaagttcatc    2040
gagcgcaacc tggtggacac ccgctacgcc agccgcgtgg tgctgaacgc cctgcaggag    2100
cacttccgcg cccacaagat cgacaccaag gtgagcgtgg tgcgcggcca gttcaccagc    2160
cagctgcgcc gccactgggg catcgagaag acccgcgaca cctaccacca ccacgccgtg    2220
gacgccctga tcattgcggc ttctagccag ctgaacctgt ggaagaagca agagaacacc    2280
```

```
ctggtgagct acagcgagga ccagctgctg gacatcgaga ccggcgagct gatcagcgac    2340
gacgagtaca aggagagcgt gttcaaggcc cctaccagc acttcgtgga caccctgaag    2400
agcaaggagt tcgaggacag catcctgttc agctaccagg tggacagcaa gttcaaccgc    2460
aagatcagcg acgccaccat ctacgccacc cgccaggcca aggtgggcaa ggacaaggcc    2520
gacgagacct acgtgctggg caagatcaag gacatctaca cccaggacgg ctacgacgcc    2580
ttcatgaaga tctacaagaa ggacaagagc aagttcctga tgtaccgcca cgaccccag    2640 accttcgaga aggtgatcga gcccatcctg gagaactacc caacaagca gatcaacgat    2700 aaaggcaagg aggtgccctg caacccttc ctgaagtaca aggaggagca cggctacatc    2760
cgcaagtaca gcaagaaggg caacggcccc gagatcaaga gcctgaagta ctacgacagc    2820
aagctgggca ccacatcga catcaccccc aaggacagca caacaaggt ggtgctgcag    2880 agcgtgagcc cctggcgcgc cgacgtgtac ttcaacaaga ccaccggcaa gtacgagatc    2940
ctgggcctga gtacgccga cctgcagttt gataagggca ccggcaccta caagatcagc    3000
caggagaagt acaacgacat caagaagaag gagggcgtgg acagcgacag cgagttcaag    3060
ttcaccctgt acaagaacga ccttctgctg gtgaaggaca ccgagaccaa ggagcaacag    3120
ctgttccgct tcctgagccg caccatgccc aagcagaagc actacgtgga gctgaagccc    3180
tacgacaagc agaagttcga gggcggcgag gccctgatca aggtgctggg caacgtggcc    3240
aacagcggcc agtgcaagaa gggcctgggc aagagcaaca tcagcatcta aaggtgcgc    3300 accgacgtgc tgggcaacca gcacatcatc aagaacgagg gcgacaagcc caagctggac    3360
ttctaa                                                             3366

<210> SEQ ID NO 10
<211> LENGTH: 3366
<212> TYPE: DNA
<213> ORGANISM: Streptococcus thermophilus

<400> SEQUENCE: 10
atgagcgacc tggtgctggg cctggccatc ggcatcggca gcgtgggcgt gggcatcctg      60
aacaaggtga ccggcgagat catccacaag aacagtcgca tcttccctgc tgctcaggct    120
gagaacaacc tggtgcgccg caccaaccgc cagggtcgcc ggcttgctcg ccgcaagaag    180
caccggcgcg tgcgcctgaa ccgcctgttc gaggagagcg gcctgatcac cgacttcacc    240
aagatcagca tcaacctgaa ccccctaccag ctgcgcgtga agggcctgac cgacgagctg    300
agcaacgagg agctgttcat cgccctgaag aacatggtga agcaccgcgg catcagctac    360
ctggacgacg ccagcgacga cggcaacagc agcgtgggcg actacgccca gatcgtgaag    420
gagaacagca gcagctgga gaccaagacc cccggccaga tccagctgga gcgctaccag    480
acctacggcc agctgcgcgg cgacttcacc gtggagaagg acggcaagaa gcaccgcctg    540
atcaacgtgt cccccaccag cgcctaccgc agcgaggccc tgcgcatcct gcagacccag    600
caggagttca cccccagat caccgacgag ttcatcaacc gctacctgga gatcctgacc    660
ggcaagcgca agtactacca cggccccggc aacgagaaga gccgcaccga ctacggccgc    720
taccgcacca gcgcgagac cctgacaac atcttcggca tcctgatcgg caagtgcacc    780
ttctaccccg acgagttccg cgccgccaag gccagctaca ccgcccagga gttcaacctg    840
ctgaacgacc tgaacaacct gaccgtgccc accgagacca agaagctgag caaggagcag    900
aagaaccaga tcatcaacta cgtgaagaac gagaaggcca tgggccccgc caagctgttc    960
```

-continued

```
aagtacatcg ccaagctgct gagctgcgac gtggccgaca tcaagggcta ccgcatcgac    1020
aagagcggca aggccgagat ccacaccttc gaggcctacc gcaagatgaa gaccctggag    1080
accctggaca tcgagcagat ggaccgcgag accctggaca agctggccta cgtgctgacc    1140
ctgaacaccg agcgcgaggg catccaggag gccctggagc acgagttcgc cgacggcagc    1200
ttcagccaga agcaggtgga cgagctggtg cagttccgca aggccaacag cagcatcttc    1260
ggcaagggct ggcacaactt cagcgtgaag ctgatgatgg agctgatccc cgagctgtac    1320
gagaccagcg aggagcagat gaccatcctg acccgcctgg gcaagcagaa gaccaccagc    1380
agcagcaaca agaccaagta catcgacgag aagctgctga ccgaggagat ctacaacccc    1440
gtggtggcca agagcgtgcg ccaggccatc aagatcgtga acgccgccat caaggagtac    1500
ggcgacttcg acaacatcgt gatcgagatg gcccgcgaga ccaacgagga cgacgagaag    1560
aaggccatcc agaagatcca gaaggccaac aaggacgaga aggacgccgc catgctgaag    1620
gccgccaacc agtacaacgg caaggccgag ctgccccaca gcgtgttcca cggccacaag    1680
cagctggcca ccaagatccg cctgtggcac cagcagggcg agcgctgcct gtacaccggc    1740
aagaccatca gcatccacga cctgatcaac aacagcaacc agttcgaggt ggctgccatc    1800
ctgcccctga gcatcacctt cgacgacagc ctggccaaca aggtgctggt gtacgccacc    1860
gccgctcagg agaagggcca gcgcacccccc taccaggccc tggacagcat ggacgacgcc    1920
tggagcttcc gcgagctgaa ggccttcgtg cgcgagagca gaccctgag caacaagaag    1980 aaggagtacc tgctgaccga ggaggacatc agcaagttcg acgtgcgcaa gaagttcatc    2040
gagcgcaacc tggtggacac ccgctacgcc agccgcgtgg tgctgaacgc cctgcaggag    2100
cacttccgcg cccacaagat cgacaccaag gtgagcgtgg tgcgcggcca gttcaccagc    2160
cagctgcgcc gccactgggg catcgagaag acccgcgaca cctaccacca ccacgccgtg    2220
gacgccctga tcattgcggc ttctagccag ctgaacctgt ggaagaagca gaagaacacc    2280
ctggtgagct acagcgagga ccagctgctg gacatcgaga ccggcgagct gatcagcgac    2340
gacgagtaca aggagagcgt gttcaaggcc ccctaccagc acttcgtgga cacccctgaag    2400 agcaaggagt tcgaggacag catcctgttc agctaccagg tggacagcaa gttcaaccgc    2460
aagatcagcg acgccaccat ctacgccacc cgccaggcca aggtgggcaa ggacaaggcc    2520
gacgagacct acgtgctggg caagatcaag gacatctaca cccaggacgg ctacgacgcc    2580
ttcatgaaga tctacaagaa ggacaagagc aagttcctga tgtaccgcca cgacccccag    2640
accttcgaga aggtgatcga gcccatcctg gagaactacc ccaacaagca gatcaacgat    2700
aaaggcaagg aggtgcccctg caacccccttc ctgaagtaca aggaggagca cggctacatc    2760
cgcaagtaca gcaagaaggg caacggcccc gagatcaaga gcctgaagta ctacgacagc    2820
aagctgggca ccacatcga catcacccccc aaggacagca caacaaggt ggtgctgcag    2880 agcgtgagcc cctggcgcgc cgacgtgtac ttcaacaaga ccaccggcaa gtacgagatc    2940
ctgggcctga gtacgccga cctgcagttt gataagggca ccggcaccta caagatcagc    3000
caggagaagt acaacgacat caagaagaag gagggcgtgg acagcgacag cgagttcaag    3060 ttcacccctgt acaagaacga cctctgctg gtgaaggaca ccgagaccaa ggagcaacag    3120
ctgttccgct tcctgagccg caccatgccc aagcagaagc actacgtgga gctgaagccc    3180
tacgacaagc agaagttcga gggcggcgag gccctgatca aggtgctggg caacgtggcc    3240
aacagcggcc agtgcaagaa gggcctgggc aagagcaaca tcagcatcta caaggtgcgc    3300
accgacgtgc tgggcaacca gcacatcatc aagaacgagg gcgacaagcc caagctggac    3360
``` ttctaa 3366

<210> SEQ ID NO 11
<211> LENGTH: 3249
<212> TYPE: DNA
<213> ORGANISM: Neisseria meningitidis

<400> SEQUENCE: 11

| | | | | | |
|---|---|---|---|---|---|
| atggccgcct | tcaagcccaa | ccccatcaac | tacatcctgg | gcctggacat | cggcatcgcc | 60 |
| agcgtgggct | gggccatggt | ggagatcgac | gaggacgaga | ccccatctg | cctgatcgac | 120 |
| ctgggtgtgc | gcgtgttcga | gcgcgctgag | gtgcccaaga | ctggtgacag | tctggctatg | 180 |
| gctcgccggc | ttgctcgctc | tgttcggcgc | cttactcgcc | ggcgcgctca | ccgccttctg | 240 |
| cgcgctcgcc | gcctgctgaa | gcgcgagggt | gtgctgcagg | ctgccgactt | cgacgagaac | 300 |
| ggcctgatca | agagcctgcc | caacactcct | tggcagctgc | gcgctgccgc | tctggaccgc | 360 |
| aagctgactc | ctctggagtg | gagcgccgtg | ctgctgcacc | tgatcaagca | ccgcggctac | 420 |
| ctgagccagc | gcaagaacga | gggcgagacc | gccgacaagg | agctgggtgc | tctgctgaag | 480 |
| ggcgtggccg | acaacgccca | cgccctgcag | actggtgact | ccgcactcc | tgctgagctg | 540 |
| gccctgaaca | agttcgagaa | ggagagcggc | cacatccgca | accagcgcgg | cgactacagc | 600 |
| cacaccttca | gccgcaagga | cctgcaggcc | gagctgatcc | tgctgttcga | gaagcagaag | 660 |
| gagttcggca | accccacgt | gagcggcggc | ctgaaggagg | gcatcgagac | cctgctgatg | 720 |
| acccagcgcc | ccgccctgag | cggcgacgcc | gtgcagaaga | tgctgggcca | ctgcaccttc | 780 |
| gagccagccg | agcccaaggc | cgccaagaac | acctacaccg | ccgagcgctt | catctggctg | 840 |
| accaagctga | caacctgcg | catcctggag | cagggcagcg | agcgcccct | gaccgacacc | 900 |
| gagcgcgcca | cctgatgga | cgagccctac | cgcaagagca | agctgaccta | cgcccaggcc | 960 |
| cgcaagctgc | tgggtctgga | ggacaccgcc | ttcttcaagg | gcctgcgcta | cggcaaggac | 1020 |
| aacgccgagg | ccagcaccct | gatggagatg | aaggcctacc | acgccatcag | ccgcgccctg | 1080 |
| gagaaggagg | gcctgaagga | caagaagagt | cctctgaacc | tgagccccga | gctgcaggac | 1140 |
| gagatcggca | ccgccttcag | cctgttcaag | accgacgagg | acatcaccgg | ccgcctgaag | 1200 |
| gaccgcatcc | agcccgagat | cctggaggcc | ctgctgaagc | acatcagctt | cgacaagttc | 1260 |
| gtgcagatca | gcctgaaggc | cctgcgccgc | atcgtgcccc | tgatggagca | gggcaagcgc | 1320 |
| tacgacgagg | cctgcgccga | gatctacggc | gaccactacg | gcaagaagaa | caccgaggag | 1380 |
| aagatctacc | tgcctcctat | ccccgccgac | gagatccgca | ccccgtggt | gctgcgcgcc | 1440 |
| ctgagccagg | cccgcaaggt | gatcaacggc | gtggtgcgcc | gctacggcag | ccccgcccgc | 1500 |
| atccacatcg | agaccgcccg | cgaggtgggc | aagagcttca | aggaccgcaa | ggagatcgag | 1560 |
| aagcgccagg | aggagaaccg | caaggaccgc | gagaaggccg | ccgccaagtt | ccgcgagtac | 1620 |
| ttccccaact | tcgtgggcga | gcccaagagc | aaggacatcc | tgaagctgcg | cctgtacgag | 1680 |
| cagcagcacg | gcaagtgcct | gtacagcggc | aaggagatca | acctgggccg | cctgaacgag | 1740 |
| aagggctacg | tggagatcga | ccacgccctg | cccttcagcc | gcacctggga | cgacagcttc | 1800 |
| aacaacaagg | tgctggtgct | gggcagcgag | aaccagaaca | gggcaacca | gacccctac | 1860 |
| gagtacttca | cggcaagga | caacagccgc | gagtggcagg | agttcaaggc | ccgcgtggag | 1920 |
| accagccgct | tccccgcag | caagaagcag | cgcatcctgc | tgcagaagtt | cgacgaggac | 1980 |
| ggcttcaagg | agcgcaacct | gaacgacacc | cgctacgtga | accgcttcct | gtgccagttc | 2040 |

| | | |
|---|---|---|
| gtggccgacc gcatgcgcct gaccggcaag ggcaagaagc gcgtgttcgc cagcaacggc | 2100 | |
| cagatcacca acctgctgcg cggcttctgg ggcctgcgca aggtgcgcgc cgagaacgac | 2160 | |
| cgccaccacg ccctggacgc cgtggtggtg gcctgcagca ccgtggccat gcagcagaag | 2220 | |
| atcacccgct tcgtgcgcta caaggagatg aacgccttcg acggtaaaac catcgacaag | 2280 | |
| gagaccggcg aggtgctgca ccagaagacc cacttccccc agccctggga gttcttcgcc | 2340 | |
| caggaggtga tgatccgcgt gttcggcaag cccgacggca agcccgagtt cgaggaggcc | 2400 | |
| gacacccccg agaagctgcg caccctgctg gccgagaagc tgagcagccg ccctgaggcc | 2460 | |
| gtgcacgagt acgtgactcc tctgttcgtg agccgcgccc ccaaccgcaa gatgagcggt | 2520 | |
| cagggtcaca tggagaccgt gaagagcgcc aagcgcctgg acgagggcgt gagcgtgctg | 2580 | |
| cgcgtgcccc tgacccagct gaagctgaag gacctggaga gatggtgaa ccgcgagcgc | 2640 | |
| gagcccaagc tgtacgaggc cctgaaggcc cgcctggagg cccacaagga cgaccccgcc | 2700 | |
| aaggccttcg ccgagccctt ctacaagtac gacaaggccg gcaaccgcac cagcaggtg | 2760 | |
| aaggccgtgc gcgtggagca ggtgcagaag accggcgtgt gggtgcgcaa ccacaacggc | 2820 | |
| atcgccgaca cgccaccat ggtgcgcgtg gacgtgttcg agaagggcga caagtactac | 2880 | |
| ctggtgccca tctacagctg gcaggtggcc aagggcatcc tgcccgaccg cgccgtggtg | 2940 | |
| cagggcaagg acgaggagga ctggcagctg atcgacgaca gcttcaactt caagttcagc | 3000 | |
| ctgcaccccca acgacctggt ggaggtgatc accaagaagg cccgcatgtt cggctacttc | 3060 | |
| gccagctgcc accgcggcac cggcaacatc aacatccgca tccacgacct ggaccacaag | 3120 | |
| atcggcaaga acggcatcct ggagggcatc ggcgtgaaga ccgccctgag cttccagaag | 3180 | |
| taccagatcg acgagctggg caaggagatc cgcccctgcc gcctgaagaa gcgccctcct | 3240 | |
| gtgcgctaa | 3249 | |

<210> SEQ ID NO 12
<211> LENGTH: 3249
<212> TYPE: DNA
<213> ORGANISM: Neisseria meningitidis

<400> SEQUENCE: 12

| | | |
|---|---|---|
| atggccgcct tcaagcccaa ccccatcaac tacatcctgg gcctggccat cggcatcgcc | 60 | |
| agcgtgggct gggccatggt ggagatcgac gaggacgaga ccccatctg cctgatcgac | 120 | |
| ctgggtgtgc gcgtgttcga gcgcgctgag gtgcccaaga ctggtgacag tctggctatg | 180 | |
| gctcgccggc ttgctcgctc tgttcggcgc cttactcgcc ggcgcgctca ccgccttctg | 240 | |
| cgcgctcgcc gcctgctgaa gcgcgagggt gtgctgcagg ctgccgactt cgacgagaac | 300 | |
| ggcctgatca agagcctgcc caacactcct tggcagctgc gcgctgccgc tctgaccgc | 360 | |
| aagctgactc ctctggagtg gagcgccgtg ctgctgcacc tgatcaagca ccgcggctac | 420 | |
| ctgagccagc gcaagaacga gggcgagacc gccgacaagg agctgggtgc tctgctgaag | 480 | |
| ggcgtggccg acaacgccca cgccctgcag actggtgact ccgcactcc tgctgagctg | 540 | |
| gccctgaaca agttcgagaa ggagagcggc acatccgca accagcgcgg cgactacagc | 600 | |
| cacaccttca gccgcaagga cctgcaggcc gagctgatcc tgctgttcga aagcagaag | 660 | |
| gagttcggca accccacgt gagcggcggc ctgaaggagg gcatcgagac cctgctgatg | 720 | |
| acccagcgcc ccgccctgag cggcgacgcc gtgcagaaga tgctgggcca ctgcaccttc | 780 | |
| gagccagccg agcccaaggc cgccaagaac acctacaccg ccgagcgctt catctggctg | 840 | |
| accaagctga caacctgcg catcctggag cagggcagcg agcgccccct gaccgacacc | 900 | |

-continued

```
gagcgcgcca ccctgatgga cgagccctac cgcaagagca agctgaccta cgcccaggcc    960
cgcaagctgc tgggtctgga ggacaccgcc ttcttcaagg gcctgcgcta cggcaaggac   1020
aacgccgagg ccagcaccct gatggagatg aaggcctacc acgccatcag ccgcgccctg   1080
gagaaggagg gcctgaagga caagaagagt cctctgaacc tgagcccga gctgcaggac    1140
gagatcggca ccgccttcag cctgttcaag accgacgagg acatcaccgg ccgcctgaag   1200
gaccgcatcc agcccgagat cctggaggcc ctgctgaagc acatcagctt cgacaagttc   1260
gtgcagatca gcctgaaggc cctgcgccgc atcgtgcccc tgatggagca gggcaagcgc   1320
tacgacgagg cctgcgccga gatctacggc gaccactacg gcaagaagaa caccgaggag   1380
aagatctacc tgcctcctat ccccgccgac gagatccgca accccgtggt gctgcgcgcc   1440
ctgagccagg cccgcaaggt gatcaacggc gtggtgcgcc gctacggcag ccccgcccgc   1500
atccacatcg agaccgcccg cgaggtgggc aagagcttca aggaccgcaa ggagatcgag   1560
aagcgccagg aggagaaccg caaggaccgc gagaaggccg ccgccaagtt ccgcgagtac   1620
ttccccaact tcgtgggcga gcccaagagc aaggacatcc tgaagctgcg cctgtacgag   1680
cagcagcacg gcaagtgcct gtacagcggc aaggagatca acctgggccg cctgaacgag   1740
aagggctacg tggagatcgc cgctgccctg cccttcagcc gcacctggga cgacagcttc   1800
aacaacaagg tgctggtgct gggcagcgag gctcagaaca agggcaacca gacccctac    1860
gagtacttca cggcaagga caacagccgc gagtggcagg agttcaaggc ccgcgtggag   1920
accagccgct ccccccgcag caagaagcag cgcatcctgc tgcagaagtt cgacgaggac   1980
ggcttcaagg agcgcaacct gaacgacacc cgctacgtga accgcttcct gtgccagttc   2040
gtggccgacc gcatgcgcct gaccggcaag ggcaagaagc gcgtgttcgc cagcaacggc   2100
cagatcacca acctgctgcg cggcttctgg ggcctgcgca aggtgcgcgc cgagaacgac   2160
cgccaccacg ccctggacgc cgtggtggtg cctgcagca ccgtggccat gcagcagaag   2220
atcacccgct tcgtgcgcta caaggagatg aacgccttcg acggtaaaac catcgacaag   2280
gagaccggcg aggtgctgca ccagaagacc cacttccccc agccctggga gttcttcgcc   2340
caggaggtga tgatccgcgt gttcggcaag cccgacggca gcccgagtt cgaggaggcc   2400
gacacccccg agaagctgcg caccctgctg ccgagaagc tgagcagccg ccctgaggcc   2460
gtgcacgagt acgtgactcc tctgttcgtg agccgcgccc ccaaccgcaa gatgagcggt   2520
cagggtcaca tggagaccgt gaagagcgcc aagcgcctgg acgagggcgt gagcgtgctg   2580
cgcgtgcccc tgacccagct gaagctgaag gacctggaga gatggtgaa ccgcgagcgc    2640
gagcccaagc tgtacgaggc cctgaaggcc cgcctggagg cccacaagga cgaccccgcc   2700
aaggccttcg ccgagccctt ctacaagtac gacaaggccg gcaaccgcac ccagcaggtg   2760
aaggccgtgc gcgtggagca ggtgcagaag accggcgtgt gggtgcgcaa ccacaacggc   2820
atcgccgaca cgccaccat ggtgcgcgtg gacgtgttcg agaagggcga caagtactac   2880
ctggtgccca tctacagctg gcaggtggcc aagggcatcc tgcccgaccg cgccgtggtg   2940
cagggcaagg acgaggagga ctggcagctg atcgacgaca gcttcaactt caagttcagc   3000
ctgcaccca acgacctggt ggaggtgatc accaagaagg cccgcatgtt cggctacttc   3060
gccagctgcc accgcggcac cggcaacatc aacatccgca tccacgacct ggaccacaag   3120
atcggcaaga acggcatcct ggagggcatc ggcgtgaaga ccgccctgag cttccagaag   3180
taccagatcg acgagctggg caaggagatc cgcccctgcc gcctgaagaa gcgccctcct   3240
```

| | |
|---|---:|
| gtgcgctaa | 3249 |

<210> SEQ ID NO 13
<211> LENGTH: 4188
<212> TYPE: DNA
<213> ORGANISM: Treponema denticola

<400> SEQUENCE: 13

| | |
|---|---:|
| atgaagaagg agatcaagga ctacttcctg ggcctggacg tgggcaccgg cagcgtgggc | 60 |
| tgggccgtga ccgacaccga ctacaagctg ctgaaggcca accgcaagga cctgtggggc | 120 |
| atgcgctgct tcgagactgc tgagaccgcc gaggtgcgcc ggctgcaccg cggtgctcgc | 180 |
| cggcgcatcg agcgccgcaa gaagcgcatc aagctgctgc aggagctgtt cagccaggag | 240 |
| atcgccaaga ccgacgaggg cttcttccag cgcatgaagg agagcccctt ctacgccgag | 300 |
| gacaagacca tcctgcagga gaacaccctg ttcaacgaca aggacttcgc cgacaagacc | 360 |
| taccacaagg cctaccccac catcaaccac ctgatcaagg cctggatcga gaacaaggtg | 420 |
| aagcccgacc tcgcctgct gtacctggcc tgccacaaca tcatcaagaa gcgcggccac | 480 |
| ttcctgttcg agggcgactt cgacagcgag aaccagttcg acaccagcat ccaggccctg | 540 |
| ttcgagtacc tgcgcgagga catggaggtg acatcgacg ccgacagcca gaaggtgaag | 600 |
| gagatcctga ggacagcag cctgaagaac agcgagaagc agagccgcct gaacaagatc | 660 |
| ctgggcctga gcccagcga caagcagaag aaggccatca ccaacctgat cagcggcaac | 720 |
| aagatcaact cgccgaccct gtacgacaac cccgacctga ggacgccga gaagaacagc | 780 |
| atcagcttca gcaaggacga cttcgacgcc ctgagcgacg acctggccag catcctgggc | 840 |
| gacagcttcg agctgctgct gaaggccaag gccgtgtaca actgcagcgt gctgagcaag | 900 |
| gtgatcggcg acgagcagta cctgagcttc gccaaggtga agatctacga agcacaag | 960 |
| accgacctta ccaagctgaa gaacgtgatc aagaagcact cccccaagga ctacaagaag | 1020 |
| gtgttcggct acaacaagaa cgagaagaac aacaacaact cagcggcta cgtgggcgtg | 1080 |
| tgcaagacca agagcaagaa gctgatcatc aacaacagcg tgaaccagga ggacttctac | 1140 |
| aagttcctga gaccatcct gagcgccaag agcgagatca aggaggtgaa cgacatcctg | 1200 |
| accgagatcg agaccggcac cttcctgccc aagcagatca gcaagagcaa cgccgagatc | 1260 |
| ccctaccagc tgcgcaagat ggagctggag aagatcctga gcaacgccga gaagcacttc | 1320 |
| agcttcctga gcagaagga cgagaagggc ctgagccaca gcgagaagat catcatgctg | 1380 |
| ctgaccttca gatcccta ctacatcggc cccatcaacg acaaccacaa gaagttcttc | 1440 |
| cccgaccgct gctgggtggt gaagaaggag aagagcccca gcggcaagac caccccctgg | 1500 |
| aacttcttcg accacatcga caaggagaag accgccgagg ccttcatcac cagccgcacc | 1560 |
| aacttctgca catacctggt gggcgagagc gtgctgccca gagcagcct gctgtacagc | 1620 |
| gagtacaccg tgctgaacga gatcaacaac ctgcagatca tcatcgacgg caagaacatc | 1680 |
| tgcgacatca agctgaagca gaagatctac gaggacctgt tcaagaagta caagaagatc | 1740 |
| acccagaagc agatcagcac cttcatcaag cacgagggca tctgcaacaa gaccgacgag | 1800 |
| gtgatcatcc tggcatcga caaggagtgc accagcagcc tgaagagcta catcgagctg | 1860 |
| aagaacatct tcggcaagca ggtggacgag atcagcacca gaacatgct ggaggagatc | 1920 |
| atccgctggg ccaccatcta cgacgaggc gagggcaaga ccatcctgaa gaccaagatc | 1980 |
| aaggccgagt acggcaagta ctgcagcgac gagcagatca gaagatcct gaacctgaag | 2040 |
| ttcagcggct ggggccgcct gagccgcaag ttcctggaga ccgtgaccag cgagatgccc | 2100 |

```
ggcttcagcg agcccgtgaa catcatcacc gccatgcgcg agacccagaa caacctgatg    2160
gagctgctga gcagcgagtt caccttcacc gagaacatca agaagatcaa cagcggcttc    2220
gaggacgccg agaagcagtt cagctacgac ggcctggtga agcccctgtt cctgagcccc    2280
agcgtgaaga agatgctgtg gcagaccctg aagctggtga aggagatcag ccacatcacc    2340
caggctcctc ctaagaagat cttcatcgag atggccaagg gcgccgagct ggagcctgct    2400
cgcaccaaga cccgcctgaa gatcctgcag gacctgtaca caactgcaa gaacgacgcc    2460 gacgcattca gcagcgagat caaggacctg agcggcaaga tcgagaacga ggacaacctg    2520
cgcctgcgca cgacaagct gtacctgtac tacacccagc tgggcaagtg catgtactgc    2580
ggcaagccca tcgagatcgg ccacgtgttc gacaccagca actacgacat cgaccacatc    2640
tacccccaga gcaagatcaa ggacgacagc atcagcaacc gcgtgctggt gtgcagcagc    2700
tgcaacaaga caaggagga caagtaccct ctgaagagcg agatccagag caagcagcgc    2760
ggcttctgga acttcctgca gcgcaacaac ttcatcagcc tggagaagct gaaccgcctg    2820
acccgcgcca cccccatcag cgacgacgag accgccaagt tcatcgcccg ccagctggtg    2880
gagactcgcc aagctaccaa ggtggccgcc aaggtgctgg agaagatgtt ccccgagacc    2940
aagatcgtgt acagcaaggc cgagaccgtg agcatgttcc gcaacaagtt cgacatcgtg    3000
aagtgccgcg agatcaacga cttccaccac gcccacgacg cctacctgaa catcgtggtg    3060
ggcaacgtgt acaacaccaa gttcaccaac aaccccctgga atttcattaa ggagaagcgc    3120
gacaacccca agatcgccga cacctacaac tactacaagg tgttcgacta cgacgtgaag    3180
cgcaacaaca tcaccgcctg ggagaagggc aagaccatca tcaccgtgaa ggacatgctg    3240
aagcgcaaca cccccatcta cacccgccag gccgcctgca agaagggcga gctgttcaac    3300
cagaccatca tgaagaaggg cctgggccag cacccctga agaaggaggg ccccttcagc    3360
aacatcagca gtacggcgg ctacaacaag gtgagcgccg cctactacac cctgatcgag    3420
tacgaggaga agggcaacaa gatccgcagc ctggagacca tcccctgta cctggtgaag    3480 gacatccaga aggaccagga cgtgctgaag agctacctga ccgacctgct gggcaagaag    3540
gagttcaaga tcctggtgcc caagatcaag atcaacagcc tgctgaagat caacggcttc    3600
ccctgccaca tcaccggcaa gaccaacgac agcttcctgc tgcgccccgc cgtgcagttc    3660
tgctgcagca acaacgaggt gctgtacttc aagaagatca tccgcttcag cgagatccgc    3720
agccagcgcg agaagatcgg caagaccatc agcccctacg aggacctgag cttccgcagc    3780
tacatcaagg agaacctgtg gaagaagacc aagaacgacg agatcggcga aaggagttc    3840 tacgacctgc tgcagaagaa gaacctggag atctacgaca tgctgctgac caagcacaag    3900
gacaccatct acaagaagcg ccccaacagc gccaccatcg acatcctggt gaagggcaag    3960
gagaagttca gagcctgat catcgagaac cagttcgagg tgatcctgga gatcctgaag    4020
ctgttcagcg ccaccgcaa cgtgagcgac ctgcagcaca tcggcggcag caagtacagc    4080
ggcgtggcca agatcggcaa caagatcagc agcctggaca actgcatcct gatctaccag    4140
agcatcaccg gcatcttcga gaagcgcatc gacctgctga aggtgtaa                4188
```

<210> SEQ ID NO 14
<211> LENGTH: 4188
<212> TYPE: DNA
<213> ORGANISM: Treponema denticola

<400> SEQUENCE: 14

-continued

| | |
|---|---|
| atgaagaagg agatcaagga ctacttcctg ggcctggccg tgggcaccgg cagcgtgggc | 60 |
| tgggccgtga ccgacaccga ctacaagctg ctgaaggcca accgcaagga cctgtggggc | 120 |
| atgcgctgct tcgagactgc tgagaccgcc gaggtgcgcc ggctgcaccg cggtgctcgc | 180 |
| cggcgcatcg agcgccgcaa gaagcgcatc aagctgctgc aggagctgtt cagccaggag | 240 |
| atcgccaaga ccgacgaggg cttcttccag cgcatgaagg agagccccct ctacgccgag | 300 |
| gacaagacca tcctgcagga gaacaccctg ttcaacgaca aggacttcgc cgacaagacc | 360 |
| taccacaagg cctaccccac catcaaccac ctgatcaagg cctggatcga gaacaaggtg | 420 |
| aagcccgacc tcgcctgct gtacctggcc tgccacaaca tcatcaagaa gcgcggccac | 480 |
| ttcctgttcg agggcgactt cgacagcgag aaccagttcg acaccagcat ccaggccctg | 540 |
| ttcgagtacc tgcgcgagga catggaggtg acatcgacg ccgacagcca gaaggtgaag | 600 |
| gagatcctga aggacagcag cctgaagaac agcgagaagc agagccgcct gaacaagatc | 660 |
| ctgggcctga agcccagcga caagcagaag aaggccatca ccaacctgat cagcggcaac | 720 |
| aagatcaact tcgccgacct gtacgacaac cccgacctga aggacgccga agaacagc | 780 |
| atcagcttca gcaaggacga cttcgacgcc ctgagcgacg acctggccag catcctgggc | 840 |
| gacagcttcg agctgctgct gaaggccaag gccgtgtaca ctgcagcgt gctgagcaag | 900 |
| gtgatcggcg acgagcagta cctgagcttc gccaaggtga agatctacga gaagcacaag | 960 |
| accgaccta ccaagctgaa gaacgtgatc aagaagcact cccccaagga ctacaagaag | 1020 |
| gtgttcggct acaacaagaa cgagaagaac aacaacaact acagcggcta cgtgggcgtg | 1080 |
| tgcaagacca gagcaagaa gctgatcatc aacaacagcg tgaaccagga ggacttctac | 1140 |
| aagttcctga gaccatcct gagcgccaag agcgagatca aggaggtgaa cgacatcctg | 1200 |
| accgagatcg agaccggcac cttcctgccc aagcagatca gcaagagcaa cgccgagatc | 1260 |
| ccctaccagc tgcgcaagat ggagctggag aagatcctga gcaacgccga gaagcacttc | 1320 |
| agcttcctga gcagaagga cgagaagggc ctgagccaca gcgagaagat catcatgctg | 1380 |
| ctgaccttca gatccccta ctacatcggc cccatcaacg acaaccacaa gaagttcttc | 1440 |
| cccgaccgct gctgggtggt gaagaaggag aagagcccca gcggcaagac caccccctgg | 1500 |
| aacttcttcg accacatcga caaggagaag accgccgagg ccttcatcac cagccgcacc | 1560 |
| aacttctgca cataccctggt gggcgagagc gtgctgccca gagcagcct gctgtacagc | 1620 |
| gagtacaccg tgctgaacga gatcaacaac ctgcagatca tcatcgacgg caagaacatc | 1680 |
| tgcgacatca gctgaagca gaagatctac gaggacctgt tcaagaagta caagaagatc | 1740 |
| acccagaagc agatcagcac cttcatcaag cacgagggca tctgcaacaa gaccgacgag | 1800 |
| gtgatcatcc tggcatcga caaggagtgc accagcagcc tgaagagcta catcgagctg | 1860 |
| aagaacatct tcggcaagca ggtggacgag atcagcacca gaacatgct ggaggagatc | 1920 |
| atccgctggg ccaccatcta cgacgagggc gagggcaaga ccatcctgaa gaccaagatc | 1980 |
| aaggccgagt acgcaagta ctgcagcgac gagcagatca agaagatcct gaacctgaag | 2040 |
| ttcagcggct ggggccgcct gagccgcaag ttcctggaga ccgtgaccag cgagatgccc | 2100 |
| ggcttcagcg agcccgtgaa catcatcacc gccatgcgcg agacccagaa caacctgatg | 2160 |
| gagctgctga gcagcgagtt caccttcacc gagaacatca agaagatcaa cagcggcttc | 2220 |
| gaggacgccg agaagcagtt cagctacgac ggcctggtga gcccctgtt cctgagcccc | 2280 |
| agcgtgaaga agatgctgtg gcagaccctg aagctggtga aggagatcag ccacatcacc | 2340 |
| caggctcctc ctaagaagat cttcatcgag atggccaagg gcgccgagct ggagcctgct | 2400 |

```
cgcaccaaga cccgcctgaa gatcctgcag gacctgtaca acaactgcaa gaacgacgcc    2460
gacgcattca gcagcgagat caaggacctg agcggcaaga tcgagaacga ggacaacctg    2520
cgcctgcgca gcgacaagct gtacctgtac tacacccagc tgggcaagtg catgtactgc    2580
ggcaagccca tcgagatcgg ccacgtgttc gacaccagca actacgacat cgctgctatc    2640
tacccccaga gcaagatcaa ggacgacagc atcagcaacc gcgtgctggt gtgcagcagc    2700
tgcgccaaga caaggagga caagtaccct ctgaagagcg agatccagag caagcagcgc    2760
ggcttctgga acttcctgca gcgcaacaac ttcatcagcc tggagaagct gaaccgcctg    2820
acccgcgcca cccccatcag cgacgacgag accgccaagt catcgcccg ccagctggtg    2880 gagactcgcc aagctaccaa ggtggccgcc aaggtgctgg agaagatgtt ccccgagacc    2940
aagatcgtgt acagcaaggc cgagaccgtg agcatgttcc gcaacaagtt cgacatcgtg    3000
aagtgccgcg agatcaacga cttccaccac gcccacgacg cctacctgaa catcgtggtg    3060
ggcaacgtgt acaacaccaa gttccaccaac acccctgga atttcattaa ggagaagcgc    3120
gacaacccca agatcgccga cacctacaac tactacaagg tgttcgacta cgacgtgaag    3180
cgcaacaaca tcaccgcctg ggagaagggc aagaccatca tcaccgtgaa ggacatgctg    3240
aagcgcaaca ccccatcta cacccgccag gccgcctgca agaagggcga gctgttcaac    3300
cagaccatca tgaagaaggg cctgggccag caccccctga gaaggaggg ccccttcagc    3360 aacatcagca agtacggcgg ctacaacaag gtgagcgccg cctactacac cctgatcgag    3420
tacgaggaga agggcaacaa gatccgcagc ctggagacca tccccctgta cctggtgaag    3480
gacatccaga aggaccagga cgtgctgaag agctacctga ccgacctgct gggcaagaag    3540
gagttcaaga tcctggtgcc caagatcaag atcaacagcc tgctgaagat caacggcttc    3600
ccctgccaca tcaccggcaa gaccaacgac agcttcctgc tgcgccccgc cgtgcagttc    3660
tgctgcagca caacgaggt gctgtacttc aagaagatca tccgcttcag cgagatccgc    3720
agccagcgcg agaagatcgg caagaccatc agcccctacg aggacctgag cttccgcagc    3780
tacatcaagg agaacctgtg gaagaagacc aagaacgacg agatcggcga aaggagttc    3840 tacgacctgc tgcagaagaa gaacctggag atctacgaca tgctgctgac cagcacaag    3900 gacaccatct acaagaagcg ccccaacagc gccaccatcg acatcctggt gagggcaag    3960 gagaagttca gagcctgat catcgagaac cagttcgagg tgatcctgga gatcctgaag    4020
ctgttcagcg ccacccgcaa cgtgagcgac ctgcagcaca tcggcggcag caagtacagc    4080
ggcgtggcca agatcggcaa caagatcagc agcctggaca ctgcatcct gatctaccag    4140 agcatcaccg gcatcttcga gaagcgcatc gacctgctga aggtgtaa                4188
```

`<210> SEQ ID NO 15`
`<211> LENGTH: 20`
`<212> TYPE: DNA`
`<213> ORGANISM: Artificial Sequence`
`<220> FEATURE:`
`<223> OTHER INFORMATION: Synthetic guide sequence`

`<400> SEQUENCE: 15`

```
aacaaatgtg tcacaaagta                                                  20
```

`<210> SEQ ID NO 16`
`<211> LENGTH: 20`
`<212> TYPE: DNA`
`<213> ORGANISM: Artificial Sequence`
`<220> FEATURE:`

<223> OTHER INFORMATION: Synthetic guide sequence

<400> SEQUENCE: 16
acaaaactgt gctagacatg                                        20

<210> SEQ ID NO 17
<211> LENGTH: 20
<212> TYPE: DNA
<213> ORGANISM: Artificial Sequence
<220> FEATURE:
<223> OTHER INFORMATION: Synthetic guide sequence

<400> SEQUENCE: 17
tgtgctagac atgaggtcta                                        20

<210> SEQ ID NO 18
<211> LENGTH: 4
<212> TYPE: DNA
<213> ORGANISM: Artificial Sequence
<220> FEATURE:
<223> OTHER INFORMATION: AciI sequence recognition site

<400> SEQUENCE: 18 ccgc                                                          4

<210> SEQ ID NO 19
<211> LENGTH: 4
<212> TYPE: DNA
<213> ORGANISM: Artificial Sequence
<220> FEATURE:
<223> OTHER INFORMATION: AciI sequence recognition site

<400> SEQUENCE: 19 gcgg                                                          4

<210> SEQ ID NO 20
<211> LENGTH: 4
<212> TYPE: DNA
<213> ORGANISM: Artificial Sequence
<220> FEATURE:
<223> OTHER INFORMATION: MnlI sequence recognition site

<400> SEQUENCE: 20 cctc                                                          4

<210> SEQ ID NO 21
<211> LENGTH: 11
<212> TYPE: DNA
<213> ORGANISM: Artificial Sequence
<220> FEATURE:
<223> OTHER INFORMATION: MnlI Sequence cut site
<220> FEATURE:
<221> NAME/KEY: misc_feature
<222> LOCATION: 5-11
<223> OTHER INFORMATION: n = a, c, t, or g

<400> SEQUENCE: 21
cctcnnnnnn n                                                 11

<210> SEQ ID NO 22
<211> LENGTH: 11
<212> TYPE: DNA
<213> ORGANISM: Artificial Sequence
<220> FEATURE:
<223> OTHER INFORMATION: MnlI sequence cut site template strand
<220> FEATURE:
<221> NAME/KEY: misc_feature

```
<222> LOCATION: 1-7
<223> OTHER INFORMATION: n = a, c, t, or g

<400> SEQUENCE: 22
nnnnnnngag g                                                            11

<210> SEQ ID NO 23
<211> LENGTH: 5
<212> TYPE: DNA
<213> ORGANISM: Artificial Sequence
<220> FEATURE:
<223> OTHER INFORMATION: AlwI recognition site

<400> SEQUENCE: 23 ggatc                                                                    5

<210> SEQ ID NO 24
<211> LENGTH: 10
<212> TYPE: DNA
<213> ORGANISM: Artificial Sequence
<220> FEATURE:
<223> OTHER INFORMATION: AlwI sequence cut site
<220> FEATURE:
<221> NAME/KEY: misc_feature
<222> LOCATION: 6-10
<223> OTHER INFORMATION: n = a, c, t, or g

<400> SEQUENCE: 24 ggatcnnnnn                                                              10

<210> SEQ ID NO 25
<211> LENGTH: 10
<212> TYPE: DNA
<213> ORGANISM: Artificial Sequence
<220> FEATURE:
<223> OTHER INFORMATION: AlwI Sequence template cut site
<220> FEATURE:
<221> NAME/KEY: misc_feature
<222> LOCATION: 1-5
<223> OTHER INFORMATION: n = a, c, t, or g

<400> SEQUENCE: 25 nnnnngatcc                                                              10

<210> SEQ ID NO 26
<211> LENGTH: 5
<212> TYPE: DNA
<213> ORGANISM: Artificial Sequence
<220> FEATURE:
<223> OTHER INFORMATION: BbvI

<400> SEQUENCE: 26 gcagc                                                                    5

<210> SEQ ID NO 27
<211> LENGTH: 17
<212> TYPE: DNA
<213> ORGANISM: Artificial Sequence
<220> FEATURE:
<223> OTHER INFORMATION: BbvI
<220> FEATURE:
<221> NAME/KEY: misc_feature
<222> LOCATION: 6-17
<223> OTHER INFORMATION: n = a, c, t, or g

<400> SEQUENCE: 27
gcagcnnnnn nnnnnnn                                                      17
```

<210> SEQ ID NO 28
<211> LENGTH: 17
<212> TYPE: DNA
<213> ORGANISM: Artificial Sequence
<220> FEATURE:
<223> OTHER INFORMATION: BbvI
<220> FEATURE:
<221> NAME/KEY: misc_feature
<222> LOCATION: 1-12
<223> OTHER INFORMATION: n = a, c, t, or g

<400> SEQUENCE: 28
nnnnnnnnnn nngctgc                                                17

<210> SEQ ID NO 29
<211> LENGTH: 5
<212> TYPE: DNA
<213> ORGANISM: Artificial Sequence
<220> FEATURE:
<223> OTHER INFORMATION: BccI

<400> SEQUENCE: 29 ccatc                                                              5

<210> SEQ ID NO 30
<211> LENGTH: 17
<212> TYPE: DNA
<213> ORGANISM: Artificial Sequence
<220> FEATURE:
<223> OTHER INFORMATION: BccI
<220> FEATURE:
<221> NAME/KEY: misc_feature
<222> LOCATION: 6-17
<223> OTHER INFORMATION: n = a, c, t, or g

<400> SEQUENCE: 30 gcagcnnnn nnnnnnn                                                 17

<210> SEQ ID NO 31
<211> LENGTH: 17
<212> TYPE: DNA
<213> ORGANISM: Artificial Sequence
<220> FEATURE:
<223> OTHER INFORMATION: BccI
<220> FEATURE:
<221> NAME/KEY: misc_feature
<222> LOCATION: 1-12
<223> OTHER INFORMATION: n = a, c, t, or g

<400> SEQUENCE: 31
nnnnnnnnnn nngctgc                                                17

<210> SEQ ID NO 32
<211> LENGTH: 5
<212> TYPE: DNA
<213> ORGANISM: Artificial Sequence
<220> FEATURE:
<223> OTHER INFORMATION: BceAI

<400> SEQUENCE: 32 acggc                                                              5

<210> SEQ ID NO 33
<211> LENGTH: 19
<212> TYPE: DNA
<213> ORGANISM: Artificial Sequence
<220> FEATURE:
<223> OTHER INFORMATION: BceAI

```
<220> FEATURE:
<221> NAME/KEY: misc_feature
<222> LOCATION: 6-19
<223> OTHER INFORMATION: n = a, c, t, or g

<400> SEQUENCE: 33
acggcnnnnn nnnnnnnnn                                                19

<210> SEQ ID NO 34
<211> LENGTH: 19
<212> TYPE: DNA
<213> ORGANISM: Artificial Sequence
<220> FEATURE:
<223> OTHER INFORMATION: BceAI
<220> FEATURE:
<221> NAME/KEY: misc_feature
<222> LOCATION: 1-14
<223> OTHER INFORMATION: n = a, c, t, or g

<400> SEQUENCE: 34
nnnnnnnnnn nnnngccgt                                                19

<210> SEQ ID NO 35
<211> LENGTH: 5
<212> TYPE: DNA
<213> ORGANISM: Artificial Sequence
<220> FEATURE:
<223> OTHER INFORMATION: BsmAI

<400> SEQUENCE: 35 gtctc                                                                5

<210> SEQ ID NO 36
<211> LENGTH: 10
<212> TYPE: DNA
<213> ORGANISM: Artificial Sequence
<220> FEATURE:
<223> OTHER INFORMATION: BsmAI
<220> FEATURE:
<221> NAME/KEY: misc_feature
<222> LOCATION: 6-10
<223> OTHER INFORMATION: n = a, c, t, or g

<400> SEQUENCE: 36 gtctcnnnnn                                                          10

<210> SEQ ID NO 37
<211> LENGTH: 10
<212> TYPE: DNA
<213> ORGANISM: Artificial Sequence
<220> FEATURE:
<223> OTHER INFORMATION: BsmAI
<220> FEATURE:
<221> NAME/KEY: misc_feature
<222> LOCATION: 1-5
<223> OTHER INFORMATION: n = a, c, t, or g

<400> SEQUENCE: 37 nnnnngagac                                                          10

<210> SEQ ID NO 38
<211> LENGTH: 5
<212> TYPE: DNA
<213> ORGANISM: Artificial Sequence
<220> FEATURE:
<223> OTHER INFORMATION: BsmFI

<400> SEQUENCE: 38
```

-continued gggac 5

<210> SEQ ID NO 39
<211> LENGTH: 19
<212> TYPE: DNA
<213> ORGANISM: Artificial Sequence
<220> FEATURE:
<223> OTHER INFORMATION: BsmFI
<220> FEATURE:
<221> NAME/KEY: misc_feature
<222> LOCATION: 6-19
<223> OTHER INFORMATION: n = a, c, t, or g

<400> SEQUENCE: 39
gggacnnnnn nnnnnnnnn 19

<210> SEQ ID NO 40
<211> LENGTH: 19
<212> TYPE: DNA
<213> ORGANISM: Artificial Sequence
<220> FEATURE:
<223> OTHER INFORMATION: BsmFI
<220> FEATURE:
<221> NAME/KEY: misc_feature
<222> LOCATION: 1-14
<223> OTHER INFORMATION: n = a, c, t, or g

<400> SEQUENCE: 40
nnnnnnnnnn nnnngtccc 19

<210> SEQ ID NO 41
<211> LENGTH: 5
<212> TYPE: DNA
<213> ORGANISM: Artificial Sequence
<220> FEATURE:
<223> OTHER INFORMATION: BspCNI

<400> SEQUENCE: 41 ctcag 5

<210> SEQ ID NO 42
<211> LENGTH: 14
<212> TYPE: DNA
<213> ORGANISM: Artificial Sequence
<220> FEATURE:
<223> OTHER INFORMATION: BspCNI
<220> FEATURE:
<221> NAME/KEY: misc_feature
<222> LOCATION: 6-14
<223> OTHER INFORMATION: n = a, c, t, or g

<400> SEQUENCE: 42
ctcagnnnnn nnnn 14

<210> SEQ ID NO 43
<211> LENGTH: 14
<212> TYPE: DNA
<213> ORGANISM: Artificial Sequence
<220> FEATURE:
<223> OTHER INFORMATION: BspCNI
<220> FEATURE:
<221> NAME/KEY: misc_feature
<222> LOCATION: 1-9
<223> OTHER INFORMATION: n = a, c, t, or g

<400> SEQUENCE: 43
nnnnnnnnnc tgag 14

```
<210> SEQ ID NO 44
<211> LENGTH: 5
<212> TYPE: DNA
<213> ORGANISM: Artificial Sequence
<220> FEATURE:
<223> OTHER INFORMATION: BsrI

<400> SEQUENCE: 44 actgg                                                                    5

<210> SEQ ID NO 45
<211> LENGTH: 6
<212> TYPE: DNA
<213> ORGANISM: Artificial Sequence
<220> FEATURE:
<223> OTHER INFORMATION: BsrI
<220> FEATURE:
<221> NAME/KEY: misc_feature
<222> LOCATION: 6
<223> OTHER INFORMATION: n = a, c, t, or g

<400> SEQUENCE: 45 actggn                                                                   6

<210> SEQ ID NO 46
<211> LENGTH: 6
<212> TYPE: DNA
<213> ORGANISM: Artificial Sequence
<220> FEATURE:
<223> OTHER INFORMATION: BsrI
<220> FEATURE:
<221> NAME/KEY: misc_feature
<222> LOCATION: 1
<223> OTHER INFORMATION: n = a, c, t, or g

<400> SEQUENCE: 46 nccagt                                                                   6

<210> SEQ ID NO 47
<211> LENGTH: 5
<212> TYPE: DNA
<213> ORGANISM: Artificial Sequence
<220> FEATURE:
<223> OTHER INFORMATION: BtsCI

<400> SEQUENCE: 47 ggatg                                                                    5

<210> SEQ ID NO 48
<211> LENGTH: 7
<212> TYPE: DNA
<213> ORGANISM: Artificial Sequence
<220> FEATURE:
<223> OTHER INFORMATION: BtsCI
<220> FEATURE:
<221> NAME/KEY: misc_feature
<222> LOCATION: 6-7
<223> OTHER INFORMATION: n = a, c, t, or g

<400> SEQUENCE: 48 ggatgnn                                                                  7

<210> SEQ ID NO 49
<211> LENGTH: 7
<212> TYPE: DNA
<213> ORGANISM: Artificial Sequence
<220> FEATURE:
<223> OTHER INFORMATION: BtsCI
<220> FEATURE:
```

```
<221> NAME/KEY: misc_feature
<222> LOCATION: 1-2
<223> OTHER INFORMATION: n = a, c, t, or g

<400> SEQUENCE: 49 nncatcc                                                                    7

<210> SEQ ID NO 50
<211> LENGTH: 5
<212> TYPE: DNA
<213> ORGANISM: Artificial Sequence
<220> FEATURE:
<223> OTHER INFORMATION: FokI

<400> SEQUENCE: 50 ggatg                                                                      5

<210> SEQ ID NO 51
<211> LENGTH: 18
<212> TYPE: DNA
<213> ORGANISM: Artificial Sequence
<220> FEATURE:
<223> OTHER INFORMATION: FokI
<220> FEATURE:
<221> NAME/KEY: misc_feature
<222> LOCATION: 6-18
<223> OTHER INFORMATION: n = a, c, t, or g

<400> SEQUENCE: 51
ggatgnnnnn nnnnnnnn                                                       18

<210> SEQ ID NO 52
<211> LENGTH: 18
<212> TYPE: DNA
<213> ORGANISM: Artificial Sequence
<220> FEATURE:
<223> OTHER INFORMATION: FokI
<220> FEATURE:
<221> NAME/KEY: misc_feature
<222> LOCATION: 1-13
<223> OTHER INFORMATION: n = a, c, t, or g

<400> SEQUENCE: 52
nnnnnnnnnn nnncatcc                                                       18

<210> SEQ ID NO 53
<211> LENGTH: 5
<212> TYPE: DNA
<213> ORGANISM: Artificial Sequence
<220> FEATURE:
<223> OTHER INFORMATION: HgaI

<400> SEQUENCE: 53 gacgc                                                                      5

<210> SEQ ID NO 54
<211> LENGTH: 15
<212> TYPE: DNA
<213> ORGANISM: Artificial Sequence
<220> FEATURE:
<223> OTHER INFORMATION: HgaI
<220> FEATURE:
<221> NAME/KEY: misc_feature
<222> LOCATION: 6-15
<223> OTHER INFORMATION: n = a, c, t, or g

<400> SEQUENCE: 54
gacgcnnnnn nnnnn                                                          15
```

```
<210> SEQ ID NO 55
<211> LENGTH: 15
<212> TYPE: DNA
<213> ORGANISM: Artificial Sequence
<220> FEATURE:
<223> OTHER INFORMATION: HgaI
<220> FEATURE:
<221> NAME/KEY: misc_feature
<222> LOCATION: 1-10
<223> OTHER INFORMATION: n = a, c, t, or g

<400> SEQUENCE: 55
nnnnnnnnnn gcgtc                                                    15

<210> SEQ ID NO 56
<211> LENGTH: 5
<212> TYPE: DNA
<213> ORGANISM: Artificial Sequence
<220> FEATURE:
<223> OTHER INFORMATION: HphI

<400> SEQUENCE: 56 ggtga                                                                5

<210> SEQ ID NO 57
<211> LENGTH: 13
<212> TYPE: DNA
<213> ORGANISM: Artificial Sequence
<220> FEATURE:
<223> OTHER INFORMATION: HphI
<220> FEATURE:
<221> NAME/KEY: misc_feature
<222> LOCATION: 6-13
<223> OTHER INFORMATION: n = a, c, t, or g

<400> SEQUENCE: 57
ggtgannnnn nnn                                                      13

<210> SEQ ID NO 58
<211> LENGTH: 9
<212> TYPE: DNA
<213> ORGANISM: Artificial Sequence
<220> FEATURE:
<223> OTHER INFORMATION: HphI
<220> FEATURE:
<221> NAME/KEY: misc_feature
<222> LOCATION: 1-8
<223> OTHER INFORMATION: n = a, c, t, or g

<400> SEQUENCE: 58 nnnnnnnnt                                                            9

<210> SEQ ID NO 59
<211> LENGTH: 5
<212> TYPE: DNA
<213> ORGANISM: Artificial Sequence
<220> FEATURE:
<223> OTHER INFORMATION: HpyAV

<400> SEQUENCE: 59 ccttc                                                                5

<210> SEQ ID NO 60
<211> LENGTH: 11
<212> TYPE: DNA
<213> ORGANISM: Artificial Sequence
<220> FEATURE:
```

```
<223> OTHER INFORMATION: HpyAV
<220> FEATURE:
<221> NAME/KEY: misc_feature
<222> LOCATION: 6-11
<223> OTHER INFORMATION: n = a, c, t, or g

<400> SEQUENCE: 60
ccttcnnnnn n                                                          11

<210> SEQ ID NO 61
<211> LENGTH: 11
<212> TYPE: DNA
<213> ORGANISM: Artificial Sequence
<220> FEATURE:
<223> OTHER INFORMATION: HpyAV
<220> FEATURE:
<221> NAME/KEY: misc_feature
<222> LOCATION: 1-6
<223> OTHER INFORMATION: n = a, c, t, or g

<400> SEQUENCE: 61
nnnnnngaag g                                                          11

<210> SEQ ID NO 62
<211> LENGTH: 5
<212> TYPE: DNA
<213> ORGANISM: Artificial Sequence
<220> FEATURE:
<223> OTHER INFORMATION: MboII

<400> SEQUENCE: 62 gaaga                                                                  5

<210> SEQ ID NO 63
<211> LENGTH: 13
<212> TYPE: DNA
<213> ORGANISM: Artificial Sequence
<220> FEATURE:
<223> OTHER INFORMATION: MboII
<220> FEATURE:
<221> NAME/KEY: misc_feature
<222> LOCATION: 6-13
<223> OTHER INFORMATION: n = a, c, t, or g

<400> SEQUENCE: 63
gaagannnnn nnn                                                        13

<210> SEQ ID NO 64
<211> LENGTH: 13
<212> TYPE: DNA
<213> ORGANISM: Artificial Sequence
<220> FEATURE:
<223> OTHER INFORMATION: MboII
<220> FEATURE:
<221> NAME/KEY: misc_feature
<222> LOCATION: 1-8
<223> OTHER INFORMATION: n = a, c, t, or g

<400> SEQUENCE: 64
nnnnnnnntc ttc                                                        13

<210> SEQ ID NO 65
<211> LENGTH: 5
<212> TYPE: DNA
<213> ORGANISM: Artificial Sequence
<220> FEATURE:
<223> OTHER INFORMATION: MlyI

<400> SEQUENCE: 65
``` gagtc                                                                           5

<210> SEQ ID NO 66
<211> LENGTH: 10
<212> TYPE: DNA
<213> ORGANISM: Artificial Sequence
<220> FEATURE:
<223> OTHER INFORMATION: MlyI
<220> FEATURE:
<221> NAME/KEY: misc_feature
<222> LOCATION: 6-10
<223> OTHER INFORMATION: n = a, c, t, or g

<400> SEQUENCE: 66 gagtcnnnnn                                                                      10

<210> SEQ ID NO 67
<211> LENGTH: 10
<212> TYPE: DNA
<213> ORGANISM: Artificial Sequence
<220> FEATURE:
<223> OTHER INFORMATION: MlyI
<220> FEATURE:
<221> NAME/KEY: misc_feature
<222> LOCATION: 1-5
<223> OTHER INFORMATION: n = a, c, t, or g

<400> SEQUENCE: 67 nnnnngactc                                                                      10

<210> SEQ ID NO 68
<211> LENGTH: 5
<212> TYPE: DNA
<213> ORGANISM: Artificial Sequence
<220> FEATURE:
<223> OTHER INFORMATION: PleI

<400> SEQUENCE: 68 gagtc                                                                           5

<210> SEQ ID NO 69
<211> LENGTH: 10
<212> TYPE: DNA
<213> ORGANISM: Artificial Sequence
<220> FEATURE:
<223> OTHER INFORMATION: PleI
<220> FEATURE:
<221> NAME/KEY: misc_feature
<222> LOCATION: 6-10
<223> OTHER INFORMATION: n = a, c, t, or g

<400> SEQUENCE: 69 gagtcnnnnn                                                                      10

<210> SEQ ID NO 70
<211> LENGTH: 10
<212> TYPE: DNA
<213> ORGANISM: Artificial Sequence
<220> FEATURE:
<223> OTHER INFORMATION: PleI
<220> FEATURE:
<221> NAME/KEY: misc_feature
<222> LOCATION: 1-5
<223> OTHER INFORMATION: n = a, c, t, or g

<400> SEQUENCE: 70 nnnnngactc                                                                      10

<210> SEQ ID NO 71
<211> LENGTH: 5
<212> TYPE: DNA
<213> ORGANISM: Artificial Sequence
<220> FEATURE:
<223> OTHER INFORMATION: SfaNI

<400> SEQUENCE: 71 gcatc                                                                    5

<210> SEQ ID NO 72
<211> LENGTH: 14
<212> TYPE: DNA
<213> ORGANISM: Artificial Sequence
<220> FEATURE:
<223> OTHER INFORMATION: SfaNI
<220> FEATURE:
<221> NAME/KEY: misc_feature
<222> LOCATION: 6-14
<223> OTHER INFORMATION: n = a, c, t, or g

<400> SEQUENCE: 72
gcatcnnnnn nnnn                                                         14

<210> SEQ ID NO 73
<211> LENGTH: 14
<212> TYPE: DNA
<213> ORGANISM: Artificial Sequence
<220> FEATURE:
<223> OTHER INFORMATION: SfaNI
<220> FEATURE:
<221> NAME/KEY: misc_feature
<222> LOCATION: 1-9
<223> OTHER INFORMATION: n = a, c, t, or g

<400> SEQUENCE: 73
nnnnnnnnng atgc                                                         14

<210> SEQ ID NO 74
<211> LENGTH: 6
<212> TYPE: DNA
<213> ORGANISM: Artificial Sequence
<220> FEATURE:
<223> OTHER INFORMATION: AcuI

<400> SEQUENCE: 74 ctgaag                                                                   6

<210> SEQ ID NO 75
<211> LENGTH: 22
<212> TYPE: DNA
<213> ORGANISM: Artificial Sequence
<220> FEATURE:
<223> OTHER INFORMATION: AcuI
<220> FEATURE:
<221> NAME/KEY: misc_feature
<222> LOCATION: 7-22
<223> OTHER INFORMATION: n = a, c, t, or g

<400> SEQUENCE: 75
ctgaagnnnn nnnnnnnnnn nn                                                22

<210> SEQ ID NO 76
<211> LENGTH: 22
<212> TYPE: DNA
<213> ORGANISM: Artificial Sequence
<220> FEATURE:
<223> OTHER INFORMATION: AcuI

```
<220> FEATURE:
<221> NAME/KEY: misc_feature
<222> LOCATION: 1-16
<223> OTHER INFORMATION: n = a, c, t, or g

<400> SEQUENCE: 76
nnnnnnnnnn nnnnnncttc ag                                              22

<210> SEQ ID NO 77
<211> LENGTH: 6
<212> TYPE: DNA
<213> ORGANISM: Artificial Sequence
<220> FEATURE:
<223> OTHER INFORMATION: BciVI

<400> SEQUENCE: 77 gtatcc                                                                 6

<210> SEQ ID NO 78
<211> LENGTH: 12
<212> TYPE: DNA
<213> ORGANISM: Artificial Sequence
<220> FEATURE:
<223> OTHER INFORMATION: BciVI
<220> FEATURE:
<221> NAME/KEY: misc_feature
<222> LOCATION: 7-12
<223> OTHER INFORMATION: n = a, c, t, or g

<400> SEQUENCE: 78
gtatccnnnn nn                                                         12

<210> SEQ ID NO 79
<211> LENGTH: 12
<212> TYPE: DNA
<213> ORGANISM: Artificial Sequence
<220> FEATURE:
<223> OTHER INFORMATION: BciVI
<220> FEATURE:
<221> NAME/KEY: misc_feature
<222> LOCATION: 1-6
<223> OTHER INFORMATION: n = a, c, t, or g

<400> SEQUENCE: 79
nnnnnnggat ac                                                         12

<210> SEQ ID NO 80
<211> LENGTH: 6
<212> TYPE: DNA
<213> ORGANISM: Artificial Sequence
<220> FEATURE:
<223> OTHER INFORMATION: BfuAI

<400> SEQUENCE: 80 acctgc                                                                 6

<210> SEQ ID NO 81
<211> LENGTH: 14
<212> TYPE: DNA
<213> ORGANISM: Artificial Sequence
<220> FEATURE:
<223> OTHER INFORMATION: BfuAI
<220> FEATURE:
<221> NAME/KEY: misc_feature
<222> LOCATION: 7-14
<223> OTHER INFORMATION: n = a, c, t, or g

<400> SEQUENCE: 81
```
acctgcnnnn nnnn                                                              14

<210> SEQ ID NO 82
<211> LENGTH: 14
<212> TYPE: DNA
<213> ORGANISM: Artificial Sequence
<220> FEATURE:
<223> OTHER INFORMATION: BfuAI
<220> FEATURE:
<221> NAME/KEY: misc_feature
<222> LOCATION: 1-8
<223> OTHER INFORMATION: n = a, c, t, or g

<400> SEQUENCE: 82
nnnnnnnngc aggt                                                              14

<210> SEQ ID NO 83
<211> LENGTH: 6
<212> TYPE: DNA
<213> ORGANISM: Artificial Sequence
<220> FEATURE:
<223> OTHER INFORMATION: BmgBI

<400> SEQUENCE: 83 cacgtc                                                                        6

<210> SEQ ID NO 84
<211> LENGTH: 6
<212> TYPE: DNA
<213> ORGANISM: Artificial Sequence
<220> FEATURE:
<223> OTHER INFORMATION: BmgBI

<400> SEQUENCE: 84 cacgtc                                                                        6

<210> SEQ ID NO 85
<211> LENGTH: 6
<212> TYPE: DNA
<213> ORGANISM: Artificial Sequence
<220> FEATURE:
<223> OTHER INFORMATION: BmgBI

<400> SEQUENCE: 85 gacgtg                                                                        6

<210> SEQ ID NO 86
<211> LENGTH: 6
<212> TYPE: DNA
<213> ORGANISM: Artificial Sequence
<220> FEATURE:
<223> OTHER INFORMATION: BmrI

<400> SEQUENCE: 86 actggg                                                                        6

<210> SEQ ID NO 87
<211> LENGTH: 11
<212> TYPE: DNA
<213> ORGANISM: Artificial Sequence
<220> FEATURE:
<223> OTHER INFORMATION: BmrI
<220> FEATURE:
<221> NAME/KEY: misc_feature
<222> LOCATION: 7-11
<223> OTHER INFORMATION: n = a, c, t, or g

<400> SEQUENCE: 87

```
actgggnnnn n                                                               11

<210> SEQ ID NO 88
<211> LENGTH: 11
<212> TYPE: DNA
<213> ORGANISM: Artificial Sequence
<220> FEATURE:
<223> OTHER INFORMATION: BmrI
<220> FEATURE:
<221> NAME/KEY: misc_feature
<222> LOCATION: 1-5
<223> OTHER INFORMATION: n = a, c, t, or g

<400> SEQUENCE: 88
nnnnncccag t                                                               11

<210> SEQ ID NO 89
<211> LENGTH: 6
<212> TYPE: DNA
<213> ORGANISM: Artificial Sequence
<220> FEATURE:
<223> OTHER INFORMATION: BpmI

<400> SEQUENCE: 89 ctggag                                                                      6

<210> SEQ ID NO 90
<211> LENGTH: 22
<212> TYPE: DNA
<213> ORGANISM: Artificial Sequence
<220> FEATURE:
<223> OTHER INFORMATION: BpmI
<220> FEATURE:
<221> NAME/KEY: misc_feature
<222> LOCATION: 7-22
<223> OTHER INFORMATION: n = a, c, t, or g

<400> SEQUENCE: 90
ctggagnnnn nnnnnnnnnn nn                                                   22

<210> SEQ ID NO 91
<211> LENGTH: 22
<212> TYPE: DNA
<213> ORGANISM: Artificial Sequence
<220> FEATURE:
<223> OTHER INFORMATION: BpmI
<220> FEATURE:
<221> NAME/KEY: misc_feature
<222> LOCATION: 1-16
<223> OTHER INFORMATION: n = a, c, t, or g

<400> SEQUENCE: 91
nnnnnnnnnn nnnnnnctcc ag                                                   22

<210> SEQ ID NO 92
<211> LENGTH: 6
<212> TYPE: DNA
<213> ORGANISM: Artificial Sequence
<220> FEATURE:
<223> OTHER INFORMATION: BpuEI

<400> SEQUENCE: 92 cttgag                                                                      6

<210> SEQ ID NO 93
<211> LENGTH: 22
<212> TYPE: DNA
```

```
<213> ORGANISM: Artificial Sequence
<220> FEATURE:
<223> OTHER INFORMATION: BpuEI
<220> FEATURE:
<221> NAME/KEY: misc_feature
<222> LOCATION: 7-22
<223> OTHER INFORMATION: n = a, c, t, or g

<400> SEQUENCE: 93
cttgagnnnn nnnnnnnnnn nn                                              22

<210> SEQ ID NO 94
<211> LENGTH: 22
<212> TYPE: DNA
<213> ORGANISM: Artificial Sequence
<220> FEATURE:
<223> OTHER INFORMATION: BpuEI
<220> FEATURE:
<221> NAME/KEY: misc_feature
<222> LOCATION: 1-16
<223> OTHER INFORMATION: n = a, c, t, or g

<400> SEQUENCE: 94
nnnnnnnnnn nnnnnnctca ag                                              22

<210> SEQ ID NO 95
<211> LENGTH: 6
<212> TYPE: DNA
<213> ORGANISM: Artificial Sequence
<220> FEATURE:
<223> OTHER INFORMATION: BsaI

<400> SEQUENCE: 95 ggtctc                                                                 6

<210> SEQ ID NO 96
<211> LENGTH: 11
<212> TYPE: DNA
<213> ORGANISM: Artificial Sequence
<220> FEATURE:
<223> OTHER INFORMATION: BsaI
<220> FEATURE:
<221> NAME/KEY: misc_feature
<222> LOCATION: 7-11
<223> OTHER INFORMATION: n = a, c, t, or g

<400> SEQUENCE: 96
ggtctcnnnn n                                                          11

<210> SEQ ID NO 97
<211> LENGTH: 11
<212> TYPE: DNA
<213> ORGANISM: Artificial Sequence
<220> FEATURE:
<223> OTHER INFORMATION: BsaI
<220> FEATURE:
<221> NAME/KEY: misc_feature
<222> LOCATION: 1-5
<223> OTHER INFORMATION: n = a, c, t, or g

<400> SEQUENCE: 97
nnnnngagac c                                                          11

<210> SEQ ID NO 98
<211> LENGTH: 6
<212> TYPE: DNA
<213> ORGANISM: Artificial Sequence
<220> FEATURE:
<223> OTHER INFORMATION: BseRI
```

```
<400> SEQUENCE: 98 gaggag                                                              6

<210> SEQ ID NO 99
<211> LENGTH: 16
<212> TYPE: DNA
<213> ORGANISM: Artificial Sequence
<220> FEATURE:
<223> OTHER INFORMATION: BseRI
<220> FEATURE:
<221> NAME/KEY: misc_feature
<222> LOCATION: 7-16
<223> OTHER INFORMATION: n = a, c, t, or g

<400> SEQUENCE: 99
gaggagnnnn nnnnnn                                                  16

<210> SEQ ID NO 100
<211> LENGTH: 16
<212> TYPE: DNA
<213> ORGANISM: Artificial Sequence
<220> FEATURE:
<223> OTHER INFORMATION: BseRI
<220> FEATURE:
<221> NAME/KEY: misc_feature
<222> LOCATION: 1-10
<223> OTHER INFORMATION: n = a, c, t, or g

<400> SEQUENCE: 100
nnnnnnnnnn ctcctc                                                  16

<210> SEQ ID NO 101
<211> LENGTH: 6
<212> TYPE: DNA
<213> ORGANISM: Artificial Sequence
<220> FEATURE:
<223> OTHER INFORMATION: BsgI

<400> SEQUENCE: 101 gtgcag                                                              6

<210> SEQ ID NO 102
<211> LENGTH: 22
<212> TYPE: DNA
<213> ORGANISM: Artificial Sequence
<220> FEATURE:
<223> OTHER INFORMATION: BsgI
<220> FEATURE:
<221> NAME/KEY: misc_feature
<222> LOCATION: 7-22
<223> OTHER INFORMATION: n = a, c, t, or g

<400> SEQUENCE: 102
gtgcagnnnn nnnnnnnnnn nn                                           22

<210> SEQ ID NO 103
<211> LENGTH: 22
<212> TYPE: DNA
<213> ORGANISM: Artificial Sequence
<220> FEATURE:
<223> OTHER INFORMATION: BsgI
<220> FEATURE:
<221> NAME/KEY: misc_feature
<222> LOCATION: 1-16
<223> OTHER INFORMATION: n = a, c, t, or g

<400> SEQUENCE: 103
```

```
nnnnnnnnnn nnnnnnctgc ac                                          22

<210> SEQ ID NO 104
<211> LENGTH: 6
<212> TYPE: DNA
<213> ORGANISM: Artificial Sequence
<220> FEATURE:
<223> OTHER INFORMATION: BsmI

<400> SEQUENCE: 104 gaatgc                                                             6

<210> SEQ ID NO 105
<211> LENGTH: 7
<212> TYPE: DNA
<213> ORGANISM: Artificial Sequence
<220> FEATURE:
<223> OTHER INFORMATION: BsmI
<220> FEATURE:
<221> NAME/KEY: misc_feature
<222> LOCATION: 7
<223> OTHER INFORMATION: n = a, c, t, or g

<400> SEQUENCE: 105 gaatgcn                                                            7

<210> SEQ ID NO 106
<211> LENGTH: 7
<212> TYPE: DNA
<213> ORGANISM: Artificial Sequence
<220> FEATURE:
<223> OTHER INFORMATION: BsmI
<220> FEATURE:
<221> NAME/KEY: misc_feature
<222> LOCATION: 1
<223> OTHER INFORMATION: n = a, c, t, or g

<400> SEQUENCE: 106 ngcattc                                                            7

<210> SEQ ID NO 107
<211> LENGTH: 6
<212> TYPE: DNA
<213> ORGANISM: Artificial Sequence
<220> FEATURE:
<223> OTHER INFORMATION: BspMI

<400> SEQUENCE: 107 acctgc                                                             6

<210> SEQ ID NO 108
<211> LENGTH: 14
<212> TYPE: DNA
<213> ORGANISM: Artificial Sequence
<220> FEATURE:
<223> OTHER INFORMATION: BspMI
<220> FEATURE:
<221> NAME/KEY: misc_feature
<222> LOCATION: 7-14
<223> OTHER INFORMATION: n = a, c, t, or g

<400> SEQUENCE: 108
acctgcnnnn nnnn                                                   14

<210> SEQ ID NO 109
<211> LENGTH: 14
<212> TYPE: DNA
<213> ORGANISM: Artificial Sequence
```

```
<220> FEATURE:
<223> OTHER INFORMATION: BspMI
<220> FEATURE:
<221> NAME/KEY: misc_feature
<222> LOCATION: 1-8
<223> OTHER INFORMATION: n = a, c, t, or g

<400> SEQUENCE: 109
nnnnnnnngc aggt                                                        14

<210> SEQ ID NO 110
<211> LENGTH: 6
<212> TYPE: DNA
<213> ORGANISM: Artificial Sequence
<220> FEATURE:
<223> OTHER INFORMATION: BsrBI

<400> SEQUENCE: 110 ccgctc                                                                  6

<210> SEQ ID NO 111
<211> LENGTH: 6
<212> TYPE: DNA
<213> ORGANISM: Artificial Sequence
<220> FEATURE:
<223> OTHER INFORMATION: BsrBI

<400> SEQUENCE: 111 gagcgg                                                                  6

<210> SEQ ID NO 112
<211> LENGTH: 6
<212> TYPE: DNA
<213> ORGANISM: Artificial Sequence
<220> FEATURE:
<223> OTHER INFORMATION: BsrDI

<400> SEQUENCE: 112 gcaatg                                                                  6

<210> SEQ ID NO 113
<211> LENGTH: 8
<212> TYPE: DNA
<213> ORGANISM: Artificial Sequence
<220> FEATURE:
<223> OTHER INFORMATION: BsrDI
<220> FEATURE:
<221> NAME/KEY: misc_feature
<222> LOCATION: 7-8
<223> OTHER INFORMATION: n = a, c, t, or g

<400> SEQUENCE: 113 gcaatgnn                                                                8

<210> SEQ ID NO 114
<211> LENGTH: 8
<212> TYPE: DNA
<213> ORGANISM: Artificial Sequence
<220> FEATURE:
<223> OTHER INFORMATION: BsrDI
<220> FEATURE:
<221> NAME/KEY: misc_feature
<222> LOCATION: 1-2
<223> OTHER INFORMATION: n = a, c, t, or g

<400> SEQUENCE: 114 nncattgc                                                                8
```

<210> SEQ ID NO 115
<211> LENGTH: 6
<212> TYPE: DNA
<213> ORGANISM: Artificial Sequence
<220> FEATURE:
<223> OTHER INFORMATION: BtgZI

<400> SEQUENCE: 115 gcgatg                                                                    6

<210> SEQ ID NO 116
<211> LENGTH: 20
<212> TYPE: DNA
<213> ORGANISM: Artificial Sequence
<220> FEATURE:
<223> OTHER INFORMATION: BtgZI
<220> FEATURE:
<221> NAME/KEY: misc_feature
<222> LOCATION: 7-20
<223> OTHER INFORMATION: n = a, c, t, or g

<400> SEQUENCE: 116
gcgatgnnnn nnnnnnnnnn                                                    20

<210> SEQ ID NO 117
<211> LENGTH: 20
<212> TYPE: DNA
<213> ORGANISM: Artificial Sequence
<220> FEATURE:
<223> OTHER INFORMATION: BtgZI
<220> FEATURE:
<221> NAME/KEY: misc_feature
<222> LOCATION: 1-14
<223> OTHER INFORMATION: n = a, c, t, or g

<400> SEQUENCE: 117
nnnnnnnnnn nnnncatcgc                                                    20

<210> SEQ ID NO 118
<211> LENGTH: 6
<212> TYPE: DNA
<213> ORGANISM: Artificial Sequence
<220> FEATURE:
<223> OTHER INFORMATION: BtsI

<400> SEQUENCE: 118 gcagtg                                                                    6

<210> SEQ ID NO 119
<211> LENGTH: 8
<212> TYPE: DNA
<213> ORGANISM: Artificial Sequence
<220> FEATURE:
<223> OTHER INFORMATION: BtsI
<220> FEATURE:
<221> NAME/KEY: misc_feature
<222> LOCATION: 7-8
<223> OTHER INFORMATION: n = a, c, t, or g

<400> SEQUENCE: 119 gcagtgnn                                                                  8

<210> SEQ ID NO 120
<211> LENGTH: 8
<212> TYPE: DNA
<213> ORGANISM: Artificial Sequence
<220> FEATURE:
<223> OTHER INFORMATION: BtsI

```
<220> FEATURE:
<221> NAME/KEY: misc_feature
<222> LOCATION: 1-2
<223> OTHER INFORMATION: n = a, c, t, or g

<400> SEQUENCE: 120 nncactgc                                                                 8

<210> SEQ ID NO 121
<211> LENGTH: 6
<212> TYPE: DNA
<213> ORGANISM: Artificial Sequence
<220> FEATURE:
<223> OTHER INFORMATION: EarI

<400> SEQUENCE: 121 ctcttc                                                                   6

<210> SEQ ID NO 122
<211> LENGTH: 10
<212> TYPE: DNA
<213> ORGANISM: Artificial Sequence
<220> FEATURE:
<223> OTHER INFORMATION: EarI
<220> FEATURE:
<221> NAME/KEY: misc_feature
<222> LOCATION: 7-10
<223> OTHER INFORMATION: n = a, c, t, or g

<400> SEQUENCE: 122 ctcttcnnnn                                                              10

<210> SEQ ID NO 123
<211> LENGTH: 10
<212> TYPE: DNA
<213> ORGANISM: Artificial Sequence
<220> FEATURE:
<223> OTHER INFORMATION: EarI
<220> FEATURE:
<221> NAME/KEY: misc_feature
<222> LOCATION: 1-4
<223> OTHER INFORMATION: n = a, c, t, or g

<400> SEQUENCE: 123 nnnngaagag                                                              10

<210> SEQ ID NO 124
<211> LENGTH: 6
<212> TYPE: DNA
<213> ORGANISM: Artificial Sequence
<220> FEATURE:
<223> OTHER INFORMATION: EciI

<400> SEQUENCE: 124 ggcgga                                                                   6

<210> SEQ ID NO 125
<211> LENGTH: 17
<212> TYPE: DNA
<213> ORGANISM: Artificial Sequence
<220> FEATURE:
<223> OTHER INFORMATION: EciI
<220> FEATURE:
<221> NAME/KEY: misc_feature
<222> LOCATION: 7-17
<223> OTHER INFORMATION: n = a, c, t, or g

<400> SEQUENCE: 125
```

```
ggcggannnn nnnnnnn                                              17

<210> SEQ ID NO 126
<211> LENGTH: 17
<212> TYPE: DNA
<213> ORGANISM: Artificial Sequence
<220> FEATURE:
<223> OTHER INFORMATION: EciI
<220> FEATURE:
<221> NAME/KEY: misc_feature
<222> LOCATION: 1-11
<223> OTHER INFORMATION: n = a, c, t, or g

<400> SEQUENCE: 126
nnnnnnnnnn ntccgcc                                              17

<210> SEQ ID NO 127
<211> LENGTH: 6
<212> TYPE: DNA
<213> ORGANISM: Artificial Sequence
<220> FEATURE:
<223> OTHER INFORMATION: MmeI
<220> FEATURE:
<221> NAME/KEY: misc_feature
<222> LOCATION: 4
<223> OTHER INFORMATION: n = a, c, t, or g

<400> SEQUENCE: 127 tccnac                                                           6

<210> SEQ ID NO 128
<211> LENGTH: 26
<212> TYPE: DNA
<213> ORGANISM: Artificial Sequence
<220> FEATURE:
<223> OTHER INFORMATION: MmeI
<220> FEATURE:
<221> NAME/KEY: misc_feature
<222> LOCATION: 7-26
<223> OTHER INFORMATION: n = a, c, t, or g

<400> SEQUENCE: 128
tccracnnnn nnnnnnnnnn nnnnnn                                    26

<210> SEQ ID NO 129
<211> LENGTH: 26
<212> TYPE: DNA
<213> ORGANISM: Artificial Sequence
<220> FEATURE:
<223> OTHER INFORMATION: MmeI
<220> FEATURE:
<221> NAME/KEY: misc_feature
<222> LOCATION: 1-20
<223> OTHER INFORMATION: n = a, c, t, or g

<400> SEQUENCE: 129
nnnnnnnnnn nnnnnnnnnn gtygga                                    26

<210> SEQ ID NO 130
<211> LENGTH: 6
<212> TYPE: DNA
<213> ORGANISM: Artificial Sequence
<220> FEATURE:
<223> OTHER INFORMATION: NmeAIII

<400> SEQUENCE: 130 gccgag                                                           6
```

```
<210> SEQ ID NO 131
<211> LENGTH: 27
<212> TYPE: DNA
<213> ORGANISM: Artificial Sequence
<220> FEATURE:
<223> OTHER INFORMATION: NmeAIII
<220> FEATURE:
<221> NAME/KEY: misc_feature
<222> LOCATION: 7-27
<223> OTHER INFORMATION: n = a, c, t, or g

<400> SEQUENCE: 131
gccgagnnnn nnnnnnnnnn nnnnnnn                                27

<210> SEQ ID NO 132
<211> LENGTH: 27
<212> TYPE: DNA
<213> ORGANISM: Artificial Sequence
<220> FEATURE:
<223> OTHER INFORMATION: NmeAIII
<220> FEATURE:
<221> NAME/KEY: misc_feature
<222> LOCATION: 1-21
<223> OTHER INFORMATION: n = a, c, t, or g

<400> SEQUENCE: 132
nnnnnnnnnn nnnnnnnnnn nctcggc                                27

<210> SEQ ID NO 133
<211> LENGTH: 7
<212> TYPE: DNA
<213> ORGANISM: Artificial Sequence
<220> FEATURE:
<223> OTHER INFORMATION: BbvCI

<400> SEQUENCE: 133 cctcagc                                                       7

<210> SEQ ID NO 134
<211> LENGTH: 7
<212> TYPE: DNA
<213> ORGANISM: Artificial Sequence
<220> FEATURE:
<223> OTHER INFORMATION: BbvCI

<400> SEQUENCE: 134 gctgagg                                                       7

<210> SEQ ID NO 135
<211> LENGTH: 7
<212> TYPE: DNA
<213> ORGANISM: Artificial Sequence
<220> FEATURE:
<223> OTHER INFORMATION: Bpu10I
<220> FEATURE:
<221> NAME/KEY: misc_feature
<222> LOCATION: 4
<223> OTHER INFORMATION: n = a, c, t, or g

<400> SEQUENCE: 135 cctnagc                                                       7

<210> SEQ ID NO 136
<211> LENGTH: 7
<212> TYPE: DNA
<213> ORGANISM: Artificial Sequence
<220> FEATURE:
<223> OTHER INFORMATION: Bpu10I
<220> FEATURE:
```

```
<221> NAME/KEY: misc_feature
<222> LOCATION: 4
<223> OTHER INFORMATION: n = a, c, t, or g

<400> SEQUENCE: 136 gctnagg                                                                    7

<210> SEQ ID NO 137
<211> LENGTH: 7
<212> TYPE: DNA
<213> ORGANISM: Artificial Sequence
<220> FEATURE:
<223> OTHER INFORMATION: BspQI

<400> SEQUENCE: 137 gctcttc                                                                    7

<210> SEQ ID NO 138
<211> LENGTH: 11
<212> TYPE: DNA
<213> ORGANISM: Artificial Sequence
<220> FEATURE:
<223> OTHER INFORMATION: BspQI
<220> FEATURE:
<221> NAME/KEY: misc_feature
<222> LOCATION: 8-11
<223> OTHER INFORMATION: n = a, c, t, or g

<400> SEQUENCE: 138
gctcttcnnn n                                                              11

<210> SEQ ID NO 139
<211> LENGTH: 11
<212> TYPE: DNA
<213> ORGANISM: Artificial Sequence
<220> FEATURE:
<223> OTHER INFORMATION: BspQI
<220> FEATURE:
<221> NAME/KEY: misc_feature
<222> LOCATION: 1-4
<223> OTHER INFORMATION: n = a, c, t, or g

<400> SEQUENCE: 139
nnnngaagag c                                                              11

<210> SEQ ID NO 140
<211> LENGTH: 7
<212> TYPE: DNA
<213> ORGANISM: Artificial Sequence
<220> FEATURE:
<223> OTHER INFORMATION: SapI

<400> SEQUENCE: 140 gctcttc                                                                    7

<210> SEQ ID NO 141
<211> LENGTH: 11
<212> TYPE: DNA
<213> ORGANISM: Artificial Sequence
<220> FEATURE:
<223> OTHER INFORMATION: SapI
<220> FEATURE:
<221> NAME/KEY: misc_feature
<222> LOCATION: 8-11
<223> OTHER INFORMATION: n = a, c, t, or g

<400> SEQUENCE: 141
gctcttcnnn n                                                              11
```

```
<210> SEQ ID NO 142
<211> LENGTH: 11
<212> TYPE: DNA
<213> ORGANISM: Artificial Sequence
<220> FEATURE:
<223> OTHER INFORMATION: SapI
<220> FEATURE:
<221> NAME/KEY: misc_feature
<222> LOCATION: 1-4
<223> OTHER INFORMATION: n = a, c, t, or g

<400> SEQUENCE: 142
nnnngaagag c                                                          11

<210> SEQ ID NO 143
<211> LENGTH: 11
<212> TYPE: DNA
<213> ORGANISM: Artificial Sequence
<220> FEATURE:
<223> OTHER INFORMATION: BaeI
<220> FEATURE:
<221> NAME/KEY: misc_feature
<222> LOCATION: 3-6
<223> OTHER INFORMATION: n = a, c, t, or g

<400> SEQUENCE: 143
acnnnngtay c                                                          11

<210> SEQ ID NO 144
<211> LENGTH: 37
<212> TYPE: DNA
<213> ORGANISM: Artificial Sequence
<220> FEATURE:
<223> OTHER INFORMATION: BaeI
<220> FEATURE:
<221> NAME/KEY: misc_feature
<222> LOCATION: 1-13, 17-21, 26-37
<223> OTHER INFORMATION: n = a, c, t, or g

<400> SEQUENCE: 144
nnnnnnnnnn nnncaannnn ngtggnnnnn nnnnnnn                              37

<210> SEQ ID NO 145
<211> LENGTH: 37
<212> TYPE: DNA
<213> ORGANISM: Artificial Sequence
<220> FEATURE:
<223> OTHER INFORMATION: BaeI
<220> FEATURE:
<221> NAME/KEY: misc_feature
<222> LOCATION: 1-12, 17-21, 25-37
<223> OTHER INFORMATION: n = a, c, t, or g

<400> SEQUENCE: 145
nnnnnnnnnn nnccacnnnn nttgnnnnnn nnnnnnn                              37

<210> SEQ ID NO 146
<211> LENGTH: 11
<212> TYPE: DNA
<213> ORGANISM: Artificial Sequence
<220> FEATURE:
<223> OTHER INFORMATION: BsaXI
<220> FEATURE:
<221> NAME/KEY: misc_feature
<222> LOCATION: 3-7
<223> OTHER INFORMATION: n = a, c, t, or g

<400> SEQUENCE: 146
```
acnnnnnctc c                                                           11

<210> SEQ ID NO 147
<211> LENGTH: 33
<212> TYPE: DNA
<213> ORGANISM: Artificial Sequence
<220> FEATURE:
<223> OTHER INFORMATION: BsaXI
<220> FEATURE:
<221> NAME/KEY: misc_feature
<222> LOCATION: 1-12, 15-19, 24-33
<223> OTHER INFORMATION: n = a, c, t, or g

<400> SEQUENCE: 147
nnnnnnnnnn nnacnnnnnc tcnnnnnnnn nnn                                   33

<210> SEQ ID NO 148
<211> LENGTH: 33
<212> TYPE: DNA
<213> ORGANISM: Artificial Sequence
<220> FEATURE:
<223> OTHER INFORMATION: BsaXI
<220> FEATURE:
<221> NAME/KEY: misc_feature
<222> LOCATION: 1-10, 15-19, 22-33
<223> OTHER INFORMATION: n = a, c, t, or g

<400> SEQUENCE: 148
nnnnnnnnnn ggagnnnnng tnnnnnnnnn nnn                                   33

<210> SEQ ID NO 149
<211> LENGTH: 12
<212> TYPE: DNA
<213> ORGANISM: Artificial Sequence
<220> FEATURE:
<223> OTHER INFORMATION: CspCI
<220> FEATURE:
<221> NAME/KEY: misc_feature
<222> LOCATION: 4-8
<223> OTHER INFORMATION: n = a, c, t, or g

<400> SEQUENCE: 149
caannnnngt gg                                                          12

<210> SEQ ID NO 150
<211> LENGTH: 37
<212> TYPE: DNA
<213> ORGANISM: Artificial Sequence
<220> FEATURE:
<223> OTHER INFORMATION: CspCI
<220> FEATURE:
<221> NAME/KEY: misc_feature
<222> LOCATION: 1-13, 17-21, 26-37
<223> OTHER INFORMATION: n = a, c, t, or g

<400> SEQUENCE: 150
nnnnnnnnnn nnncaannnn ngtggnnnnn nnnnnnn                               37

<210> SEQ ID NO 151
<211> LENGTH: 37
<212> TYPE: DNA
<213> ORGANISM: Artificial Sequence
<220> FEATURE:
<223> OTHER INFORMATION: CspCI
<220> FEATURE:
<221> NAME/KEY: misc_feature
<222> LOCATION: 1-12, 17-21, 25-37
<223> OTHER INFORMATION: n = a, c, t, or g

<400> SEQUENCE: 151

```
nnnnnnnnnn nnccacnnnn nttgnnnnnn nnnnnn                              37
```

<210> SEQ ID NO 152
<211> LENGTH: 4
<212> TYPE: DNA
<213> ORGANISM: Artificial Sequence
<220> FEATURE:
<223> OTHER INFORMATION: AccII

<400> SEQUENCE: 152

```
cgcg                                                                  4
```

<210> SEQ ID NO 153
<211> LENGTH: 4
<212> TYPE: DNA
<213> ORGANISM: Artificial Sequence
<220> FEATURE:
<223> OTHER INFORMATION: AfaI

<400> SEQUENCE: 153

```
gtac                                                                  4
```

<210> SEQ ID NO 154
<211> LENGTH: 4
<212> TYPE: DNA
<213> ORGANISM: Artificial Sequence
<220> FEATURE:
<223> OTHER INFORMATION: AluBI

<400> SEQUENCE: 154

```
agct                                                                  4
```

<210> SEQ ID NO 155
<211> LENGTH: 4
<212> TYPE: DNA
<213> ORGANISM: Artificial Sequence
<220> FEATURE:
<223> OTHER INFORMATION: AspLEI

<400> SEQUENCE: 155

```
gcgc                                                                  4
```

<210> SEQ ID NO 156
<211> LENGTH: 4
<212> TYPE: DNA
<213> ORGANISM: Artificial Sequence
<220> FEATURE:
<223> OTHER INFORMATION: BscFI

<400> SEQUENCE: 156

```
gatc                                                                  4
```

<210> SEQ ID NO 157
<211> LENGTH: 4
<212> TYPE: DNA
<213> ORGANISM: Artificial Sequence
<220> FEATURE:
<223> OTHER INFORMATION: Bsh1236I

<400> SEQUENCE: 157

```
cgcg                                                                  4
```

<210> SEQ ID NO 158
<211> LENGTH: 4
<212> TYPE: DNA

```
<213> ORGANISM: Artificial Sequence
<220> FEATURE:
<223> OTHER INFORMATION: BshFI

<400> SEQUENCE: 158 ggcc                                                                    4

<210> SEQ ID NO 159
<211> LENGTH: 4
<212> TYPE: DNA
<213> ORGANISM: Artificial Sequence
<220> FEATURE:
<223> OTHER INFORMATION: BshI

<400> SEQUENCE: 159 ggcc                                                                    4

<210> SEQ ID NO 160
<211> LENGTH: 4
<212> TYPE: DNA
<213> ORGANISM: Artificial Sequence
<220> FEATURE:
<223> OTHER INFORMATION: BsiSI

<400> SEQUENCE: 160 ccgg                                                                    4

<210> SEQ ID NO 161
<211> LENGTH: 4
<212> TYPE: DNA
<213> ORGANISM: Artificial Sequence
<220> FEATURE:
<223> OTHER INFORMATION: BsnI

<400> SEQUENCE: 161 ggcc                                                                    4

<210> SEQ ID NO 162
<211> LENGTH: 4
<212> TYPE: DNA
<213> ORGANISM: Artificial Sequence
<220> FEATURE:
<223> OTHER INFORMATION: Bsp143I

<400> SEQUENCE: 162 gatc                                                                    4

<210> SEQ ID NO 163
<211> LENGTH: 4
<212> TYPE: DNA
<213> ORGANISM: Artificial Sequence
<220> FEATURE:
<223> OTHER INFORMATION: BspACI

<400> SEQUENCE: 163 ccgc                                                                    4

<210> SEQ ID NO 164
<211> LENGTH: 4
<212> TYPE: DNA
<213> ORGANISM: Artificial Sequence
<220> FEATURE:
<223> OTHER INFORMATION: BspANI

<400> SEQUENCE: 164 ggcc                                                                    4
```

```
<210> SEQ ID NO 165
<211> LENGTH: 4
<212> TYPE: DNA
<213> ORGANISM: Artificial Sequence
<220> FEATURE:
<223> OTHER INFORMATION: BspFNI

<400> SEQUENCE: 165 cgcg                                                                    4

<210> SEQ ID NO 166
<211> LENGTH: 4
<212> TYPE: DNA
<213> ORGANISM: Artificial Sequence
<220> FEATURE:
<223> OTHER INFORMATION: BssMI

<400> SEQUENCE: 166 gatc                                                                    4

<210> SEQ ID NO 167
<211> LENGTH: 4
<212> TYPE: DNA
<213> ORGANISM: Artificial Sequence
<220> FEATURE:
<223> OTHER INFORMATION: BstENII

<400> SEQUENCE: 167 gatc                                                                    4

<210> SEQ ID NO 168
<211> LENGTH: 4
<212> TYPE: DNA
<213> ORGANISM: Artificial Sequence
<220> FEATURE:
<223> OTHER INFORMATION: BstFNI

<400> SEQUENCE: 168 cgcg                                                                    4

<210> SEQ ID NO 169
<211> LENGTH: 4
<212> TYPE: DNA
<213> ORGANISM: Artificial Sequence
<220> FEATURE:
<223> OTHER INFORMATION: BstHHI

<400> SEQUENCE: 169 gcgc                                                                    4

<210> SEQ ID NO 170
<211> LENGTH: 4
<212> TYPE: DNA
<213> ORGANISM: Artificial Sequence
<220> FEATURE:
<223> OTHER INFORMATION: BstKTI

<400> SEQUENCE: 170 gatc                                                                    4

<210> SEQ ID NO 171
<211> LENGTH: 4
<212> TYPE: DNA
<213> ORGANISM: Artificial Sequence
<220> FEATURE:
```

```
<223> OTHER INFORMATION: BstMBI

<400> SEQUENCE: 171 gatc                                                                    4

<210> SEQ ID NO 172
<211> LENGTH: 4
<212> TYPE: DNA
<213> ORGANISM: Artificial Sequence
<220> FEATURE:
<223> OTHER INFORMATION: BsuRI

<400> SEQUENCE: 172 ggcc                                                                    4

<210> SEQ ID NO 173
<211> LENGTH: 4
<212> TYPE: DNA
<213> ORGANISM: Artificial Sequence
<220> FEATURE:
<223> OTHER INFORMATION: CfoI

<400> SEQUENCE: 173 gcgc                                                                    4

<210> SEQ ID NO 174
<211> LENGTH: 4
<212> TYPE: DNA
<213> ORGANISM: Artificial Sequence
<220> FEATURE:
<223> OTHER INFORMATION: Csp6I

<400> SEQUENCE: 174 gtac                                                                    4

<210> SEQ ID NO 175
<211> LENGTH: 4
<212> TYPE: DNA
<213> ORGANISM: Artificial Sequence
<220> FEATURE:
<223> OTHER INFORMATION: FaeI

<400> SEQUENCE: 175 catg                                                                    4

<210> SEQ ID NO 176
<211> LENGTH: 4
<212> TYPE: DNA
<213> ORGANISM: Artificial Sequence
<220> FEATURE:
<223> OTHER INFORMATION: FaiI

<400> SEQUENCE: 176 yatr                                                                    4

<210> SEQ ID NO 177
<211> LENGTH: 4
<212> TYPE: DNA
<213> ORGANISM: Artificial Sequence
<220> FEATURE:
<223> OTHER INFORMATION: FnuDII

<400> SEQUENCE: 177 cgcg                                                                    4
```

```
<210> SEQ ID NO 178
<211> LENGTH: 4
<212> TYPE: DNA
<213> ORGANISM: Artificial Sequence
<220> FEATURE:
<223> OTHER INFORMATION: FspBI

<400> SEQUENCE: 178 ctag                                                                    4

<210> SEQ ID NO 179
<211> LENGTH: 4
<212> TYPE: DNA
<213> ORGANISM: Artificial Sequence
<220> FEATURE:
<223> OTHER INFORMATION: GlaI

<400> SEQUENCE: 179 gcgc                                                                    4

<210> SEQ ID NO 180
<211> LENGTH: 4
<212> TYPE: DNA
<213> ORGANISM: Artificial Sequence
<220> FEATURE:
<223> OTHER INFORMATION: HapII

<400> SEQUENCE: 180 ccgg                                                                    4

<210> SEQ ID NO 181
<211> LENGTH: 4
<212> TYPE: DNA
<213> ORGANISM: Artificial Sequence
<220> FEATURE:
<223> OTHER INFORMATION: Hin1II

<400> SEQUENCE: 181 catg                                                                    4

<210> SEQ ID NO 182
<211> LENGTH: 4
<212> TYPE: DNA
<213> ORGANISM: Artificial Sequence
<220> FEATURE:
<223> OTHER INFORMATION: R9529

<400> SEQUENCE: 182 gcgc                                                                    4

<210> SEQ ID NO 183
<211> LENGTH: 4
<212> TYPE: DNA
<213> ORGANISM: Artificial Sequence
<220> FEATURE:
<223> OTHER INFORMATION: Hsp92II

<400> SEQUENCE: 183 catg                                                                    4

<210> SEQ ID NO 184
<211> LENGTH: 4
<212> TYPE: DNA
<213> ORGANISM: Artificial Sequence
<220> FEATURE:
<223> OTHER INFORMATION: HspAI
```

```
<400> SEQUENCE: 184 gcgc                                                                    4

<210> SEQ ID NO 185
<211> LENGTH: 4
<212> TYPE: DNA
<213> ORGANISM: Artificial Sequence
<220> FEATURE:
<223> OTHER INFORMATION: MaeI

<400> SEQUENCE: 185 ctag                                                                    4

<210> SEQ ID NO 186
<211> LENGTH: 4
<212> TYPE: DNA
<213> ORGANISM: Artificial Sequence
<220> FEATURE:
<223> OTHER INFORMATION: MaeII

<400> SEQUENCE: 186 acgt                                                                    4

<210> SEQ ID NO 187
<211> LENGTH: 4
<212> TYPE: DNA
<213> ORGANISM: Artificial Sequence
<220> FEATURE:
<223> OTHER INFORMATION: MvnI

<400> SEQUENCE: 187 cgcg                                                                    4

<210> SEQ ID NO 188
<211> LENGTH: 4
<212> TYPE: DNA
<213> ORGANISM: Artificial Sequence
<220> FEATURE:
<223> OTHER INFORMATION: PalI

<400> SEQUENCE: 188 ggcc                                                                    4

<210> SEQ ID NO 189
<211> LENGTH: 4
<212> TYPE: DNA
<213> ORGANISM: Artificial Sequence
<220> FEATURE:
<223> OTHER INFORMATION: RsaNI

<400> SEQUENCE: 189 gtac                                                                    4

<210> SEQ ID NO 190
<211> LENGTH: 4
<212> TYPE: DNA
<213> ORGANISM: Artificial Sequence
<220> FEATURE:
<223> OTHER INFORMATION: SetI

<400> SEQUENCE: 190 asst                                                                    4

<210> SEQ ID NO 191
<211> LENGTH: 4
```

```
<212> TYPE: DNA
<213> ORGANISM: Artificial Sequence
<220> FEATURE:
<223> OTHER INFORMATION: SgeI
<220> FEATURE:
<221> NAME/KEY: misc_feature
<222> LOCATION: 2-3
<223> OTHER INFORMATION: n = a, c, t, or g

<400> SEQUENCE: 191 cnng                                                                      4

<210> SEQ ID NO 192
<211> LENGTH: 17
<212> TYPE: DNA
<213> ORGANISM: Artificial Sequence
<220> FEATURE:
<223> OTHER INFORMATION: SgeI
<220> FEATURE:
<221> NAME/KEY: misc_feature
<222> LOCATION: 2-3, 5-17
<223> OTHER INFORMATION: n = a, c, t, or g

<400> SEQUENCE: 192
cnngnnnnnn nnnnnnn                                                       17

<210> SEQ ID NO 193
<211> LENGTH: 17
<212> TYPE: DNA
<213> ORGANISM: Artificial Sequence
<220> FEATURE:
<223> OTHER INFORMATION: SgeI
<220> FEATURE:
<221> NAME/KEY: misc_feature
<222> LOCATION: 1-13, 15-16
<223> OTHER INFORMATION: n = a, c, t, or g

<400> SEQUENCE: 193
nnnnnnnnnn nnncnng                                                       17

<210> SEQ ID NO 194
<211> LENGTH: 4
<212> TYPE: DNA
<213> ORGANISM: Artificial Sequence
<220> FEATURE:
<223> OTHER INFORMATION: Sse9I

<400> SEQUENCE: 194 aatt                                                                      4

<210> SEQ ID NO 195
<211> LENGTH: 4
<212> TYPE: DNA
<213> ORGANISM: Artificial Sequence
<220> FEATURE:
<223> OTHER INFORMATION: ThaI

<400> SEQUENCE: 195 cgcg                                                                      4

<210> SEQ ID NO 196
<211> LENGTH: 4
<212> TYPE: DNA
<213> ORGANISM: Artificial Sequence
<220> FEATURE:
<223> OTHER INFORMATION: Tru1I

<400> SEQUENCE: 196
``` ttaa                                                                    4

<210> SEQ ID NO 197
<211> LENGTH: 4
<212> TYPE: DNA
<213> ORGANISM: Artificial Sequence
<220> FEATURE:
<223> OTHER INFORMATION: Tru9I

<400> SEQUENCE: 197 ttaa                                                                    4

<210> SEQ ID NO 198
<211> LENGTH: 4
<212> TYPE: DNA
<213> ORGANISM: Artificial Sequence
<220> FEATURE:
<223> OTHER INFORMATION: TscI

<400> SEQUENCE: 198 acgt                                                                    4

<210> SEQ ID NO 199
<211> LENGTH: 4
<212> TYPE: DNA
<213> ORGANISM: Artificial Sequence
<220> FEATURE:
<223> OTHER INFORMATION: TspEI

<400> SEQUENCE: 199 aatt                                                                    4

<210> SEQ ID NO 200
<211> LENGTH: 4
<212> TYPE: DNA
<213> ORGANISM: Artificial Sequence
<220> FEATURE:
<223> OTHER INFORMATION: TthHB8I

<400> SEQUENCE: 200 tcga                                                                    4

<210> SEQ ID NO 201
<211> LENGTH: 4
<212> TYPE: DNA
<213> ORGANISM: Artificial Sequence
<220> FEATURE:
<223> OTHER INFORMATION: XspI

<400> SEQUENCE: 201 ctag                                                                    4

<210> SEQ ID NO 202
<211> LENGTH: 5
<212> TYPE: DNA
<213> ORGANISM: Artificial Sequence
<220> FEATURE:
<223> OTHER INFORMATION: AflI

<400> SEQUENCE: 202 ggwcc                                                                   5

<210> SEQ ID NO 203
<211> LENGTH: 5
<212> TYPE: DNA
<213> ORGANISM: Artificial Sequence

```
<220> FEATURE:
<223> OTHER INFORMATION: AgsI

<400> SEQUENCE: 203 ttsaa                                                                 5

<210> SEQ ID NO 204
<211> LENGTH: 5
<212> TYPE: DNA
<213> ORGANISM: Artificial Sequence
<220> FEATURE:
<223> OTHER INFORMATION: AspS9I
<220> FEATURE:
<221> NAME/KEY: misc_feature
<222> LOCATION: 3
<223> OTHER INFORMATION: n = a, c, t, or g

<400> SEQUENCE: 204 ggncc                                                                 5

<210> SEQ ID NO 205
<211> LENGTH: 5
<212> TYPE: DNA
<213> ORGANISM: Artificial Sequence
<220> FEATURE:
<223> OTHER INFORMATION: AsuC2I

<400> SEQUENCE: 205 ccsgg                                                                 5

<210> SEQ ID NO 206
<211> LENGTH: 5
<212> TYPE: DNA
<213> ORGANISM: Artificial Sequence
<220> FEATURE:
<223> OTHER INFORMATION: AsuI
<220> FEATURE:
<221> NAME/KEY: misc_feature
<222> LOCATION: 3
<223> OTHER INFORMATION: n = a, c, t, or g

<400> SEQUENCE: 206 ggncc                                                                 5

<210> SEQ ID NO 207
<211> LENGTH: 5
<212> TYPE: DNA
<213> ORGANISM: Artificial Sequence
<220> FEATURE:
<223> OTHER INFORMATION: BcefI

<400> SEQUENCE: 207 acggc                                                                 5

<210> SEQ ID NO 208
<211> LENGTH: 18
<212> TYPE: DNA
<213> ORGANISM: Artificial Sequence
<220> FEATURE:
<223> OTHER INFORMATION: BcefI
<220> FEATURE:
<221> NAME/KEY: misc_feature
<222> LOCATION: 6-18
<223> OTHER INFORMATION: n = a, c, t, or g

<400> SEQUENCE: 208
acggcnnnnn nnnnnnnn                                                  18
```

<210> SEQ ID NO 209
<211> LENGTH: 18
<212> TYPE: DNA
<213> ORGANISM: Artificial Sequence
<220> FEATURE:
<223> OTHER INFORMATION: BcefI
<220> FEATURE:
<221> NAME/KEY: misc_feature
<222> LOCATION: 1-13
<223> OTHER INFORMATION: n = a, c, t, or g

<400> SEQUENCE: 209
nnnnnnnnnn nnngccgt                                           18

<210> SEQ ID NO 210

<400> SEQUENCE: 210

000

<210> SEQ ID NO 211

<400> SEQUENCE: 211

000

<210> SEQ ID NO 212

<400> SEQUENCE: 212

000

<210> SEQ ID NO 213

<400> SEQUENCE: 213

000

<210> SEQ ID NO 214

<400> SEQUENCE: 214

000

<210> SEQ ID NO 215

<400> SEQUENCE: 215

000

<210> SEQ ID NO 216

<400> SEQUENCE: 216

000

<210> SEQ ID NO 217

<400> SEQUENCE: 217

000

<210> SEQ ID NO 218

<400> SEQUENCE: 218

000

<210> SEQ ID NO 219

<400> SEQUENCE: 219

000

<210> SEQ ID NO 220

<400> SEQUENCE: 220

000

<210> SEQ ID NO 221

<400> SEQUENCE: 221

000

<210> SEQ ID NO 222

<400> SEQUENCE: 222

000

<210> SEQ ID NO 223

<400> SEQUENCE: 223

000

<210> SEQ ID NO 224

<400> SEQUENCE: 224

000

<210> SEQ ID NO 225

<400> SEQUENCE: 225

000

<210> SEQ ID NO 226

<400> SEQUENCE: 226

000

<210> SEQ ID NO 227

<400> SEQUENCE: 227

000

<210> SEQ ID NO 228

<400> SEQUENCE: 228

000

<210> SEQ ID NO 229

<400> SEQUENCE: 229

000

<210> SEQ ID NO 230

```
<211> LENGTH: 5
<212> TYPE: DNA
<213> ORGANISM: Artificial Sequence
<220> FEATURE:
<223> OTHER INFORMATION: BcnI

<400> SEQUENCE: 230 ccsgg                                                                    5

<210> SEQ ID NO 231
<211> LENGTH: 5
<212> TYPE: DNA
<213> ORGANISM: Artificial Sequence
<220> FEATURE:
<223> OTHER INFORMATION: BisI
<220> FEATURE:
<221> NAME/KEY: misc_feature
<222> LOCATION: 3
<223> OTHER INFORMATION: n = a, c, t, or g

<400> SEQUENCE: 231 gcngc                                                                    5

<210> SEQ ID NO 232
<211> LENGTH: 5
<212> TYPE: DNA
<213> ORGANISM: Artificial Sequence
<220> FEATURE:
<223> OTHER INFORMATION: BlsI
<220> FEATURE:
<221> NAME/KEY: misc_feature
<222> LOCATION: 3
<223> OTHER INFORMATION: n = a, c, t, or g

<400> SEQUENCE: 232 gcngc                                                                    5

<210> SEQ ID NO 233
<211> LENGTH: 5
<212> TYPE: DNA
<213> ORGANISM: Artificial Sequence
<220> FEATURE:
<223> OTHER INFORMATION: Bme1390I
<220> FEATURE:
<221> NAME/KEY: misc_feature
<222> LOCATION: 3
<223> OTHER INFORMATION: n = a, c, t, or g

<400> SEQUENCE: 233 ccngg                                                                    5

<210> SEQ ID NO 234
<211> LENGTH: 5
<212> TYPE: DNA
<213> ORGANISM: Artificial Sequence
<220> FEATURE:
<223> OTHER INFORMATION: Bme18I

<400> SEQUENCE: 234 ggwcc                                                                    5

<210> SEQ ID NO 235
<211> LENGTH: 5
<212> TYPE: DNA
<213> ORGANISM: Artificial Sequence
<220> FEATURE:
<223> OTHER INFORMATION: BmrFI
<220> FEATURE:
<221> NAME/KEY: misc_feature
```

```
<222> LOCATION: 3
<223> OTHER INFORMATION: n = a, c, t, or g

<400> SEQUENCE: 235 ccngg                                                                    5

<210> SEQ ID NO 236
<211> LENGTH: 5
<212> TYPE: DNA
<213> ORGANISM: Artificial Sequence
<220> FEATURE:
<223> OTHER INFORMATION: BscGI

<400> SEQUENCE: 236 cccgt                                                                    5

<210> SEQ ID NO 237
<211> LENGTH: 6
<212> TYPE: DNA
<213> ORGANISM: Artificial Sequence
<220> FEATURE:
<223> OTHER INFORMATION: BscGI
<220> FEATURE:
<221> NAME/KEY: misc_feature
<222> LOCATION: 6
<223> OTHER INFORMATION: n = a, c, t, or g

<400> SEQUENCE: 237 cccgtn                                                                   6

<210> SEQ ID NO 238
<211> LENGTH: 6
<212> TYPE: DNA
<213> ORGANISM: Artificial Sequence
<220> FEATURE:
<223> OTHER INFORMATION: BscGI
<220> FEATURE:
<221> NAME/KEY: misc_feature
<222> LOCATION: 1
<223> OTHER INFORMATION: n = a, c, t, or g

<400> SEQUENCE: 238 nacggg                                                                   6

<210> SEQ ID NO 239
<211> LENGTH: 5
<212> TYPE: DNA
<213> ORGANISM: Artificial Sequence
<220> FEATURE:
<223> OTHER INFORMATION: BseBI

<400> SEQUENCE: 239 ccwgg                                                                    5

<210> SEQ ID NO 240
<211> LENGTH: 5
<212> TYPE: DNA
<213> ORGANISM: Artificial Sequence
<220> FEATURE:
<223> OTHER INFORMATION: BsiLI

<400> SEQUENCE: 240 ccwgg                                                                    5

<210> SEQ ID NO 241
<211> LENGTH: 5
<212> TYPE: DNA
```

```
<213> ORGANISM: Artificial Sequence
<220> FEATURE:
<223> OTHER INFORMATION: BsiZI
<220> FEATURE:
<221> NAME/KEY: misc_feature
<222> LOCATION: 3
<223> OTHER INFORMATION: n = a, c, t, or g

<400> SEQUENCE: 241 ggncc                                                                     5

<210> SEQ ID NO 242
<211> LENGTH: 5
<212> TYPE: DNA
<213> ORGANISM: Artificial Sequence
<220> FEATURE:
<223> OTHER INFORMATION: BslFI

<400> SEQUENCE: 242 gggac                                                                     5

<210> SEQ ID NO 243
<211> LENGTH: 19
<212> TYPE: DNA
<213> ORGANISM: Artificial Sequence
<220> FEATURE:
<223> OTHER INFORMATION: BslFI
<220> FEATURE:
<221> NAME/KEY: misc_feature
<222> LOCATION: 6-19
<223> OTHER INFORMATION: n = a, c, t, or g

<400> SEQUENCE: 243
gggacnnnnn nnnnnnnnn                                                     19

<210> SEQ ID NO 244
<211> LENGTH: 19
<212> TYPE: DNA
<213> ORGANISM: Artificial Sequence
<220> FEATURE:
<223> OTHER INFORMATION: BslFI
<220> FEATURE:
<221> NAME/KEY: misc_feature
<222> LOCATION: 1-14
<223> OTHER INFORMATION: n = a, c, t, or g

<400> SEQUENCE: 244
nnnnnnnnnn nnnngtccc                                                     19

<210> SEQ ID NO 245
<211> LENGTH: 5
<212> TYPE: DNA
<213> ORGANISM: Artificial Sequence
<220> FEATURE:
<223> OTHER INFORMATION: BsoMAI

<400> SEQUENCE: 245 gtctc                                                                     5

<210> SEQ ID NO 246
<211> LENGTH: 10
<212> TYPE: DNA
<213> ORGANISM: Artificial Sequence
<220> FEATURE:
<223> OTHER INFORMATION: BsoMAI
<220> FEATURE:
<221> NAME/KEY: misc_feature
<222> LOCATION: 6-10
<223> OTHER INFORMATION: n = a, c, t, or g
```

```
<400> SEQUENCE: 246 gtctcnnnnn                                                          10

<210> SEQ ID NO 247
<211> LENGTH: 10
<212> TYPE: DNA
<213> ORGANISM: Artificial Sequence
<220> FEATURE:
<223> OTHER INFORMATION: BsoMAI
<220> FEATURE:
<221> NAME/KEY: misc_feature
<222> LOCATION: 1-5
<223> OTHER INFORMATION: n = a, c, t, or g

<400> SEQUENCE: 247 nnnnngagac                                                          10

<210> SEQ ID NO 248
<211> LENGTH: 5
<212> TYPE: DNA
<213> ORGANISM: Artificial Sequence
<220> FEATURE:
<223> OTHER INFORMATION: BspNCI

<400> SEQUENCE: 248 ccaga                                                                5

<210> SEQ ID NO 249
<211> LENGTH: 6
<212> TYPE: DNA
<213> ORGANISM: Artificial Sequence
<220> FEATURE:
<223> OTHER INFORMATION: BspNCI
<220> FEATURE:
<221> NAME/KEY: misc_feature
<222> LOCATION: 6
<223> OTHER INFORMATION: n = a, c, t, or g

<400> SEQUENCE: 249 ccagan                                                               6

<210> SEQ ID NO 250
<211> LENGTH: 6
<212> TYPE: DNA
<213> ORGANISM: Artificial Sequence
<220> FEATURE:
<223> OTHER INFORMATION: BspNCI
<220> FEATURE:
<221> NAME/KEY: misc_feature
<222> LOCATION: 1
<223> OTHER INFORMATION: n = a, c, t, or g

<400> SEQUENCE: 250 ntctgg                                                               6

<210> SEQ ID NO 251
<211> LENGTH: 5
<212> TYPE: DNA
<213> ORGANISM: Artificial Sequence
<220> FEATURE:
<223> OTHER INFORMATION: Bst2UI

<400> SEQUENCE: 251 ccwgg                                                                5

<210> SEQ ID NO 252
```

```
<211> LENGTH: 5
<212> TYPE: DNA
<213> ORGANISM: Artificial Sequence
<220> FEATURE:
<223> OTHER INFORMATION: Bst71I

<400> SEQUENCE: 252 gcagc                                                                     5

<210> SEQ ID NO 253
<211> LENGTH: 17
<212> TYPE: DNA
<213> ORGANISM: Artificial Sequence
<220> FEATURE:
<223> OTHER INFORMATION: Bst71I
<220> FEATURE:
<221> NAME/KEY: misc_feature
<222> LOCATION: 6-17
<223> OTHER INFORMATION: n = a, c, t, or g

<400> SEQUENCE: 253 gcagcnnnn nnnnnnn                                                        17

<210> SEQ ID NO 254
<211> LENGTH: 17
<212> TYPE: DNA
<213> ORGANISM: Artificial Sequence
<220> FEATURE:
<223> OTHER INFORMATION: Bst71I
<220> FEATURE:
<221> NAME/KEY: misc_feature
<222> LOCATION: 1-12
<223> OTHER INFORMATION: n = a, c, t, or g

<400> SEQUENCE: 254
nnnnnnnnnn nngctgc                                                       17

<210> SEQ ID NO 255
<211> LENGTH: 5
<212> TYPE: DNA
<213> ORGANISM: Artificial Sequence
<220> FEATURE:
<223> OTHER INFORMATION: BstDEI
<220> FEATURE:
<221> NAME/KEY: misc_feature
<222> LOCATION: 3
<223> OTHER INFORMATION: n = a, c, t, or g

<400> SEQUENCE: 255 ctnag                                                                     5

<210> SEQ ID NO 256
<211> LENGTH: 5
<212> TYPE: DNA
<213> ORGANISM: Artificial Sequence
<220> FEATURE:
<223> OTHER INFORMATION: BstOI

<400> SEQUENCE: 256 ccwgg                                                                     5

<210> SEQ ID NO 257
<211> LENGTH: 5
<212> TYPE: DNA
<213> ORGANISM: Artificial Sequence
<220> FEATURE:
<223> OTHER INFORMATION: BstSCI
<220> FEATURE:
<221> NAME/KEY: misc_feature
```

```
<222> LOCATION: 3
<223> OTHER INFORMATION: n = a, c, t, or g

<400> SEQUENCE: 257 ccngg                                                                        5

<210> SEQ ID NO 258
<211> LENGTH: 5
<212> TYPE: DNA
<213> ORGANISM: Artificial Sequence
<220> FEATURE:
<223> OTHER INFORMATION: CauII

<400> SEQUENCE: 258 ccsgg                                                                        5

<210> SEQ ID NO 259
<211> LENGTH: 5
<212> TYPE: DNA
<213> ORGANISM: Artificial Sequence
<220> FEATURE:
<223> OTHER INFORMATION: CdiI

<400> SEQUENCE: 259 catcg                                                                        5

<210> SEQ ID NO 260
<211> LENGTH: 5
<212> TYPE: DNA
<213> ORGANISM: Artificial Sequence
<220> FEATURE:
<223> OTHER INFORMATION: CdiI

<400> SEQUENCE: 260 cgatg                                                                        5

<210> SEQ ID NO 261
<211> LENGTH: 5
<212> TYPE: DNA
<213> ORGANISM: Artificial Sequence
<220> FEATURE:
<223> OTHER INFORMATION: Cfr13I
<220> FEATURE:
<221> NAME/KEY: misc_feature
<222> LOCATION: 3
<223> OTHER INFORMATION: n = a, c, t, or g

<400> SEQUENCE: 261 ggncc                                                                        5

<210> SEQ ID NO 262
<211> LENGTH: 5
<212> TYPE: DNA
<213> ORGANISM: Artificial Sequence
<220> FEATURE:
<223> OTHER INFORMATION: Eco47I

<400> SEQUENCE: 262 ggwcc                                                                        5

<210> SEQ ID NO 263
<211> LENGTH: 5
<212> TYPE: DNA
<213> ORGANISM: Artificial Sequence
<220> FEATURE:
<223> OTHER INFORMATION: EcoRII
```

```
<400> SEQUENCE: 263 ccwgg                                                                      5

<210> SEQ ID NO 264
<211> LENGTH: 5
<212> TYPE: DNA
<213> ORGANISM: Artificial Sequence
<220> FEATURE:
<223> OTHER INFORMATION: FaqI

<400> SEQUENCE: 264 gggac                                                                      5

<210> SEQ ID NO 265
<211> LENGTH: 19
<212> TYPE: DNA
<213> ORGANISM: Artificial Sequence
<220> FEATURE:
<223> OTHER INFORMATION: FaqI
<220> FEATURE:
<221> NAME/KEY: misc_feature
<222> LOCATION: 6-19
<223> OTHER INFORMATION: n = a, c, t, or g

<400> SEQUENCE: 265 gggacnnnn nnnnnnnn                                                        19

<210> SEQ ID NO 266
<211> LENGTH: 19
<212> TYPE: DNA
<213> ORGANISM: Artificial Sequence
<220> FEATURE:
<223> OTHER INFORMATION: FaqI
<220> FEATURE:
<221> NAME/KEY: misc_feature
<222> LOCATION: 1-14
<223> OTHER INFORMATION: n = a, c, t, or g

<400> SEQUENCE: 266
nnnnnnnnnn nnnngtccc                                                      19

<210> SEQ ID NO 267
<211> LENGTH: 5
<212> TYPE: DNA
<213> ORGANISM: Artificial Sequence
<220> FEATURE:
<223> OTHER INFORMATION: FinI

<400> SEQUENCE: 267 gggac                                                                      5

<210> SEQ ID NO 268
<211> LENGTH: 6
<212> TYPE: DNA
<213> ORGANISM: Artificial Sequence
<220> FEATURE:
<223> OTHER INFORMATION: FinI
<220> FEATURE:
<221> NAME/KEY: misc_feature
<222> LOCATION: 6
<223> OTHER INFORMATION: n = a, c, t, or g

<400> SEQUENCE: 268 gggacn                                                                     6

<210> SEQ ID NO 269
<211> LENGTH: 6
```

```
<212> TYPE: DNA
<213> ORGANISM: Artificial Sequence
<220> FEATURE:
<223> OTHER INFORMATION: FinI
<220> FEATURE:
<221> NAME/KEY: misc_feature
<222> LOCATION: 1
<223> OTHER INFORMATION: n = a, c, t, or g

<400> SEQUENCE: 269 ngtccc                                                                    6

<210> SEQ ID NO 270
<211> LENGTH: 5
<212> TYPE: DNA
<213> ORGANISM: Artificial Sequence
<220> FEATURE:
<223> OTHER INFORMATION: Fsp4HI
<220> FEATURE:
<221> NAME/KEY: misc_feature
<222> LOCATION: 3
<223> OTHER INFORMATION: n = a, c, t, or g

<400> SEQUENCE: 270 gcngc                                                                     5

<210> SEQ ID NO 271
<211> LENGTH: 5
<212> TYPE: DNA
<213> ORGANISM: Artificial Sequence
<220> FEATURE:
<223> OTHER INFORMATION: GluI
<220> FEATURE:
<221> NAME/KEY: misc_feature
<222> LOCATION: 3
<223> OTHER INFORMATION: n = a, c, t, or g

<400> SEQUENCE: 271 gcngc                                                                     5

<210> SEQ ID NO 272
<211> LENGTH: 5
<212> TYPE: DNA
<213> ORGANISM: Artificial Sequence
<220> FEATURE:
<223> OTHER INFORMATION: Hin4II

<400> SEQUENCE: 272 ccttc                                                                     5

<210> SEQ ID NO 273
<211> LENGTH: 11
<212> TYPE: DNA
<213> ORGANISM: Artificial Sequence
<220> FEATURE:
<223> OTHER INFORMATION: Hin4II
<220> FEATURE:
<221> NAME/KEY: misc_feature
<222> LOCATION: 6-11
<223> OTHER INFORMATION: n = a, c, t, or g

<400> SEQUENCE: 273
ccttcnnnnn n                                                             11

<210> SEQ ID NO 274
<211> LENGTH: 11
<212> TYPE: DNA
<213> ORGANISM: Artificial Sequence
<220> FEATURE:
```

<223> OTHER INFORMATION: Hin4II
<220> FEATURE:
<221> NAME/KEY: misc_feature
<222> LOCATION: 1-6
<223> OTHER INFORMATION: n = a, c, t, or g

<400> SEQUENCE: 274
nnnnnngaag g                                                               11

<210> SEQ ID NO 275
<211> LENGTH: 5
<212> TYPE: DNA
<213> ORGANISM: Artificial Sequence
<220> FEATURE:
<223> OTHER INFORMATION: HpyF3I
<220> FEATURE:
<221> NAME/KEY: misc_feature
<222> LOCATION: 3
<223> OTHER INFORMATION: n = a, c, t, or g

<400> SEQUENCE: 275 ctnag                                                                       5

<210> SEQ ID NO 276
<211> LENGTH: 5
<212> TYPE: DNA
<213> ORGANISM: Artificial Sequence
<220> FEATURE:
<223> OTHER INFORMATION: ItaI
<220> FEATURE:
<221> NAME/KEY: misc_feature
<222> LOCATION: 3
<223> OTHER INFORMATION: n = a, c, t, or g

<400> SEQUENCE: 276 gcngc                                                                       5

<210> SEQ ID NO 277
<211> LENGTH: 5
<212> TYPE: DNA
<213> ORGANISM: Artificial Sequence
<220> FEATURE:
<223> OTHER INFORMATION: MaeIII
<220> FEATURE:
<221> NAME/KEY: misc_feature
<222> LOCATION: 3
<223> OTHER INFORMATION: n = a, c, t, or g

<400> SEQUENCE: 277 gtnac                                                                       5

<210> SEQ ID NO 278
<211> LENGTH: 5
<212> TYPE: DNA
<213> ORGANISM: Artificial Sequence
<220> FEATURE:
<223> OTHER INFORMATION: MspR9I
<220> FEATURE:
<221> NAME/KEY: misc_feature
<222> LOCATION: 3
<223> OTHER INFORMATION: n = a, c, t, or g

<400> SEQUENCE: 278 ccngg                                                                       5

<210> SEQ ID NO 279
<211> LENGTH: 5
<212> TYPE: DNA
<213> ORGANISM: Artificial Sequence

```
<220> FEATURE:
<223> OTHER INFORMATION: MvaI

<400> SEQUENCE: 279 ccwgg                                                                    5

<210> SEQ ID NO 280
<211> LENGTH: 5
<212> TYPE: DNA
<213> ORGANISM: Artificial Sequence
<220> FEATURE:
<223> OTHER INFORMATION: NmuCI

<400> SEQUENCE: 280 gtsac                                                                    5

<210> SEQ ID NO 281
<211> LENGTH: 5
<212> TYPE: DNA
<213> ORGANISM: Artificial Sequence
<220> FEATURE:
<223> OTHER INFORMATION: Psp6I

<400> SEQUENCE: 281 ccwgg                                                                    5

<210> SEQ ID NO 282
<211> LENGTH: 5
<212> TYPE: DNA
<213> ORGANISM: Artificial Sequence
<220> FEATURE:
<223> OTHER INFORMATION: PspPI
<220> FEATURE:
<221> NAME/KEY: misc_feature
<222> LOCATION: 3
<223> OTHER INFORMATION: n = a, c, t, or g

<400> SEQUENCE: 282 ggncc                                                                    5

<210> SEQ ID NO 283
<211> LENGTH: 5
<212> TYPE: DNA
<213> ORGANISM: Artificial Sequence
<220> FEATURE:
<223> OTHER INFORMATION: SatI
<220> FEATURE:
<221> NAME/KEY: misc_feature
<222> LOCATION: 3
<223> OTHER INFORMATION: n = a, c, t, or g

<400> SEQUENCE: 283 gcngc                                                                    5

<210> SEQ ID NO 284
<211> LENGTH: 5
<212> TYPE: DNA
<213> ORGANISM: Artificial Sequence
<220> FEATURE:
<223> OTHER INFORMATION: SinI

<400> SEQUENCE: 284 ggwcc                                                                    5

<210> SEQ ID NO 285
<211> LENGTH: 5
<212> TYPE: DNA
```

```
<213> ORGANISM: Artificial Sequence
<220> FEATURE:
<223> OTHER INFORMATION: TscAI

<400> SEQUENCE: 285 castg                                                                  5

<210> SEQ ID NO 286
<211> LENGTH: 9
<212> TYPE: DNA
<213> ORGANISM: Artificial Sequence
<220> FEATURE:
<223> OTHER INFORMATION: TscAI
<220> FEATURE:
<221> NAME/KEY: misc_feature
<222> LOCATION: 1-2, 8-9
<223> OTHER INFORMATION: n = a, c, t, or g

<400> SEQUENCE: 286 nncastgnn                                                              9

<210> SEQ ID NO 287
<211> LENGTH: 5
<212> TYPE: DNA
<213> ORGANISM: Artificial Sequence
<220> FEATURE:
<223> OTHER INFORMATION: VpaK11BI

<400> SEQUENCE: 287 ggwcc                                                                  5

<210> SEQ ID NO 288
<211> LENGTH: 6
<212> TYPE: DNA
<213> ORGANISM: Artificial Sequence
<220> FEATURE:
<223> OTHER INFORMATION: AanI

<400> SEQUENCE: 288 ttataa                                                                 6

<210> SEQ ID NO 289
<211> LENGTH: 6
<212> TYPE: DNA
<213> ORGANISM: Artificial Sequence
<220> FEATURE:
<223> OTHER INFORMATION: AatI

<400> SEQUENCE: 289 aggcct                                                                 6

<210> SEQ ID NO 290
<211> LENGTH: 6
<212> TYPE: DNA
<213> ORGANISM: Artificial Sequence
<220> FEATURE:
<223> OTHER INFORMATION: AauI

<400> SEQUENCE: 290 tgtaca                                                                 6

<210> SEQ ID NO 291
<211> LENGTH: 6
<212> TYPE: DNA
<213> ORGANISM: Artificial Sequence
<220> FEATURE:
<223> OTHER INFORMATION: Acc113I
```

```
<400> SEQUENCE: 291 agtact                                                                   6

<210> SEQ ID NO 292
<211> LENGTH: 6
<212> TYPE: DNA
<213> ORGANISM: Artificial Sequence
<220> FEATURE:
<223> OTHER INFORMATION: Acc16I

<400> SEQUENCE: 292 tgcgca                                                                   6

<210> SEQ ID NO 293
<211> LENGTH: 6
<212> TYPE: DNA
<213> ORGANISM: Artificial Sequence
<220> FEATURE:
<223> OTHER INFORMATION: AccB1I

<400> SEQUENCE: 293 ggyrcc                                                                   6

<210> SEQ ID NO 294
<211> LENGTH: 6
<212> TYPE: DNA
<213> ORGANISM: Artificial Sequence
<220> FEATURE:
<223> OTHER INFORMATION: AceIII

<400> SEQUENCE: 294 cagctc                                                                   6

<210> SEQ ID NO 295
<211> LENGTH: 17
<212> TYPE: DNA
<213> ORGANISM: Artificial Sequence
<220> FEATURE:
<223> OTHER INFORMATION: AceIII
<220> FEATURE:
<221> NAME/KEY: misc_feature
<222> LOCATION: 7-17
<223> OTHER INFORMATION: n = a, c, t, or g

<400> SEQUENCE: 295
cagctcnnnn nnnnnnn                                                      17

<210> SEQ ID NO 296
<211> LENGTH: 17
<212> TYPE: DNA
<213> ORGANISM: Artificial Sequence
<220> FEATURE:
<223> OTHER INFORMATION: AceIII
<220> FEATURE:
<221> NAME/KEY: misc_feature
<222> LOCATION: 1-11
<223> OTHER INFORMATION: n = a, c, t, or g

<400> SEQUENCE: 296
nnnnnnnnnn ngagctg                                                      17

<210> SEQ ID NO 297
<211> LENGTH: 6
<212> TYPE: DNA
<213> ORGANISM: Artificial Sequence
<220> FEATURE:
```

```
<223> OTHER INFORMATION: AcsI

<400> SEQUENCE: 297 raatty                                                              6

<210> SEQ ID NO 298
<211> LENGTH: 6
<212> TYPE: DNA
<213> ORGANISM: Artificial Sequence
<220> FEATURE:
<223> OTHER INFORMATION: AcsI

<400> SEQUENCE: 298 raatty                                                              6

<210> SEQ ID NO 299
<211> LENGTH: 6
<212> TYPE: DNA
<213> ORGANISM: Artificial Sequence
<220> FEATURE:
<223> OTHER INFORMATION: AcvI

<400> SEQUENCE: 299 cacgtg                                                              6

<210> SEQ ID NO 300
<211> LENGTH: 6
<212> TYPE: DNA
<213> ORGANISM: Artificial Sequence
<220> FEATURE:
<223> OTHER INFORMATION: AcyI

<400> SEQUENCE: 300 grcgyc                                                              6

<210> SEQ ID NO 301
<211> LENGTH: 6
<212> TYPE: DNA
<213> ORGANISM: Artificial Sequence
<220> FEATURE:
<223> OTHER INFORMATION: AhlI

<400> SEQUENCE: 301 actagt                                                              6

<210> SEQ ID NO 302
<211> LENGTH: 6
<212> TYPE: DNA
<213> ORGANISM: Artificial Sequence
<220> FEATURE:
<223> OTHER INFORMATION: Alw21I

<400> SEQUENCE: 302 gwgcwc                                                              6

<210> SEQ ID NO 303
<211> LENGTH: 6
<212> TYPE: DNA
<213> ORGANISM: Artificial Sequence
<220> FEATURE:
<223> OTHER INFORMATION: Alw44I

<400> SEQUENCE: 303 gtgcac                                                              6
```

```
<210> SEQ ID NO 304
<211> LENGTH: 6
<212> TYPE: DNA
<213> ORGANISM: Artificial Sequence
<220> FEATURE:
<223> OTHER INFORMATION: Ama87I

<400> SEQUENCE: 304 cycgrg                                                                    6

<210> SEQ ID NO 305
<211> LENGTH: 6
<212> TYPE: DNA
<213> ORGANISM: Artificial Sequence
<220> FEATURE:
<223> OTHER INFORMATION: Aor51HI

<400> SEQUENCE: 305 agcgct                                                                    6

<210> SEQ ID NO 306
<211> LENGTH: 6
<212> TYPE: DNA
<213> ORGANISM: Artificial Sequence
<220> FEATURE:
<223> OTHER INFORMATION: AsiAI

<400> SEQUENCE: 306 accggt                                                                    6

<210> SEQ ID NO 307
<211> LENGTH: 6
<212> TYPE: DNA
<213> ORGANISM: Artificial Sequence
<220> FEATURE:
<223> OTHER INFORMATION: AsnI

<400> SEQUENCE: 307 attaat                                                                    6

<210> SEQ ID NO 308
<211> LENGTH: 6
<212> TYPE: DNA
<213> ORGANISM: Artificial Sequence
<220> FEATURE:
<223> OTHER INFORMATION: Asp718I

<400> SEQUENCE: 308 ggtacc                                                                    6

<210> SEQ ID NO 309
<211> LENGTH: 6
<212> TYPE: DNA
<213> ORGANISM: Artificial Sequence
<220> FEATURE:
<223> OTHER INFORMATION: AspHI

<400> SEQUENCE: 309 gwgcwc                                                                    6

<210> SEQ ID NO 310
<211> LENGTH: 6
<212> TYPE: DNA
<213> ORGANISM: Artificial Sequence
<220> FEATURE:
<223> OTHER INFORMATION: AsuII
```

```
<400> SEQUENCE: 310 ttcgaa                                                                      6

<210> SEQ ID NO 311
<211> LENGTH: 6
<212> TYPE: DNA
<213> ORGANISM: Artificial Sequence
<220> FEATURE:
<223> OTHER INFORMATION: AsuNHI

<400> SEQUENCE: 311 gctagc                                                                      6

<210> SEQ ID NO 312
<211> LENGTH: 6
<212> TYPE: DNA
<213> ORGANISM: Artificial Sequence
<220> FEATURE:
<223> OTHER INFORMATION: AvaIII

<400> SEQUENCE: 312 atgcat                                                                      6

<210> SEQ ID NO 313
<211> LENGTH: 6
<212> TYPE: DNA
<213> ORGANISM: Artificial Sequence
<220> FEATURE:
<223> OTHER INFORMATION: AviII

<400> SEQUENCE: 313 tgcgca                                                                      6

<210> SEQ ID NO 314
<211> LENGTH: 6
<212> TYPE: DNA
<213> ORGANISM: Artificial Sequence
<220> FEATURE:
<223> OTHER INFORMATION: BalI

<400> SEQUENCE: 314 tggcca                                                                      6

<210> SEQ ID NO 315
<211> LENGTH: 6
<212> TYPE: DNA
<213> ORGANISM: Artificial Sequence
<220> FEATURE:
<223> OTHER INFORMATION: BanIII

<400> SEQUENCE: 315 atcgat                                                                      6

<210> SEQ ID NO 316
<211> LENGTH: 6
<212> TYPE: DNA
<213> ORGANISM: Artificial Sequence
<220> FEATURE:
<223> OTHER INFORMATION: BauI

<400> SEQUENCE: 316 cacgag                                                                      6

<210> SEQ ID NO 317
<211> LENGTH: 6
```

```
<212> TYPE: DNA
<213> ORGANISM: Artificial Sequence
<220> FEATURE:
<223> OTHER INFORMATION: BauI

<400> SEQUENCE: 317 cacgag                                                               6

<210> SEQ ID NO 318
<211> LENGTH: 6
<212> TYPE: DNA
<213> ORGANISM: Artificial Sequence
<220> FEATURE:
<223> OTHER INFORMATION: BauI

<400> SEQUENCE: 318 ctcgtg                                                               6

<210> SEQ ID NO 319
<211> LENGTH: 6
<212> TYPE: DNA
<213> ORGANISM: Artificial Sequence
<220> FEATURE:
<223> OTHER INFORMATION: BbeI

<400> SEQUENCE: 319 ggcgcc                                                               6

<210> SEQ ID NO 320
<211> LENGTH: 6
<212> TYPE: DNA
<213> ORGANISM: Artificial Sequence
<220> FEATURE:
<223> OTHER INFORMATION: BbeI

<400> SEQUENCE: 320 ggcgcc                                                               6

<210> SEQ ID NO 321
<211> LENGTH: 6
<212> TYPE: DNA
<213> ORGANISM: Artificial Sequence
<220> FEATURE:
<223> OTHER INFORMATION: BbrPI

<400> SEQUENCE: 321 cacgtg                                                               6

<210> SEQ ID NO 322
<211> LENGTH: 6
<212> TYPE: DNA
<213> ORGANISM: Artificial Sequence
<220> FEATURE:
<223> OTHER INFORMATION: BbuI

<400> SEQUENCE: 322 gcatgc                                                               6

<210> SEQ ID NO 323
<211> LENGTH: 6
<212> TYPE: DNA
<213> ORGANISM: Artificial Sequence
<220> FEATURE:
<223> OTHER INFORMATION: Bbv12I

<400> SEQUENCE: 323
```

```
gwgcwc                                                              6

<210> SEQ ID NO 324
<211> LENGTH: 6
<212> TYPE: DNA
<213> ORGANISM: Artificial Sequence
<220> FEATURE:
<223> OTHER INFORMATION: BbvII

<400> SEQUENCE: 324 gaagac                                                              6

<210> SEQ ID NO 325
<211> LENGTH: 12
<212> TYPE: DNA
<213> ORGANISM: Artificial Sequence
<220> FEATURE:
<223> OTHER INFORMATION: BbvII
<220> FEATURE:
<221> NAME/KEY: misc_feature
<222> LOCATION: 7-12
<223> OTHER INFORMATION: n = a, c, t, or g

<400> SEQUENCE: 325
gaagacnnnn nn                                                      12

<210> SEQ ID NO 326
<211> LENGTH: 12
<212> TYPE: DNA
<213> ORGANISM: Artificial Sequence
<220> FEATURE:
<223> OTHER INFORMATION: BbvII
<220> FEATURE:
<221> NAME/KEY: misc_feature
<222> LOCATION: 1-6
<223> OTHER INFORMATION: n = a, c, t, or g

<400> SEQUENCE: 326
nnnnnngtct tc                                                      12

<210> SEQ ID NO 327
<211> LENGTH: 6
<212> TYPE: DNA
<213> ORGANISM: Artificial Sequence
<220> FEATURE:
<223> OTHER INFORMATION: Bce83I

<400> SEQUENCE: 327 cttgag                                                              6

<210> SEQ ID NO 328
<211> LENGTH: 22
<212> TYPE: DNA
<213> ORGANISM: Artificial Sequence
<220> FEATURE:
<223> OTHER INFORMATION: Bce83I
<220> FEATURE:
<221> NAME/KEY: misc_feature
<222> LOCATION: 7-22
<223> OTHER INFORMATION: n = a, c, t, or g

<400> SEQUENCE: 328
cttgagnnnn nnnnnnnnnn nn                                           22

<210> SEQ ID NO 329
<211> LENGTH: 22
<212> TYPE: DNA
<213> ORGANISM: Artificial Sequence
```

```
<220> FEATURE:
<223> OTHER INFORMATION: Bce83I
<220> FEATURE:
<221> NAME/KEY: misc_feature
<222> LOCATION: 1-16
<223> OTHER INFORMATION: n = a, c, t, or g

<400> SEQUENCE: 329
nnnnnnnnnn nnnnnnctca ag                                              22

<210> SEQ ID NO 330
<211> LENGTH: 6
<212> TYPE: DNA
<213> ORGANISM: Artificial Sequence
<220> FEATURE:
<223> OTHER INFORMATION: BcoI

<400> SEQUENCE: 330 cycgrg                                                                 6

<210> SEQ ID NO 331
<211> LENGTH: 6
<212> TYPE: DNA
<213> ORGANISM: Artificial Sequence
<220> FEATURE:
<223> OTHER INFORMATION: BcuI

<400> SEQUENCE: 331 actagt                                                                 6

<210> SEQ ID NO 332
<211> LENGTH: 6
<212> TYPE: DNA
<213> ORGANISM: Artificial Sequence
<220> FEATURE:
<223> OTHER INFORMATION: BfmI

<400> SEQUENCE: 332 ctryag                                                                 6

<210> SEQ ID NO 333
<211> LENGTH: 6
<212> TYPE: DNA
<213> ORGANISM: Artificial Sequence
<220> FEATURE:
<223> OTHER INFORMATION: BfrBl

<400> SEQUENCE: 333 atgcat                                                                 6

<210> SEQ ID NO 334
<211> LENGTH: 6
<212> TYPE: DNA
<213> ORGANISM: Artificial Sequence
<220> FEATURE:
<223> OTHER INFORMATION: BfrI

<400> SEQUENCE: 334 cttaag                                                                 6

<210> SEQ ID NO 335
<211> LENGTH: 6
<212> TYPE: DNA
<213> ORGANISM: Artificial Sequence
<220> FEATURE:
<223> OTHER INFORMATION: BlnI
```

```
<400> SEQUENCE: 335 cctagg                                                                    6

<210> SEQ ID NO 336
<211> LENGTH: 6
<212> TYPE: DNA
<213> ORGANISM: Artificial Sequence
<220> FEATURE:
<223> OTHER INFORMATION: BmcAI

<400> SEQUENCE: 336 agtact                                                                    6

<210> SEQ ID NO 337
<211> LENGTH: 6
<212> TYPE: DNA
<213> ORGANISM: Artificial Sequence
<220> FEATURE:
<223> OTHER INFORMATION: BmeT11I

<400> SEQUENCE: 337 cycgrg                                                                    6

<210> SEQ ID NO 338
<211> LENGTH: 6
<212> TYPE: DNA
<213> ORGANISM: Artificial Sequence
<220> FEATURE:
<223> OTHER INFORMATION: BmiI
<220> FEATURE:
<221> NAME/KEY: misc_feature
<222> LOCATION: 3-4
<223> OTHER INFORMATION: n = a, c, t, or g

<400> SEQUENCE: 338 ggnncc                                                                    6

<210> SEQ ID NO 339
<211> LENGTH: 6
<212> TYPE: DNA
<213> ORGANISM: Artificial Sequence
<220> FEATURE:
<223> OTHER INFORMATION: BmuI

<400> SEQUENCE: 339 actggg                                                                    6

<210> SEQ ID NO 340
<211> LENGTH: 6
<212> TYPE: DNA
<213> ORGANISM: Artificial Sequence
<220> FEATURE:
<223> OTHER INFORMATION: BmyI

<400> SEQUENCE: 340 gdgchc                                                                    6

<210> SEQ ID NO 341
<211> LENGTH: 6
<212> TYPE: DNA
<213> ORGANISM: Artificial Sequence
<220> FEATURE:
<223> OTHER INFORMATION: Bpu14I

<400> SEQUENCE: 341 ttcgaa                                                                    6
```

```
<210> SEQ ID NO 342
<211> LENGTH: 6
<212> TYPE: DNA
<213> ORGANISM: Artificial Sequence
<220> FEATURE:
<223> OTHER INFORMATION: BpvUI

<400> SEQUENCE: 342 cgatcg                                                                     6

<210> SEQ ID NO 343
<211> LENGTH: 6
<212> TYPE: DNA
<213> ORGANISM: Artificial Sequence
<220> FEATURE:
<223> OTHER INFORMATION: Bsa29I

<400> SEQUENCE: 343 atcgat                                                                     6

<210> SEQ ID NO 344
<211> LENGTH: 6
<212> TYPE: DNA
<213> ORGANISM: Artificial Sequence
<220> FEATURE:
<223> OTHER INFORMATION: BsaOI

<400> SEQUENCE: 344 cgrycg                                                                     6

<210> SEQ ID NO 345
<211> LENGTH: 6
<212> TYPE: DNA
<213> ORGANISM: Artificial Sequence
<220> FEATURE:
<223> OTHER INFORMATION: BsbI

<400> SEQUENCE: 345 caacac                                                                     6

<210> SEQ ID NO 346
<211> LENGTH: 27
<212> TYPE: DNA
<213> ORGANISM: Artificial Sequence
<220> FEATURE:
<223> OTHER INFORMATION: BsbI
<220> FEATURE:
<221> NAME/KEY: misc_feature
<222> LOCATION: 7-27
<223> OTHER INFORMATION: n = a, c, t, or g

<400> SEQUENCE: 346
caacacnnnn nnnnnnnnnn nnnnnnn                                              27

<210> SEQ ID NO 347
<211> LENGTH: 27
<212> TYPE: DNA
<213> ORGANISM: Artificial Sequence
<220> FEATURE:
<223> OTHER INFORMATION: BsbI
<220> FEATURE:
<221> NAME/KEY: misc_feature
<222> LOCATION: 1-21
<223> OTHER INFORMATION: n = a, c, t, or g

<400> SEQUENCE: 347
```

```
nnnnnnnnnn nnnnnnnnnn ngtgttg                                              27

<210> SEQ ID NO 348
<211> LENGTH: 6
<212> TYPE: DNA
<213> ORGANISM: Artificial Sequence
<220> FEATURE:
<223> OTHER INFORMATION: BscBI
<220> FEATURE:
<221> NAME/KEY: misc_feature
<222> LOCATION: 3-4
<223> OTHER INFORMATION: n = a, c, t, or g

<400> SEQUENCE: 348 ggnncc                                                                      6

<210> SEQ ID NO 349
<211> LENGTH: 6
<212> TYPE: DNA
<213> ORGANISM: Artificial Sequence
<220> FEATURE:
<223> OTHER INFORMATION: BscCI

<400> SEQUENCE: 349 gaatgc                                                                      6

<210> SEQ ID NO 350
<211> LENGTH: 7
<212> TYPE: DNA
<213> ORGANISM: Artificial Sequence
<220> FEATURE:
<223> OTHER INFORMATION: BscCI
<220> FEATURE:
<221> NAME/KEY: misc_feature
<222> LOCATION: 7
<223> OTHER INFORMATION: n = a, c, t, or g

<400> SEQUENCE: 350 gaatgcn                                                                     7

<210> SEQ ID NO 351
<211> LENGTH: 7
<212> TYPE: DNA
<213> ORGANISM: Artificial Sequence
<220> FEATURE:
<223> OTHER INFORMATION: BscCI
<220> FEATURE:
<221> NAME/KEY: misc_feature
<222> LOCATION: 1
<223> OTHER INFORMATION: n = a, c, t, or g

<400> SEQUENCE: 351 ngcattc                                                                     7

<210> SEQ ID NO 352
<211> LENGTH: 6
<212> TYPE: DNA
<213> ORGANISM: Artificial Sequence
<220> FEATURE:
<223> OTHER INFORMATION: Bse118I

<400> SEQUENCE: 352 rccggy                                                                      6

<210> SEQ ID NO 353
<211> LENGTH: 6
<212> TYPE: DNA
<213> ORGANISM: Artificial Sequence
```

```
<220> FEATURE:
<223> OTHER INFORMATION: BseAI

<400> SEQUENCE: 353 tccgga                                                                    6

<210> SEQ ID NO 354
<211> LENGTH: 6
<212> TYPE: DNA
<213> ORGANISM: Artificial Sequence
<220> FEATURE:
<223> OTHER INFORMATION: BseCI

<400> SEQUENCE: 354 atcgat                                                                    6

<210> SEQ ID NO 355
<211> LENGTH: 6
<212> TYPE: DNA
<213> ORGANISM: Artificial Sequence
<220> FEATURE:
<223> OTHER INFORMATION: BseDI
<220> FEATURE:
<221> NAME/KEY: misc_feature
<222> LOCATION: 3-4
<223> OTHER INFORMATION: n = a, c, t, or g

<400> SEQUENCE: 355 ccnngg                                                                    6

<210> SEQ ID NO 356
<211> LENGTH: 6
<212> TYPE: DNA
<213> ORGANISM: Artificial Sequence
<220> FEATURE:
<223> OTHER INFORMATION: BsePI

<400> SEQUENCE: 356 gcgcgc                                                                    6

<210> SEQ ID NO 357
<211> LENGTH: 6
<212> TYPE: DNA
<213> ORGANISM: Artificial Sequence
<220> FEATURE:
<223> OTHER INFORMATION: BseSI

<400> SEQUENCE: 357 gkgcmc                                                                    6

<210> SEQ ID NO 358
<211> LENGTH: 6
<212> TYPE: DNA
<213> ORGANISM: Artificial Sequence
<220> FEATURE:
<223> OTHER INFORMATION: BseX3I

<400> SEQUENCE: 358 cggccg                                                                    6

<210> SEQ ID NO 359
<211> LENGTH: 6
<212> TYPE: DNA
<213> ORGANISM: Artificial Sequence
<220> FEATURE:
<223> OTHER INFORMATION: Bsh1285I
```

```
<400> SEQUENCE: 359 cgrycg                                                                    6

<210> SEQ ID NO 360
<211> LENGTH: 6
<212> TYPE: DNA
<213> ORGANISM: Artificial Sequence
<220> FEATURE:
<223> OTHER INFORMATION: BshNI

<400> SEQUENCE: 360 ggyrcc                                                                    6

<210> SEQ ID NO 361
<211> LENGTH: 6
<212> TYPE: DNA
<213> ORGANISM: Artificial Sequence
<220> FEATURE:
<223> OTHER INFORMATION: BshTI

<400> SEQUENCE: 361 accggt                                                                    6

<210> SEQ ID NO 362
<211> LENGTH: 6
<212> TYPE: DNA
<213> ORGANISM: Artificial Sequence
<220> FEATURE:
<223> OTHER INFORMATION: BshVI

<400> SEQUENCE: 362 atcgat                                                                    6

<210> SEQ ID NO 363
<211> LENGTH: 6
<212> TYPE: DNA
<213> ORGANISM: Artificial Sequence
<220> FEATURE:
<223> OTHER INFORMATION: BsiCI

<400> SEQUENCE: 363 ttcgaa                                                                    6

<210> SEQ ID NO 364
<211> LENGTH: 6
<212> TYPE: DNA
<213> ORGANISM: Artificial Sequence
<220> FEATURE:
<223> OTHER INFORMATION: BsiHKCI

<400> SEQUENCE: 364 cycgrg                                                                    6

<210> SEQ ID NO 365
<211> LENGTH: 6
<212> TYPE: DNA
<213> ORGANISM: Artificial Sequence
<220> FEATURE:
<223> OTHER INFORMATION: BsiMI

<400> SEQUENCE: 365 tccgga                                                                    6

<210> SEQ ID NO 366
<211> LENGTH: 6
```

-continued

```
<212> TYPE: DNA
<213> ORGANISM: Artificial Sequence
<220> FEATURE:
<223> OTHER INFORMATION: BsiQI

<400> SEQUENCE: 366 tgatca                                                                     6

<210> SEQ ID NO 367
<211> LENGTH: 6
<212> TYPE: DNA
<213> ORGANISM: Artificial Sequence
<220> FEATURE:
<223> OTHER INFORMATION: BsiXI

<400> SEQUENCE: 367 atcgat                                                                     6

<210> SEQ ID NO 368
<211> LENGTH: 6
<212> TYPE: DNA
<213> ORGANISM: Artificial Sequence
<220> FEATURE:
<223> OTHER INFORMATION: Bsp106I

<400> SEQUENCE: 368 atcgat                                                                     6

<210> SEQ ID NO 369
<211> LENGTH: 6
<212> TYPE: DNA
<213> ORGANISM: Artificial Sequence
<220> FEATURE:
<223> OTHER INFORMATION: Bsp119I

<400> SEQUENCE: 369 ttcgaa                                                                     6

<210> SEQ ID NO 370
<211> LENGTH: 6
<212> TYPE: DNA
<213> ORGANISM: Artificial Sequence
<220> FEATURE:
<223> OTHER INFORMATION: Bsp120I

<400> SEQUENCE: 370 gggccc                                                                     6

<210> SEQ ID NO 371
<211> LENGTH: 6
<212> TYPE: DNA
<213> ORGANISM: Artificial Sequence
<220> FEATURE:
<223> OTHER INFORMATION: Bsp13I

<400> SEQUENCE: 371 tccgga                                                                     6

<210> SEQ ID NO 372
<211> LENGTH: 6
<212> TYPE: DNA
<213> ORGANISM: Artificial Sequence
<220> FEATURE:
<223> OTHER INFORMATION: Bsp1407I

<400> SEQUENCE: 372
```

```
tgtaca                                                                     6

<210> SEQ ID NO 373
<211> LENGTH: 6
<212> TYPE: DNA
<213> ORGANISM: Artificial Sequence
<220> FEATURE:
<223> OTHER INFORMATION: Bsp143II

<400> SEQUENCE: 373 rgcgcy                                                                     6

<210> SEQ ID NO 374
<211> LENGTH: 6
<212> TYPE: DNA
<213> ORGANISM: Artificial Sequence
<220> FEATURE:
<223> OTHER INFORMATION: Bsp19I

<400> SEQUENCE: 374 ccatgg                                                                     6

<210> SEQ ID NO 375
<211> LENGTH: 6
<212> TYPE: DNA
<213> ORGANISM: Artificial Sequence
<220> FEATURE:
<223> OTHER INFORMATION: Bsp68I

<400> SEQUENCE: 375 tcgcga                                                                     6

<210> SEQ ID NO 376
<211> LENGTH: 6
<212> TYPE: DNA
<213> ORGANISM: Artificial Sequence
<220> FEATURE:
<223> OTHER INFORMATION: BspA2I

<400> SEQUENCE: 376 cctagg                                                                     6

<210> SEQ ID NO 377
<211> LENGTH: 6
<212> TYPE: DNA
<213> ORGANISM: Artificial Sequence
<220> FEATURE:
<223> OTHER INFORMATION: BspCI

<400> SEQUENCE: 377 cgatcg                                                                     6

<210> SEQ ID NO 378
<211> LENGTH: 6
<212> TYPE: DNA
<213> ORGANISM: Artificial Sequence
<220> FEATURE:
<223> OTHER INFORMATION: BspGI

<400> SEQUENCE: 378 ctggac                                                                     6

<210> SEQ ID NO 379
<211> LENGTH: 7
<212> TYPE: DNA
<213> ORGANISM: Artificial Sequence
```

```
<220> FEATURE:
<223> OTHER INFORMATION: BspGI
<220> FEATURE:
<221> NAME/KEY: misc_feature
<222> LOCATION: 7
<223> OTHER INFORMATION: n = a, c, t, or g

<400> SEQUENCE: 379 ctggacn                                                                    7

<210> SEQ ID NO 380
<211> LENGTH: 7
<212> TYPE: DNA
<213> ORGANISM: Artificial Sequence
<220> FEATURE:
<223> OTHER INFORMATION: BspGI
<220> FEATURE:
<221> NAME/KEY: misc_feature
<222> LOCATION: 1
<223> OTHER INFORMATION: n = a, c, t, or g

<400> SEQUENCE: 380 ngtccag                                                                    7

<210> SEQ ID NO 381
<211> LENGTH: 6
<212> TYPE: DNA
<213> ORGANISM: Artificial Sequence
<220> FEATURE:
<223> OTHER INFORMATION: BspLU11I

<400> SEQUENCE: 381 acatgt                                                                     6

<210> SEQ ID NO 382
<211> LENGTH: 6
<212> TYPE: DNA
<213> ORGANISM: Artificial Sequence
<220> FEATURE:
<223> OTHER INFORMATION: BspMAI

<400> SEQUENCE: 382 ctgcag                                                                     6

<210> SEQ ID NO 383
<211> LENGTH: 6
<212> TYPE: DNA
<213> ORGANISM: Artificial Sequence
<220> FEATURE:
<223> OTHER INFORMATION: BspMII

<400> SEQUENCE: 383 tccgga                                                                     6

<210> SEQ ID NO 384
<211> LENGTH: 6
<212> TYPE: DNA
<213> ORGANISM: Artificial Sequence
<220> FEATURE:
<223> OTHER INFORMATION: BspOI

<400> SEQUENCE: 384 gctagc                                                                     6

<210> SEQ ID NO 385
<211> LENGTH: 6
<212> TYPE: DNA
```

```
<213> ORGANISM: Artificial Sequence
<220> FEATURE:
<223> OTHER INFORMATION: BspT104I

<400> SEQUENCE: 385 ttcgaa                                                                     6

<210> SEQ ID NO 386
<211> LENGTH: 6
<212> TYPE: DNA
<213> ORGANISM: Artificial Sequence
<220> FEATURE:
<223> OTHER INFORMATION: BspT107I

<400> SEQUENCE: 386 ggyrcc                                                                     6

<210> SEQ ID NO 387
<211> LENGTH: 6
<212> TYPE: DNA
<213> ORGANISM: Artificial Sequence
<220> FEATURE:
<223> OTHER INFORMATION: BspTI

<400> SEQUENCE: 387 cttaag                                                                     6

<210> SEQ ID NO 388
<211> LENGTH: 6
<212> TYPE: DNA
<213> ORGANISM: Artificial Sequence
<220> FEATURE:
<223> OTHER INFORMATION: BspXI

<400> SEQUENCE: 388 atcgat                                                                     6

<210> SEQ ID NO 389
<211> LENGTH: 6
<212> TYPE: DNA
<213> ORGANISM: Artificial Sequence
<220> FEATURE:
<223> OTHER INFORMATION: BssAI

<400> SEQUENCE: 389 rccggy                                                                     6

<210> SEQ ID NO 390
<211> LENGTH: 6
<212> TYPE: DNA
<213> ORGANISM: Artificial Sequence
<220> FEATURE:
<223> OTHER INFORMATION: BssHI

<400> SEQUENCE: 390 ctcgag                                                                     6

<210> SEQ ID NO 391
<211> LENGTH: 6
<212> TYPE: DNA
<213> ORGANISM: Artificial Sequence
<220> FEATURE:
<223> OTHER INFORMATION: BssNAI

<400> SEQUENCE: 391 gtatac                                                                     6
```

<210> SEQ ID NO 392
<211> LENGTH: 6
<212> TYPE: DNA
<213> ORGANISM: Artificial Sequence
<220> FEATURE:
<223> OTHER INFORMATION: BssNI

<400> SEQUENCE: 392 grcgyc                                                                    6

<210> SEQ ID NO 393
<211> LENGTH: 6
<212> TYPE: DNA
<213> ORGANISM: Artificial Sequence
<220> FEATURE:
<223> OTHER INFORMATION: BssT1I

<400> SEQUENCE: 393 ccwwgg                                                                    6

<210> SEQ ID NO 394
<211> LENGTH: 6
<212> TYPE: DNA
<213> ORGANISM: Artificial Sequence
<220> FEATURE:
<223> OTHER INFORMATION: Bst1107I

<400> SEQUENCE: 394 gtatac                                                                    6

<210> SEQ ID NO 395
<211> LENGTH: 6
<212> TYPE: DNA
<213> ORGANISM: Artificial Sequence
<220> FEATURE:
<223> OTHER INFORMATION: Bst98I

<400> SEQUENCE: 395 cttaag                                                                    6

<210> SEQ ID NO 396
<211> LENGTH: 6
<212> TYPE: DNA
<213> ORGANISM: Artificial Sequence
<220> FEATURE:
<223> OTHER INFORMATION: BstACI

<400> SEQUENCE: 396 grcgyc                                                                    6

<210> SEQ ID NO 397
<211> LENGTH: 6
<212> TYPE: DNA
<213> ORGANISM: Artificial Sequence
<220> FEATURE:
<223> OTHER INFORMATION: BstAFI

<400> SEQUENCE: 397 cttaag                                                                    6

<210> SEQ ID NO 398
<211> LENGTH: 6
<212> TYPE: DNA
<213> ORGANISM: Artificial Sequence
<220> FEATURE:

```
<223> OTHER INFORMATION: BstAUI

<400> SEQUENCE: 398 tgtaca                                                                    6

<210> SEQ ID NO 399
<211> LENGTH: 6
<212> TYPE: DNA
<213> ORGANISM: Artificial Sequence
<220> FEATURE:
<223> OTHER INFORMATION: BstBAI

<400> SEQUENCE: 399 yacgtr                                                                    6

<210> SEQ ID NO 400
<211> LENGTH: 6
<212> TYPE: DNA
<213> ORGANISM: Artificial Sequence
<220> FEATURE:
<223> OTHER INFORMATION: BstC8I
<220> FEATURE:
<221> NAME/KEY: misc_feature
<222> LOCATION: 3-4
<223> OTHER INFORMATION: n = a, c, t, or g

<400> SEQUENCE: 400 gcnngc                                                                    6

<210> SEQ ID NO 401
<211> LENGTH: 6
<212> TYPE: DNA
<213> ORGANISM: Artificial Sequence
<220> FEATURE:
<223> OTHER INFORMATION: BstDSI

<400> SEQUENCE: 401 ccrygg                                                                    6

<210> SEQ ID NO 402
<211> LENGTH: 6
<212> TYPE: DNA
<213> ORGANISM: Artificial Sequence
<220> FEATURE:
<223> OTHER INFORMATION: BstH2I

<400> SEQUENCE: 402 rgcgcy                                                                    6

<210> SEQ ID NO 403
<211> LENGTH: 6
<212> TYPE: DNA
<213> ORGANISM: Artificial Sequence
<220> FEATURE:
<223> OTHER INFORMATION: BstHPI

<400> SEQUENCE: 403 gttaac                                                                    6

<210> SEQ ID NO 404
<211> LENGTH: 6
<212> TYPE: DNA
<213> ORGANISM: Artificial Sequence
<220> FEATURE:
<223> OTHER INFORMATION: BstNSI

<400> SEQUENCE: 404
```

```
rcatgy                                                          6

<210> SEQ ID NO 405
<211> LENGTH: 6
<212> TYPE: DNA
<213> ORGANISM: Artificial Sequence
<220> FEATURE:
<223> OTHER INFORMATION: BstSFI

<400> SEQUENCE: 405 ctryag                                                          6

<210> SEQ ID NO 406
<211> LENGTH: 6
<212> TYPE: DNA
<213> ORGANISM: Artificial Sequence
<220> FEATURE:
<223> OTHER INFORMATION: BstSLI

<400> SEQUENCE: 406 gkgcmc                                                          6

<210> SEQ ID NO 407
<211> LENGTH: 6
<212> TYPE: DNA
<213> ORGANISM: Artificial Sequence
<220> FEATURE:
<223> OTHER INFORMATION: BstSNI

<400> SEQUENCE: 407 tacgta                                                          6

<210> SEQ ID NO 408
<211> LENGTH: 6
<212> TYPE: DNA
<213> ORGANISM: Artificial Sequence
<220> FEATURE:
<223> OTHER INFORMATION: BstX2I

<400> SEQUENCE: 408 rgatcy                                                          6

<210> SEQ ID NO 409
<211> LENGTH: 6
<212> TYPE: DNA
<213> ORGANISM: Artificial Sequence
<220> FEATURE:
<223> OTHER INFORMATION: BstZI

<400> SEQUENCE: 409 cggccg                                                          6

<210> SEQ ID NO 410
<211> LENGTH: 6
<212> TYPE: DNA
<213> ORGANISM: Artificial Sequence
<220> FEATURE:
<223> OTHER INFORMATION: BsuTUI

<400> SEQUENCE: 410 atcgat                                                          6

<210> SEQ ID NO 411
<211> LENGTH: 6
<212> TYPE: DNA
```

```
<213> ORGANISM: Artificial Sequence
<220> FEATURE:
<223> OTHER INFORMATION: BtuMI

<400> SEQUENCE: 411 tcgcga                                                                    6

<210> SEQ ID NO 412
<211> LENGTH: 6
<212> TYPE: DNA
<213> ORGANISM: Artificial Sequence
<220> FEATURE:
<223> OTHER INFORMATION: BveI

<400> SEQUENCE: 412 acctgc                                                                    6

<210> SEQ ID NO 413
<211> LENGTH: 14
<212> TYPE: DNA
<213> ORGANISM: Artificial Sequence
<220> FEATURE:
<223> OTHER INFORMATION: BveI
<220> FEATURE:
<221> NAME/KEY: misc_feature
<222> LOCATION: 7-14
<223> OTHER INFORMATION: n = a, c, t, or g

<400> SEQUENCE: 413
acctgcnnnn nnnn                                                          14

<210> SEQ ID NO 414
<211> LENGTH: 14
<212> TYPE: DNA
<213> ORGANISM: Artificial Sequence
<220> FEATURE:
<223> OTHER INFORMATION: BveI
<220> FEATURE:
<221> NAME/KEY: misc_feature
<222> LOCATION: 1-8
<223> OTHER INFORMATION: n = a, c, t, or g

<400> SEQUENCE: 414
nnnnnnnngc aggt                                                          14

<210> SEQ ID NO 415
<211> LENGTH: 6
<212> TYPE: DNA
<213> ORGANISM: Artificial Sequence
<220> FEATURE:
<223> OTHER INFORMATION: CciI

<400> SEQUENCE: 415 tcatga                                                                    6

<210> SEQ ID NO 416
<211> LENGTH: 6
<212> TYPE: DNA
<213> ORGANISM: Artificial Sequence
<220> FEATURE:
<223> OTHER INFORMATION: Cfr10I

<400> SEQUENCE: 416 rccggy                                                                    6

<210> SEQ ID NO 417
<211> LENGTH: 6
```

```
<212> TYPE: DNA
<213> ORGANISM: Artificial Sequence
<220> FEATURE:
<223> OTHER INFORMATION: Cfr42I

<400> SEQUENCE: 417 ccgcgg                                                                   6

<210> SEQ ID NO 418
<211> LENGTH: 6
<212> TYPE: DNA
<213> ORGANISM: Artificial Sequence
<220> FEATURE:
<223> OTHER INFORMATION: Cfr9I

<400> SEQUENCE: 418 cccggg                                                                   6

<210> SEQ ID NO 419
<211> LENGTH: 6
<212> TYPE: DNA
<213> ORGANISM: Artificial Sequence
<220> FEATURE:
<223> OTHER INFORMATION: CfrI

<400> SEQUENCE: 419 yggccr                                                                   6

<210> SEQ ID NO 420
<211> LENGTH: 6
<212> TYPE: DNA
<213> ORGANISM: Artificial Sequence
<220> FEATURE:
<223> OTHER INFORMATION: Csp45I

<400> SEQUENCE: 420 ttcgaa                                                                   6

<210> SEQ ID NO 421
<211> LENGTH: 6
<212> TYPE: DNA
<213> ORGANISM: Artificial Sequence
<220> FEATURE:
<223> OTHER INFORMATION: CspAI

<400> SEQUENCE: 421 accggt                                                                   6

<210> SEQ ID NO 422
<211> LENGTH: 6
<212> TYPE: DNA
<213> ORGANISM: Artificial Sequence
<220> FEATURE:
<223> OTHER INFORMATION: DinI

<400> SEQUENCE: 422 ggcgcc                                                                   6

<210> SEQ ID NO 423
<211> LENGTH: 6
<212> TYPE: DNA
<213> ORGANISM: Artificial Sequence
<220> FEATURE:
<223> OTHER INFORMATION: DrdII

<400> SEQUENCE: 423
``` gaacca                                                                   6

<210> SEQ ID NO 424
<211> LENGTH: 7
<212> TYPE: DNA
<213> ORGANISM: Artificial Sequence
<220> FEATURE:
<223> OTHER INFORMATION: DrdII
<220> FEATURE:
<221> NAME/KEY: misc_feature
<222> LOCATION: 7
<223> OTHER INFORMATION: n = a, c, t, or g

<400> SEQUENCE: 424 gaaccan                                                                  7

<210> SEQ ID NO 425
<211> LENGTH: 7
<212> TYPE: DNA
<213> ORGANISM: Artificial Sequence
<220> FEATURE:
<223> OTHER INFORMATION: DrdII
<220> FEATURE:
<221> NAME/KEY: misc_feature
<222> LOCATION: 1
<223> OTHER INFORMATION: n = a, c, t, or g

<400> SEQUENCE: 425 ntggttc                                                                  7

<210> SEQ ID NO 426
<211> LENGTH: 6
<212> TYPE: DNA
<213> ORGANISM: Artificial Sequence
<220> FEATURE:
<223> OTHER INFORMATION: DsaI

<400> SEQUENCE: 426 ccrygg                                                                   6

<210> SEQ ID NO 427
<211> LENGTH: 6
<212> TYPE: DNA
<213> ORGANISM: Artificial Sequence
<220> FEATURE:
<223> OTHER INFORMATION: Ecl136II

<400> SEQUENCE: 427 gagctc                                                                   6

<210> SEQ ID NO 428
<211> LENGTH: 6
<212> TYPE: DNA
<213> ORGANISM: Artificial Sequence
<220> FEATURE:
<223> OTHER INFORMATION: EclXI

<400> SEQUENCE: 428 cggccg                                                                   6

<210> SEQ ID NO 429
<211> LENGTH: 6
<212> TYPE: DNA
<213> ORGANISM: Artificial Sequence
<220> FEATURE:
<223> OTHER INFORMATION: Eco105I

<400> SEQUENCE: 429

```
tacgta                                                              6

<210> SEQ ID NO 430
<211> LENGTH: 6
<212> TYPE: DNA
<213> ORGANISM: Artificial Sequence
<220> FEATURE:
<223> OTHER INFORMATION: Eco130I

<400> SEQUENCE: 430 ccwwgg                                                              6

<210> SEQ ID NO 431
<211> LENGTH: 6
<212> TYPE: DNA
<213> ORGANISM: Artificial Sequence
<220> FEATURE:
<223> OTHER INFORMATION: Eco147I

<400> SEQUENCE: 431 aggcct                                                              6

<210> SEQ ID NO 432
<211> LENGTH: 6
<212> TYPE: DNA
<213> ORGANISM: Artificial Sequence
<220> FEATURE:
<223> OTHER INFORMATION: Eco24I

<400> SEQUENCE: 432 grgcyc                                                              6

<210> SEQ ID NO 433
<211> LENGTH: 6
<212> TYPE: DNA
<213> ORGANISM: Artificial Sequence
<220> FEATURE:
<223> OTHER INFORMATION: Eco32I

<400> SEQUENCE: 433 gatatc                                                              6

<210> SEQ ID NO 434
<211> LENGTH: 6
<212> TYPE: DNA
<213> ORGANISM: Artificial Sequence
<220> FEATURE:
<223> OTHER INFORMATION: Eco47III

<400> SEQUENCE: 434 agcgct                                                              6

<210> SEQ ID NO 435
<211> LENGTH: 6
<212> TYPE: DNA
<213> ORGANISM: Artificial Sequence
<220> FEATURE:
<223> OTHER INFORMATION: Eco52I

<400> SEQUENCE: 435 cggccg                                                              6

<210> SEQ ID NO 436
<211> LENGTH: 6
<212> TYPE: DNA
```

```
<213> ORGANISM: Artificial Sequence
<220> FEATURE:
<223> OTHER INFORMATION: Eco72I

<400> SEQUENCE: 436 cacgtg                                                                      6

<210> SEQ ID NO 437
<211> LENGTH: 6
<212> TYPE: DNA
<213> ORGANISM: Artificial Sequence
<220> FEATURE:
<223> OTHER INFORMATION: Eco88I

<400> SEQUENCE: 437 cycgrg                                                                      6

<210> SEQ ID NO 438
<211> LENGTH: 6
<212> TYPE: DNA
<213> ORGANISM: Artificial Sequence
<220> FEATURE:
<223> OTHER INFORMATION: EcoICRI

<400> SEQUENCE: 438 gagctc                                                                      6

<210> SEQ ID NO 439
<211> LENGTH: 6
<212> TYPE: DNA
<213> ORGANISM: Artificial Sequence
<220> FEATURE:
<223> OTHER INFORMATION: EcoT14I

<400> SEQUENCE: 439 ccwwgg                                                                      6

<210> SEQ ID NO 440
<211> LENGTH: 6
<212> TYPE: DNA
<213> ORGANISM: Artificial Sequence
<220> FEATURE:
<223> OTHER INFORMATION: EcoT22I

<400> SEQUENCE: 440 atgcat                                                                      6

<210> SEQ ID NO 441
<211> LENGTH: 6
<212> TYPE: DNA
<213> ORGANISM: Artificial Sequence
<220> FEATURE:
<223> OTHER INFORMATION: EcoT38I

<400> SEQUENCE: 441 grgcyc                                                                      6

<210> SEQ ID NO 442
<211> LENGTH: 6
<212> TYPE: DNA
<213> ORGANISM: Artificial Sequence
<220> FEATURE:
<223> OTHER INFORMATION: EgeI

<400> SEQUENCE: 442 ggcgcc                                                                      6
```

```
<210> SEQ ID NO 443
<211> LENGTH: 6
<212> TYPE: DNA
<213> ORGANISM: Artificial Sequence
<220> FEATURE:
<223> OTHER INFORMATION: EheI

<400> SEQUENCE: 443 ggcgcc                                                                   6

<210> SEQ ID NO 444
<211> LENGTH: 6
<212> TYPE: DNA
<213> ORGANISM: Artificial Sequence
<220> FEATURE:
<223> OTHER INFORMATION: ErhI

<400> SEQUENCE: 444 ccwwgg                                                                   6

<210> SEQ ID NO 445
<211> LENGTH: 6
<212> TYPE: DNA
<213> ORGANISM: Artificial Sequence
<220> FEATURE:
<223> OTHER INFORMATION: FauNDI

<400> SEQUENCE: 445 catatg                                                                   6

<210> SEQ ID NO 446
<211> LENGTH: 6
<212> TYPE: DNA
<213> ORGANISM: Artificial Sequence
<220> FEATURE:
<223> OTHER INFORMATION: FbaI

<400> SEQUENCE: 446 tgatca                                                                   6

<210> SEQ ID NO 447
<211> LENGTH: 6
<212> TYPE: DNA
<213> ORGANISM: Artificial Sequence
<220> FEATURE:
<223> OTHER INFORMATION: FblI

<400> SEQUENCE: 447 gtmkac                                                                   6

<210> SEQ ID NO 448
<211> LENGTH: 6
<212> TYPE: DNA
<213> ORGANISM: Artificial Sequence
<220> FEATURE:
<223> OTHER INFORMATION: FriOI

<400> SEQUENCE: 448 grgcyc                                                                   6

<210> SEQ ID NO 449
<211> LENGTH: 6
<212> TYPE: DNA
<213> ORGANISM: Artificial Sequence
<220> FEATURE:
```

```
<223> OTHER INFORMATION: FunI

<400> SEQUENCE: 449 agcgct                                                                    6

<210> SEQ ID NO 450
<211> LENGTH: 6
<212> TYPE: DNA
<213> ORGANISM: Artificial Sequence
<220> FEATURE:
<223> OTHER INFORMATION: FunII

<400> SEQUENCE: 450 gaattc                                                                    6

<210> SEQ ID NO 451
<211> LENGTH: 6
<212> TYPE: DNA
<213> ORGANISM: Artificial Sequence
<220> FEATURE:
<223> OTHER INFORMATION: GdiII

<400> SEQUENCE: 451 cggccr                                                                    6

<210> SEQ ID NO 452
<211> LENGTH: 6
<212> TYPE: DNA
<213> ORGANISM: Artificial Sequence
<220> FEATURE:
<223> OTHER INFORMATION: GdiII

<400> SEQUENCE: 452 yggccg                                                                    6

<210> SEQ ID NO 453
<211> LENGTH: 6
<212> TYPE: DNA
<213> ORGANISM: Artificial Sequence
<220> FEATURE:
<223> OTHER INFORMATION: GsaI

<400> SEQUENCE: 453 cccagc                                                                    6

<210> SEQ ID NO 454
<211> LENGTH: 6
<212> TYPE: DNA
<213> ORGANISM: Artificial Sequence
<220> FEATURE:
<223> OTHER INFORMATION: GsaI

<400> SEQUENCE: 454 gctggg                                                                    6

<210> SEQ ID NO 455
<211> LENGTH: 6
<212> TYPE: DNA
<213> ORGANISM: Artificial Sequence
<220> FEATURE:
<223> OTHER INFORMATION: HaeI

<400> SEQUENCE: 455 wggccw                                                                    6
```

```
<210> SEQ ID NO 456
<211> LENGTH: 6
<212> TYPE: DNA
<213> ORGANISM: Artificial Sequence
<220> FEATURE:
<223> OTHER INFORMATION: HgiAI

<400> SEQUENCE: 456 gwgcwc                                                                    6

<210> SEQ ID NO 457
<211> LENGTH: 6
<212> TYPE: DNA
<213> ORGANISM: Artificial Sequence
<220> FEATURE:
<223> OTHER INFORMATION: Hin1I

<400> SEQUENCE: 457 grcgyc                                                                    6

<210> SEQ ID NO 458
<211> LENGTH: 6
<212> TYPE: DNA
<213> ORGANISM: Artificial Sequence
<220> FEATURE:
<223> OTHER INFORMATION: HindII

<400> SEQUENCE: 458 gtyrac                                                                    6

<210> SEQ ID NO 459
<211> LENGTH: 6
<212> TYPE: DNA
<213> ORGANISM: Artificial Sequence
<220> FEATURE:
<223> OTHER INFORMATION: Hpy178III
<220> FEATURE:
<221> NAME/KEY: misc_feature
<222> LOCATION: 3-4
<223> OTHER INFORMATION: n = a, c, t, or g

<400> SEQUENCE: 459 tcnnga                                                                    6

<210> SEQ ID NO 460
<211> LENGTH: 6
<212> TYPE: DNA
<213> ORGANISM: Artificial Sequence
<220> FEATURE:
<223> OTHER INFORMATION: Hpy8I
<220> FEATURE:
<221> NAME/KEY: misc_feature
<222> LOCATION: 3-4
<223> OTHER INFORMATION: n = a, c, t, or g

<400> SEQUENCE: 460 gtnnac                                                                    6

<210> SEQ ID NO 461
<211> LENGTH: 6
<212> TYPE: DNA
<213> ORGANISM: Artificial Sequence
<220> FEATURE:
<223> OTHER INFORMATION: Hsp92I

<400> SEQUENCE: 461 grcgyc                                                                    6
```

<210> SEQ ID NO 462
<211> LENGTH: 6
<212> TYPE: DNA
<213> ORGANISM: Artificial Sequence
<220> FEATURE:
<223> OTHER INFORMATION: Kpn2I

<400> SEQUENCE: 462 tccgga                                                                        6

<210> SEQ ID NO 463
<211> LENGTH: 6
<212> TYPE: DNA
<213> ORGANISM: Artificial Sequence
<220> FEATURE:
<223> OTHER INFORMATION: Ksp22I

<400> SEQUENCE: 463 tgatca                                                                        6

<210> SEQ ID NO 464
<211> LENGTH: 6
<212> TYPE: DNA
<213> ORGANISM: Artificial Sequence
<220> FEATURE:
<223> OTHER INFORMATION: KspAI

<400> SEQUENCE: 464 gttaac                                                                        6

<210> SEQ ID NO 465
<211> LENGTH: 6
<212> TYPE: DNA
<213> ORGANISM: Artificial Sequence
<220> FEATURE:
<223> OTHER INFORMATION: MflI

<400> SEQUENCE: 465 rgatcy                                                                        6

<210> SEQ ID NO 466
<211> LENGTH: 6
<212> TYPE: DNA
<213> ORGANISM: Artificial Sequence
<220> FEATURE:
<223> OTHER INFORMATION: MhlI

<400> SEQUENCE: 466 gdgchc                                                                        6

<210> SEQ ID NO 467
<211> LENGTH: 6
<212> TYPE: DNA
<213> ORGANISM: Artificial Sequence
<220> FEATURE:
<223> OTHER INFORMATION: MlsI

<400> SEQUENCE: 467 tggcca                                                                        6

<210> SEQ ID NO 468
<211> LENGTH: 6
<212> TYPE: DNA
<213> ORGANISM: Artificial Sequence
<220> FEATURE:
<223> OTHER INFORMATION: MluNI

```
<400> SEQUENCE: 468 tggcca                                                                    6

<210> SEQ ID NO 469
<211> LENGTH: 6
<212> TYPE: DNA
<213> ORGANISM: Artificial Sequence
<220> FEATURE:
<223> OTHER INFORMATION: Mly113I

<400> SEQUENCE: 469 ggcgcc                                                                    6

<210> SEQ ID NO 470
<211> LENGTH: 6
<212> TYPE: DNA
<213> ORGANISM: Artificial Sequence
<220> FEATURE:
<223> OTHER INFORMATION: Mph1103I

<400> SEQUENCE: 470 atgcat                                                                    6

<210> SEQ ID NO 471
<211> LENGTH: 6
<212> TYPE: DNA
<213> ORGANISM: Artificial Sequence
<220> FEATURE:
<223> OTHER INFORMATION: MroI

<400> SEQUENCE: 471 tccgga                                                                    6

<210> SEQ ID NO 472
<211> LENGTH: 6
<212> TYPE: DNA
<213> ORGANISM: Artificial Sequence
<220> FEATURE:
<223> OTHER INFORMATION: MroNI

<400> SEQUENCE: 472 gccggc                                                                    6

<210> SEQ ID NO 473
<211> LENGTH: 6
<212> TYPE: DNA
<213> ORGANISM: Artificial Sequence
<220> FEATURE:
<223> OTHER INFORMATION: Msp20I

<400> SEQUENCE: 473 tggcca                                                                    6

<210> SEQ ID NO 474
<211> LENGTH: 6
<212> TYPE: DNA
<213> ORGANISM: Artificial Sequence
<220> FEATURE:
<223> OTHER INFORMATION: MspCI

<400> SEQUENCE: 474 cttaag                                                                    6

<210> SEQ ID NO 475
```

```
<211> LENGTH: 6
<212> TYPE: DNA
<213> ORGANISM: Artificial Sequence
<220> FEATURE:
<223> OTHER INFORMATION: MstI

<400> SEQUENCE: 475 tgcgca                                                                      6

<210> SEQ ID NO 476
<211> LENGTH: 6
<212> TYPE: DNA
<213> ORGANISM: Artificial Sequence
<220> FEATURE:
<223> OTHER INFORMATION: MunI

<400> SEQUENCE: 476 caattg                                                                      6

<210> SEQ ID NO 477
<211> LENGTH: 6
<212> TYPE: DNA
<213> ORGANISM: Artificial Sequence
<220> FEATURE:
<223> OTHER INFORMATION: MvrI

<400> SEQUENCE: 477 cgatcg                                                                      6

<210> SEQ ID NO 478
<211> LENGTH: 6
<212> TYPE: DNA
<213> ORGANISM: Artificial Sequence
<220> FEATURE:
<223> OTHER INFORMATION: NgoAIV

<400> SEQUENCE: 478 gccggc                                                                      6

<210> SEQ ID NO 479
<211> LENGTH: 6
<212> TYPE: DNA
<213> ORGANISM: Artificial Sequence
<220> FEATURE:
<223> OTHER INFORMATION: NsbI

<400> SEQUENCE: 479 tgcgca                                                                      6

<210> SEQ ID NO 480
<211> LENGTH: 6
<212> TYPE: DNA
<213> ORGANISM: Artificial Sequence
<220> FEATURE:
<223> OTHER INFORMATION: NspIII

<400> SEQUENCE: 480 cycgrg                                                                      6

<210> SEQ ID NO 481
<211> LENGTH: 6
<212> TYPE: DNA
<213> ORGANISM: Artificial Sequence
<220> FEATURE:
<223> OTHER INFORMATION: NspV

<400> SEQUENCE: 481
```

```
ttcgaa                                                              6

<210> SEQ ID NO 482
<211> LENGTH: 6
<212> TYPE: DNA
<213> ORGANISM: Artificial Sequence
<220> FEATURE:
<223> OTHER INFORMATION: PagI

<400> SEQUENCE: 482 tcatga                                                              6

<210> SEQ ID NO 483
<211> LENGTH: 6
<212> TYPE: DNA
<213> ORGANISM: Artificial Sequence
<220> FEATURE:
<223> OTHER INFORMATION: PauI

<400> SEQUENCE: 483 gcgcgc                                                              6

<210> SEQ ID NO 484
<211> LENGTH: 6
<212> TYPE: DNA
<213> ORGANISM: Artificial Sequence
<220> FEATURE:
<223> OTHER INFORMATION: PceI

<400> SEQUENCE: 484 aggcct                                                              6

<210> SEQ ID NO 485
<211> LENGTH: 6
<212> TYPE: DNA
<213> ORGANISM: Artificial Sequence
<220> FEATURE:
<223> OTHER INFORMATION: PdiI

<400> SEQUENCE: 485 gccggc                                                              6

<210> SEQ ID NO 486
<211> LENGTH: 6
<212> TYPE: DNA
<213> ORGANISM: Artificial Sequence
<220> FEATURE:
<223> OTHER INFORMATION: Pfl23II

<400> SEQUENCE: 486 cgtacg                                                              6

<210> SEQ ID NO 487
<211> LENGTH: 6
<212> TYPE: DNA
<213> ORGANISM: Artificial Sequence
<220> FEATURE:
<223> OTHER INFORMATION: PinAI

<400> SEQUENCE: 487 accggt                                                              6

<210> SEQ ID NO 488
<211> LENGTH: 6
<212> TYPE: DNA
```

```
<213> ORGANISM: Artificial Sequence
<220> FEATURE:
<223> OTHER INFORMATION: Ple19I

<400> SEQUENCE: 488 cgatcg                                                                     6

<210> SEQ ID NO 489
<211> LENGTH: 6
<212> TYPE: DNA
<213> ORGANISM: Artificial Sequence
<220> FEATURE:
<223> OTHER INFORMATION: PmaCI

<400> SEQUENCE: 489 cacgtg                                                                     6

<210> SEQ ID NO 490
<211> LENGTH: 6
<212> TYPE: DNA
<213> ORGANISM: Artificial Sequence
<220> FEATURE:
<223> OTHER INFORMATION: PshBI

<400> SEQUENCE: 490 attaat                                                                     6

<210> SEQ ID NO 491
<211> LENGTH: 6
<212> TYPE: DNA
<213> ORGANISM: Artificial Sequence
<220> FEATURE:
<223> OTHER INFORMATION: Psp124BI

<400> SEQUENCE: 491 gagctc                                                                     6

<210> SEQ ID NO 492
<211> LENGTH: 6
<212> TYPE: DNA
<213> ORGANISM: Artificial Sequence
<220> FEATURE:
<223> OTHER INFORMATION: Psp1406I

<400> SEQUENCE: 492 aacgtt                                                                     6

<210> SEQ ID NO 493
<211> LENGTH: 6
<212> TYPE: DNA
<213> ORGANISM: Artificial Sequence
<220> FEATURE:
<223> OTHER INFORMATION: PspAI

<400> SEQUENCE: 493 cccggg                                                                     6

<210> SEQ ID NO 494
<211> LENGTH: 6
<212> TYPE: DNA
<213> ORGANISM: Artificial Sequence
<220> FEATURE:
<223> OTHER INFORMATION: PspLI

<400> SEQUENCE: 494 cgtacg                                                                     6
```

```
<210> SEQ ID NO 495
<211> LENGTH: 6
<212> TYPE: DNA
<213> ORGANISM: Artificial Sequence
<220> FEATURE:
<223> OTHER INFORMATION: PspN4I
<220> FEATURE:
<221> NAME/KEY: misc_feature
<222> LOCATION: 3-4
<223> OTHER INFORMATION: n = a, c, t, or g

<400> SEQUENCE: 495 ggnncc                                                                       6

<210> SEQ ID NO 496
<211> LENGTH: 6
<212> TYPE: DNA
<213> ORGANISM: Artificial Sequence
<220> FEATURE:
<223> OTHER INFORMATION: PsuI

<400> SEQUENCE: 496 rgatcy                                                                       6

<210> SEQ ID NO 497
<211> LENGTH: 6
<212> TYPE: DNA
<213> ORGANISM: Artificial Sequence
<220> FEATURE:
<223> OTHER INFORMATION: RcaI

<400> SEQUENCE: 497 tcatga                                                                       6

<210> SEQ ID NO 498
<211> LENGTH: 6
<212> TYPE: DNA
<213> ORGANISM: Artificial Sequence
<220> FEATURE:
<223> OTHER INFORMATION: SduI

<400> SEQUENCE: 498 gdgchc                                                                       6

<210> SEQ ID NO 499
<211> LENGTH: 6
<212> TYPE: DNA
<213> ORGANISM: Artificial Sequence
<220> FEATURE:
<223> OTHER INFORMATION: Sfr274I

<400> SEQUENCE: 499 ctcgag                                                                       6

<210> SEQ ID NO 500
<211> LENGTH: 6
<212> TYPE: DNA
<213> ORGANISM: Artificial Sequence
<220> FEATURE:
<223> OTHER INFORMATION: Sfr303I

<400> SEQUENCE: 500 ccgcgg                                                                       6

<210> SEQ ID NO 501
```

```
<211> LENGTH: 6
<212> TYPE: DNA
<213> ORGANISM: Artificial Sequence
<220> FEATURE:
<223> OTHER INFORMATION: SfuI

<400> SEQUENCE: 501 ttcgaa                                                                      6

<210> SEQ ID NO 502
<211> LENGTH: 6
<212> TYPE: DNA
<213> ORGANISM: Artificial Sequence
<220> FEATURE:
<223> OTHER INFORMATION: SgrBI

<400> SEQUENCE: 502 ccgcgg                                                                      6

<210> SEQ ID NO 503
<211> LENGTH: 6
<212> TYPE: DNA
<213> ORGANISM: Artificial Sequence
<220> FEATURE:
<223> OTHER INFORMATION: SlaI

<400> SEQUENCE: 503 ctcgag                                                                      6

<210> SEQ ID NO 504
<211> LENGTH: 6
<212> TYPE: DNA
<213> ORGANISM: Artificial Sequence
<220> FEATURE:
<223> OTHER INFORMATION: SpaHI

<400> SEQUENCE: 504 gcatgc                                                                      6

<210> SEQ ID NO 505
<211> LENGTH: 6
<212> TYPE: DNA
<213> ORGANISM: Artificial Sequence
<220> FEATURE:
<223> OTHER INFORMATION: SseBI

<400> SEQUENCE: 505 aggcct                                                                      6

<210> SEQ ID NO 506
<211> LENGTH: 6
<212> TYPE: DNA
<213> ORGANISM: Artificial Sequence
<220> FEATURE:
<223> OTHER INFORMATION: SspBI

<400> SEQUENCE: 506 tgtaca                                                                      6

<210> SEQ ID NO 507
<211> LENGTH: 6
<212> TYPE: DNA
<213> ORGANISM: Artificial Sequence
<220> FEATURE:
<223> OTHER INFORMATION: SstI

<400> SEQUENCE: 507
```

```
gagctc                                                              6

<210> SEQ ID NO 508
<211> LENGTH: 6
<212> TYPE: DNA
<213> ORGANISM: Artificial Sequence
<220> FEATURE:
<223> OTHER INFORMATION: SstII

<400> SEQUENCE: 508 ccgcgg                                                              6

<210> SEQ ID NO 509
<211> LENGTH: 6
<212> TYPE: DNA
<213> ORGANISM: Artificial Sequence
<220> FEATURE:
<223> OTHER INFORMATION: SunI

<400> SEQUENCE: 509 cgtacg                                                              6

<210> SEQ ID NO 510
<211> LENGTH: 6
<212> TYPE: DNA
<213> ORGANISM: Artificial Sequence
<220> FEATURE:
<223> OTHER INFORMATION: TatI

<400> SEQUENCE: 510 wgtacw                                                              6

<210> SEQ ID NO 511
<211> LENGTH: 6
<212> TYPE: DNA
<213> ORGANISM: Artificial Sequence
<220> FEATURE:
<223> OTHER INFORMATION: Vha464I

<400> SEQUENCE: 511 cttaag                                                              6

<210> SEQ ID NO 512
<211> LENGTH: 6
<212> TYPE: DNA
<213> ORGANISM: Artificial Sequence
<220> FEATURE:
<223> OTHER INFORMATION: VneI

<400> SEQUENCE: 512 gtgcac                                                              6

<210> SEQ ID NO 513
<211> LENGTH: 6
<212> TYPE: DNA
<213> ORGANISM: Artificial Sequence
<220> FEATURE:
<223> OTHER INFORMATION: VspI

<400> SEQUENCE: 513 attaat                                                              6

<210> SEQ ID NO 514
<211> LENGTH: 6
<212> TYPE: DNA
```

```
<213> ORGANISM: Artificial Sequence
<220> FEATURE:
<223> OTHER INFORMATION: XapI

<400> SEQUENCE: 514 raatty                                                                        6

<210> SEQ ID NO 515
<211> LENGTH: 6
<212> TYPE: DNA
<213> ORGANISM: Artificial Sequence
<220> FEATURE:
<223> OTHER INFORMATION: XhoII

<400> SEQUENCE: 515 rgatcy                                                                        6

<210> SEQ ID NO 516
<211> LENGTH: 6
<212> TYPE: DNA
<213> ORGANISM: Artificial Sequence
<220> FEATURE:
<223> OTHER INFORMATION: XmaCI

<400> SEQUENCE: 516 cccggg                                                                        6

<210> SEQ ID NO 517
<211> LENGTH: 6
<212> TYPE: DNA
<213> ORGANISM: Artificial Sequence
<220> FEATURE:
<223> OTHER INFORMATION: XmaIII

<400> SEQUENCE: 517 cggccg                                                                        6

<210> SEQ ID NO 518
<211> LENGTH: 6
<212> TYPE: DNA
<213> ORGANISM: Artificial Sequence
<220> FEATURE:
<223> OTHER INFORMATION: XmaJI

<400> SEQUENCE: 518 cctagg                                                                        6

<210> SEQ ID NO 519
<211> LENGTH: 6
<212> TYPE: DNA
<213> ORGANISM: Artificial Sequence
<220> FEATURE:
<223> OTHER INFORMATION: XmiI

<400> SEQUENCE: 519 gtmkac                                                                        6

<210> SEQ ID NO 520
<211> LENGTH: 6
<212> TYPE: DNA
<213> ORGANISM: Artificial Sequence
<220> FEATURE:
<223> OTHER INFORMATION: ZhoI

<400> SEQUENCE: 520 atcgat                                                                        6
```

```
<210> SEQ ID NO 521
<211> LENGTH: 6
<212> TYPE: DNA
<213> ORGANISM: Artificial Sequence
<220> FEATURE:
<223> OTHER INFORMATION: Zsp2I

<400> SEQUENCE: 521 atgcat                                                                  6

<210> SEQ ID NO 522
<211> LENGTH: 7
<212> TYPE: DNA
<213> ORGANISM: Artificial Sequence
<220> FEATURE:
<223> OTHER INFORMATION: AocI
<220> FEATURE:
<221> NAME/KEY: misc_feature
<222> LOCATION: 4
<223> OTHER INFORMATION: n = a, c, t, or g

<400> SEQUENCE: 522 cctnagg                                                                 7

<210> SEQ ID NO 523
<211> LENGTH: 7
<212> TYPE: DNA
<213> ORGANISM: Artificial Sequence
<220> FEATURE:
<223> OTHER INFORMATION: AxyI
<220> FEATURE:
<221> NAME/KEY: misc_feature
<222> LOCATION: 4
<223> OTHER INFORMATION: n = a, c, t, or g

<400> SEQUENCE: 523 cctnagg                                                                 7

<210> SEQ ID NO 524
<211> LENGTH: 7
<212> TYPE: DNA
<213> ORGANISM: Artificial Sequence
<220> FEATURE:
<223> OTHER INFORMATION: Bpu1102I
<220> FEATURE:
<221> NAME/KEY: misc_feature
<222> LOCATION: 4
<223> OTHER INFORMATION: n = a, c, t, or g

<400> SEQUENCE: 524 gctnagc                                                                 7

<210> SEQ ID NO 525
<211> LENGTH: 7
<212> TYPE: DNA
<213> ORGANISM: Artificial Sequence
<220> FEATURE:
<223> OTHER INFORMATION: Bse21I
<220> FEATURE:
<221> NAME/KEY: misc_feature
<222> LOCATION: 4
<223> OTHER INFORMATION: n = a, c, t, or g

<400> SEQUENCE: 525 cctnagg                                                                 7

<210> SEQ ID NO 526
```

```
<211> LENGTH: 7
<212> TYPE: DNA
<213> ORGANISM: Artificial Sequence
<220> FEATURE:
<223> OTHER INFORMATION: Bsp1720I
<220> FEATURE:
<221> NAME/KEY: misc_feature
<222> LOCATION: 4
<223> OTHER INFORMATION: n = a, c, t, or g

<400> SEQUENCE: 526 gctnagc                                                                    7

<210> SEQ ID NO 527
<211> LENGTH: 7
<212> TYPE: DNA
<213> ORGANISM: Artificial Sequence
<220> FEATURE:
<223> OTHER INFORMATION: BstPI
<220> FEATURE:
<221> NAME/KEY: misc_feature
<222> LOCATION: 4
<223> OTHER INFORMATION: n = a, c, t, or g

<400> SEQUENCE: 527 ggtnacc                                                                    7

<210> SEQ ID NO 528
<211> LENGTH: 7
<212> TYPE: DNA
<213> ORGANISM: Artificial Sequence
<220> FEATURE:
<223> OTHER INFORMATION: CelII
<220> FEATURE:
<221> NAME/KEY: misc_feature
<222> LOCATION: 4
<223> OTHER INFORMATION: n = a, c, t, or g

<400> SEQUENCE: 528 gctnagc                                                                    7

<210> SEQ ID NO 529
<211> LENGTH: 7
<212> TYPE: DNA
<213> ORGANISM: Artificial Sequence
<220> FEATURE:
<223> OTHER INFORMATION: CpoI

<400> SEQUENCE: 529 cggwccg                                                                    7

<210> SEQ ID NO 530
<211> LENGTH: 7
<212> TYPE: DNA
<213> ORGANISM: Artificial Sequence
<220> FEATURE:
<223> OTHER INFORMATION: CspI

<400> SEQUENCE: 530 cggwccg                                                                    7

<210> SEQ ID NO 531
<211> LENGTH: 7
<212> TYPE: DNA
<213> ORGANISM: Artificial Sequence
<220> FEATURE:
<223> OTHER INFORMATION: DraII
<220> FEATURE:
<221> NAME/KEY: misc_feature
```

-continued

<222> LOCATION: 4
<223> OTHER INFORMATION: n = a, c, t, or g

<400> SEQUENCE: 531 rggnccy                                                                  7

<210> SEQ ID NO 532
<211> LENGTH: 7
<212> TYPE: DNA
<213> ORGANISM: Artificial Sequence
<220> FEATURE:
<223> OTHER INFORMATION: Eco065I
<220> FEATURE:
<221> NAME/KEY: misc_feature
<222> LOCATION: 4
<223> OTHER INFORMATION: n = a, c, t, or g

<400> SEQUENCE: 532 ggtnacc                                                                  7

<210> SEQ ID NO 533
<211> LENGTH: 7
<212> TYPE: DNA
<213> ORGANISM: Artificial Sequence
<220> FEATURE:
<223> OTHER INFORMATION: Eco81I
<220> FEATURE:
<221> NAME/KEY: misc_feature
<222> LOCATION: 4
<223> OTHER INFORMATION: n = a, c, t, or g

<400> SEQUENCE: 533 cctnagg                                                                  7

<210> SEQ ID NO 534
<211> LENGTH: 7
<212> TYPE: DNA
<213> ORGANISM: Artificial Sequence
<220> FEATURE:
<223> OTHER INFORMATION: Eco91I
<220> FEATURE:
<221> NAME/KEY: misc_feature
<222> LOCATION: 4
<223> OTHER INFORMATION: n = a, c, t, or g

<400> SEQUENCE: 534 ggtnacc                                                                  7

<210> SEQ ID NO 535
<211> LENGTH: 7
<212> TYPE: DNA
<213> ORGANISM: Artificial Sequence
<220> FEATURE:
<223> OTHER INFORMATION: EspI
<220> FEATURE:
<221> NAME/KEY: misc_feature
<222> LOCATION: 4
<223> OTHER INFORMATION: n = a, c, t, or g

<400> SEQUENCE: 535 gctnagc                                                                  7

<210> SEQ ID NO 536
<211> LENGTH: 7
<212> TYPE: DNA
<213> ORGANISM: Artificial Sequence
<220> FEATURE:
<223> OTHER INFORMATION: KflI

```
<400> SEQUENCE: 536 gggwccc                                                              7

<210> SEQ ID NO 537

<400> SEQUENCE: 537

000

<210> SEQ ID NO 538

<400> SEQUENCE: 538

000

<210> SEQ ID NO 539
<211> LENGTH: 7
<212> TYPE: DNA
<213> ORGANISM: Artificial Sequence
<220> FEATURE:
<223> OTHER INFORMATION: MabI

<400> SEQUENCE: 539 accwggt                                                              7

<210> SEQ ID NO 540
<211> LENGTH: 7
<212> TYPE: DNA
<213> ORGANISM: Artificial Sequence
<220> FEATURE:
<223> OTHER INFORMATION: PpuXI

<400> SEQUENCE: 540 rggwccy                                                              7

<210> SEQ ID NO 541
<211> LENGTH: 7
<212> TYPE: DNA
<213> ORGANISM: Artificial Sequence
<220> FEATURE:
<223> OTHER INFORMATION: Psp5II

<400> SEQUENCE: 541 rggwccy                                                              7

<210> SEQ ID NO 542
<211> LENGTH: 7
<212> TYPE: DNA
<213> ORGANISM: Artificial Sequence
<220> FEATURE:
<223> OTHER INFORMATION: PspEI
<220> FEATURE:
<221> NAME/KEY: misc_feature
<222> LOCATION: 4
<223> OTHER INFORMATION: n = a, c, t, or g

<400> SEQUENCE: 542 ggtnacc                                                              7

<210> SEQ ID NO 543
<211> LENGTH: 7
<212> TYPE: DNA
<213> ORGANISM: Artificial Sequence
<220> FEATURE:
<223> OTHER INFORMATION: Rsr2I

<400> SEQUENCE: 543
``` cggwccg                                                                          7

<210> SEQ ID NO 544
<211> LENGTH: 7
<212> TYPE: DNA
<213> ORGANISM: Artificial Sequence
<220> FEATURE:
<223> OTHER INFORMATION: SauI
<220> FEATURE:
<221> NAME/KEY: misc_feature
<222> LOCATION: 4
<223> OTHER INFORMATION: n = a, c, t, or g

<400> SEQUENCE: 544 cctnagg                                                                          7

<210> SEQ ID NO 545
<211> LENGTH: 8
<212> TYPE: DNA
<213> ORGANISM: Artificial Sequence
<220> FEATURE:
<223> OTHER INFORMATION: AbsI

<400> SEQUENCE: 545 cctcgagg                                                                         8

<210> SEQ ID NO 546
<211> LENGTH: 8
<212> TYPE: DNA
<213> ORGANISM: Artificial Sequence
<220> FEATURE:
<223> OTHER INFORMATION: CciNI

<400> SEQUENCE: 546 gcggccgc                                                                         8

<210> SEQ ID NO 547
<211> LENGTH: 8
<212> TYPE: DNA
<213> ORGANISM: Artificial Sequence
<220> FEATURE:
<223> OTHER INFORMATION: FspAI

<400> SEQUENCE: 547 rtgcgcay                                                                         8

<210> SEQ ID NO 548
<211> LENGTH: 8
<212> TYPE: DNA
<213> ORGANISM: Artificial Sequence
<220> FEATURE:
<223> OTHER INFORMATION: MauBI

<400> SEQUENCE: 548 cgcgcgcg                                                                         8

<210> SEQ ID NO 549
<211> LENGTH: 8
<212> TYPE: DNA
<213> ORGANISM: Artificial Sequence
<220> FEATURE:
<223> OTHER INFORMATION: MreI

<400> SEQUENCE: 549 cgccggcg                                                                         8

```
<210> SEQ ID NO 550
<211> LENGTH: 8
<212> TYPE: DNA
<213> ORGANISM: Artificial Sequence
<220> FEATURE:
<223> OTHER INFORMATION: MssI

<400> SEQUENCE: 550 gtttaaac                                                               8

<210> SEQ ID NO 551
<211> LENGTH: 8
<212> TYPE: DNA
<213> ORGANISM: Artificial Sequence
<220> FEATURE:
<223> OTHER INFORMATION: RgaI

<400> SEQUENCE: 551 gcgatcgc                                                               8

<210> SEQ ID NO 552
<211> LENGTH: 8
<212> TYPE: DNA
<213> ORGANISM: Artificial Sequence
<220> FEATURE:
<223> OTHER INFORMATION: SdaI

<400> SEQUENCE: 552 cctgcagg                                                               8

<210> SEQ ID NO 553
<211> LENGTH: 8
<212> TYPE: DNA
<213> ORGANISM: Artificial Sequence
<220> FEATURE:
<223> OTHER INFORMATION: SfaAI

<400> SEQUENCE: 553 gcgatcgc                                                               8

<210> SEQ ID NO 554
<211> LENGTH: 8
<212> TYPE: DNA
<213> ORGANISM: Artificial Sequence
<220> FEATURE:
<223> OTHER INFORMATION: SgfI

<400> SEQUENCE: 554 gcgatcgc                                                               8

<210> SEQ ID NO 555
<211> LENGTH: 8
<212> TYPE: DNA
<213> ORGANISM: Artificial Sequence
<220> FEATURE:
<223> OTHER INFORMATION: SmiI

<400> SEQUENCE: 555 atttaaat                                                               8

<210> SEQ ID NO 556
<211> LENGTH: 8
<212> TYPE: DNA
<213> ORGANISM: Artificial Sequence
<220> FEATURE:
<223> OTHER INFORMATION: Sse232I
```

```
<400> SEQUENCE: 556 cgccggcg                                                                8

<210> SEQ ID NO 557
<211> LENGTH: 9
<212> TYPE: DNA
<213> ORGANISM: Artificial Sequence
<220> FEATURE:
<223> OTHER INFORMATION: AdeI
<220> FEATURE:
<221> NAME/KEY: misc_feature
<222> LOCATION: 4-6
<223> OTHER INFORMATION: n = a, c, t, or g

<400> SEQUENCE: 557 cacnnngtg                                                               9

<210> SEQ ID NO 558
<211> LENGTH: 9
<212> TYPE: DNA
<213> ORGANISM: Artificial Sequence
<220> FEATURE:
<223> OTHER INFORMATION: AspI
<220> FEATURE:
<221> NAME/KEY: misc_feature
<222> LOCATION: 4-6
<223> OTHER INFORMATION: n = a, c, t, or g

<400> SEQUENCE: 558 gacnnngtc                                                               9

<210> SEQ ID NO 559
<211> LENGTH: 9
<212> TYPE: DNA
<213> ORGANISM: Artificial Sequence
<220> FEATURE:
<223> OTHER INFORMATION: CaiI
<220> FEATURE:
<221> NAME/KEY: misc_feature
<222> LOCATION: 4-6
<223> OTHER INFORMATION: n = a, c, t, or g

<400> SEQUENCE: 559 cagnnnctg                                                               9

<210> SEQ ID NO 560
<211> LENGTH: 9
<212> TYPE: DNA
<213> ORGANISM: Artificial Sequence
<220> FEATURE:
<223> OTHER INFORMATION: PsyI
<220> FEATURE:
<221> NAME/KEY: misc_feature
<222> LOCATION: 4-6
<223> OTHER INFORMATION: n = a, c, t, or g

<400> SEQUENCE: 560 gacnnngtc                                                               9

<210> SEQ ID NO 561
<211> LENGTH: 9
<212> TYPE: DNA
<213> ORGANISM: Artificial Sequence
<220> FEATURE:
<223> OTHER INFORMATION: TelI
<220> FEATURE:
<221> NAME/KEY: misc_feature
<222> LOCATION: 4-6
```

```
<223> OTHER INFORMATION: n = a, c, t, or g

<400> SEQUENCE: 561 gacnnngtc                                                                                    9

<210> SEQ ID NO 562
<211> LENGTH: 10
<212> TYPE: DNA
<213> ORGANISM: Artificial Sequence
<220> FEATURE:
<223> OTHER INFORMATION: Asp700I
<220> FEATURE:
<221> NAME/KEY: misc_feature
<222> LOCATION: 4-7
<223> OTHER INFORMATION: n = a, c, t, or g

<400> SEQUENCE: 562 gaannnnttc                                                                                  10

<210> SEQ ID NO 563
<211> LENGTH: 10
<212> TYPE: DNA
<213> ORGANISM: Artificial Sequence
<220> FEATURE:
<223> OTHER INFORMATION: BoxI
<220> FEATURE:
<221> NAME/KEY: misc_feature
<222> LOCATION: 4-7
<223> OTHER INFORMATION: n = a, c, t, or g

<400> SEQUENCE: 563 gacnnnngtc                                                                                  10

<210> SEQ ID NO 564
<211> LENGTH: 10
<212> TYPE: DNA
<213> ORGANISM: Artificial Sequence
<220> FEATURE:
<223> OTHER INFORMATION: Bse8I
<220> FEATURE:
<221> NAME/KEY: misc_feature
<222> LOCATION: 4-7
<223> OTHER INFORMATION: n = a, c, t, or g

<400> SEQUENCE: 564 gatnnnnatc                                                                                  10

<210> SEQ ID NO 565
<211> LENGTH: 10
<212> TYPE: DNA
<213> ORGANISM: Artificial Sequence
<220> FEATURE:
<223> OTHER INFORMATION: BseJI
<220> FEATURE:
<221> NAME/KEY: misc_feature
<222> LOCATION: 4-7
<223> OTHER INFORMATION: n = a, c, t, or g

<400> SEQUENCE: 565 gatnnnnatc                                                                                  10

<210> SEQ ID NO 566
<211> LENGTH: 10
<212> TYPE: DNA
<213> ORGANISM: Artificial Sequence
<220> FEATURE:
<223> OTHER INFORMATION: BsiBI
<220> FEATURE:
<221> NAME/KEY: misc_feature
```

-continued

```
<222> LOCATION: 4-7
<223> OTHER INFORMATION: n = a, c, t, or g

<400> SEQUENCE: 566 gatnnnnatc                                                             10

<210> SEQ ID NO 567
<211> LENGTH: 10
<212> TYPE: DNA
<213> ORGANISM: Artificial Sequence
<220> FEATURE:
<223> OTHER INFORMATION: BsrBRI
<220> FEATURE:
<221> NAME/KEY: misc_feature
<222> LOCATION: 4-7
<223> OTHER INFORMATION: n = a, c, t, or g

<400> SEQUENCE: 567 gatnnnnatc                                                             10

<210> SEQ ID NO 568
<211> LENGTH: 10
<212> TYPE: DNA
<213> ORGANISM: Artificial Sequence
<220> FEATURE:
<223> OTHER INFORMATION: BstPAI
<220> FEATURE:
<221> NAME/KEY: misc_feature
<222> LOCATION: 4-7
<223> OTHER INFORMATION: n = a, c, t, or g

<400> SEQUENCE: 568 gacnnnngtc                                                             10

<210> SEQ ID NO 569
<211> LENGTH: 10
<212> TYPE: DNA
<213> ORGANISM: Artificial Sequence
<220> FEATURE:
<223> OTHER INFORMATION: CjeNII
<220> FEATURE:
<221> NAME/KEY: misc_feature
<222> LOCATION: 4-8
<223> OTHER INFORMATION: n = a, c, t, or g

<400> SEQUENCE: 569 gagnnnnngt                                                             10

<210> SEQ ID NO 570
<211> LENGTH: 10
<212> TYPE: DNA
<213> ORGANISM: Artificial Sequence
<220> FEATURE:
<223> OTHER INFORMATION: MamI
<220> FEATURE:
<221> NAME/KEY: misc_feature
<222> LOCATION: 4-7
<223> OTHER INFORMATION: n = a, c, t, or g

<400> SEQUENCE: 570 gatnnnnatc                                                             10

<210> SEQ ID NO 571
<211> LENGTH: 10
<212> TYPE: DNA
<213> ORGANISM: Artificial Sequence
<220> FEATURE:
<223> OTHER INFORMATION: MroXI
<220> FEATURE:
```

```
<221> NAME/KEY: misc_feature
<222> LOCATION: 4-7
<223> OTHER INFORMATION: n = a, c, t, or g

<400> SEQUENCE: 571 gaannnnttc                                                              10

<210> SEQ ID NO 572
<211> LENGTH: 10
<212> TYPE: DNA
<213> ORGANISM: Artificial Sequence
<220> FEATURE:
<223> OTHER INFORMATION: OliI
<220> FEATURE:
<221> NAME/KEY: misc_feature
<222> LOCATION: 4-7
<223> OTHER INFORMATION: n = a, c, t, or g

<400> SEQUENCE: 572 cacnnnngtg                                                              10

<210> SEQ ID NO 573
<211> LENGTH: 10
<212> TYPE: DNA
<213> ORGANISM: Artificial Sequence
<220> FEATURE:
<223> OTHER INFORMATION: PdmI
<220> FEATURE:
<221> NAME/KEY: misc_feature
<222> LOCATION: 4-7
<223> OTHER INFORMATION: n = a, c, t, or g

<400> SEQUENCE: 573 gaannnnttc                                                              10

<210> SEQ ID NO 574
<211> LENGTH: 10
<212> TYPE: DNA
<213> ORGANISM: Artificial Sequence
<220> FEATURE:
<223> OTHER INFORMATION: RseI
<220> FEATURE:
<221> NAME/KEY: misc_feature
<222> LOCATION: 4-7
<223> OTHER INFORMATION: n = a, c, t, or g

<400> SEQUENCE: 574 caynnnnrtg                                                              10

<210> SEQ ID NO 575
<211> LENGTH: 10
<212> TYPE: DNA
<213> ORGANISM: Artificial Sequence
<220> FEATURE:
<223> OTHER INFORMATION: SmiMI
<220> FEATURE:
<221> NAME/KEY: misc_feature
<222> LOCATION: 4-7
<223> OTHER INFORMATION: n = a, c, t, or g

<400> SEQUENCE: 575 caynnnnrtg                                                              10

<210> SEQ ID NO 576
<211> LENGTH: 11
<212> TYPE: DNA
<213> ORGANISM: Artificial Sequence
<220> FEATURE:
<223> OTHER INFORMATION: AccB7I
```

```
<220> FEATURE:
<221> NAME/KEY: misc_feature
<222> LOCATION: 4-8
<223> OTHER INFORMATION: n = a, c, t, or g

<400> SEQUENCE: 576
ccannnnntg g                                                              11

<210> SEQ ID NO 577
<211> LENGTH: 11
<212> TYPE: DNA
<213> ORGANISM: Artificial Sequence
<220> FEATURE:
<223> OTHER INFORMATION: AspEI
<220> FEATURE:
<221> NAME/KEY: misc_feature
<222> LOCATION: 4-8
<223> OTHER INFORMATION: n = a, c, t, or g

<400> SEQUENCE: 577
gacnnnnngt c                                                              11

<210> SEQ ID NO 578
<211> LENGTH: 11
<212> TYPE: DNA
<213> ORGANISM: Artificial Sequence
<220> FEATURE:
<223> OTHER INFORMATION: BasI
<220> FEATURE:
<221> NAME/KEY: misc_feature
<222> LOCATION: 4-8
<223> OTHER INFORMATION: n = a, c, t, or g

<400> SEQUENCE: 578
ccannnnntg g                                                              11

<210> SEQ ID NO 579
<211> LENGTH: 11
<212> TYPE: DNA
<213> ORGANISM: Artificial Sequence
<220> FEATURE:
<223> OTHER INFORMATION: BmeRI
<220> FEATURE:
<221> NAME/KEY: misc_feature
<222> LOCATION: 4-8
<223> OTHER INFORMATION: n = a, c, t, or g

<400> SEQUENCE: 579
gacnnnnngt c                                                              11

<210> SEQ ID NO 580
<211> LENGTH: 11
<212> TYPE: DNA
<213> ORGANISM: Artificial Sequence
<220> FEATURE:
<223> OTHER INFORMATION: BplI
<220> FEATURE:
<221> NAME/KEY: misc_feature
<222> LOCATION: 4-8
<223> OTHER INFORMATION: n = a, c, t, or g

<400> SEQUENCE: 580
gagnnnnnct c                                                              11

<210> SEQ ID NO 581
<211> LENGTH: 37
<212> TYPE: DNA
<213> ORGANISM: Artificial Sequence
<220> FEATURE:
```

<223> OTHER INFORMATION: BplI
<220> FEATURE:
<221> NAME/KEY: misc_feature
<222> LOCATION: 1-13, 17-21, 25-37
<223> OTHER INFORMATION: n = a, c, t, or g

<400> SEQUENCE: 581
nnnnnnnnnn nnngagnnnn nctcnnnnnn nnnnnnn                37

<210> SEQ ID NO 582
<211> LENGTH: 37
<212> TYPE: DNA
<213> ORGANISM: Artificial Sequence
<220> FEATURE:
<223> OTHER INFORMATION: BplI
<220> FEATURE:
<221> NAME/KEY: misc_feature
<222> LOCATION: 1-13, 17-21, 25-37
<223> OTHER INFORMATION: n = a, c, t, or g

<400> SEQUENCE: 582
nnnnnnnnnn nnngagnnnn nctcnnnnnn nnnnnnn                37

<210> SEQ ID NO 583
<211> LENGTH: 11
<212> TYPE: DNA
<213> ORGANISM: Artificial Sequence
<220> FEATURE:
<223> OTHER INFORMATION: Bsc4I
<220> FEATURE:
<221> NAME/KEY: misc_feature
<222> LOCATION: 3-9
<223> OTHER INFORMATION: n = a, c, t, or g

<400> SEQUENCE: 583
ccnnnnnnng g                                            11

<210> SEQ ID NO 584
<211> LENGTH: 11
<212> TYPE: DNA
<213> ORGANISM: Artificial Sequence
<220> FEATURE:
<223> OTHER INFORMATION: BseLI
<220> FEATURE:
<221> NAME/KEY: misc_feature
<222> LOCATION: 3-9
<223> OTHER INFORMATION: n = a, c, t, or g

<400> SEQUENCE: 584
ccnnnnnnng g                                            11

<210> SEQ ID NO 585
<211> LENGTH: 11
<212> TYPE: DNA
<213> ORGANISM: Artificial Sequence
<220> FEATURE:
<223> OTHER INFORMATION: BsiYI
<220> FEATURE:
<221> NAME/KEY: misc_feature
<222> LOCATION: 3-9
<223> OTHER INFORMATION: n = a, c, t, or g

<400> SEQUENCE: 585
ccnnnnnnng g                                            11

<210> SEQ ID NO 586
<211> LENGTH: 11
<212> TYPE: DNA
<213> ORGANISM: Artificial Sequence

```
<220> FEATURE:
<223> OTHER INFORMATION: BstENI
<220> FEATURE:
<221> NAME/KEY: misc_feature
<222> LOCATION: 4-8
<223> OTHER INFORMATION: n = a, c, t, or g

<400> SEQUENCE: 586
cctnnnnnag g                                                            11

<210> SEQ ID NO 587
<211> LENGTH: 11
<212> TYPE: DNA
<213> ORGANISM: Artificial Sequence
<220> FEATURE:
<223> OTHER INFORMATION: BstMWI
<220> FEATURE:
<221> NAME/KEY: misc_feature
<222> LOCATION: 3-9
<223> OTHER INFORMATION: n = a, c, t, or g

<400> SEQUENCE: 587
gcnnnnnnng c                                                            11

<210> SEQ ID NO 588
<211> LENGTH: 11
<212> TYPE: DNA
<213> ORGANISM: Artificial Sequence
<220> FEATURE:
<223> OTHER INFORMATION: CjeI
<220> FEATURE:
<221> NAME/KEY: misc_feature
<222> LOCATION: 4-9
<223> OTHER INFORMATION: n = a, c, t, or g

<400> SEQUENCE: 588
ccannnnnng t                                                            11

<210> SEQ ID NO 589
<211> LENGTH: 40
<212> TYPE: DNA
<213> ORGANISM: Artificial Sequence
<220> FEATURE:
<223> OTHER INFORMATION: CjeI
<220> FEATURE:
<221> NAME/KEY: misc_feature
<222> LOCATION: 1-14, 18-23, 26-40
<223> OTHER INFORMATION: n = a, c, t, or g

<400> SEQUENCE: 589
nnnnnnnnnn nnnnccannn nnngtnnnnn nnnnnnnnnn                             40

<210> SEQ ID NO 590
<211> LENGTH: 40
<212> TYPE: DNA
<213> ORGANISM: Artificial Sequence
<220> FEATURE:
<223> OTHER INFORMATION: CjeI
<220> FEATURE:
<221> NAME/KEY: misc_feature
<222> LOCATION: 1-15, 18-23, 27-40
<223> OTHER INFORMATION: n = a, c, t, or g

<400> SEQUENCE: 590
nnnnnnnnnn nnnnnacnnn nnntggnnnn nnnnnnnnnn                             40

<210> SEQ ID NO 591
<211> LENGTH: 11
<212> TYPE: DNA
```

```
<213> ORGANISM: Artificial Sequence
<220> FEATURE:
<223> OTHER INFORMATION: CjuI
<220> FEATURE:
<221> NAME/KEY: misc_feature
<222> LOCATION: 4-8
<223> OTHER INFORMATION: n = a, c, t, or g

<400> SEQUENCE: 591
caynnnnnrt g                                                              11

<210> SEQ ID NO 592
<211> LENGTH: 11
<212> TYPE: DNA
<213> ORGANISM: Artificial Sequence
<220> FEATURE:
<223> OTHER INFORMATION: CjuII
<220> FEATURE:
<221> NAME/KEY: misc_feature
<222> LOCATION: 4-8
<223> OTHER INFORMATION: n = a, c, t, or g

<400> SEQUENCE: 592
caynnnnnct c                                                              11

<210> SEQ ID NO 593
<211> LENGTH: 11
<212> TYPE: DNA
<213> ORGANISM: Artificial Sequence
<220> FEATURE:
<223> OTHER INFORMATION: CjuII
<220> FEATURE:
<221> NAME/KEY: misc_feature
<222> LOCATION: 4-8
<223> OTHER INFORMATION: n = a, c, t, or g

<400> SEQUENCE: 593
gagnnnnnrt g                                                              11

<210> SEQ ID NO 594
<211> LENGTH: 11
<212> TYPE: DNA
<213> ORGANISM: Artificial Sequence
<220> FEATURE:
<223> OTHER INFORMATION: DriI
<220> FEATURE:
<221> NAME/KEY: misc_feature
<222> LOCATION: 4-8
<223> OTHER INFORMATION: n = a, c, t, or g

<400> SEQUENCE: 594
gacnnnnngt c                                                              11

<210> SEQ ID NO 595
<211> LENGTH: 11
<212> TYPE: DNA
<213> ORGANISM: Artificial Sequence
<220> FEATURE:
<223> OTHER INFORMATION: Eam1105I
<220> FEATURE:
<221> NAME/KEY: misc_feature
<222> LOCATION: 4-8
<223> OTHER INFORMATION: n = a, c, t, or g

<400> SEQUENCE: 595
gacnnnnngt c                                                              11

<210> SEQ ID NO 596
<211> LENGTH: 11
```

```
<212> TYPE: DNA
<213> ORGANISM: Artificial Sequence
<220> FEATURE:
<223> OTHER INFORMATION: EclHKI
<220> FEATURE:
<221> NAME/KEY: misc_feature
<222> LOCATION: 4-8
<223> OTHER INFORMATION: n = a, c, t, or g

<400> SEQUENCE: 596
gacnnnnngt c                                                            11

<210> SEQ ID NO 597
<211> LENGTH: 11
<212> TYPE: DNA
<213> ORGANISM: Artificial Sequence
<220> FEATURE:
<223> OTHER INFORMATION: FalI
<220> FEATURE:
<221> NAME/KEY: misc_feature
<222> LOCATION: 4-8
<223> OTHER INFORMATION: n = a, c, t, or g

<400> SEQUENCE: 597
aagnnnnnct t                                                            11

<210> SEQ ID NO 598
<211> LENGTH: 37
<212> TYPE: DNA
<213> ORGANISM: Artificial Sequence
<220> FEATURE:
<223> OTHER INFORMATION: FalI
<220> FEATURE:
<221> NAME/KEY: misc_feature
<222> LOCATION: 1-13, 17-21, 25-37
<223> OTHER INFORMATION: n = a, c, t, or g

<400> SEQUENCE: 598
nnnnnnnnnn nnnaagnnnn ncttnnnnnn nnnnnnn                                37

<210> SEQ ID NO 599
<211> LENGTH: 37
<212> TYPE: DNA
<213> ORGANISM: Artificial Sequence
<220> FEATURE:
<223> OTHER INFORMATION: FalI
<220> FEATURE:
<221> NAME/KEY: misc_feature
<222> LOCATION: 1-13, 17-21, 25-37
<223> OTHER INFORMATION: n = a, c, t, or g

<400> SEQUENCE: 599
nnnnnnnnnn nnnaagnnnn ncttnnnnnn nnnnnnn                                37

<210> SEQ ID NO 600
<211> LENGTH: 11
<212> TYPE: DNA
<213> ORGANISM: Artificial Sequence
<220> FEATURE:
<223> OTHER INFORMATION: HpyF10VI
<220> FEATURE:
<221> NAME/KEY: misc_feature
<222> LOCATION: 3-9
<223> OTHER INFORMATION: n = a, c, t, or g

<400> SEQUENCE: 600
gcnnnnnnng c                                                            11

<210> SEQ ID NO 601
```

```
<211> LENGTH: 11
<212> TYPE: DNA
<213> ORGANISM: Artificial Sequence
<220> FEATURE:
<223> OTHER INFORMATION: NgoAVIII
<220> FEATURE:
<221> NAME/KEY: misc_feature
<222> LOCATION: 4-8
<223> OTHER INFORMATION: n = a, c, t, or g

<400> SEQUENCE: 601
gacnnnnntg a                                                              11

<210> SEQ ID NO 602
<211> LENGTH: 38
<212> TYPE: DNA
<213> ORGANISM: Artificial Sequence
<220> FEATURE:
<223> OTHER INFORMATION: NgoAVIII
<220> FEATURE:
<221> NAME/KEY: misc_feature
<222> LOCATION: 1-14, 18-22, 26-38
<223> OTHER INFORMATION: n = a, c, t, or g

<400> SEQUENCE: 602
nnnnnnnnnn nnnngacnnn nntgannnnn nnnnnnnn                                 38

<210> SEQ ID NO 603
<211> LENGTH: 38
<212> TYPE: DNA
<213> ORGANISM: Artificial Sequence
<220> FEATURE:
<223> OTHER INFORMATION: NgoAVIII
<220> FEATURE:
<221> NAME/KEY: misc_feature
<222> LOCATION: 1-13, 17-21, 25-38
<223> OTHER INFORMATION: n = a, c, t, or g

<400> SEQUENCE: 603
nnnnnnnnnn nnntcannnn ngtcnnnnnn nnnnnnnn                                 38

<210> SEQ ID NO 604
<211> LENGTH: 11
<212> TYPE: DNA
<213> ORGANISM: Artificial Sequence
<220> FEATURE:
<223> OTHER INFORMATION: NruGI
<220> FEATURE:
<221> NAME/KEY: misc_feature
<222> LOCATION: 4-8
<223> OTHER INFORMATION: n = a, c, t, or g

<400> SEQUENCE: 604
gacnnnnngt c                                                              11

<210> SEQ ID NO 605
<211> LENGTH: 11
<212> TYPE: DNA
<213> ORGANISM: Artificial Sequence
<220> FEATURE:
<223> OTHER INFORMATION: PflBI
<220> FEATURE:
<221> NAME/KEY: misc_feature
<222> LOCATION: 4-8
<223> OTHER INFORMATION: n = a, c, t, or g

<400> SEQUENCE: 605
ccannnnntg g                                                              11
```

```
<210> SEQ ID NO 606
<211> LENGTH: 11
<212> TYPE: DNA
<213> ORGANISM: Artificial Sequence
<220> FEATURE:
<223> OTHER INFORMATION: UbaF14I
<220> FEATURE:
<221> NAME/KEY: misc_feature
<222> LOCATION: 4-8
<223> OTHER INFORMATION: n = a, c, t, or g

<400> SEQUENCE: 606
ccannnnntc g                                                          11

<210> SEQ ID NO 607
<211> LENGTH: 11
<212> TYPE: DNA
<213> ORGANISM: Artificial Sequence
<220> FEATURE:
<223> OTHER INFORMATION: UbaF14I
<220> FEATURE:
<221> NAME/KEY: misc_feature
<222> LOCATION: 4-8
<223> OTHER INFORMATION: n = a, c, t, or g

<400> SEQUENCE: 607
cgannnnntg g                                                          11

<210> SEQ ID NO 608
<211> LENGTH: 11
<212> TYPE: DNA
<213> ORGANISM: Artificial Sequence
<220> FEATURE:
<223> OTHER INFORMATION: XagI
<220> FEATURE:
<221> NAME/KEY: misc_feature
<222> LOCATION: 4-8
<223> OTHER INFORMATION: n = a, c, t, or g

<400> SEQUENCE: 608
cctnnnnnag g                                                          11

<210> SEQ ID NO 609
<211> LENGTH: 12
<212> TYPE: DNA
<213> ORGANISM: Artificial Sequence
<220> FEATURE:
<223> OTHER INFORMATION: AasI
<220> FEATURE:
<221> NAME/KEY: misc_feature
<222> LOCATION: 4-9
<223> OTHER INFORMATION: n = a, c, t, or g

<400> SEQUENCE: 609
gacnnnnnng tc                                                         12

<210> SEQ ID NO 610
<211> LENGTH: 12
<212> TYPE: DNA
<213> ORGANISM: Artificial Sequence
<220> FEATURE:
<223> OTHER INFORMATION: BdaI
<220> FEATURE:
<221> NAME/KEY: misc_feature
<222> LOCATION: 4-9
<223> OTHER INFORMATION: n = a, c, t, or g

<400> SEQUENCE: 610
tgannnnnnt ca                                                         12
```

```
<210> SEQ ID NO 611
<211> LENGTH: 36
<212> TYPE: DNA
<213> ORGANISM: Artificial Sequence
<220> FEATURE:
<223> OTHER INFORMATION: BdaI
<220> FEATURE:
<221> NAME/KEY: misc_feature
<222> LOCATION: 1-12, 16-21, 25-36
<223> OTHER INFORMATION: n = a, c, t, or g

<400> SEQUENCE: 611
nnnnnnnnnn nntgannnnn ntcannnnnn nnnnnn                              36

<210> SEQ ID NO 612
<211> LENGTH: 36
<212> TYPE: DNA
<213> ORGANISM: Artificial Sequence
<220> FEATURE:
<223> OTHER INFORMATION: BdaI
<220> FEATURE:
<221> NAME/KEY: misc_feature
<222> LOCATION: 1-12, 16-21, 25-36
<223> OTHER INFORMATION: n = a, c, t, or g

<400> SEQUENCE: 612
nnnnnnnnnn nntgannnnn ntcannnnnn nnnnnn                              36

<210> SEQ ID NO 613
<211> LENGTH: 12
<212> TYPE: DNA
<213> ORGANISM: Artificial Sequence
<220> FEATURE:
<223> OTHER INFORMATION: Bsp24I
<220> FEATURE:
<221> NAME/KEY: misc_feature
<222> LOCATION: 4-9
<223> OTHER INFORMATION: n = a, c, t, or g

<400> SEQUENCE: 613
gacnnnnnnt gg                                                        12

<210> SEQ ID NO 614
<211> LENGTH: 37
<212> TYPE: DNA
<213> ORGANISM: Artificial Sequence
<220> FEATURE:
<223> OTHER INFORMATION: Bsp24I
<220> FEATURE:
<221> NAME/KEY: misc_feature
<222> LOCATION: 1-13, 17-22, 26-37
<223> OTHER INFORMATION: n = a, c, t, or g

<400> SEQUENCE: 614
nnnnnnnnnn nnngacnnnn nntggnnnnn nnnnnnn                             37

<210> SEQ ID NO 615
<211> LENGTH: 37
<212> TYPE: DNA
<213> ORGANISM: Artificial Sequence
<220> FEATURE:
<223> OTHER INFORMATION: Bsp24I
<220> FEATURE:
<221> NAME/KEY: misc_feature
<222> LOCATION: 1-12, 16-21, 25-37
<223> OTHER INFORMATION: n = a, c, t, or g

<400> SEQUENCE: 615
nnnnnnnnnn nnccannnnn ngtcnnnnnn nnnnnnn                             37
```

```
<210> SEQ ID NO 616
<211> LENGTH: 12
<212> TYPE: DNA
<213> ORGANISM: Artificial Sequence
<220> FEATURE:
<223> OTHER INFORMATION: CjePI
<220> FEATURE:
<221> NAME/KEY: misc_feature
<222> LOCATION: 4-10
<223> OTHER INFORMATION: n = a, c, t, or g

<400> SEQUENCE: 616
ccannnnnnn tc                                                              12

<210> SEQ ID NO 617
<211> LENGTH: 39
<212> TYPE: DNA
<213> ORGANISM: Artificial Sequence
<220> FEATURE:
<223> OTHER INFORMATION: CjePI
<220> FEATURE:
<221> NAME/KEY: misc_feature
<222> LOCATION: 1-13, 17-23, 26-39
<223> OTHER INFORMATION: n = a, c, t, or g

<400> SEQUENCE: 617
nnnnnnnnnn nnnccannnn nnntcnnnnn nnnnnnnnn                                 39

<210> SEQ ID NO 618
<211> LENGTH: 39
<212> TYPE: DNA
<213> ORGANISM: Artificial Sequence
<220> FEATURE:
<223> OTHER INFORMATION: CjePI
<220> FEATURE:
<221> NAME/KEY: misc_feature
<222> LOCATION: 1-14, 17-23, 27-39
<223> OTHER INFORMATION: n = a, c, t, or g

<400> SEQUENCE: 618
nnnnnnnnnn nnnngannnn nnntggnnnn nnnnnnnnn                                 39

<210> SEQ ID NO 619
<211> LENGTH: 12
<212> TYPE: DNA
<213> ORGANISM: Artificial Sequence
<220> FEATURE:
<223> OTHER INFORMATION: DseDI
<220> FEATURE:
<221> NAME/KEY: misc_feature
<222> LOCATION: 4-9
<223> OTHER INFORMATION: n = a, c, t, or g

<400> SEQUENCE: 619
gacnnnnnng tc                                                              12

<210> SEQ ID NO 620
<211> LENGTH: 12
<212> TYPE: DNA
<213> ORGANISM: Artificial Sequence
<220> FEATURE:
<223> OTHER INFORMATION: UbaF9I
<220> FEATURE:
<221> NAME/KEY: misc_feature
<222> LOCATION: 4-8
<223> OTHER INFORMATION: n = a, c, t, or g

<400> SEQUENCE: 620
```
tacnnnnnrt gt                                                                    12

<210> SEQ ID NO 621
<211> LENGTH: 12
<212> TYPE: DNA
<213> ORGANISM: Artificial Sequence
<220> FEATURE:
<223> OTHER INFORMATION: UbaF9I
<220> FEATURE:
<221> NAME/KEY: misc_feature
<222> LOCATION: 5-9
<223> OTHER INFORMATION: n = a, c, t, or g

<400> SEQUENCE: 621
acaynnnnng ta                                                                    12

<210> SEQ ID NO 622
<211> LENGTH: 13
<212> TYPE: DNA
<213> ORGANISM: Artificial Sequence
<220> FEATURE:
<223> OTHER INFORMATION: ArsI
<220> FEATURE:
<221> NAME/KEY: misc_feature
<222> LOCATION: 4-9
<223> OTHER INFORMATION: n = a, c, t, or g

<400> SEQUENCE: 622
gacnnnnnnt tyg                                                                   13

<210> SEQ ID NO 623
<211> LENGTH: 37
<212> TYPE: DNA
<213> ORGANISM: Artificial Sequence
<220> FEATURE:
<223> OTHER INFORMATION: ArsI
<220> FEATURE:
<221> NAME/KEY: misc_feature
<222> LOCATION: 1-13, 17-22, 27-37
<223> OTHER INFORMATION: n = a, c, t, or g

<400> SEQUENCE: 623
nnnnnnnnnn nnngacnnnn nnttygnnnn nnnnnnn                                         37

<210> SEQ ID NO 624
<211> LENGTH: 37
<212> TYPE: DNA
<213> ORGANISM: Artificial Sequence
<220> FEATURE:
<223> OTHER INFORMATION: ArsI
<220> FEATURE:
<221> NAME/KEY: misc_feature
<222> LOCATION: 1-11, 16-21, 25-37
<223> OTHER INFORMATION: n = a, c, t, or g

<400> SEQUENCE: 624
nnnnnnnnnn ncraannnnn ngtcnnnnnn nnnnnnn                                         37

<210> SEQ ID NO 625
<211> LENGTH: 13
<212> TYPE: DNA
<213> ORGANISM: Artificial Sequence
<220> FEATURE:
<223> OTHER INFORMATION: BarI
<220> FEATURE:
<221> NAME/KEY: misc_feature
<222> LOCATION: 5-10
<223> OTHER INFORMATION: n = a, c, t, or g

<400> SEQUENCE: 625
gaagnnnnnn tac    13

<210> SEQ ID NO 626
<211> LENGTH: 37
<212> TYPE: DNA
<213> ORGANISM: Artificial Sequence
<220> FEATURE:
<223> OTHER INFORMATION: BarI
<220> FEATURE:
<221> NAME/KEY: misc_feature
<222> LOCATION: 1-12, 17-22, 26-37
<223> OTHER INFORMATION: n = a, c, t, or g

<400> SEQUENCE: 626
nnnnnnnnnn nngaagnnnn nntacnnnnn nnnnnnn    37

<210> SEQ ID NO 627
<211> LENGTH: 37
<212> TYPE: DNA
<213> ORGANISM: Artificial Sequence
<220> FEATURE:
<223> OTHER INFORMATION: BarI
<220> FEATURE:
<221> NAME/KEY: misc_feature
<222> LOCATION: 1-12, 16-21, 26-37
<223> OTHER INFORMATION: n = a, c, t, or g

<400> SEQUENCE: 627
nnnnnnnnnn nngtannnnn ncttcnnnnn nnnnnnn    37

<210> SEQ ID NO 628
<211> LENGTH: 13
<212> TYPE: DNA
<213> ORGANISM: Artificial Sequence
<220> FEATURE:
<223> OTHER INFORMATION: PcsI
<220> FEATURE:
<221> NAME/KEY: misc_feature
<222> LOCATION: 4-10
<223> OTHER INFORMATION: n = a, c, t, or g

<400> SEQUENCE: 628
wcgnnnnnnn cgw    13

<210> SEQ ID NO 629
<211> LENGTH: 13
<212> TYPE: DNA
<213> ORGANISM: Artificial Sequence
<220> FEATURE:
<223> OTHER INFORMATION: UbaF13I
<220> FEATURE:
<221> NAME/KEY: misc_feature
<222> LOCATION: 4-9
<223> OTHER INFORMATION: n = a, c, t, or g

<400> SEQUENCE: 629
gagnnnnnnc tgg    13

<210> SEQ ID NO 630
<211> LENGTH: 13
<212> TYPE: DNA
<213> ORGANISM: Artificial Sequence
<220> FEATURE:
<223> OTHER INFORMATION: UbaF13I
<220> FEATURE:
<221> NAME/KEY: misc_feature
<222> LOCATION: 5-10
<223> OTHER INFORMATION: n = a, c, t, or g

```
<400> SEQUENCE: 630 ccagnnnnn ctc                                                          13

<210> SEQ ID NO 631
<211> LENGTH: 6
<212> TYPE: DNA
<213> ORGANISM: Artificial Sequence
<220> FEATURE:
<223> OTHER INFORMATION: KspI

<400> SEQUENCE: 631 ccgcgg                                                                  6

<210> SEQ ID NO 632
<211> LENGTH: 6
<212> TYPE: DNA
<213> ORGANISM: Artificial Sequence
<220> FEATURE:
<223> OTHER INFORMATION: PaeI

<400> SEQUENCE: 632 gcatgc                                                                  6

<210> SEQ ID NO 633
<211> LENGTH: 6
<212> TYPE: DNA
<213> ORGANISM: Artificial Sequence
<220> FEATURE:
<223> OTHER INFORMATION: StuI

<400> SEQUENCE: 633 aggcct                                                                  6

<210> SEQ ID NO 634
<211> LENGTH: 7
<212> TYPE: DNA
<213> ORGANISM: Artificial Sequence
<220> FEATURE:
<223> OTHER INFORMATION: LguI

<400> SEQUENCE: 634 gctcttc                                                                 7

<210> SEQ ID NO 635
<211> LENGTH: 11
<212> TYPE: DNA
<213> ORGANISM: Artificial Sequence
<220> FEATURE:
<223> OTHER INFORMATION: LguI
<220> FEATURE:
<221> NAME/KEY: misc_feature
<222> LOCATION: 8-11
<223> OTHER INFORMATION: n = a, c, t, or g

<400> SEQUENCE: 635
gctcttcnnn n                                                           11

<210> SEQ ID NO 636
<211> LENGTH: 11
<212> TYPE: DNA
<213> ORGANISM: Artificial Sequence
<220> FEATURE:
<223> OTHER INFORMATION: LguI
<220> FEATURE:
<221> NAME/KEY: misc_feature
<222> LOCATION: 1-4
<223> OTHER INFORMATION: n = a, c, t, or g
```

```
<400> SEQUENCE: 636
nnnngaagag c                                                               11

<210> SEQ ID NO 637
<211> LENGTH: 553
<212> TYPE: DNA
<213> ORGANISM: Artificial Sequence
<220> FEATURE:
<223> OTHER INFORMATION: pEVL-300 sequence

<400> SEQUENCE: 637
gggataacct ggcaggaatc tggatatgcc aggcgtgtac tatgtcgatt accgactgga          60
acggattaag gaggctaaca atgaaaccta tgtggagcag catgaagtgg ctgtggctag         120
gtattgtgat ctgccctcca aactgggaca taaactgaat taacgtacgg aaaaaaaaaa         180
aaaaaaaaaa aaaaaaaaaa aaaaaaaaaa aaaaaaaaaa aaaaaaaaaa aaaaaaaaaa         240
aaaaaaaaaa aaaaaaaaaa aaaaaaaaaa aaaaaaaaaa aaaaaaaaaa aaaaaaaaaa         300
aaaaaaaaaa aaaaaaaaaa aaaaaaaaaa aaaaaaaaaa aaaaaaaaaa aaaaaaaaaa         360
aaaaaaaaaa aaaaaaaaaa aaaaaaaaaa aaaaaaaaaa aaaaaaaaaa aaaaaaaaaa         420
aaaaaaaaaa aaaaaaaaaa aaaaaaaaaa aaaaaaaaaa aaaaaaaaaa aaaagccccc         480
gcccccgggg ccttaaatat aagaaccccc ccccccccccc ccgggggggcg tggggggggta       540 caaataaata cct                                                            553

<210> SEQ ID NO 638
<211> LENGTH: 438
<212> TYPE: DNA
<213> ORGANISM: Artificial Sequence
<220> FEATURE:
<223> OTHER INFORMATION: pEVL-300 sequence

<400> SEQUENCE: 638
aattggaacg ggcgcttgac ttcagtctaa tggccctaag gtctcgtttt tttttttttt          60
tttttttttt tttttttttt tttttttttt tttttttttt tttttttttt tttttttttt         120
tttttttttt tttttttttt tttttttttt tttttttttt tttttttttt tttttttttt         180
tttttttttt tttttttttt tttttttttt tttttttttt tttttttttt tttttttttt         240
tttttttttt tttttttttt tttttttttt tttttttttt tttttttttt tttttttttt         300 tttttttat tttttttttt ttcttttttt tttttttttt tttttttttt tacaaaaaaa          360
aaaacctccc aatccacggg gagggagaag aaaaaaaaaa ccccaccccc cccacccca           420 gccaaaattt aatattga                                                       438
```